US012441936B2

(12) United States Patent
Sakuma

(10) Patent No.: US 12,441,936 B2
(45) Date of Patent: Oct. 14, 2025

(54) LIGHT EMITTING ELEMENT AND POLYCYCLIC COMPOUND FOR THE SAME

(71) Applicant: Samsung Display Co., Ltd., Yongin-si (KR)

(72) Inventor: Takao Sakuma, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 898 days.

(21) Appl. No.: 17/447,533

(22) Filed: Sep. 13, 2021

(65) Prior Publication Data

US 2022/0246858 A1 Aug. 4, 2022

(30) Foreign Application Priority Data

Jan. 19, 2021 (KR) ........................ 10-2021-0007281

(51) Int. Cl.
*C09K 11/06* (2006.01)
*C07D 209/86* (2006.01)
(Continued)

(52) U.S. Cl.
CPC ............ *C09K 11/06* (2013.01); *C07D 209/86* (2013.01); *C07D 405/14* (2013.01);
(Continued)

(58) Field of Classification Search
CPC .......................... H10K 85/6572; C07D 209/86
See application file for complete search history.

(56) References Cited

U.S. PATENT DOCUMENTS 8,530,063 B2 9/2013 Kim et al.
8,993,783 B2 3/2015 Lee et al.
(Continued)

FOREIGN PATENT DOCUMENTS

CN 108976212 A 12/2018
KR 10-1233380 B1 2/2013
(Continued)

OTHER PUBLICATIONS

Machine-generated English-language translation of KR-20130022232-A.*
Machine-generated English-language translation of KR-1389527-B1.*

*Primary Examiner* — Vu A Nguyen
(74) *Attorney, Agent, or Firm* — Womble Bond Dickinson (US) LLP

(57) ABSTRACT

A light emitting element includes a first electrode, a second electrode, and at least one functional layer disposed between the first electrode and the second electrode, in which the at least one functional layer includes a polycyclic compound represented by Formula 1, and the light emitting element thereby exhibits improved service life characteristics:

Formula 1

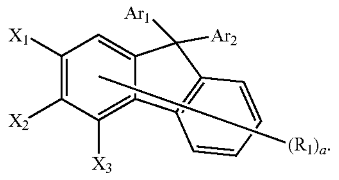

20 Claims, 6 Drawing Sheets

(51) Int. Cl.

| | |
|---|---|
| ***C07D 405/14*** | (2006.01) |
| ***H10K 50/15*** | (2023.01) |
| ***H10K 50/17*** | (2023.01) |
| ***H10K 50/18*** | (2023.01) |
| ***H10K 85/60*** | (2023.01) |

(52) U.S. Cl.

CPC ....... *H10K 85/615* (2023.02); *H10K 85/6572* (2023.02); *H10K 85/6574* (2023.02); *C09K 2211/1018* (2013.01); *H10K 50/15* (2023.02); *H10K 50/17* (2023.02); *H10K 50/18* (2023.02); *H10K 50/181* (2023.02)

(56) References Cited

U.S. PATENT DOCUMENTS

| | | | | |
|---|---|---|---|---|
| 9,455,412 | B2 | 9/2016 | Zeng et al. | |
| 10,208,026 | B2 | 2/2019 | Dyatkin et al. | |
| 2015/0243894 | A1* | 8/2015 | Zeng | C07D 209/88 548/440 |
| 2019/0185457 | A1 | 6/2019 | Irisa et al. | |
| 2020/0235303 | A1* | 7/2020 | Kim | H10K 50/15 |

FOREIGN PATENT DOCUMENTS

| | | | | |
|---|---|---|---|---|
| KR | 10-2013-0022232 | A | 3/2013 | |
| KR | 20130022232 | A * | 3/2013 | C09K 11/06 |
| KR | 10-1288567 | B1 | 7/2013 | |
| KR | 10-1389527 | B1 | 4/2014 | |
| KR | 1389527 | B1 * | 4/2014 | C09K 11/06 |
| KR | 10-2015-0099395 | A | 8/2015 | |
| KR | 10-2015-0115226 | A1 | 10/2015 | |
| KR | 10-2016-0095319 | A | 8/2016 | |
| KR | 10-1773936 | B1 | 9/2017 | |
| KR | 10-2019-0074186 | A | 6/2019 | |
| KR | 10-2020-0091544 | A | 7/2020 | |

* cited by examiner

LIGHT EMITTING ELEMENT AND POLYCYCLIC COMPOUND FOR THE SAME

CROSS-REFERENCE TO RELATED APPLICATION

This application claims priority to and the benefit of Korean Patent Application No. 10-2021-0007281, filed on Jan. 19, 2021 in the Korean Intellectual Property Office, the entire content of which is hereby incorporated by reference.

BACKGROUND

1. Field

One or more aspects of embodiments of the present disclosure relate to a light emitting element and a polycyclic compound utilized therein, and for example, to a polycyclic compound utilized in a hole transport region and a light emitting element including the same.

2. Description of Related Art

Organic electroluminescence display devices are being actively developed as image display devices. An example organic electroluminescence display device includes a so-called self-luminescent light emitting element, in which holes and electrons respectively injected from a first electrode and a second electrode recombine in an emission layer, and a luminescent material of the emission layer emits light to implement display.

In the application of a light emitting element to a display device, there is a desire for a light emitting element having a long service life (e.g., life span), and development of materials capable of stably attaining such a characteristic for a light emitting element is desired.

SUMMARY

One or more aspects of embodiments of the present disclosure are directed toward a light emitting element exhibiting a long service life characteristic.

One or more aspects of embodiments of the present disclosure are directed toward a polycyclic compound as a material for a light emitting element having a long service life characteristic.

One or more embodiments of the present disclosure provide a light emitting element including: a first electrode; a second electrode disposed on the first electrode; and at least one functional layer between the first electrode and the second electrode and including a polycyclic compound represented by Formula 1:

Formula 1

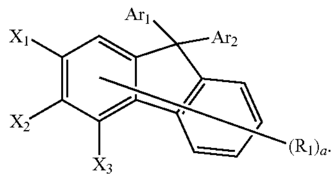

In Formula 1, $X_1$, $X_2$, and $X_3$ may each independently be $R_x$ or represented by Substituent S1, where at least one of $X_1$, $X_2$, or $X_3$ is represented by Substituent S1, $R_x$ and $R_1$ may each independently be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring, a may be an integer of 0 to 5, and $Ar_1$ and $Ar_2$ may each independently be a substituted or unsubstituted aryl group having 6 to 50 ring-forming carbon atoms, Substituent S1

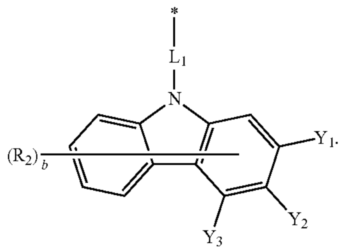

In Substituent S1, $Y_1$, $Y_2$, and $Y_3$ may each independently be $R_y$ or $L_2Z$, where any one of $Y_1$, $Y_2$, or $Y_3$ is represented by $L_2Z$, $R_2$ and $R_y$ may each independently be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring, where $R_y$ does not include (e.g., is not) a substituted or unsubstituted carbazole group, b may be an integer of 0 to 4, $L_1$ may be a direct linkage or a substituted or unsubstituted arylene group having 6 to 50 ring-forming carbon atoms, $L_2$ may be a direct linkage, a substituted or unsubstituted arylene group having 6 to 50 ring-forming carbon atoms, or a substituted or unsubstituted heteroarylene group having 2 to 50 ring-forming carbon atoms, where when $X_1$ is represented by Substituent S1 and $Y_1$ is represented by $L_2Z$, $L_2$ is a direct linkage, and when $X_1$ is represented by Substituent S1 and $Y_2$ is represented by $L_2Z$, Z is a substituted carbazole group, and in Substituent S1, "—*" is a position connected to a benzene ring in Formula 1, and Z is represented by Substituent S2, and Substituent S2

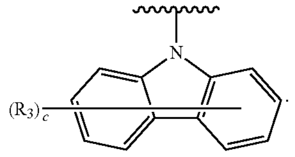

In Substituent S2, $R_3$ may be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring, c may be an integer of 0 to 8, and in Substituent S2,

is a position connected to $L_2$ in Substituent S1.

In an embodiment, the at least one functional layer may include an emission layer, a hole transport region disposed between the first electrode and the emission layer, and an electron transport region disposed between the emission layer and the second electrode, where the hole transport region may include the polycyclic compound.

In an embodiment, the hole transport region may include at least one of a hole injection layer, a hole transport layer, or an electron blocking layer, and at least one of the hole injection layer, the hole transport layer, or the electron blocking layer may include the polycyclic compound.

In an embodiment, $Ar_1$ and $Ar_2$ may each independently be a substituted or unsubstituted phenyl group.

In an embodiment, any one of $X_1$, $X_2$, or $X_3$ may be represented by Substituent S1.

In an embodiment, $R_x$, $R_y$, and $R_1$ may each independently be a hydrogen atom or a deuterium atom.

In an embodiment, $R_2$ may be a hydrogen atom, a deuterium atom, a methyl group, a cyano group, a methoxy group, or a substituted or unsubstituted carbazole group.

In an embodiment, $R_3$ may be a hydrogen atom, a deuterium atom, a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group.

In an embodiment, the polycyclic compound represented by Formula 1 may be represented by Formula 1-1:

Formula 1-1

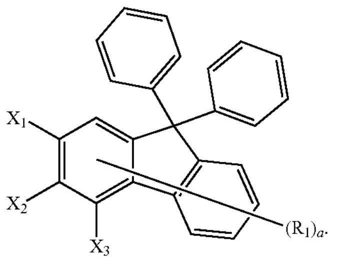

In Formula 1-1, $X_1$, $X_2$, $X_3$, $R_1$, and a may each independently be the same as defined in Formula 1.

In an embodiment, $L_1$ may be a direct linkage, a substituted or unsubstituted phenylene group, a substituted or unsubstituted divalent biphenyl group, or a substituted or unsubstituted divalent naphthyl group.

In an embodiment, $L_2$ may be a direct linkage, a substituted or unsubstituted phenylene group, a substituted or unsubstituted divalent biphenyl group, a substituted or unsubstituted divalent naphthyl group, a substituted or unsubstituted divalent dibenzofuran group, or a substituted or unsubstituted divalent dibenzothiophene group.

In an embodiment, the substituent represented by Substituent S2 may be a substituted or unsubstituted carbazole group.

In an embodiment of the present disclosure, the polycyclic compound is represented by Formula 1.

BRIEF DESCRIPTION OF THE DRAWINGS

The accompanying drawings are included to provide a further understanding of the present disclosure, and are incorporated in and constitute a part of this specification. The drawings illustrate embodiments of the present disclosure and, together with the description, serve to explain principles of the present disclosure. In the drawings.

DETAILED DESCRIPTION

Figure 1:
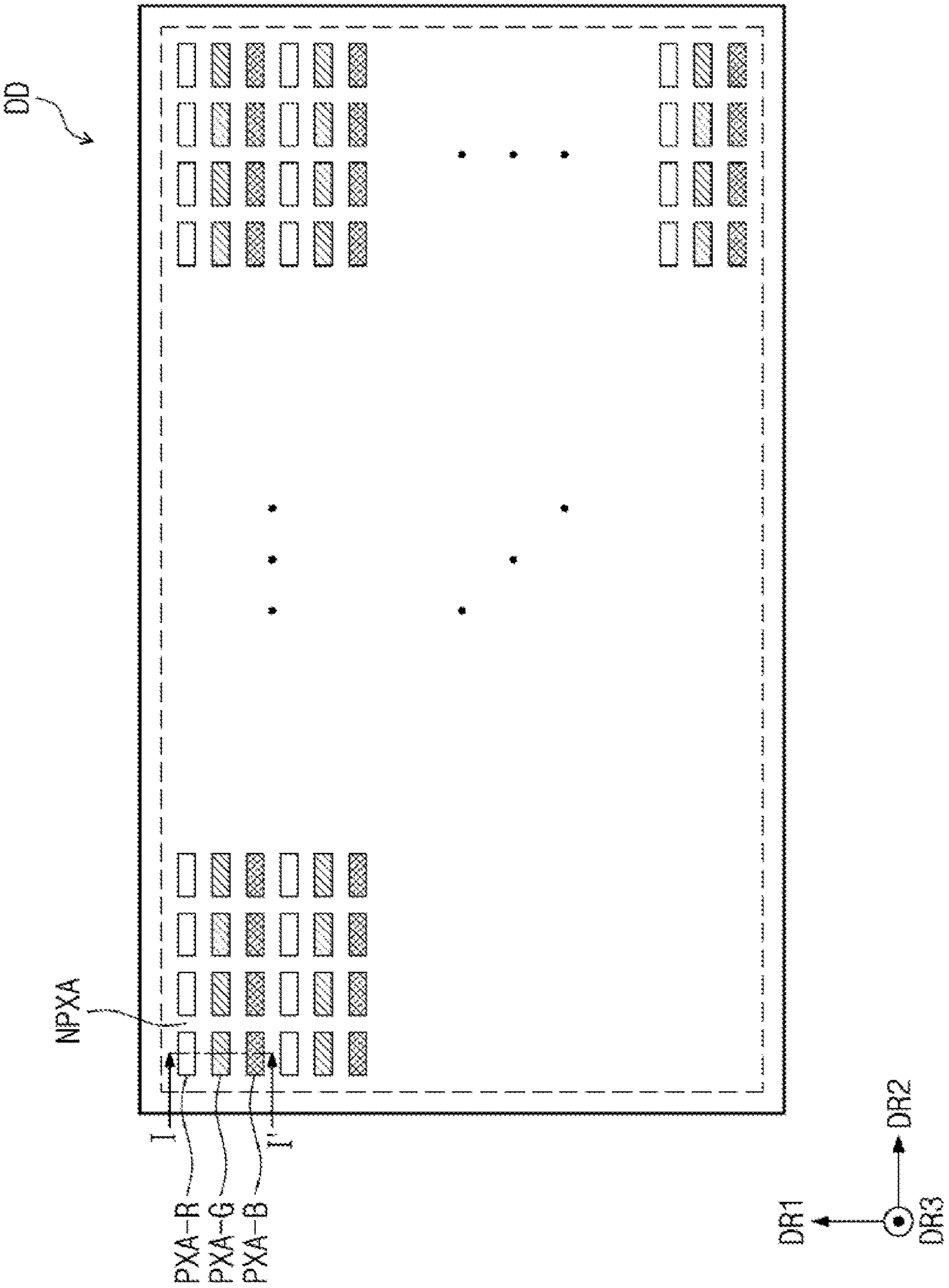
FIG. 1 is a plan view illustrating a display device according to an embodiment of the present disclosure.

The present disclosure may be modified in many alternate forms, and thus selected embodiments will be shown in the drawings and described in more detail. It should be understood, however, that the present disclosure is not limited to the particular forms disclosed, but rather, is intended to cover all modifications, equivalents, and alternatives falling within the spirit and scope of the present disclosure.

Like reference numerals in the drawings denote like elements throughout, and duplicative descriptions thereof may not be provided. Sizes and dimensions in the drawings may be exaggerated for clarity of the present disclosure. It will be understood that, although the terms "first," "second," etc. may be used herein to describe various suitable elements, these elements should not be limited by these terms. These terms are only utilized to distinguish one element from another. For example, a first element may be referred to as a second element, and, similarly, the second element may be referred to as the first element, without departing from the scope of the present disclosure. Singular forms (such as "a," "an," and "the") include the plural forms as well, unless the context clearly indicates otherwise.

In the present application, it will be understood that the terms "include," "comprise," "have," etc., specify the presence of a feature, a fixed number, a step, an operation, an element, a component, or a combination thereof disclosed in the specification, but do not exclude the possibility of presence or addition of one or more other features, fixed numbers, steps, operations, elements, components, or combination thereof.

In the present application, when a part such as a layer, a film, a region, or a plate is referred to as being "on" or "above" another part, it can be directly on the other part, or an intervening part may also be present. In contrast, when a part such as a layer, a film, a region, or a plate is referred to as being "under" or "below" another part, it can be directly under the other part, or an intervening part may also be present. It will be understood that when a part is referred to as being "on" another part, it can be disposed on the other part, or disposed under the other part as well.

As used herein, the terms "use," "using," and "used" may be considered synonymous with the terms "utilize," "utilizing," and "utilized," respectively. As used herein, expressions such as "at least one of," "one of," and "selected from," when preceding a list of elements, modify the entire list of elements and do not modify the individual elements of the list. As used herein, the term "and/or" includes any and all combinations of one or more of the associated listed items. Further, the use of "may" when describing embodiments of the present disclosure refers to "one or more embodiments of the present disclosure".

In the specification, the term "substituted or unsubstituted" may refer to being unsubstituted, or substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In some embodiments, each of the above substituents may be further substituted or unsubstituted. For example, a biphenyl group may be interpreted as a named aryl group, or as a phenyl group substituted with a phenyl group.

In the specification, the phrase "bonded to an adjacent group to form a ring" may refer to being bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In some embodiments, the rings formed by being bonded to each other may be connected to another ring to form a spiro structure.

In the specification, the term "adjacent group" may refer to a substituent on the same atom or point, a substituent on an atom that is directly connected to the base atom or point, or a substituent sterically positioned (e.g., within intramolecular bonding distance) to the corresponding substituent. For example, two methyl groups in 1,2-dimethylbenzene may be interpreted as "adjacent groups" to each other, and two ethyl groups in 1,1-diethylcyclopentane may be interpreted as "adjacent groups" to each other. Further, two methyl groups in 4,5-dimethylphenanthrene may be interpreted as "adjacent groups" to each other.

In the specification, examples of the halogen atom may include a fluorine atom, a chlorine atom, a bromine atom, and/or an iodine atom.

In the specification, the term "alkyl group" may refer to a linear, branched or cyclic alkyl group. The number of carbons in the alkyl group may be 1 to 50, 1 to 30, 1 to 20, 1 to 10, or 1 to 6. Examples of the alkyl group may include a methyl group, an ethyl group, an n-propyl group, an isopropyl group, an n-butyl group, a s-butyl group, a t-butyl group, an i-butyl group, a 2-ethylbutyl group, a 3,3-a dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but are not limited thereto.

The term "hydrocarbon ring group" may refer to any functional group or substituent derived from an aliphatic hydrocarbon ring. The hydrocarbon ring group may be a saturated hydrocarbon ring group having 5 to 20 ring-forming carbon atoms.

The term "aryl group" may refer to any functional group or substituent derived from an aromatic hydrocarbon ring. The aryl group may be a monocyclic aryl group or a polycyclic aryl group. The number of ring-forming carbon atoms in the aryl group may be 6 to 50, 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but embodiments of the present disclosure are not limited thereto.

In the specification, the fluorenyl group may be substituted (e.g., at the 9H position), and the two substituents may be bonded to each other to form a spiro structure. Examples of cases where the fluorenyl group is substituted are as follows.

However, embodiments of the present disclosure are not limited thereto.

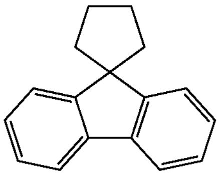

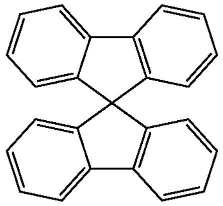

-continued

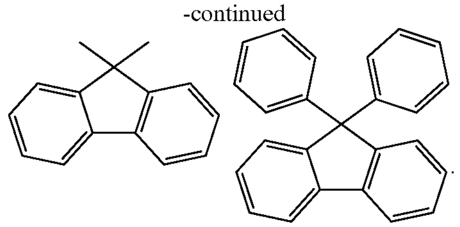

The term "heterocyclic group" may refer to any functional group or substituent derived from a ring including at least one of boron (B), oxygen (O), nitrogen (N), phosphorus (P), silicon (Si), or selenium (Se) as a heteroatom. The heterocyclic group may be an aliphatic heterocyclic group or an aromatic heterocyclic group. The aromatic heterocyclic group may be a heteroaryl group. The aliphatic heterocycle and the aromatic heterocycle may be monocyclic or polycyclic.

In the specification, the heterocyclic group may include at least one of B, O, N, P, Si or S as a heteroatom. When the heterocyclic group includes two or more heteroatoms, the two or more heteroatoms may be the same as or different from each other. The heterocyclic group may be a monocyclic heterocyclic group or a polycyclic heterocyclic group, and in some embodiments may be a heteroaryl group. The number of ring-forming carbon atoms in the heterocyclic group may be 2 to 50, 2 to 30, 2 to 20, or 2 to 10.

In the specification, the aliphatic heterocyclic group may include one or more among B, O, N, P, Si, and S as a heteroatom. The number of ring-forming carbon atoms in the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but embodiments of the present disclosure are not limited thereto.

The heteroaryl group herein may include at least one of B, O, N, P, Si, or S as a heteroatom. When the heteroaryl group contains two or more heteroatoms, the two or more heteroatoms may be the same as or different from each other. The heteroaryl group may be a monocyclic heteroaryl group or polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but embodiments of the present disclosure are not limited thereto.

In the specification, the above description with respect to the aryl group may be applied to an arylene group except that the arylene group is a divalent group. The explanation on the aforementioned heteroaryl group may be applied to the heteroarylene group except that the heteroarylene group is a divalent group.

In the specification, the silyl group includes an alkylsilyl group and an arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the specification, the number of carbon atoms in the amino group is not specifically limited, but may be 1 to 30. The amino group may include an alkyl amino group, an aryl amino group, or a heteroaryl amino group. Examples of the amino group may include a methylamino group, a dimethylamino group, a phenylamino group, a diphenylamino group, a naphthylamino group, a 9-methyl-anthracenylamino group, a triphenylamino group, etc., but are not limited thereto.

In the specification, the number of ring-forming carbon atoms in the carbonyl group is not specifically limited, but may be 1 to 40, 1 to 30, or 1 to 20. For example, the carbonyl group may have the following structures, but embodiments of the present disclosure are not limited thereto:

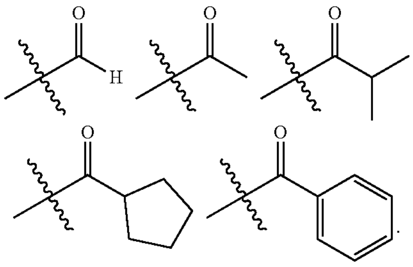

In the specification, the number of carbon atoms in the sulfinyl group and the sulfonyl group is not particularly limited, but may be 1 to 30. The term "sulfinyl group" may include an alkyl sulfinyl group and an aryl sulfinyl group. The term "sulfonyl group" may include an alkyl sulfonyl group and an aryl sulfonyl group.

The term "thio group" herein may include an alkylthio group and an arylthio group. The thio group may refer to that a sulfur atom is bonded to the alkyl group or the aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, but embodiments of the present disclosure are not limited thereto.

The term "oxy group" herein may refer to an oxygen atom bonded to an alkyl group or an aryl group as defined above. The oxy group may be an alkoxy group or an aryl oxy group. The alkoxy group may be a linear chain, a branched chain or a ring chain. The number of carbon atoms in the alkoxy group is not specifically limited, but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc., but embodiments of the present disclosure are not limited thereto.

The term "boron group" herein may refer to a boron atom bonded to an alkyl group or an aryl group as defined above.

The boron group may be an alkyl boron group or an aryl boron group. Examples of the boron group may include a trimethylboron group, a triethylboron group, a t-butyldimethylboron group, a triphenylboron group, a diphenylboron group, a phenylboron group, etc., but embodiments of the present disclosure are not limited thereto.

In the specification, the alkenyl group may be linear or branched. The number of carbon atoms in the alkynyl group is not specifically limited, but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the specification, the number of carbon atoms in an amine group is not specifically limited, but may be 1 to 30. The amine group may be an alkyl amine group or an aryl amine group. Examples of the amine group may include a methylamine group, a dimethylamine group, a phenylamine group, a diphenylamine group, a naphthylamine group, a 9-methyl-anthracenylamine group, etc., but embodiments of the present disclosure are not limited thereto.

In the specification, examples of the alkyl group included in the alkylthio group, the alkylsulfoxy group, the alkylaryl group, the alkylamino group, the alkyl boron group, the alkyl silyl group, and/or the alkyl amine group may be the same as described above.

In the specification, examples of the aryl group included in the aryloxy group, the arylthio group, the arylsulfoxy group, the arylamino group, the arylboron group, the arylsilyl group, and/or the arylamine group may be the same as described above.

A direct linkage herein may refer to a single bond.

In the specification,

" 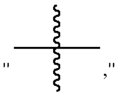 ,"

"—*,"

"  ,"

etc. herein refer to positions to be connected.

Hereinafter, embodiments of the present disclosure will be described with reference to the accompanying drawings.

Figure 2:
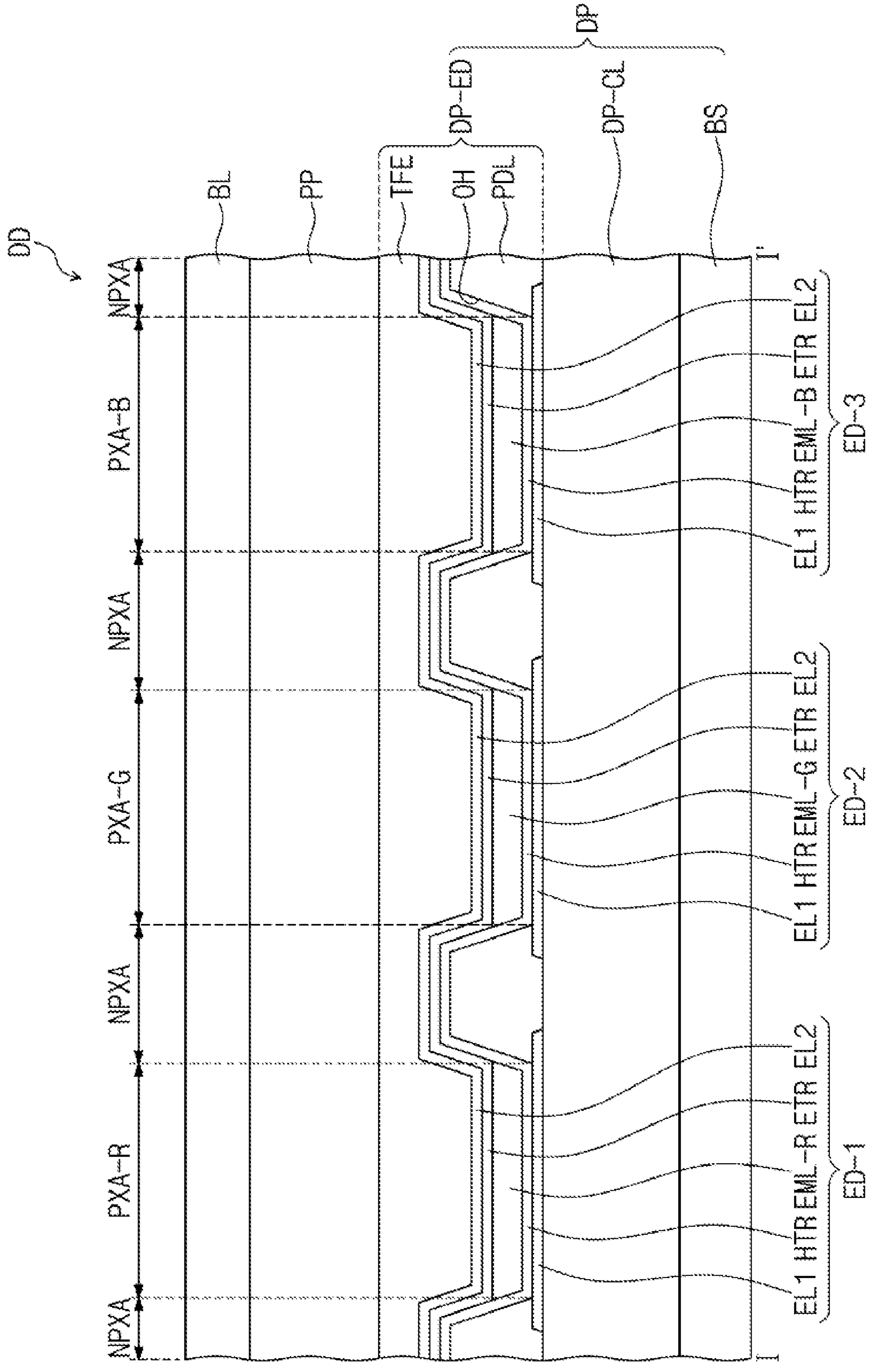
FIG. 2 is a cross-sectional view of a display device according to an embodiment of the present disclosure.

FIG. 1 is a plan view illustrating an embodiment of a display device DD. FIG. 2 is a cross-sectional view of the display device DD of the embodiment. FIG. 2 is a cross-sectional view illustrating a part taken along line I-I' of FIG. 1.

The display device DD may include a display panel DP and an optical layer PP disposed on the display panel DP. The display panel DP includes light emitting elements ED-1, ED-2, and ED-3. The display device DD may include a plurality of light emitting elements ED-1, ED-2, and ED-3. The optical layer PP may be disposed on the display panel DP and control reflected light in the display panel DP due to external light. The optical layer PP may include, for example, a polarization layer or a color filter layer. In some embodiments, the optical layer PP may not be provided in the display device DD of an embodiment.

A base substrate BL may be disposed on the optical layer PP. The base substrate BL may provide a base surface on (e.g., under) which the optical layer PP is disposed. The base substrate BL may be a glass substrate, a metal substrate, a plastic substrate, etc. However, embodiments of the present disclosure are not limited thereto, and the base substrate BL may be an inorganic layer, an organic layer, or a composite material layer. In some embodiments, the base substrate BL may not be provided.

The display device DD according to an embodiment may further include a filling layer. The filling layer may be disposed between a display element layer DP-ED and the base substrate BL. The filling layer may be an organic material layer. The filling layer may include at least one of an acrylic-based resin, a silicone-based resin, or an epoxy-based resin.

The display panel DP may include a base layer BS, a circuit layer DP-CL provided on the base layer BS, and a display element layer DP-ED. The display element layer DP-ED may include a pixel defining film PDL, the light emitting elements ED-1, ED-2, and ED-3 disposed between portions of the pixel defining film PDL, and an encapsulation layer TFE disposed on the light emitting elements ED-1, ED-2, and ED-3.

The base layer BS may provide a base surface on which the display element layer DP-ED is disposed. The base layer BS may be a glass substrate, a metal substrate, a plastic substrate, etc. However, embodiments of the present disclosure are not limited thereto, and the base layer BS may be an inorganic layer, an organic layer, or a composite material layer.

In an embodiment, the circuit layer DP-CL is disposed on the base layer BS, and the circuit layer DP-CL may include a plurality of transistors. Each of the transistors may include a control (e.g., gate) electrode, an input electrode, and an output electrode. For example, the circuit layer DP-CL may include a switching transistor and a driving transistor in order to drive the light emitting elements ED-1, ED-2, and ED-3 of the display element layer DP-ED.

Each of the light emitting elements ED-1, ED-2, and ED-3 may have a structure of a light emitting element ED of an embodiment according to any of FIGS. 3 to 6, which will be described later. Each of the light emitting elements ED-1, ED-2 and ED-3 may include a first electrode EL1, a hole transport region HTR, emission layers EML-R, EML-G and EML-B, an electron transport region ETR, and a second electrode EL2.

FIG. 2 illustrates an embodiment in which the emission layers EML-R, EML-G, and EML-B of the light emitting elements ED-1, ED-2, and ED-3 are disposed in the openings OH defined in the pixel defining film PDL, and the hole transport region HTR, the electron transport region ETR, and the second electrode EL2 are provided as a common layer in the entire light emitting elements ED-1, ED-2, and ED-3. However, embodiments of the present disclosure are not limited thereto, and for example, the hole transport region HTR and the electron transport region ETR in an embodiment may be provided by being independently patterned inside each opening hole OH defined in the pixel defining film PDL. For example, the hole transport region HTR, the emission layers EML-R, EML-G, and EML-B, and the electron transport region ETR of the light emitting elements ED-1, ED-2, and ED-3 in an embodiment may each independently be provided by being patterned in an inkjet printing method.

The encapsulation layer TFE may cover the light emitting elements ED-1, ED-2 and ED-3. The encapsulation layer TFE may seal the display element layer DP-ED. The encapsulation layer TFE may be a thin film encapsulation layer. The encapsulation layer TFE may be formed by laminating one layer or a plurality of layers. The encapsulation layer TFE may include at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film protects the display element layer DP-ED from moisture/oxygen, and the encapsulation-organic film protects the display element layer DP-ED from foreign substances (such as dust particles). The encapsulation-inorganic film may include silicon nitride, silicon oxynitride, silicon oxide, titanium oxide, aluminum oxide, and/or the like, but embodiments of the present disclosure are not particularly limited thereto. The encapsulation-organic film may include an acrylic-based compound, an epoxy-based compound, and/or the like. The encapsulation-organic film may include a photopolymerizable organic material, but embodiments of the present disclosure are not particularly limited thereto.

The encapsulation layer TFE may be disposed on the second electrode EL2 and may be disposed filling the opening hole OH.

Referring to FIGS. 1 and 2, the display device DD may include a non-light emitting region NPXA and light emitting regions PXA-R, PXA-G and PXA-B. The light emitting regions PXA-R, PXA-G and PXA-B may respectively be a region to emit light generated from the light emitting elements ED-1, ED-2 and ED-3. The light emitting regions PXA-R, PXA-G, and PXA-B may be spaced apart from each other in a plane.

Each of the light emitting regions PXA-R, PXA-G, and PXA-B may be divided (e.g., defined) by the pixel defining film PDL. The non-light emitting regions NPXA may be between the light emitting regions PXA-R, PXA-G, and PXA-B, and may correspond to portions of the pixel defining film PDL. In some embodiments, each of the light emitting regions PXA-R, PXA-G, and PXA-B may correspond to a pixel. The pixel defining film PDL may separate the light emitting elements ED-1, ED-2, and ED-3. The emission layers EML-R, EML-G and EML-B of the light emitting elements ED-1, ED-2 and ED-3 may be disposed in openings OH defined by the pixel defining film PDL and separated from each other.

The light emitting regions PXA-R, PXA-G and PXA-B may be divided into a plurality of groups according to the color of light generated from the light emitting elements ED-1, ED-2 and ED-3. In the display device DD of an embodiment shown in FIGS. 1 and 2, three light emitting regions PXA-R, PXA-G, and PXA-B to respectively emit red light, green light, and blue light are illustrated. For example, the display device DD of an embodiment may include the red light emitting region PXA-R, the green light emitting region PXA-G, and the blue light emitting region PXA-B, which are separated from one another.

In the display device DD according to an embodiment, the plurality of light emitting elements ED-1, ED-2 and ED-3 may be to emit light beams having wavelengths different from one another. For example, in an embodiment, the display device DD may include a first light emitting element ED-1 to emit red light, a second light emitting element ED-2 to emit green light, and a third light emitting element ED-3 to emit blue light. For example, the red light emitting region PXA-R, the green light emitting region PXA-G, and the blue light emitting region PXA-B of the display device DD may correspond to the first light emitting element ED-1, the second light emitting element ED-2, and the third light emitting element ED-3, respectively.

However, embodiments of the present disclosure are not limited thereto, and the first to third light emitting elements ED-1, ED-2, and ED-3 may be to emit light beams in substantially the same wavelength range, or at least one light emitting element may be to emit a light beam in a wavelength range different from the others. For example, the first to third light emitting elements ED-1, ED-2, and ED-3 may all emit blue light.

The light emitting regions PXA-R, PXA-G, and PXA-B in the display device DD according to an embodiment may be arranged in a stripe form or pattern. Referring to FIG. 1, the plurality of red light emitting regions PXA-R may be arranged with each other along a second directional axis DR2, the plurality of green light emitting regions PXA-G may be arranged with each other along the second directional axis DR, and the plurality of blue light emitting regions PXA-B may be arranged with each along the second directional axis DR2. The red light emitting region PXA-R, the green light emitting region PXA-G, and the blue light emitting region PXA-B may be alternatingly arranged with each other in this order along a first directional axis DR1.

FIGS. 1 and 2 illustrate embodiments in which all the light emitting regions PXA-R, PXA-G, and PXA-B have similar areas, but embodiments of the present disclosure are not limited thereto, and the light emitting regions PXA-R, PXA-G, and PXA-B may have different areas from each other according to a wavelength range of the emitted light. In this case, the areas of the light emitting regions PXA-R, PXA-G, and PXA-B may be the areas when viewed in (e.g., normal or perpendicular to) a plane defined by the first directional axis DR1 and the second directional axis DR2.

The arrangement form or pattern of the light emitting regions PXA-R, PXA-G, and PXA-B is not limited to the feature illustrated in FIG. 1, and the order in which the red light emitting region PXA-R, the green light emitting region PXA-G, and the blue light emitting region PXA-B are arranged may be variously combined and provided according to the desired characteristics of qualities of the display device DD. For example, the arrangement form of the light emitting regions PXA-R, PXA-G, and PXA-B may be a PENTILE® arrangement form (pattern) or a diamond arrangement form (pattern).

In some embodiments, the areas of the light emitting regions PXA-R, PXA-G, and PXA-B may be different from each other. For example, in an embodiment, the area of the green light emitting region PXA-G may be smaller than that of the blue light emitting region PXA-B, but embodiments of the present disclosure are not limited thereto.

Hereinafter, FIGS. 3 to 6 are cross-sectional views schematically illustrating light emitting elements according to embodiments of the present disclosure. The light emitting elements ED according to embodiments each may include a first electrode EL1, a second electrode EL2 facing the first electrode EL1, and at least one functional layer disposed between the first electrode EL1 and the second electrode EL2. The at least one functional layer may include a hole transport region HTR, an emission layer EML, and an electron transport region ETR that are sequentially stacked. For example, each of the light emitting elements ED of embodiments may include the first electrode EL1, the hole transport region HTR, the emission layer EML, the electron transport region ETR, and the second electrode EL2 that are sequentially stacked.

Figure 3:
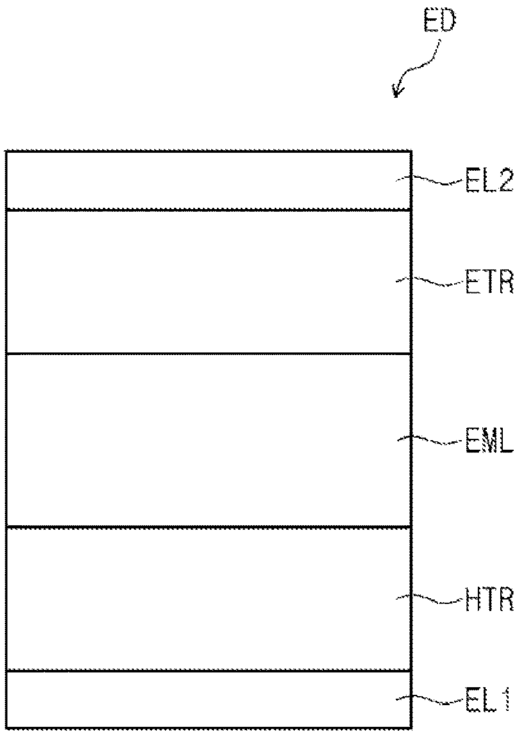
FIG. 3 is a cross-sectional view schematically illustrating a light emitting element according to an embodiment of the present disclosure.
Figure 4:
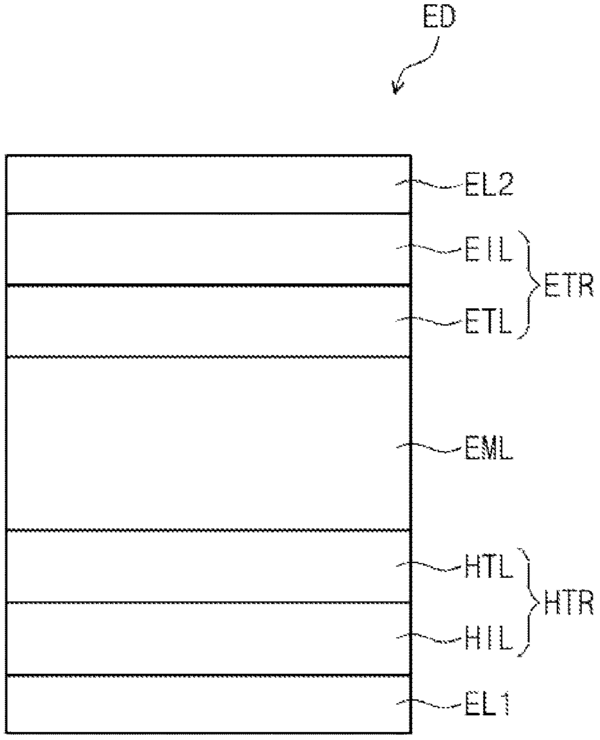
FIG. 4 is a cross-sectional view schematically illustrating a light emitting element according to an embodiment of the present disclosure.
Figure 5:
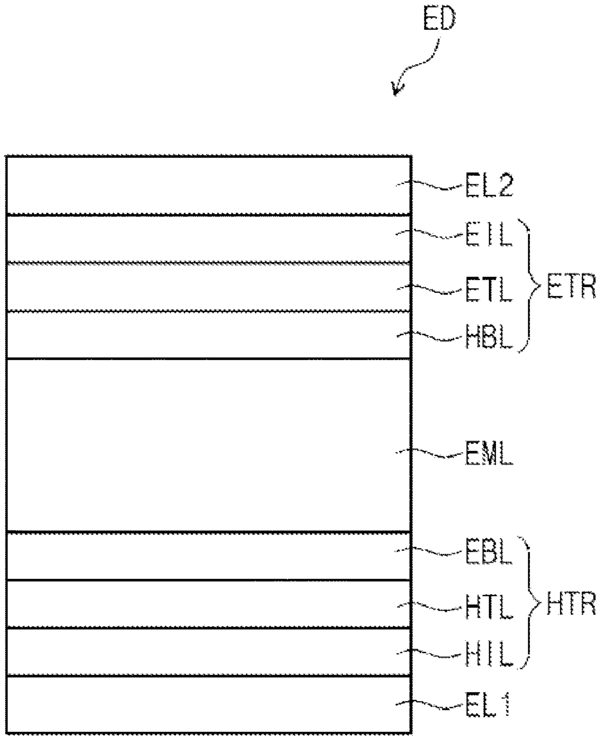
FIG. 5 is a cross-sectional view schematically illustrating a light emitting element according to an embodiment of the present disclosure.
Figure 6:
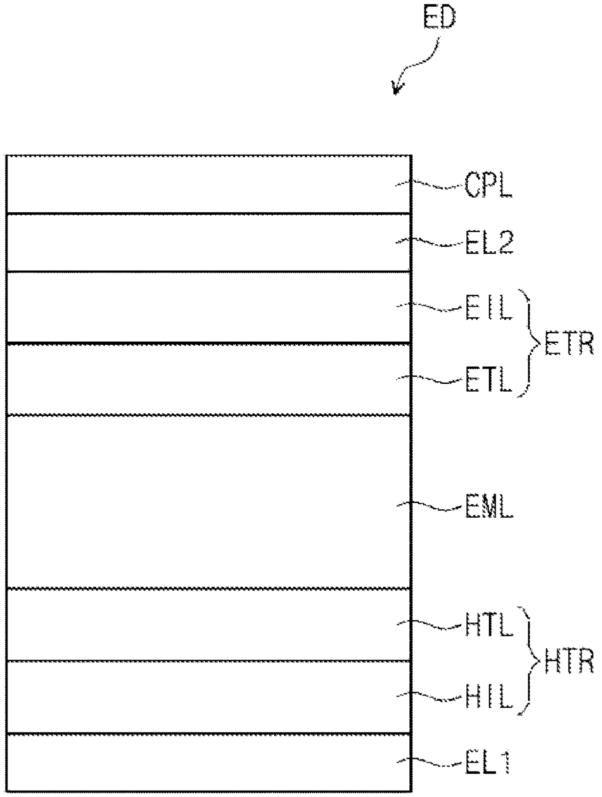
FIG. 6 is a cross-sectional view schematically illustrating a light emitting element according to an embodiment of the present disclosure.

Compared to FIG. 3, FIG. 4 illustrates a cross-sectional view of a light emitting element ED of an embodiment, in which a hole transport region HTR includes a hole injection layer HIL and a hole transport layer HTL, and an electron transport region ETR includes an electron injection layer EIL and an electron transport layer ETL. Compared to FIG. 3, FIG. 5 illustrates a cross-sectional view of a light emitting element ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 4, FIG. 6 illustrates a cross-sectional view of a light emitting element ED of an embodiment including a capping layer CPL disposed on a second electrode EL2.

The light emitting element ED of an embodiment may include the polycyclic compound of an embodiment, which will be described below, in at least one functional layer of the hole transport region HTR, the emission layer EML, the electron transport region ETR, and/or the like.

In the light emitting element ED according to an embodiment, the first electrode EL1 has conductivity. The first electrode EU may be formed of a metal material, a metal alloy, and/or a conductive compound. The first electrode EL1 may be an anode or a cathode. However, embodiments of the present disclosure are not limited thereto. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may be formed utilizing a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF, molybdenum (Mo), titanium (Ti), tungsten (W), a compound thereof, or a mixture thereof (e.g., a mixture of Ag and Mg, a mixture of LiF and Ca, a mixture of LiF and Al, etc.). In some embodiments, the first electrode EU may have a multilayer structure including a reflective film or a transflective film formed of the above-described materials, and a transparent conductive film formed of ITO, IZO, ZnO, ITZO, etc. For example, the first electrode EU may have a three-layer structure of ITO/Ag/ITO, but embodiments of the present disclosure are not limited thereto. In some embodiments, embodiments of the present disclosure are not limited thereto, and the first electrode EL1 may include the above-described metal materials, combinations of at least two of the above-described metal materials, oxides of the above-described metal materials, and/or the like. The thickness of the first electrode EL1 may be about 700 Å to about 10,000 Å. For example, the thickness of the first electrode EL1 may be about 1,000 Å to about 3,000 Å.

The hole transport region HTR is provided on the first electrode EL1. The hole transport region HTR may include at least one of a hole injection layer HIL, a hole transport layer HTL, a buffer layer, an emission-auxiliary layer, or an electron blocking layer EBL. The thickness of the hole transport region HTR may be, for example, about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of the hole injection layer HIL or the hole transport layer HTL, and may have a single layer structure formed of a hole injection material and a hole transport material. In some embodiments, the hole transport region HTR may have a single layer structure formed of a plurality of different materials, or a structure in which a hole injection layer HIL/hole transport layer HTL, a hole injection layer HIL/hole transport layer HTL/buffer layer, a hole injection layer HIL/buffer layer, a hole transport layer HTL/buffer layer, or a hole injection layer HIL/hole transport layer HTL/electron blocking layer EBL are stacked in order from the first electrode EL1, but embodiments of the present disclosure are not limited thereto.

The hole transport region HTR may be formed utilizing one or more suitable methods (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR in the light emitting element ED of an embodiment may include a polycyclic compound represented by Formula 1. In some embodiments, the hole transport region HTR in the light emitting element ED of an embodiment may include at least one of the hole injection layer HIL, the hole transport layer HTL, or electron blocking layer EBL, and at least one of the hole injection layer HIL, the hole transport layer HTL, or the electron blocking layer EBL may include the polycyclic compound represented by Formula 1 according to an embodiment. For example, the hole transport layer HTL in the light emitting element ED of an embodiment may include a polycyclic compound represented by Formula 1:

Formula 1

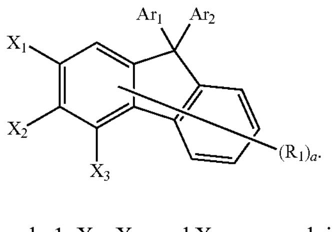

In Formula 1, $X_1$, $X_2$, and $X_3$ may each independently be $R_x$ or represented by Substituent S1, and at least one of $X_1$, $X_2$, and $X_3$ may be represented by Substituent S1. In an embodiment, any one of $X_1$, $X_2$, or $X_3$ may be represented by Substituent S1, and the other two may be represented by $R_x$. However, embodiments of the present disclosure are not limited thereto.

$R_x$ may be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring. For example, $R_x$ may be a hydrogen atom or a deuterium atom.

$Ar_1$ and $Ar_2$ may each independently be a substituted or unsubstituted aryl group having 6 to 50 ring-forming carbon atoms. For example, $Ar_1$ and $Ar_2$ may each independently be a substituted or unsubstituted phenyl group, and in some embodiments, each of $Ar_1$ and $Ar_2$ may be an unsubstituted phenyl group. For example, the polycyclic compound represented by Formula 1 may have a 9,9-diphenyl fluorene skeleton (structure). However, embodiments of the present disclosure are not limited thereto. For example, $Ar_1$ and $Ar_2$ may each be a phenyl group substituted with a deuterium atom.

$R_1$ may each independently be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring. For example, $R_1$ may be a hydrogen atom or a deuterium atom.

a may be an integer of 0 to 5. For example, a may be 0 or 1. The case where a is 0 may provide the same structure as the case where a is 1 and $R_1$ is a hydrogen atom.

Substituent S1 may be represented as follows:

Substituent S1

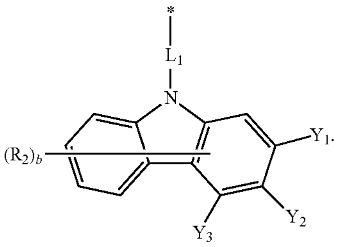

In Substituent S1, "—*" is a position connected to a benzene ring in Formula 1. For example, in Substituent S1, "—*" is a position connected to any one among the carbon atoms substituted with $X_1$, $X_2$, or $X_3$ in Formula 1.

In Substituent S1, $Y_1$, $Y_2$, and $Y_3$ may each independently be $R_y$ or $L_2Z$, and any one of $Y_1$, $Y_2$, or $Y_3$ may be represented by $L_2Z$. For example, any one of $Y_1$, $Y_2$, or $Y_3$ may be $L_2Z$, and the other two may be $R_y$. In $L_2Z$, $L_2$ may be a linker and Z may be a substituent. For example, $L_2$ may be a linker that links the substituent Z to any one among the carbon atoms substituted with $Y_1$, $Y_2$, or $Y_3$.

$R_y$ may be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring, where $R_y$ does not include a substituted or unsubstituted carbazole group. For example, $R_y$ may be a hydrogen atom or a deuterium atom.

$R_2$ may be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring. For example, $R_2$ may be a hydrogen atom, a deuterium atom, a methyl group, a cyano group, a methoxy group, or a substituted or unsubstituted carbazole group. However, embodiments of the present disclosure are not limited thereto.

b may be an integer of 0 to 4. For example, b may be 0 or 1. The case where b is 0 may provide the same structure as the case where b is 1 and $R_2$ is a hydrogen atom.

$L_1$ may be a direct linkage, or a substituted or unsubstituted arylene group having 6 to 50 ring-forming carbon atoms. For example, $L_1$ may be a direct linkage, a substituted or unsubstituted phenylene group, a substituted or unsubstituted divalent biphenyl group, or a substituted or unsubstituted divalent naphthyl group. For example, $L_1$ may include a substituted disclosed in Substituent Group L-1. However, embodiments of the present disclosure are not limited thereto.

Substituent Group L-1

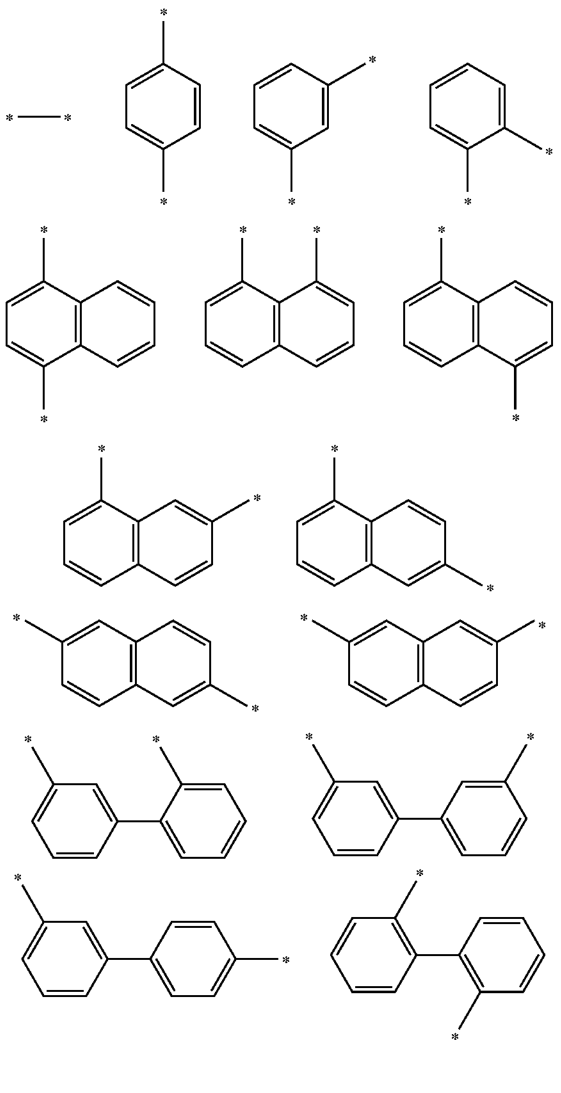

-continued

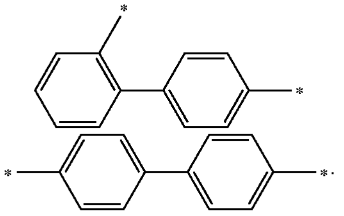

In Substituent Group L-1, "—*" is a position connected to a benzene ring in Formula 1 or a nitrogen atom in Substituent S1. For example, in Substituent Group L-1, "—*" is connected to any one among the carbon atoms substituted with $X_1$, $X_2$, or $X_3$ in Formula 1, or to the nitrogen atom at the 9-position of the carbazole group in Substituent S1.

$L_2$ may be a direct linkage, a substituted or unsubstituted arylene group having 6 to 50 ring-forming carbon atoms, or a substituted or unsubstituted heteroarylene group having 2 to 50 ring-forming carbon atoms. However, when $X_1$ is represented by Substituent S1, and $Y_1$ is represented by $L_2Z$, $L_2$ may be a direct linkage. However, when $X_1$ is represented by Substituent S1, and $Y_2$ is represented by $L_2Z$, $L_2$ may be a substituted carbazole group.

In an embodiment, $L_2$ may be a direct linkage, a substituted or unsubstituted phenylene group, a substituted or unsubstituted divalent biphenyl group, a substituted or unsubstituted divalent naphthyl group, a substituted or unsubstituted divalent dibenzofuran group, or a substituted or unsubstituted divalent dibenzothiophene group.

For example, $L_2$ may include a substituent disclosed in Substituent Group L-2. However, embodiments of the present disclosure are not limited thereto.

Substituent Group L-2

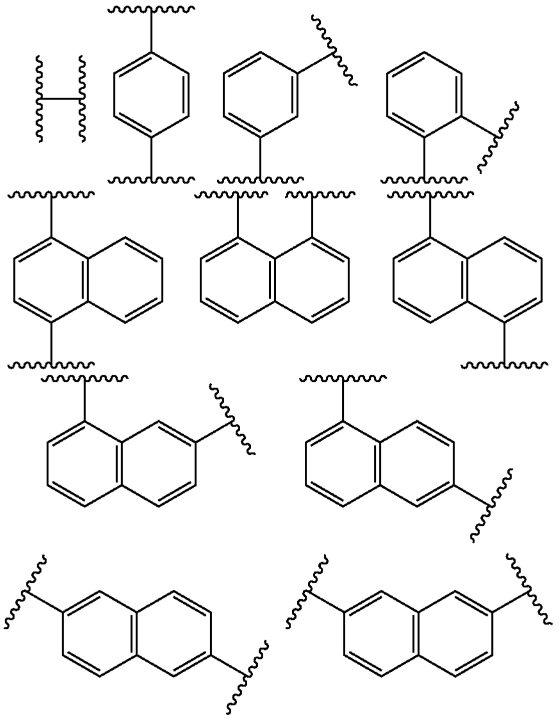

-continued

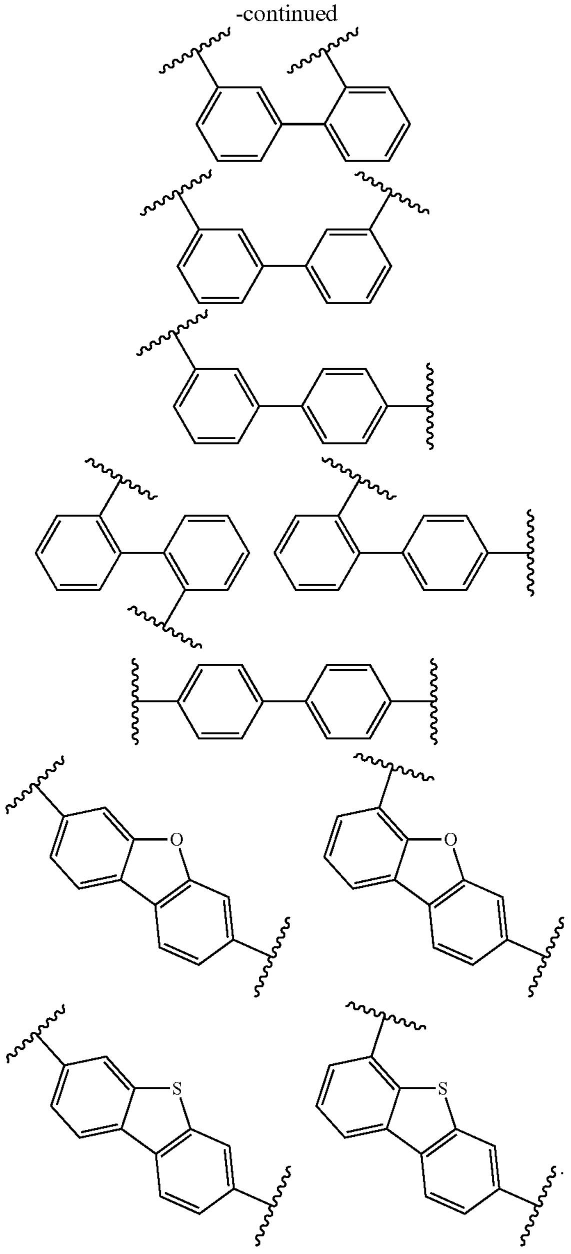

In Substituent Group L-2,

""

is a position connected to a benzene ring in Substituent S1 or a nitrogen atom in substituent S2. For example, in Substituent Group L-2, ""

is connected to any one among the carbon atoms substituted with $Y_1$, $Y_2$, or $Y_3$ in Substituent S1, or to the nitrogen atom at the 9-position of the carbazole group in Substituent S2. For example, one “  ”

may be connected to Substituent S1 and the other

“  ”

may be connected to Substituent S2.

Z may be represented by Substituent S2.

Substituent S2

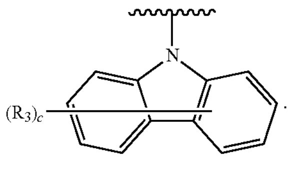

In Substituent S2,

“  ”

is a position connected to $L_2$ in Substituent S1.

$R_3$ may be a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or may be bonded to an adjacent group to form a ring.

For example, $R_3$ may be a hydrogen atom, a deuterium atom, a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group. For example, $R_3$ may be a hydrogen atom, a deuterium atom, an unsubstituted phenyl group, a phenyl group substituted with a triphenylsilyl group, a phenyl group substituted with deuterium, an unsubstituted biphenyl group, an unsubstituted naphthyl group, an unsubstituted dibenzofuran group, a dibenzofuran group substituted with an unsubstituted phenyl group, an unsubstituted dibenzothiophene group, or a dibenzophenyl group substituted with an unsubstituted phenyl group. However, embodiments of the present disclosure are not limited thereto.

c may be an integer of 0 to 8. For example, c may be 0, 1, or 2. When c is an integer of 2 or greater, a plurality of $R_3$'s may all be the same or at least one may be different from the rest. For example, a plurality of $R_3$'s may all be unsubstituted phenyl groups. In some embodiments, any one among the plurality of $R_3$'s may be an unsubstituted phenyl group, and any one may be a substituted dibenzofuran group.

In an embodiment, Substituent S2 may be a substituted or unsubstituted carbazole group.

In an embodiment, the polycyclic compound represented by Formula 1 may be represented by Formula 1-1:

Formula 1-1

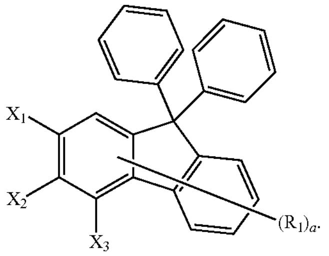

Formula 1-1 specifies the case where each of $Ar_1$ and $Ar_2$ is an unsubstituted phenyl group in Formula 1.

$X_1$, $X_2$, $X_3$, $R_1$, and a may each independently be the same as defined in Formula 1.

The polycyclic compound represented by Formula 1 of an embodiment may be represented by one among the compounds of Compound Group 1. The hole transport region HTR of the light emitting element ED of an embodiment may include at least one among the polycyclic compounds disclosed in Compound Group 1:

Compound Group 1

A1

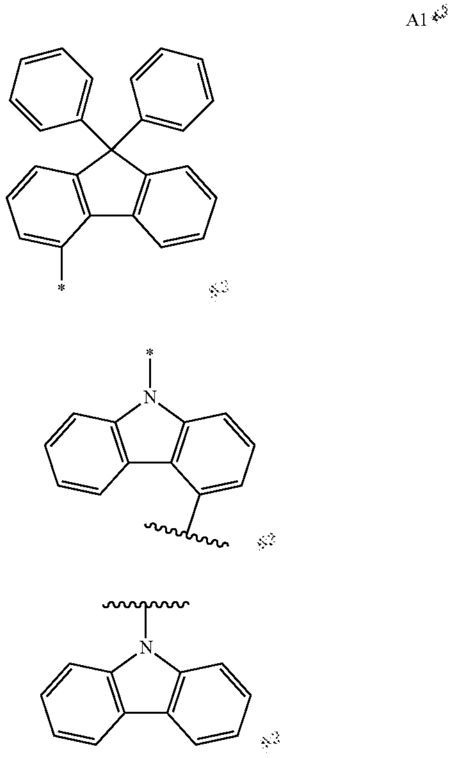

-continued
A2
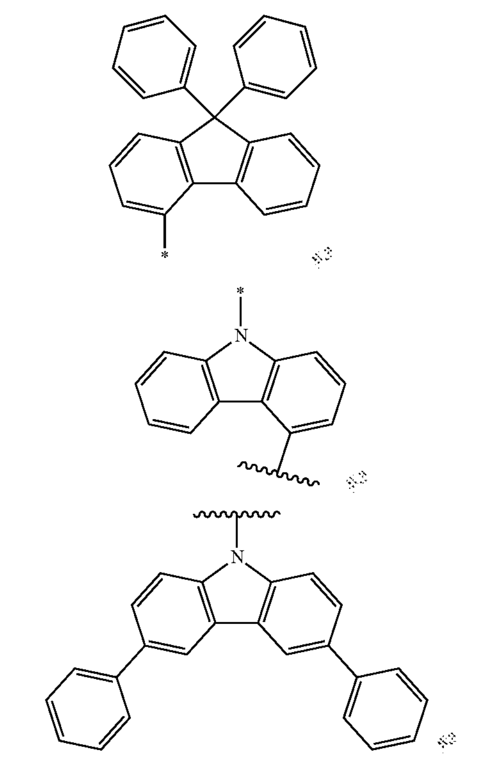
A3
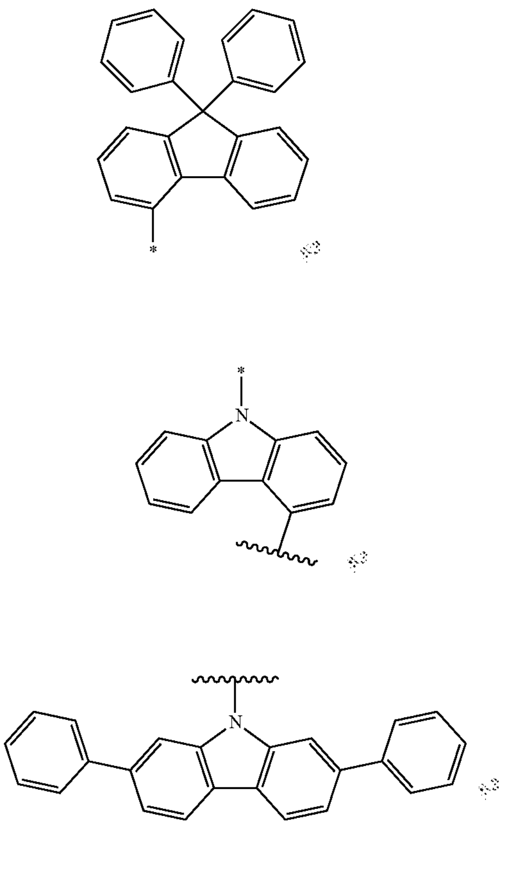
-continued
A4
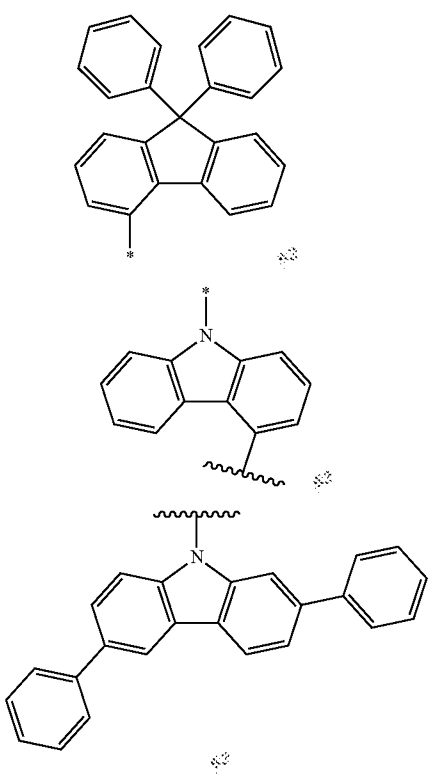
A5
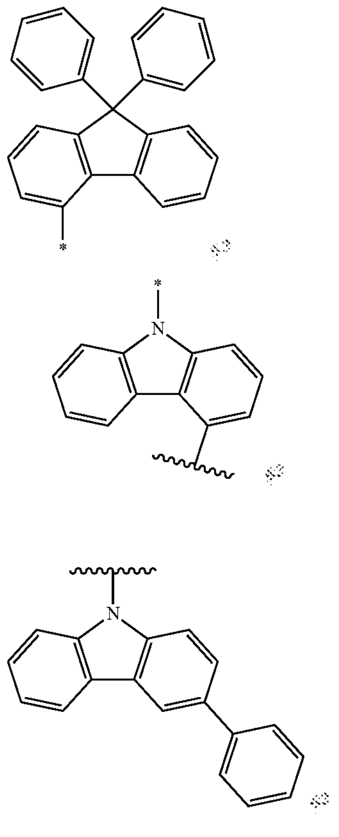

-continued
A6
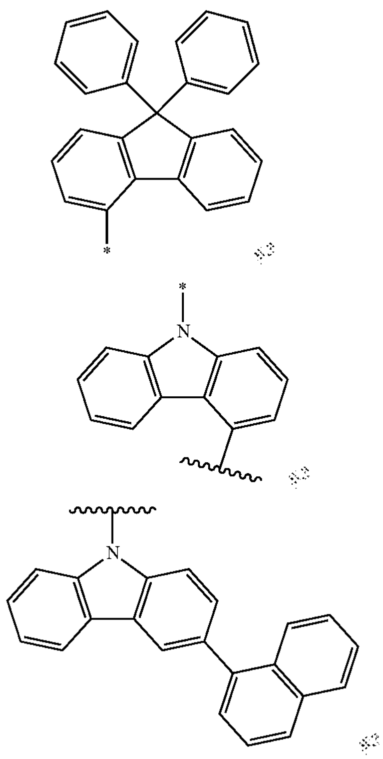
A7
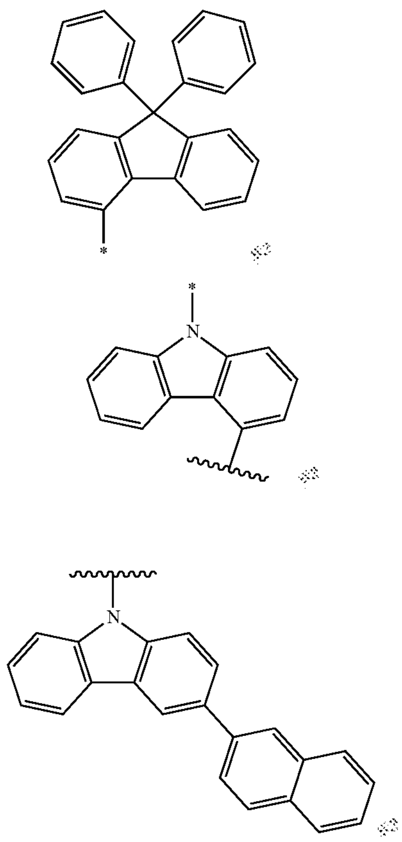
-continued
A8
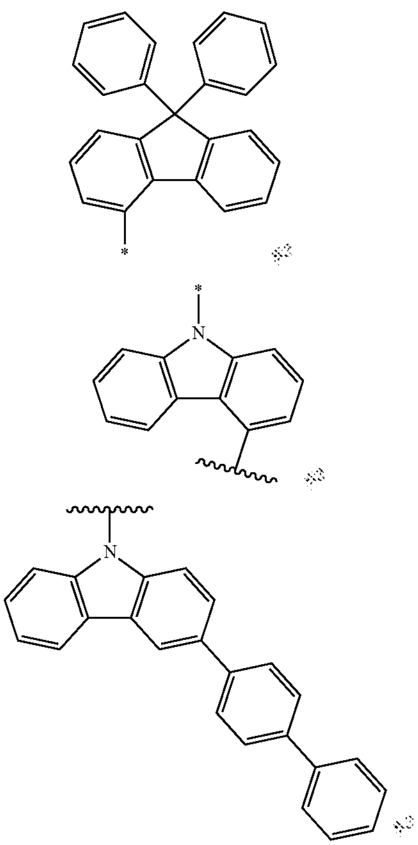
A9
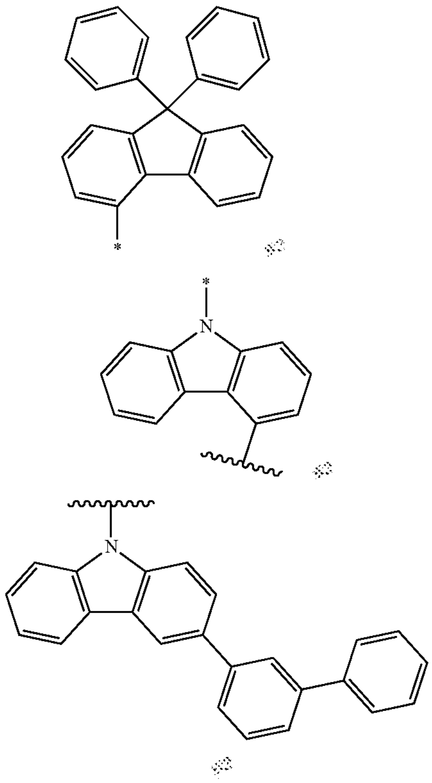

-continued
A10
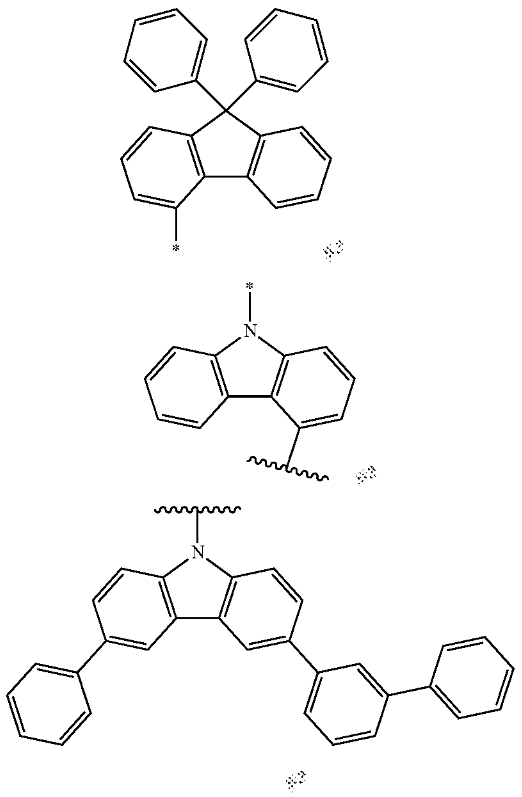
A11
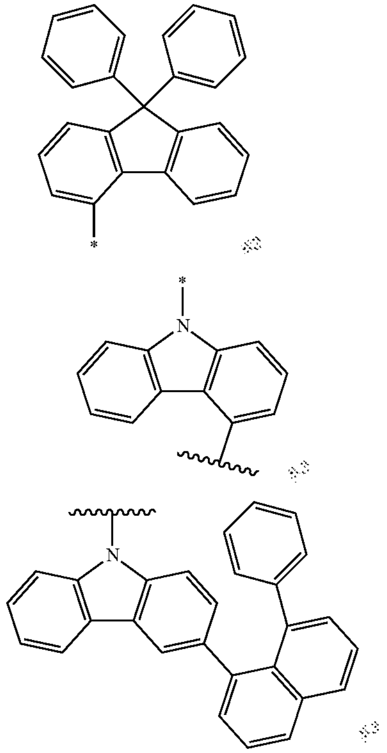
-continued
A12
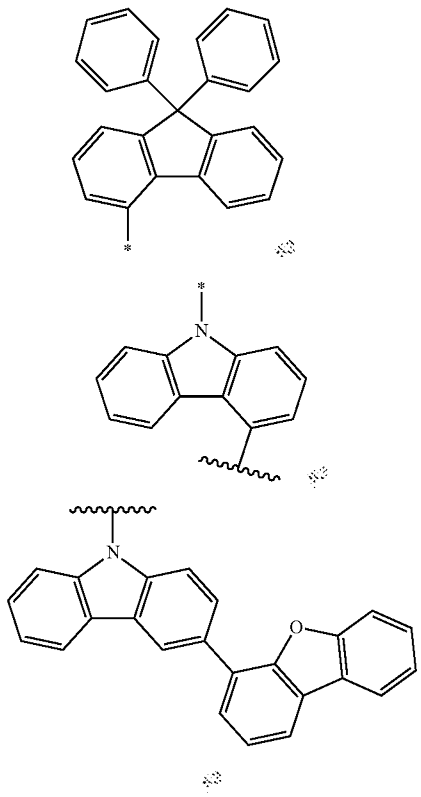
A13
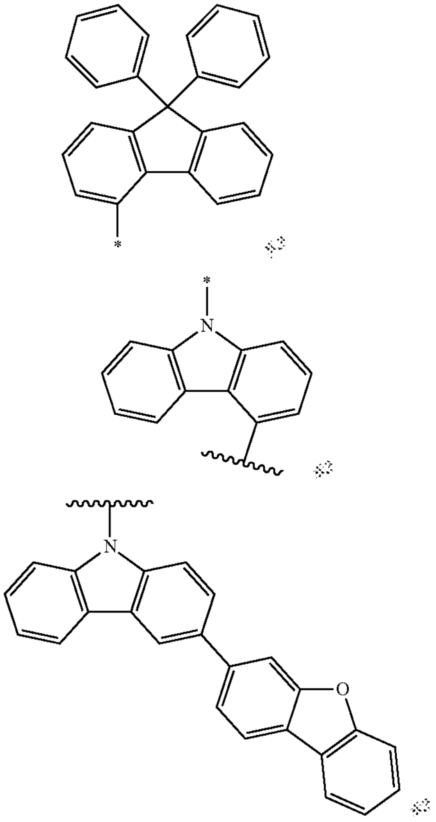

-continued
A14
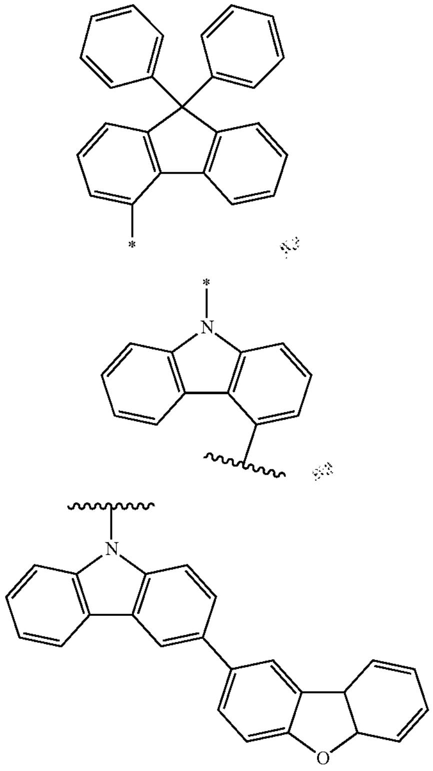
A15
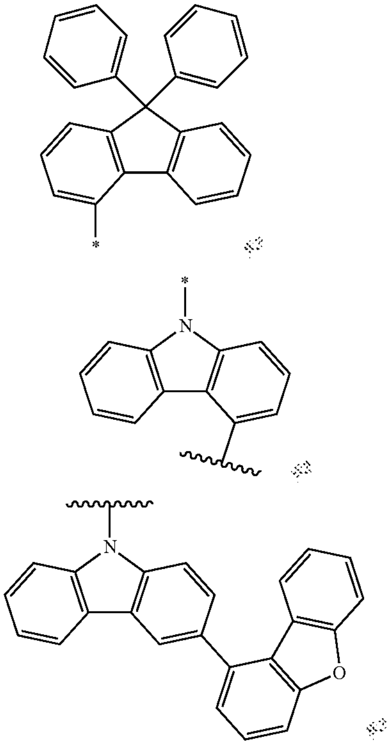
-continued
A16
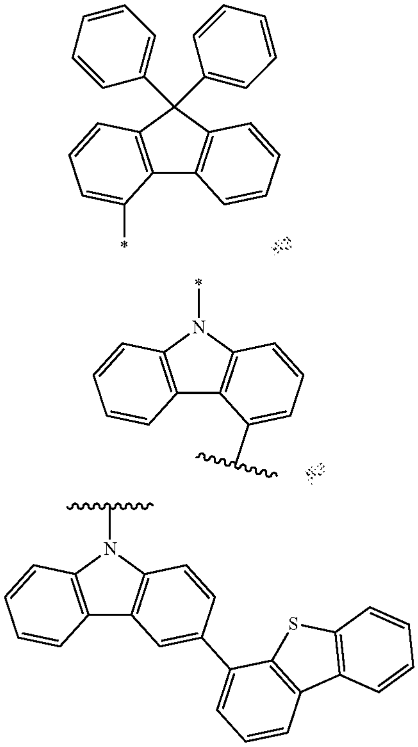
A17
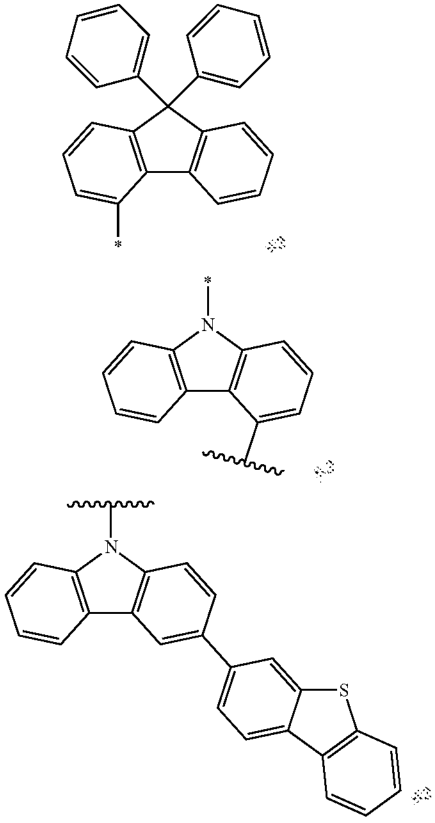

-continued
A18
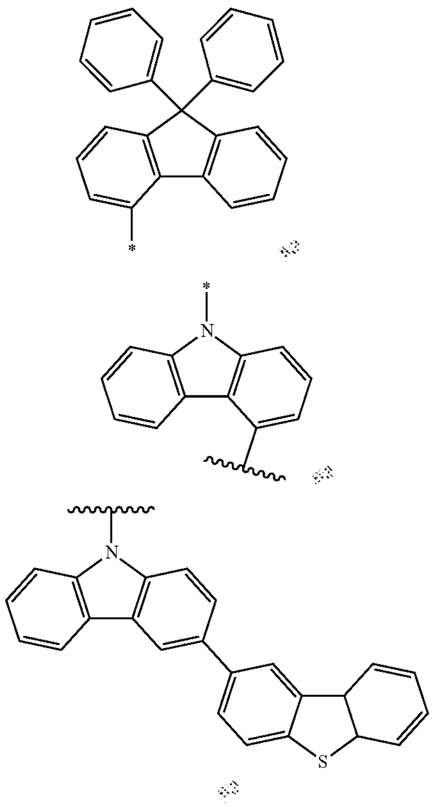
A19
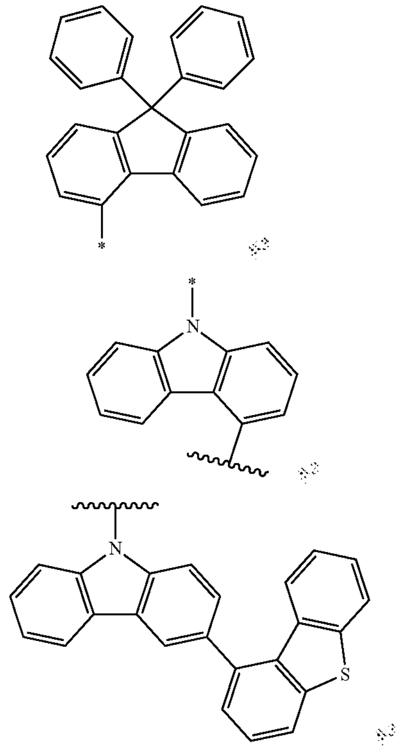
-continued
A20
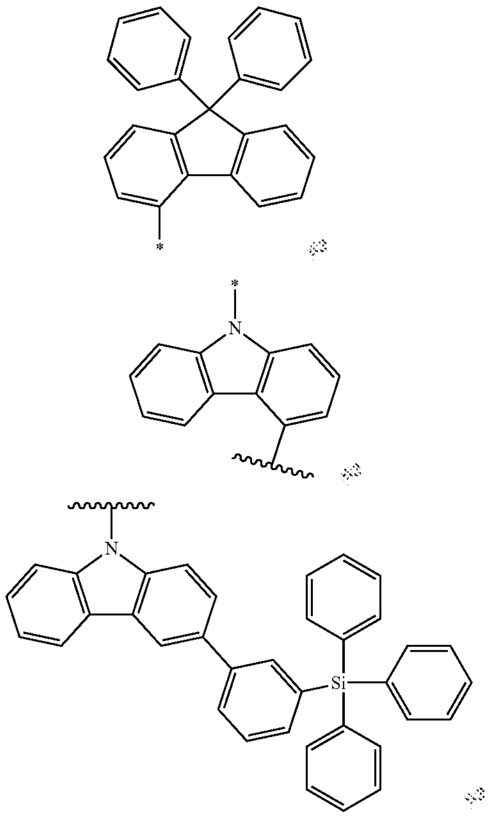
A21
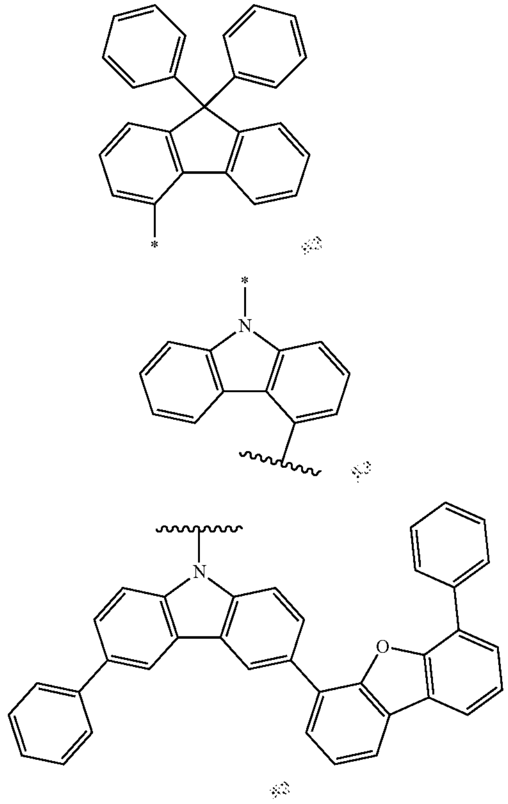

-continued
A22
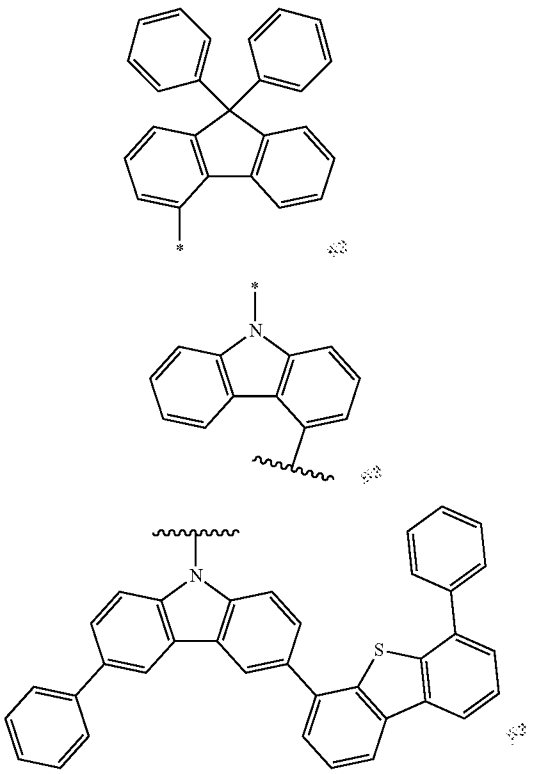
A23
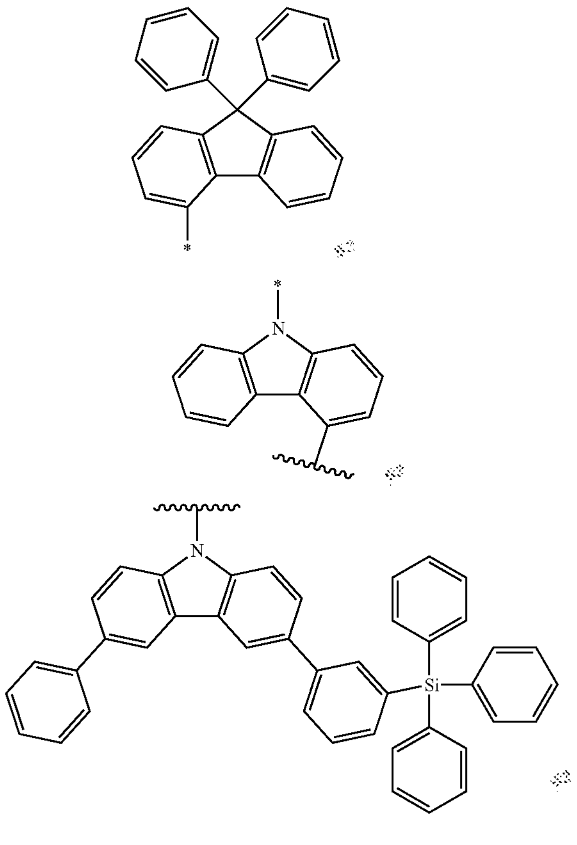
-continued
A24
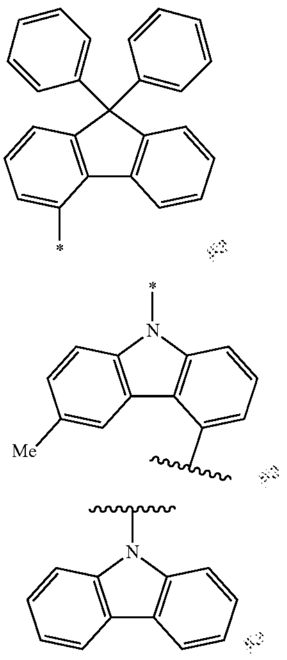
A25
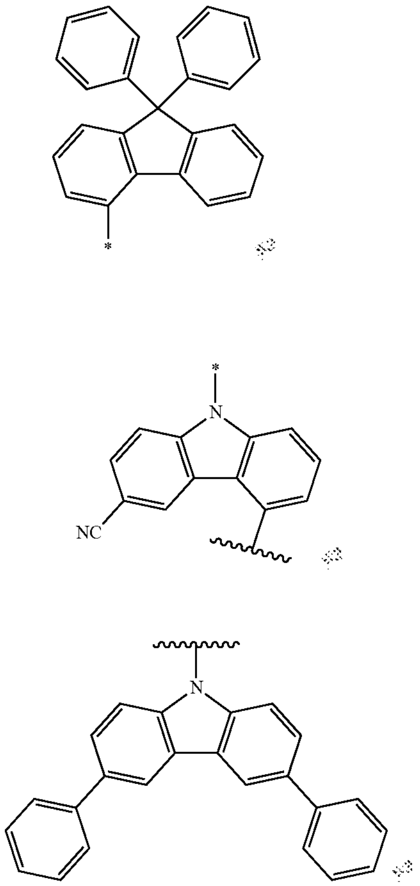

-continued
A26
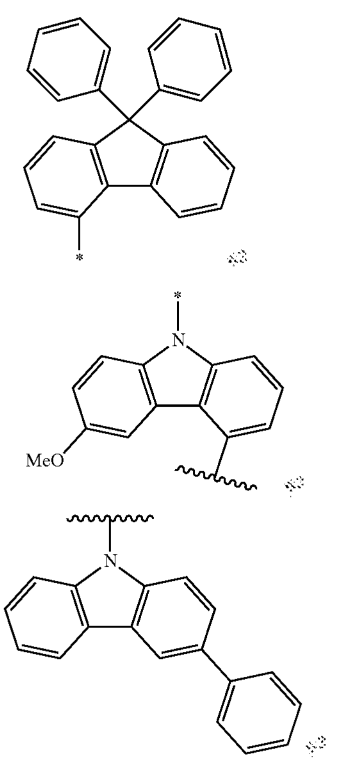
B1
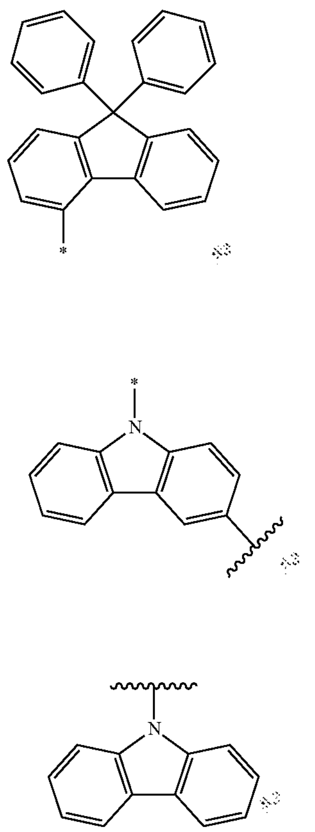
-continued
B2
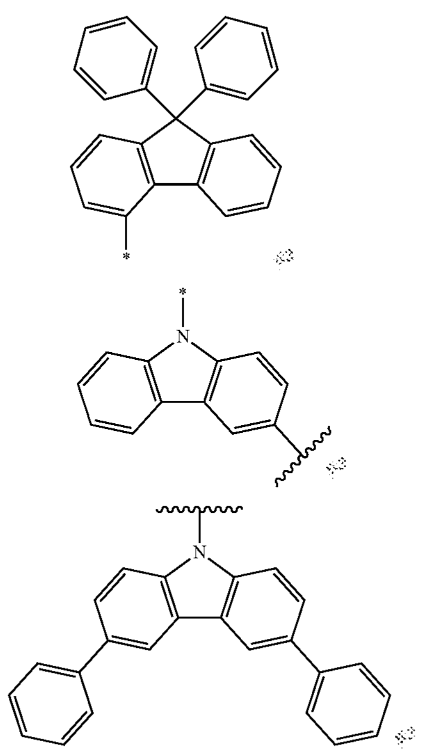
B3
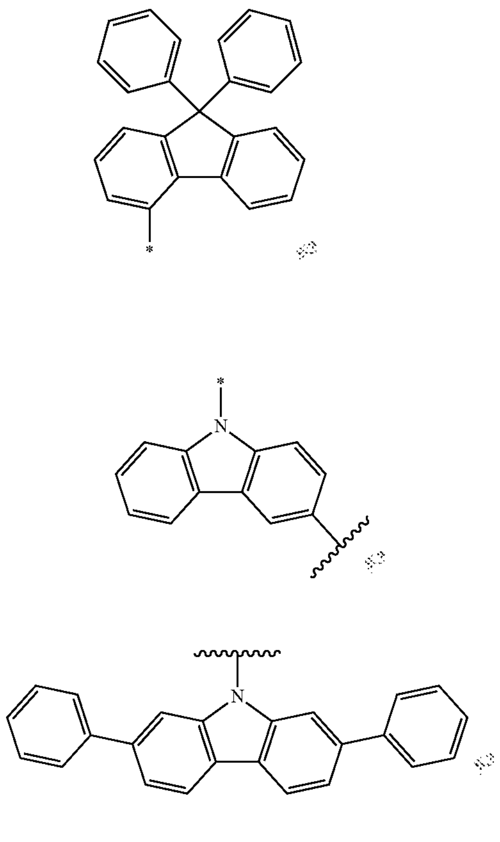

-continued
B4
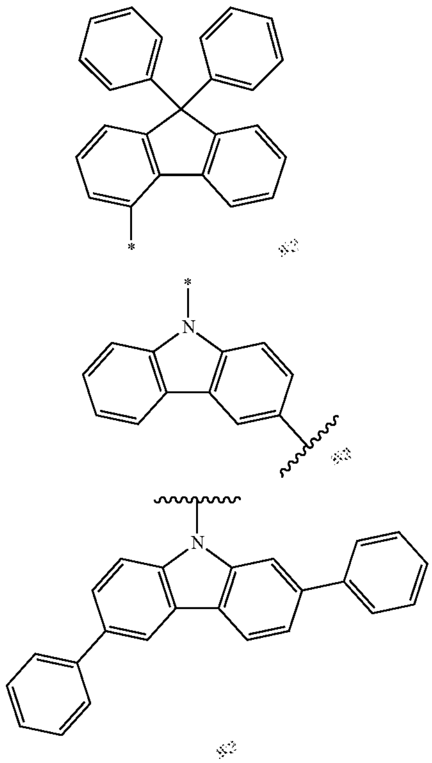
B5
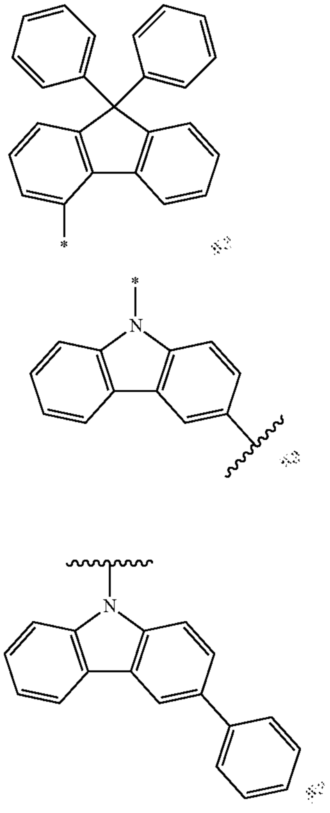
-continued
B6
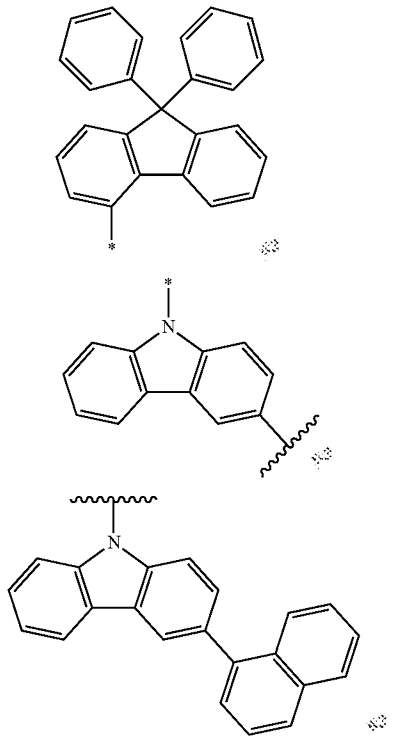
B7
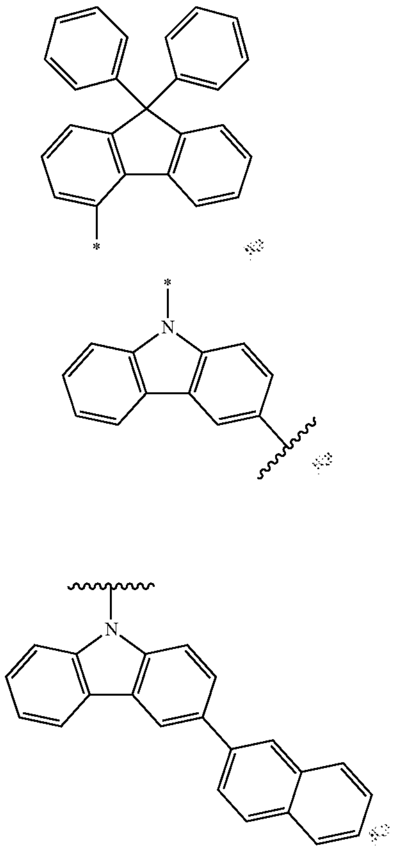

-continued
B8
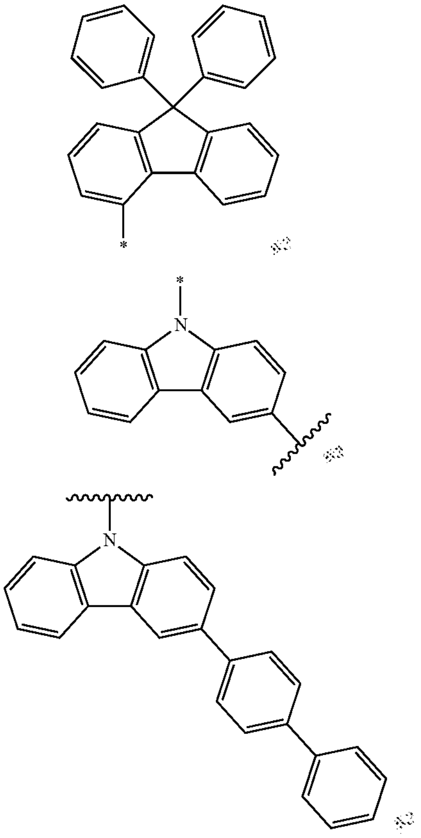
B9
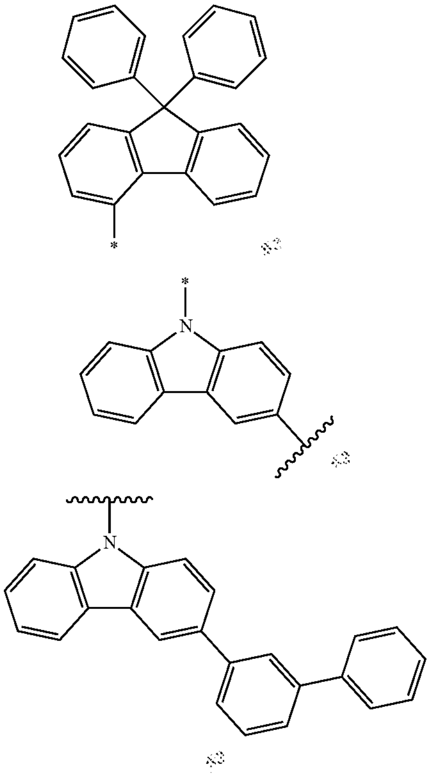
-continued
B10
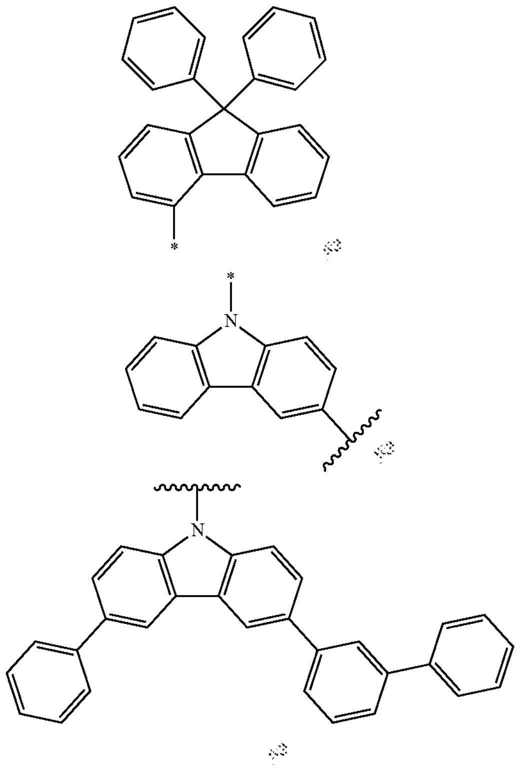
B11
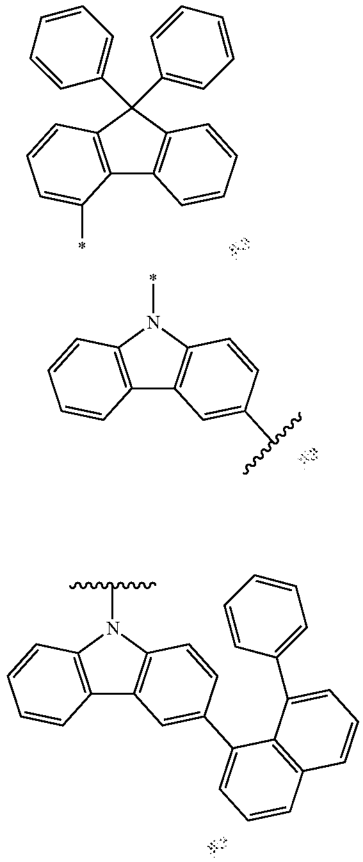

-continued
B12
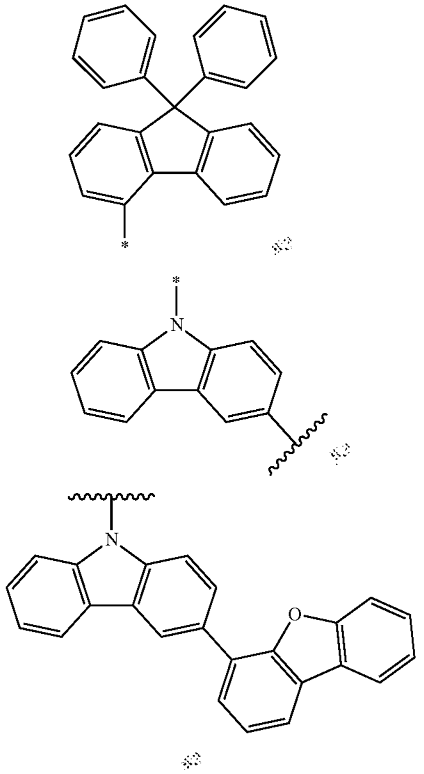
B13
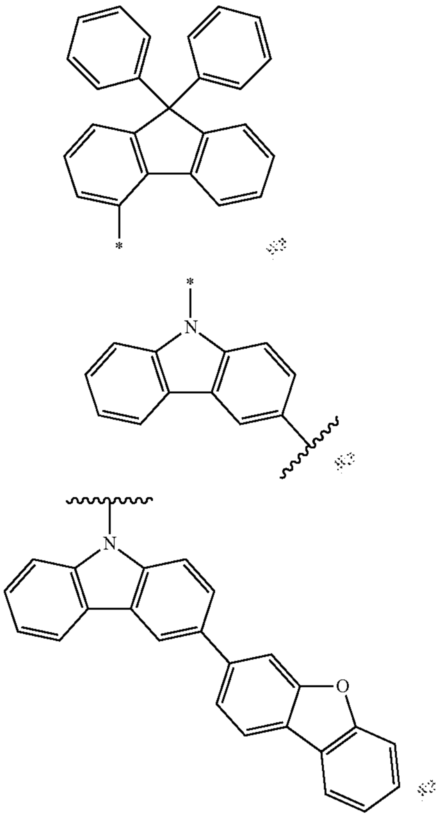
-continued
B14
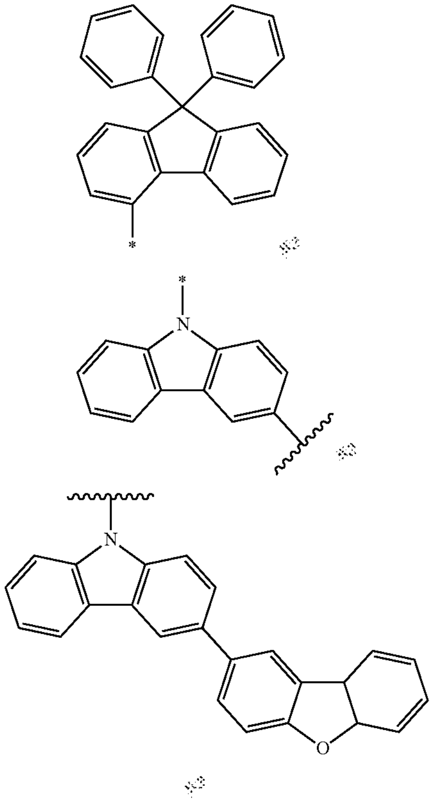
B15
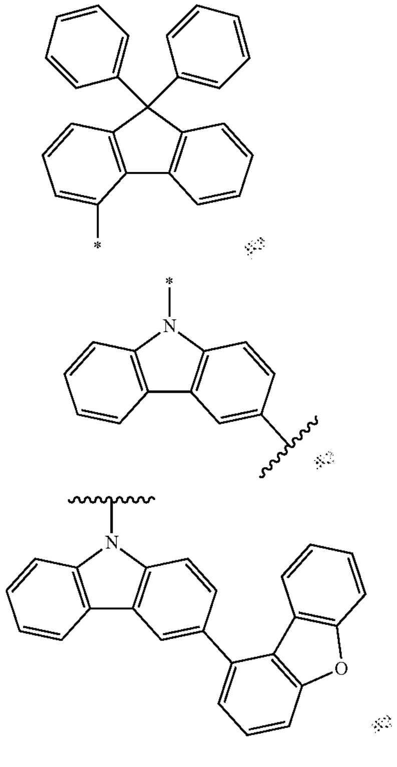

-continued
B16
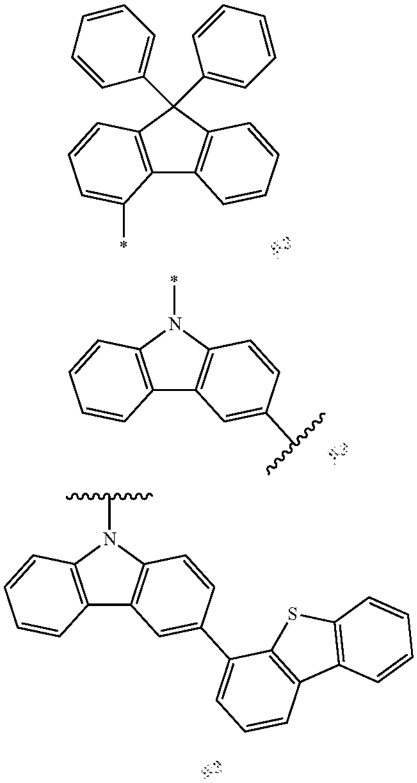
B17
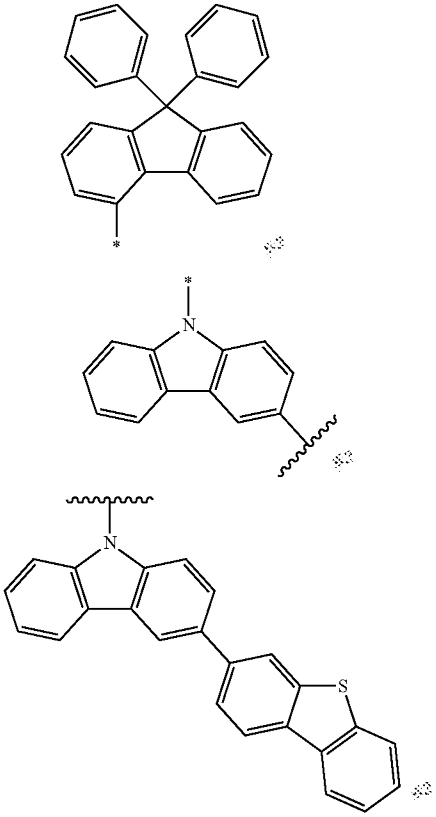
-continued
B18
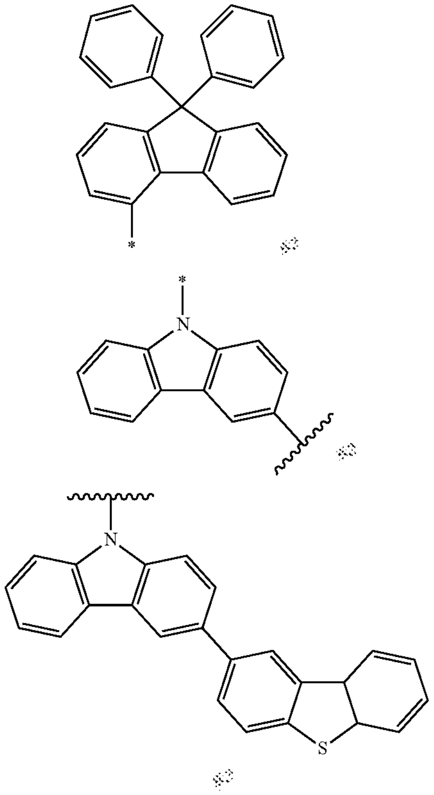
B19
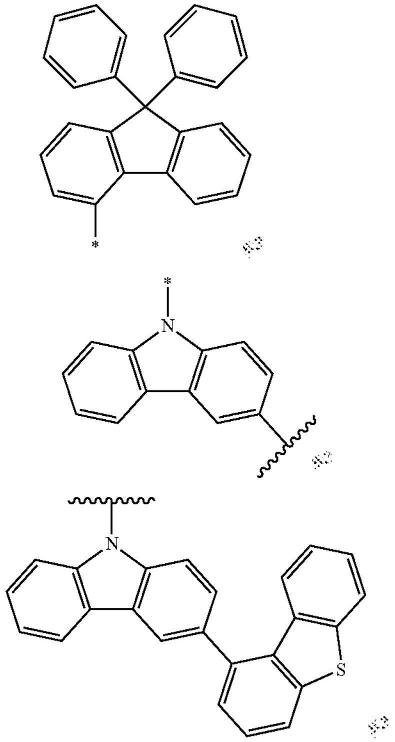

B20
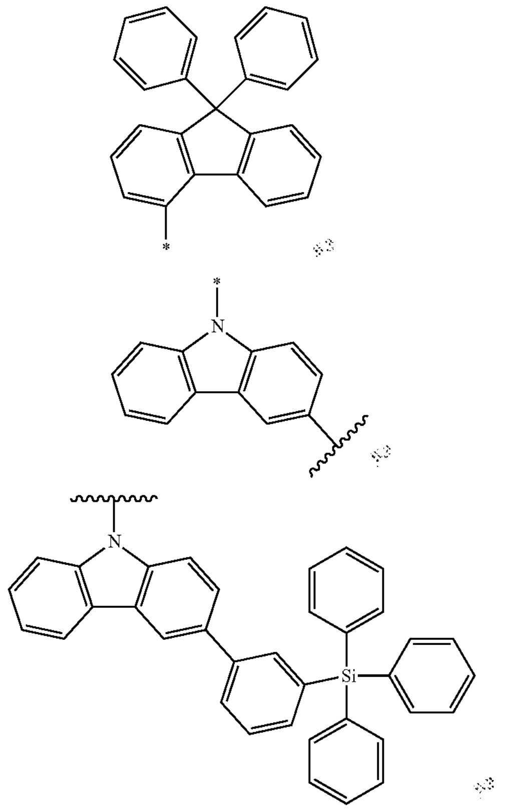
B21
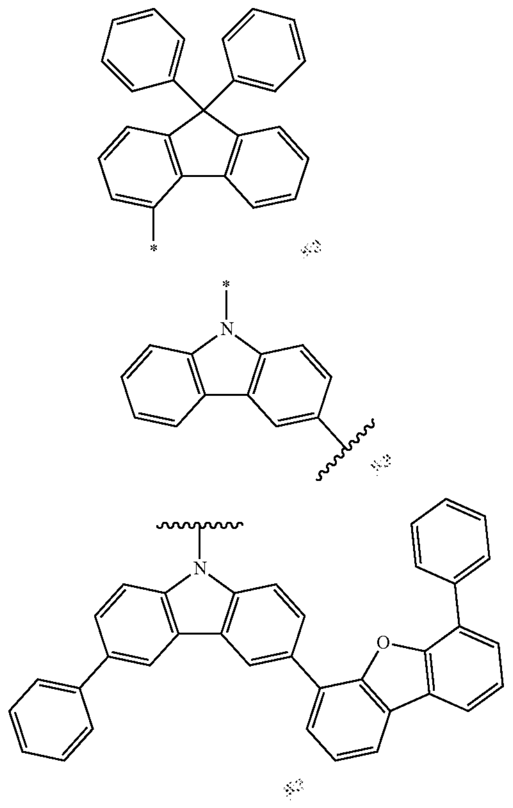
B22
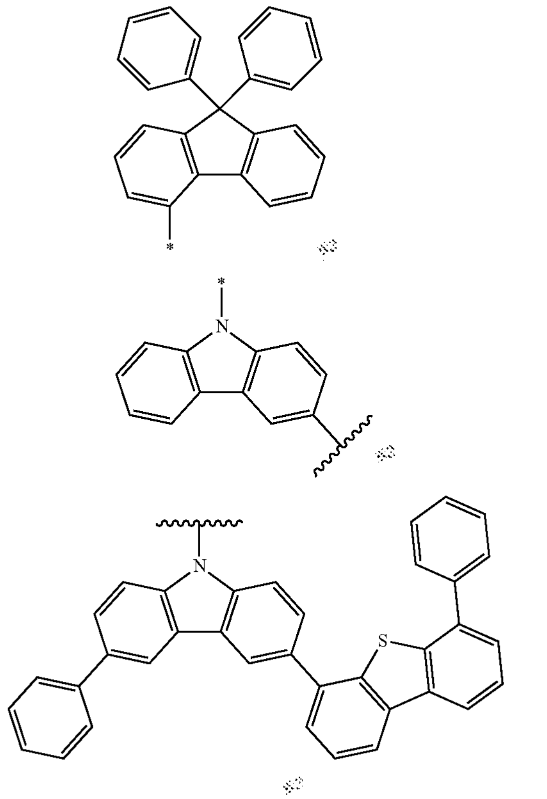
B23
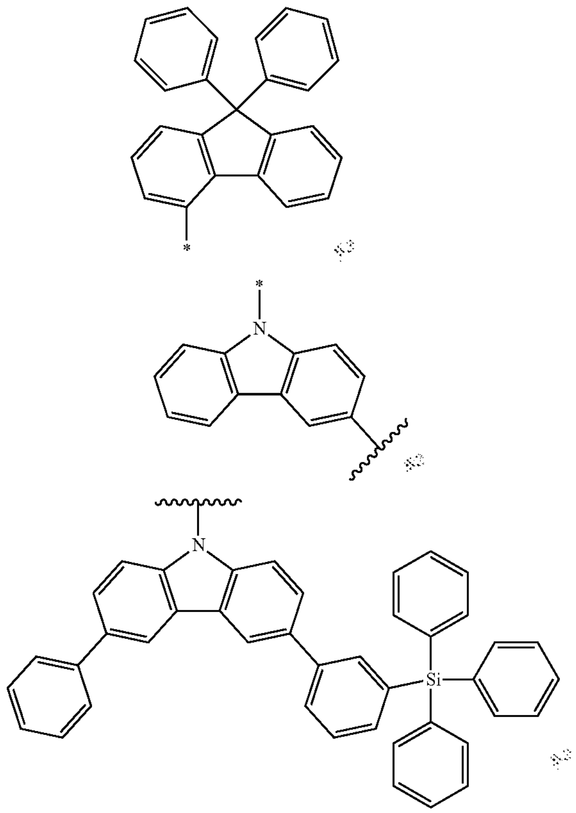

-continued
B24
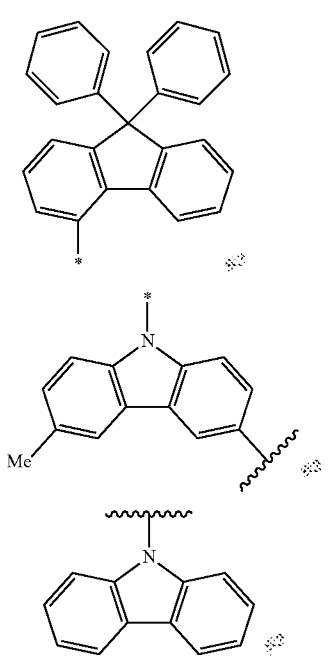
B25
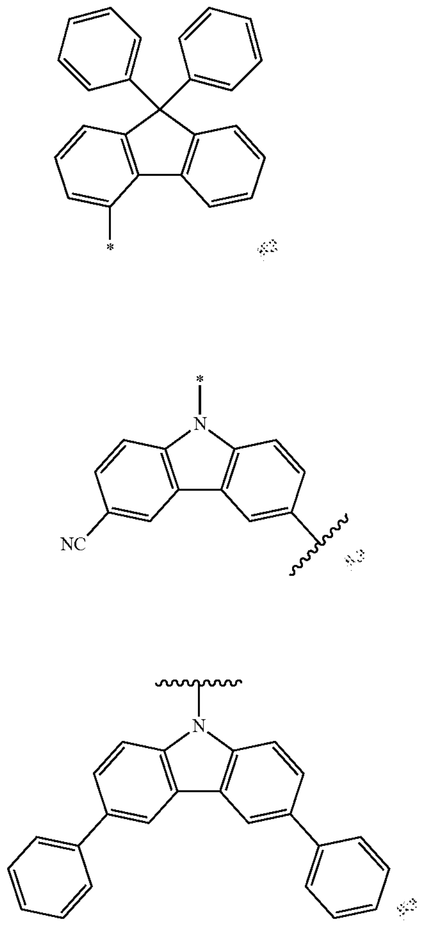
-continued
B26
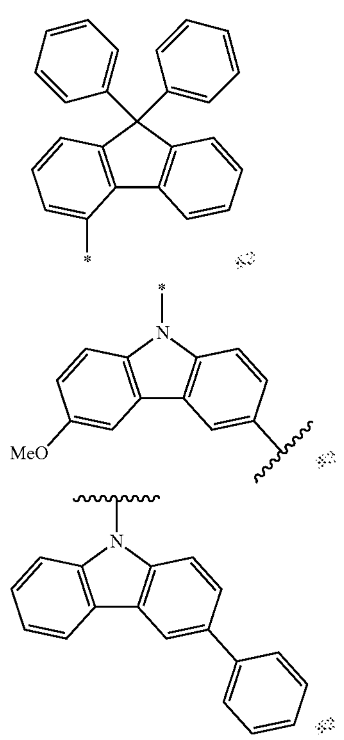
C1
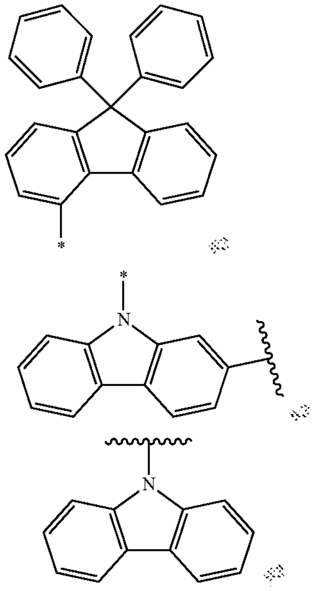
C2
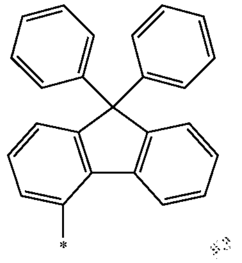

-continued
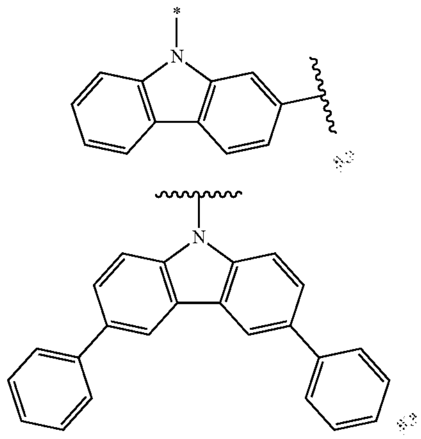
C3
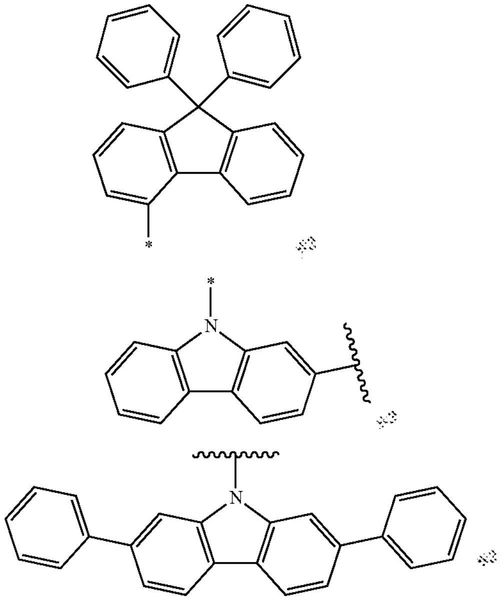
C4
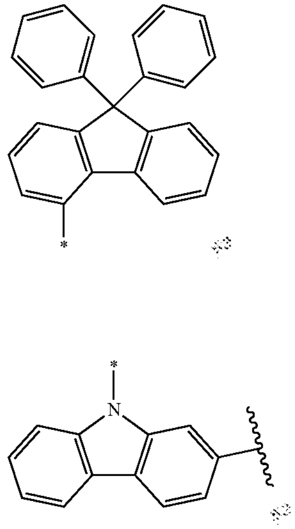
-continued
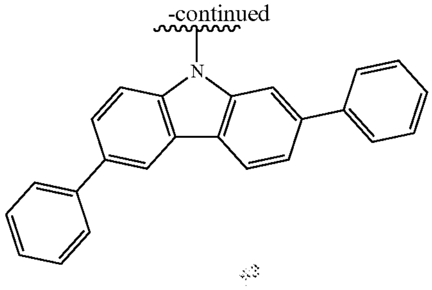
C5
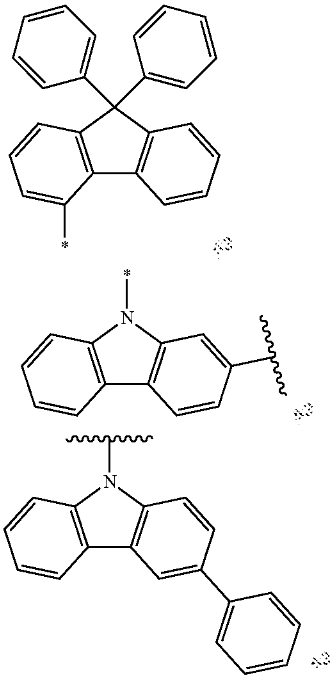
C6
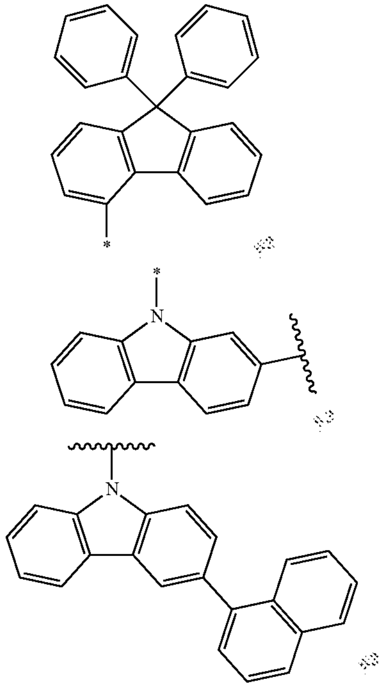

-continued
C7
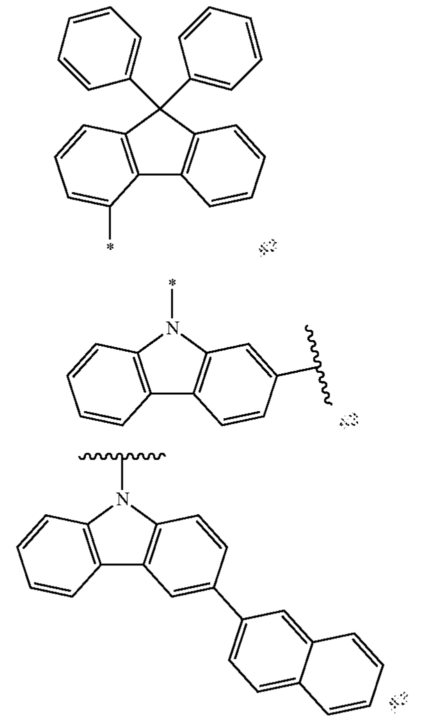
C8
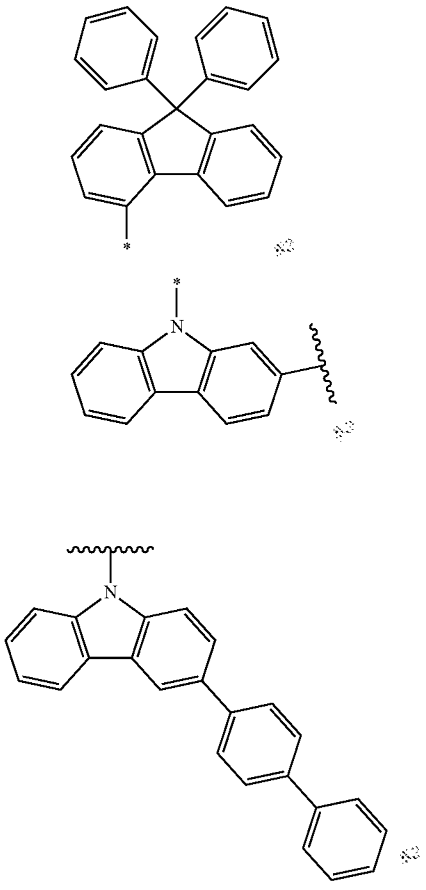
-continued
C9
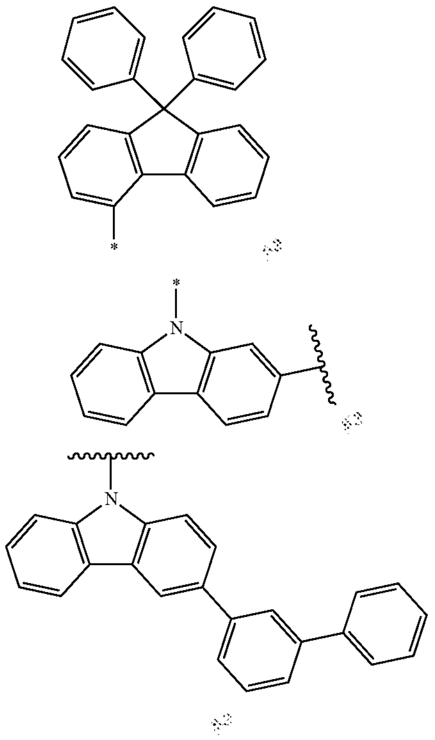
C10
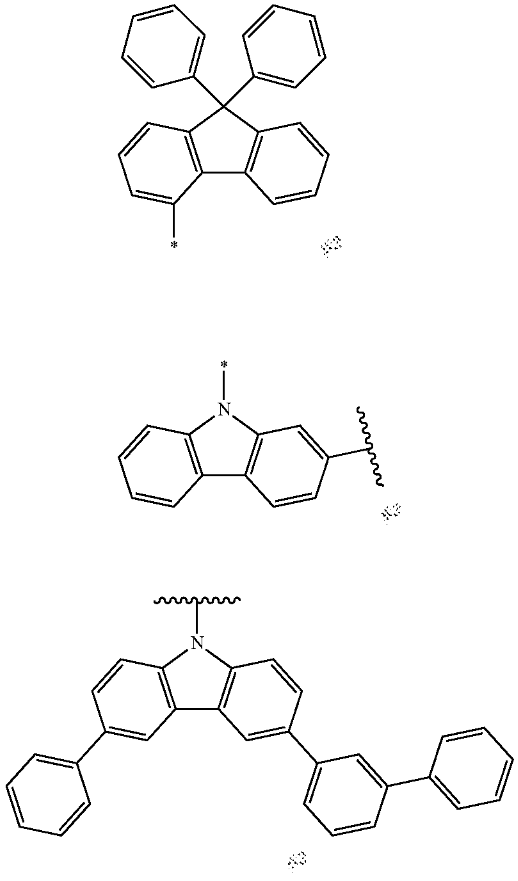

-continued
C11
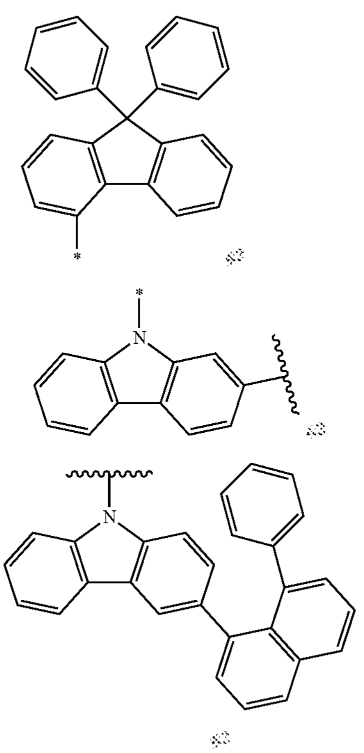
C12
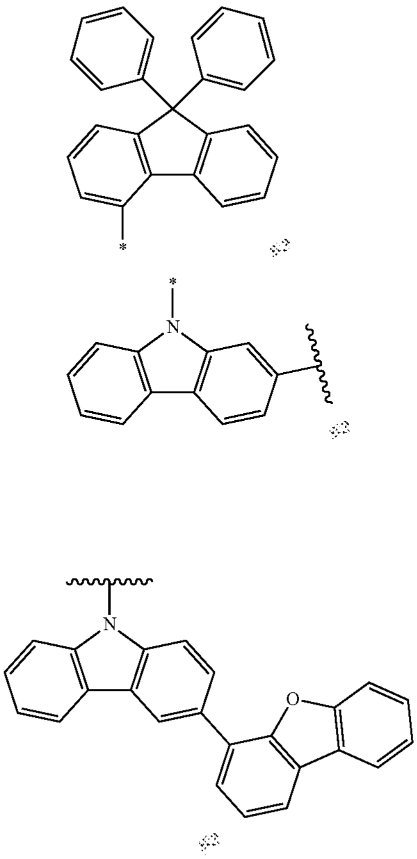
C13
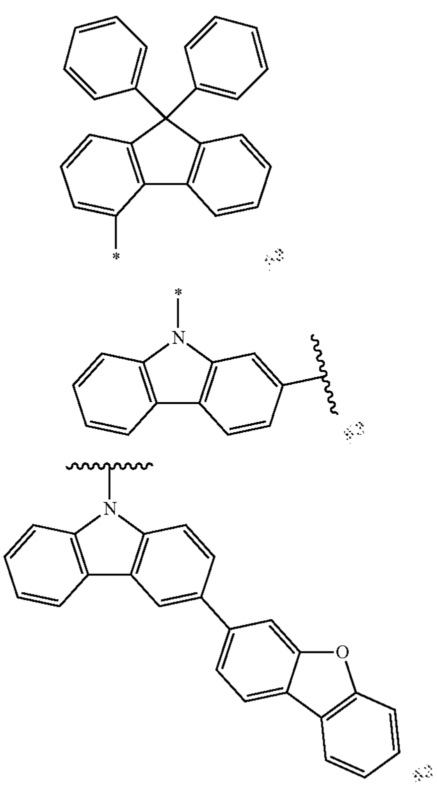
C14
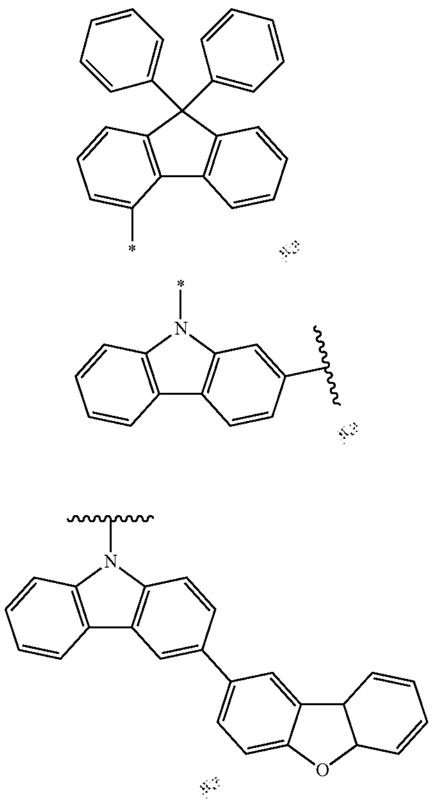

-continued
C15
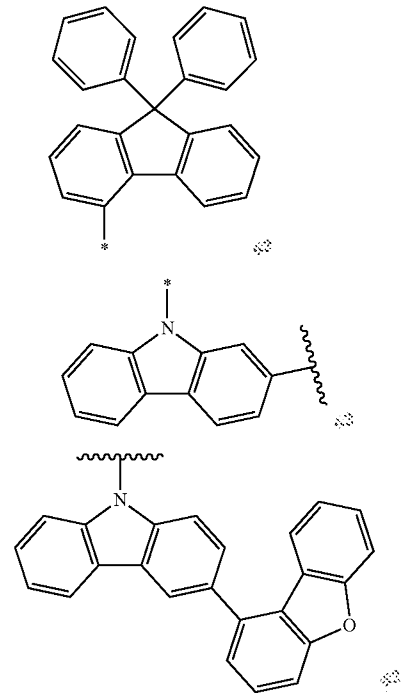
C16
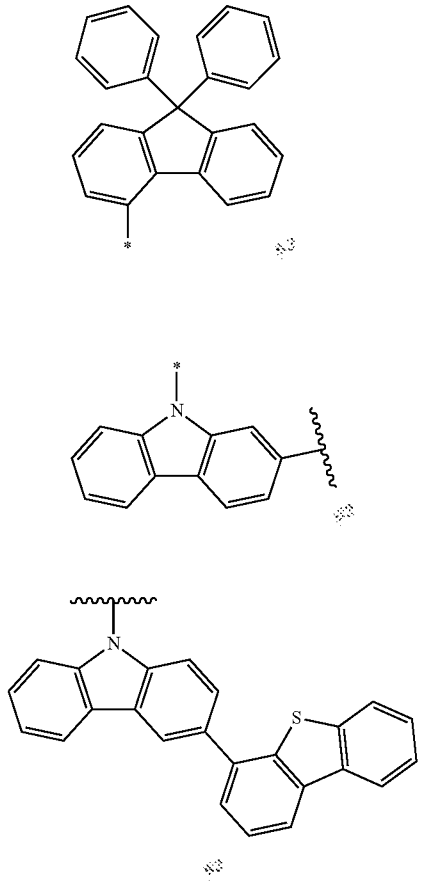
-continued
C17
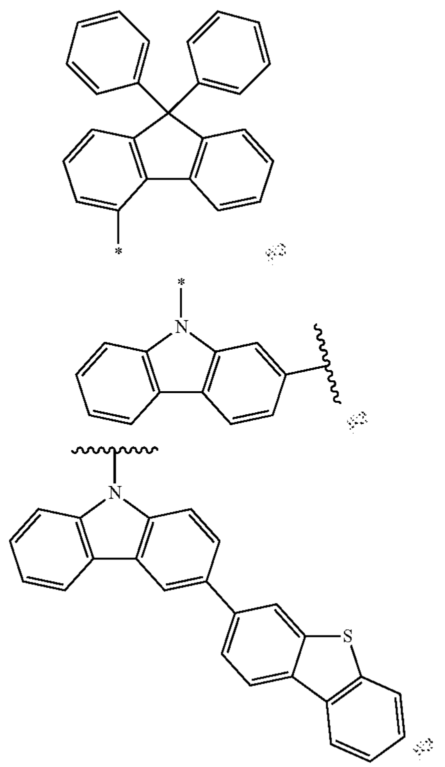
C18
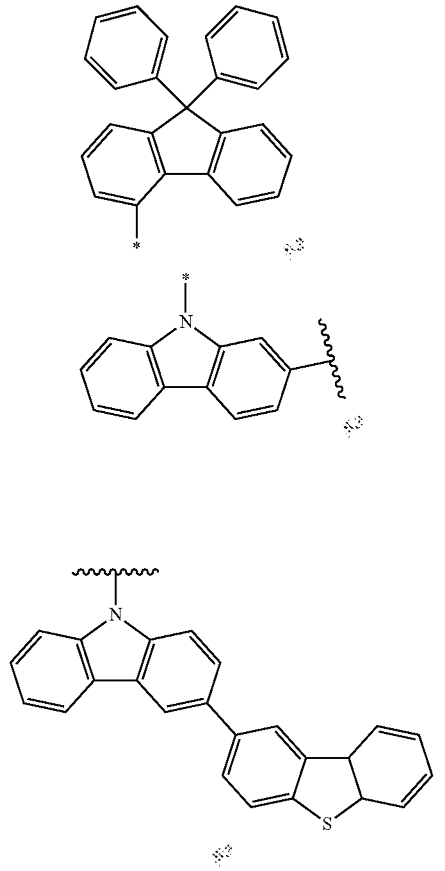

C19
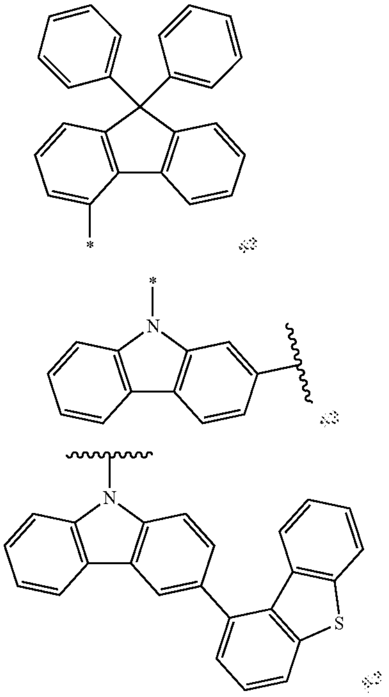
C20
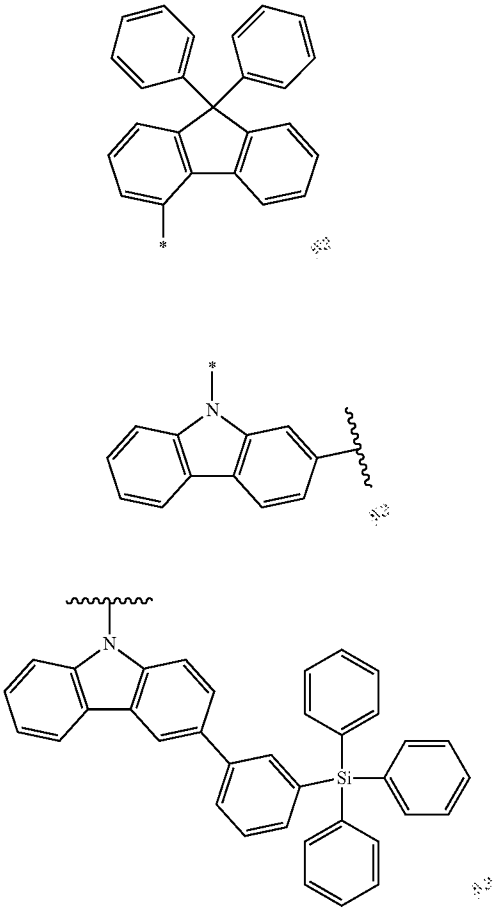
C21
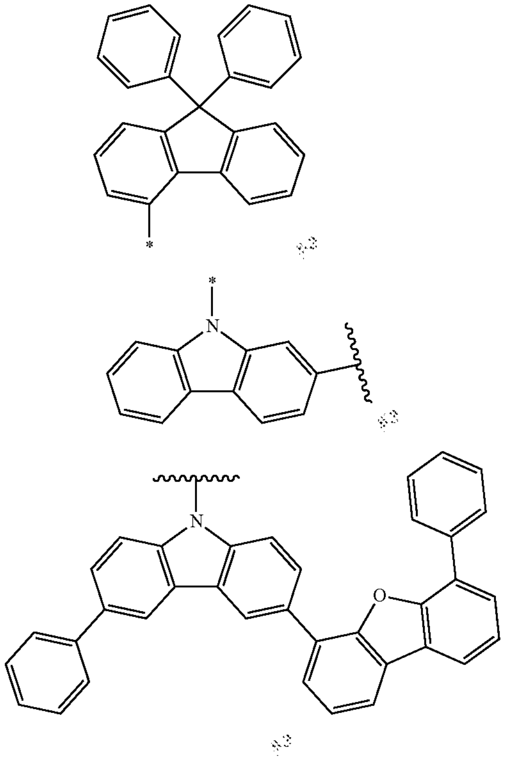
C22
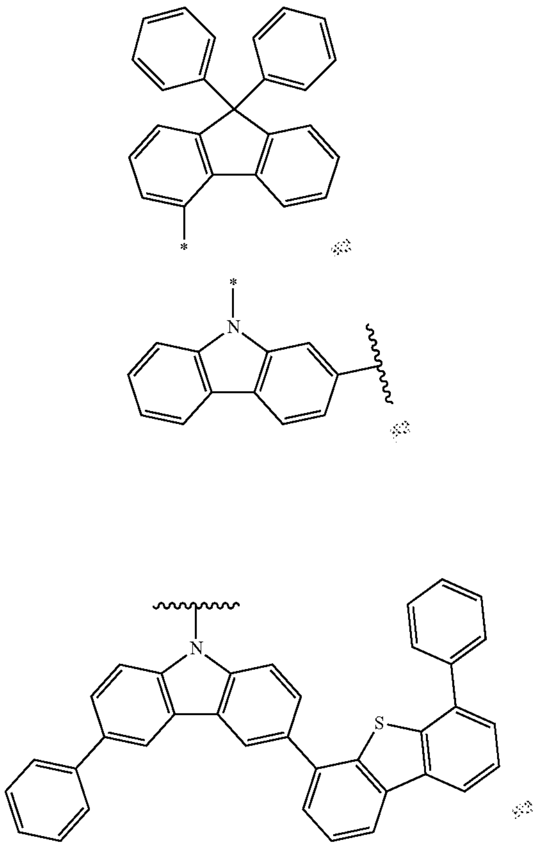

-continued
C23
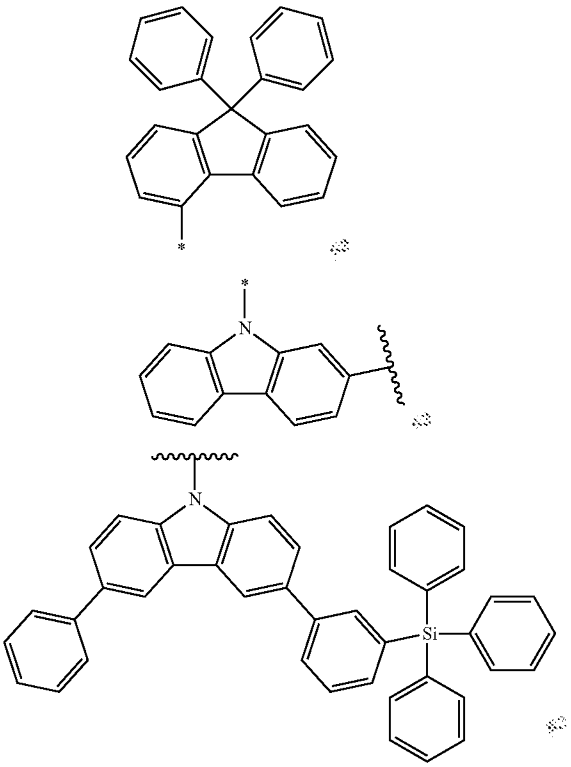
C24
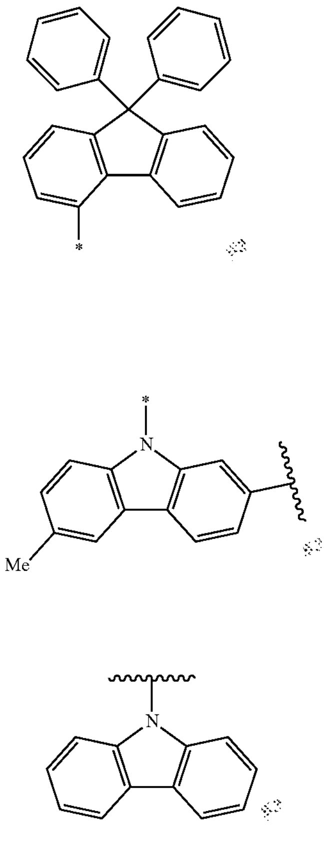
-continued
C25
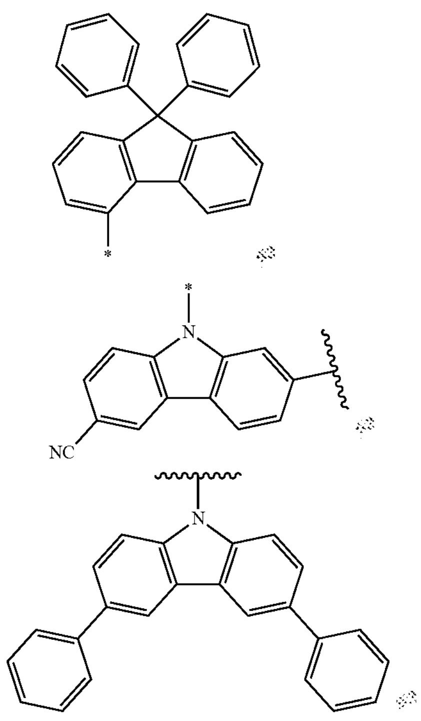
C26
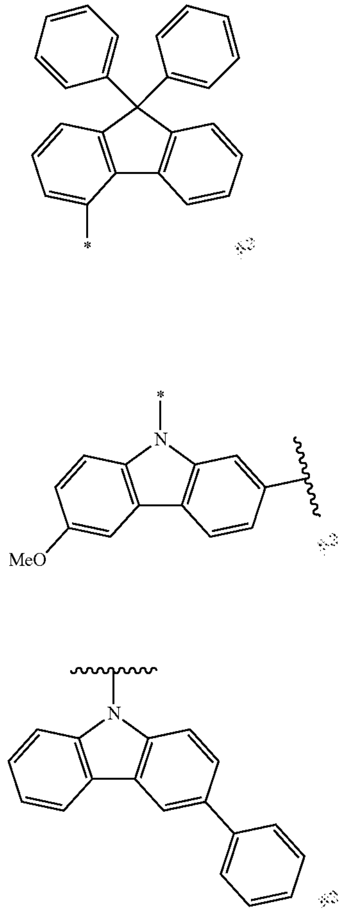

-continued
D1
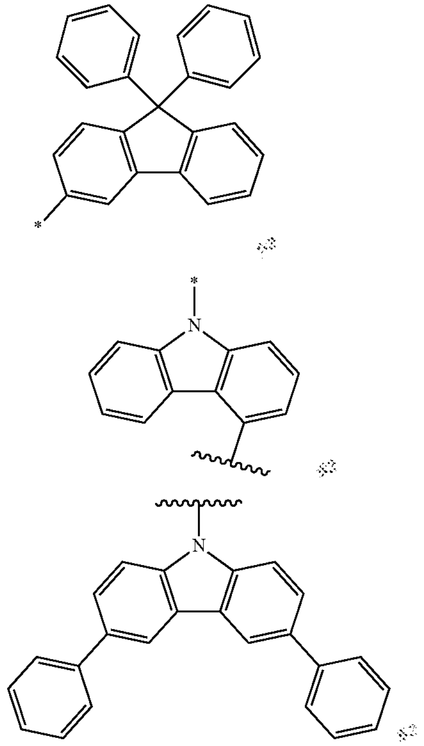
D2
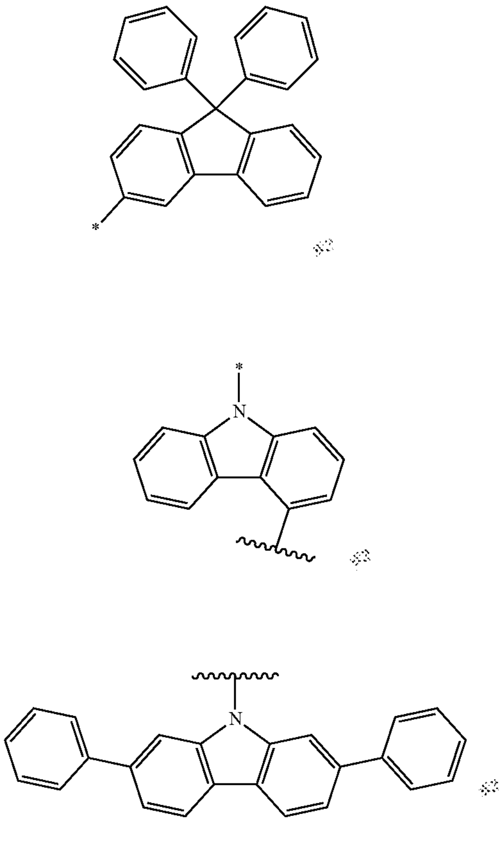
-continued
D3
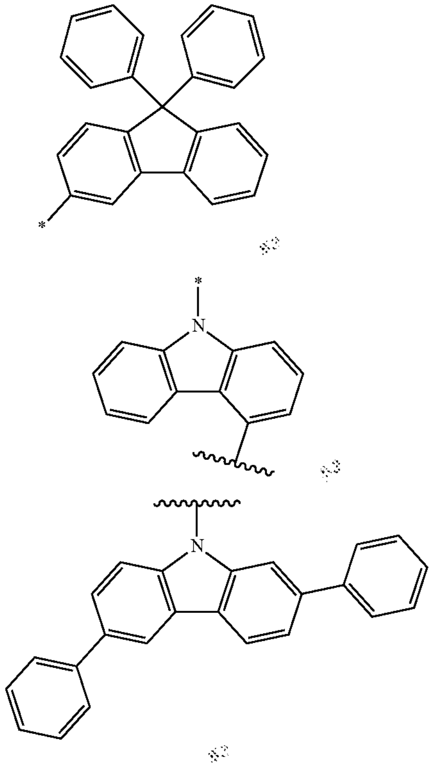
D4
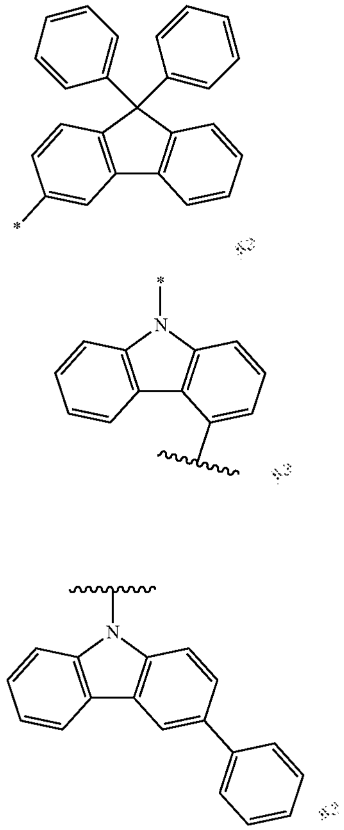

-continued
D5
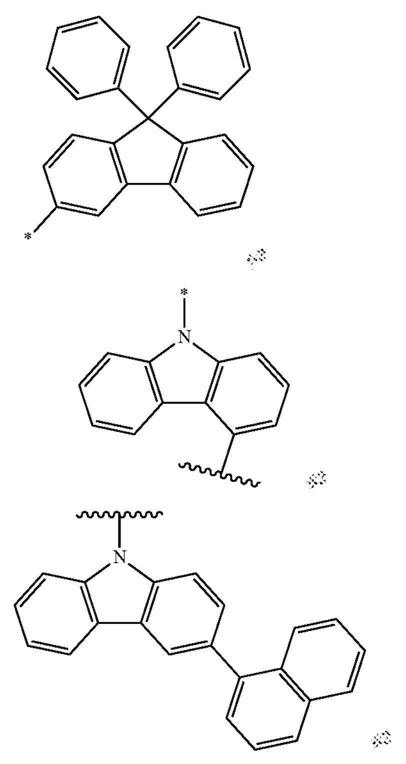
D6
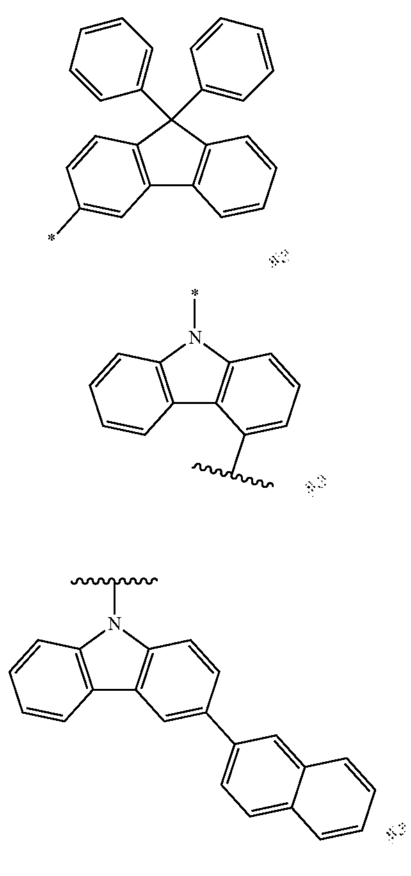
-continued
D7
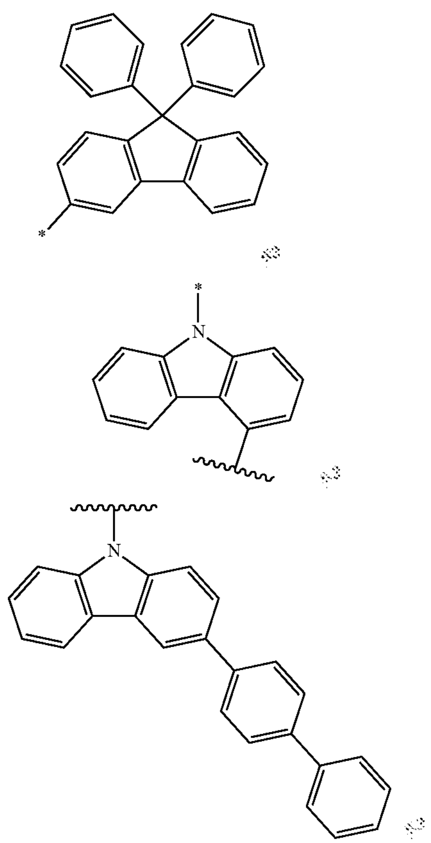
D8
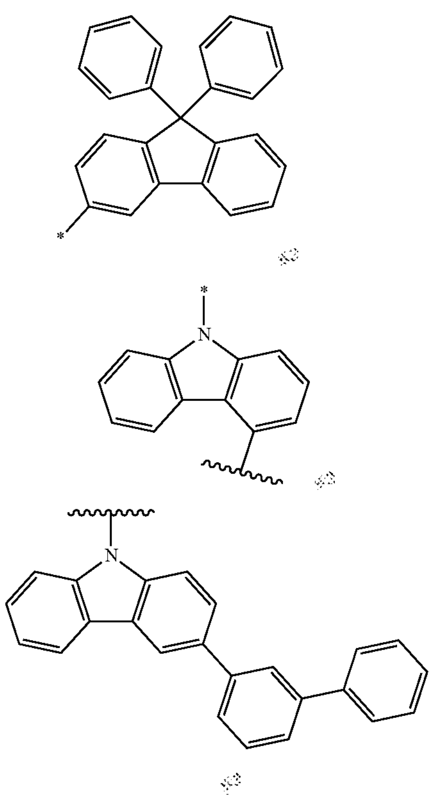

-continued
D9
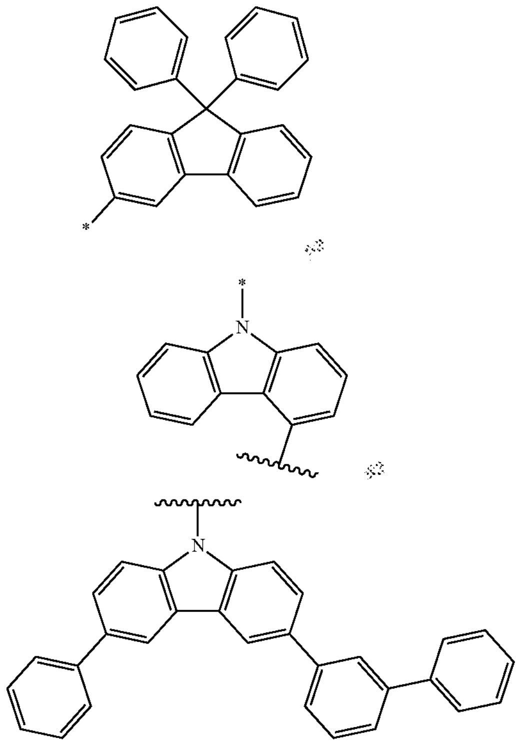
D10
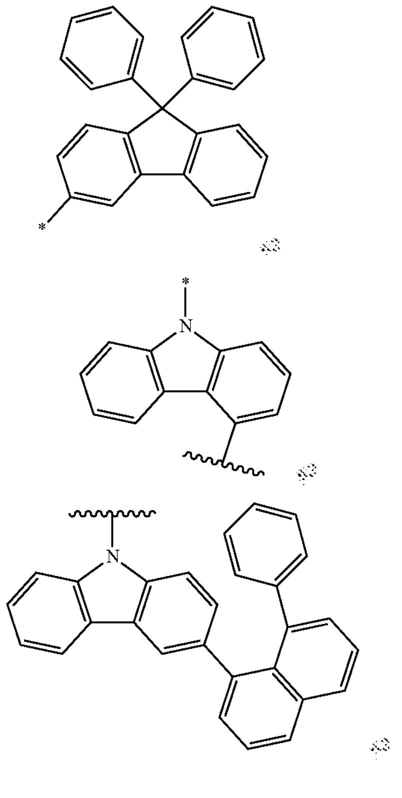
-continued
D11
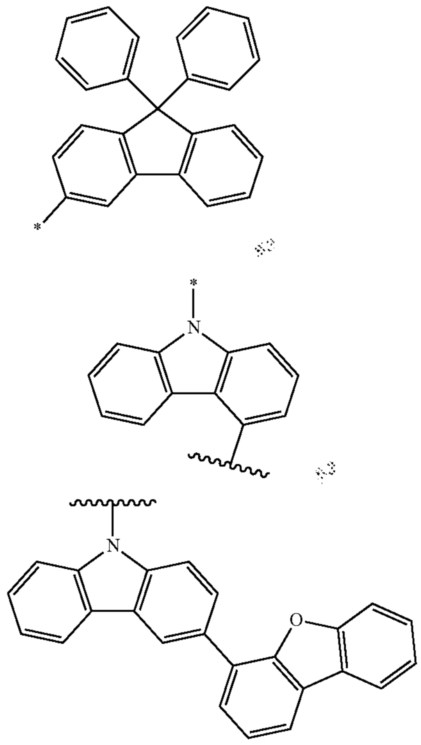
D12
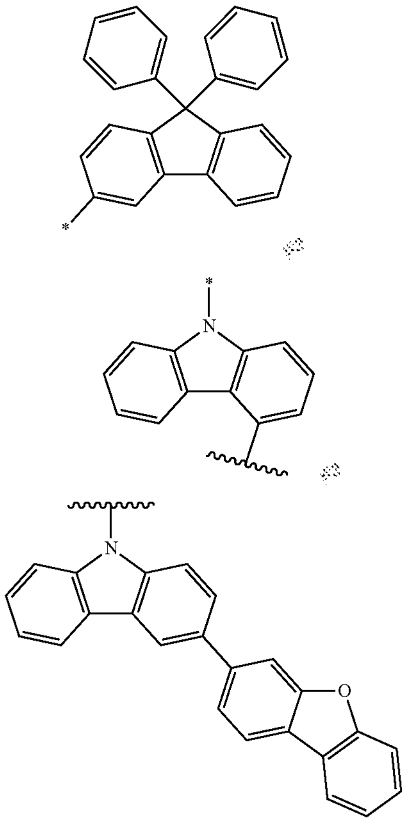

-continued
D13
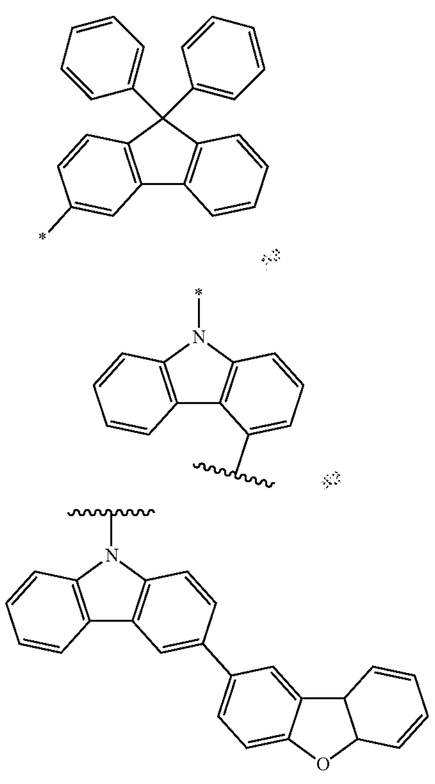
D14
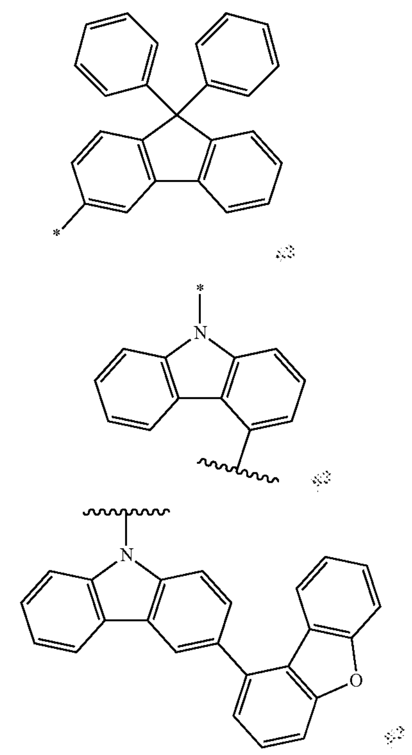
-continued
D15
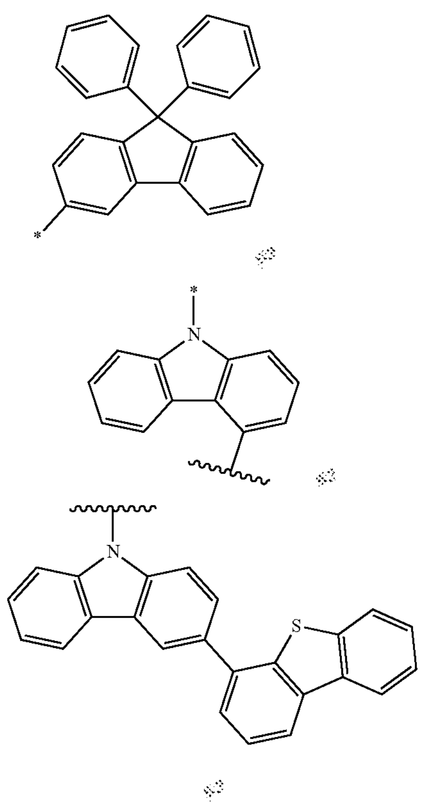
D16
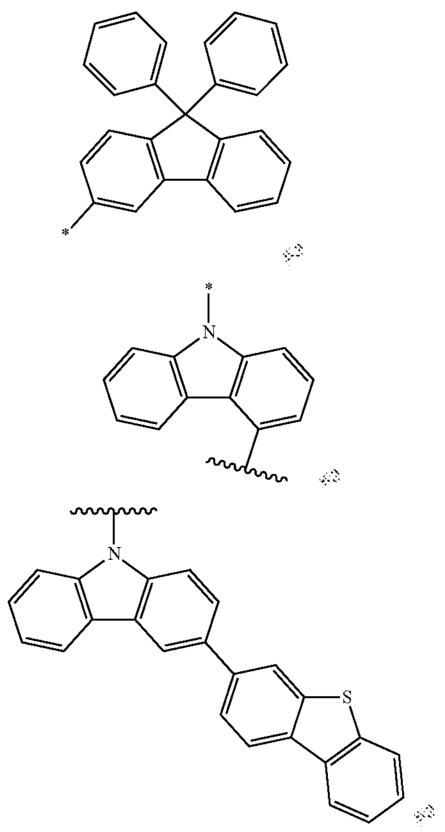

-continued
D17
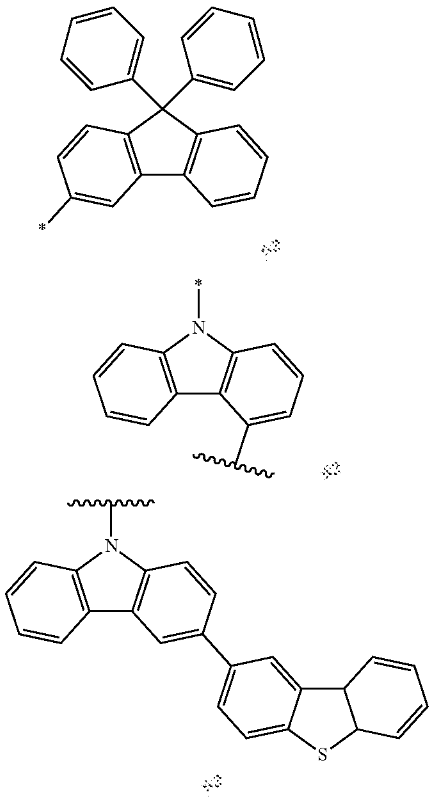
D18
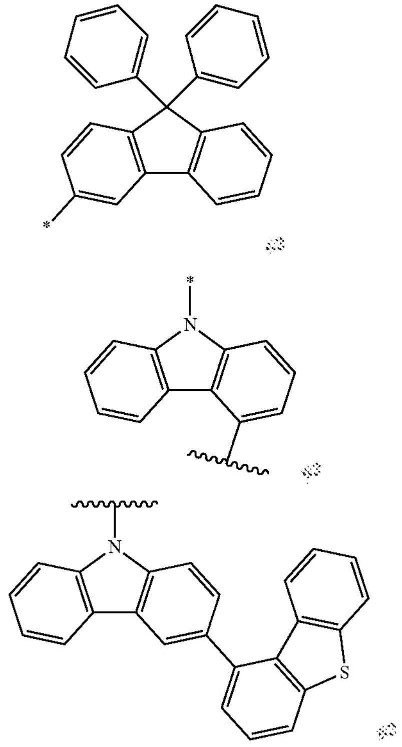
-continued
D19
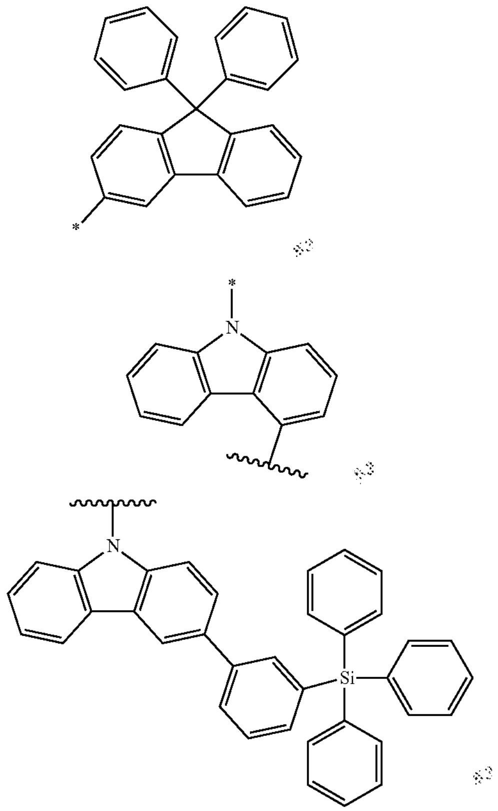
D20
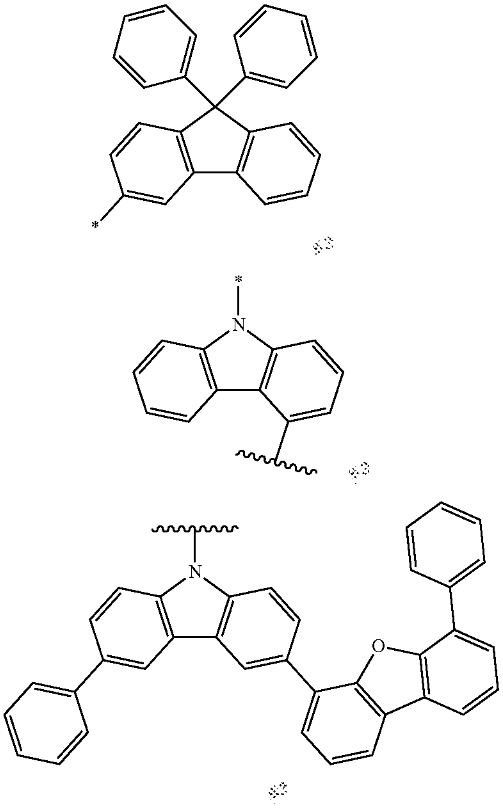

-continued
D21
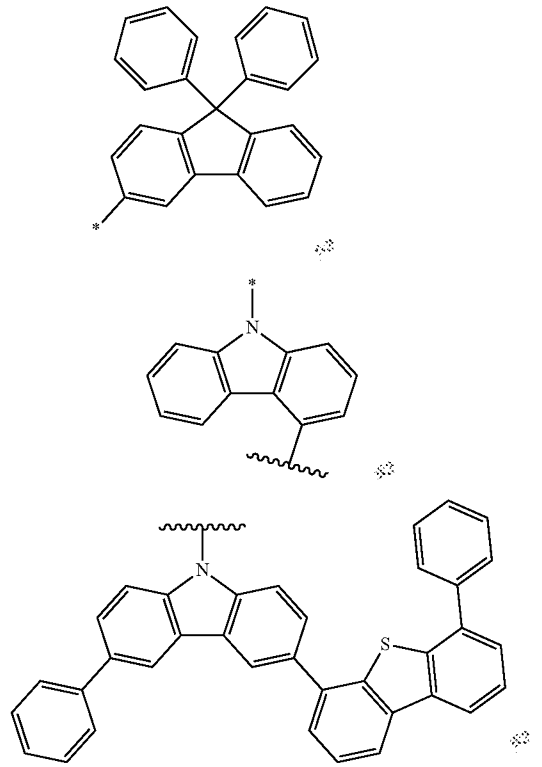
D22
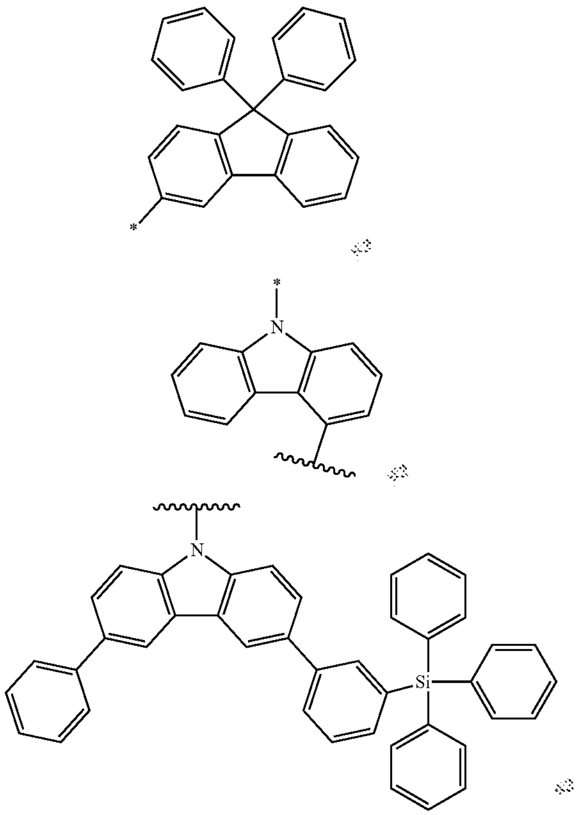
-continued
D23
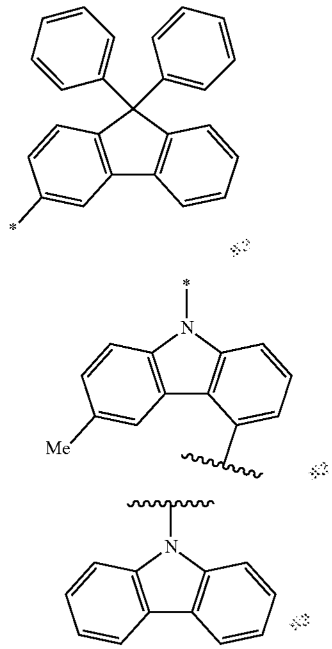
D24
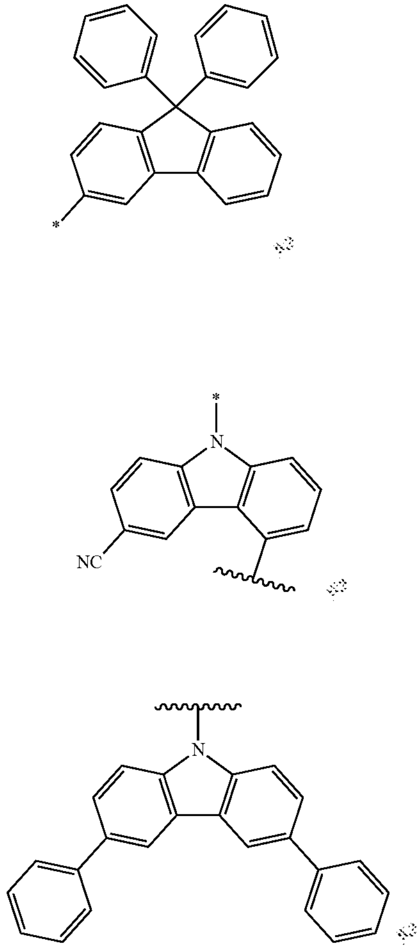

-continued
D25
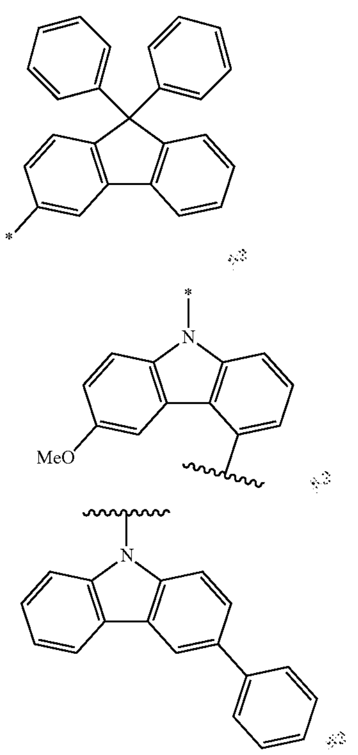
D26
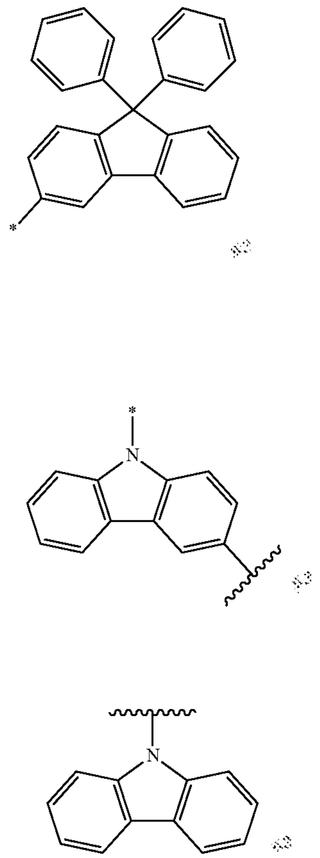
-continued
E1
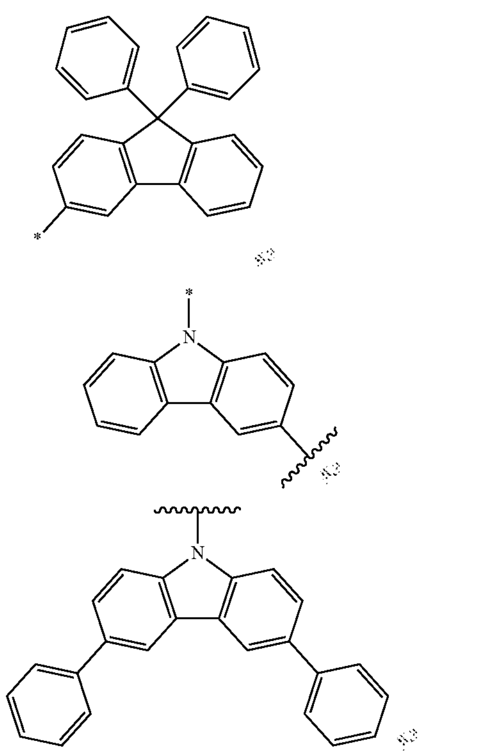
E2
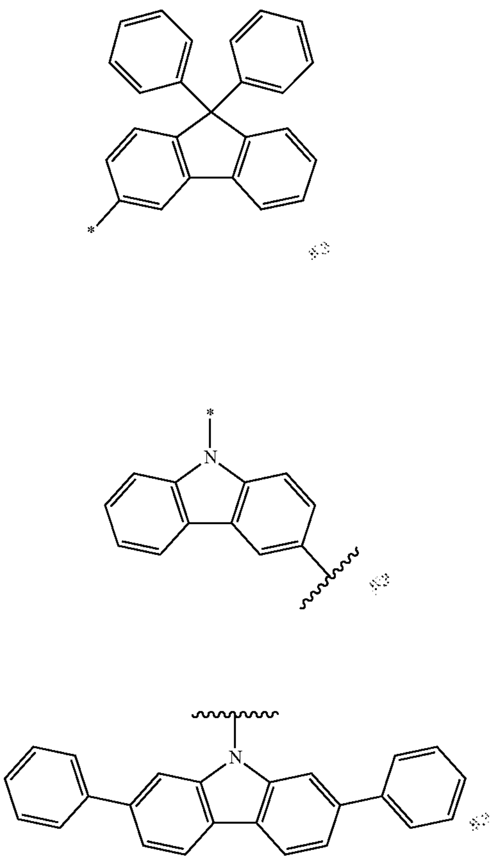

E3
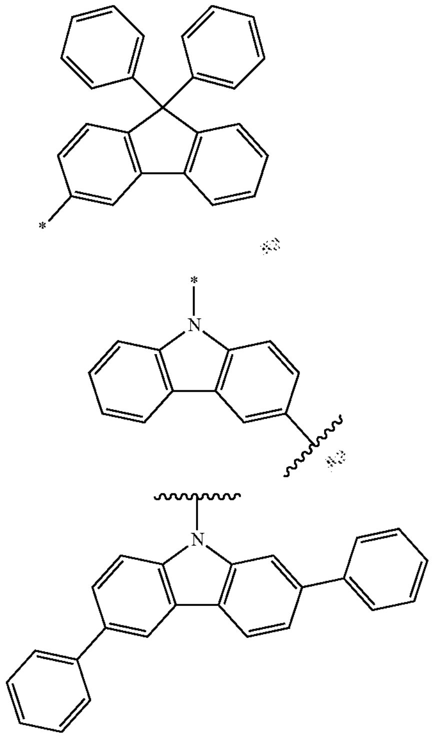
E4
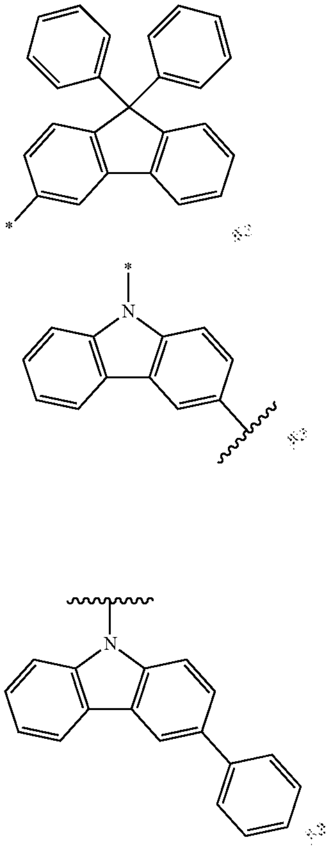
E5
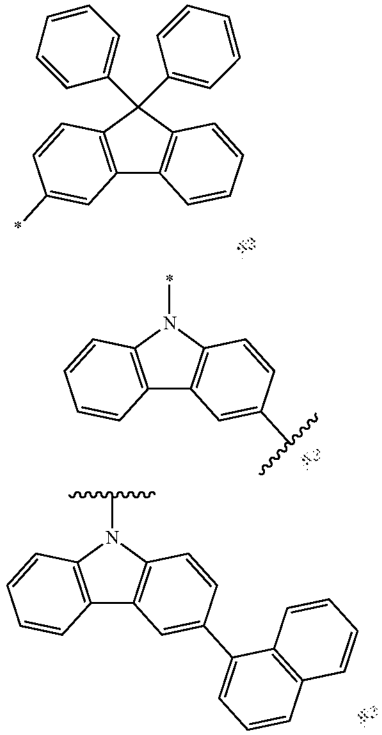
E6
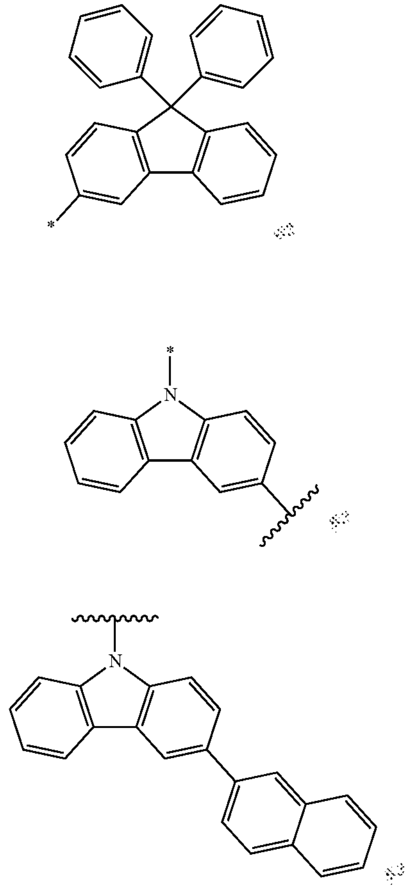

-continued
E7
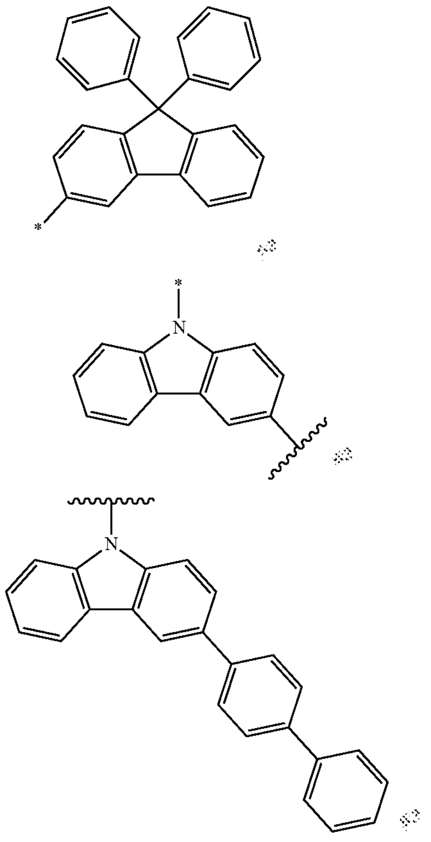
E8
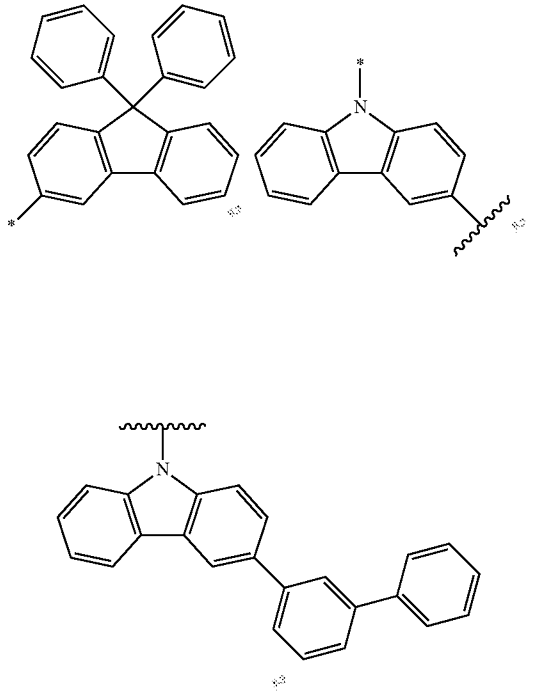
-continued
E9
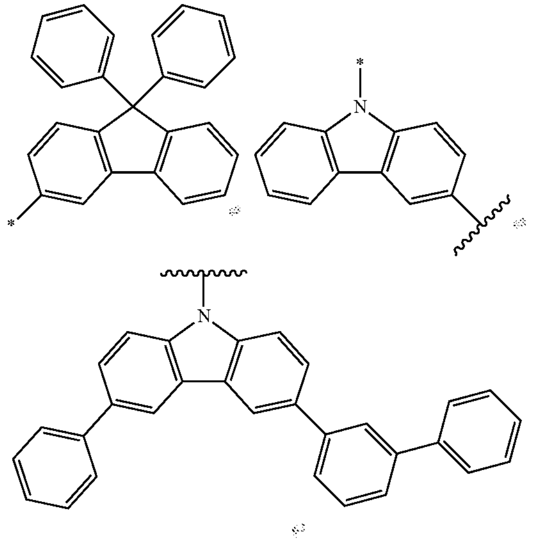
E10
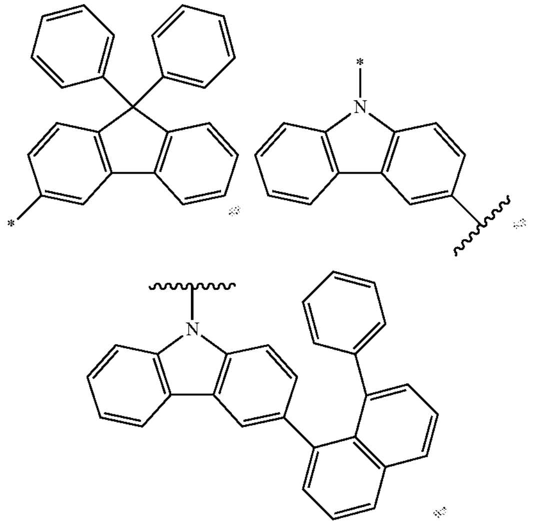
E11
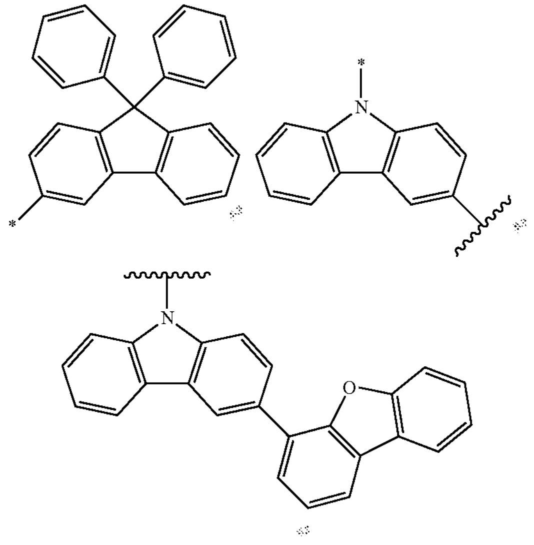

-continued
E12
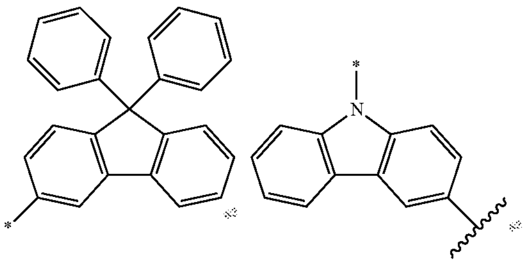
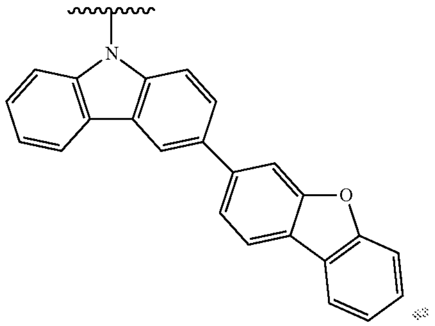
E13
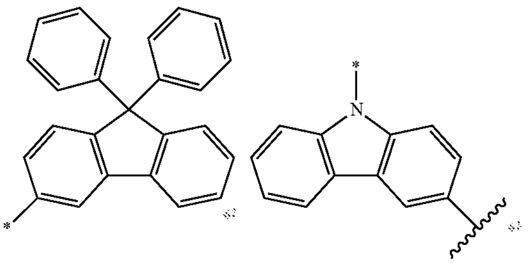
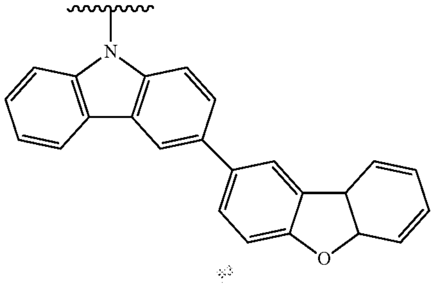
E14
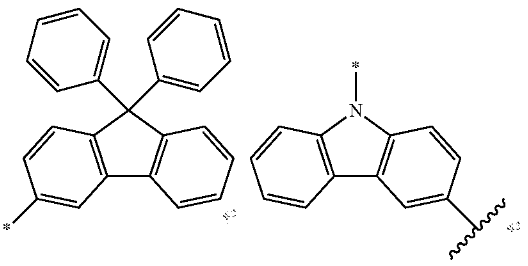
-continued
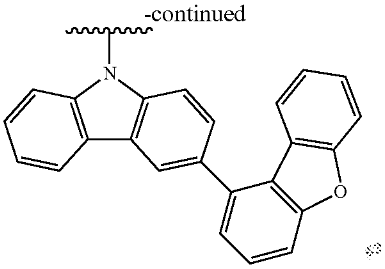
E15
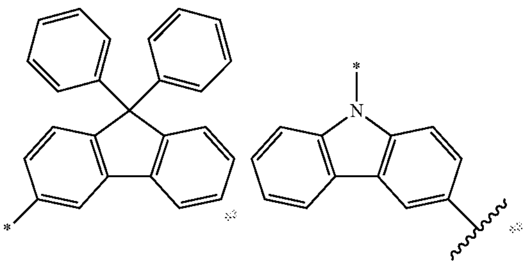
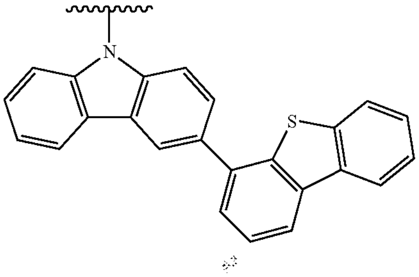
E16
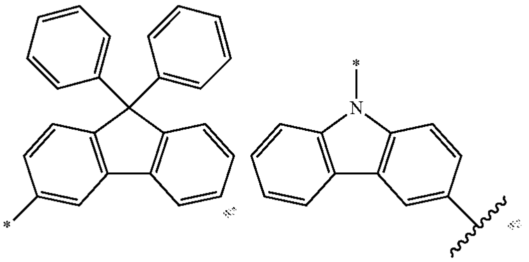
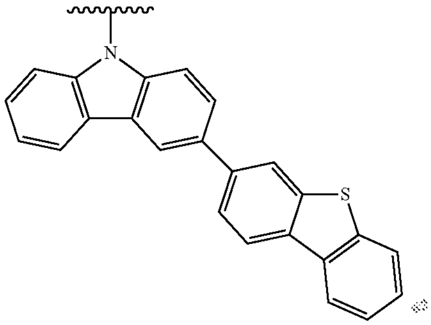
E17
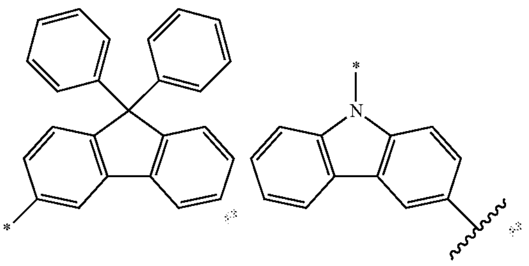

-continued
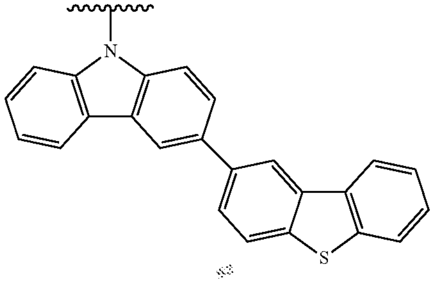
E18
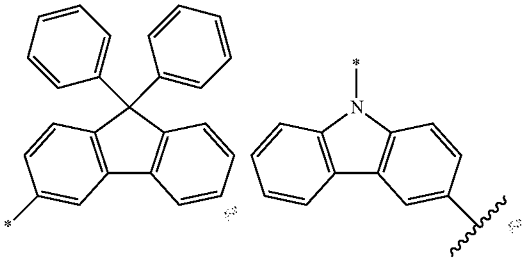
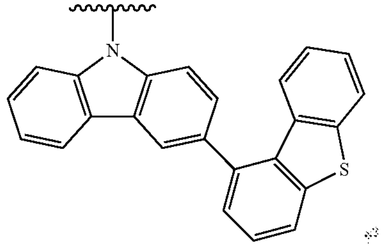
E19
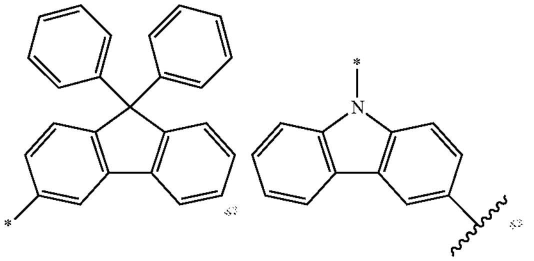
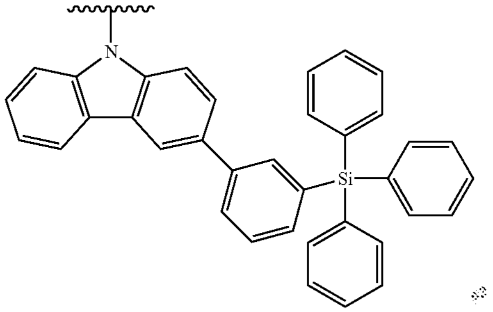
E20
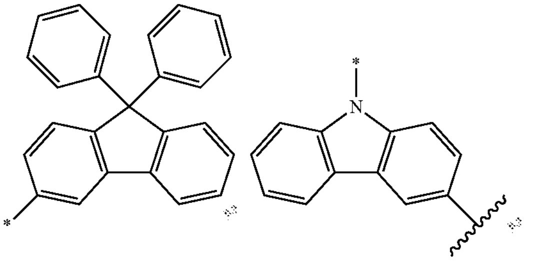
-continued
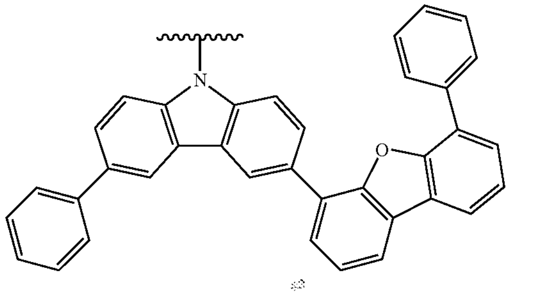
E21
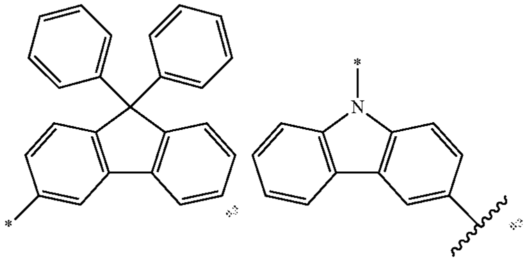
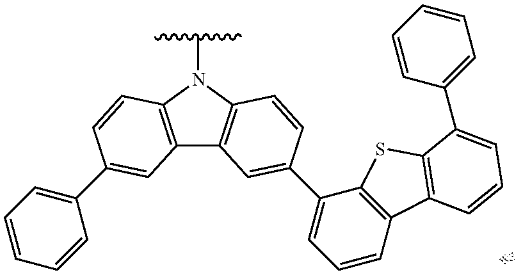
E22
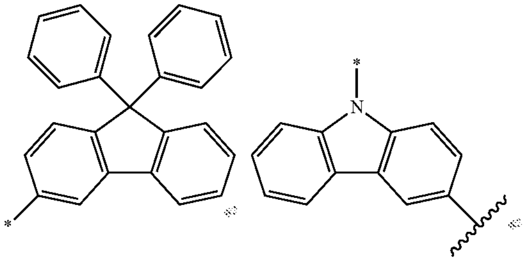
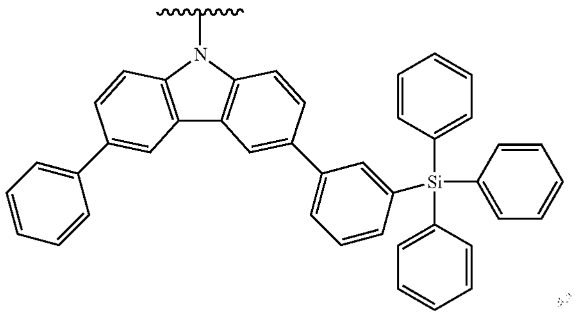

-continued
E23
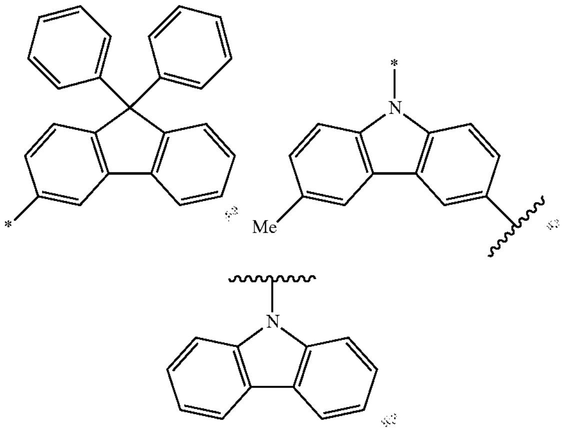
E24
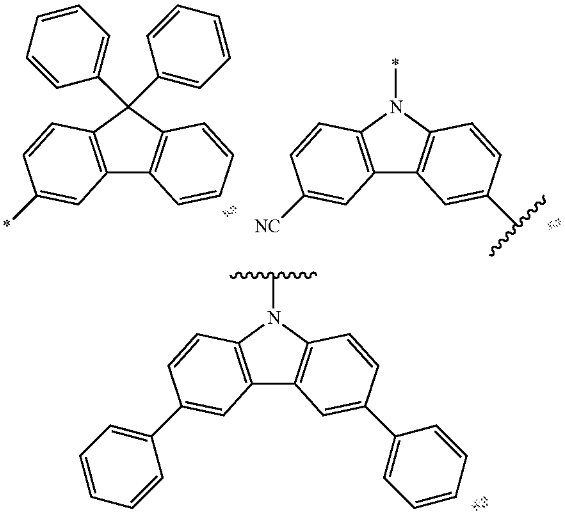
E25
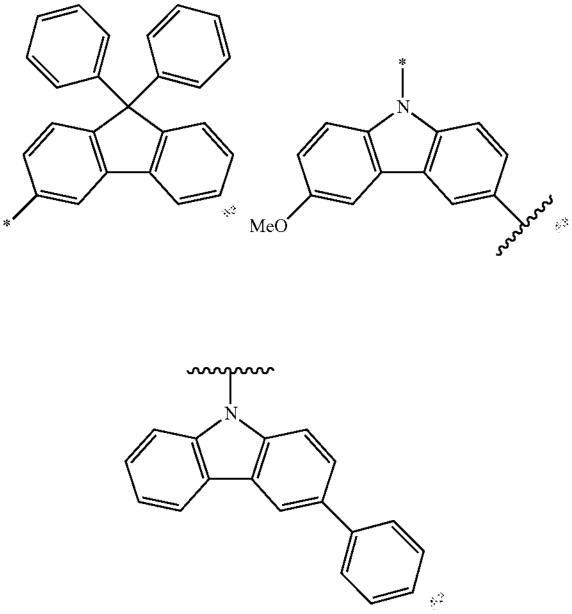
-continued
E26
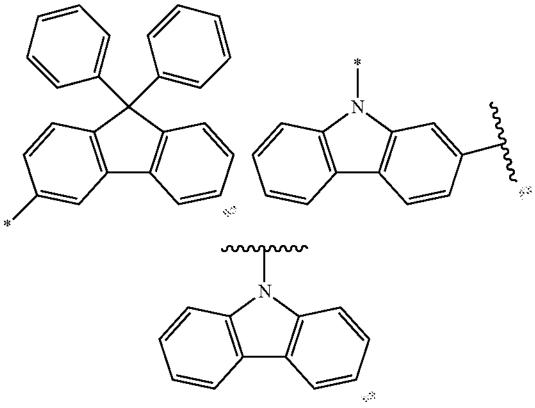
F1
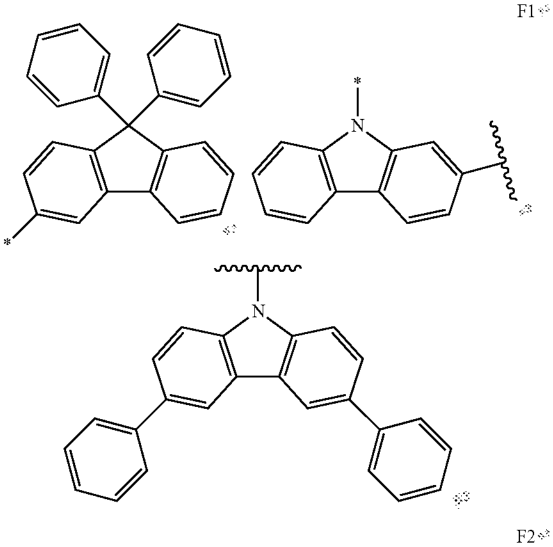
F2
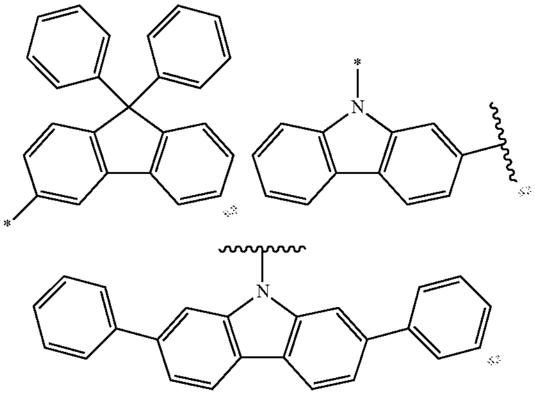
F3
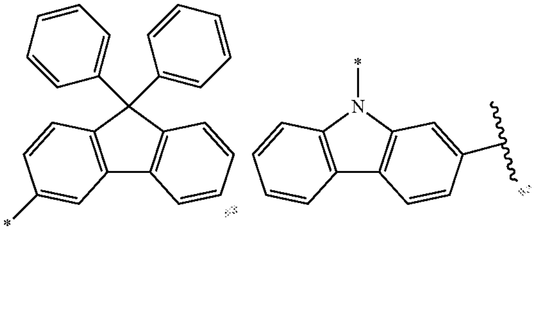

-continued
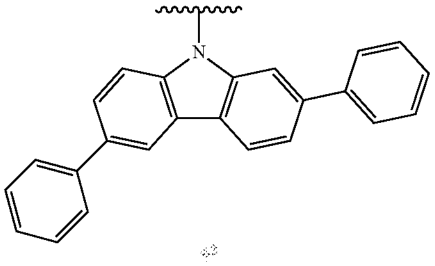
F4
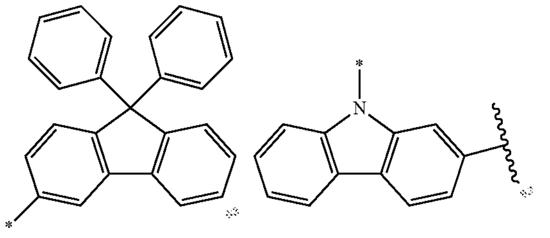
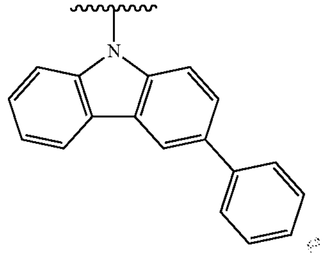
F5
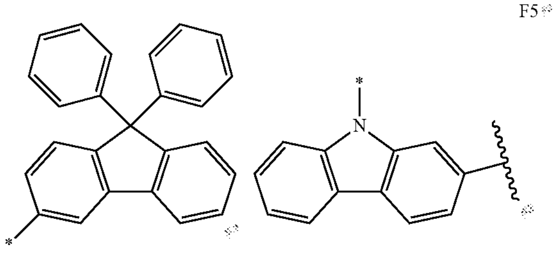
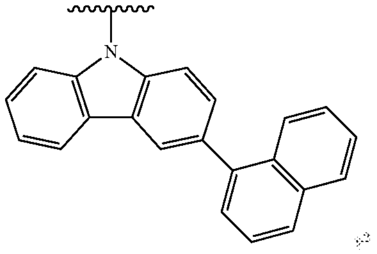
F6
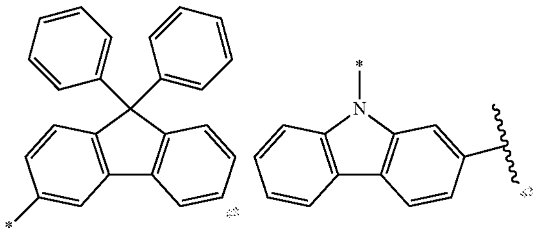
-continued
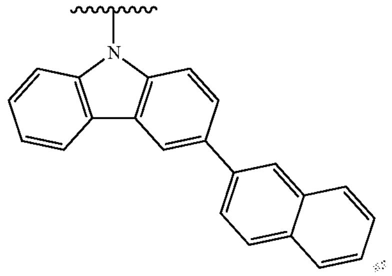
F7
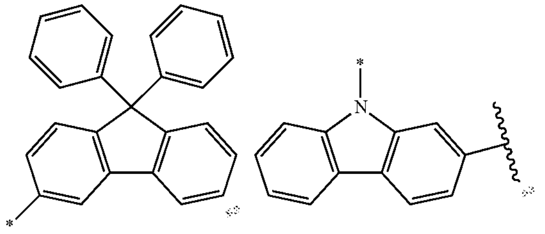
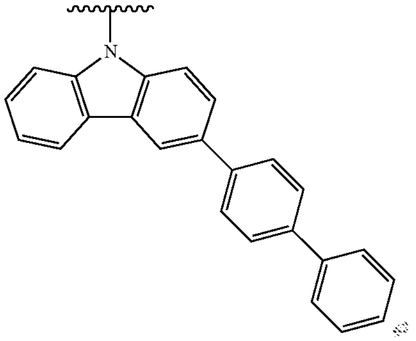
F8
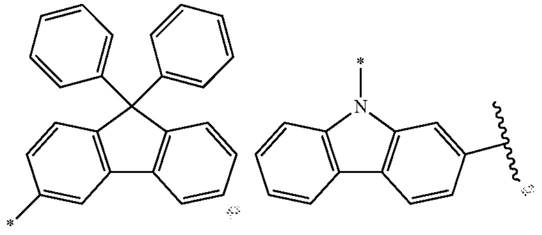
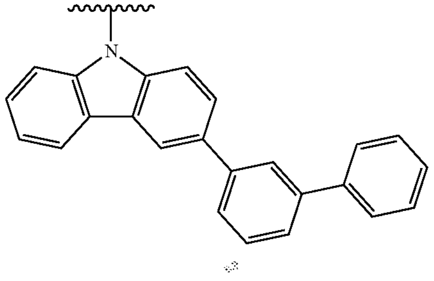
F9
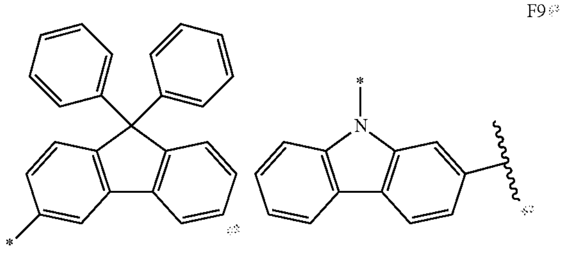

-continued
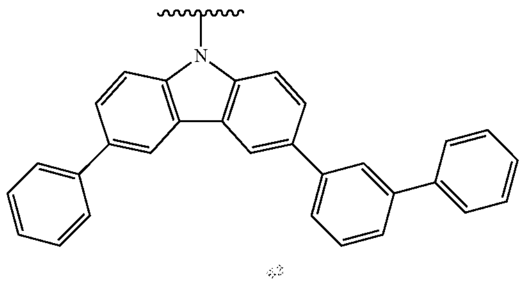
F10
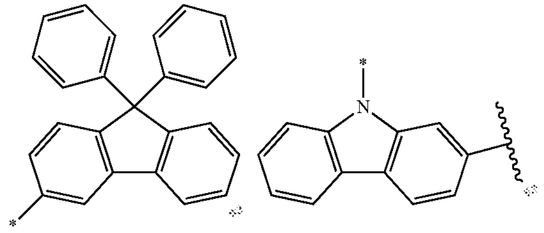
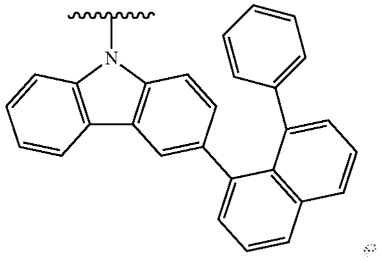
F11
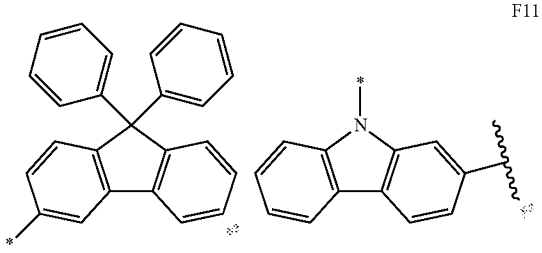
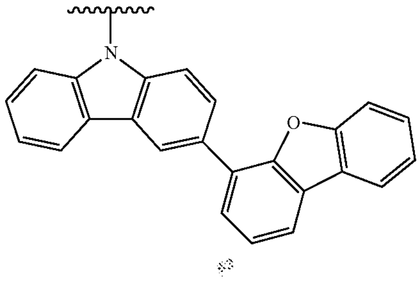
F12
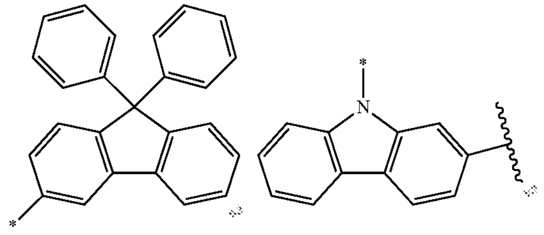
-continued
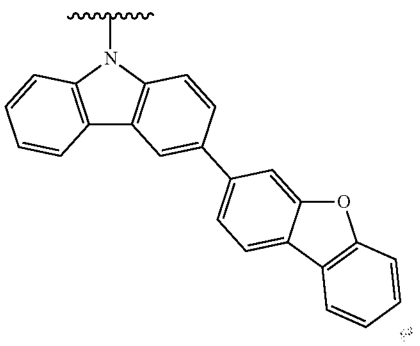
F13
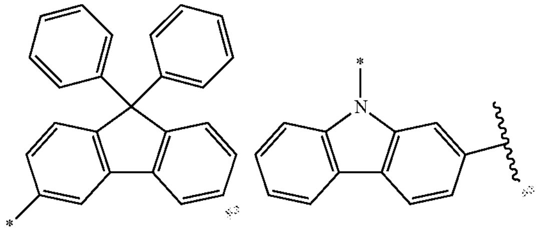
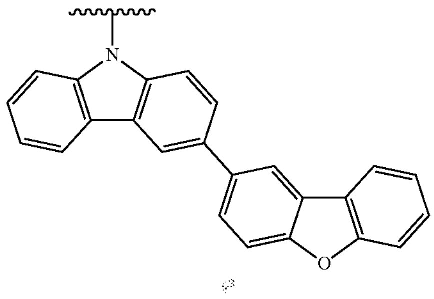
F14
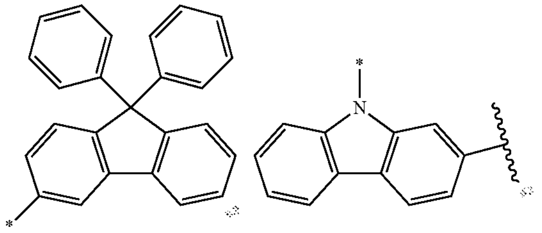
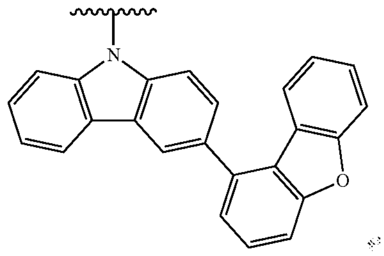
F15
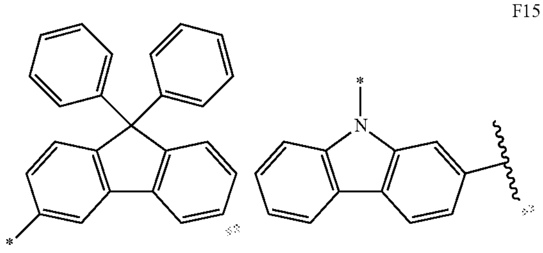

-continued
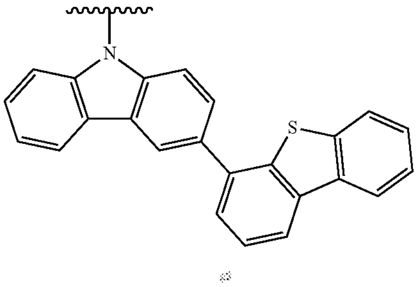
F16
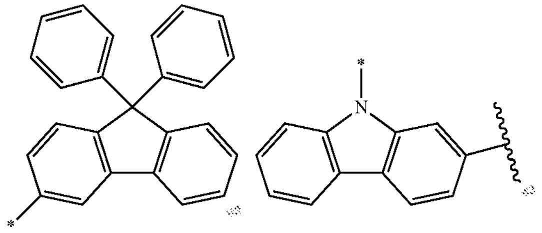
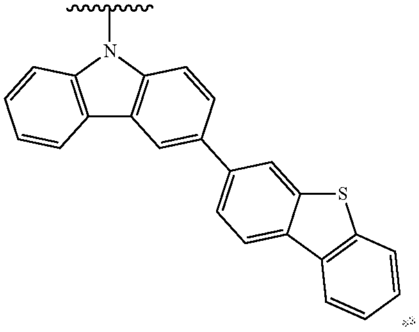
F17
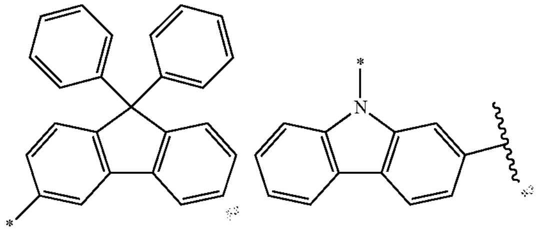
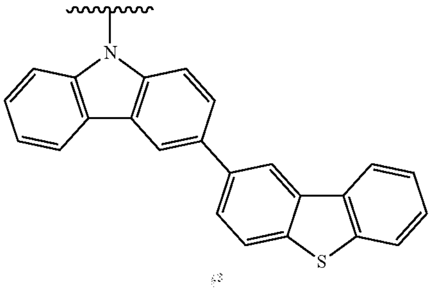
F18
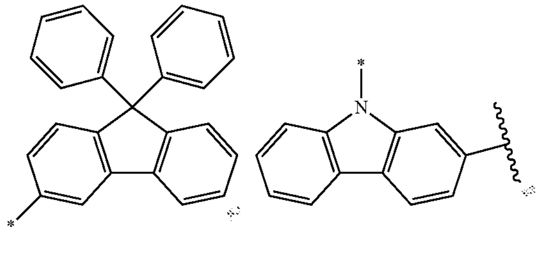
-continued
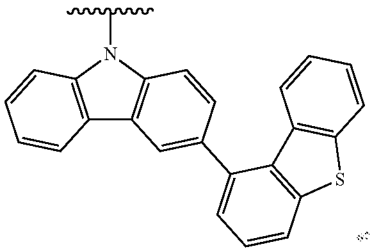
F19
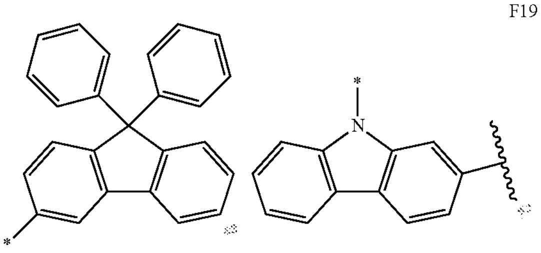
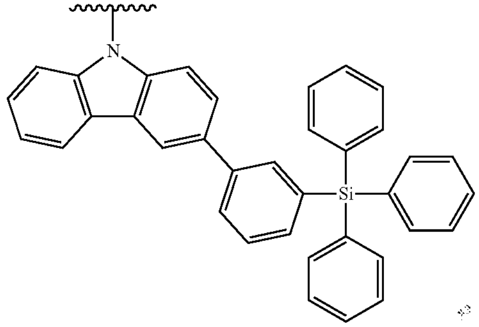
F20
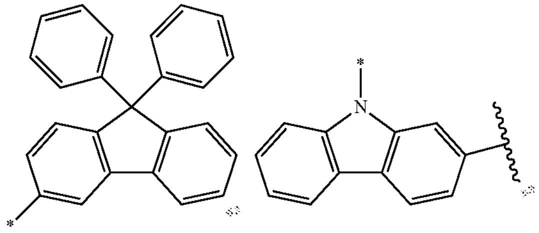
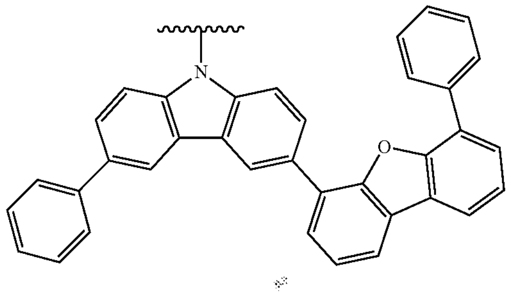
F21
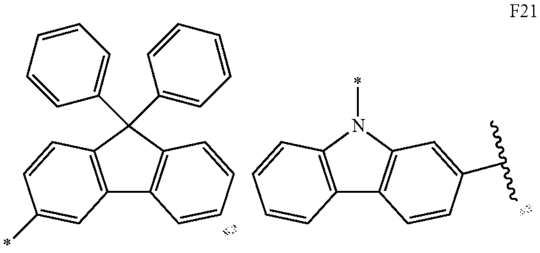

-continued
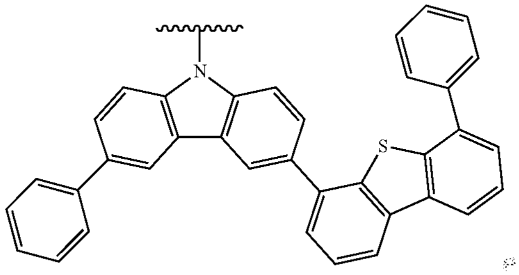
F22
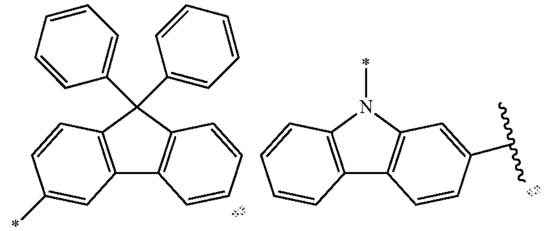
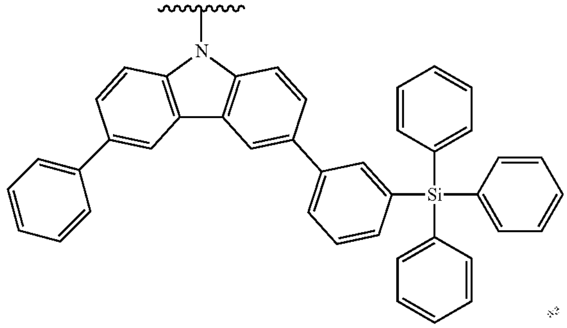
F23
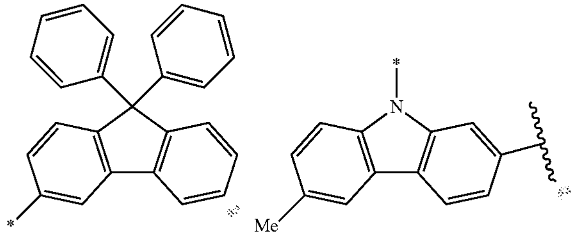
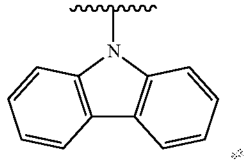
F24
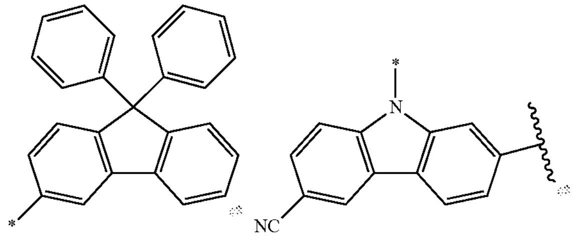
-continued
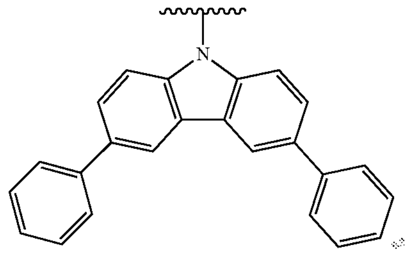
F25
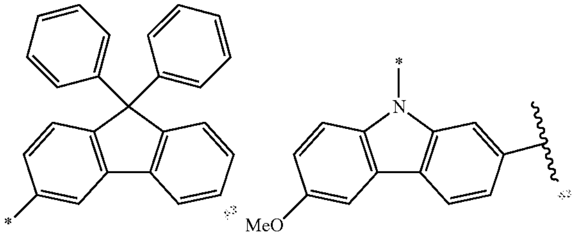
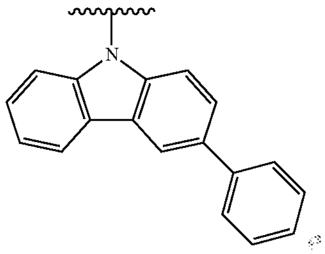
F26
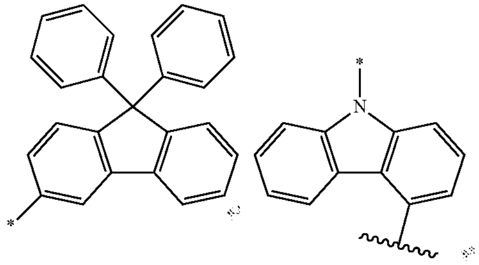
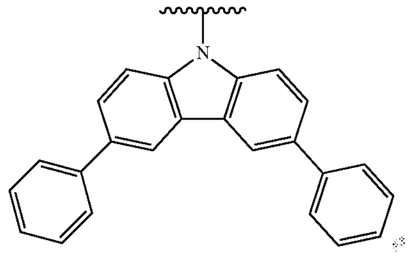
G1
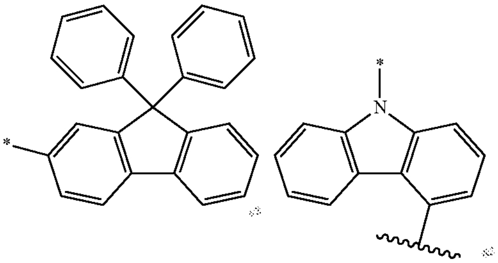

-continued
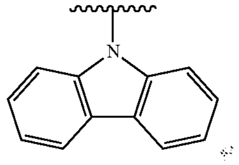
G2
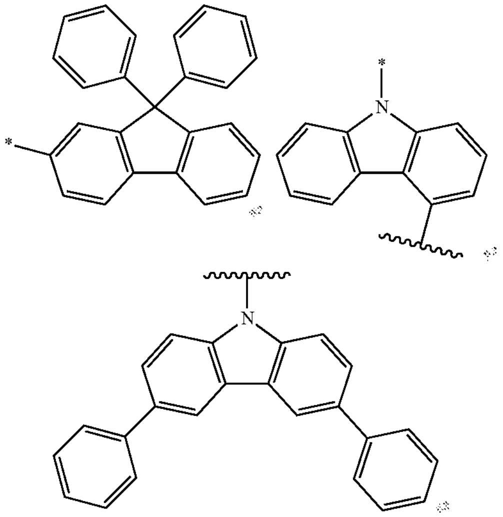
G3
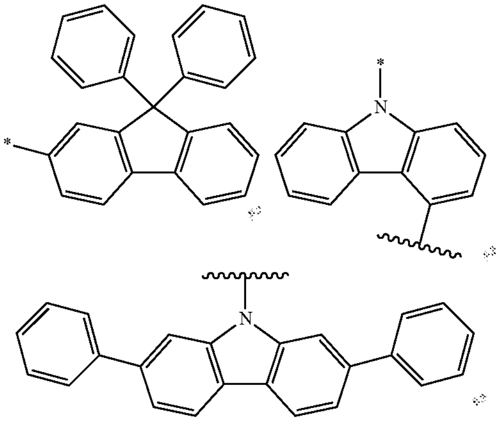
G4
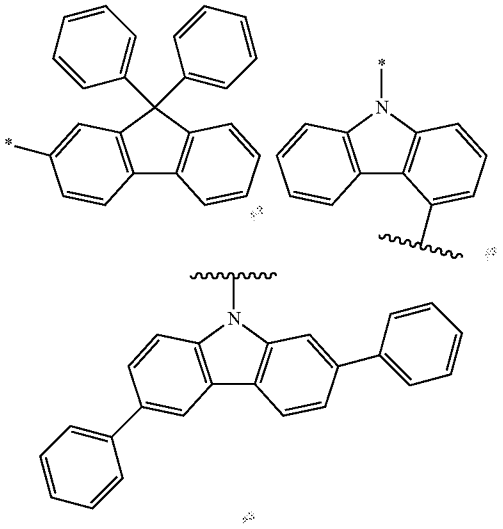
-continued
G5
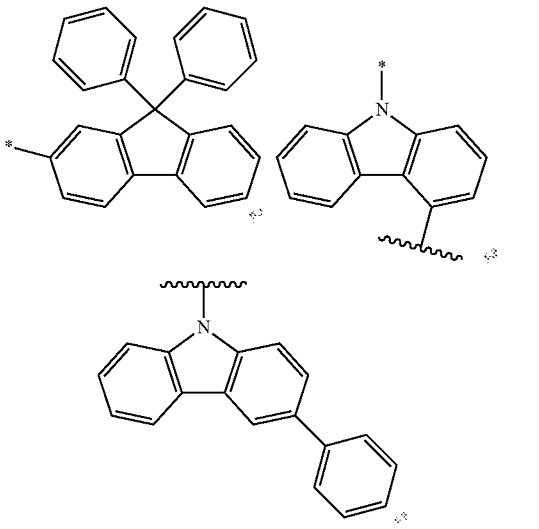
G6
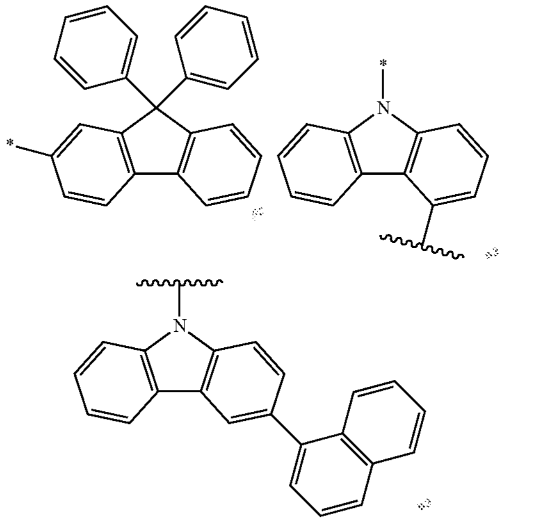
G7
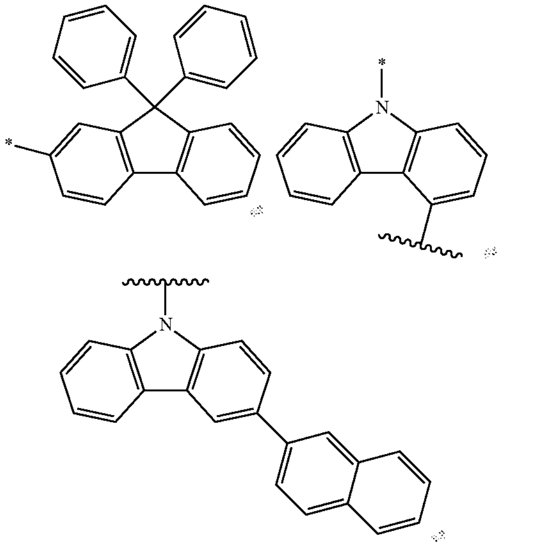

-continued
G8
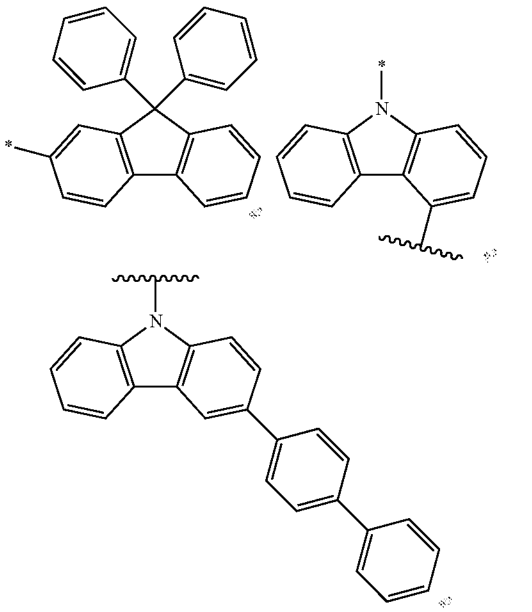
G9
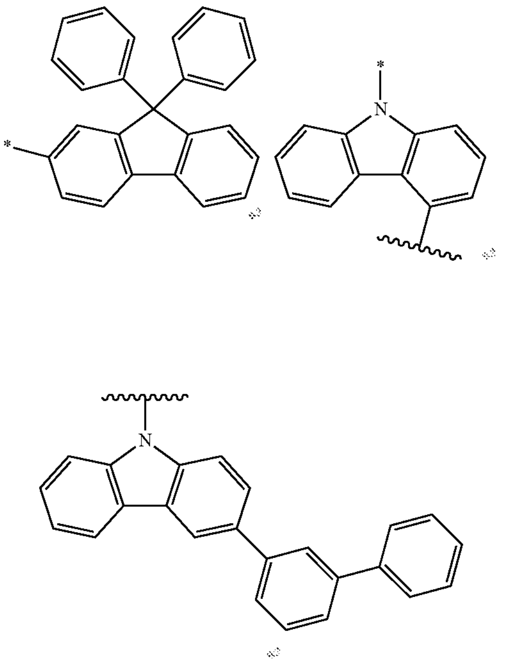
G10
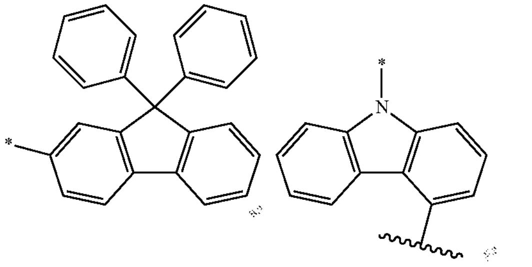
-continued
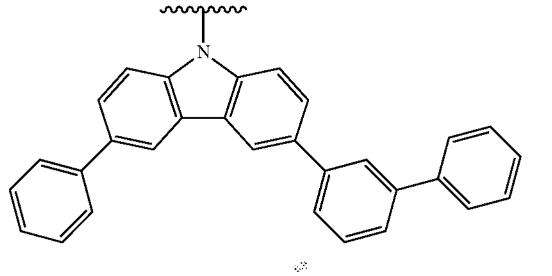
G11
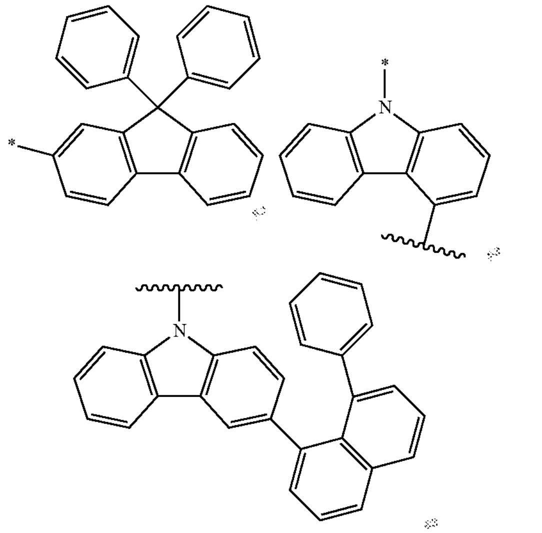
G12
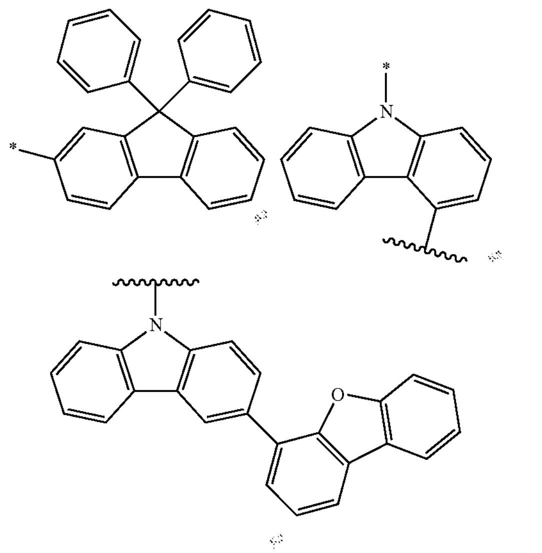
G13
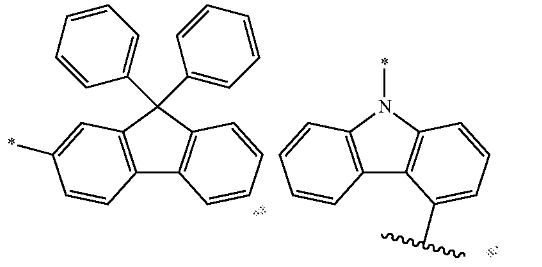

-continued
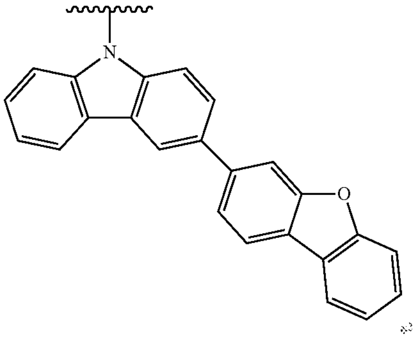
G14
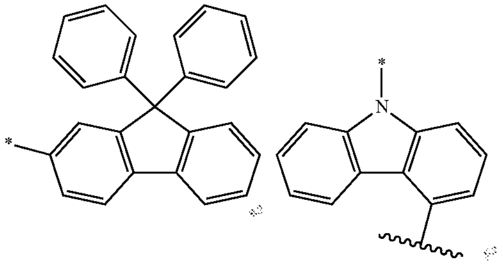
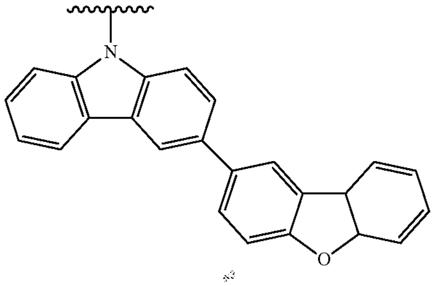
G15
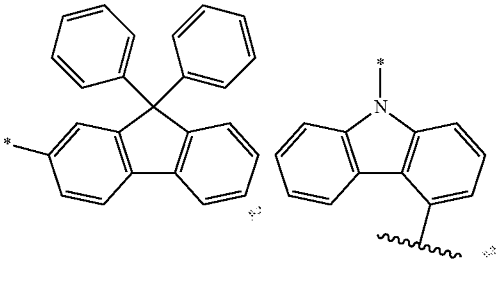
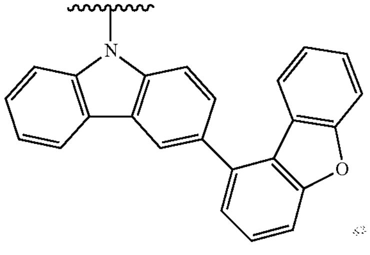
-continued
G16
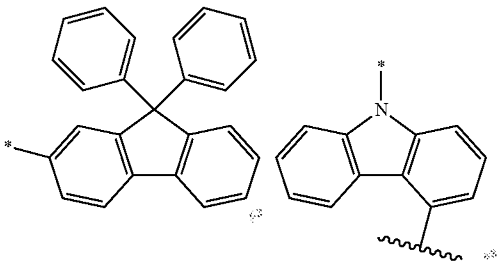
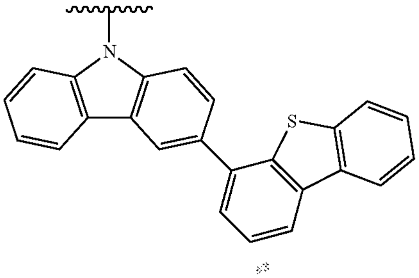
G17
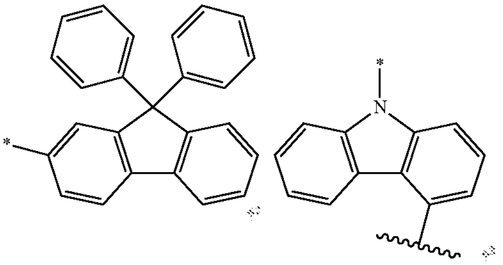
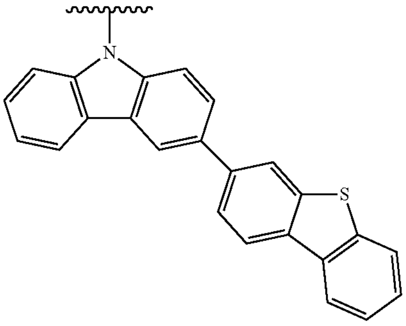
G18
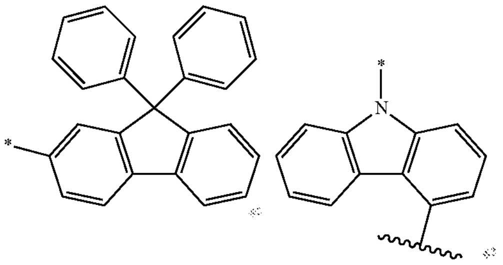

-continued
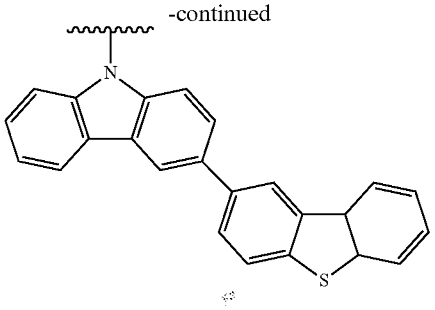
G19
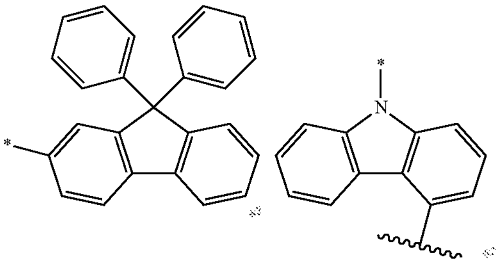
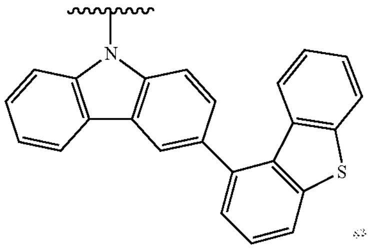
G20
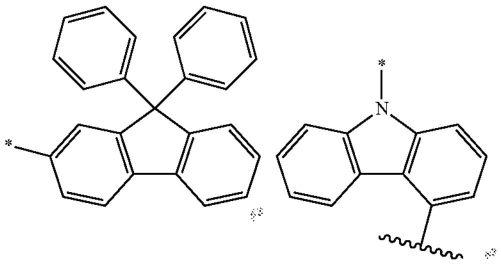
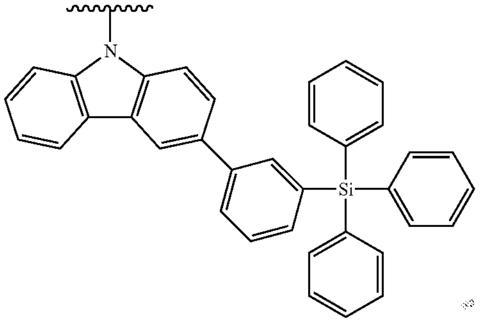
G21
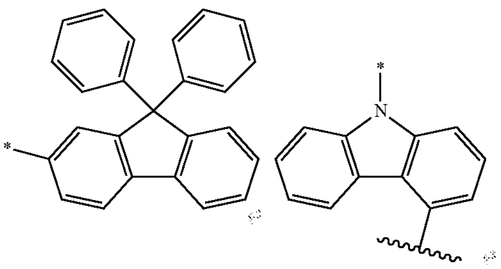
-continued
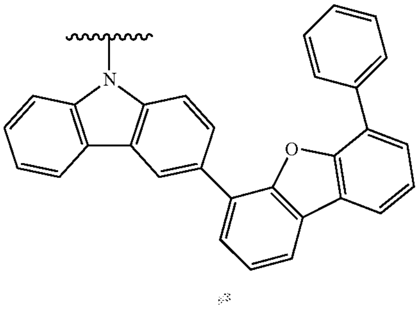
G22
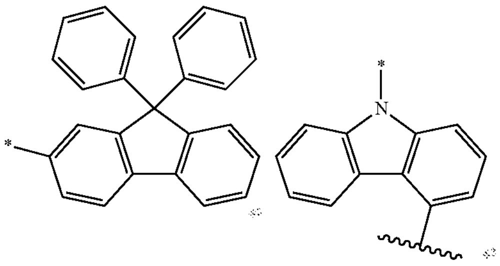
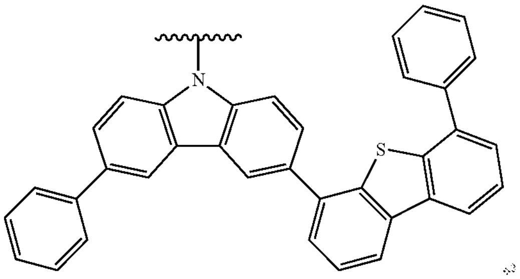
G23
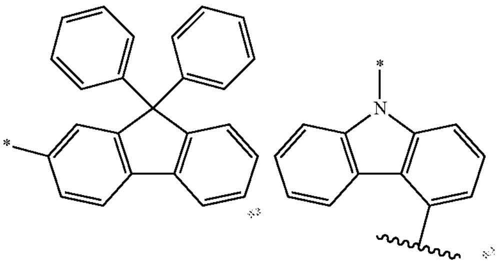
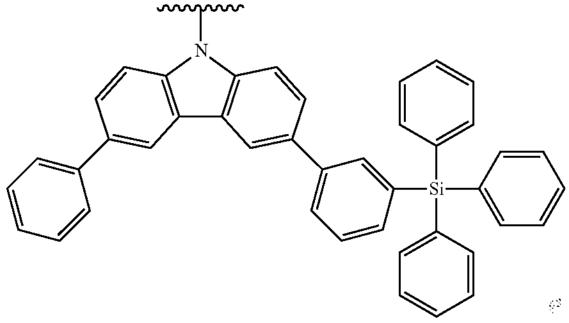

-continued
G24
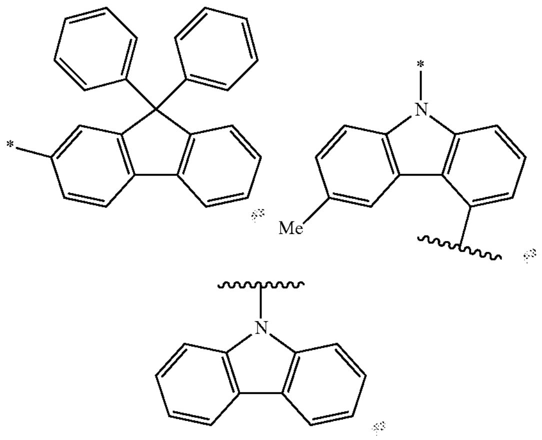
G25
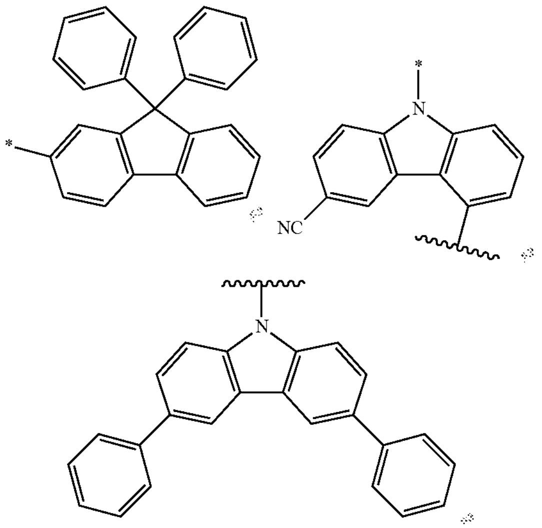
G26
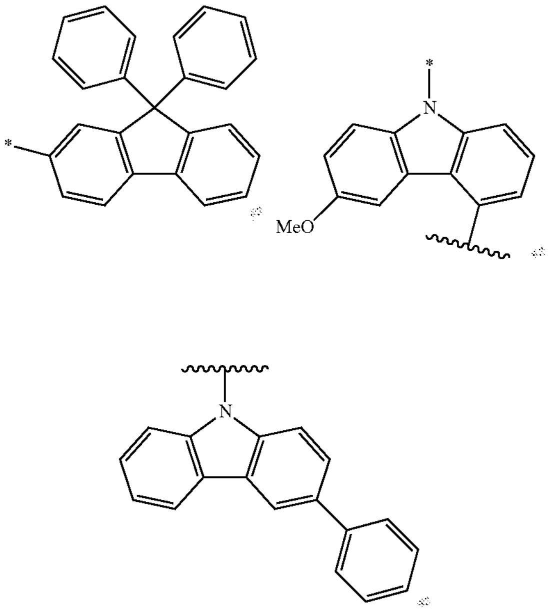
-continued
H1
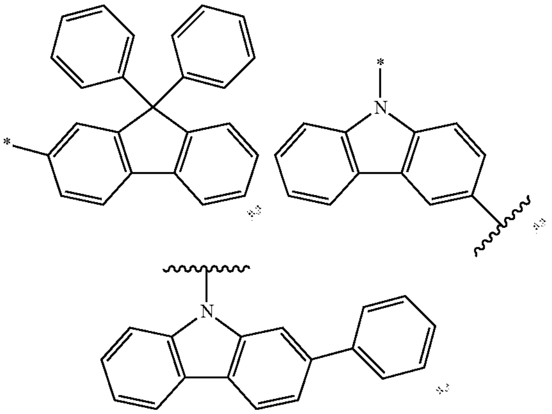
H2
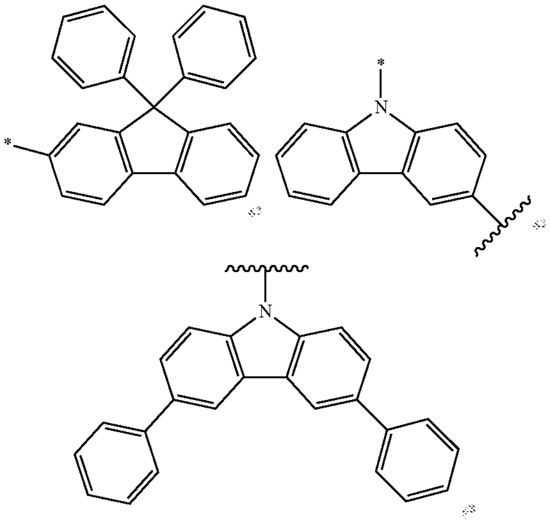
H3
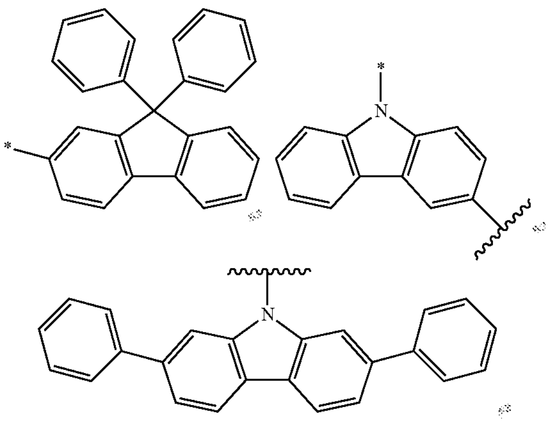
H4
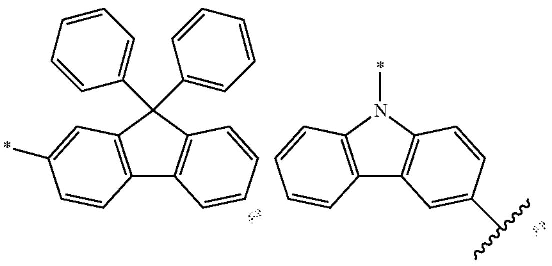

-continued
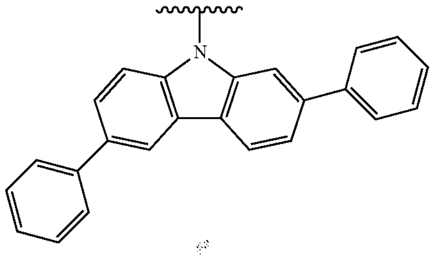
H5
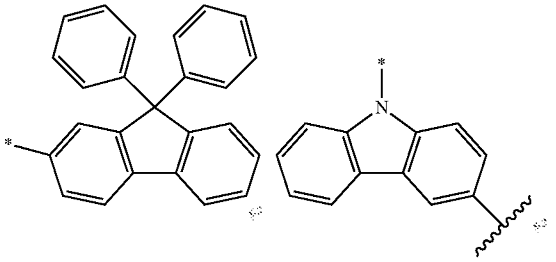
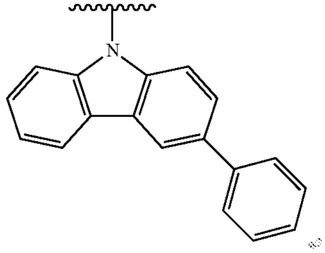
H6
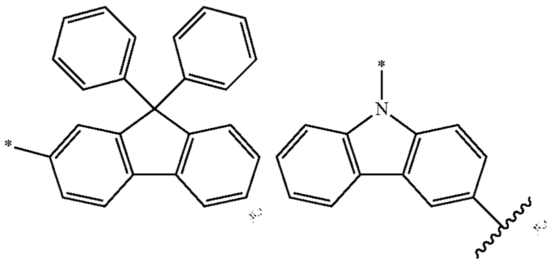
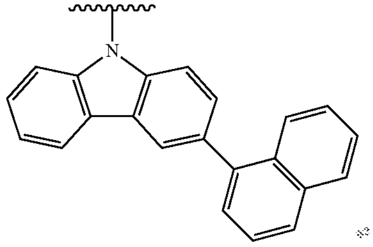
H7
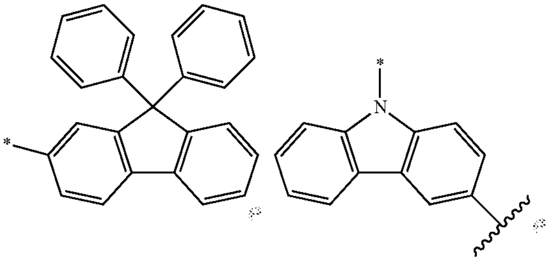
-continued
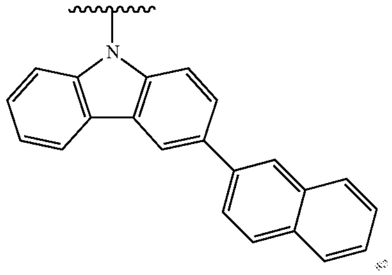
H8
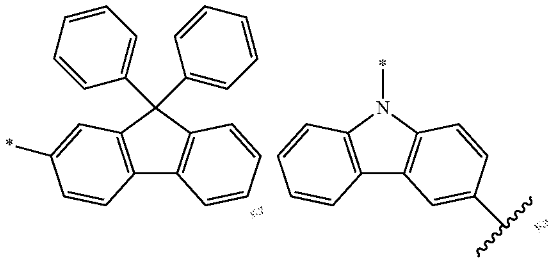
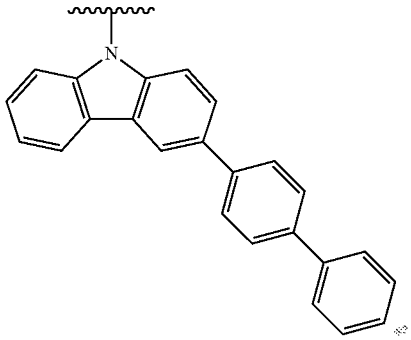
H9
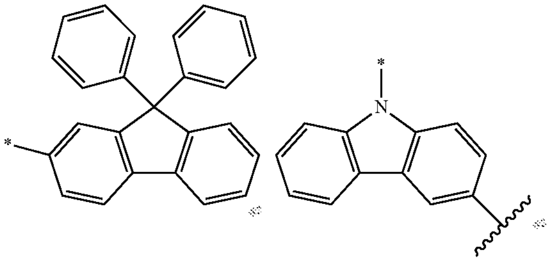
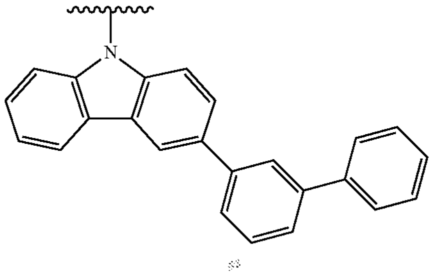

H10
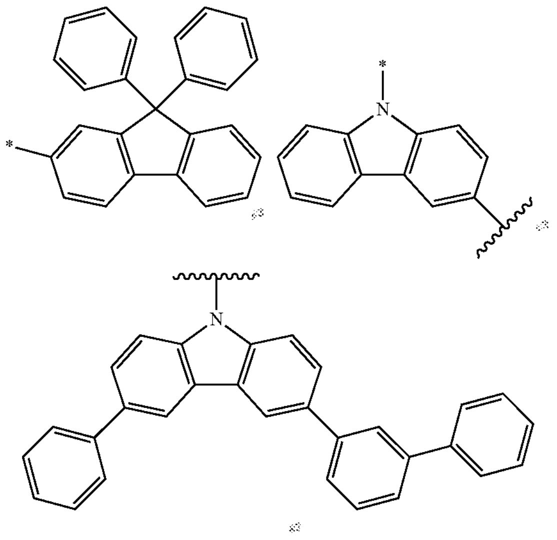
H11
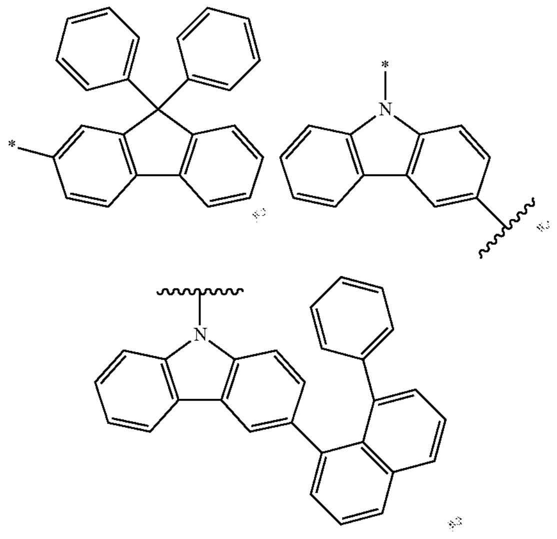
H12
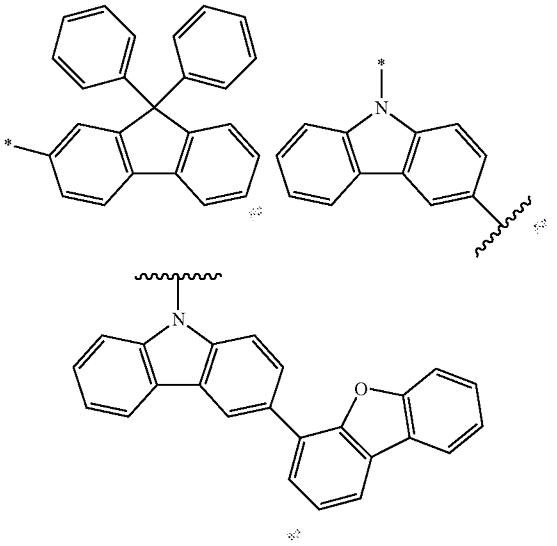
H13
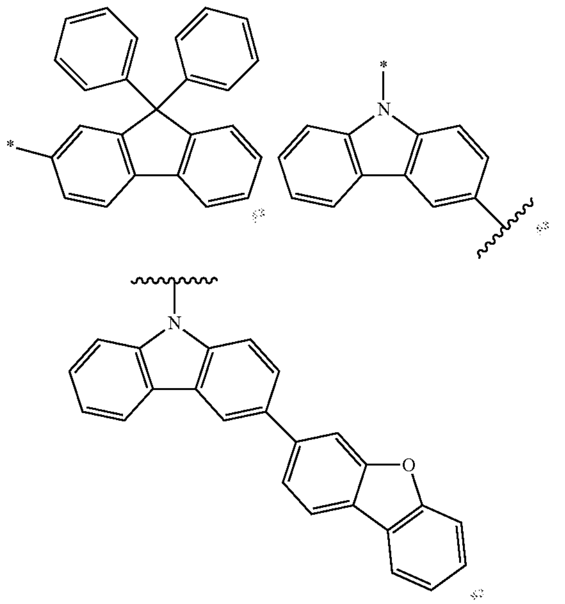
H14
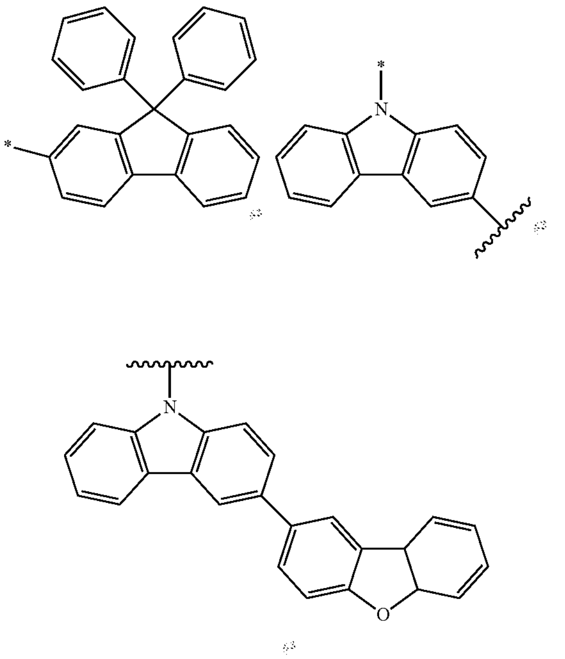
H15
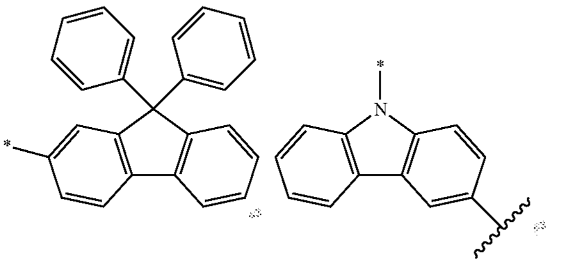

-continued
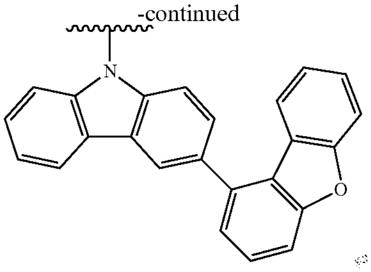
H16
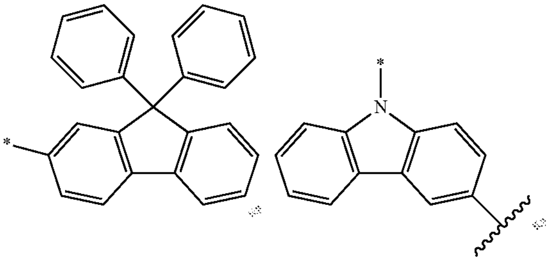
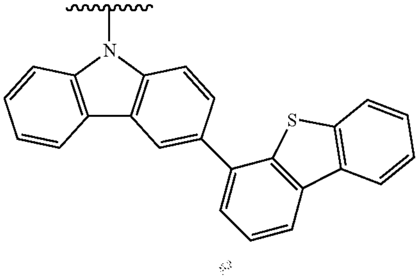
H17
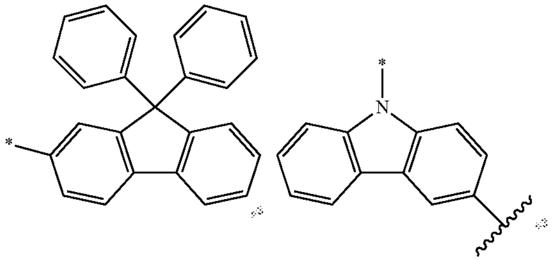
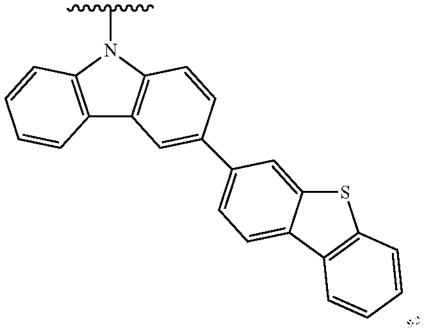
H18
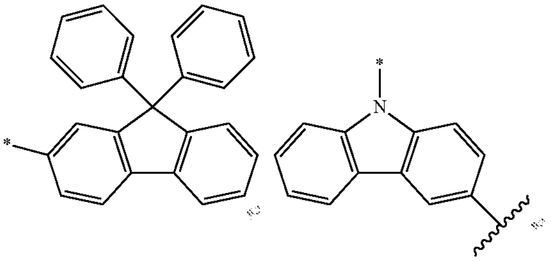
-continued
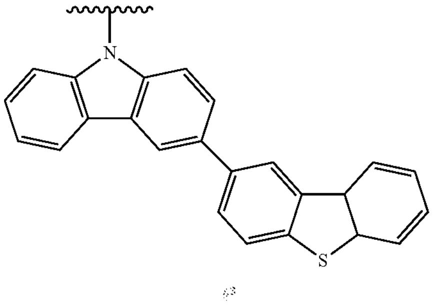
H19
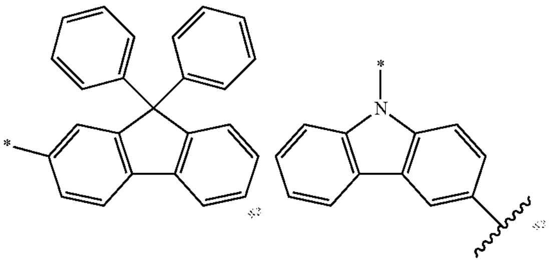
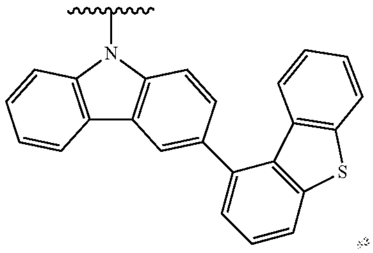
H20
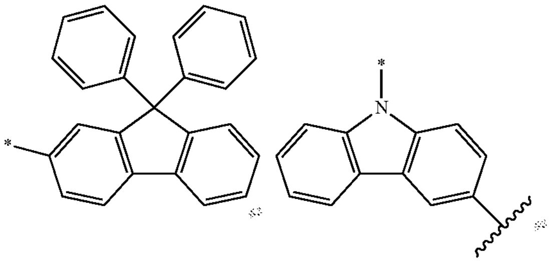
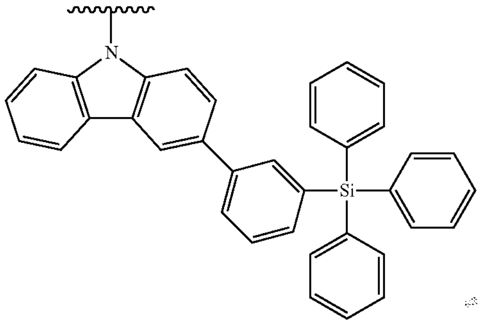

-continued
H21
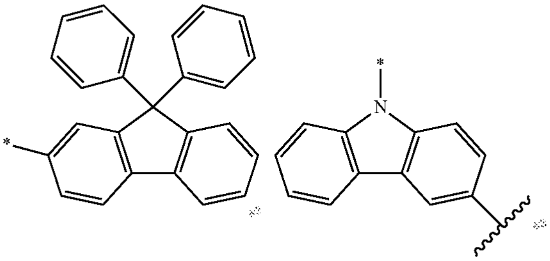
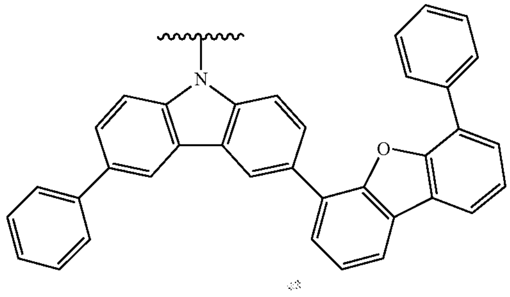
H22
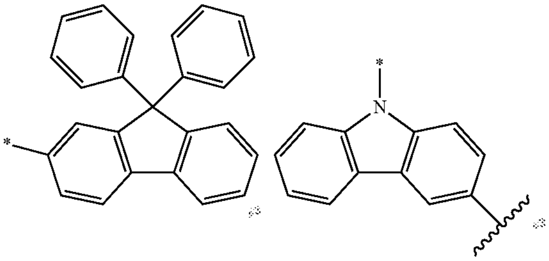
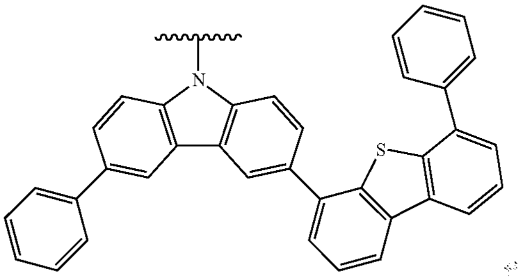
H23
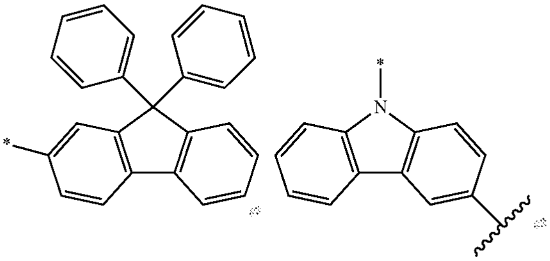
-continued
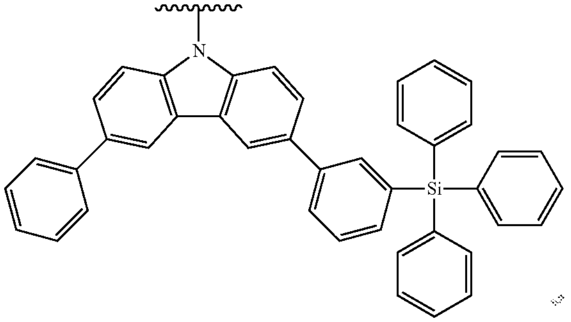
H24
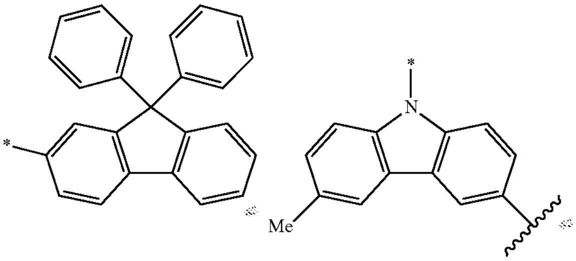
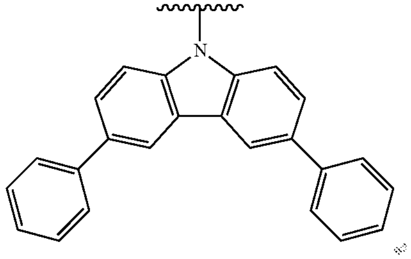
H25
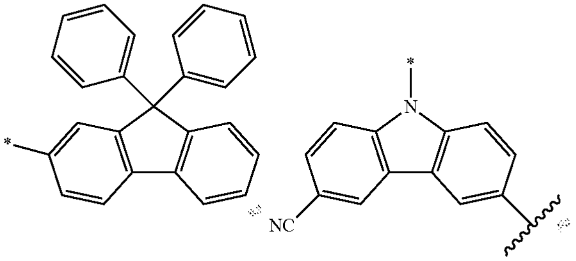
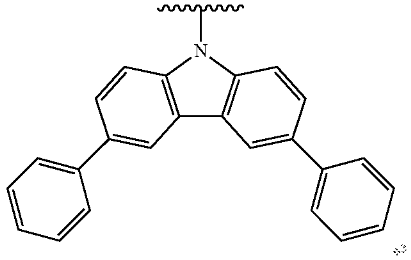
H26
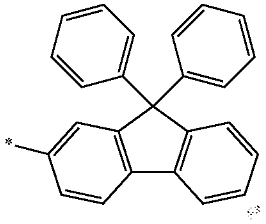

-continued
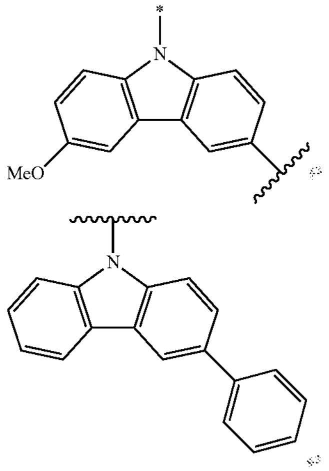
H27
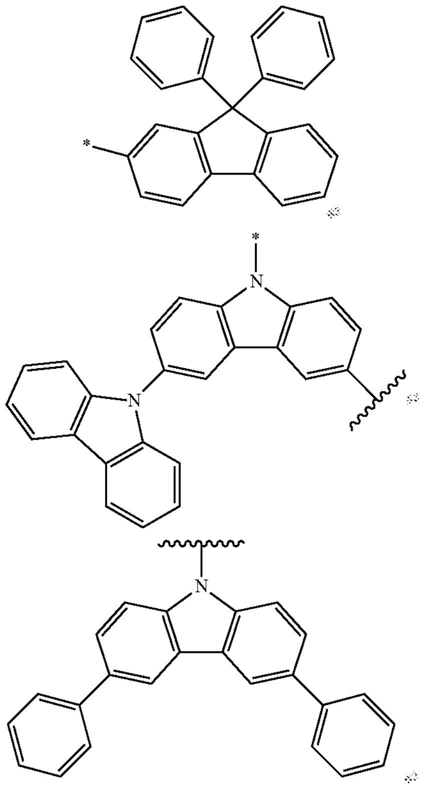
I1
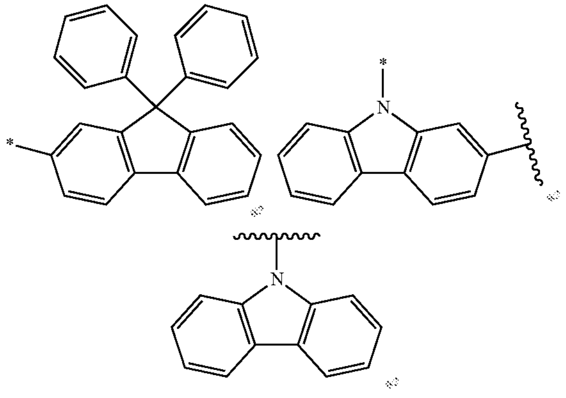
-continued
I2
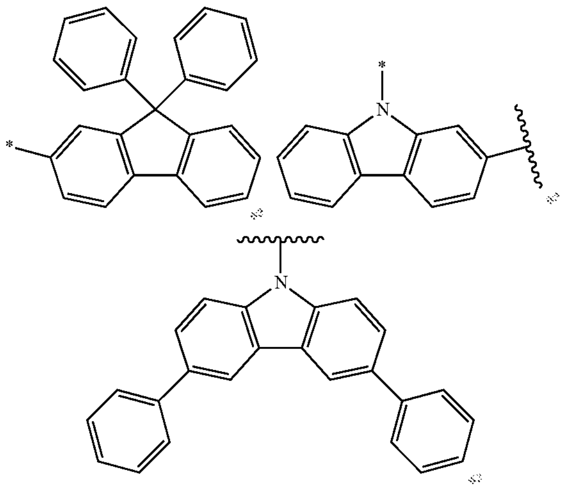
I3
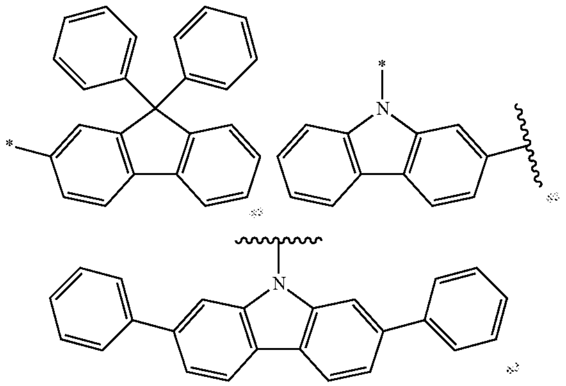
I4
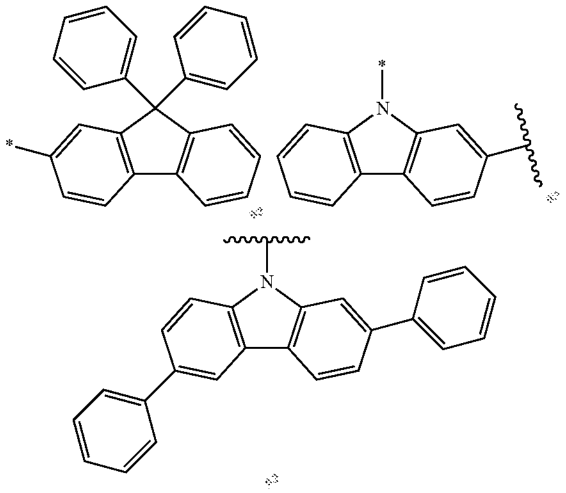
I5
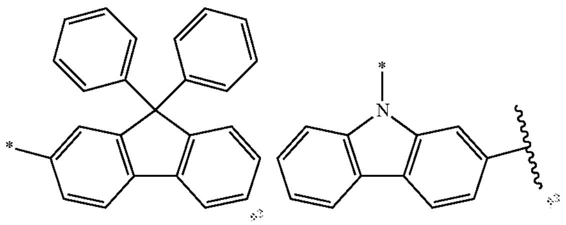

-continued
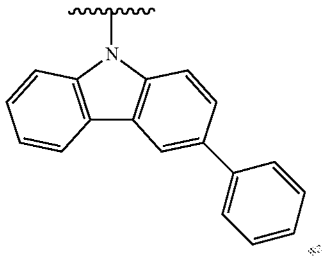
I6
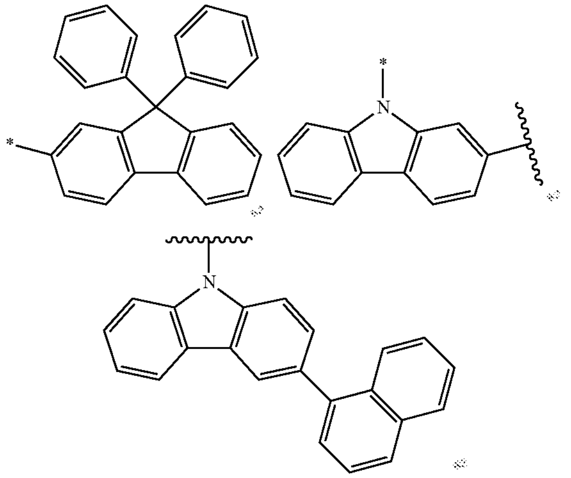
I7
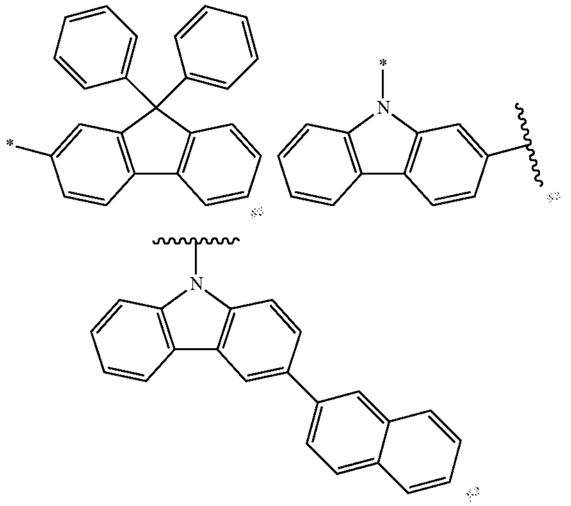
I8
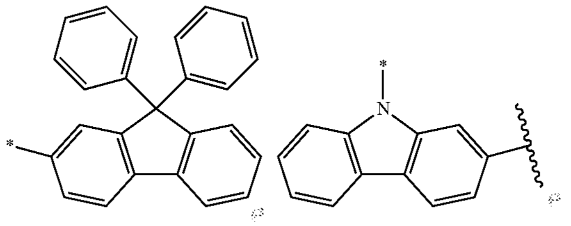
-continued
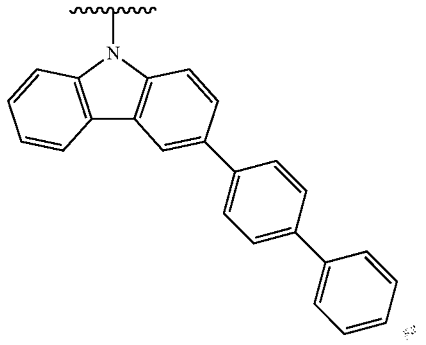
I9
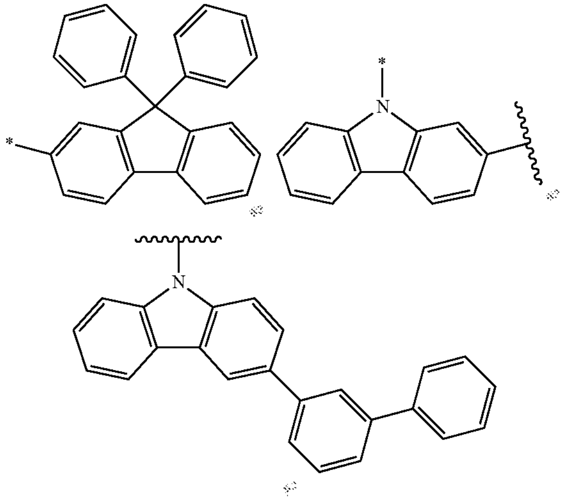
I10
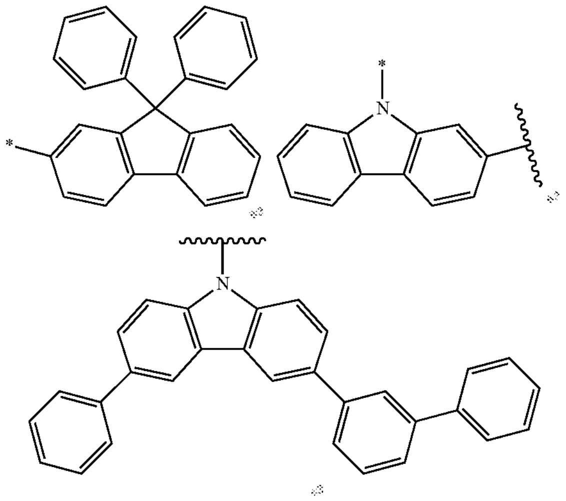
I11
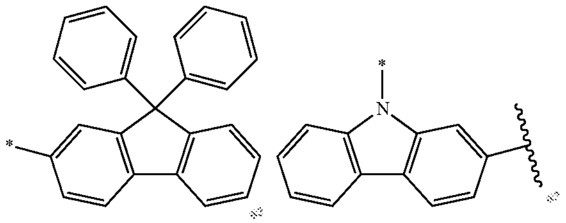

-continued
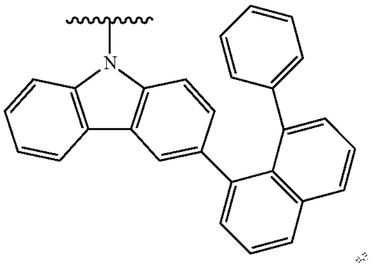
I12
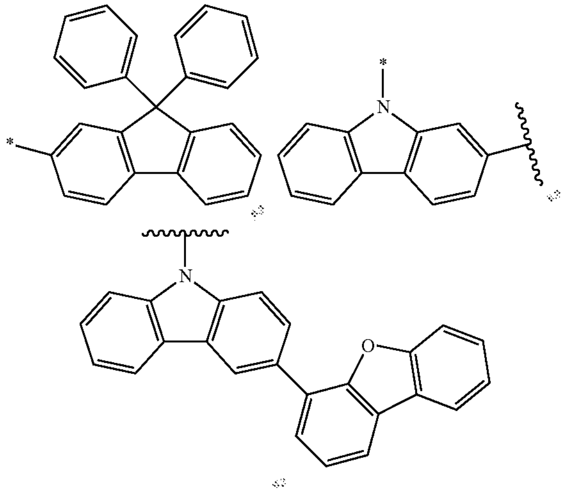
I13
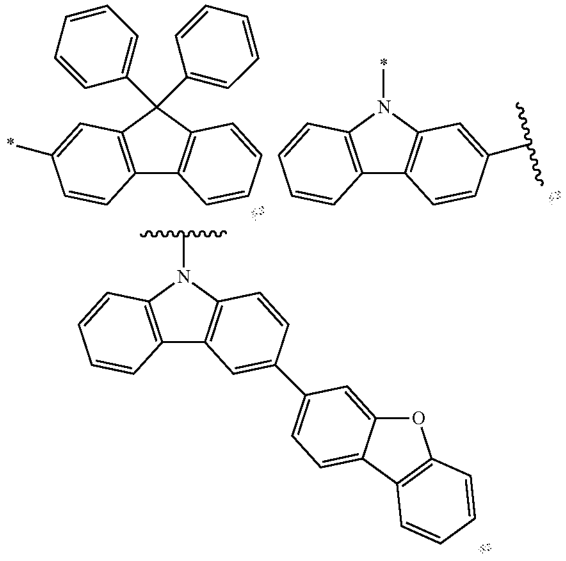
I14
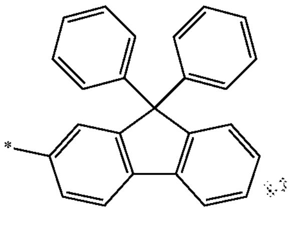
-continued
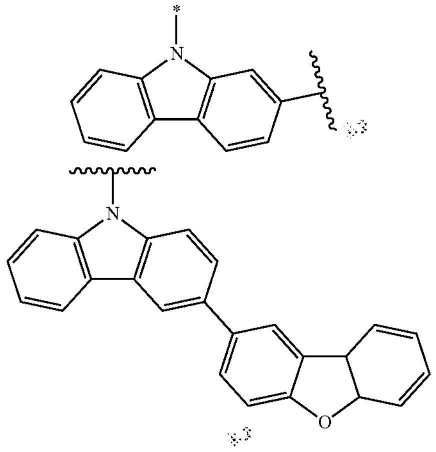
I15
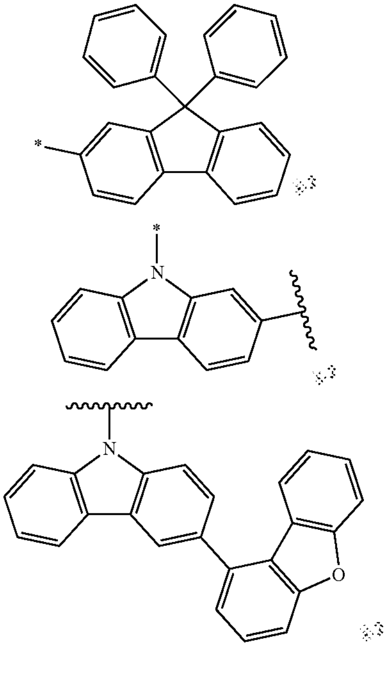
I16
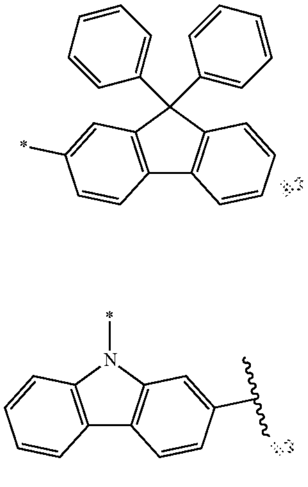

-continued
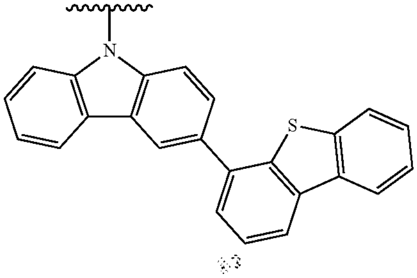
I17
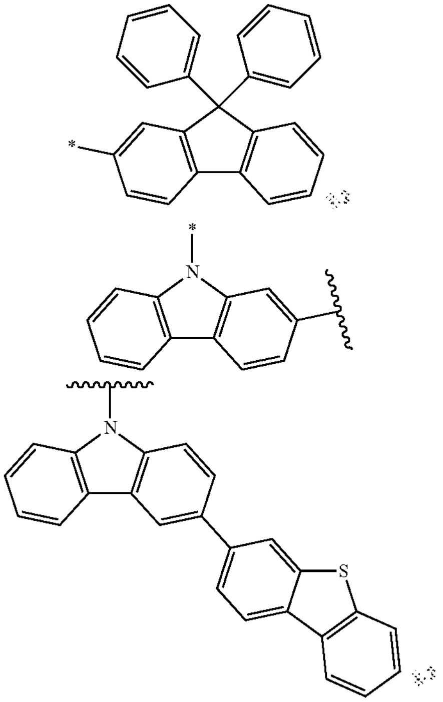
I18
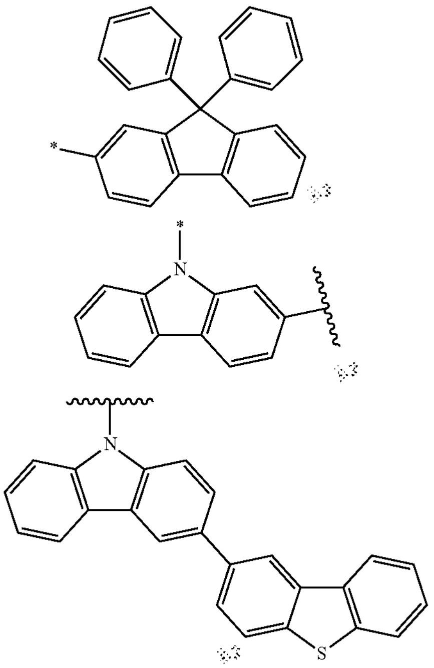
-continued
I19
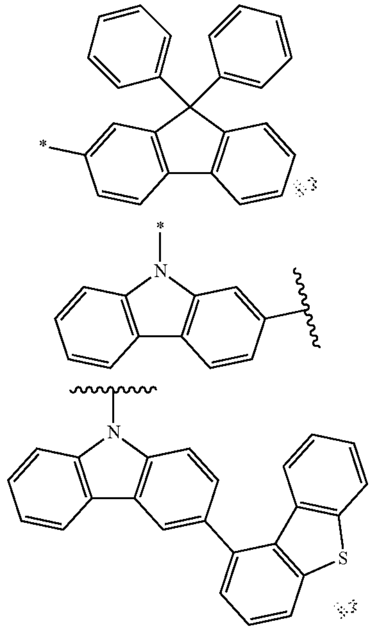
I20
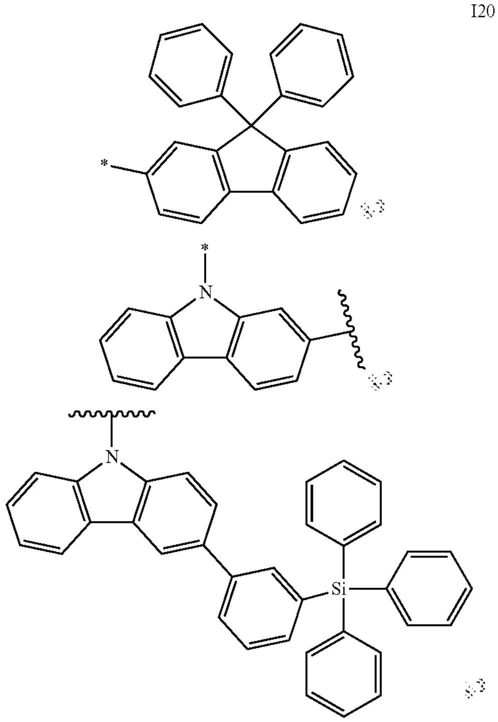
I21
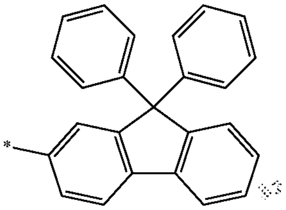

-continued
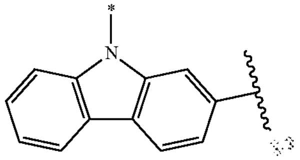
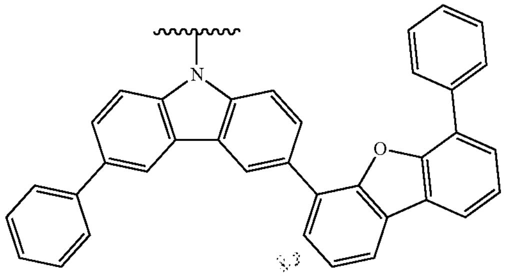
I22
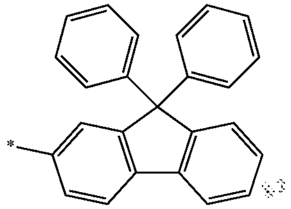
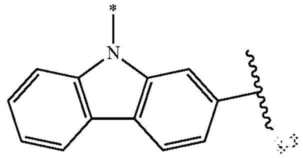
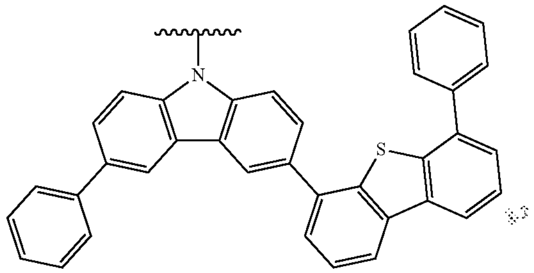
I23
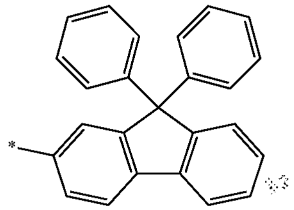
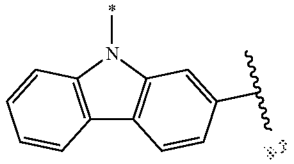
-continued
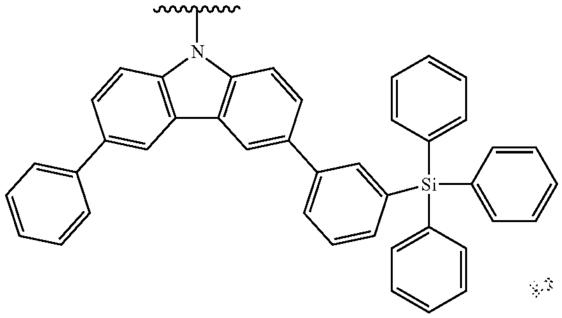
I24
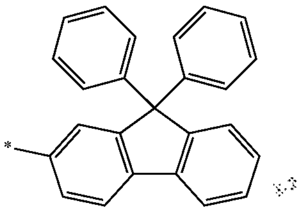
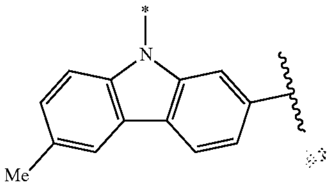
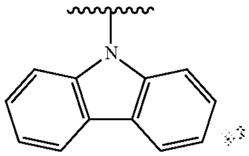
I25
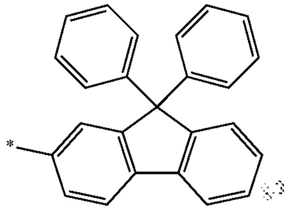
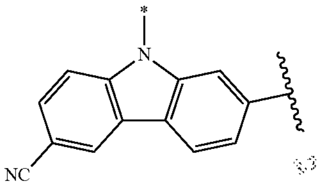
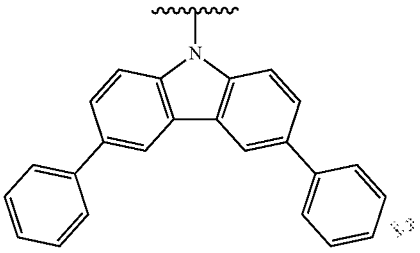

-continued
I26
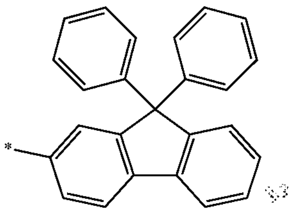
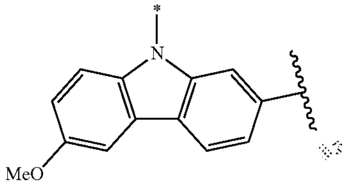
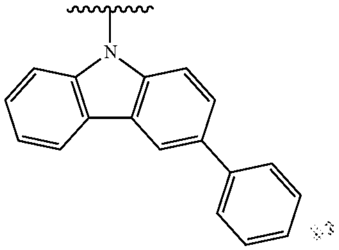
J1
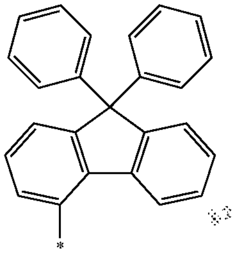
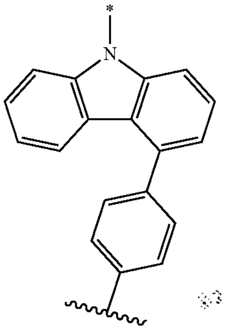
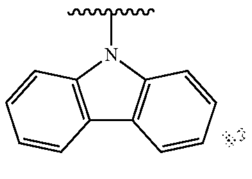
-continued
J2
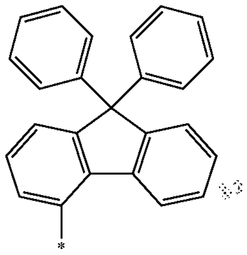
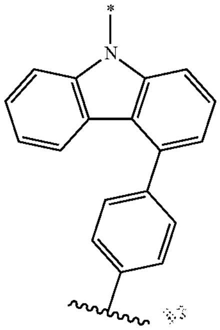
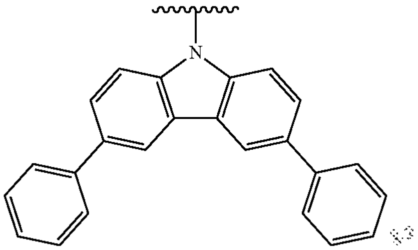
J3
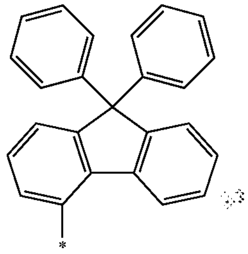
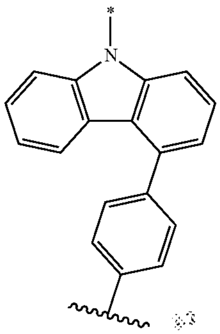
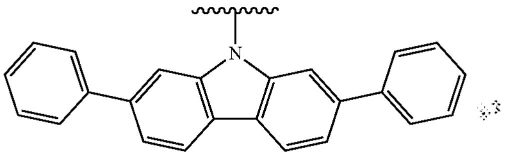

J4
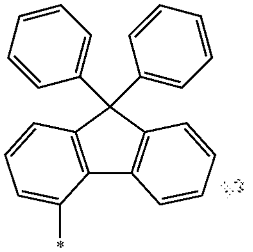
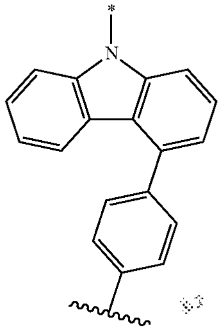
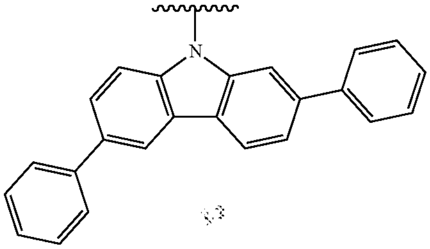
J5
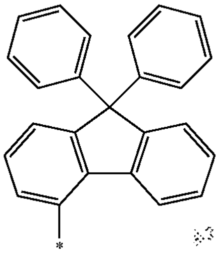
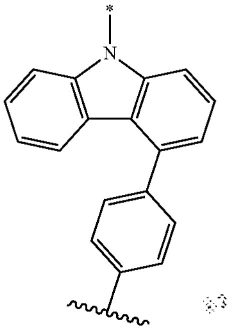
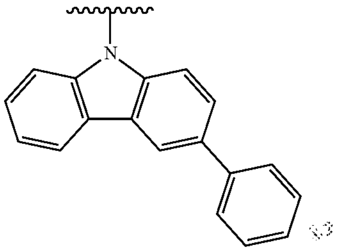
J6
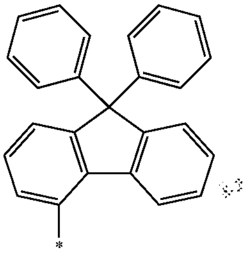
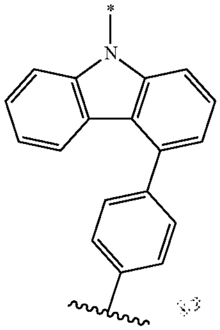
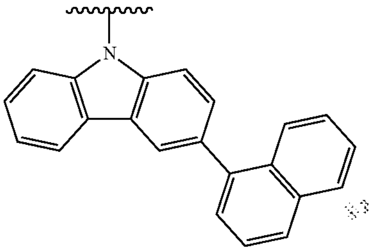
J6
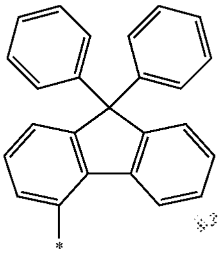

-continued
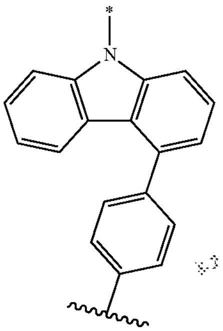
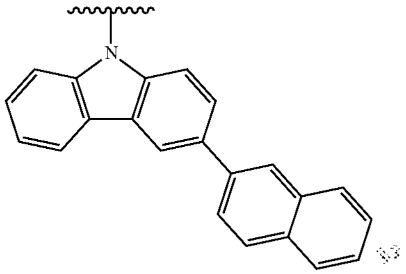
J8
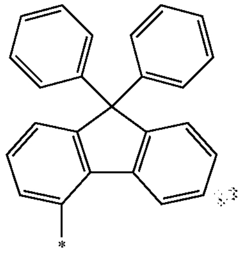
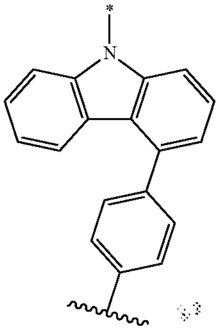
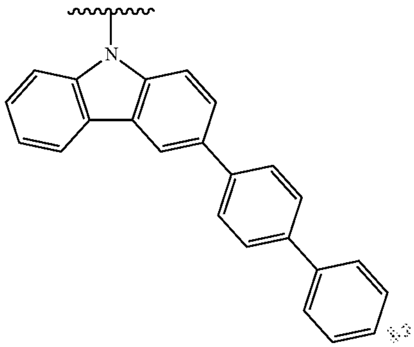
-continued
J9
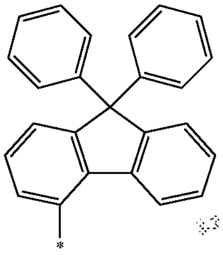
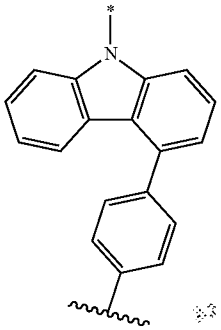
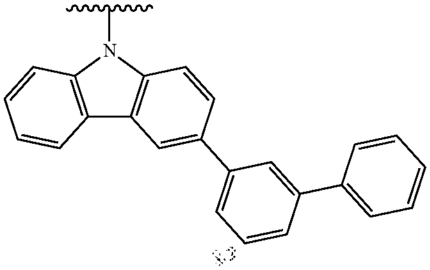
J10
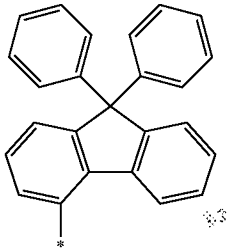
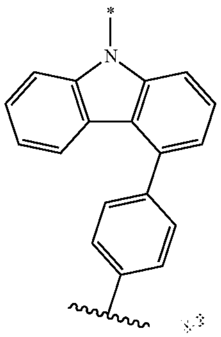

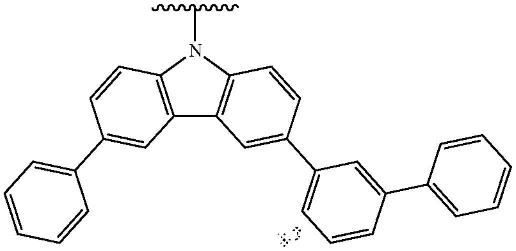
J11
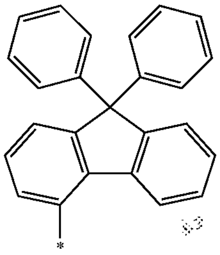
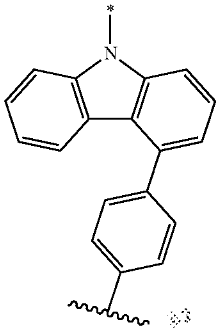
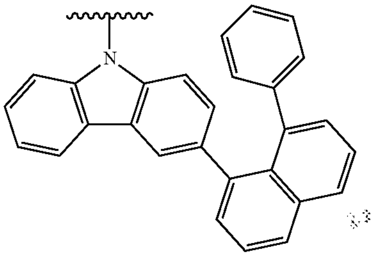
J12
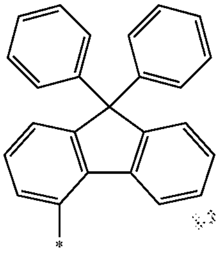
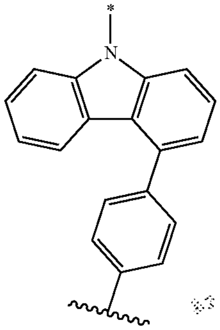
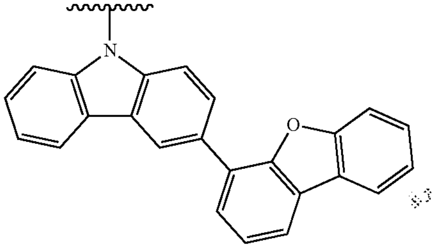
J13
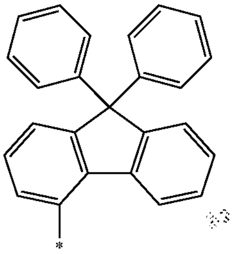
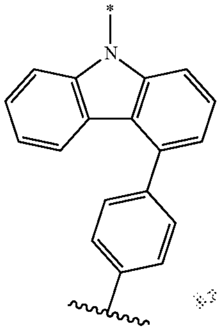
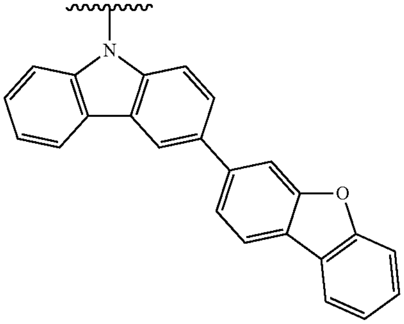

-continued
J14
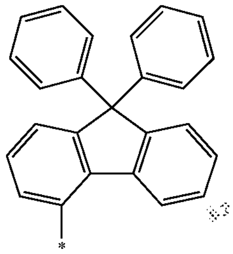
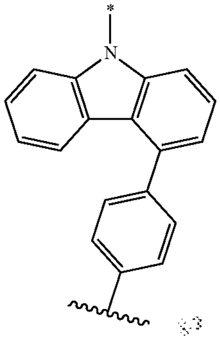
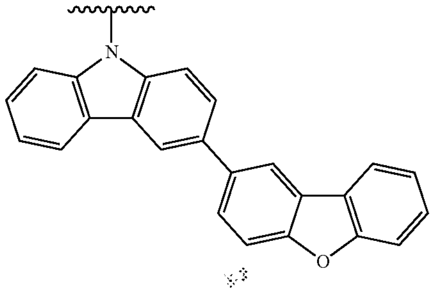
J15
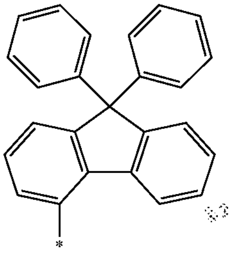
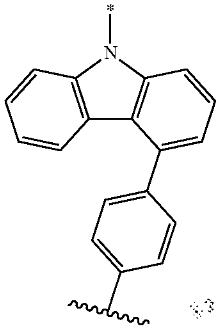
-continued
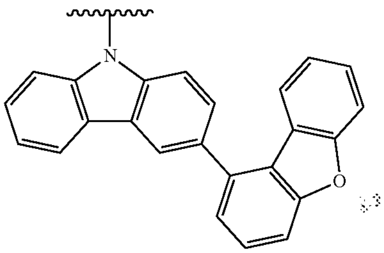
J16
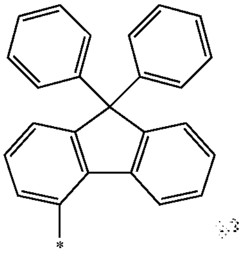
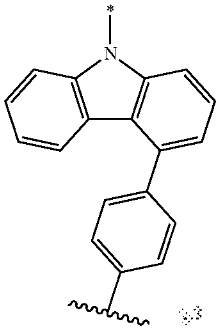
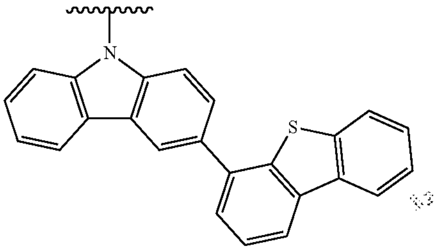
J17
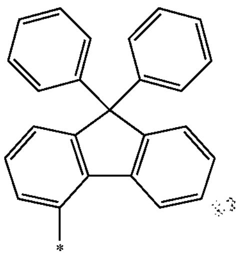

-continued
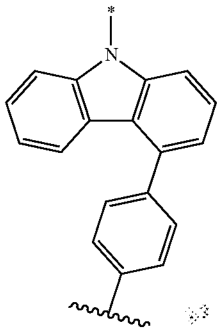
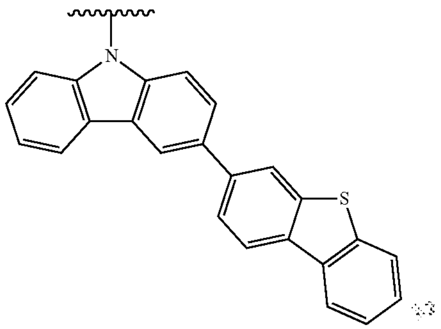
J18
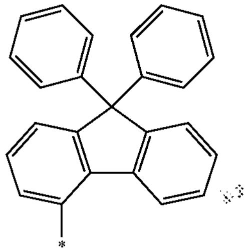
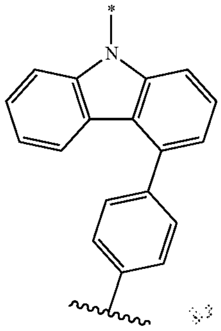
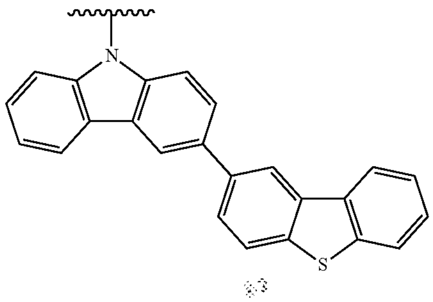
-continued
J19
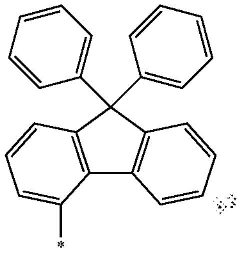
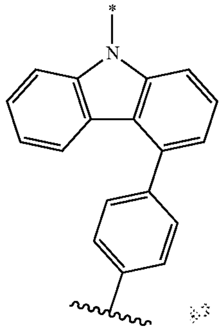
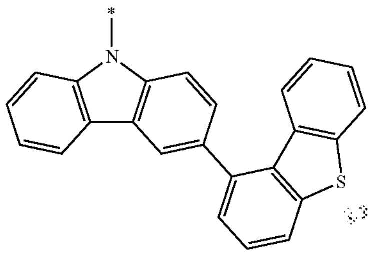
J20
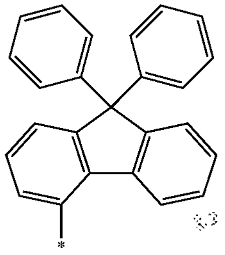
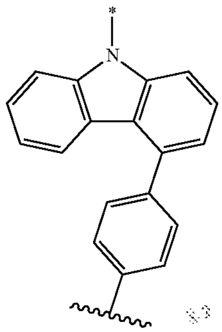

-continued
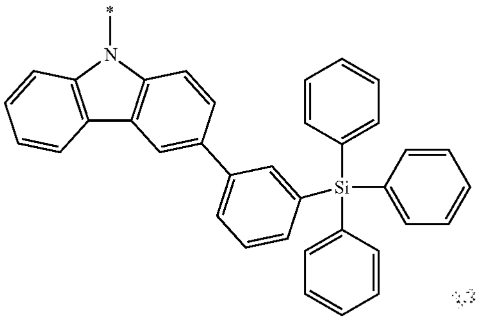
J21
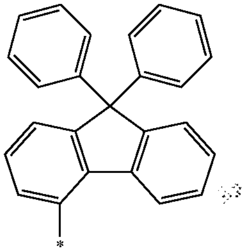
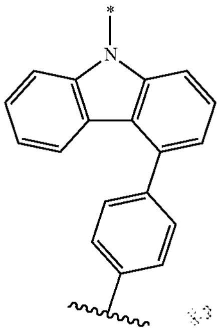
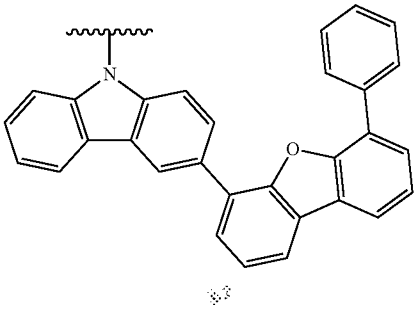
J22
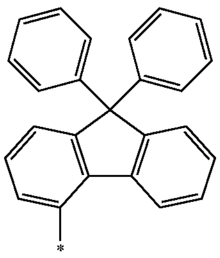
-continued
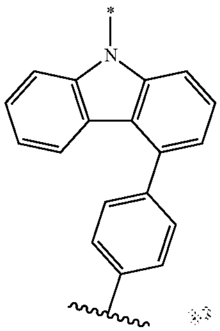
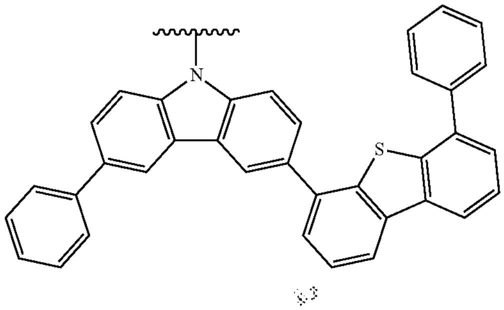
J23
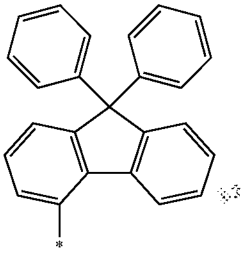
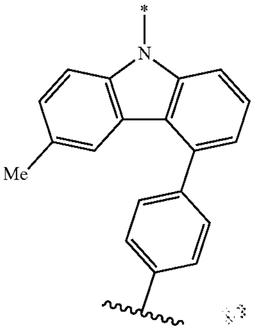
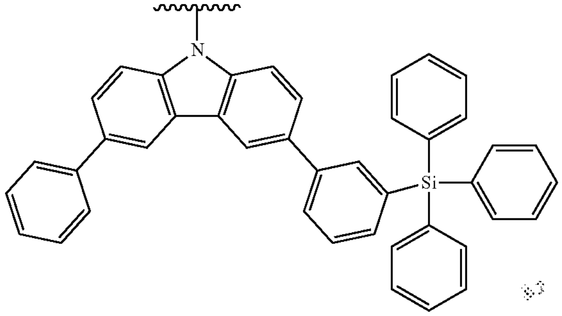

-continued
J24
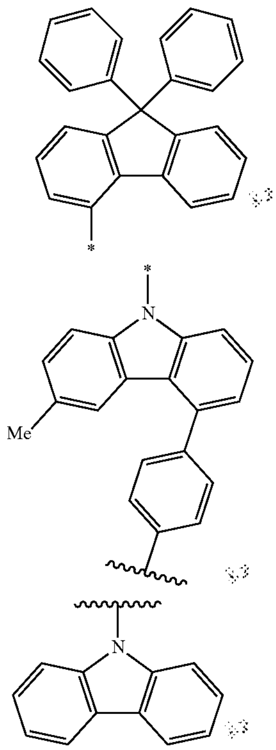
J25
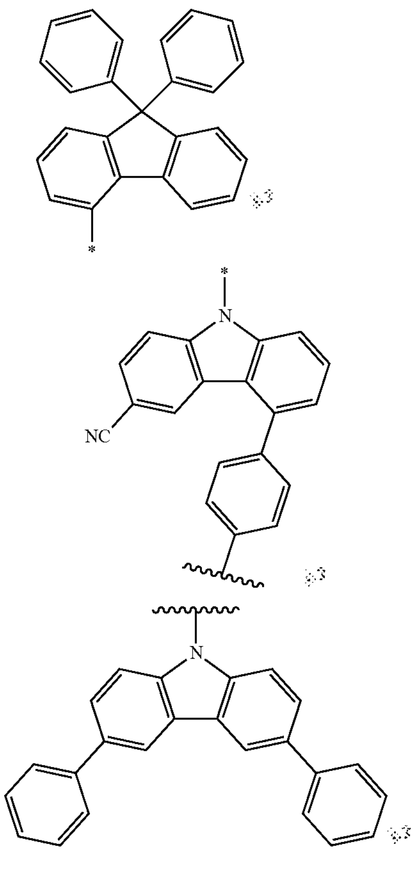
-continued
J26
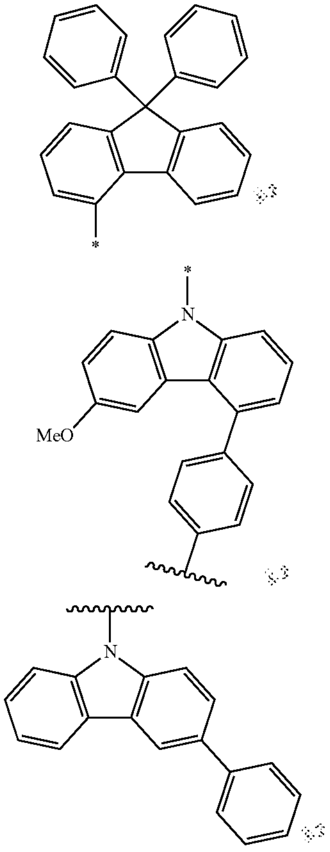
K1
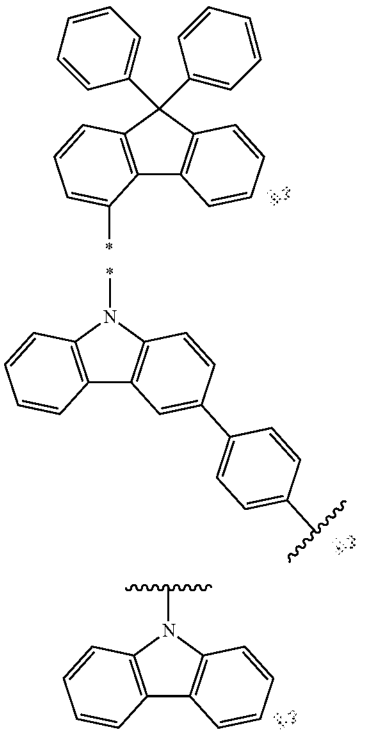

-continued
K2
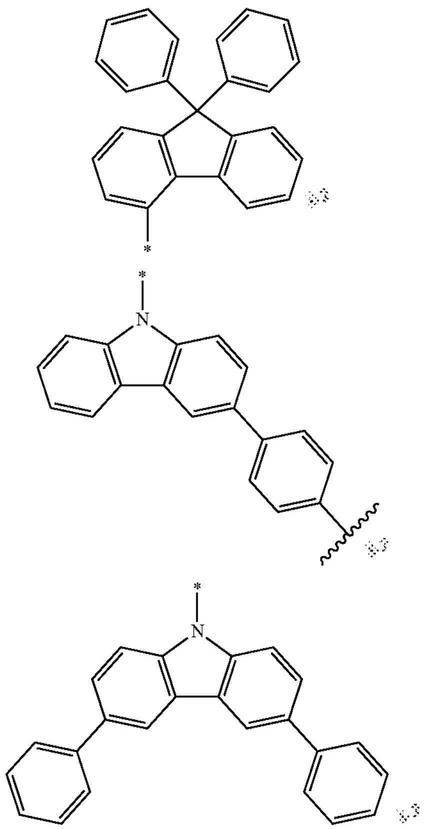
K3
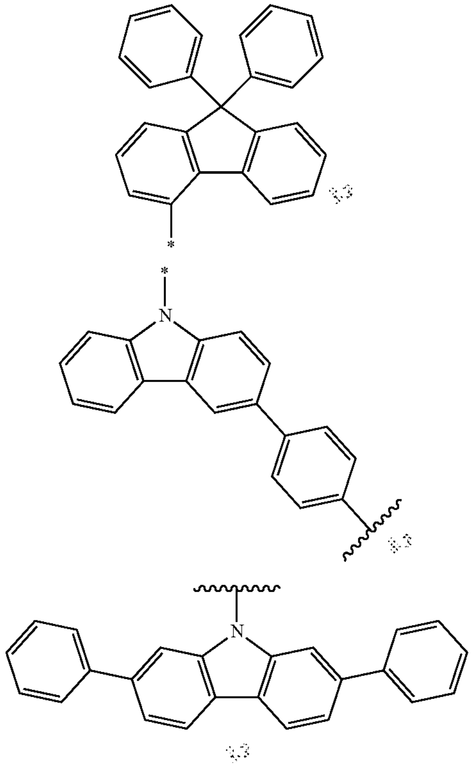
-continued
K4
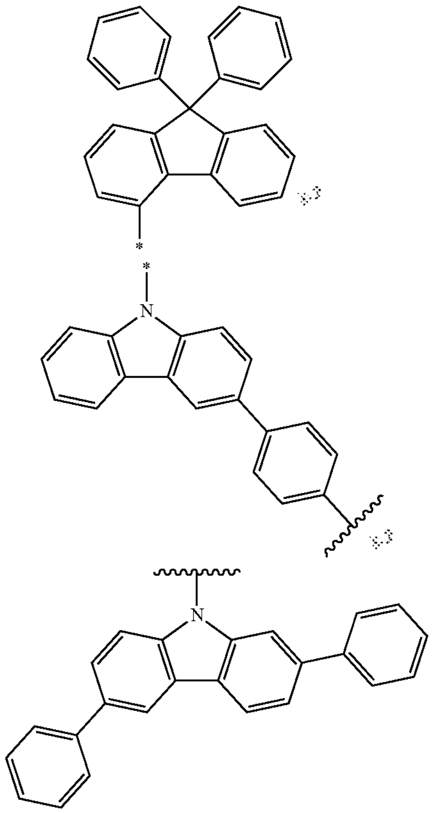
K5
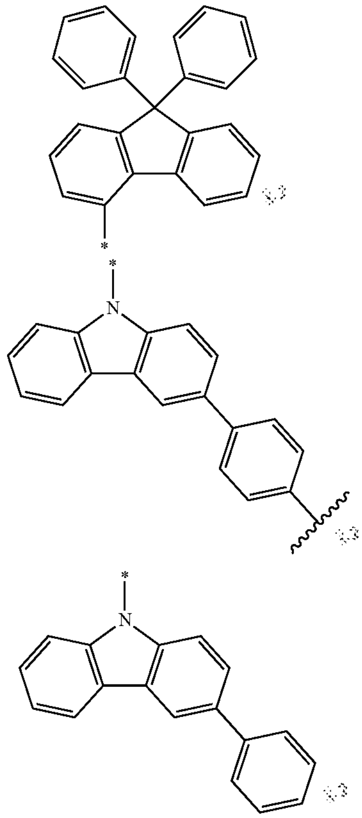

-continued
K6
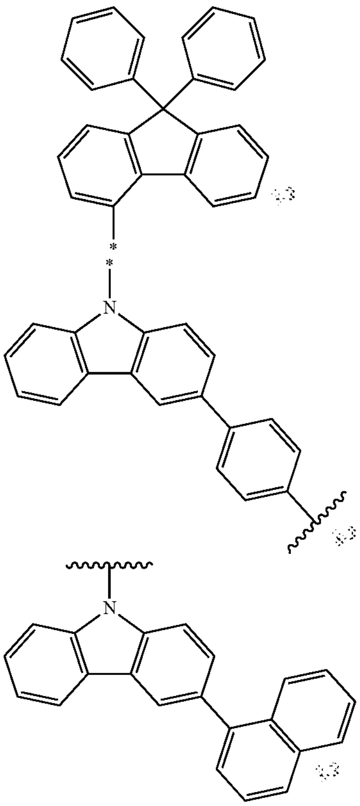
K7
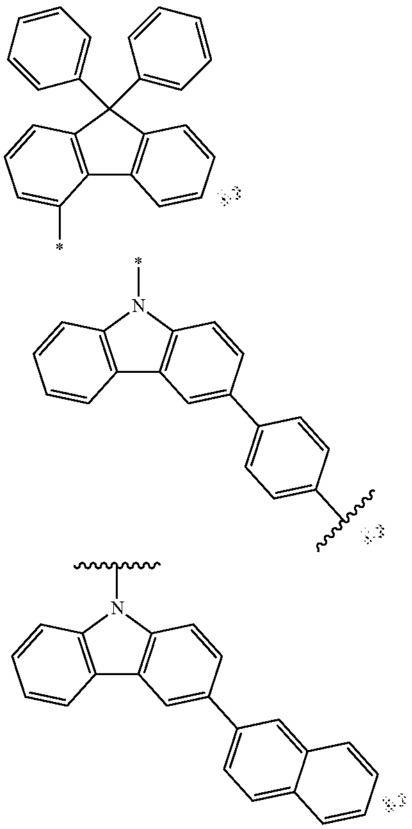
-continued
K8
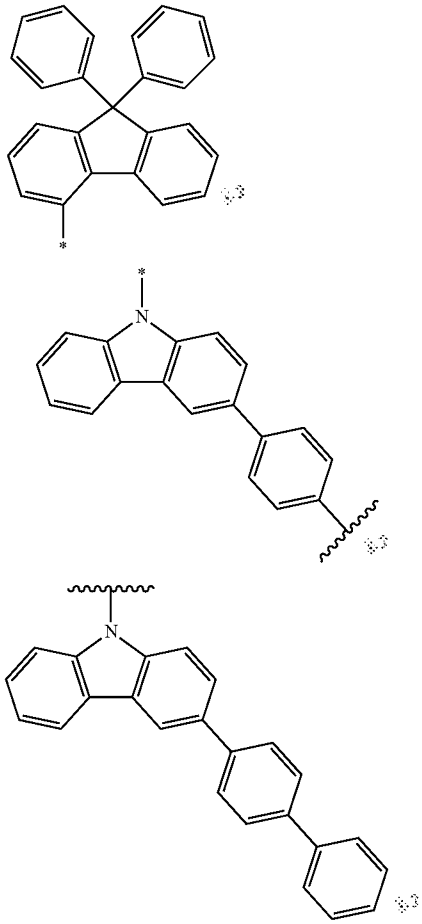
K9
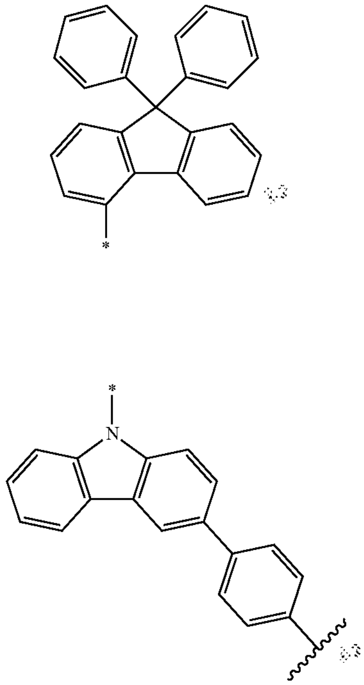

-continued
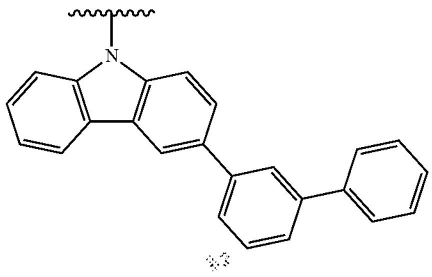
K10
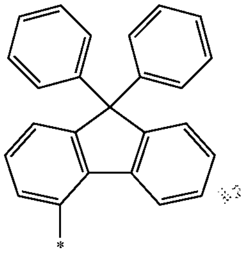
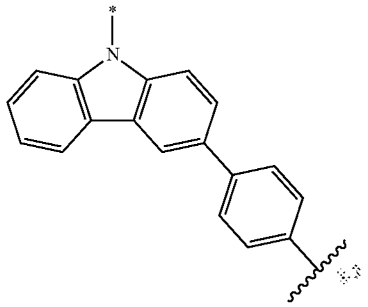
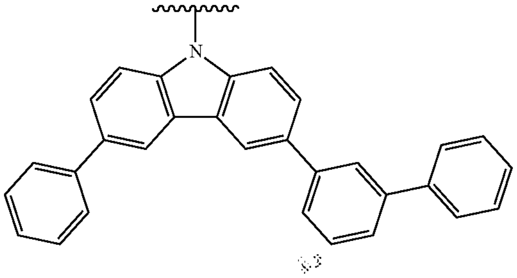
K11
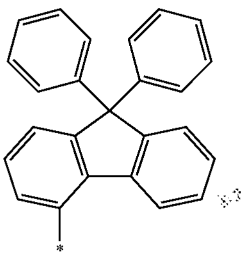
-continued
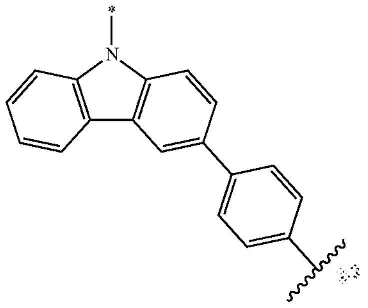
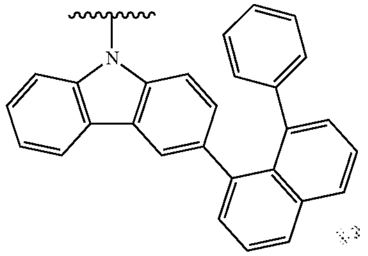
K12
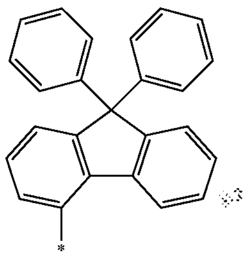
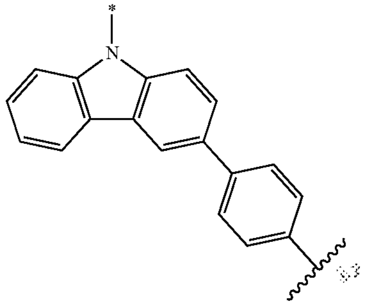
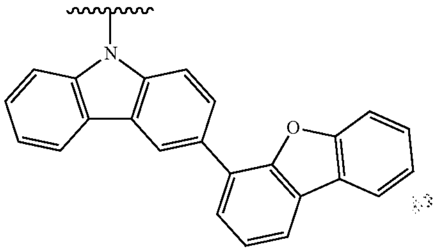
K13
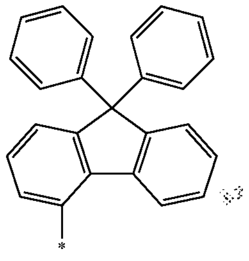

-continued
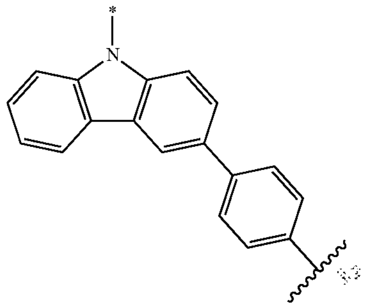
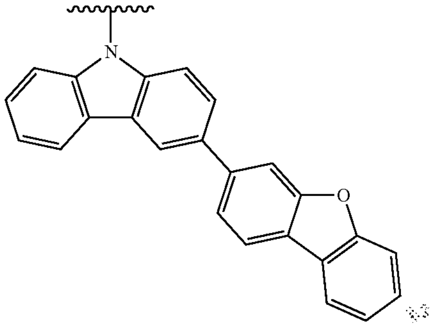
K14
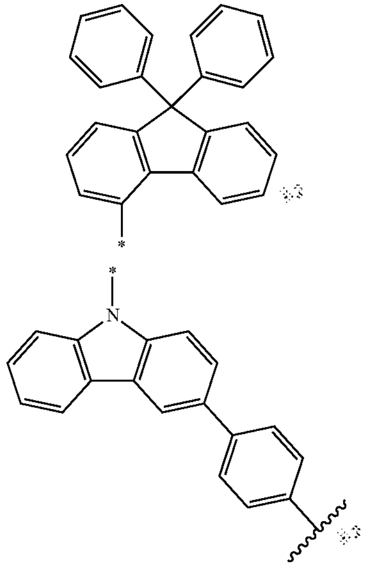
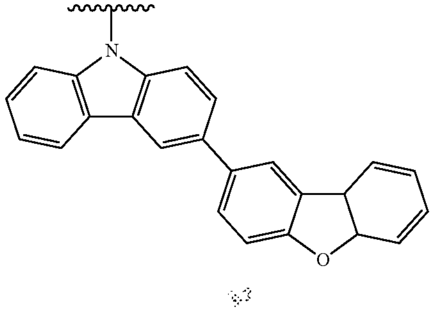
-continued
K15
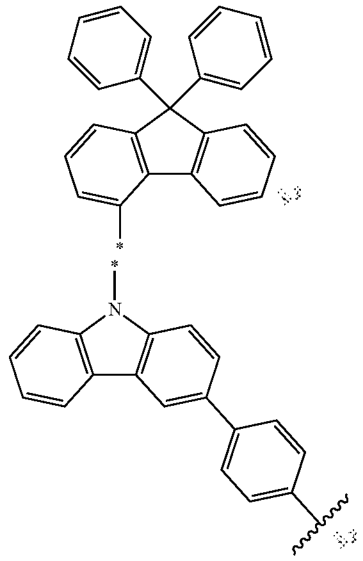
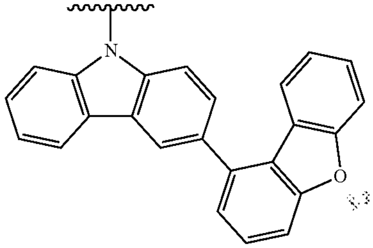
K16
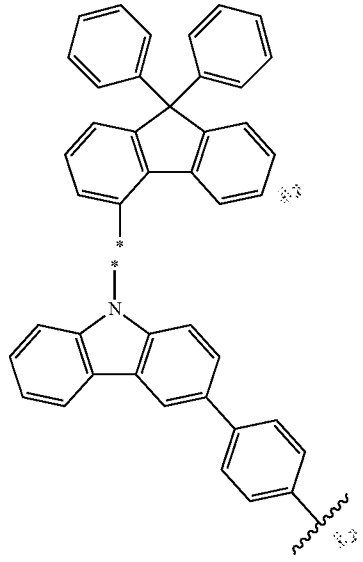
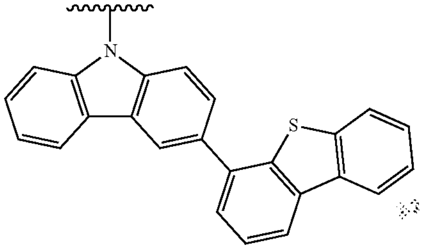

K17
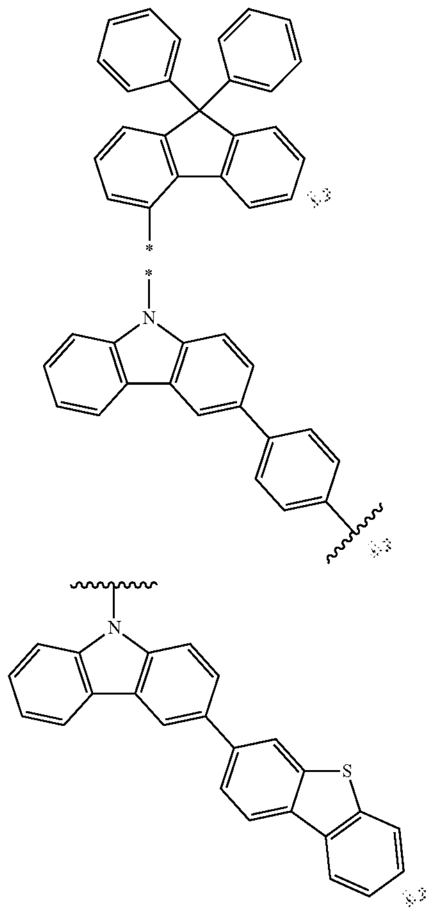
K18
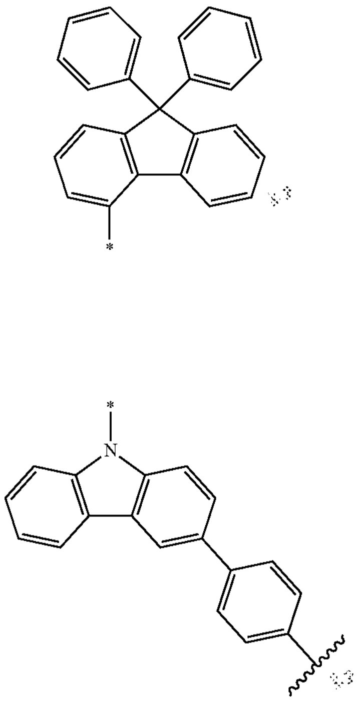
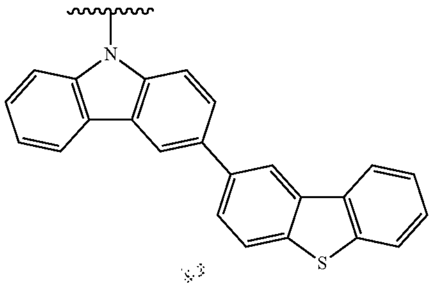
K19
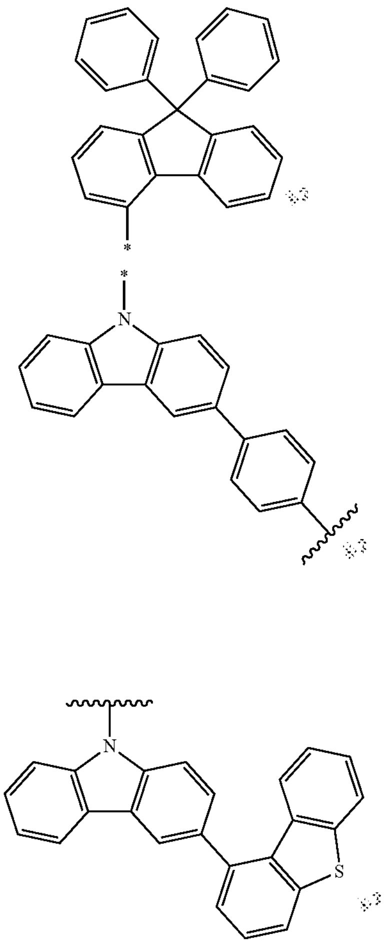
K20
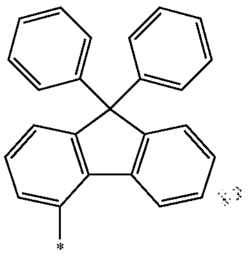

-continued
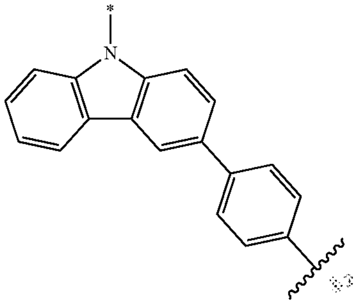
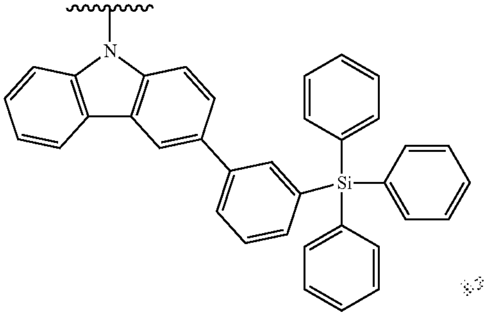
K21
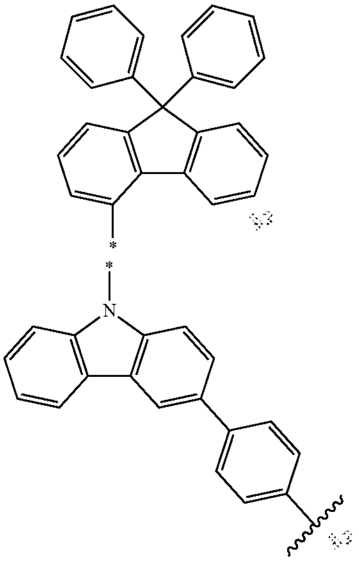
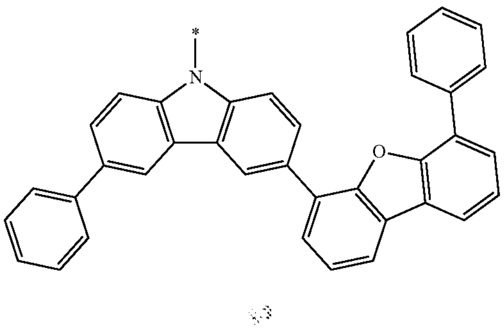
-continued
K22
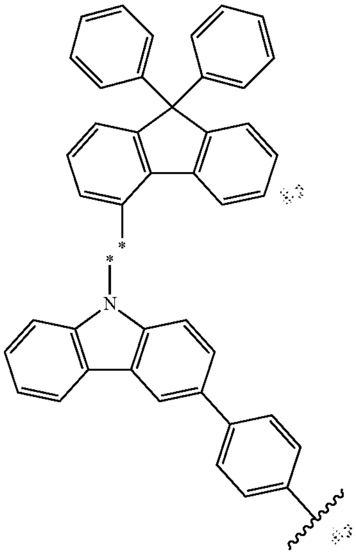
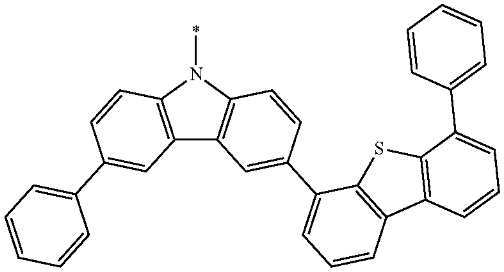
K23
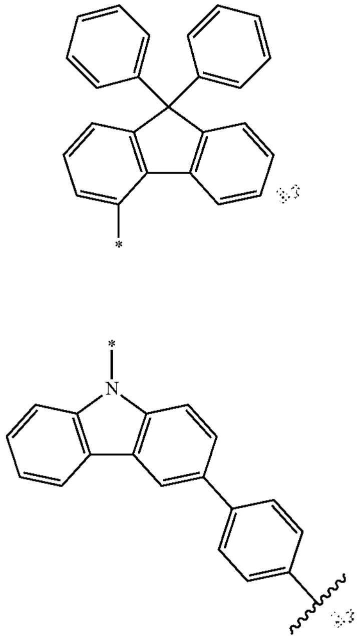

-continued
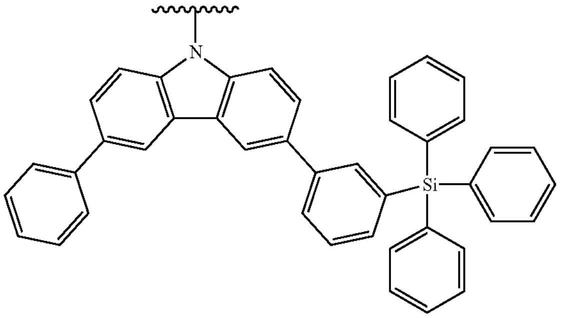
K24
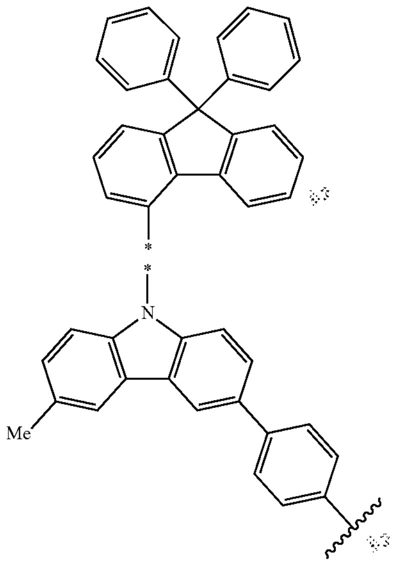
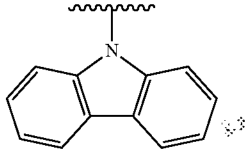
K25
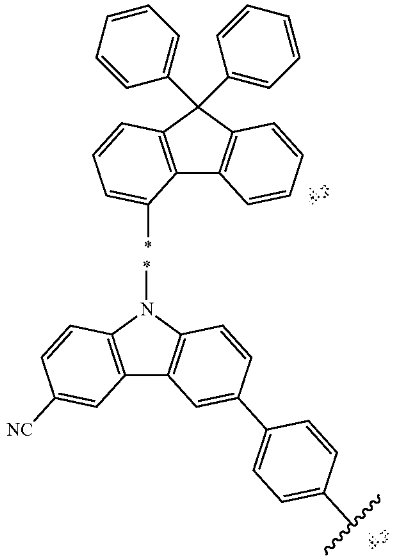
-continued
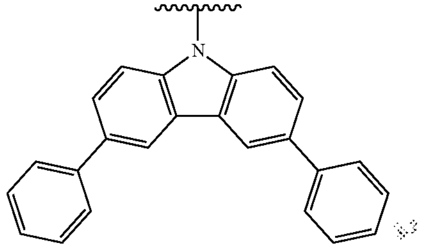
K26
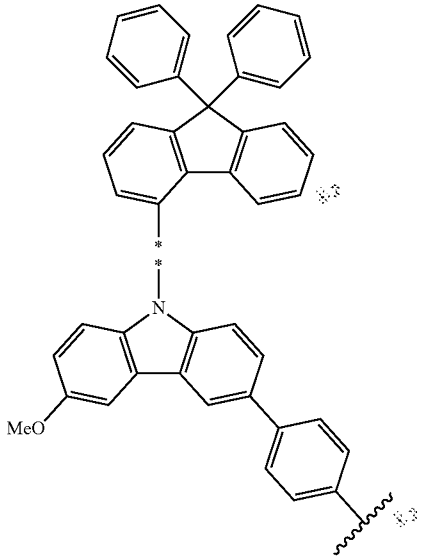
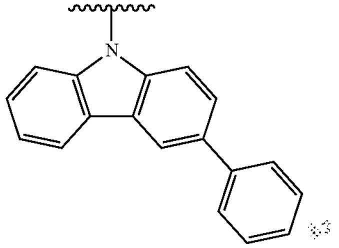
M1
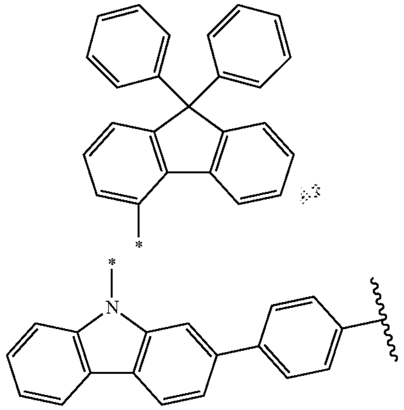
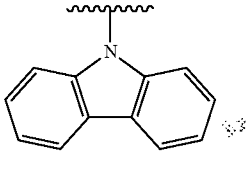

-continued
M2
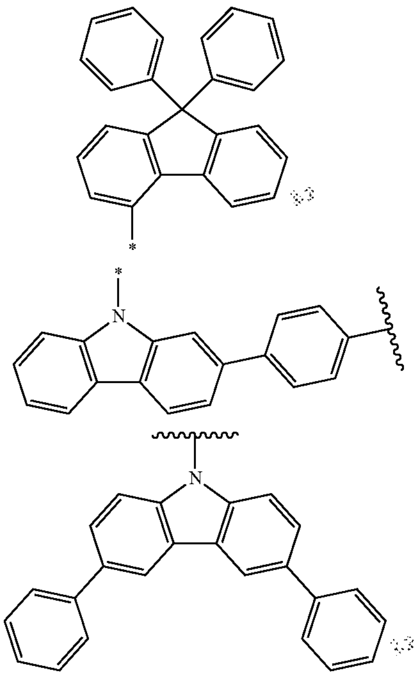
M3
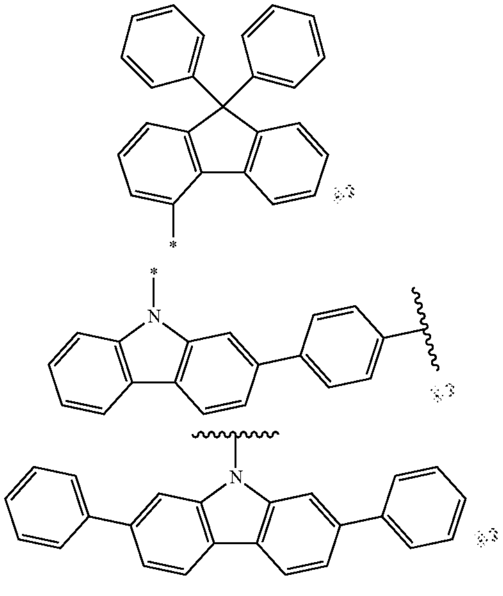
M4
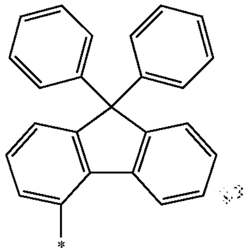
-continued
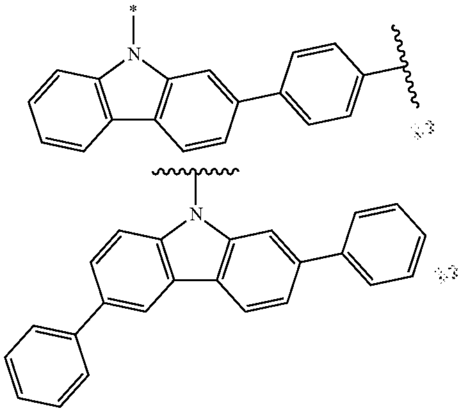
M5
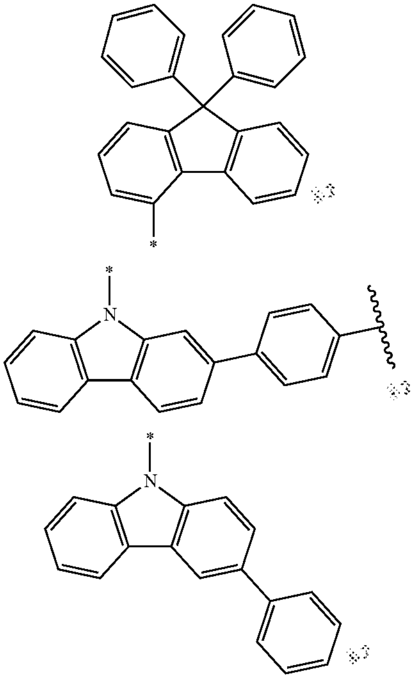
M6
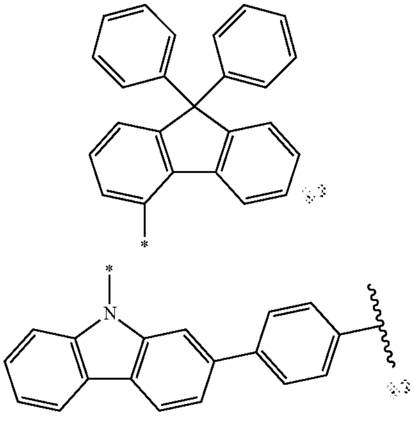

-continued
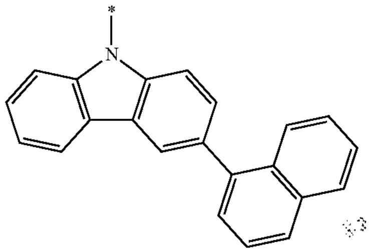
M7
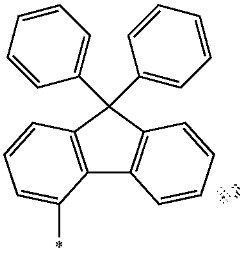
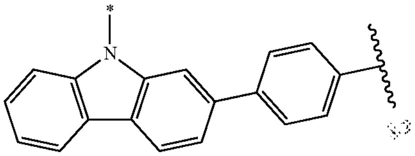
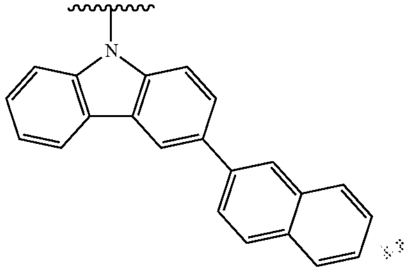
M8
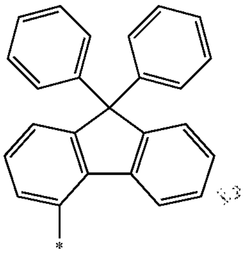
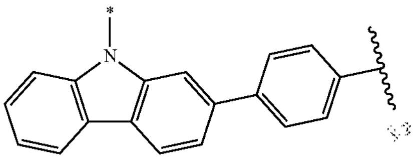
-continued
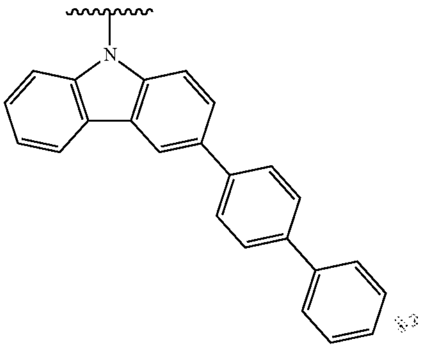
M9
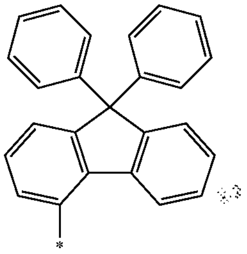
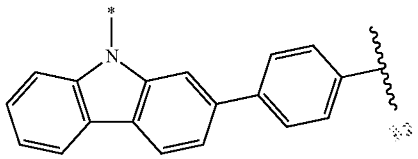
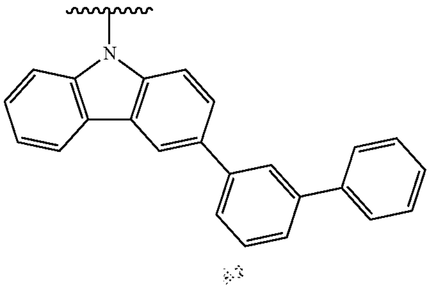
M10
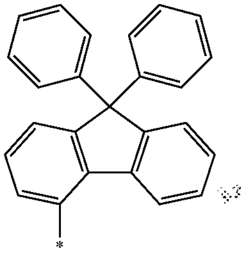
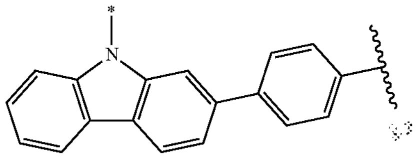

-continued
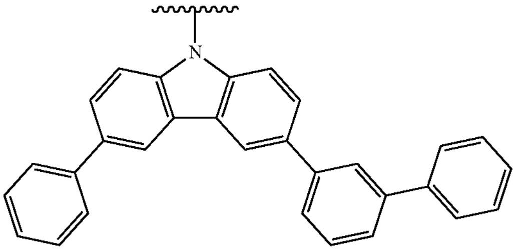
M11
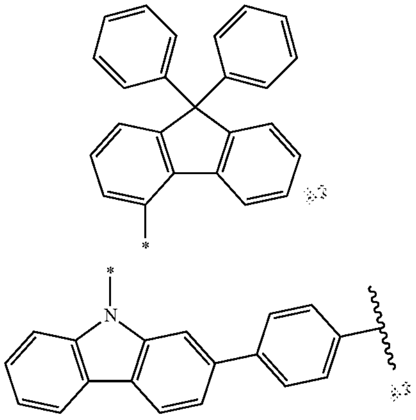
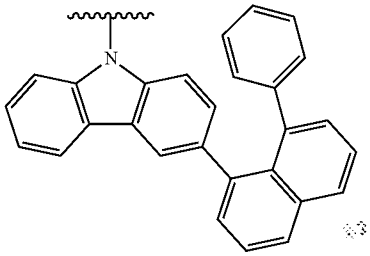
M12
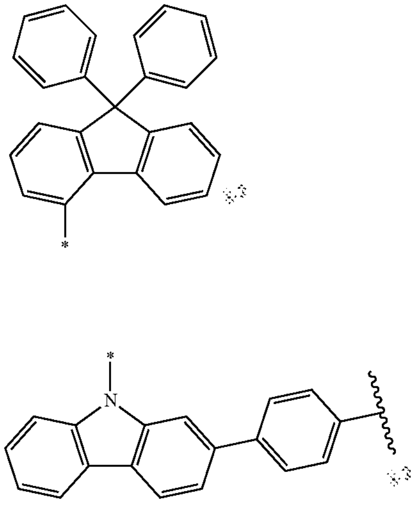
-continued
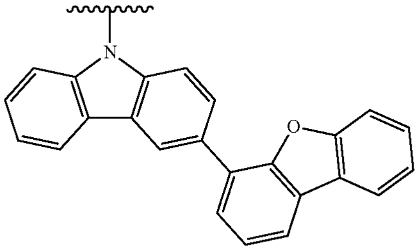
M13
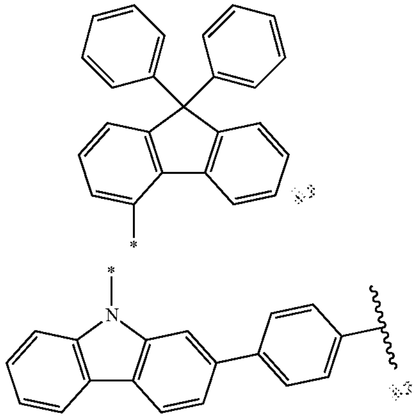
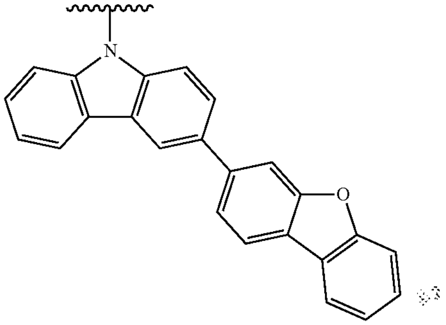
M14
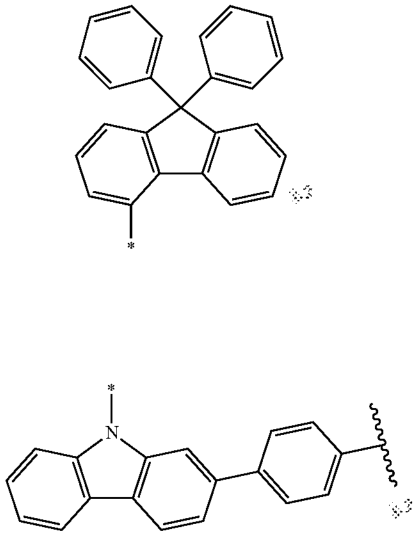

-continued
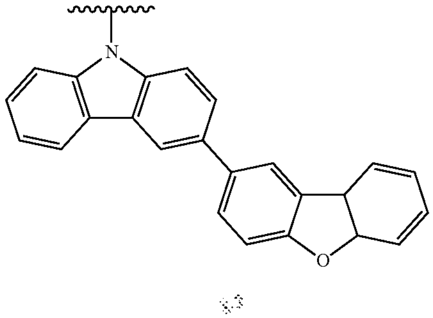
M15
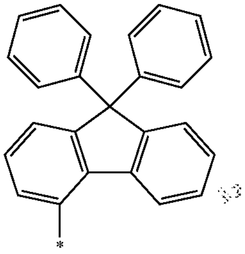
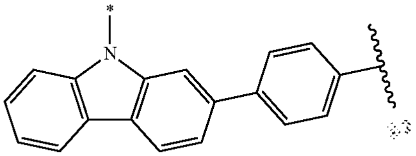
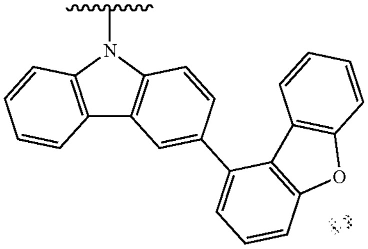
M16
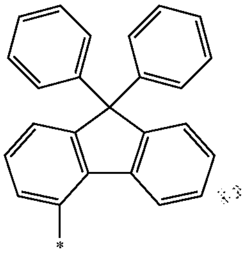
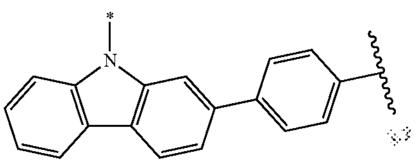
-continued
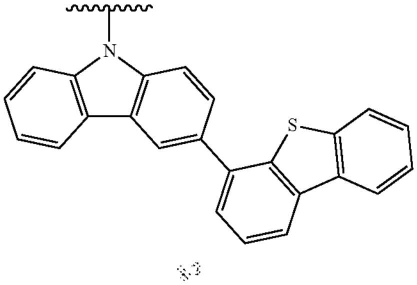
M17
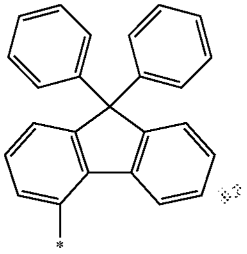
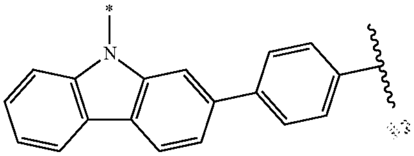
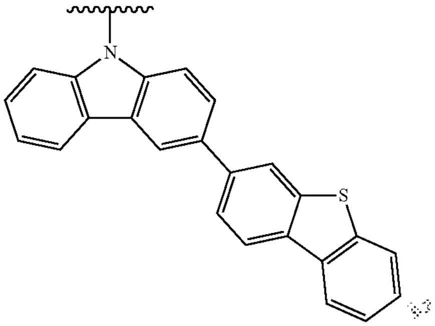
M18
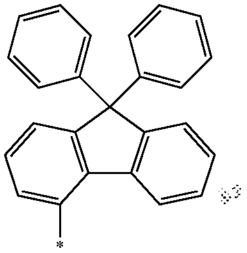
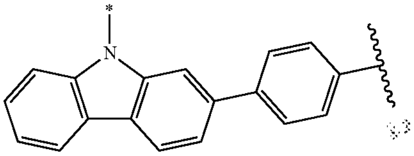

-continued
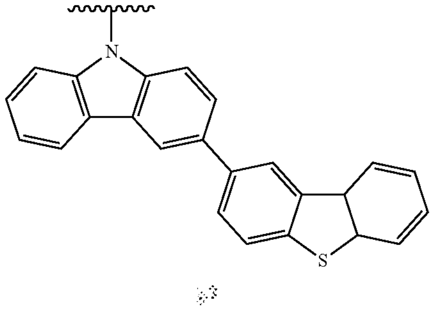
M19
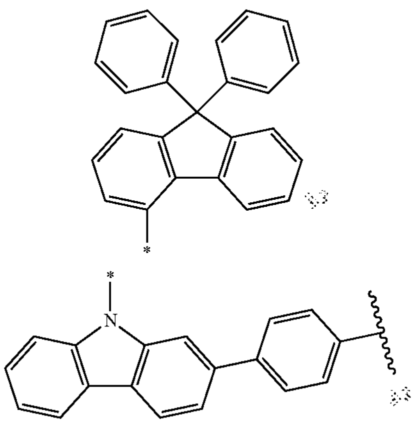
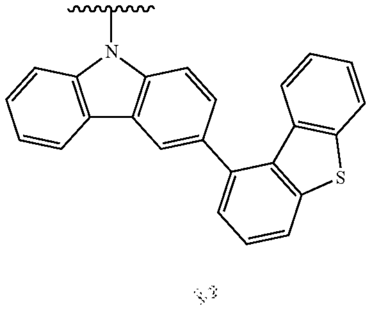
M20
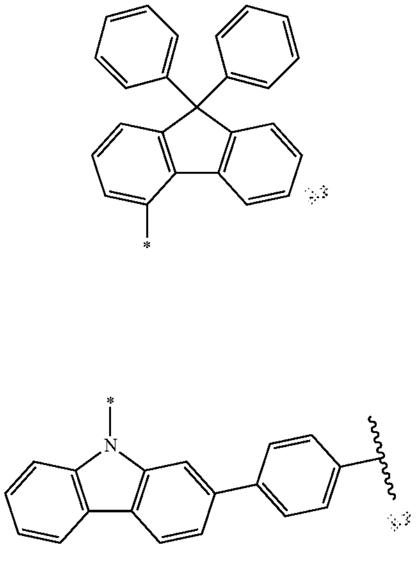
-continued
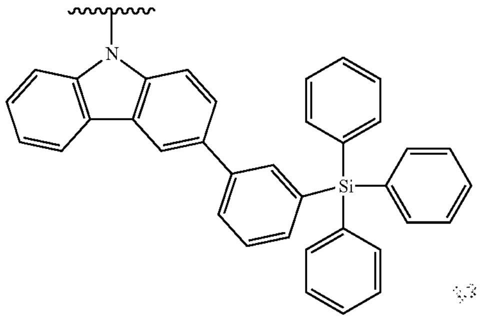
M21
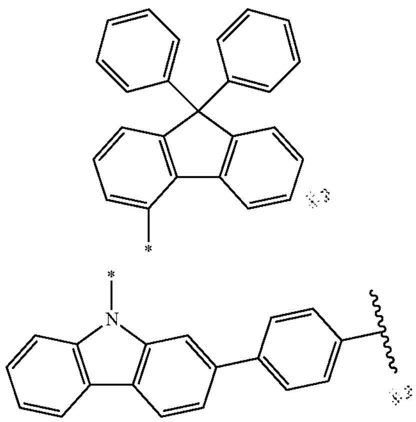
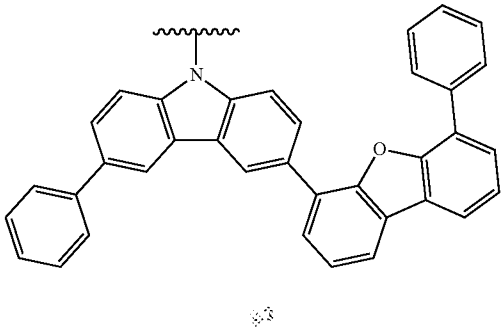
M22
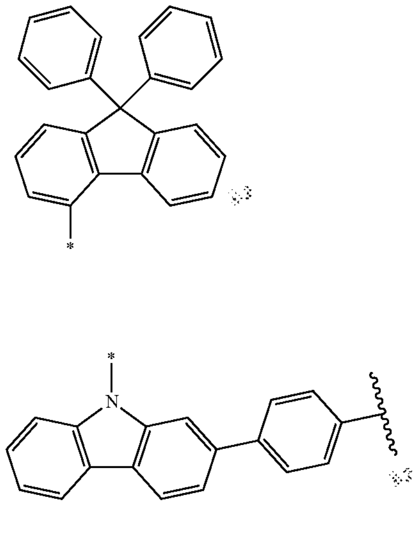

-continued
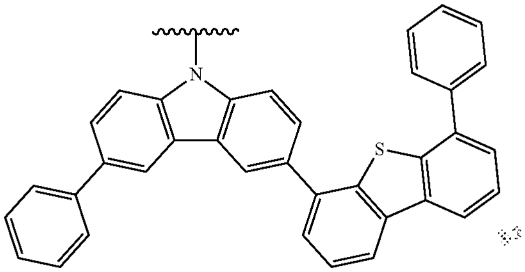
M23
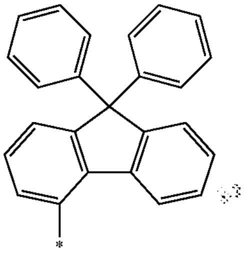
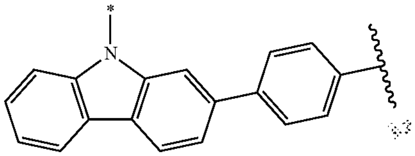
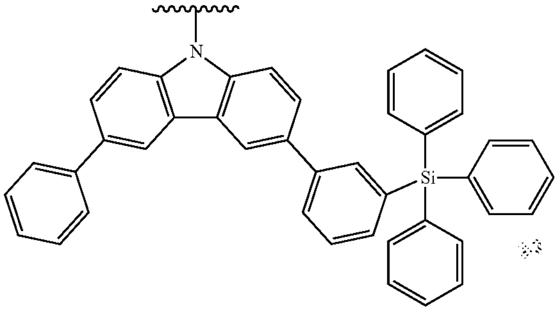
M24
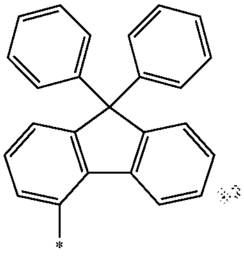
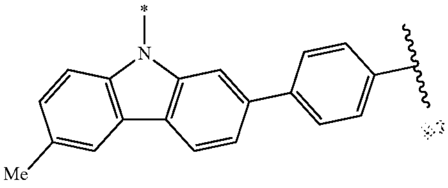
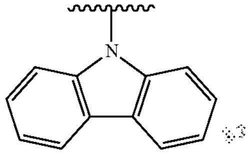
-continued
M25
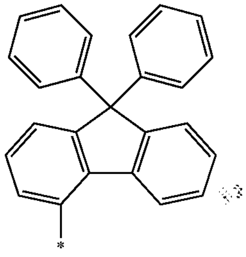
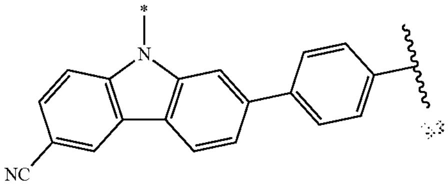
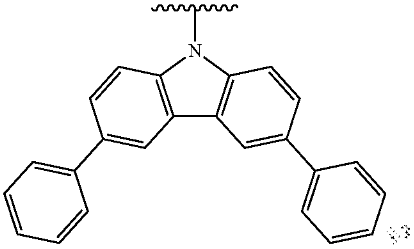
M26
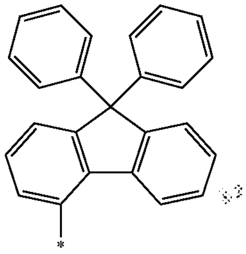
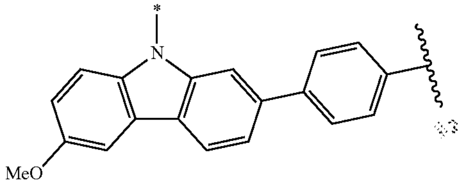
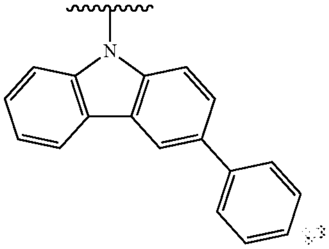

-continued
N1
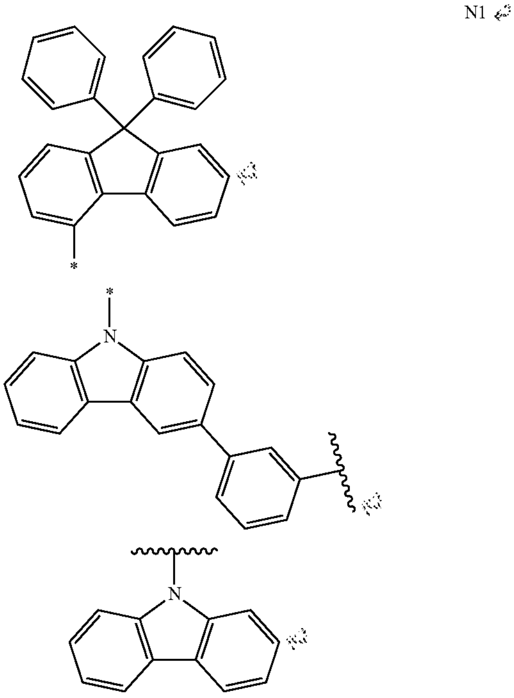
N2
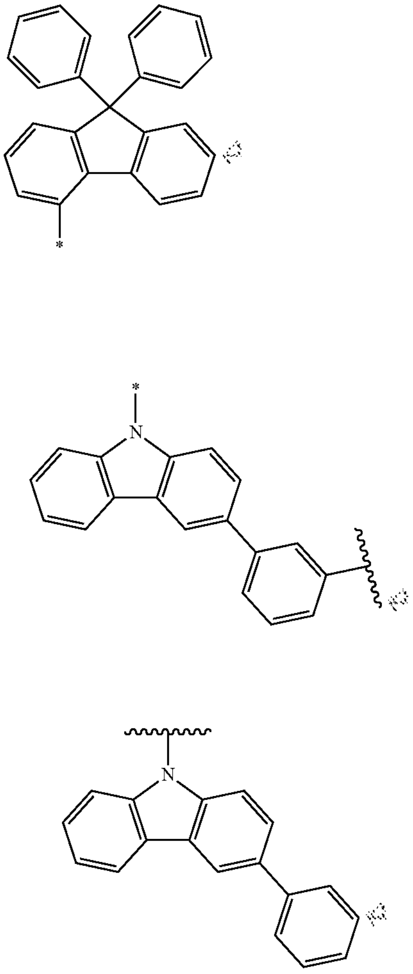
N3
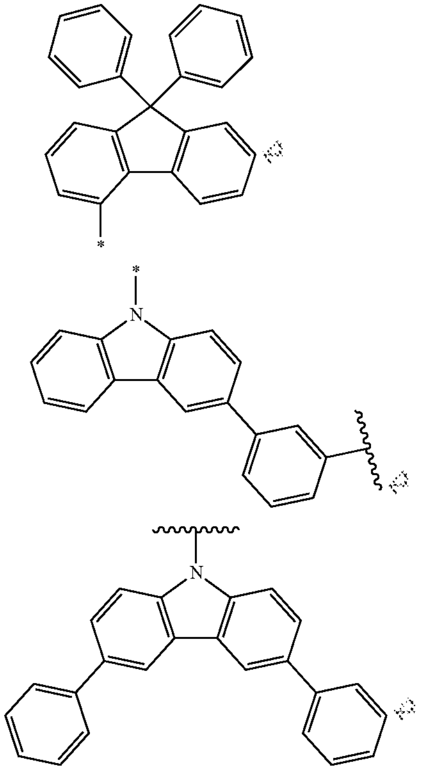
N4
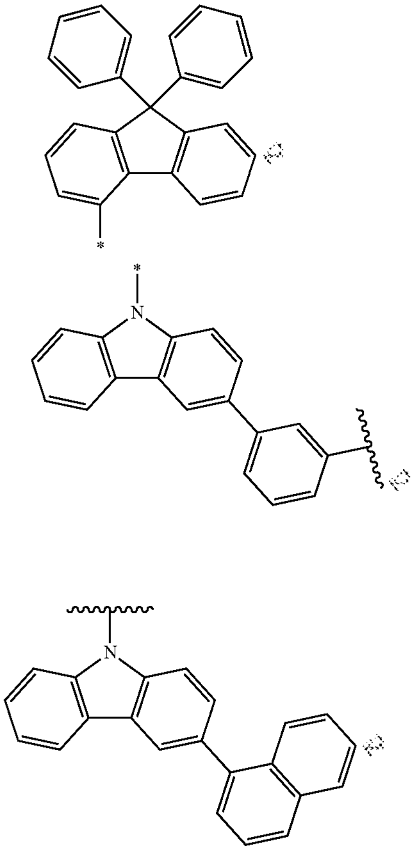

-continued
N5
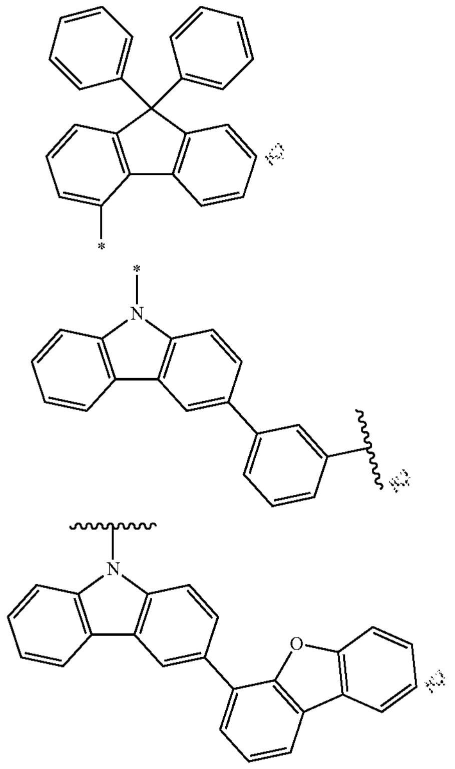
N6
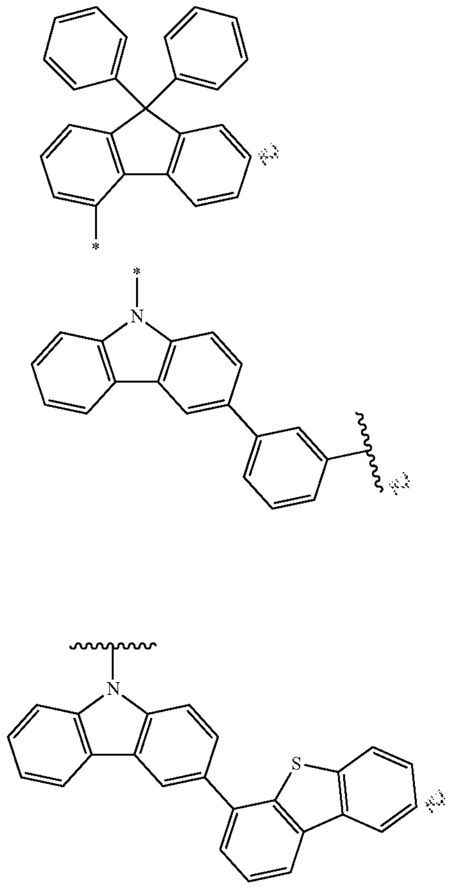
-continued
N7
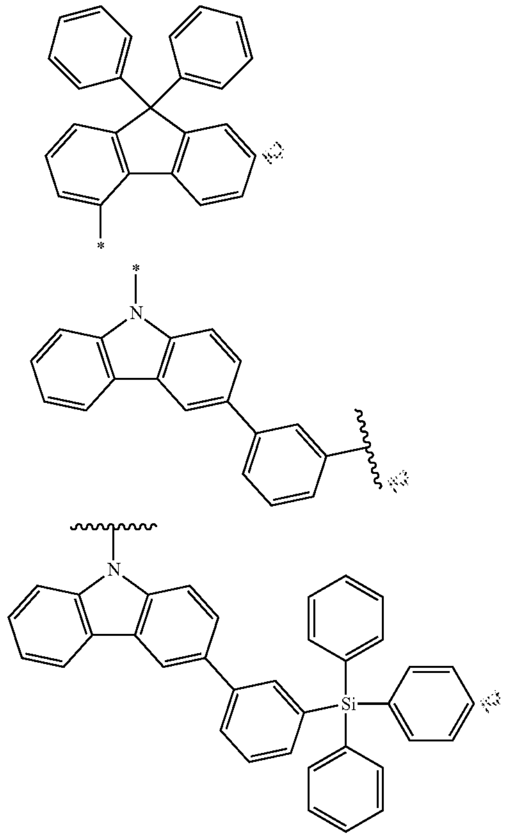
N8
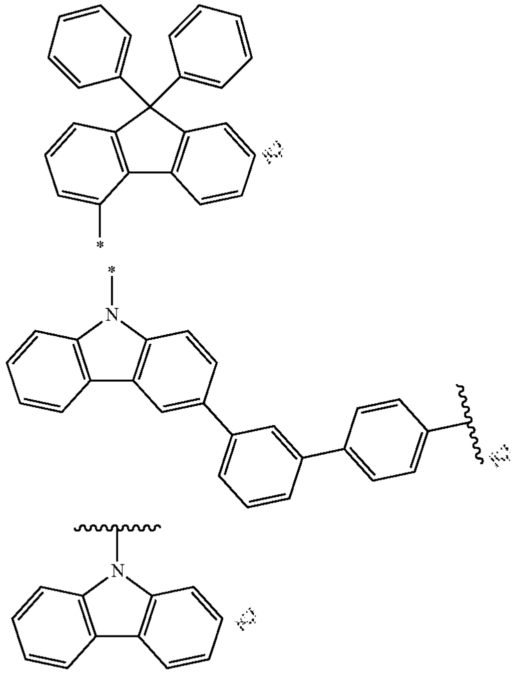

-continued
N9
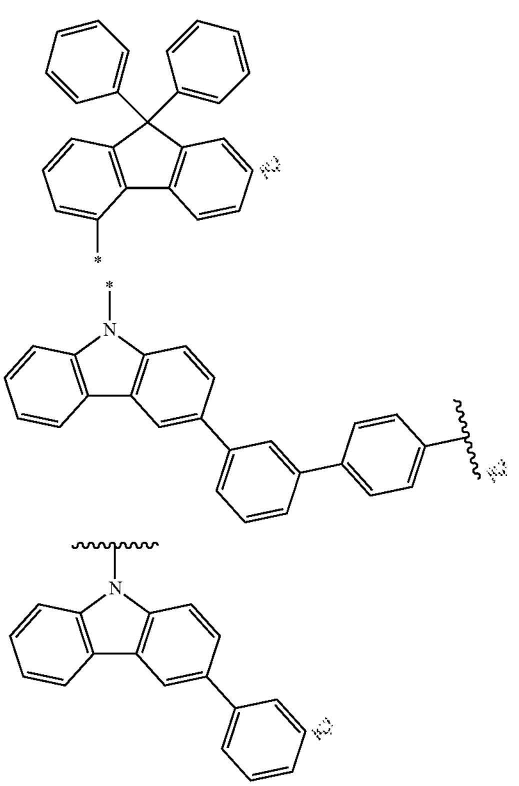
N10
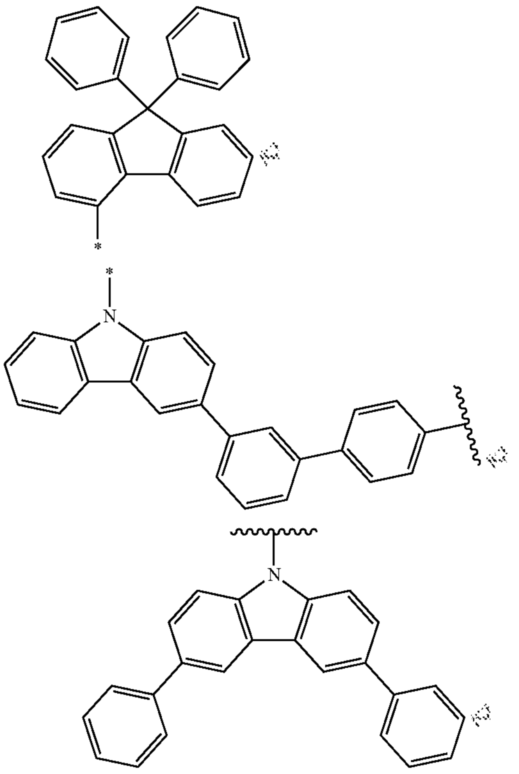
-continued
N11
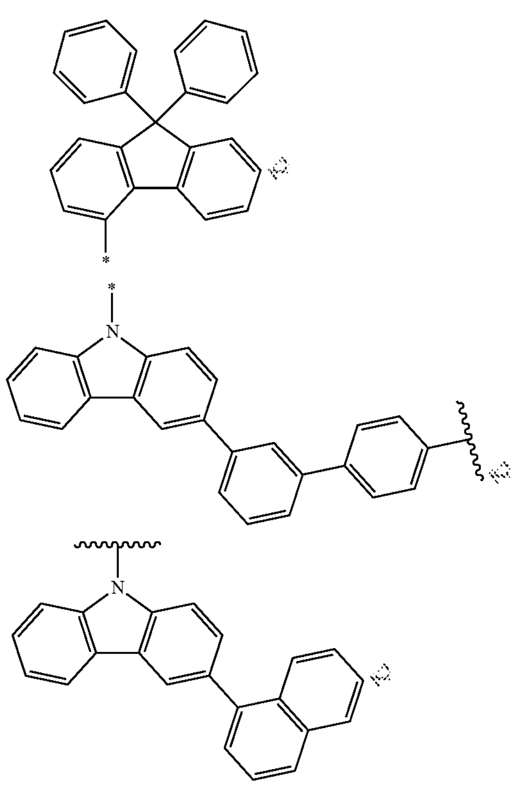
N12
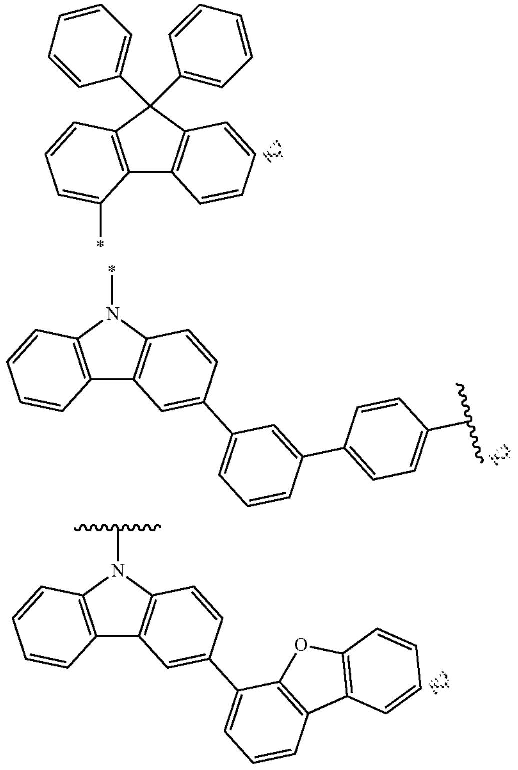

N13
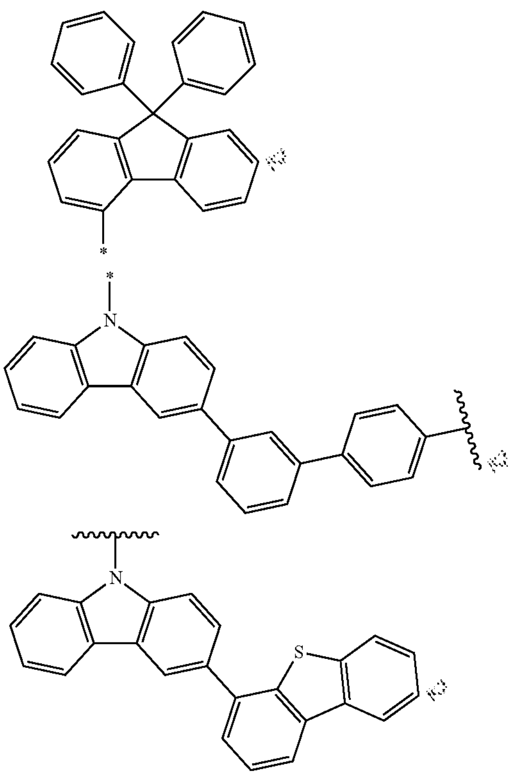
N14
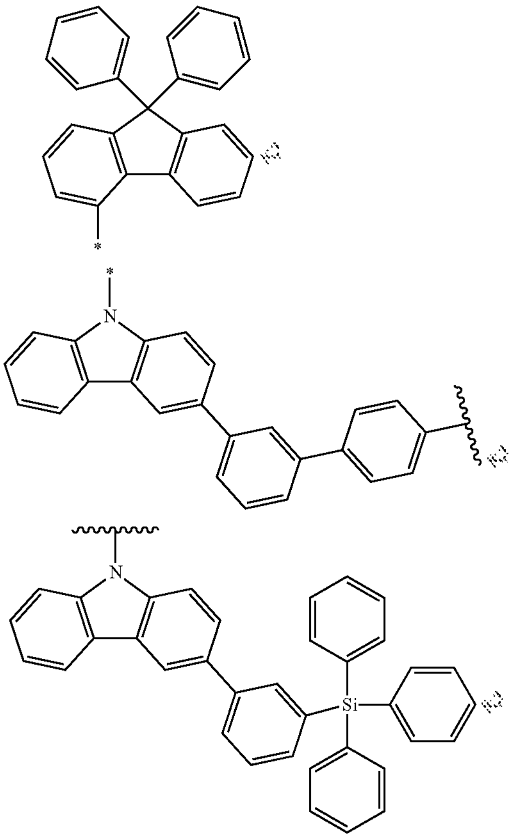
N15
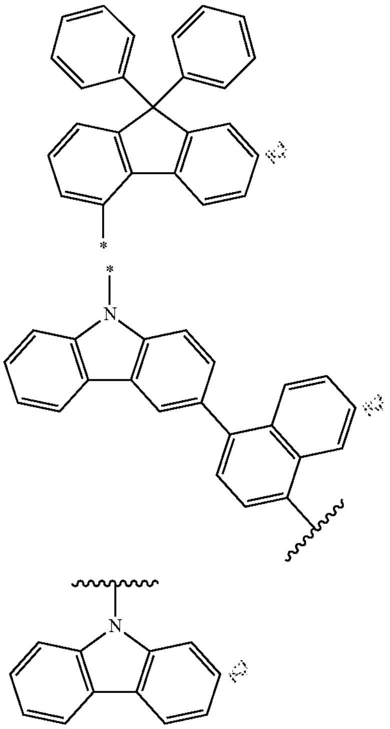
N16
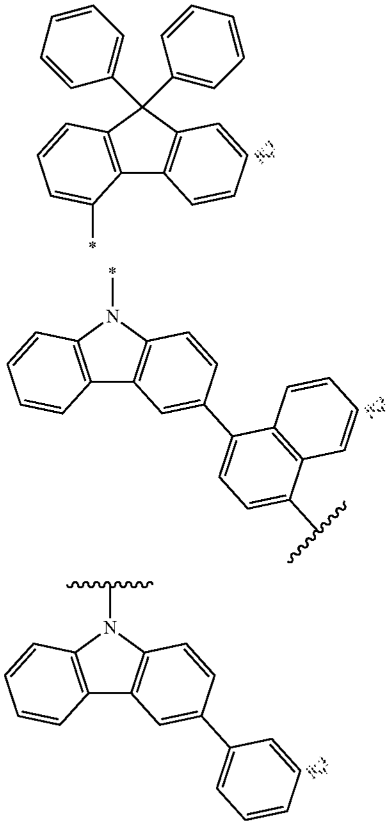

-continued
N17
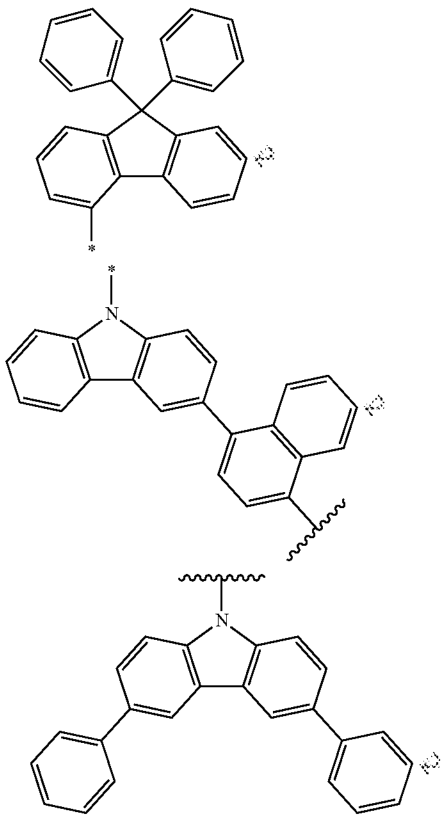
N18
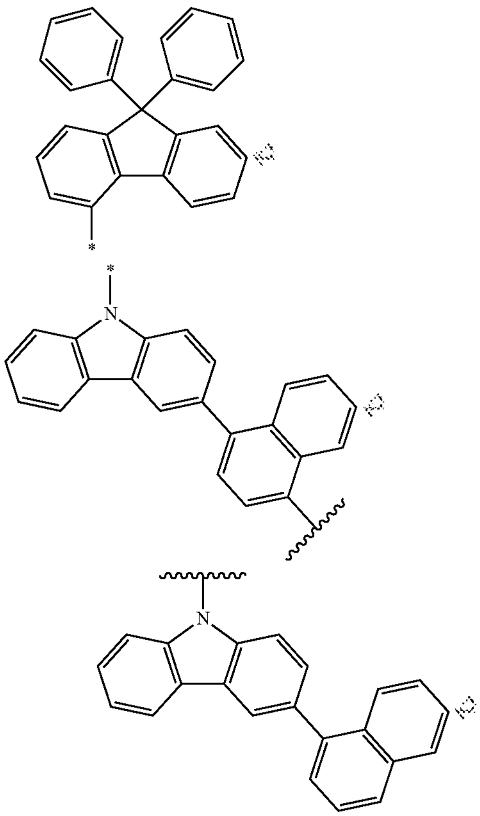
-continued
N19
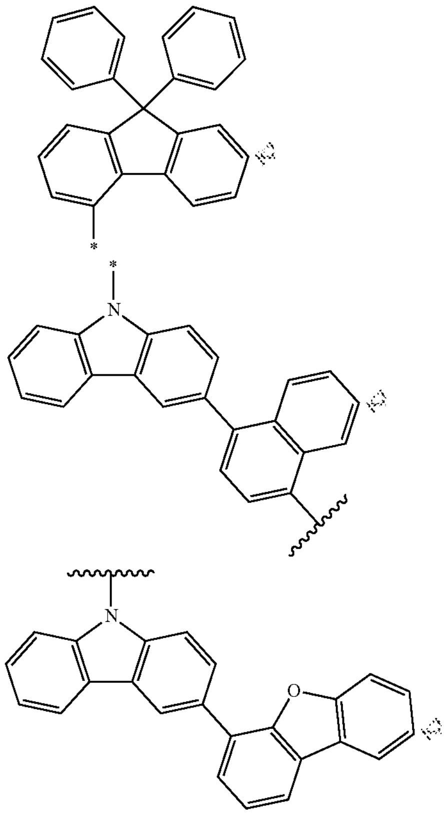
N20
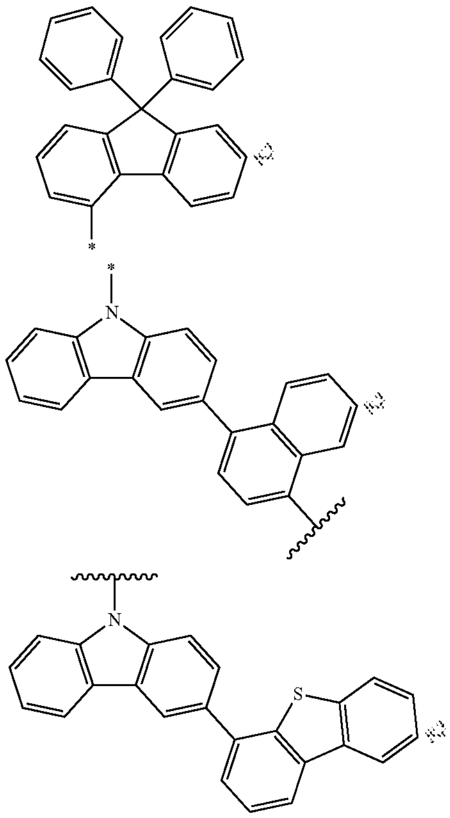

-continued
N21
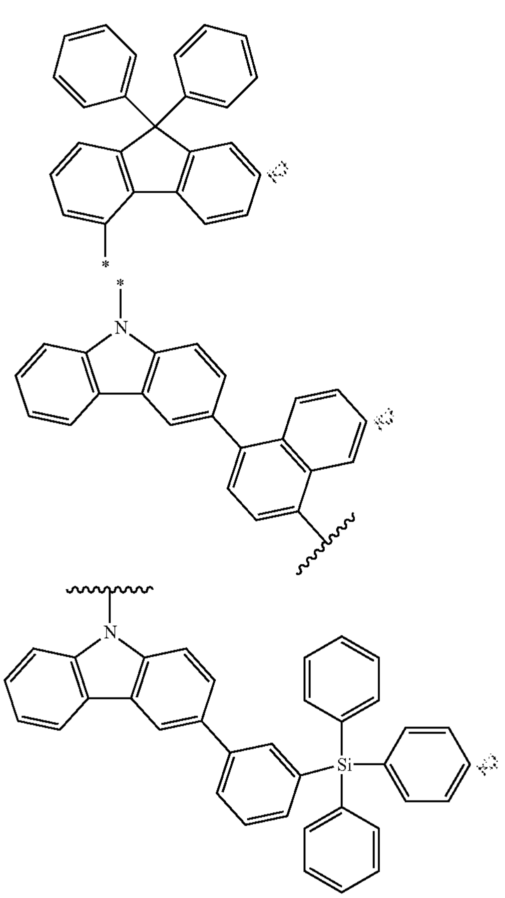
N22
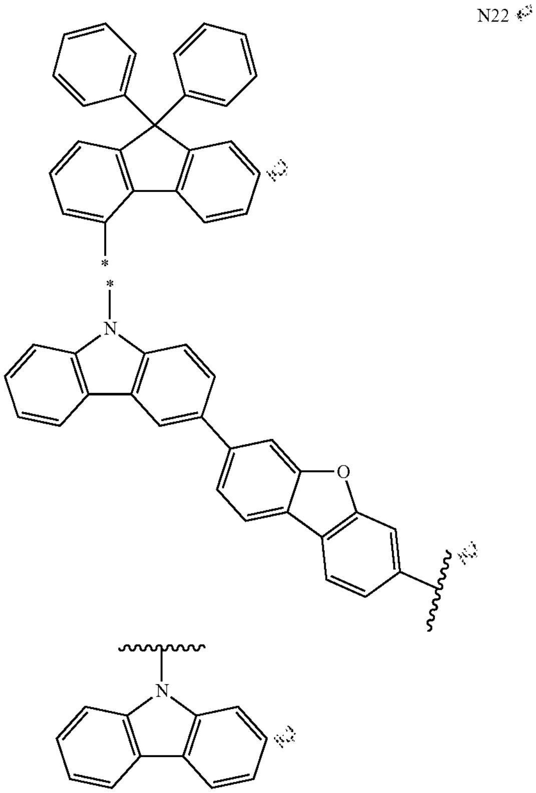
-continued
N23
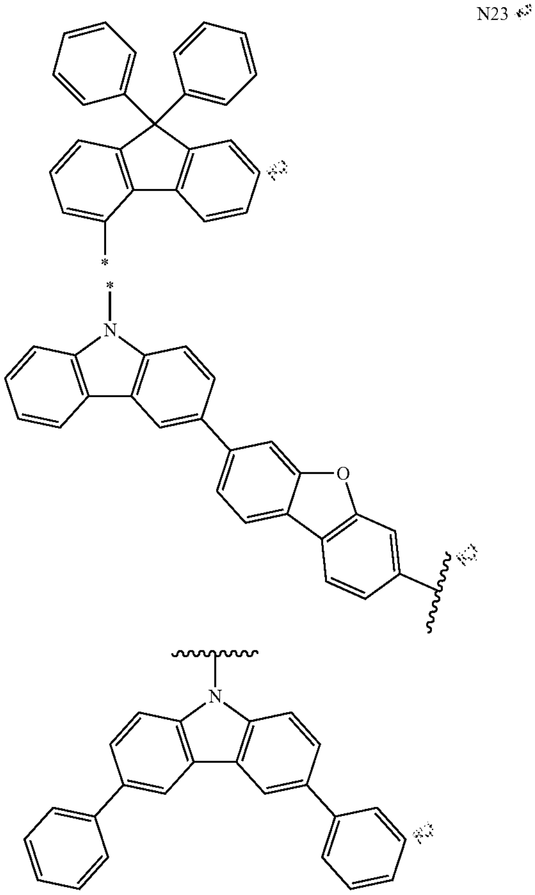
N24
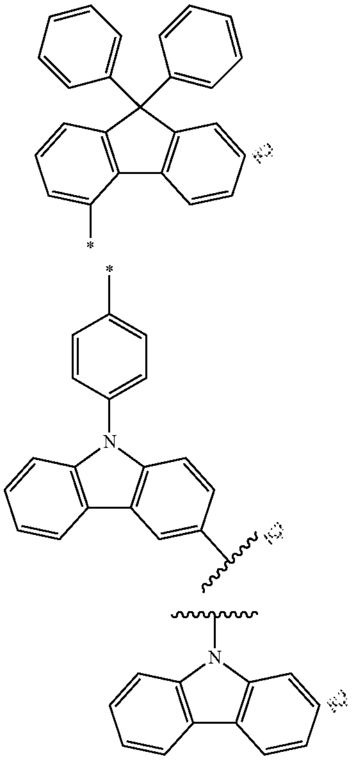

-continued
N25
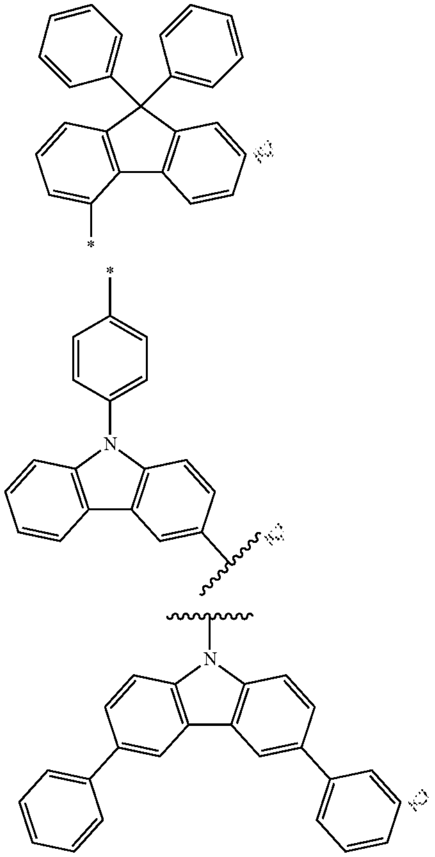
N26
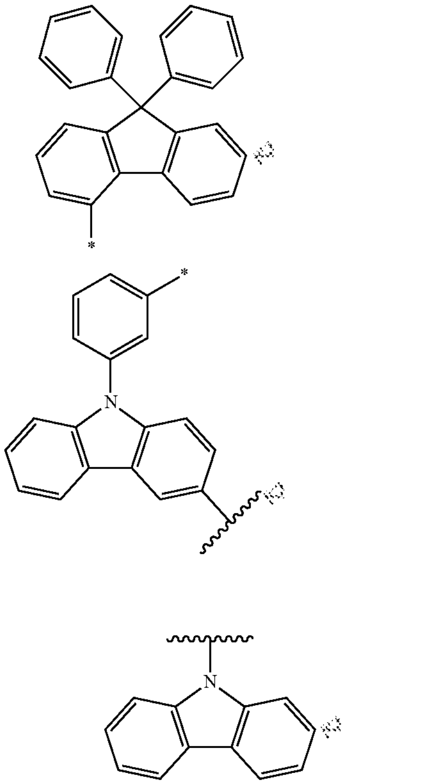
-continued
N27
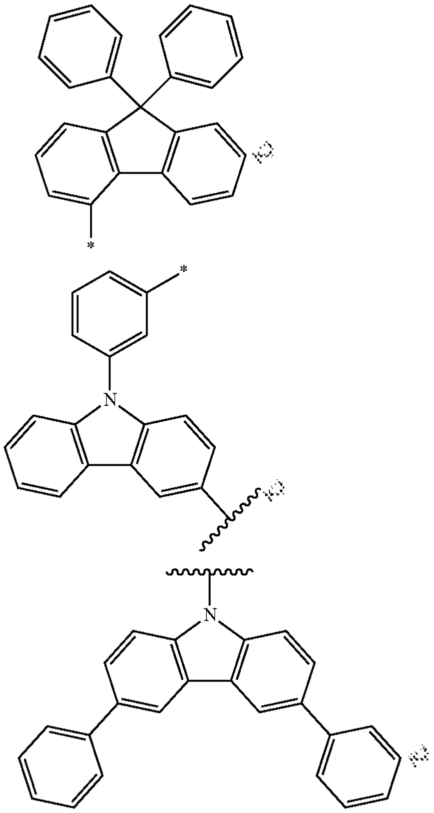
N28
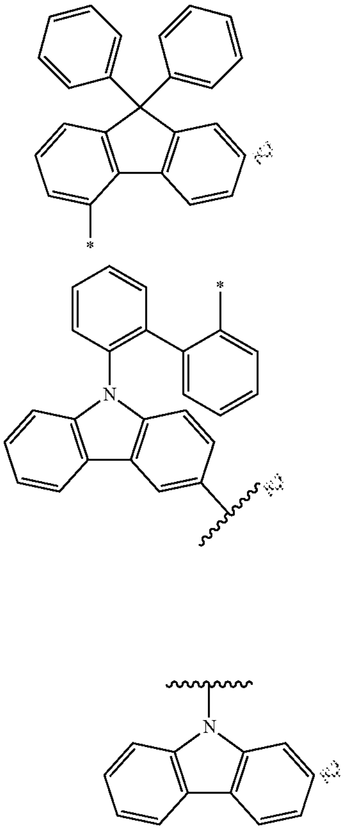

-continued
N29
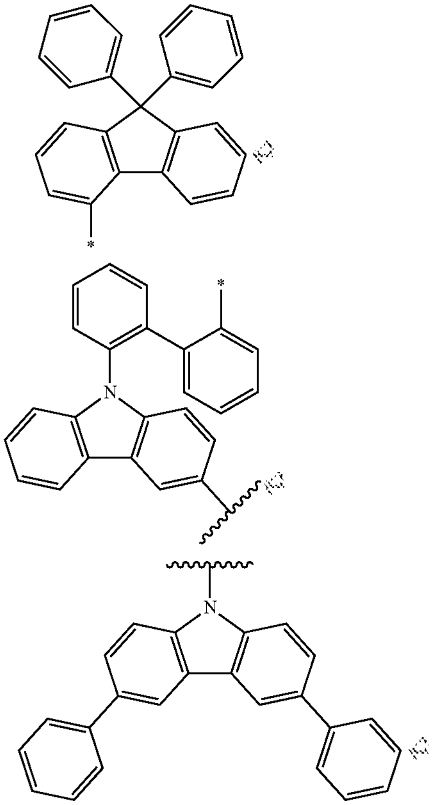
N30
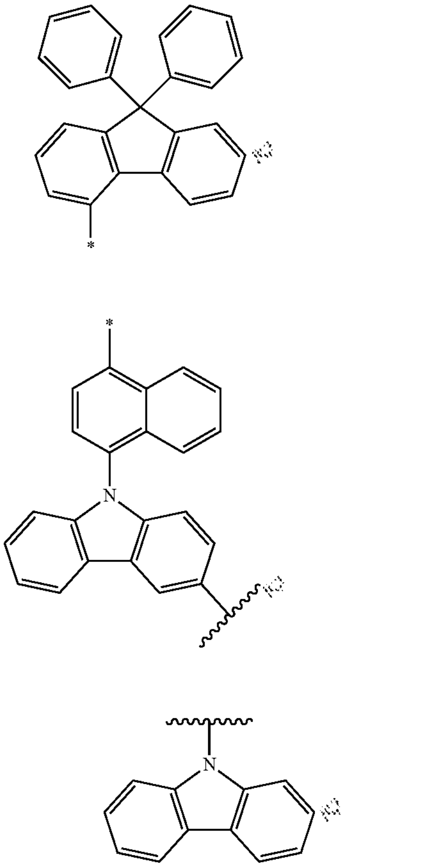
-continued
N31
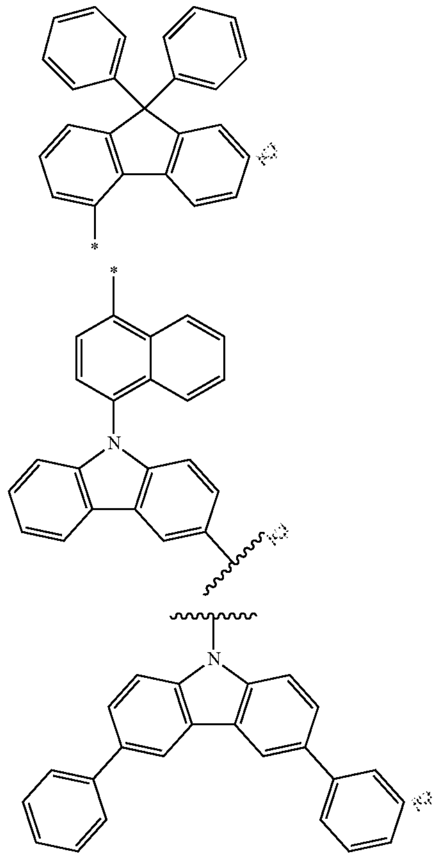
N32
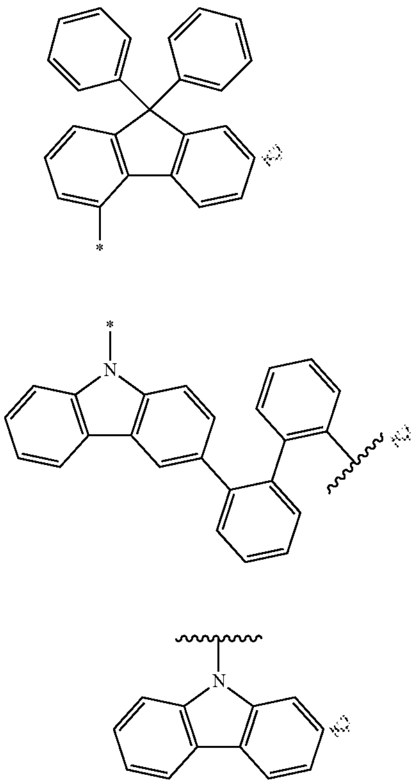

-continued
N33
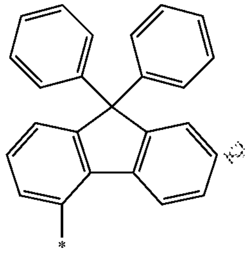
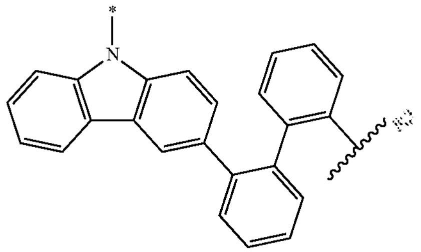
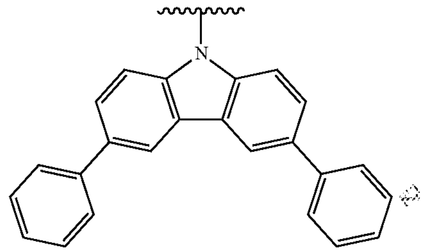
O1
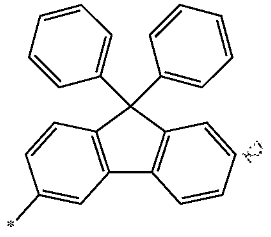
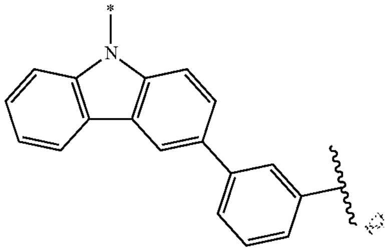
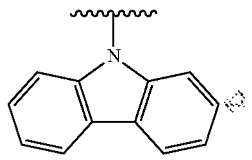
O2
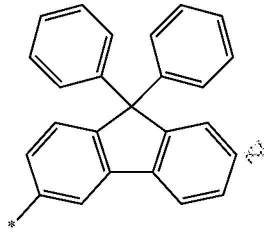
-continued
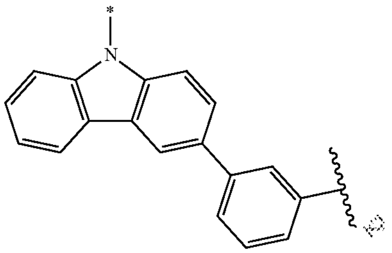
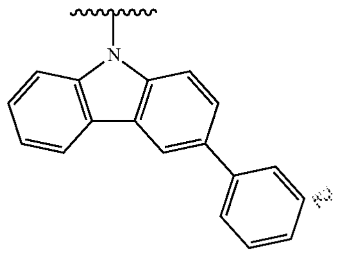
O3
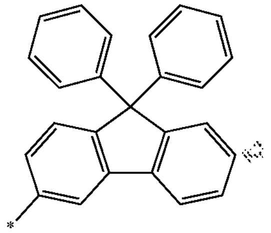
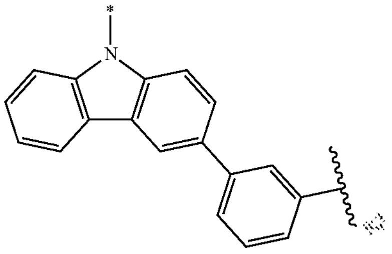
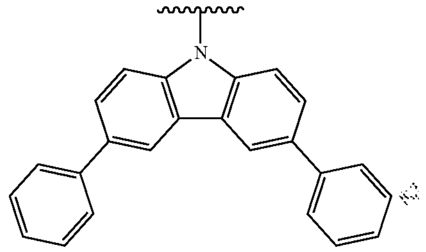
O4
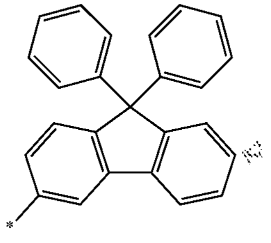

-continued
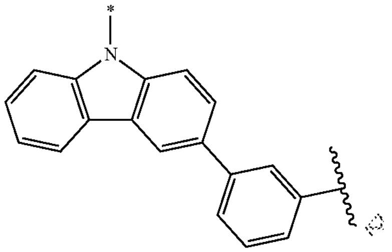
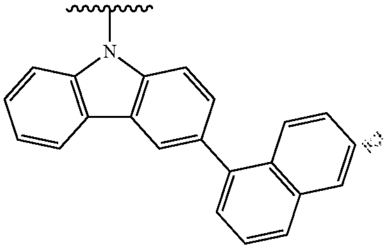
O5
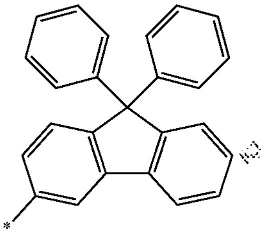
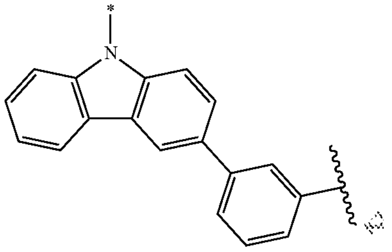
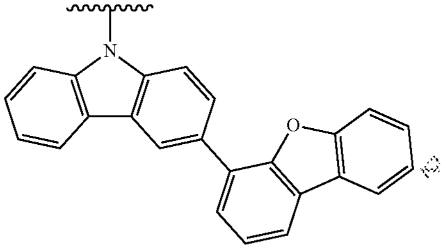
O6
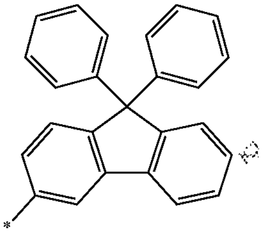
-continued
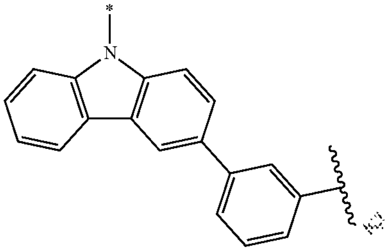
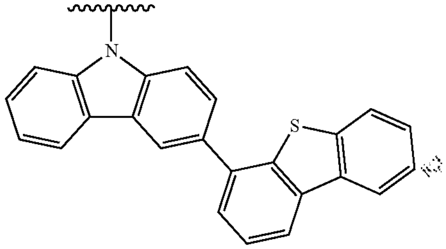
O7
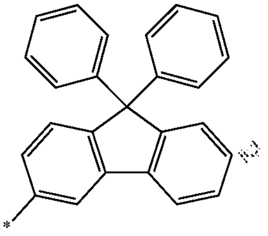
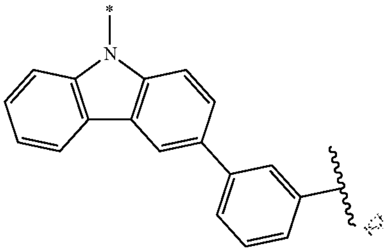
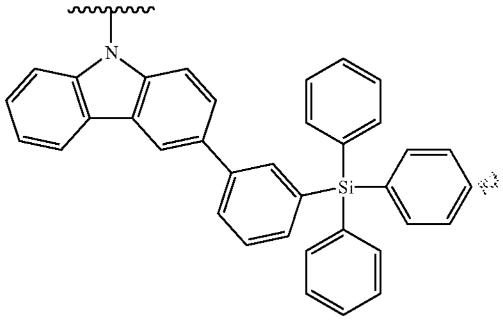
O8
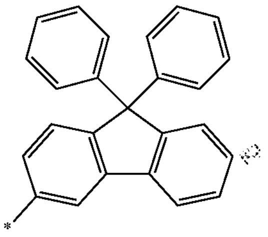

-continued
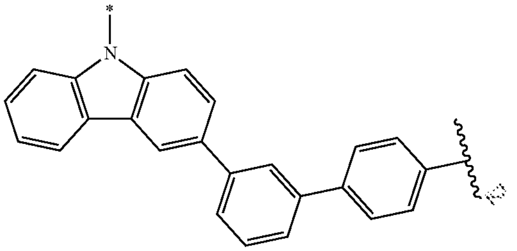
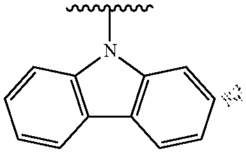
O9
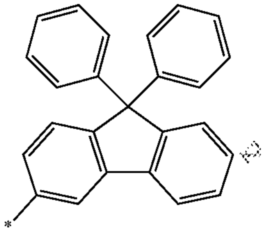
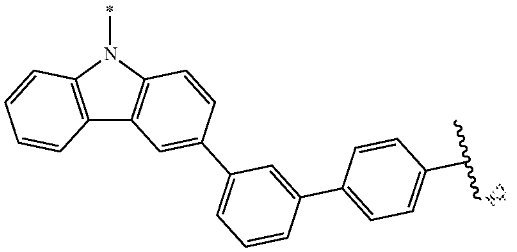
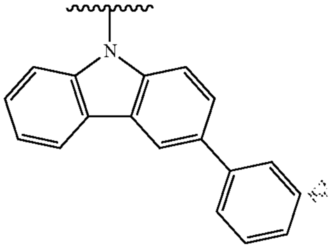
O10
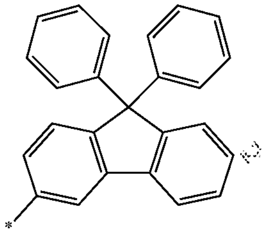
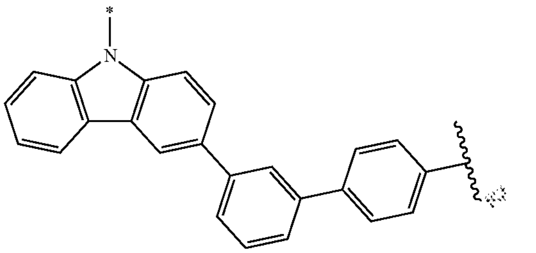
-continued
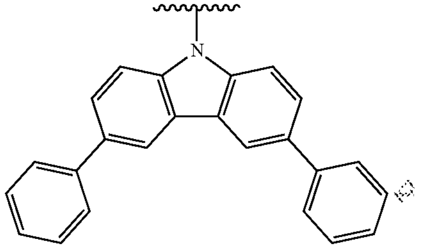
O11
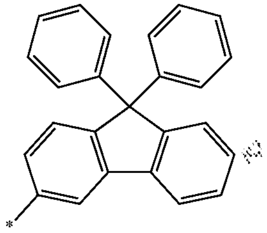
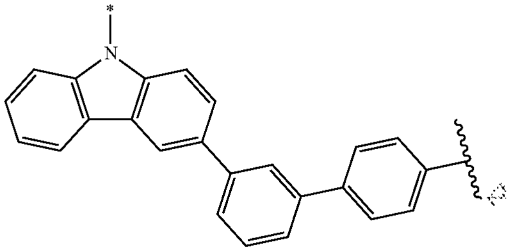
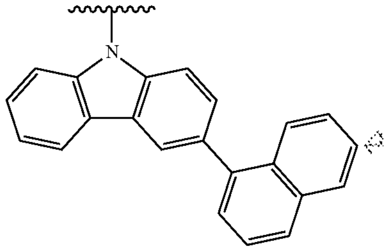
O12
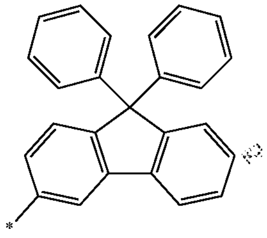
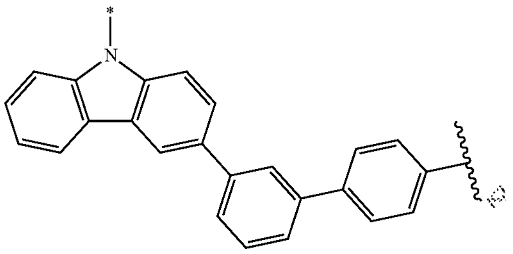

-continued
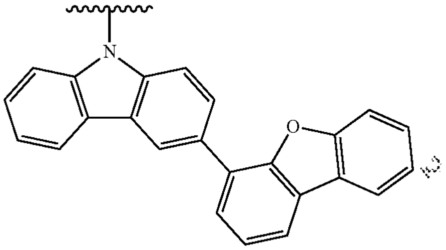
O13
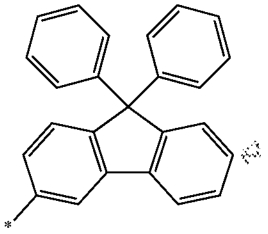
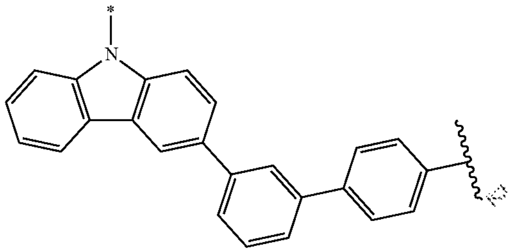
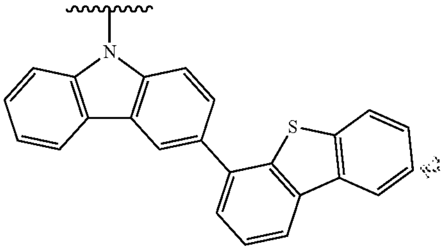
O14
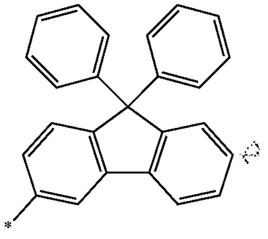
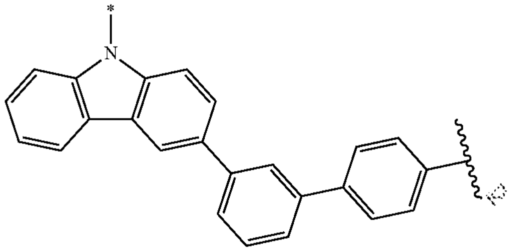
-continued
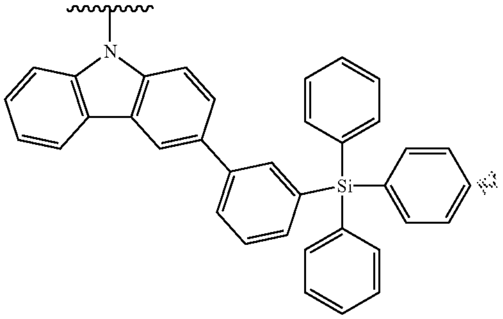
O15
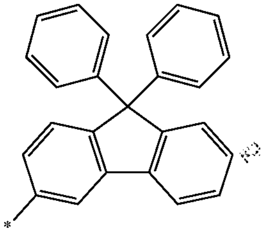
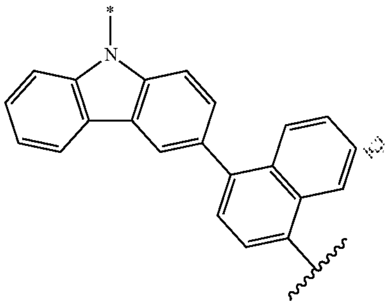
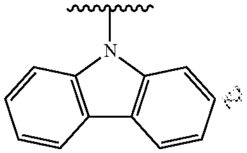
O16
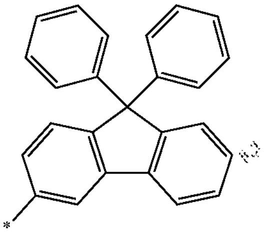
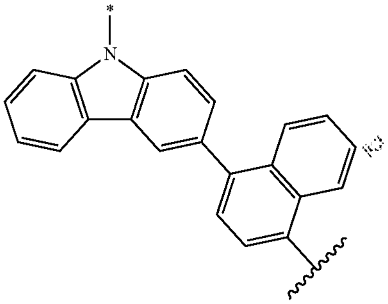

-continued
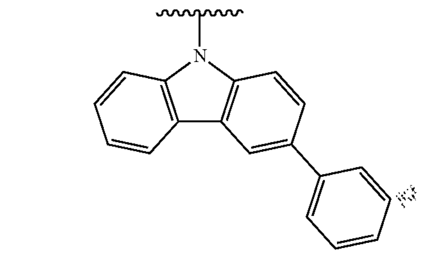
O17
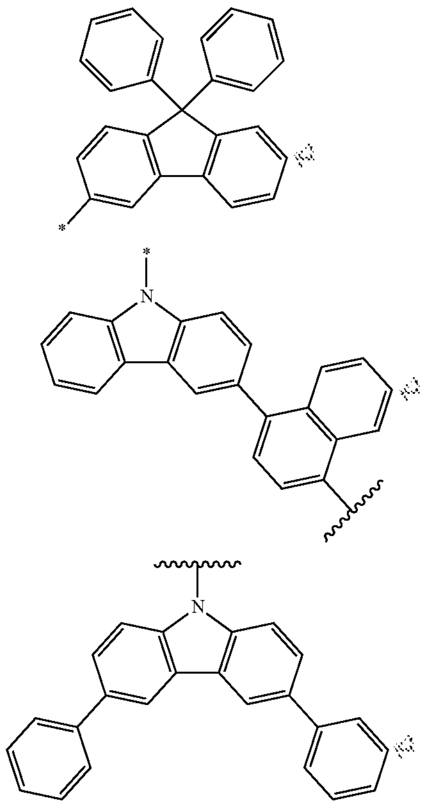
O18
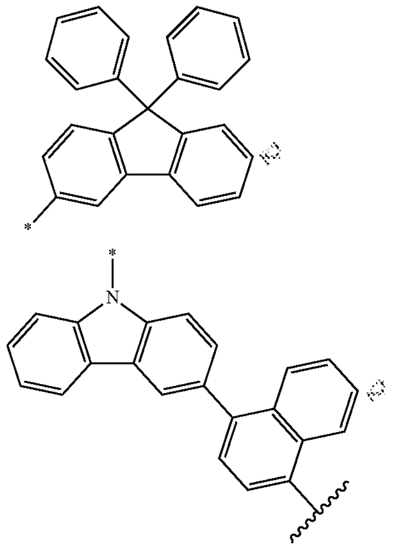
-continued
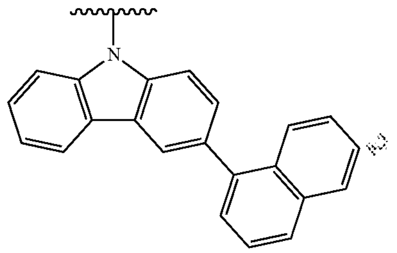
O19
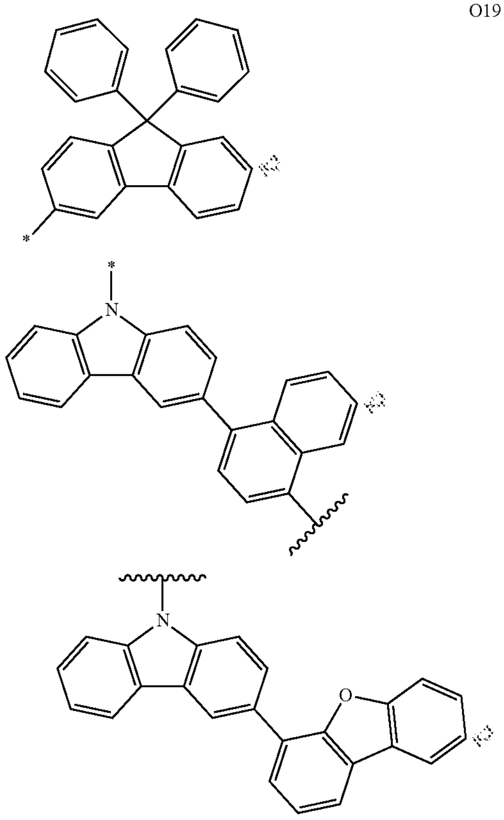
O20
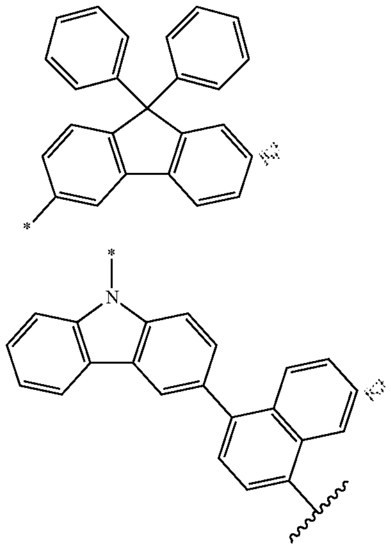

-continued
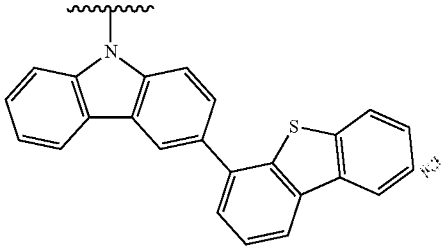
O21
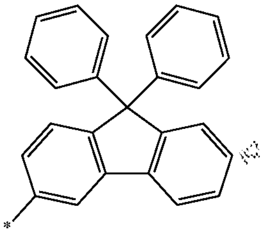
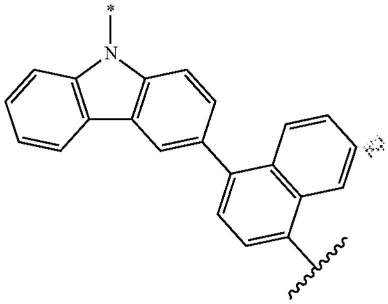
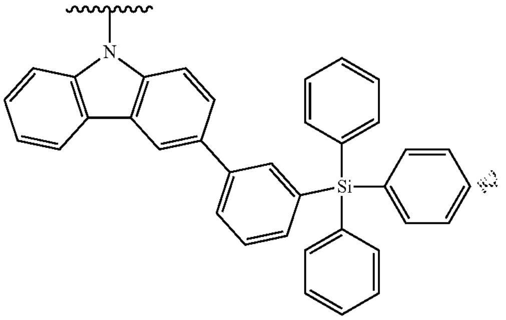
O22
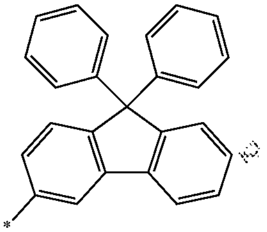
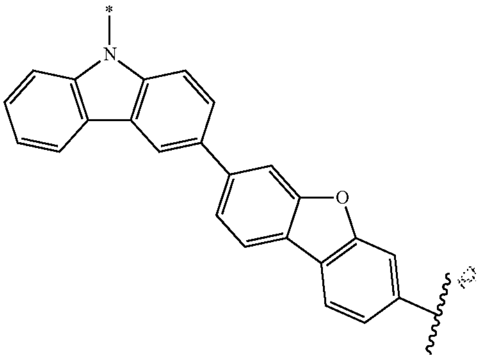
-continued
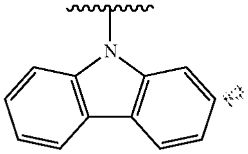
O23
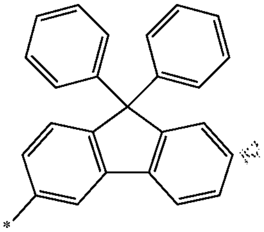
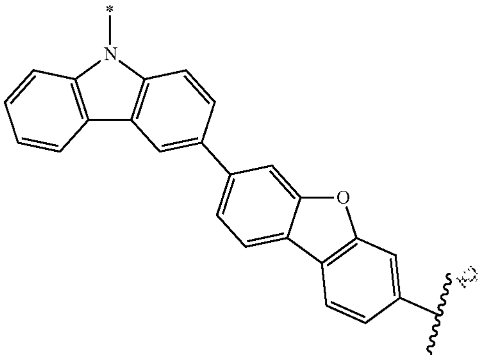
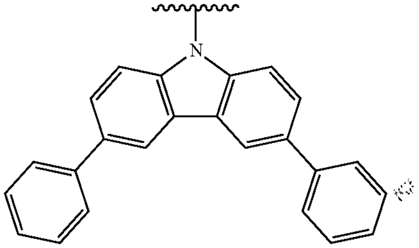
O24
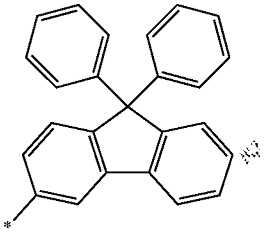
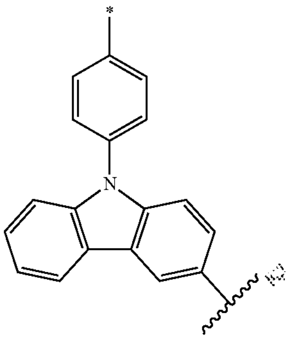

-continued
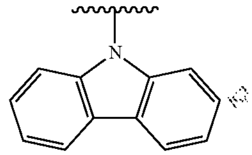
O25
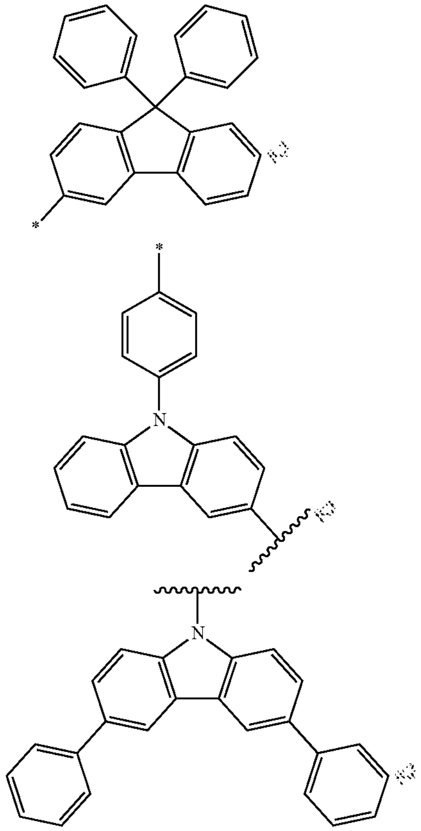
O26
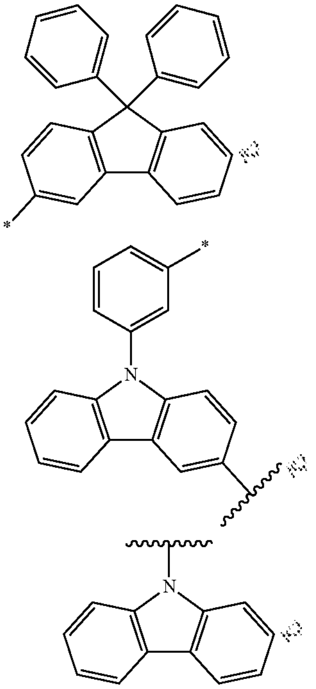
-continued
O27
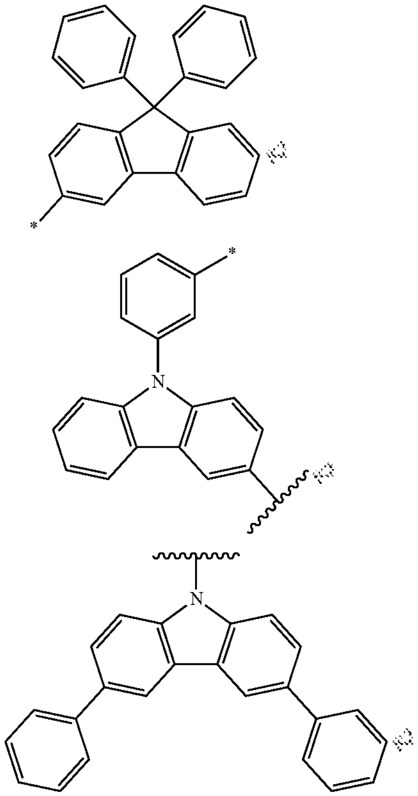
O28
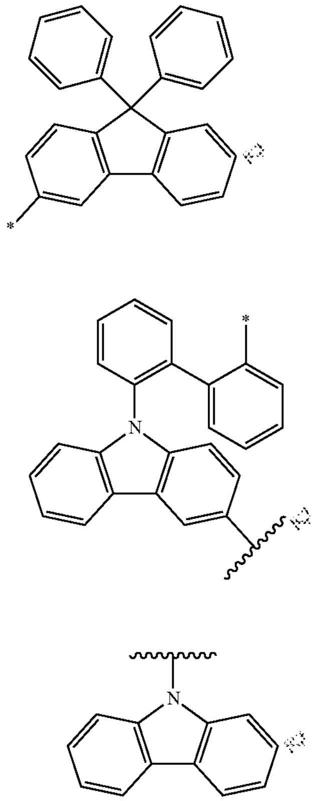

-continued
O29
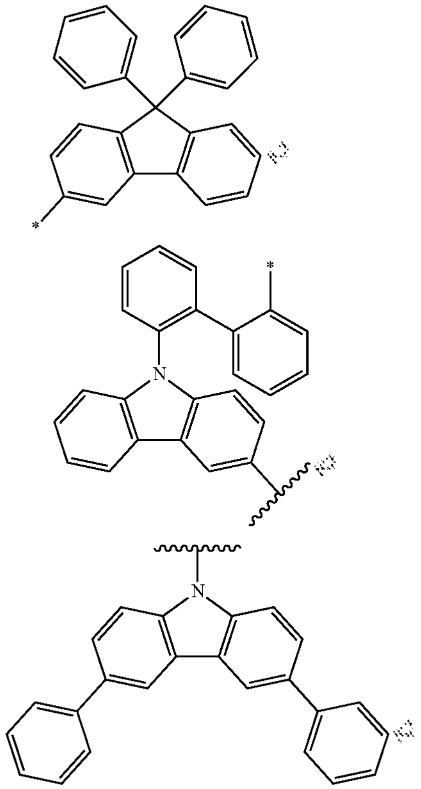
O30
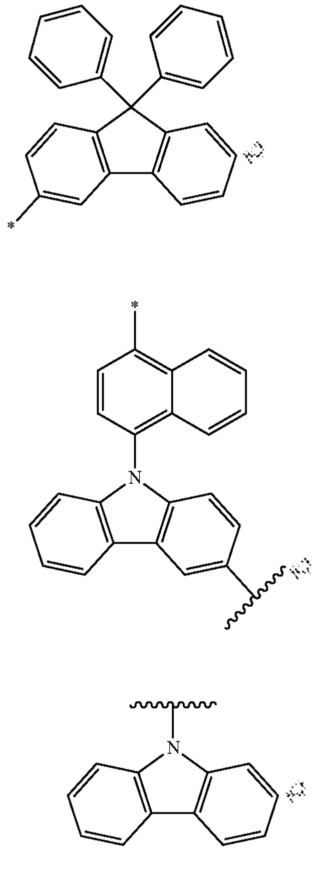
-continued
O31
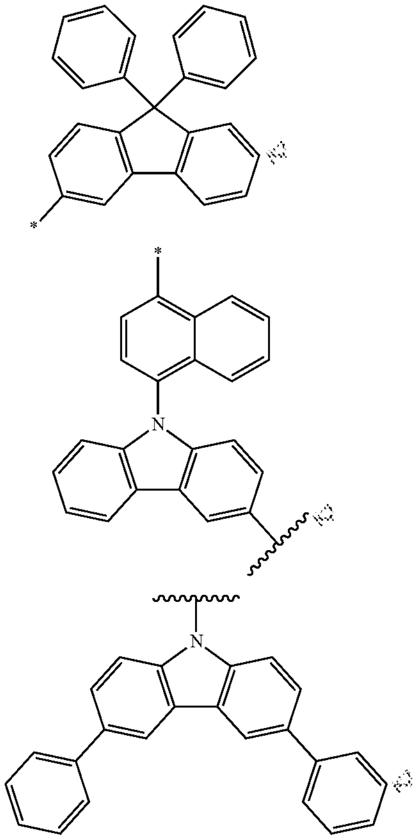
O32
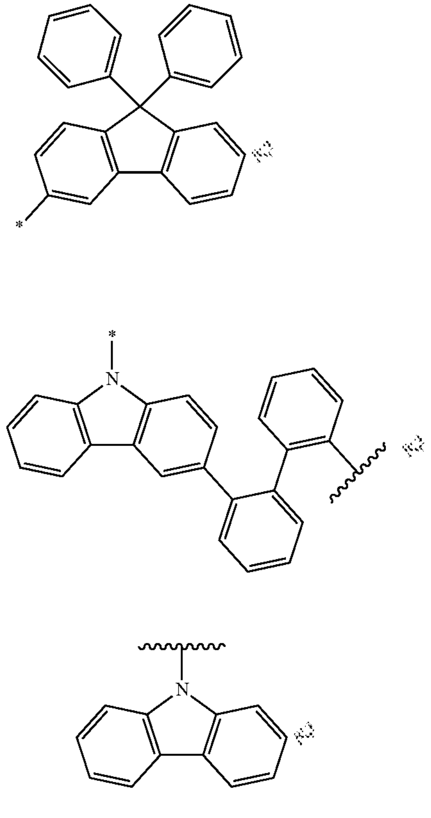

-continued
O33
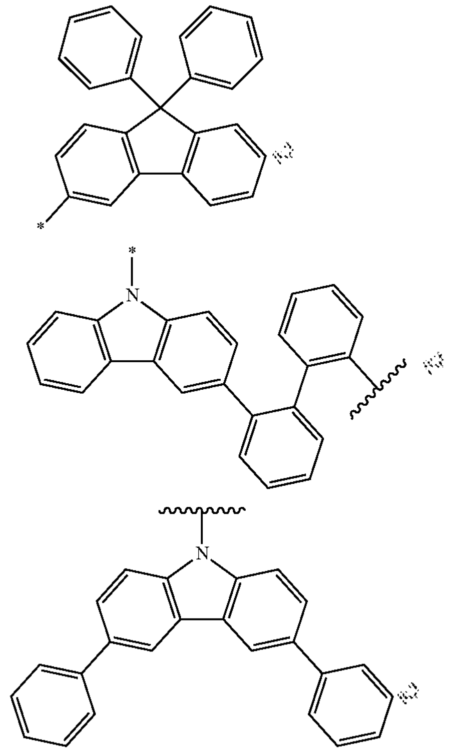
P1
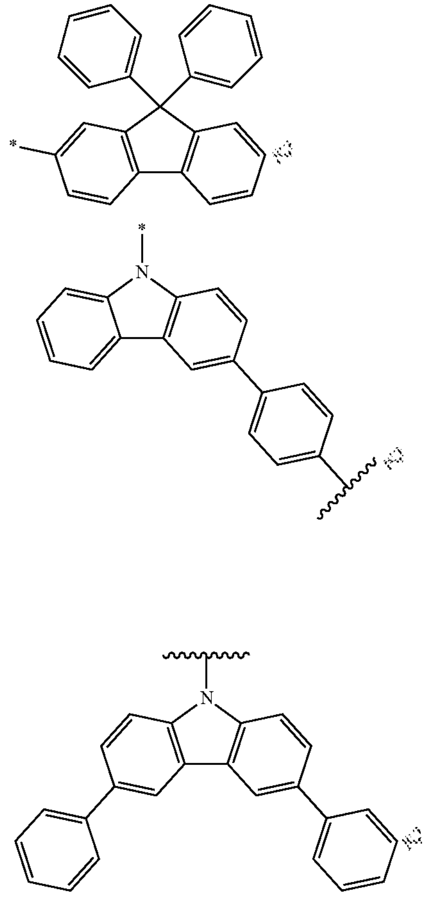
-continued
P2
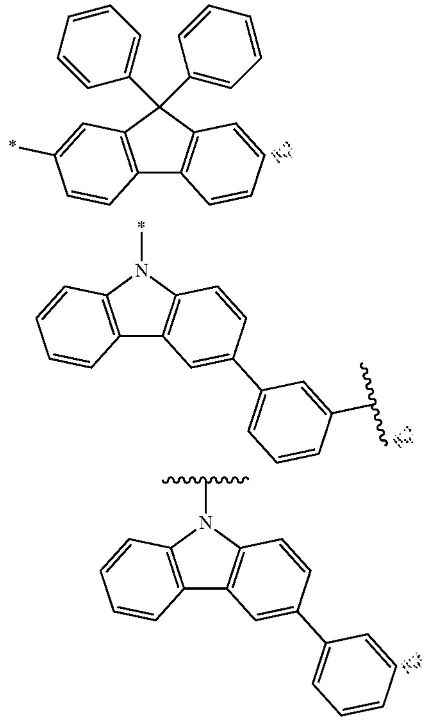
P3
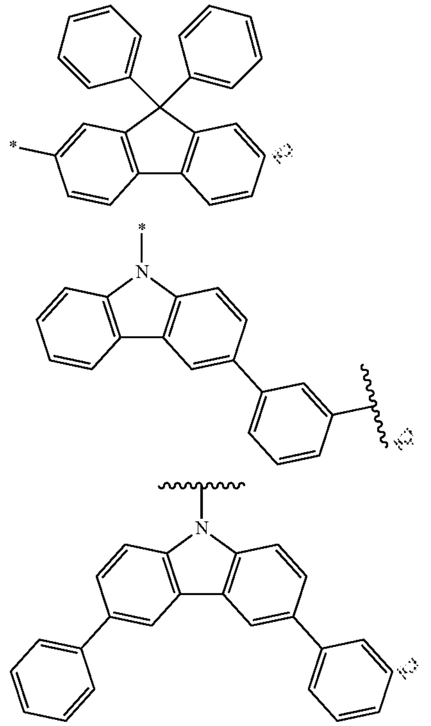
P4
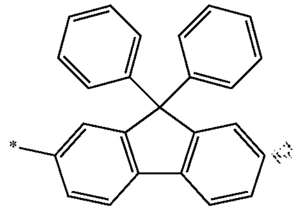

-continued
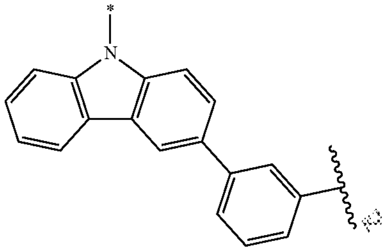
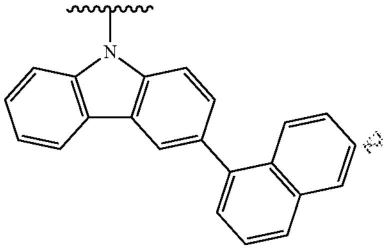
P5
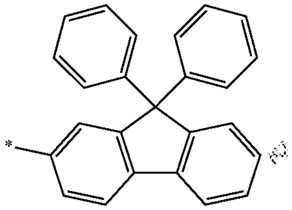
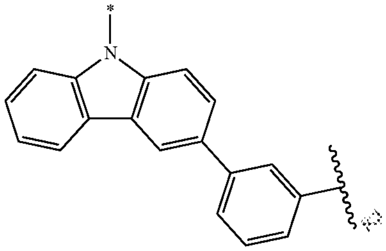
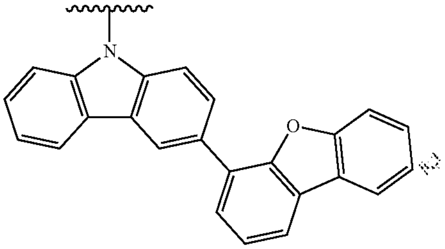
P6
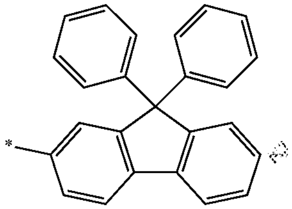
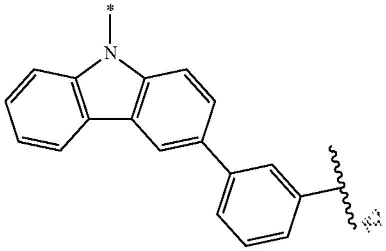
-continued
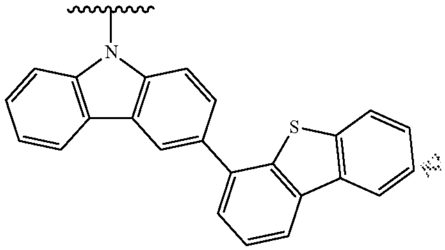
P7
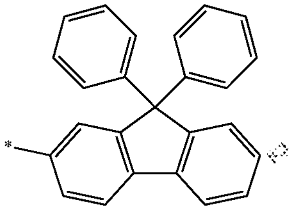
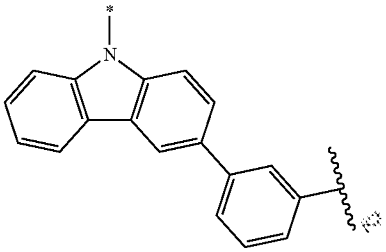
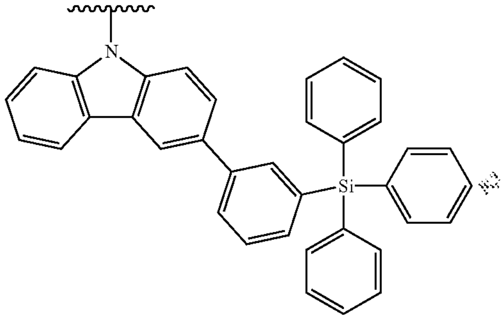
P8
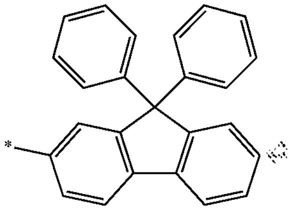
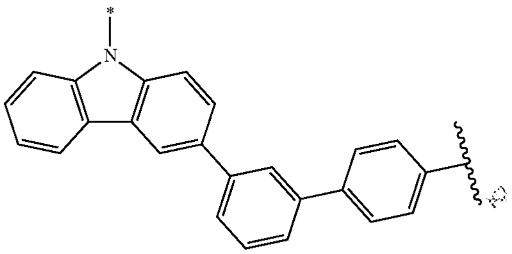
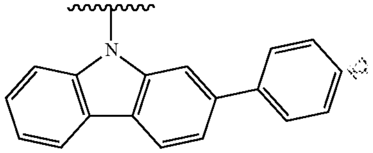

-continued
P9
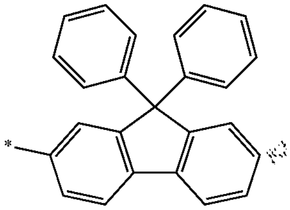
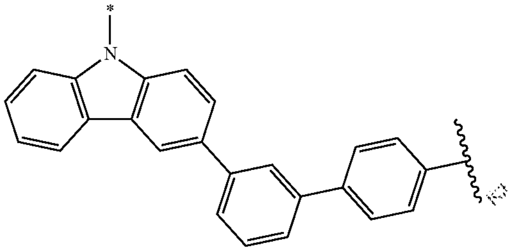
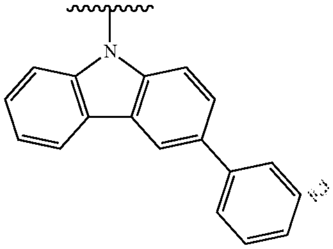
P10
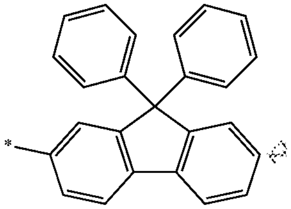
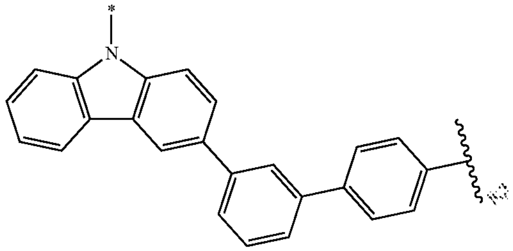
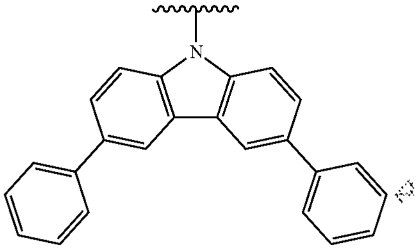
P11
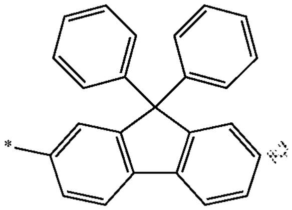
-continued
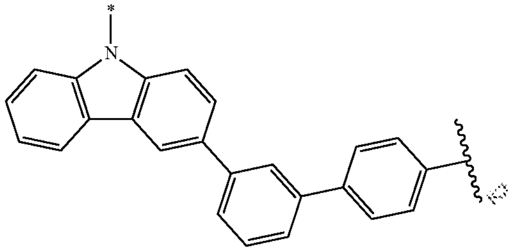
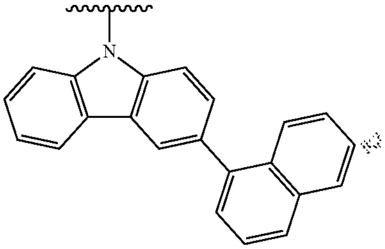
P12
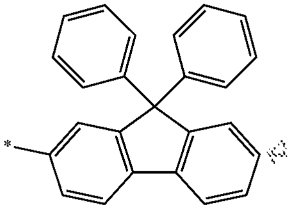
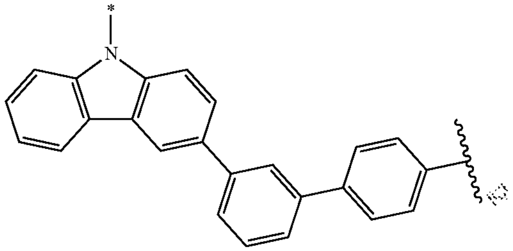
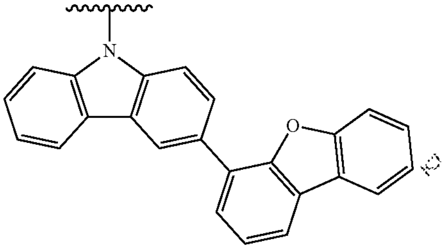
P13
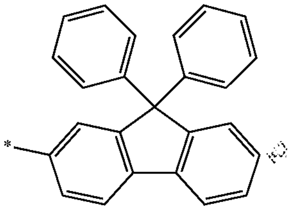
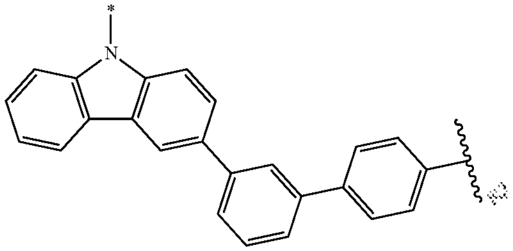

-continued
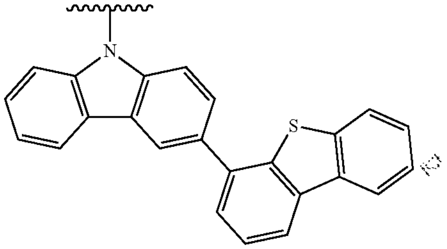
P14
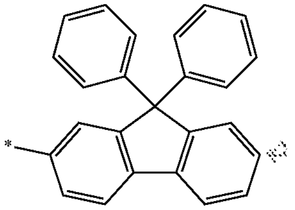
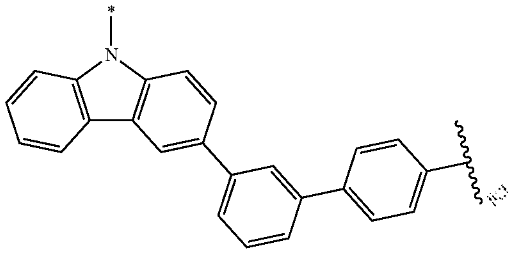
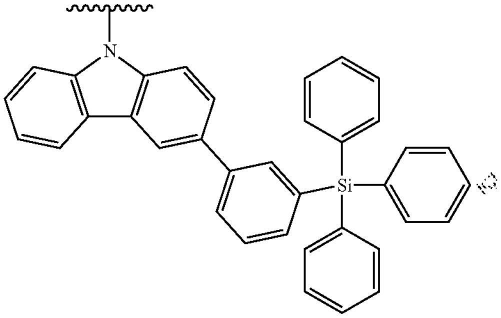
P15
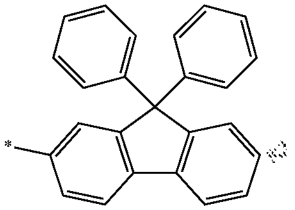
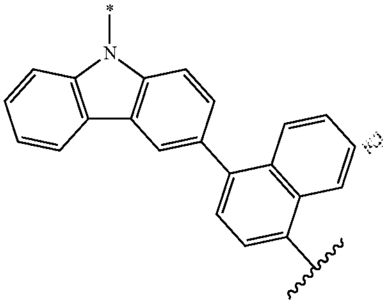
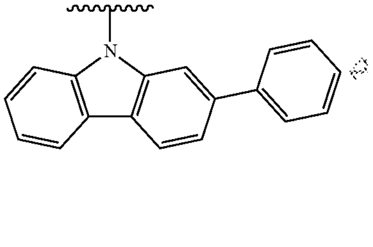
-continued
P16
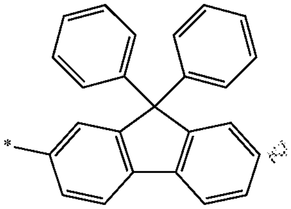
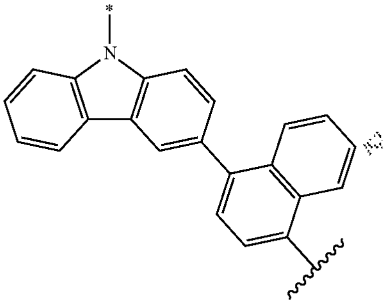
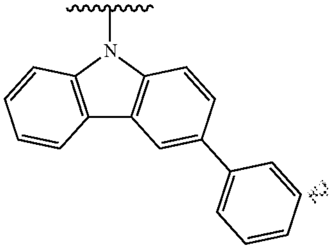
P17
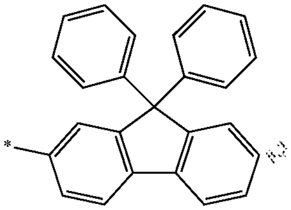
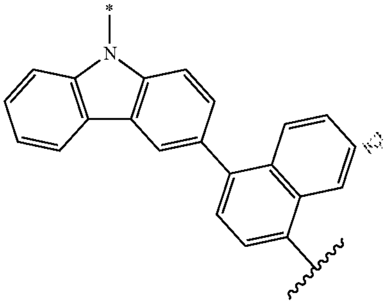
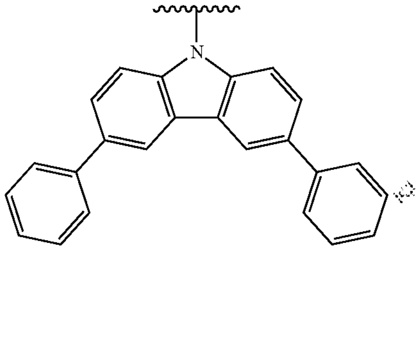

-continued
P18
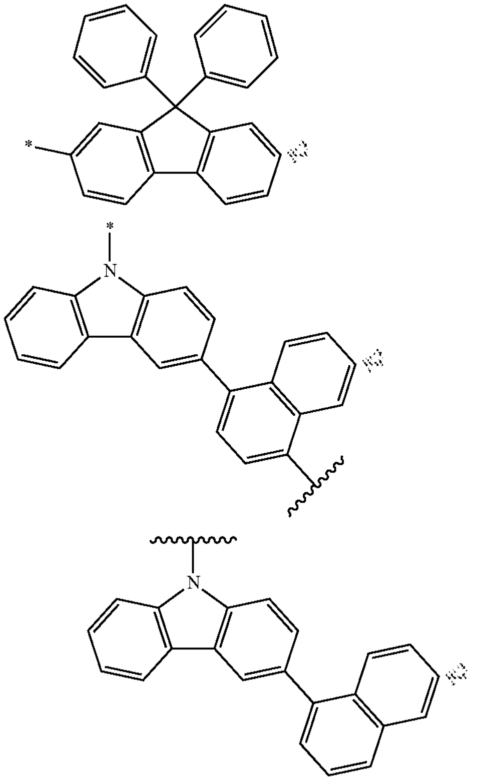
P19
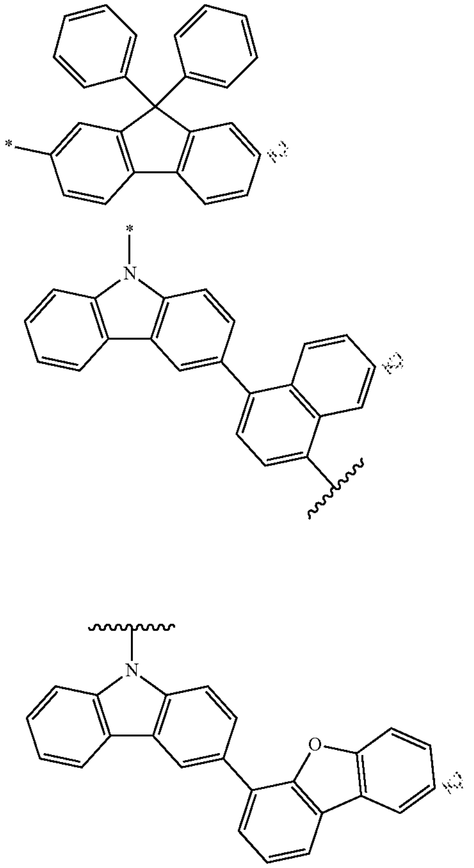
-continued
P20
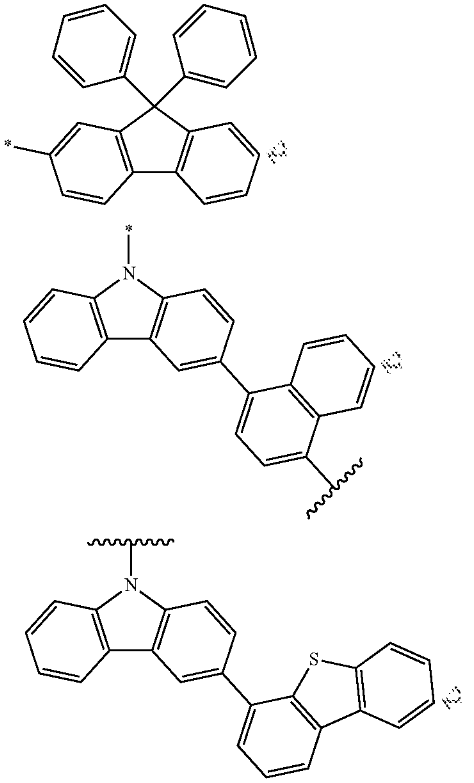
P21
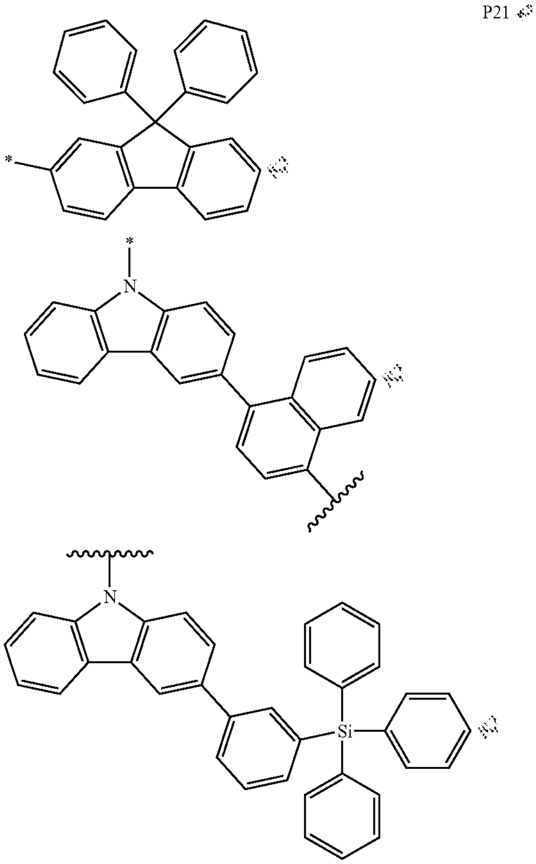

-continued
P22
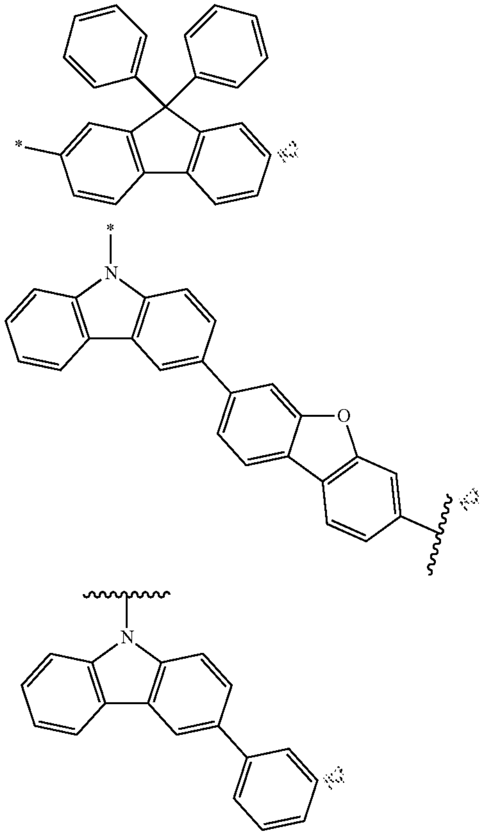
P23
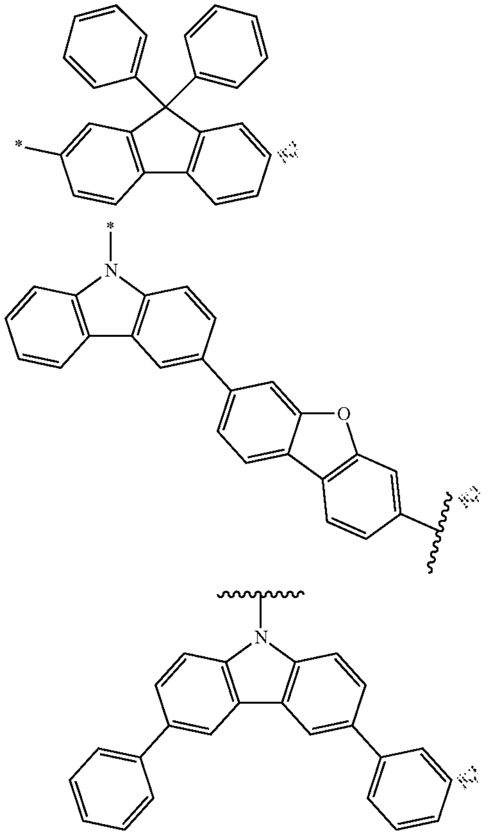
-continued
P24
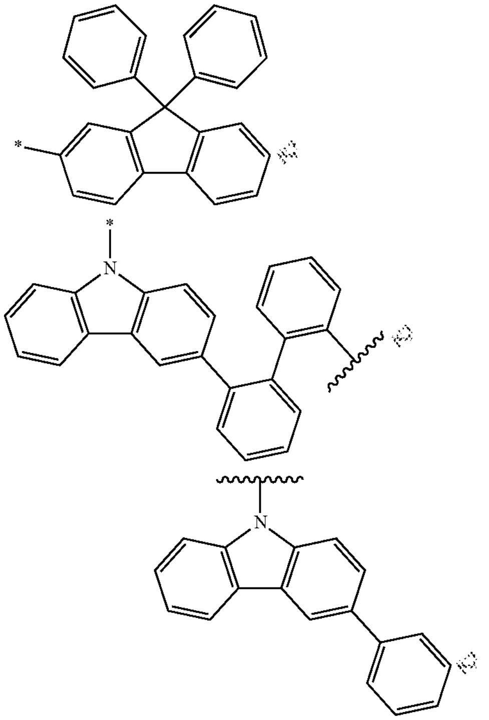
P25
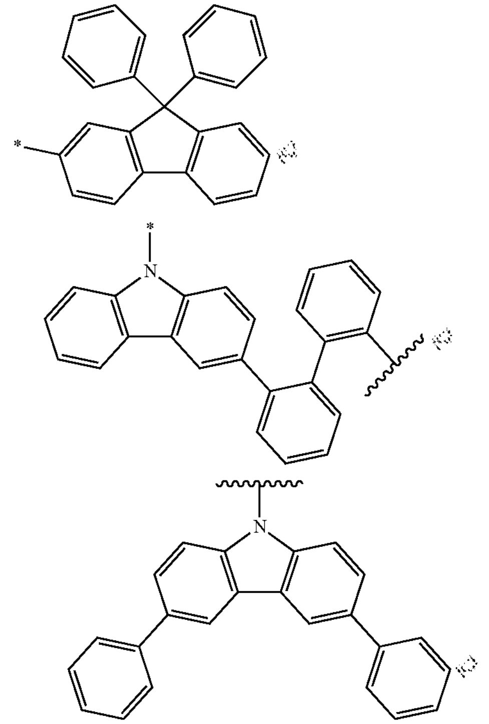
P26
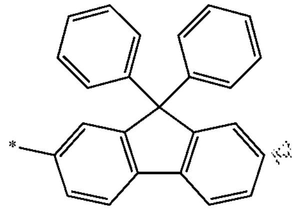

-continued
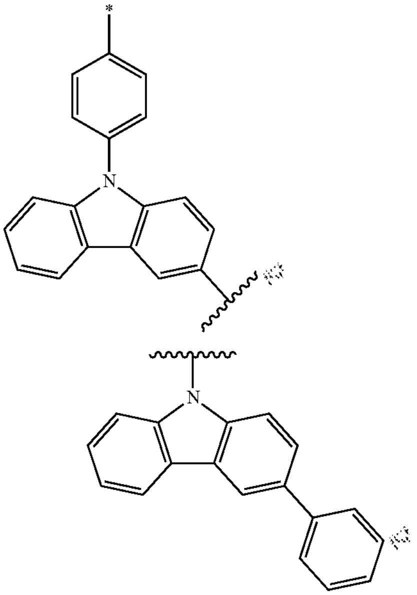
P27
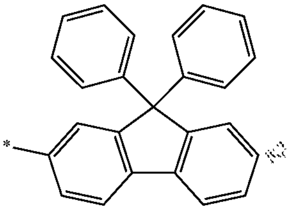
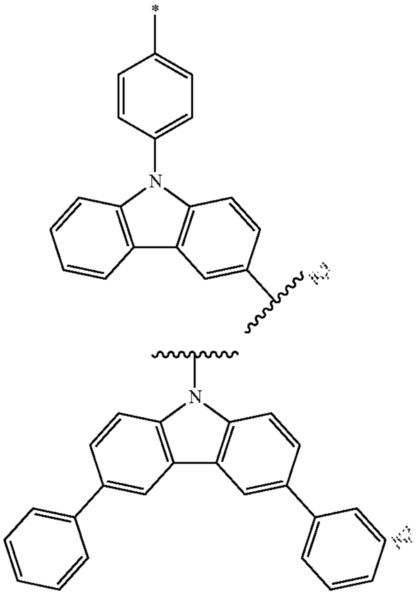
P28
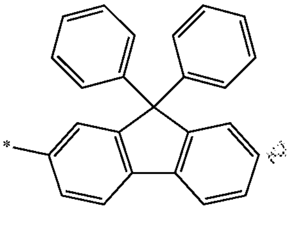
-continued
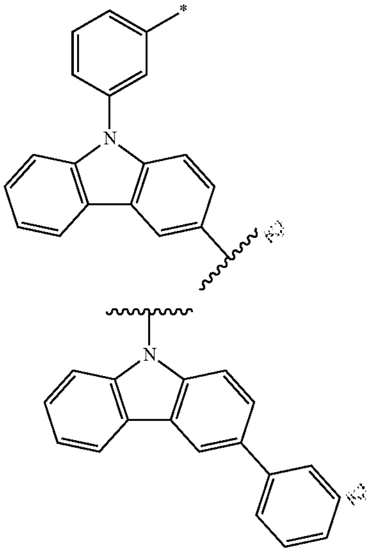
P29
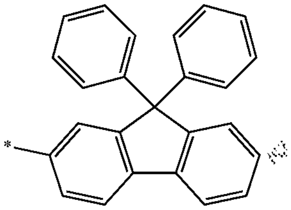
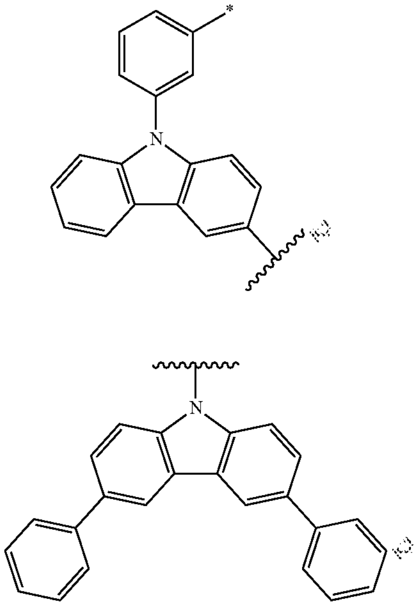
P30
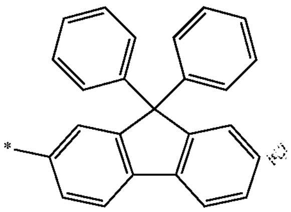

-continued
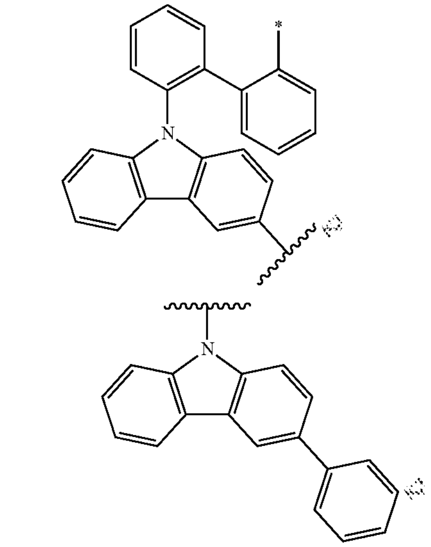
P31
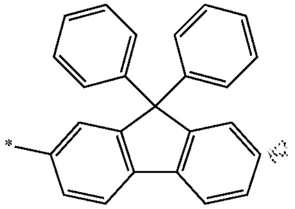
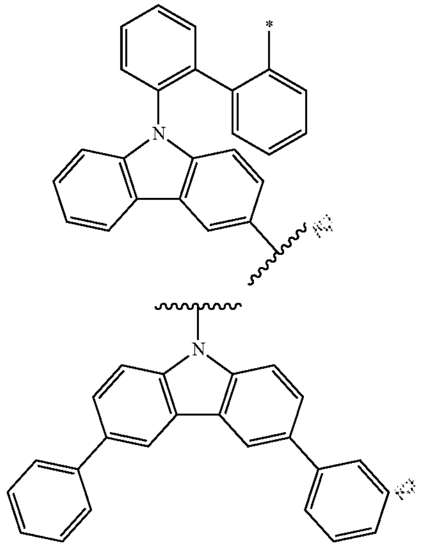
P32
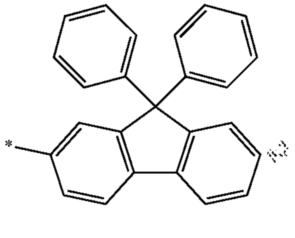
-continued
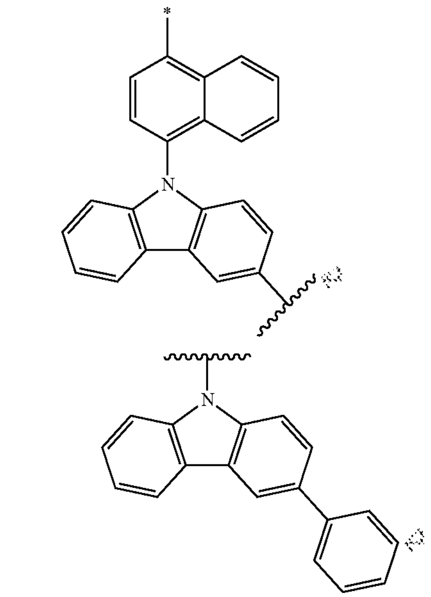
P33
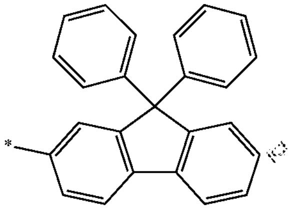
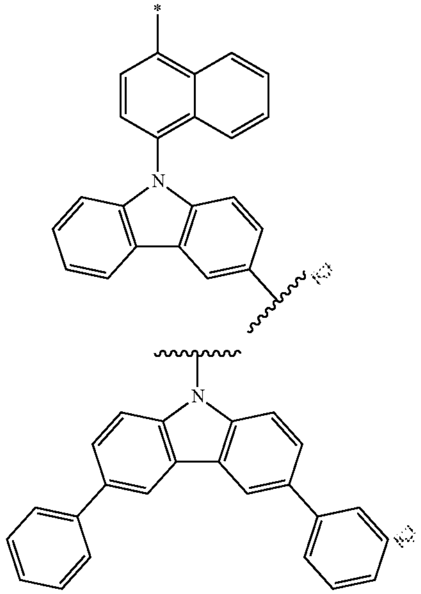
P34
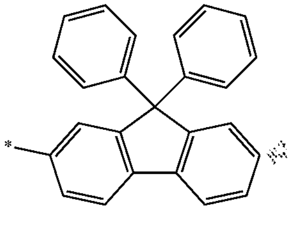

-continued

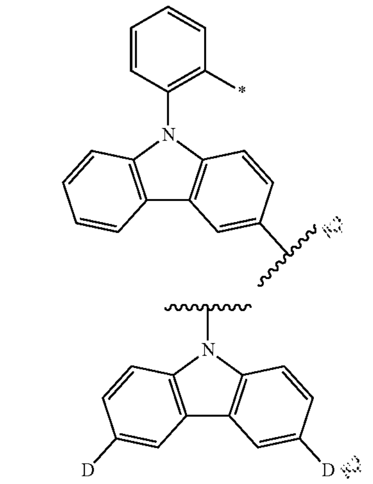

P35

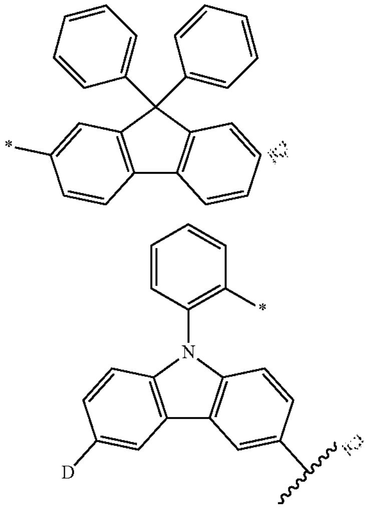

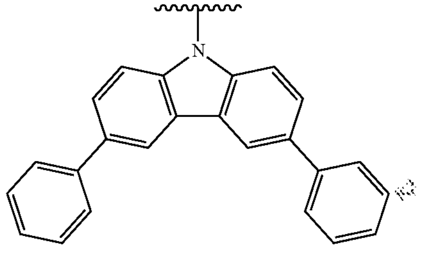

P36

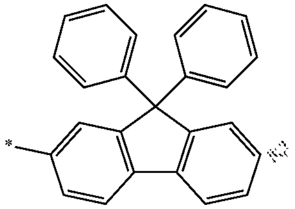

-continued

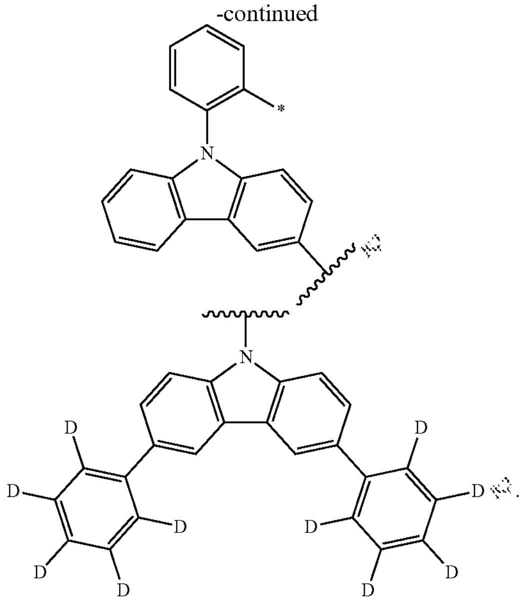

The polycyclic compound represented by Formula 1 according to an embodiment includes a structure in which at least one bis carbazole moiety is connected to a fluorenyl group. In the specification, the bis carbazole moiety may be derived from a structure in which Substituent S2 is connected (linked) to Substituent S1. In addition, the fluorenyl group has the structure in which two aryl groups are connected to (e.g., substituted at) the carbon atom at the 9H-position.

Accordingly, the polycyclic compound of an embodiment may have an excellent or suitable hole transport ability and/or good or suitable material stability. The light emitting element according to an embodiment including the polycyclic compound of an embodiment may exhibit an excellent or suitable service life characteristics.

In some embodiments, the polycyclic compound of an embodiment includes the bis carbazole moiety having a high heat and/or a charge resistance, and thus may be utilized as a hole transport material having a more excellent or suitable service life characteristic while maintaining the hole transport property of the polycyclic derivative.

In some embodiments, the light emitting element ED of an embodiment may further include materials for the hole transport region, which will be described below, in addition to the polycyclic compound of an embodiment as described above.

The hole transport region HTR may include a compound represented by Formula H-1:

Formula H-1

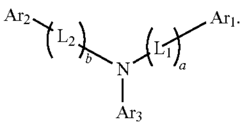

In Formula H-1 above, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms, a and b may each independently be an integer of 0 to 10. In some embodiments, when a or b is an integer of 2 or greater, a plurality of $L_1$'s and $L_2$'s may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In some embodiments, in Formula H-1, $Ar_a$ may be a substituted or unsubstituted aryl group having 6 to 30 ring-forming carbon atoms, or a substituted or unsubstituted heteroaryl group having 2 to 30 ring-forming carbon atoms.

The compound represented by Formula H-1 above may be a monoamine compound. In some embodiments, the compound represented by Formula H-1 above may be a diamine compound in which at least one among $Ar_1$ to $Ar_a$ includes the amine group as a substituent. In some embodiments, the compound represented by Formula H-1 above may be a carbazole-based compound including a substituted or unsubstituted carbazole group in at least one of $Ar_1$ or $Ar_2$, or a fluorene-based compound including a substituted or unsubstituted fluorenyl group in at least one of $Ar_1$ or $Ar_2$.

The compound represented by Formula H-1 may be represented by any one among the compounds of Compound Group H. However, the compounds listed in Compound Group H are examples, and the compounds represented by Formula H-1 are not limited to those represented by Compound Group H:

Compound Group H

H-1-1

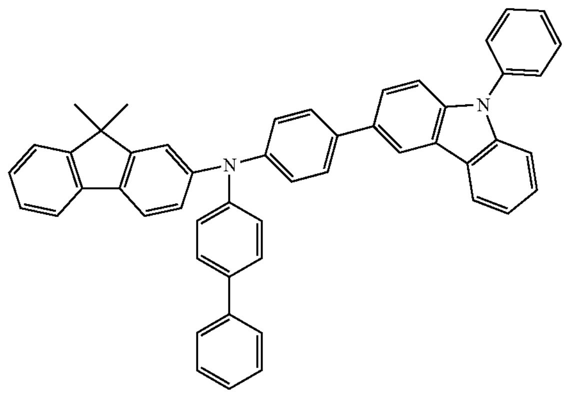

H-1-2

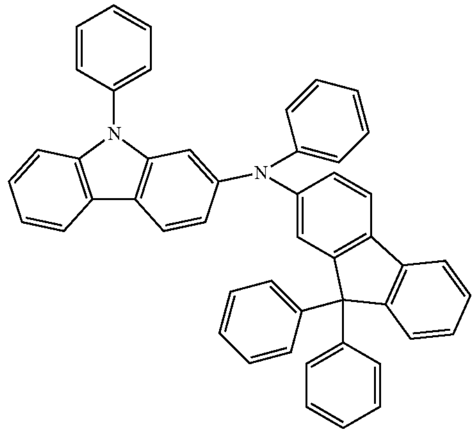

-continued

H-1-3

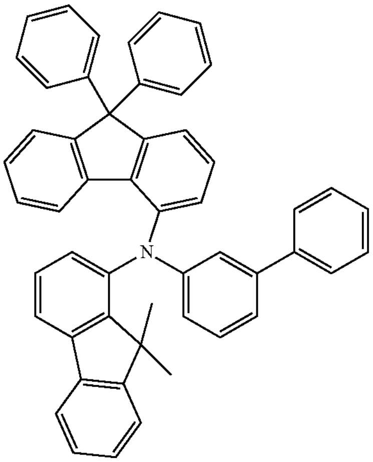

H-1-4

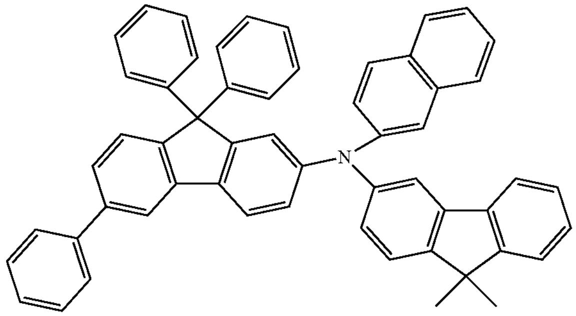

H-1-5

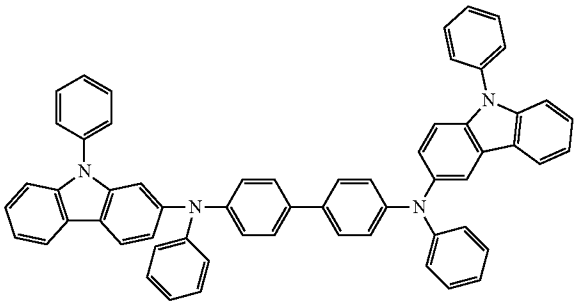

-continued

H-1-6

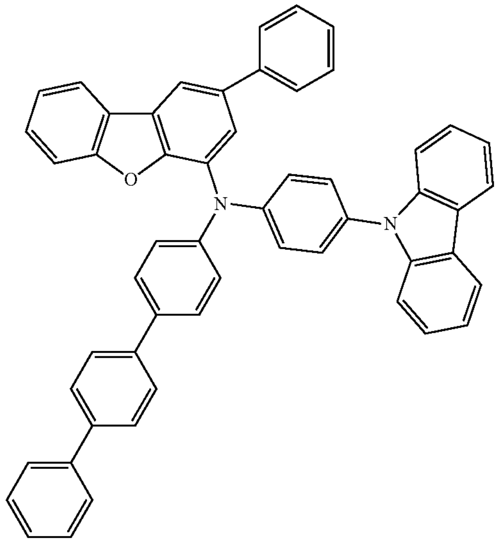

H-1-7

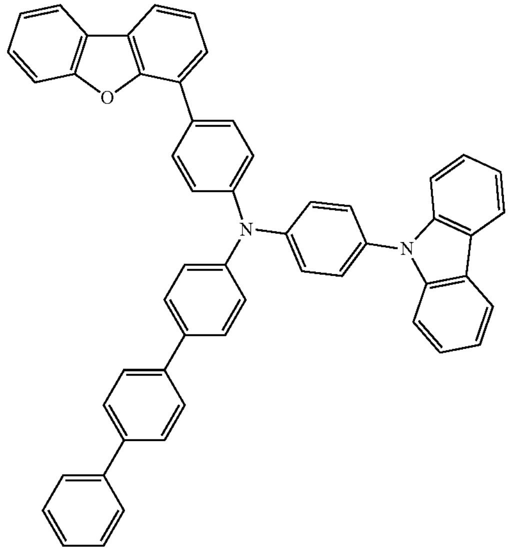

H-1-8

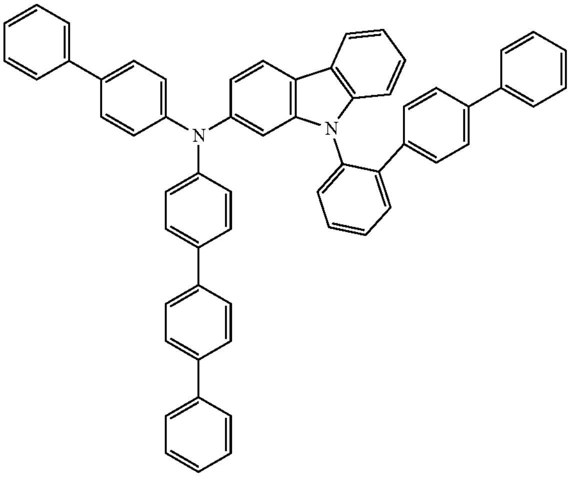

-continued

H-1-9

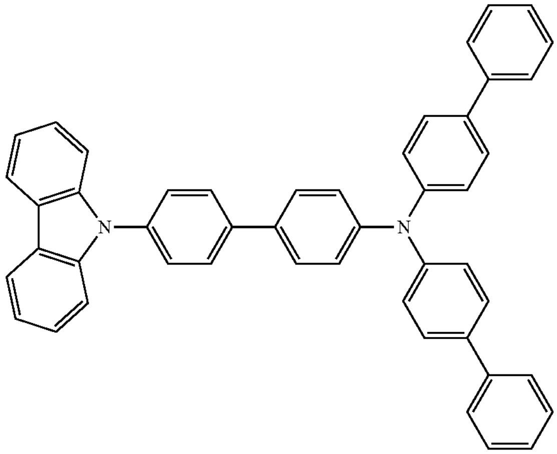

H-1-10

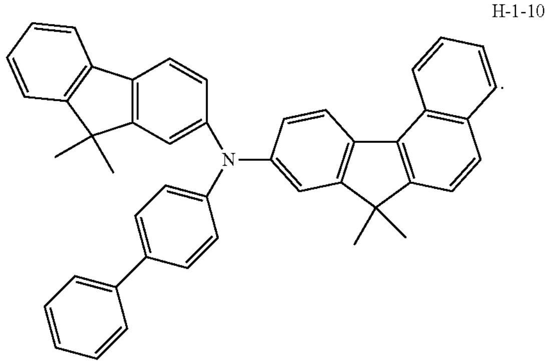

The hole transport region HTR may include a phthalocyanine compound (such as copper phthalocyanine); $N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino]triphenylamine (m-MTDATA), 4,4'4"-tris(N,N-diphenylamino)triphenylamine (TDATA), 4,4',4"-tris[N(2-naphthyl)-N-phenylamino]-triphenylamine (2-TNATA), poly(3,4-ethylene dioxythiophene)/poly(4-styrene sulfonate) (PEDOT/PSS), polyaniline/dodecylbenzene sulfonic acid (PAN I/DBSA), polyaniline/camphor sulfonic acid (PANI/CSA), polyaniline/poly(4-styrene sulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], dipyrazino[2,3-f: 2',3'-h]quinoxaline-2,3,6,7,10,11-hexacarbonitrile (HATCN), etc.

In some embodiments, the hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-Abenzene (mDCP), etc.

The hole transport region HTR may include the above-described compound of the hole transport region in at least one of a hole injection layer HIL, a hole transport layer HTL, or an electron blocking layer EBL.

The thickness of the hole transport region HTR may be about 100 Å to about 10,000 Å, for example, about 100 Å to about 5,000 Å. When the hole transport region HTR includes the hole injection layer HIL, the hole injection layer HIL may have, for example, a thickness of about 30 Å to about 1,000 Å. When the hole transport region HTR includes the hole transport layer HTL, the hole transport layer HTL may have a thickness of about 30 Å to about 1,000 Å. For example, when the hole transport region HTR includes the electron blocking layer EBL, the electron blocking layer EBL may have a thickness of about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be achieved without a substantial increase in a driving voltage.

The hole transport region HTR may further include a charge generating material to increase conductivity in addition to the above-described materials. The charge generating material may be dispersed substantially uniformly or non-uniformly in the hole transport region HTR. The charge generating material may be, for example, a p-dopant. The p-dopant may include at least one of a halogenated metal compound, a quinone derivative, a metal oxide, or a cyano group-containing compound, but embodiments of the present disclosure are not limited thereto. For example, the p-dopant may include metal halides (such as Cul and/or RbI), quinone derivatives (such as tetracyanoquinodimethane (TCNQ) and/or 2,3,5,6-tetrafluoro-7,7'8,8-tetracyanoquinodimethane (F4-TCNQ)), metal oxides (such as tungsten oxide and/or molybdenum oxide), dipyrazino[2,3-f:2',3'-h]quinoxaline-2,3,6,7,10,11-hexacarbonitrile (HATCN), 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), etc., but embodiments of the present disclosure are not limited thereto.

As described above, the hole transport region HTR may further include at least one of the buffer layer or the electron blocking layer EBL in addition to the hole injection layer HIL and the hole transport layer HTL. The buffer layer may compensate for a resonance distance of the wavelength of light emitted from the emission layer EML and may thus increase the light emission efficiency of the device. Materials that may be included in the hole transport region HTR may also be included in the buffer layer. The electron blocking layer EBL may prevent or reduce electron injection from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed of a single material, a single layer formed of a plurality of different materials, or a multilayer structure having a plurality of layers formed of a plurality of different materials.

In the light emitting element ED of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include anthracene derivatives and/or pyrene derivatives.

In each light emitting element ED of embodiments illustrated in FIGS. 3 to 6, the emission layer EML may include a host and a dopant, and the emission layer EML may include a compound represented by Formula E-1. The compound represented by Formula E-1 may be utilized as a fluorescence host material:

Formula E-1

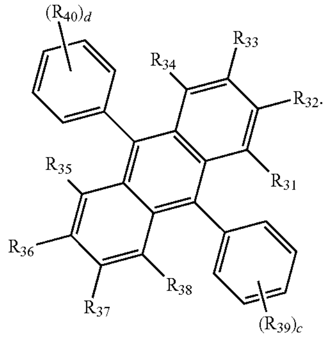

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group having 1 to 10 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. In some embodiments, $R_{31}$ to $R_{40}$ may be bonded to an adjacent group to form a saturated hydrocarbon ring, an unsaturated hydrocarbon ring, a saturated heterocycle, or an unsaturated heterocycle.

In Formula E-1, c and d may each independently be an integer of 0 to 5.

Formula E-1 may be represented by any one among Compound E1 to Compound E19:

E1

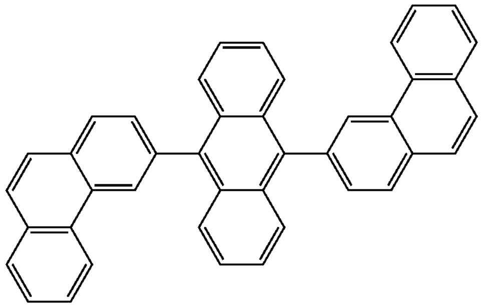

E2

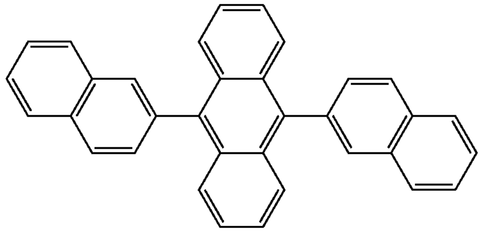

-continued
E3
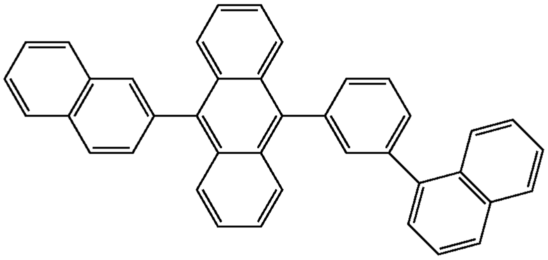
E4
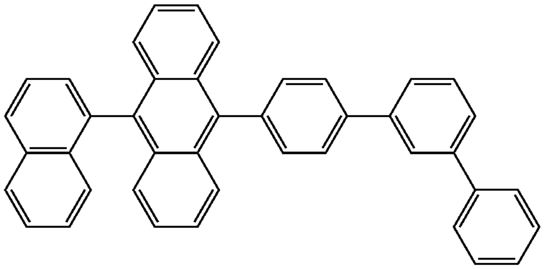
E5
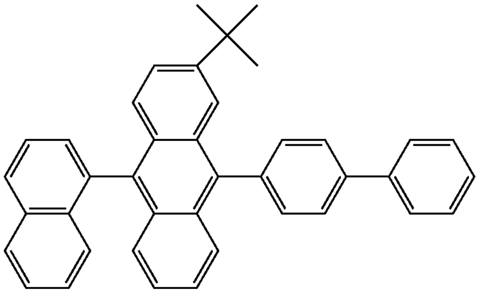
E6
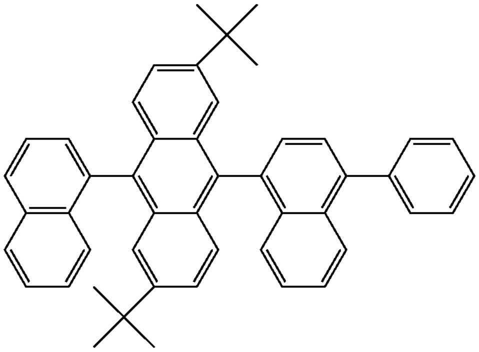
E7
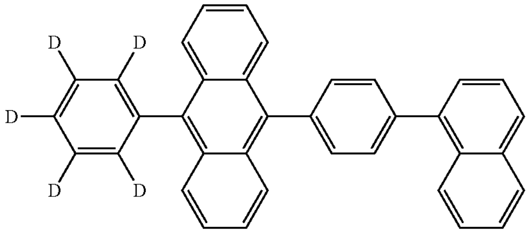
-continued
E8
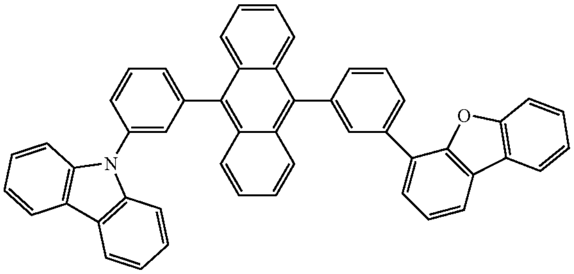
E9
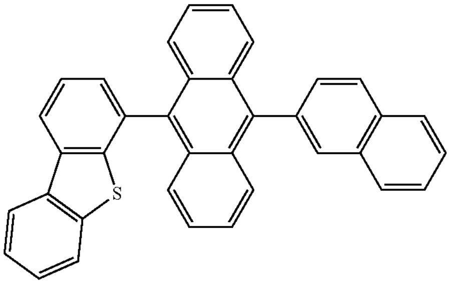
E10
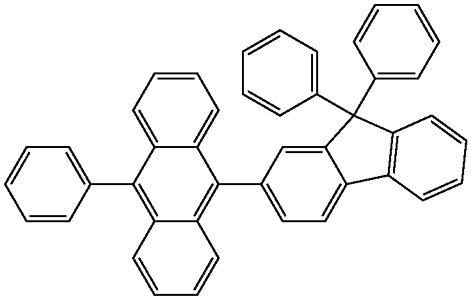
E11
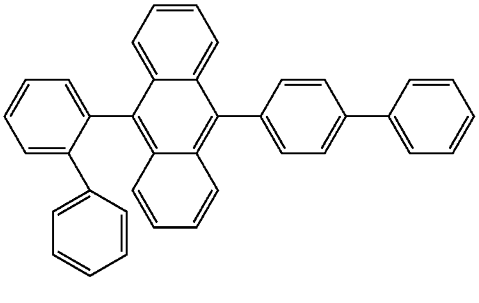
E12
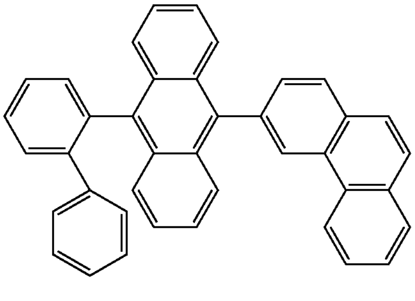

-continued
E13
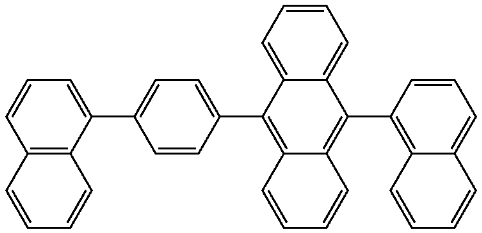
E14
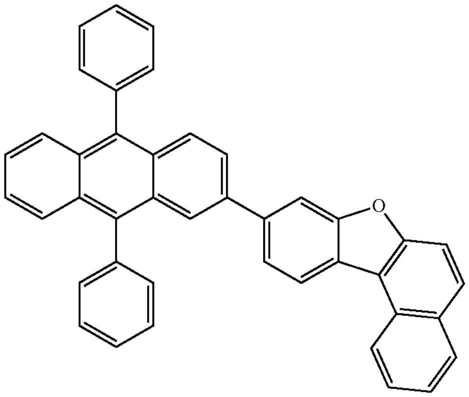
E15
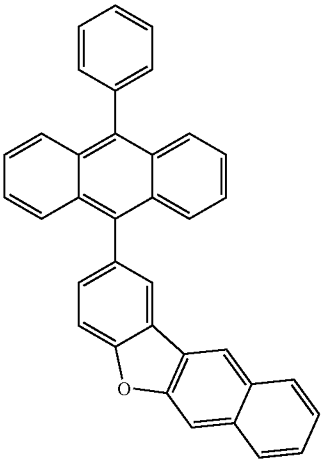
E16
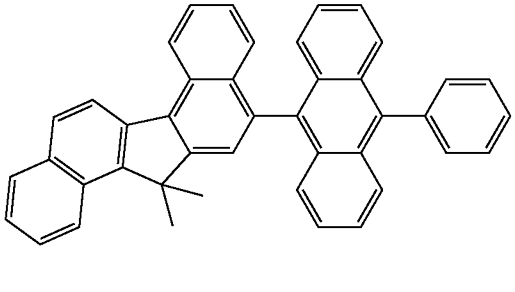
-continued
E17
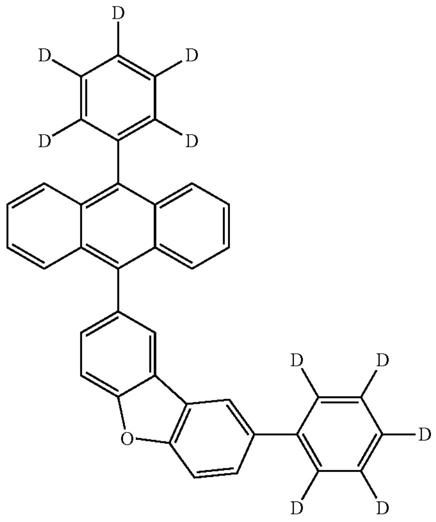
E18
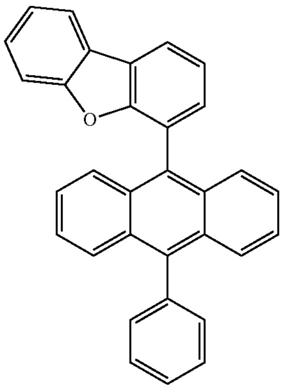
E19
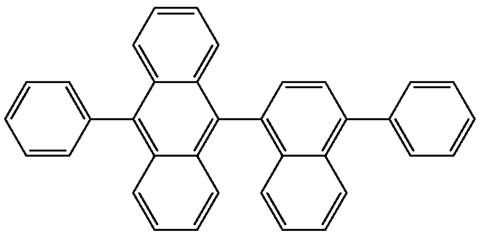.
In an embodiment, the emission layer EML may include a compound represented by Formula E-2a or Formula E-2b. The compound represented by Formula E-2a or Formula E-2b may be utilized as a phosphorescence host material:

Formula E-2a

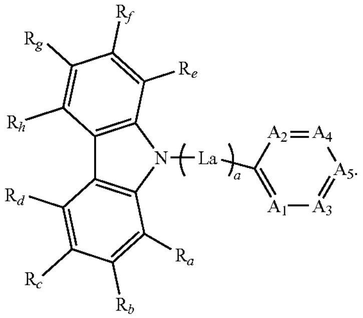

In Formula E-2a, a may be an integer of 0 to 10, $L_a$ may be a direct linkage, a substituted or unsubstituted arylene group having 6 to 30 ring-forming carbon atoms, or a substituted or unsubstituted heteroarylene group having 2 to 30 ring-forming carbon atoms. In some embodiments, when a is an integer of 2 or more, a plurality of $L_a$'s may each independently be a substituted or unsubstituted arylene group having 6 to 30 ring-forming carbon atoms, or a substituted or unsubstituted heteroarylene group having 2 to 30 ring-forming carbon atoms.

In some embodiments, in Formula E-2a, $A_1$ to $A_5$ may each independently be N or $CR_j$. $R_a$ to $R_j$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. $R_a$ to $R_i$ may be bonded to an adjacent group to form a hydrocarbon ring or a heterocycle containing N, O, S, etc. as a ring-forming atom.

In some embodiments, in Formula E-2a, two or three selected from among $A_1$ to $A_5$ may be N, and the rest may be $CR_j$.

Formula E-2b $$(Cbz1\frac{}{}\!\!)\!-\!\!(L_b)_b\!-\!\!(Cbz2).$$

In Formula E-2b, Cbz1 and Cbz2 may each independently be an unsubstituted carbazole group, or a carbazole group substituted with an aryl group having 6 to 30 ring-forming carbon atoms. $L_b$ may be a direct linkage, a substituted or unsubstituted arylene group having 6 to 30 ring-forming carbon atoms, or a substituted or unsubstituted heteroarylene group having 2 to 30 ring-forming carbon atoms. In some embodiments, b may be an integer of 0 to 10, and when b is an integer of 2 or more, a plurality of $L_b$'s may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be represented by any one among the compounds of Compound Group E-2. However, the compounds listed in Compound Group E-2 are examples, and the compound represented by Formula E-2a or Formula E-2b is not limited to those represented by Compound Group E-2:

Compound Group E-2

E-2-1

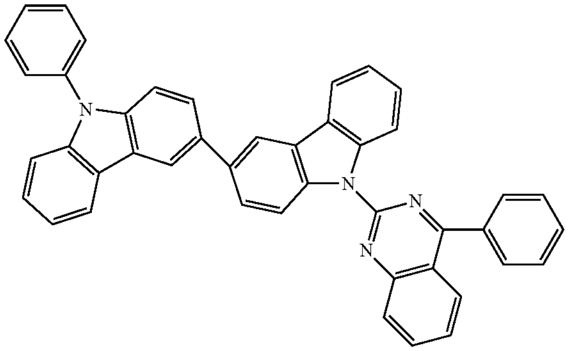

E-2-2

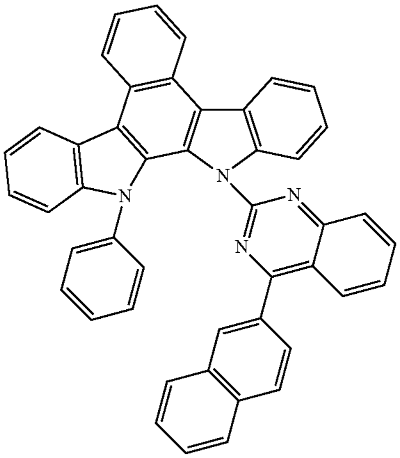

E-2-3

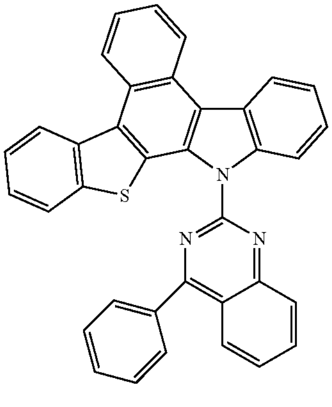

E-2-4
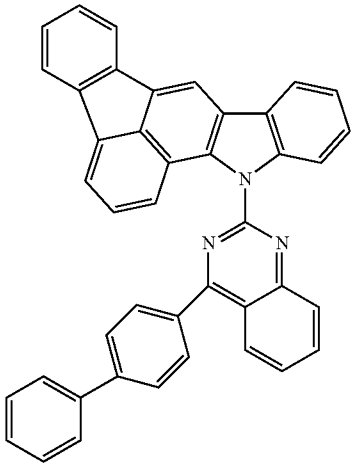
E-2-5
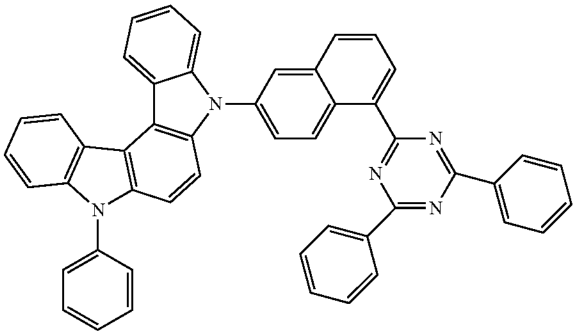
E-2-6
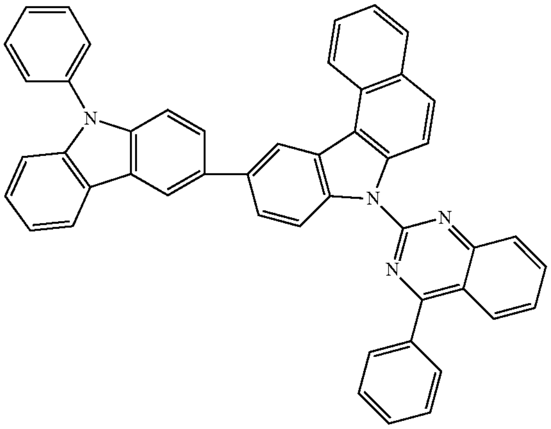
E-2-7
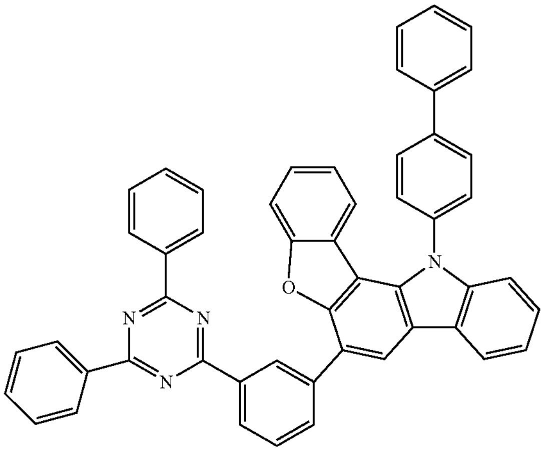
E-2-8
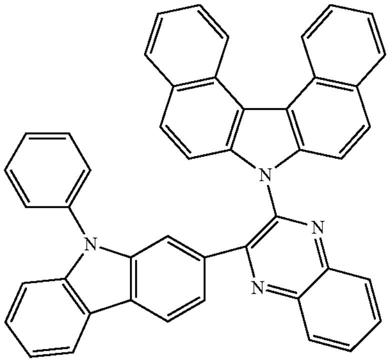
E-2-9
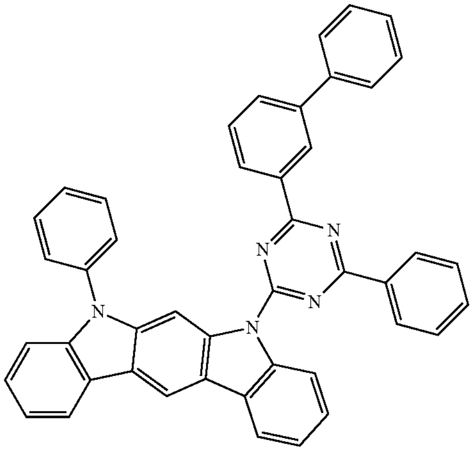

-continued
E-2-10
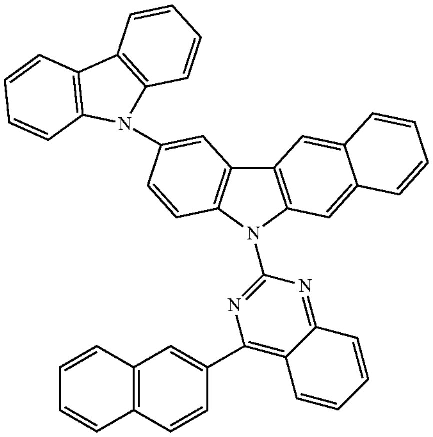
E-2-11
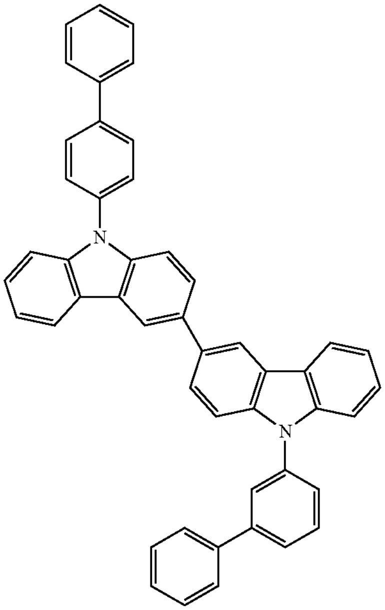
E-2-12
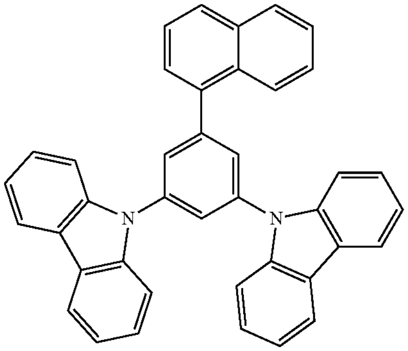
-continued
E-2-13
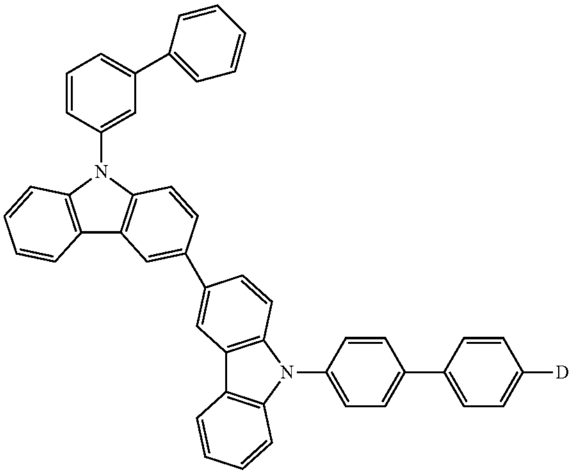
E-2-14
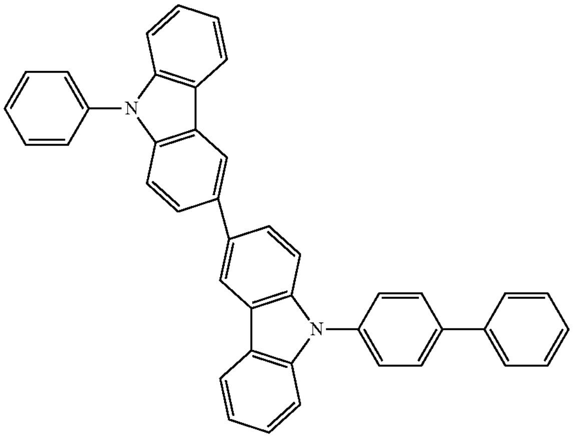
E-2-15
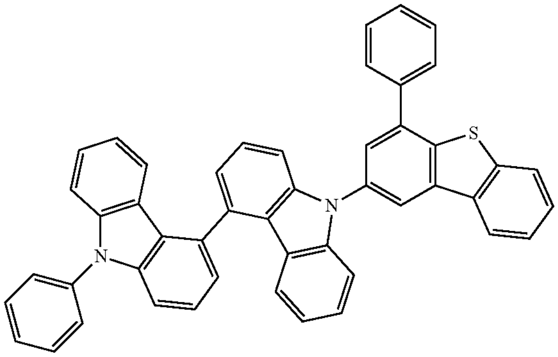

E-2-16
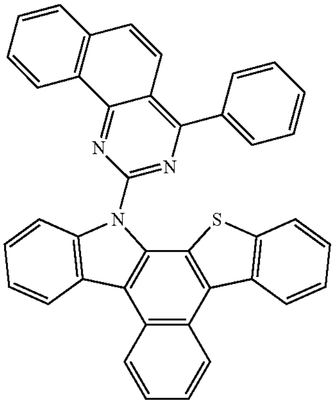
E-2-17
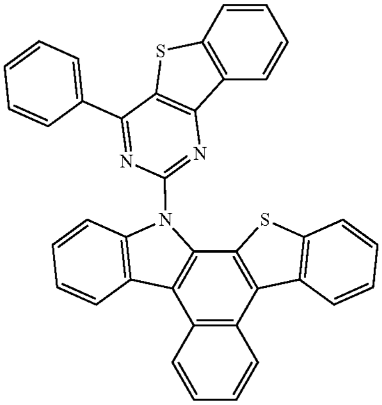
E-2-18
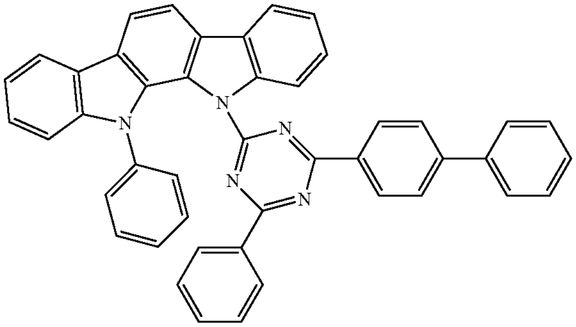
E-2-19
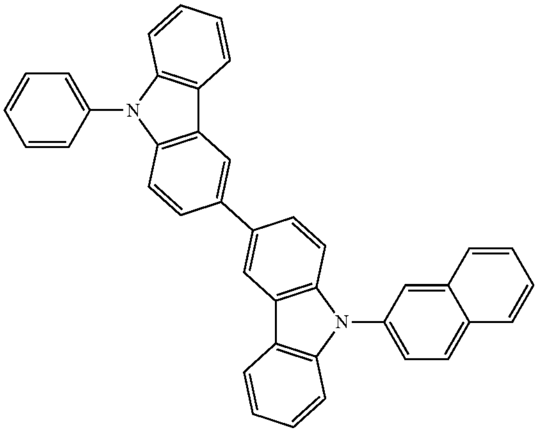
E-2-20
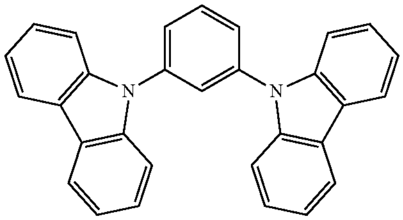
E-2-21
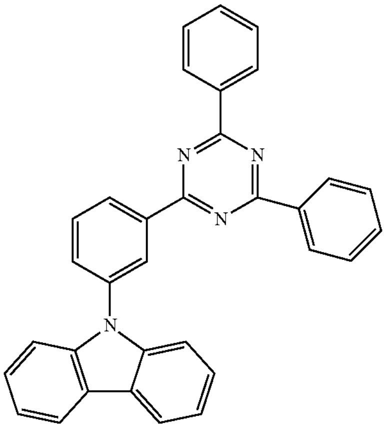
E-2-22
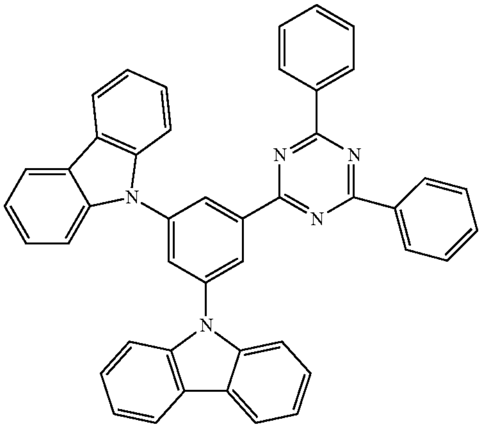
E-2-23
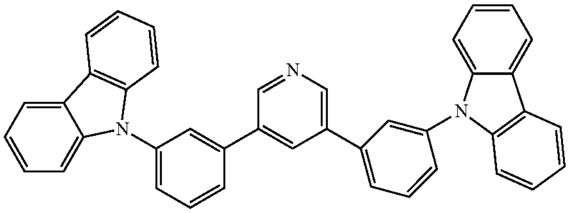

-continued

E-2-24

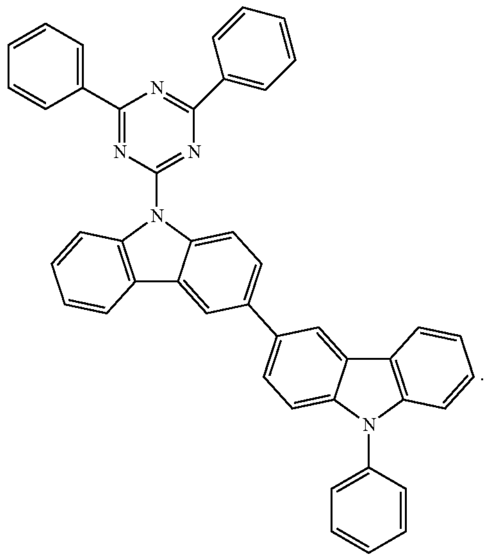

The emission layer EML may further include any suitable material in the art as a host material. For example, the emission layer EML may include, as a host material, at least one of bis[2-(diphenylphosphino)phenyl]ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, the embodiment of the present disclosure is not limited thereto, for example, tris(8-hydroxyquinolino)aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be utilized as a host material.

The emission layer EML may include a compound represented by Formula M-a or Formula M-b. The compound represented by Formula M-a or Formula M-b may be utilized as a phosphorescence dopant material:

Formula M-a

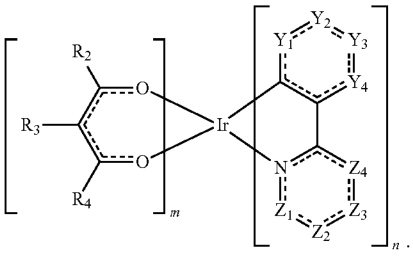

In Formula M-a above, $Y_1$ to $Y_4$ and $Z_1$ to $Z_4$ may each independently be $CR_1$ or N, $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be utilized as a phosphorescence dopant.

The compound represented by Formula M-a may be represented by any one among Compound M-a1 to Compound M-a25. However, Compounds M-a1 to M-a25 are examples, and the compound represented by Formula M-a is not limited to those represented by Compounds M-a1 to M-a25:

M-a1

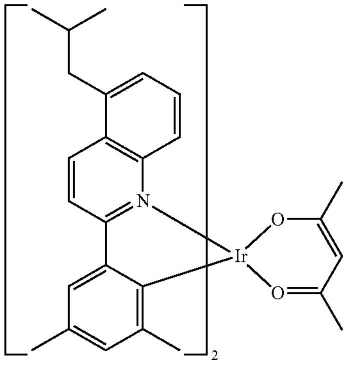

M-a2

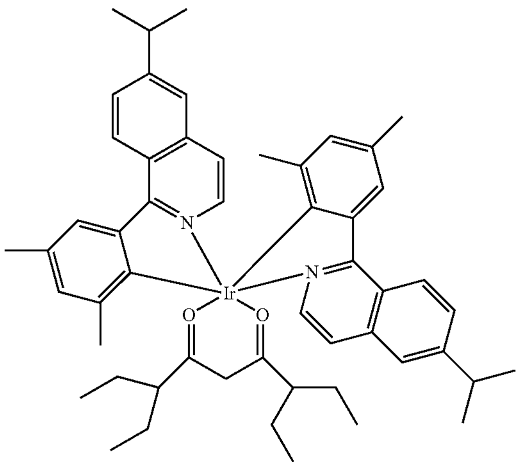

M-a3

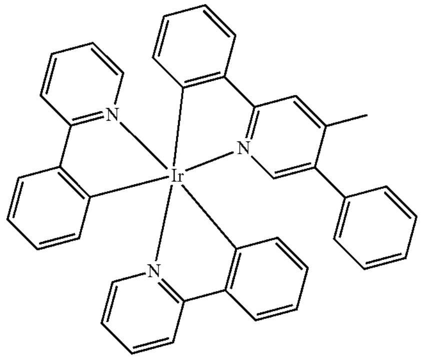

-continued
M-a4
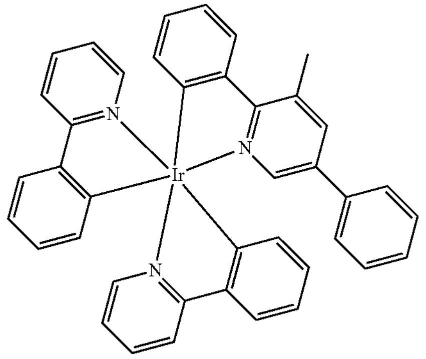
M-a5
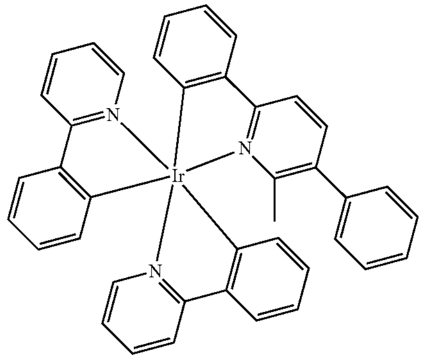
M-a6
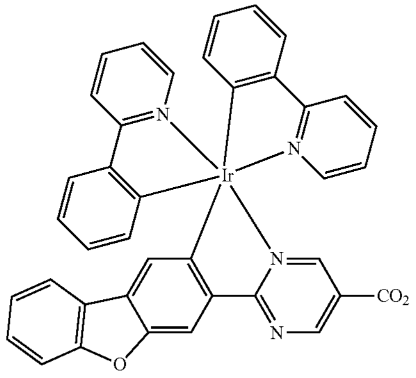
M-a7
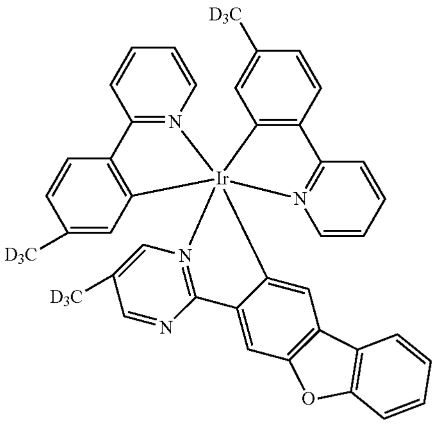
-continued
M-a8
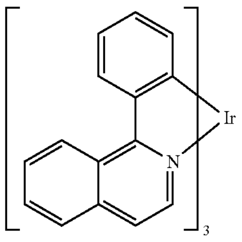
M-a9
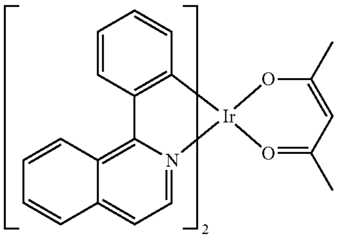
M-a10
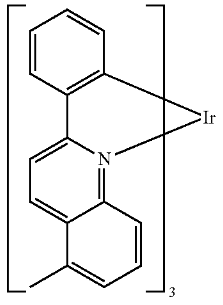
M-a11
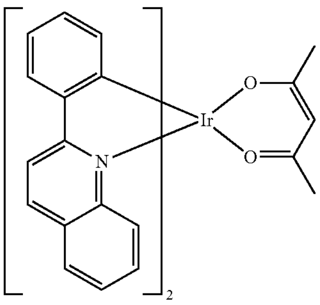
M-a12
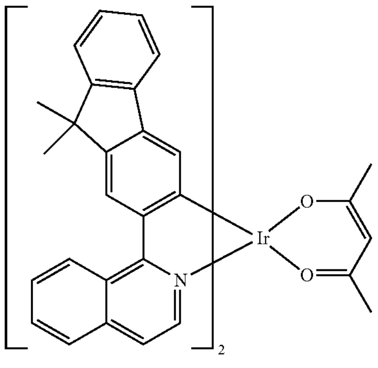

-continued
M-a13
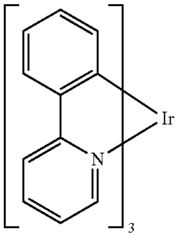
M-a14
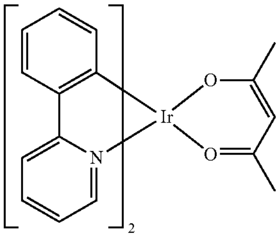
M-a15
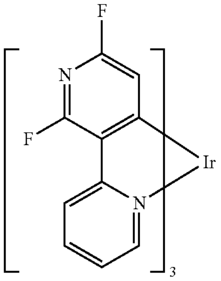
M-a16
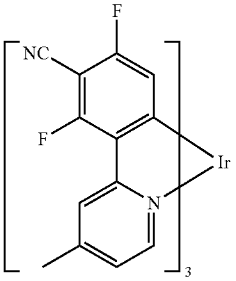
M-a17
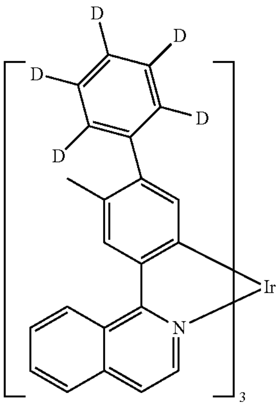
-continued
M-a18
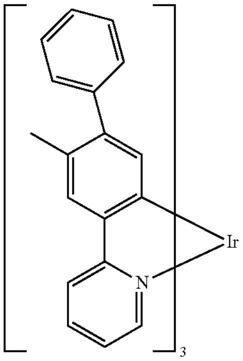
M-a19
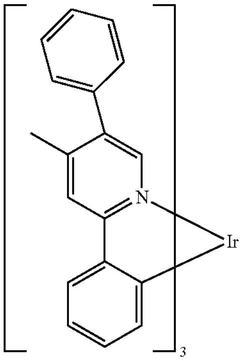
M-a0
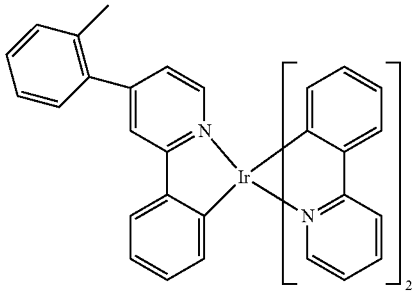
M-a21
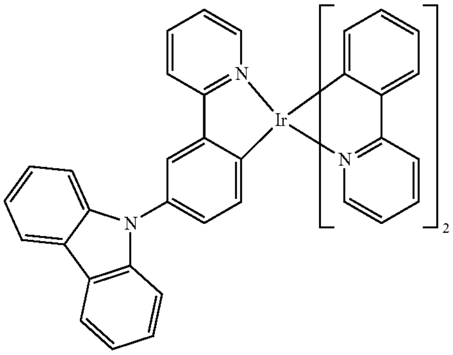

-continued

M-a22

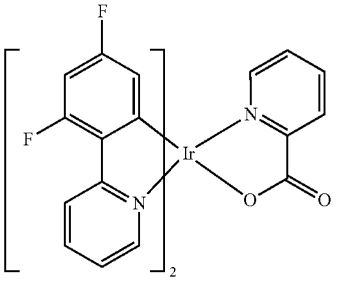

M-a23

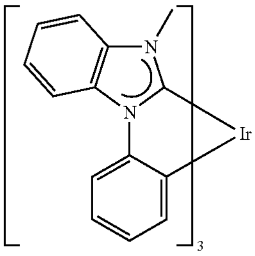

M-a24

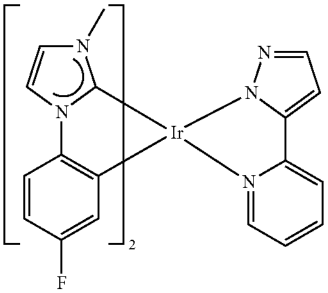

-a25

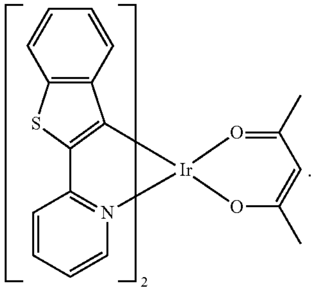

Compound M-a1 and Compound M-a2 may each be utilized as a red dopant material, and Compound M-a3 to Compound M-a7 may each be utilized as a green dopant material.

Formula M-b

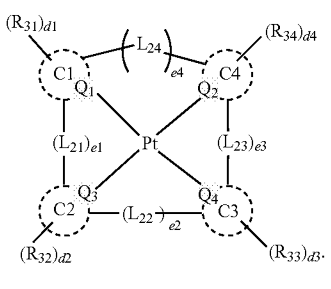

In Formula M-b, $Q_1$ to $Q_4$ may each independently be C or N, and C1 to C4 may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

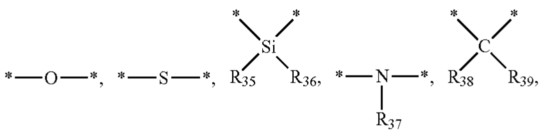

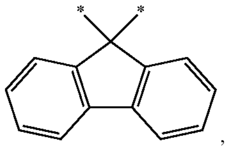

, a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring, and d1 to d4 may each independently be an integer of 0 to 4.

The compound represented by Formula M-b may be utilized as a blue phosphorescence dopant or a green phosphorescence dopant.

The compound represented by Formula M-b may be represented by any one among the compounds below. However, the compounds are examples, and the compound represented by Formula M-b is not limited to those below:

M-b-1

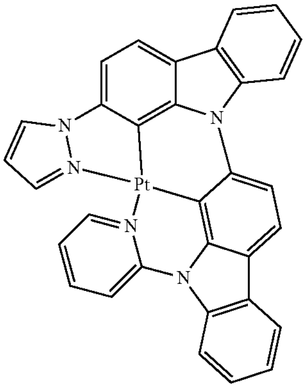

-continued
M-b-2
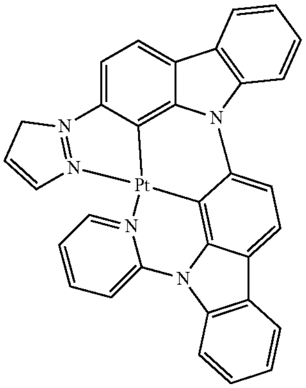
M-b-3
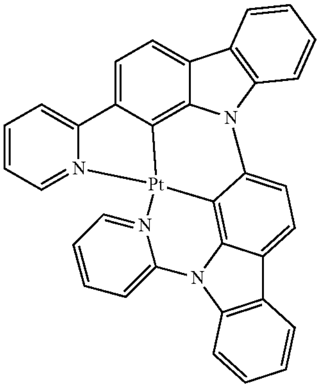
M-b-4
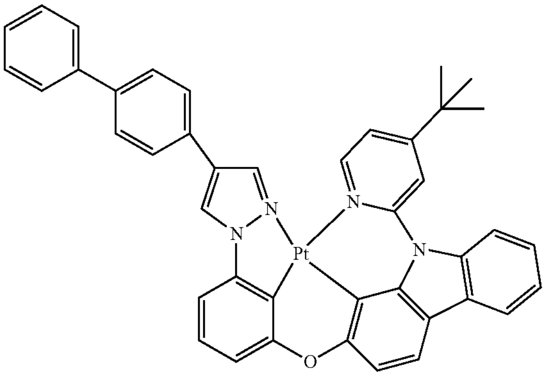
M-b-5
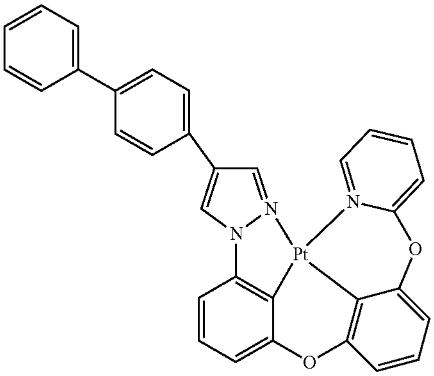
-continued
M-b-6
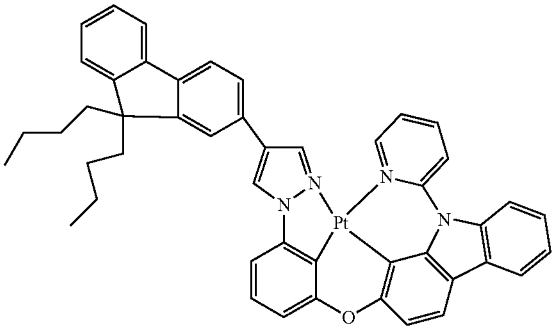
M-b-7
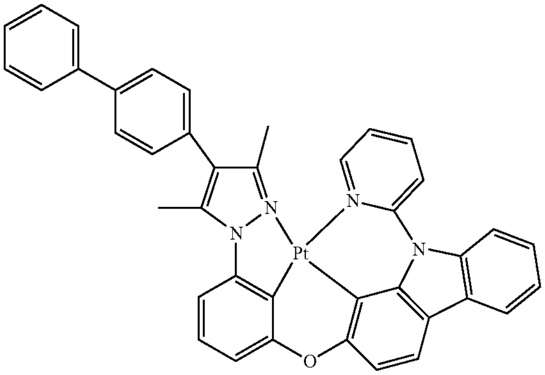
M-b-8
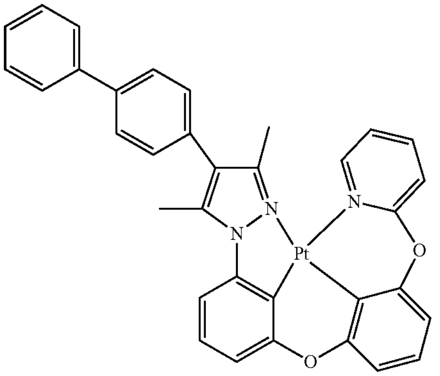
M-b-9
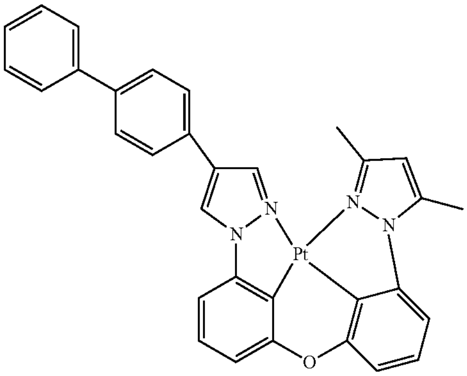

-continued

M-b-10

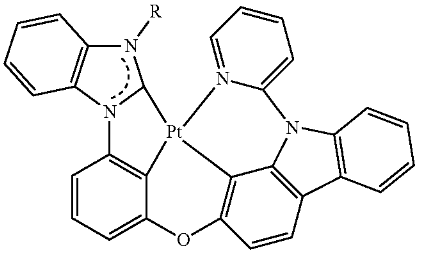

M-b-11

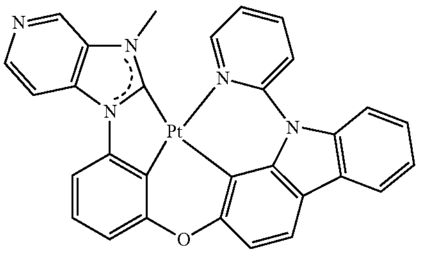

M-b-12

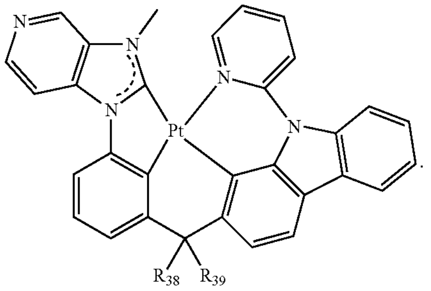

In the compounds, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

The emission layer EML may include a compound represented by any one among Formula F-a to Formula F-c. The compound represented by Formula F-a or Formula F-c may be utilized as a fluorescence dopant material.

Formula F-a

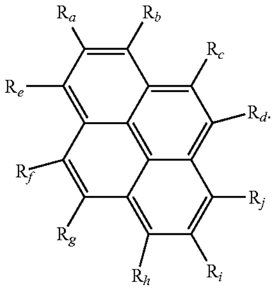

In Formula F-a, two selected from among $R_a$ to $R_j$ may each independently be substituted with *—$NAr_1Ar_2$. The others among $R_a$ to $R_j$, which are not substituted with *—$NAr_1Ar_2$, may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In *—$NAr_1Ar_2$, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing 0 or S as a ring-forming atom.

The emission layer may include, as a fluorescence dopant, at least one among Compound FD1 to Compound FD22:

FD1

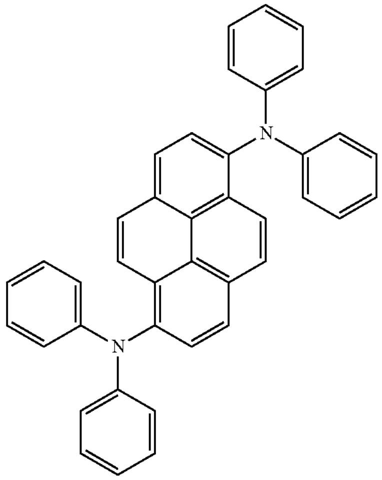

FD2

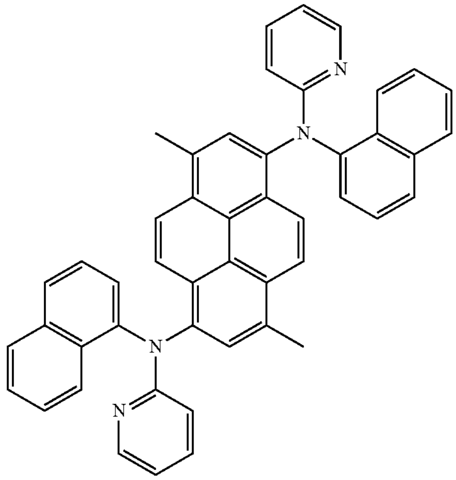

FD3
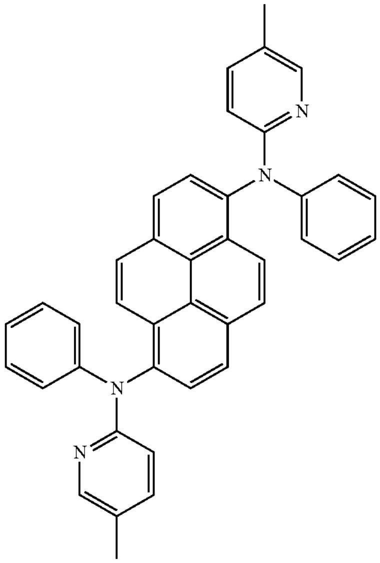
FD4
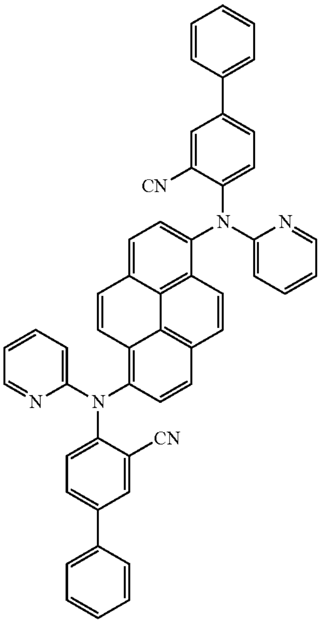
FD5
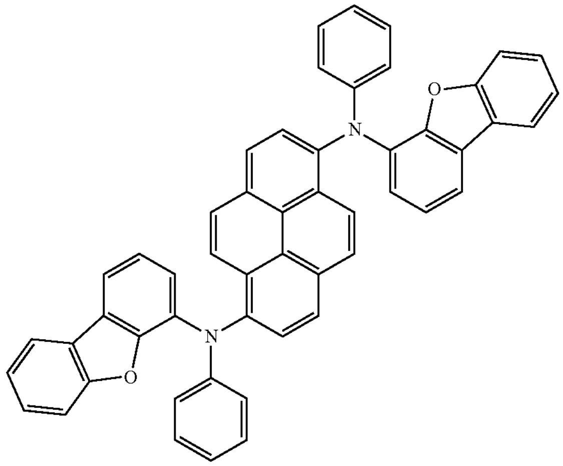
FD6
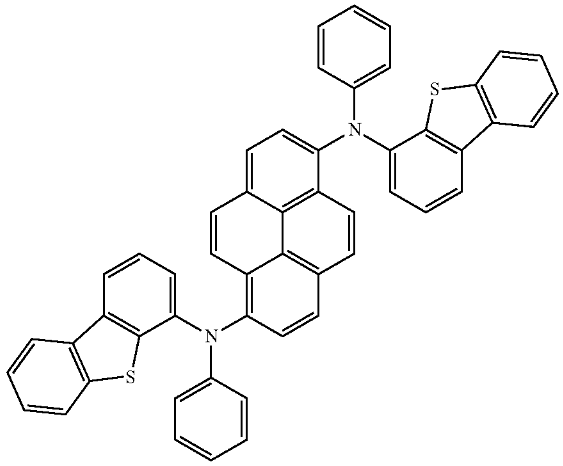
FD7
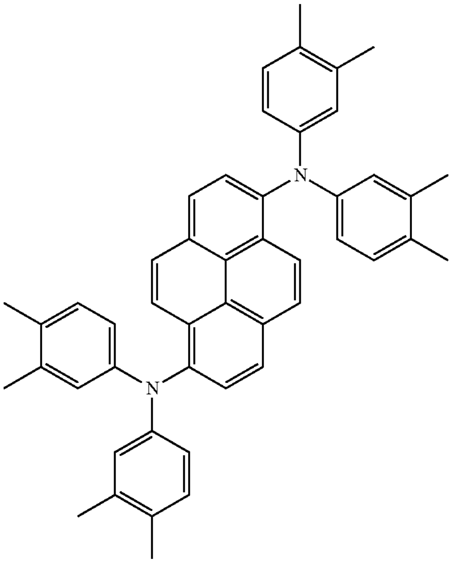

FD8
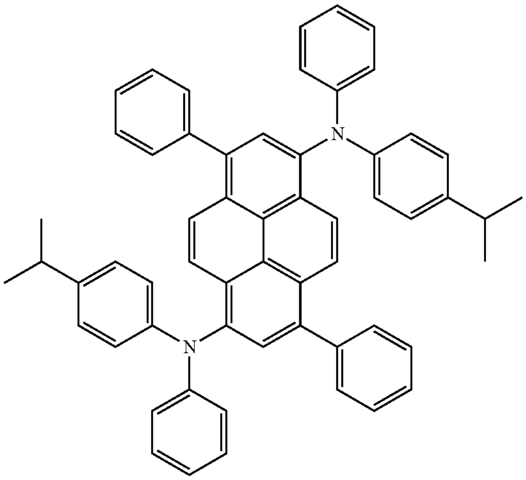
FD9
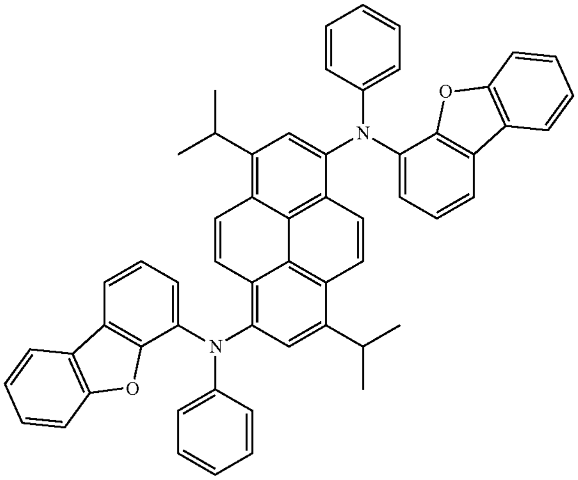
FD10
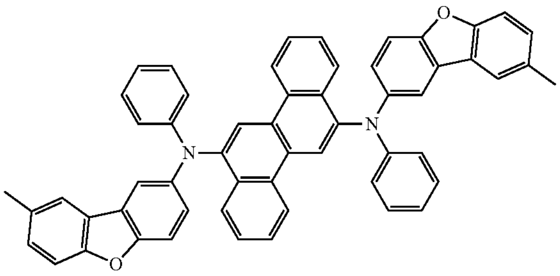
FD11
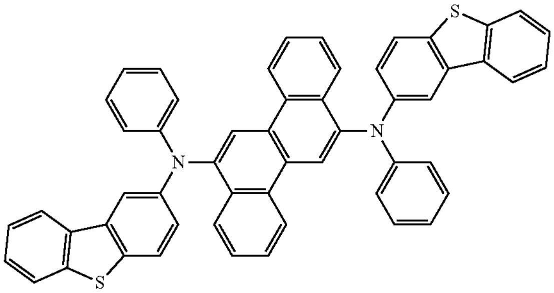
FD12
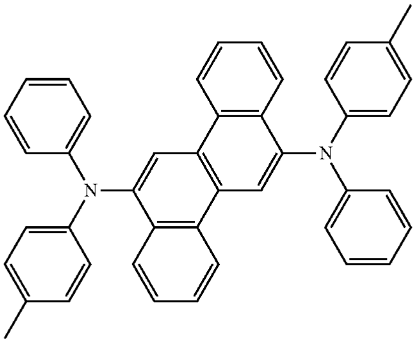
FD13
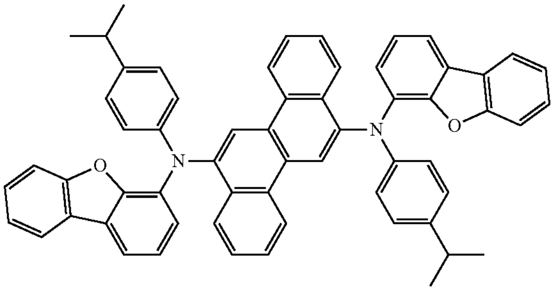
FD14
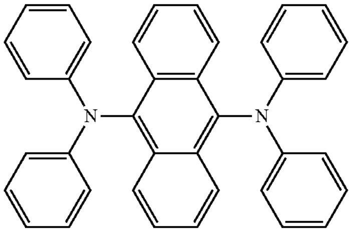
FD15
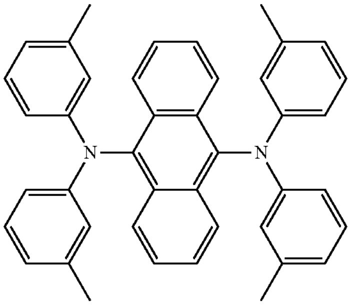
FD16
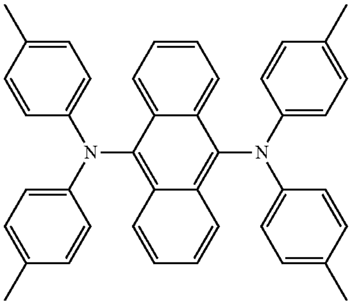

-continued

FD17

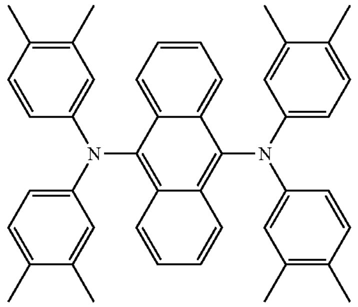

FD18

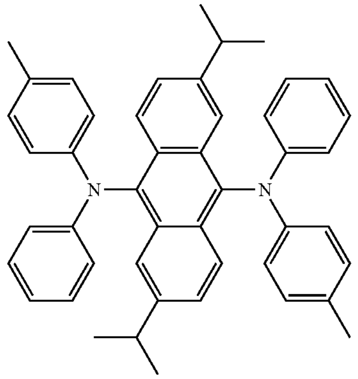

FD19

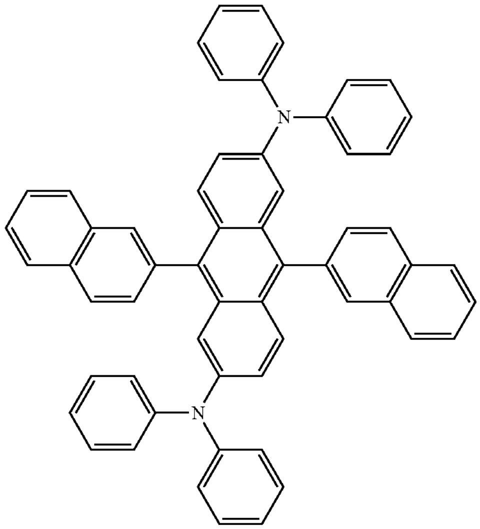

FD20

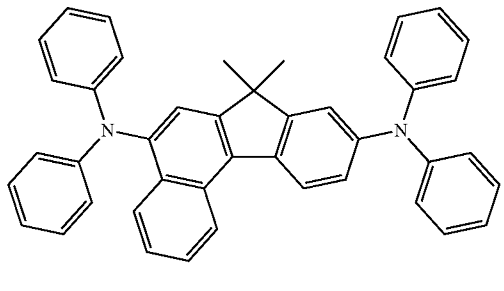

-continued

FD21

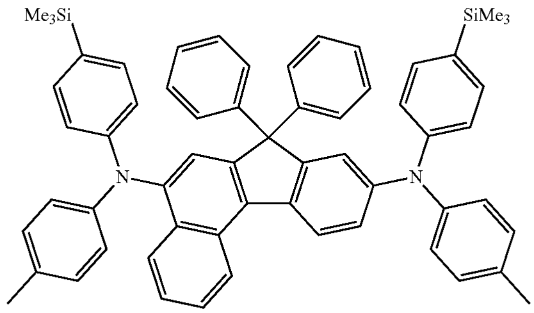

FD22

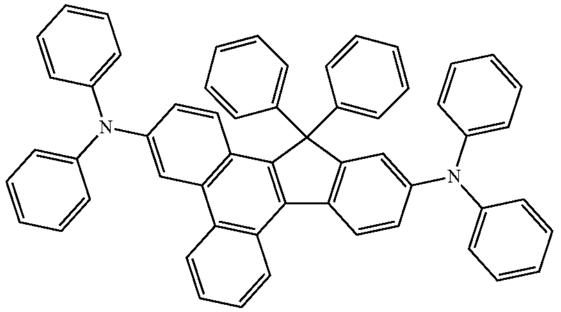

Formula F-b

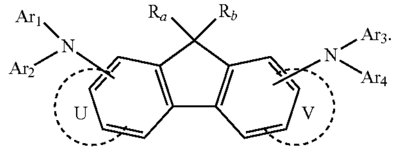

In Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring. $Ar_1$ to $Ar_4$ may each independently be a substituted or unsubstituted aryl group having 6 to 30 ring-forming carbon atoms, or a substituted or unsubstituted heteroaryl group having 2 to 30 ring-forming carbon atoms.

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the number of U or V is 1, one ring forms a condensed ring at the respective part described as U or V, and when the number of U or V is 0, a ring described as U or V is not present. For example, when the number of U is 0 and the number of V is 1, or when the number of U is 1 and the number of V is 0, the condensed ring having a fluorene core of Formula F-b may be a four-ring cyclic compound. When the number of U and V are each 0, the condensed ring of Formula F-b may be a three-ring cyclic compound. When the number of U and V are each 1, the condensed ring having a fluorene core of Formula F-b may be a five-ring cyclic compound.

Formula F-c

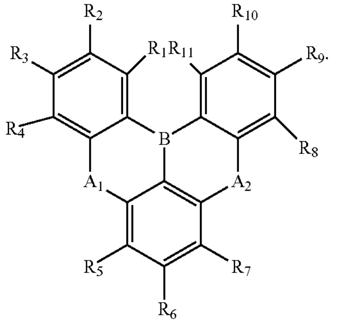

In Formula F-c, $A_1$ and $A_2$ may each independently be O, S, Se, or $NR_m$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, and/or may be bonded to an adjacent group to form a ring.

In Formula F-c, $A_1$ and $A_2$ may each independently be bonded to substituents of an adjacent ring to form a condensed ring. For example, when $A_1$ and $A_2$ are each independently $NR_m$, $A_1$ may be bonded to $R_4$ or $R_5$ to form a ring. In some embodiments, $A_2$ may be bonded to $R_7$ or $R_8$ to form a ring.

In an embodiment, the emission layer EML may include, as a suitable dopant material, styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), 4,4'-bis[2-(4-(N,N-diphenylamino)phenyl)vinyl]biphenyl(DPAVBi), perylene and/or derivatives thereof (e.g., 2,5,8,11-tetra-t-butylperylene (TBP)), pyrene and/or derivatives thereof (e.g., 1,1-dipyrene, 1,4-dipyrenylbenzene, 1,4-bis(N,N-diphenylamino)pyrene), etc.

The emission layer EML may include a suitable phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), or thulium (Tm) may be utilized as a phosphorescence dopant. For example, iridium(III) bis(4,6-difluorophenylpyridinato-N,C2') (Flrpic), bis(2,4-difluorophenylpyridinato)-tetrakis(1-pyrazolyl)borate iridium(III) (Fir6), or platinum octaethyl porphyrin (PtOEP) may be utilized as a phosphorescence dopant. However, embodiments of the present disclosure are not limited thereto.

The emission layer EML may include a quantum dot material. The core of the quantum dot may be selected from a Group II-VI compound, a Group III-VI compound, a Group I-III-IV compound, a Group III-V compound, a Group III-II-V compound, a Group IV-VI compound, a Group IV element, a Group IV compound, and combinations thereof.

The Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound (such as $In_2S_3$ and $In_2Se_3$), a ternary compound (such as $InGaS_3$ and $InGaSe_3$), or any combination thereof.

The Group compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, and a quaternary compound (such as $AgInGaS_2$ and $CuInGaS_2$).

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. In some embodiments, the Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

In this case, a binary compound, a ternary compound, and/or a quaternary compound may be present in particles in a substantially uniform concentration distribution, or may be present within the same particle in a partially different (e.g., a non-uniform) concentration distribution. In some embodiments, the quantum dot may have a core/shell structure (in which one quantum dot surrounds another quantum dot). An interface between the core and the shell may have a concentration gradient in which the concentration of an element present in the shell becomes lower towards the center.

In some embodiments, a quantum dot may have the above-described core-shell structure including a core containing nanocrystals and a shell around (e.g., surrounding) the core. The shell of the quantum dot may serve as a protection layer to prevent or reduce chemical deformation of the core so as to maintain semiconductor properties, and/or as a charging layer to impart electrophoresis properties to the quantum dot. The shell may be a single layer or a multilayer. An interface between the core and the shell may have a concentration gradient in which the concentration of an element present in the shell becomes lower (e.g., decreases) towards the center. An example of the shell of the quantum dot may include a metal or non-metal oxide, a semiconductor compound, or a combination thereof.

For example, the metal or non-metal oxide may be a binary compound (such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO), or a ternary compound (such as $MgAl_2O_4$, $CoFe_2O_4$, $NiFe_2O_4$, and/or $CoMn_2O_4$), but the present disclosure is not limited thereto.

In some embodiments, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

The quantum dot may have a full width of half maximum (FWHM) of a light emission wavelength spectrum of about 45 nm or less, about 40 nm or less, and more about 30 nm or less, and color purity or color reproducibility may be improved in the above range. Light emitted by such a quantum dot may be emitted in all directions, and thus a wide viewing angle may be improved.

The form of each quantum dot is not particularly limited as long as it is a form commonly utilized in the art, and for example, a quantum dot in the form of spherical, pyramidal, multi-arm, or cubic nanoparticles, nanotubes, nanowires, nanofibers, nanoparticles, etc. may be utilized.

The quantum dot may be to emit light corresponding to the particle size thereof, and accordingly, the quantum dot may be to emit light of one or more suitable emission colors (such as blue, red, and green).

In each light emitting element ED of embodiments illustrated in FIGS. 1 to 4, the electron transport region ETR is provided on the emission layer EML. The electron transport region ETR may include at least one of the hole blocking layer HBL, the electron transport layer ETL, or the electron injection layer EIL, but embodiments of the present disclosure are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of the electron injection layer EIL or the electron transport layer ETL, or may have a single layer structure formed of an electron injection material and an electron transport material. In some embodiments, the electron transport region ETR may have a single layer structure formed of a plurality of different materials, or may have a structure in which an electron transport layer ETL/electron injection layer EIL, a hole blocking layer HBL/electron transport layer ETL/electron injection layer EIL are stacked in order from the emission layer EML, but embodiments of the present disclosure are not limited thereto. The electron transport region ETR may have a thickness, for example, of about 1,000 Å to about 1,500 Å.

The electron transport region ETR may be formed by utilizing one or more suitable methods (such as a vacuum deposition method, a spin coating method, a cast method, a Langmuir-Blodgett (LB) method, an inkjet printing method, a laser printing method, a laser induced thermal imaging (LITI) method, etc.)

The electron transport region ETR may include a compound represented by Formula ET-1:

Formula ET-1

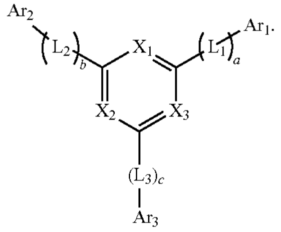

In Formula ET-1, at least one among $X_1$ to $X_3$ may be N, and the rest may be $CR_a$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. $Ar_1$ to $Ar_a$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer of 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. In some embodiments, when any of a to c are an integer of 2 or more, $L_1$ to $L_3$ may each independently be a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl) phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate ($Bebq_2$), 9,10-di(naphthalene-2-yl)anthracene (ADN), 1,3-bis[3,5-di(pyridin-3-yl)phenyl]benzene (BmPyPhB), or a mixture thereof.

The electron transport region ETR may include at least one among Compound ET1 to Compound ET36:

-continued
ET1
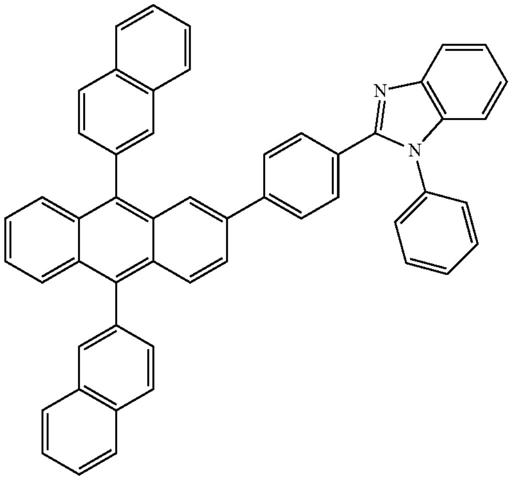
ET2
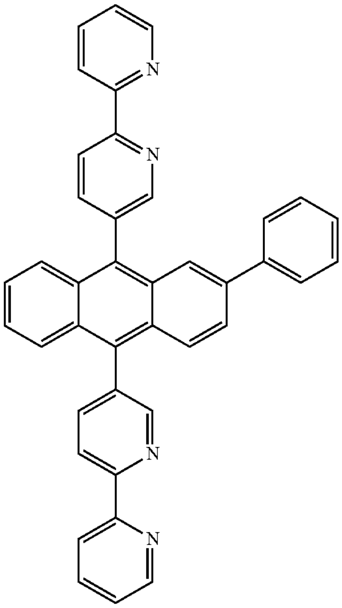
ET3
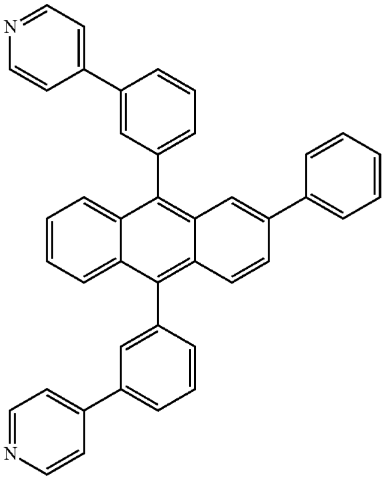
ET4
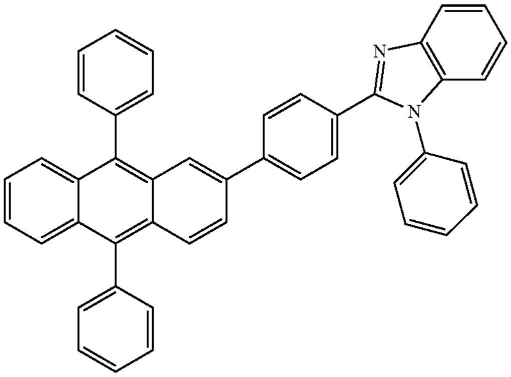
ET5
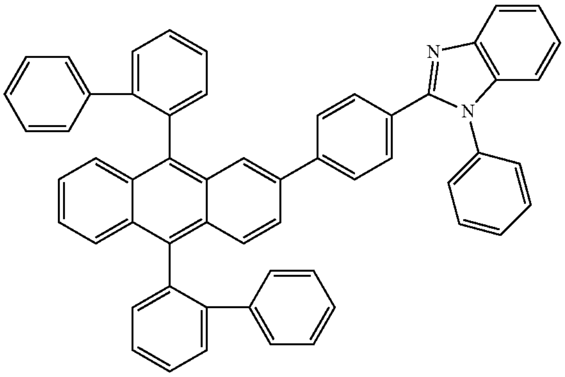
ET6
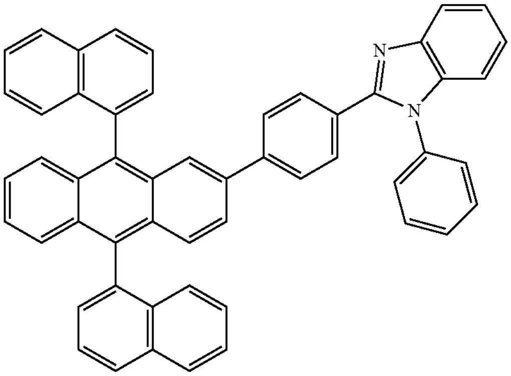

-continued
ET7
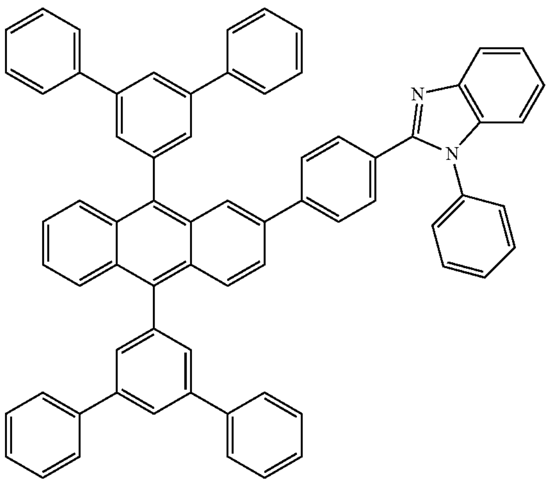
ET8
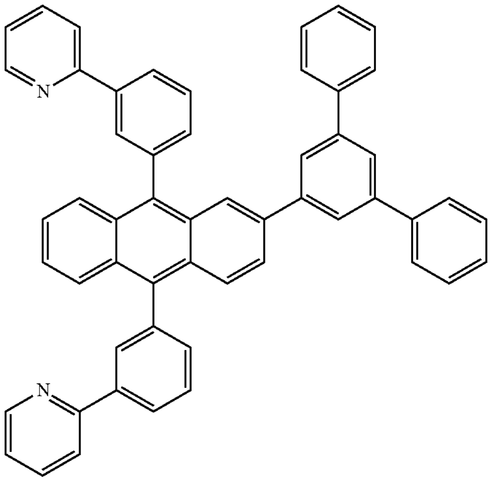
ET9
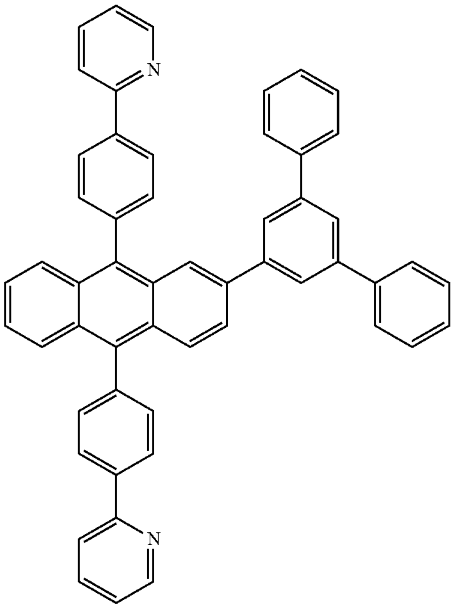
-continued
ET10
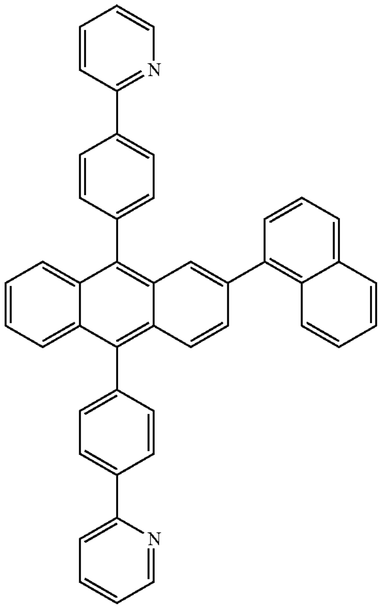
ET11
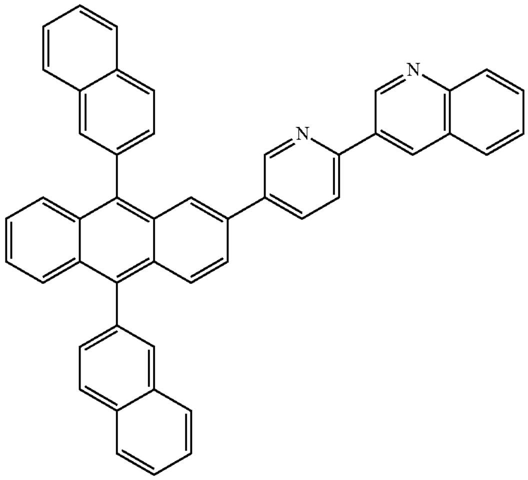
ET12
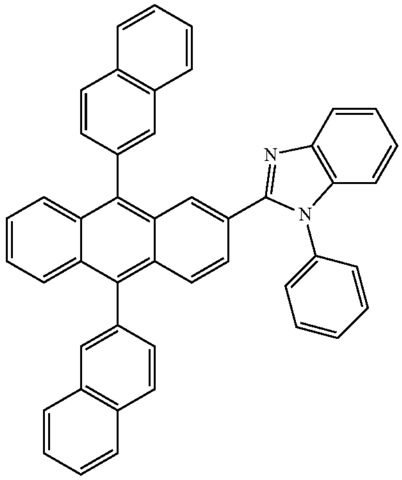

ET13
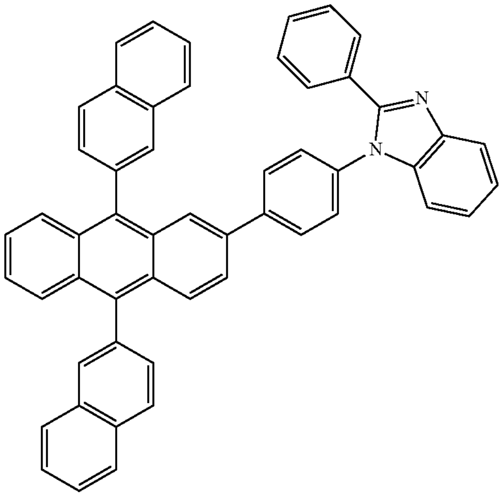
ET14
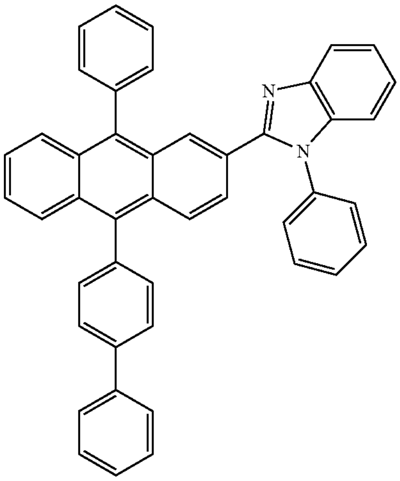
ET15
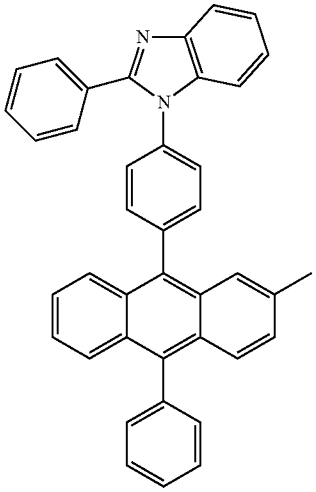
ET16
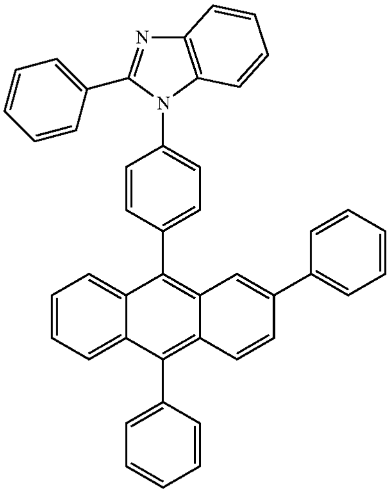
ET17
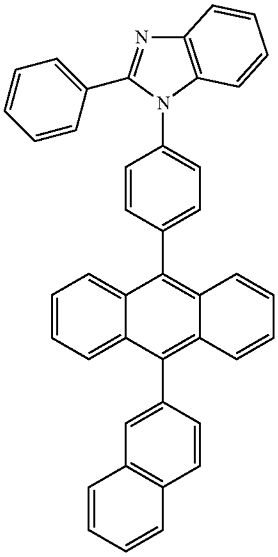
ET18
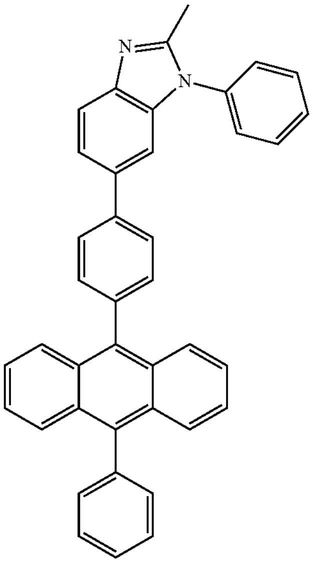

-continued
ET19
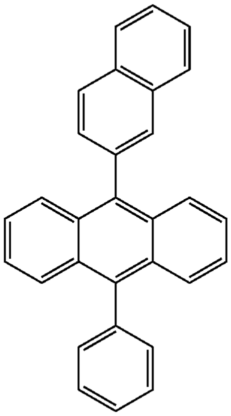
ET20
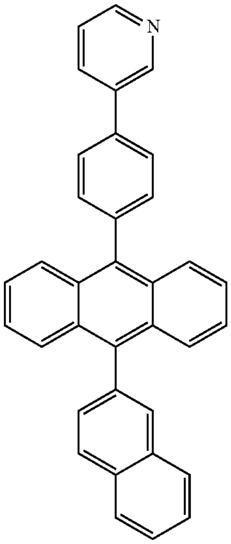
ET21
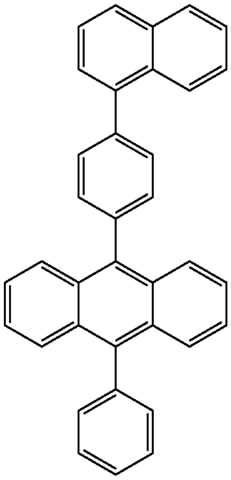
-continued
ET22
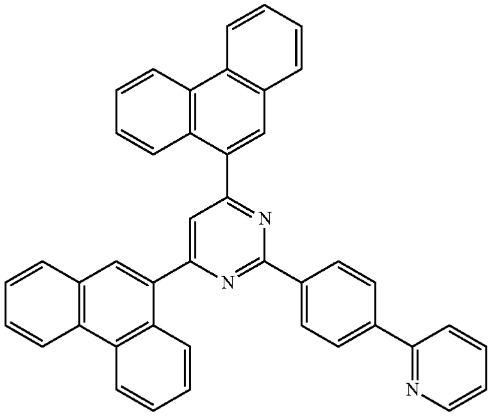
ET23
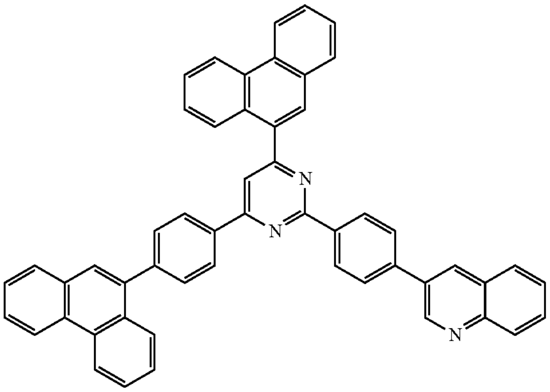
ET24
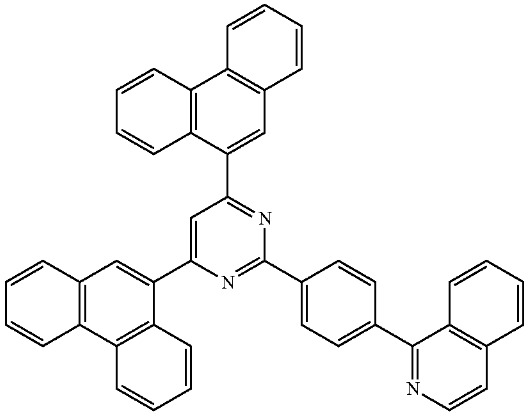

-continued
ET25
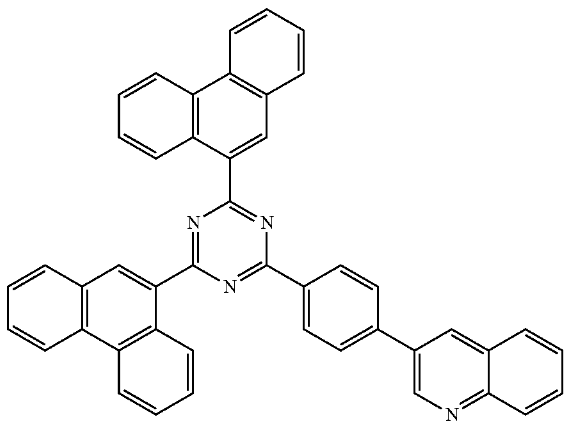
ET26
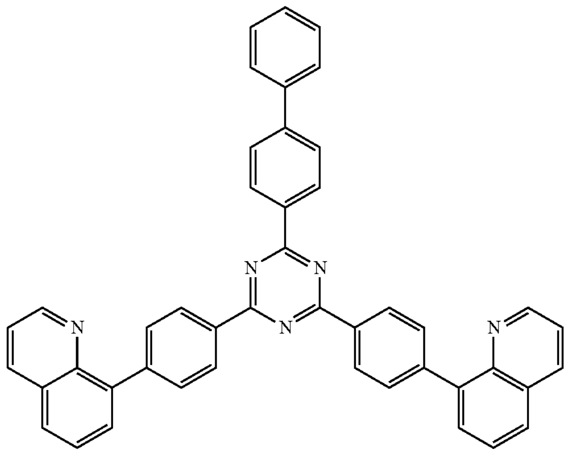
ET27
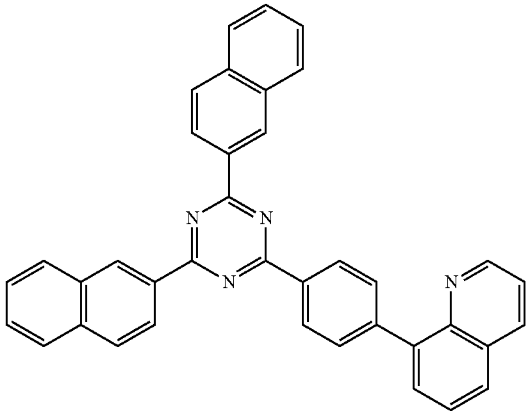
-continued
ET28
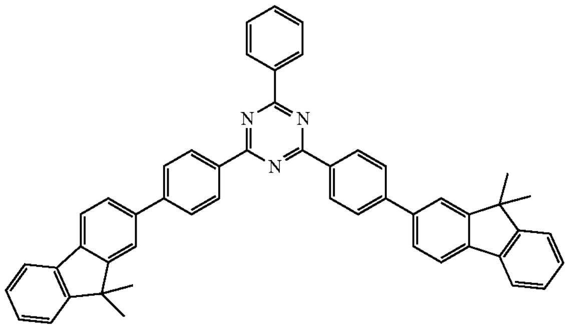
ET29
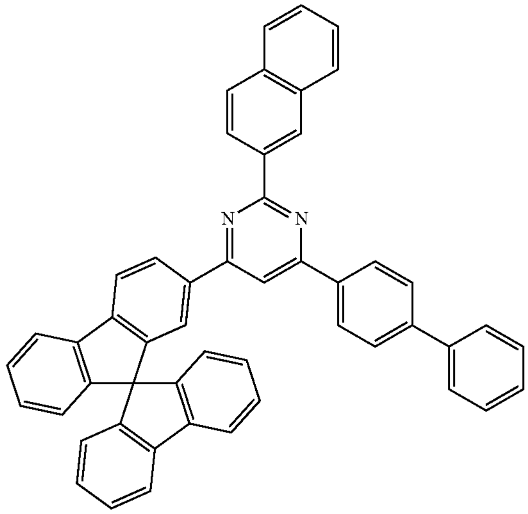
ET30
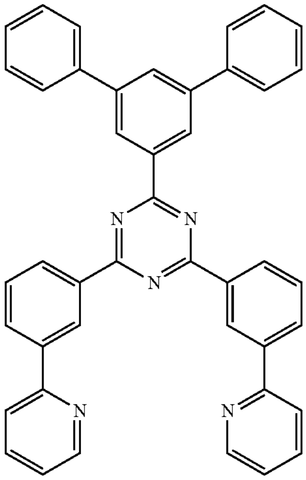

-continued

ET31

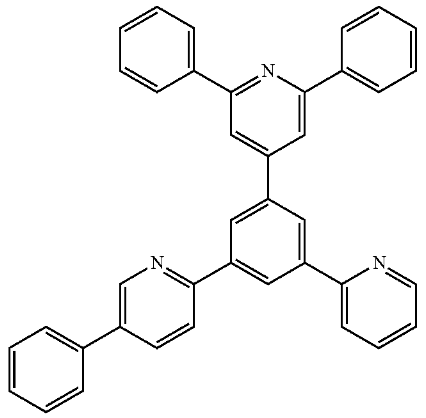

ET32

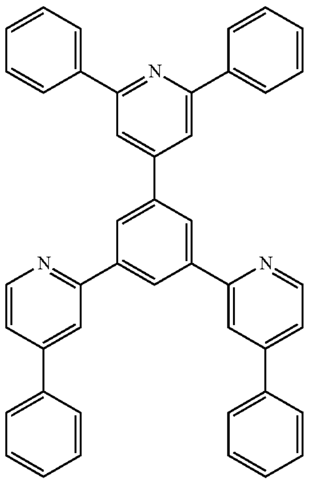

ET33

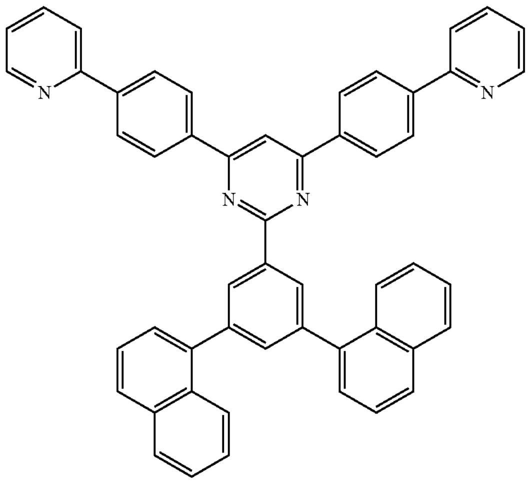

-continued

ET34

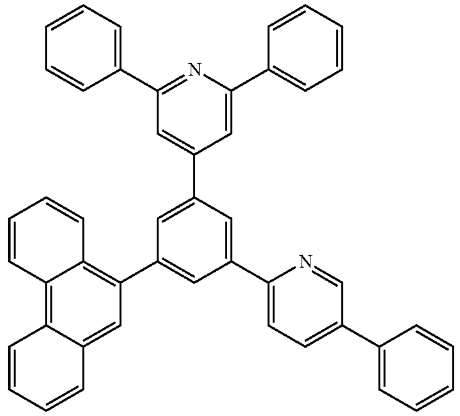

ET35

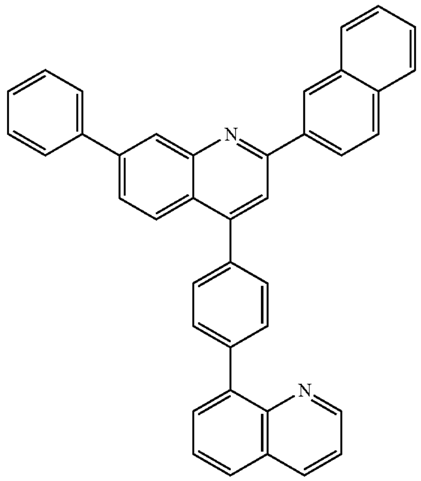

ET36

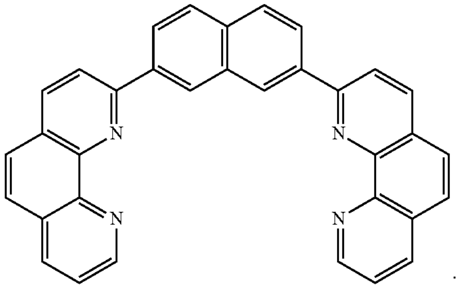

.

In some embodiments, the electron transport regions ETR may include a metal halide (such as LiF, NaCl, CsF, RbCl, RbI, CuI, and/or KI), a lanthanide metal (such as Yb), or a co-deposited material of the metal halide and the lanthanide metal. For example, the electron transport region ETR may include KI:Yb, RbI:Yb, etc. as a co-deposited material. In some embodiments, the electron transport region ETR may be formed utilizing a metal oxide (such as $Li_2O$ and/or BaO), or 8-hydroxyl-lithium quinolate (LiQ), etc., but embodiments of the present disclosure are not limited thereto.

The electron transport region ETR may also be formed of a mixture material of an electron transport material and an insulating organometallic salt. The organometallic salt may be a material having an energy band gap of about 4 eV or more. For example, the organometallic salt may include, for example, metal acetates, metal benzoates, metal acetoacetates, metal acetylacetonates, and/or metal stearates.

The electron transport region ETR may further include at least one of 2,9-dimethyl-4,7-diphenyl-1,10-phenanthroline (BCP), or 4,7-diphenyl-1,10-phenanthroline (Bphen) in addition to the above-described materials, but embodiments of the present disclosure are not limited thereto.

The electron transport region ETR may include the above-described compounds of the hole transport region in at least one of the electron injection layer EIL, the electron transport layer ETL, or the hole blocking layer HBL.

When the electron transport region ETR includes the electron transport layer ETL, the electron transport layer ETL may have a thickness of about 100 Å to about 1,000 Å, for example, about 150 Å to about 500 Å. When the thickness of the electron transport layer ETL satisfies the aforementioned range, satisfactory electron transport characteristics may be obtained without a substantial increase in driving voltage. When the electron transport region ETR includes the electron injection layer EIL, the electron injection layer EIL may have a thickness of about 1 Å to about 100 Å, for example, about 3 Å to about 90 Å. When the thickness of the electron injection layer EIL satisfies the above-described range, satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF, Mo, Ti, W, a compound thereof, or a mixture thereof (e.g., a mixture of Ag and Mg, a mixture of LiF and Ca, a mixture of LiF and Al, etc.). In some embodiments, the second electrode EL2 may have a multilayer structure including a reflective film or a transflective film formed of the above-described materials, and a transparent conductive film formed of ITO, IZO, ZnO, ITZO, etc. For example, the second electrode EL2 may include the above-described metal materials, combinations of at least two metal materials of the above-described metal materials, oxides of the above-described metal materials, and/or the like.

The second electrode EL2 may be connected with an auxiliary electrode. When the second electrode EL2 is connected with the auxiliary electrode, the resistance of the second electrode EL2 may decrease.

In some embodiments, a capping layer CPL may further be disposed on the second electrode EL2 of the light emitting element ED of an embodiment. The capping layer CPL may include a multilayer or a single layer.

In an embodiment, the capping layer CPL may be or include an organic layer and/or an inorganic layer. For example, when the capping layer CPL includes an inorganic material (e.g., includes an inorganic layer), the inorganic material may include an alkaline metal compound such as LiF, an alkaline earth metal compound such as $MgF_2$, SiON, $SiN_x$, SiOy, etc.

For example, when the capping layer CPL includes an organic material (e.g., includes an organic layer), the organic material may include α-NPD, NPB, TPD, m-MTDATA, $Alq_3$, CuPc, N4,N4,N4',N4'-tetra(biphenyl-4-yl)biphenyl-4,4'-diamine (TPD15), 4,4',4"-tris(carbazol-9-yl)triphenylamine (TCTA), etc., an epoxy resin, and/or an acrylate (such as methacrylate). However, embodiments of the present disclosure are not limited thereto, and the capping layer CPL may include at least one among Compounds P1 to P5:

P1

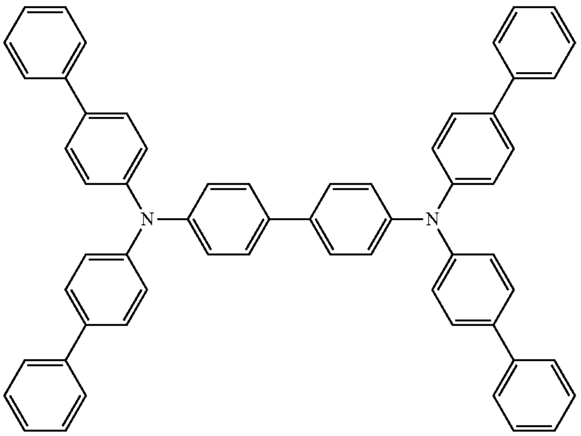

P2

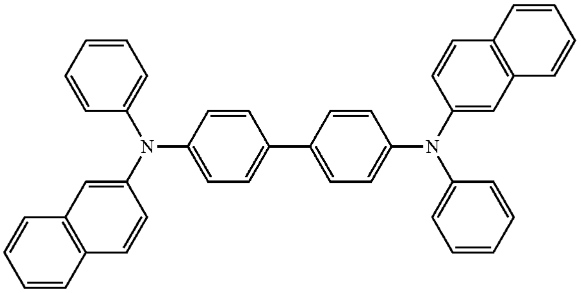

P3

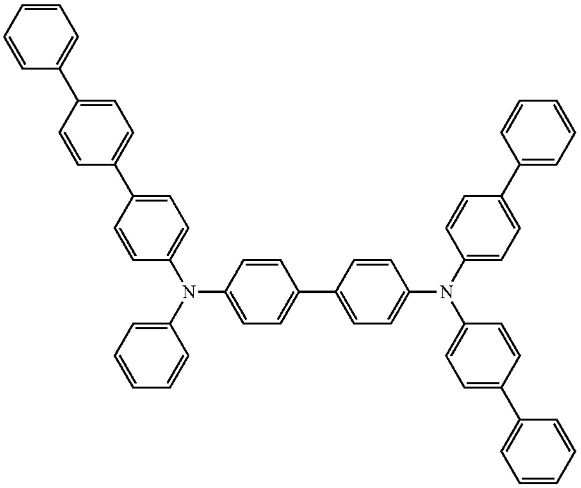

-continued

P4

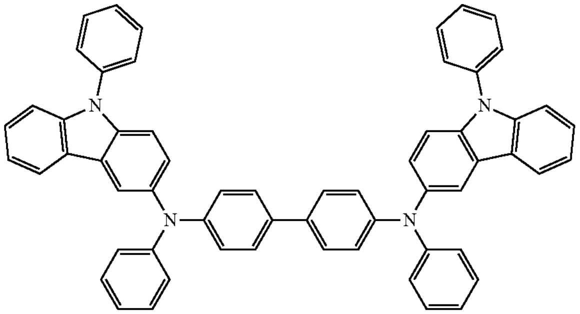

P5

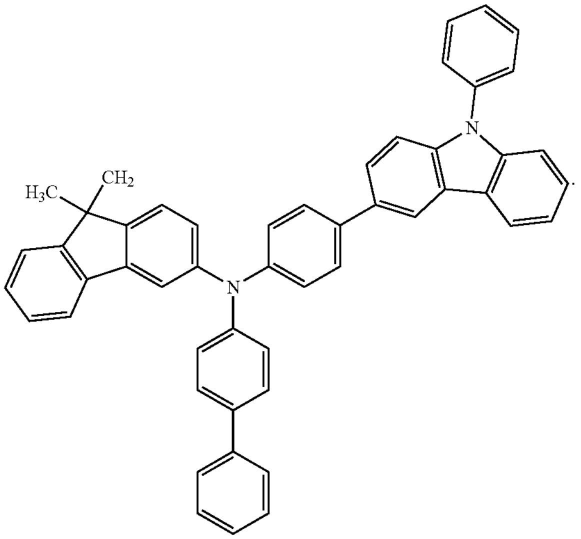

In some embodiments, the refractive index of the capping layer CPL may be about 1.6 or more. For example, the refractive index of the capping layer CPL may be about 1.6 or more with respect to light in a wavelength range of about 550 nm to about 660 nm.

Figure 7:
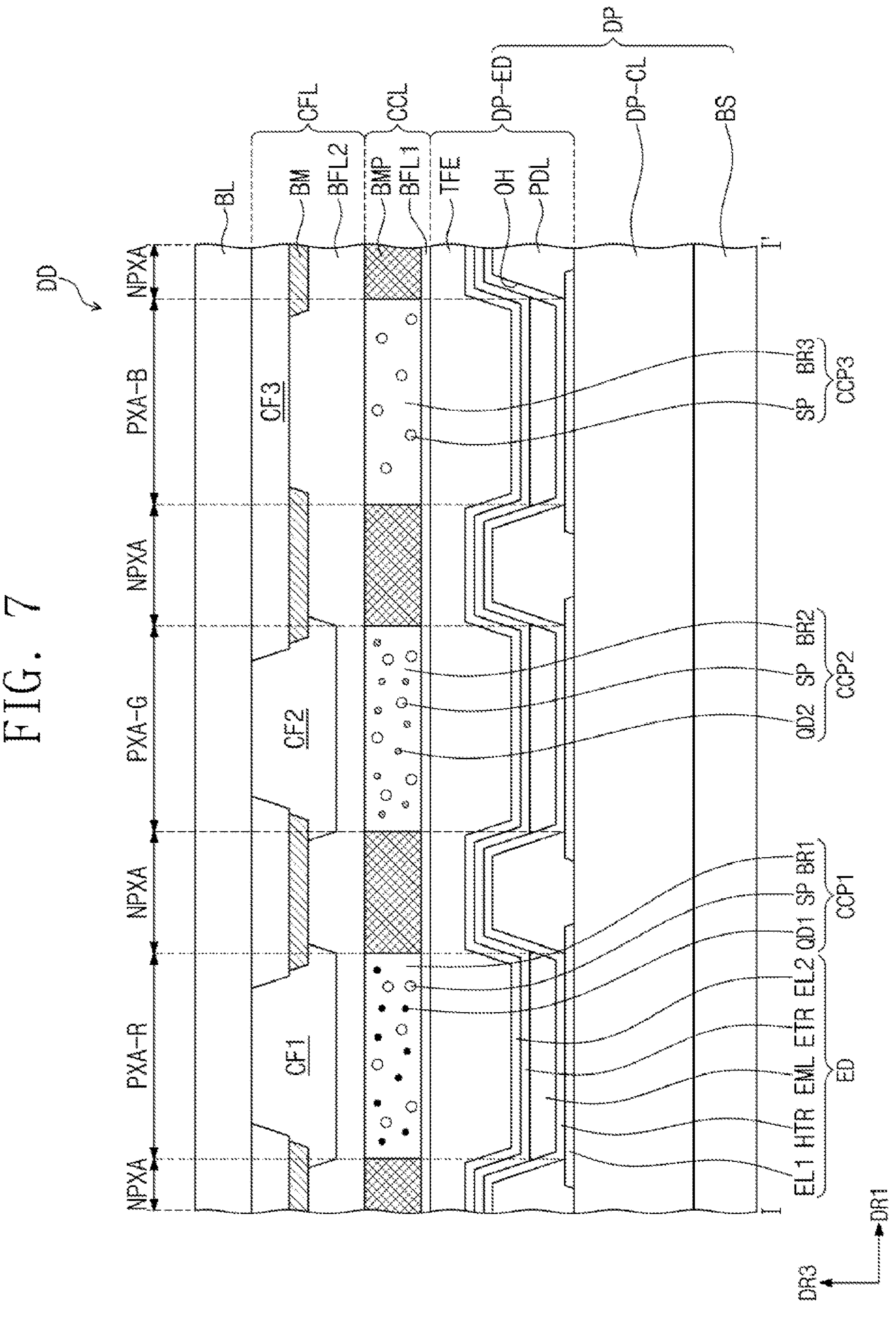
FIG. 7 is a cross-sectional view of a display device according to an embodiment of the present disclosure.
Figure 8:
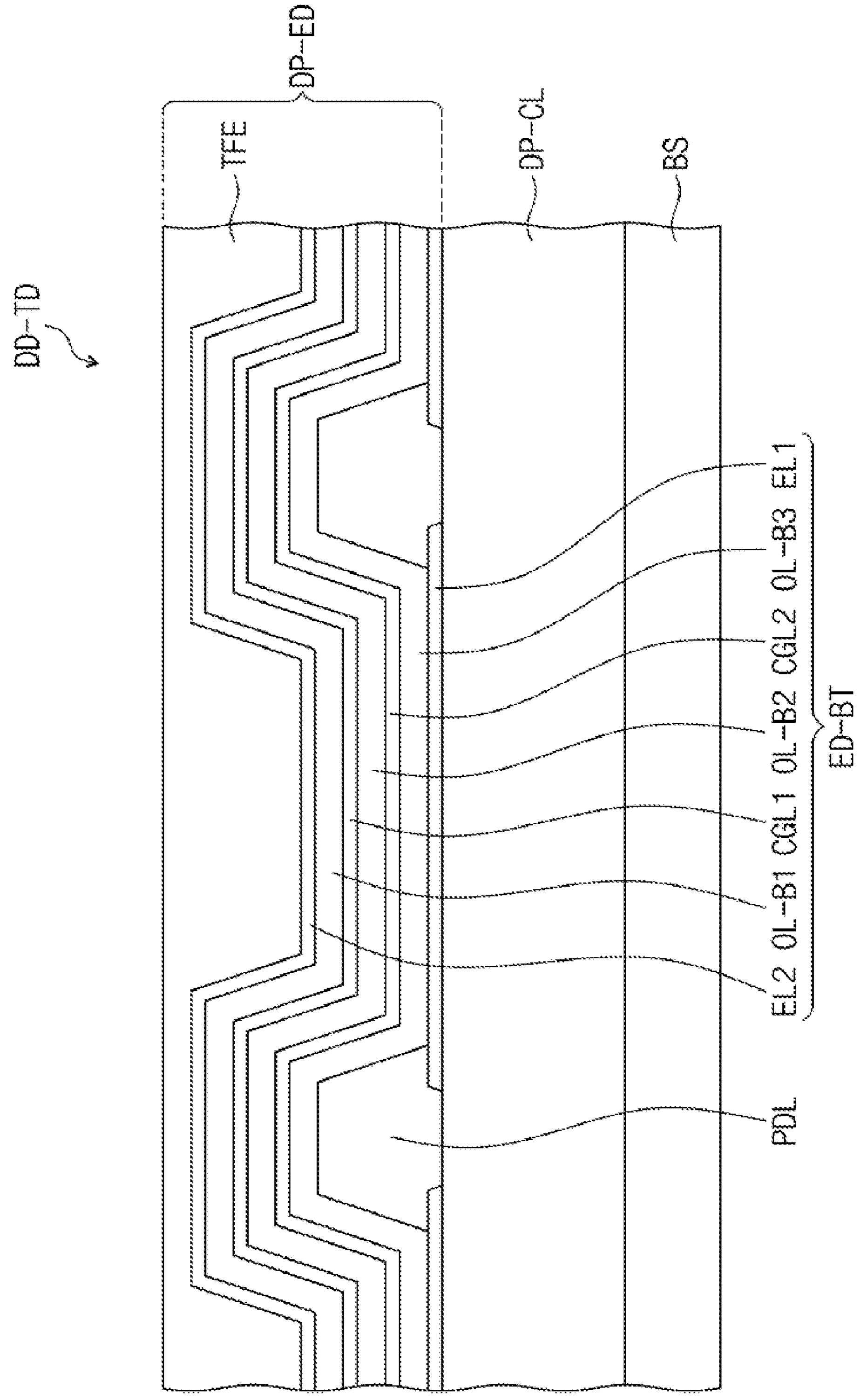
FIG. 8 is a cross-sectional view of a display device according to an embodiment of the present disclosure.

FIGS. 7 and 8 are each a cross-sectional view of a display device according to an embodiment. Hereinafter, in describing the display device of an embodiment with reference to FIGS. 7 and 8, the duplicated features which have been described in FIGS. 1 to 6 are not described again, but their differences will be mainly described.

Referring to FIG. 7, the display device DD according to an embodiment may include a display panel DP including a display element layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and the display element layer DP-ED, and the display element layer DP-ED may include a light emitting element ED.

The light emitting element ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. In some embodiments, the structures of the light emitting elements of FIGS. 3 to 6 as described above may be applied to the structure of the light emitting element ED shown in FIG. 7.

Referring to FIG. 7, the emission layer EML may be disposed in an opening OH defined in a pixel defining film PDL. For example, the emission layer EML, which is divided by the pixel defining film PDL and provided to correspond to light emitting regions PXA-R, PXA-G, and PXA-B may be to emit light in substantially the same wavelength range. In the display device DD of an embodiment, the emission layer EML may be to emit blue light. In some embodiments, the emission layer EML may be provided as a common layer to all of the light emitting regions PXA-R, PXA-G, and PXA-B.

The light control layer CCL may be disposed on the display panel DP. The light control layer CCL may include a light conversion body. The light conversion body may be a quantum dot, a phosphor, and/or the like. The light conversion body may be to emit light by converting the wavelength of light provided thereto. For example, the light control layer CCL may be a layer containing the quantum dot or a layer containing the phosphor.

The light control layer CCL may include a plurality of light control parts CCP1, CCP2 and CCP3. The light control parts CCP1, CCP2, and CCP3 may be spaced apart from one another.

Referring to FIG. 7, divided patterns BMP may define or be disposed between the light control parts CCP1, CCP2 and CCP3, which are spaced apart from each other, but embodiments of the present disclosure are not limited thereto. FIG. 7 illustrates that the divided patterns BMP do not overlap the light control parts CCP1, CCP2 and CCP3, but at least a portion of the edges of the light control parts CCP1, CCP2 and CCP3 may overlap the divided patterns BMP.

The light control layer CCL may include a first light control part CCP1 containing a first quantum dot QD1 to convert first color light provided from the light emitting element ED into second color light, a second light control part CCP2 containing a second quantum dot QD2 to convert the first color light into third color light, and a third light control part CCP3 to transmit the first color light.

In an embodiment, the first light control part CCP1 may provide red light that is the second color light, and the second light control part CCP2 may provide green light that is the third color light. The third light control part CCP3 may provide blue light by transmitting the blue light that is (e.g., is the same as) the first color light provided in the light emitting element ED. For example, the first quantum dot QD1 may be a red quantum dot, and the second quantum dot QD2 may be a green quantum dot. The same as described above may be applied with respect to the quantum dots QD1 and QD2.

In some embodiments, the light control layer CCL may further include a scatterer SP. The first light control part CCP1 may include the first quantum dot QD1 and the scatterer SP, the second light control part CCP2 may include the second quantum dot QD2 and the scatterer SP, and the third light control part CCP3 may not include any quantum dot but include the scatterer SP.

The scatterer SP may be or include inorganic particles. For example, the scatterer SP may include at least one of $TiO_2$, ZnO, $Al_2O_3$, $SiO_2$, or hollow silica. The scatterer SP may include any one of $TiO_2$, ZnO, $Al_2O_3$, $SiO_2$, or hollow silica, or may be a mixture of at least two materials selected from among $TiO_2$, ZnO, $Al_2O_3$, $SiO_2$, and hollow silica.

The first light control part CCP1, the second light control part CCP2, and the third light control part CCP3 each may include base resins BR1, BR2, and BR3 in which the quantum dots QD1 and QD2 and/or the scatterer SP are dispersed. In an embodiment, the first light control part CCP1 may include the first quantum dot QD1 and the scatterer SP dispersed in a first base resin BR1, the second light control part CCP2 may include the second quantum dot QD2 and the scatterer SP dispersed in a second base resin BR2, and the third light control part CCP3 may include the scatterer SP dispersed in a third base resin BR3. The base resins BR1, BR2, and BR3 are media in which the quantum dots QD1 and QD2 and the scatterer SP are dispersed, and may be formed of one or more suitable resin compositions, which may be generally referred to as binders. For example, the base resins BR1, BR2, and BR3 may be acrylic-based resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may be the same as or different from each other.

The light control layer CCL may include a barrier layer BFL1. The barrier layer BFL1 may serve to prevent or reduce penetration of moisture and/or oxygen (hereinafter, referred to as 'moisture/oxygen'). The barrier layer BFL1 may be disposed on the light control parts CCP1, CCP2, and CCP3 to block or reduce the light control parts CCP1, CCP2 and CCP3 from being exposed to moisture/oxygen. In some embodiments, the barrier layer BFL1 may cover the light control parts CCP1, CCP2, and CCP3. In some embodiments, the barrier layer BFL2 may be provided between the light control parts CCP1, CCP2, and CCP3 and the color filter layer CFL.

The barrier layers BFL1 and BFL2 may each independently include at least one inorganic layer. For example, the barrier layers BFL1 and BFL2 may each include an inorganic material. For example, the barrier layers BFL1 and BFL2 may each independently include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. In some embodiments, the barrier layers BFL1 and BFL2 may further include an organic film. The barrier layers BFL1 and BFL2 may be formed of a single layer or a plurality of layers.

In the display device DD of an embodiment, the color filter layer CFL may be disposed on the light control layer CCL. For example, the color filter layer CFL may be directly disposed on the light control layer CCL. In this case, the barrier layer BFL2 may not be provided.

The color filter layer CFL may include a light shielding unit BM and filters CF1, CF2, and CF3. The color filter layer CFL may include a first filter CF1 configured to transmit the second color light, a second filter CF2 configured to transmit the third color light, and a third filter CF3 configured to transmit the first color light. For example, the first filter CF1 may be a red filter, the second filter CF2 may be a green filter, and the third filter CF3 may be a blue filter. The filters CF1, CF2, and CF3 may each independently include a polymeric photosensitive resin and/or a pigment and/or dye. The first filter CF1 may include a red pigment and/or dye, the second filter CF2 may include a green pigment and/or dye, and the third filter CF3 may include a blue pigment and/or dye. In some embodiments, the third filter CF3 may not include a pigment or dye. For example, the third filter CF3 may include a polymeric photosensitive resin and may not include a pigment or dye. The third filter CF3 may be transparent. The third filter CF3 may be formed of a transparent photosensitive resin.

Furthermore, in an embodiment, the first filter CF1 and the second filter CF2 may each be a yellow filter. The first filter CF1 and the second filter CF2 may not be separated but be provided as one filter.

The light shielding unit BM may be a black matrix. The light shielding unit BM may include an organic light shielding material and/or an inorganic light shielding material containing a black pigment and/or dye. The light shielding unit BM may prevent or reduce light leakage, and may separate boundaries between the adjacent filters CF1, CF2, and CF3. In some embodiments, in an embodiment, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

A base substrate BL may be disposed on the color filter layer CFL. The base substrate BL may be a member which provides a base surface in which the color filter layer CFL, the light control layer CCL, and/or the like are disposed. The base substrate BL may be a glass substrate, a metal substrate, a plastic substrate, etc. However, embodiments of the present disclosure are not limited thereto, and the base substrate BL may be an inorganic layer, an organic layer, or a composite material layer. In some embodiments, the base substrate BL may not be provided.

FIG. 8 is a cross-sectional view illustrating a part of a display device according to an embodiment. FIG. 8 illustrates a cross-sectional view of a part corresponding to the display panel DP of FIG. 7. In the display device DD-TD of an embodiment, the light emitting element ED-BT may include a plurality of light emitting structures OL-B1, OL-B2, and OL-B3. The light emitting element ED-BT may include a first electrode EL1 and a second electrode EL2 which face each other, and the plurality of light emitting structures OL-B1, OL-B2, and OL-B3 sequentially stacked in the thickness direction between the first electrode EL1 and the second electrode EL2. The light emitting structures OL-B1, OL-B2, and OL-B3 each may include an emission layer EML (FIG. 7) and a hole transport region HTR and an electron transport region ETR disposed with the emission layer EML (FIG. 7) therebetween.

For example, the light emitting element ED-BT included in the display device DD-TD of an embodiment may be a light emitting element having a tandem structure and including a plurality of emission layers.

In an embodiment illustrated in FIG. 8, all light beams respectively emitted from the light emitting structures OL-B1, OL-B2, and OL-B3 may be blue light. However, embodiments of the present disclosure are not limited thereto, and the light beams respectively emitted from the light emitting structures OL-B1, OL-B2, and OL-B3 may have wavelength ranges different from each other. For example, the light emitting element ED-BT including the plurality of light emitting structures OL-B1, OL-B2, and OL-B3 to emit light beams having wavelength ranges different from each other may be to collectively emit white light.

A charge generation layer CGL may be disposed between the neighboring light emitting structures OL-B1, OL-B2, and OL-B3. The charge generation layer CGL may include a p-type charge generation layer and/or an n-type charge generation layer.

At least one among the light emitting structures OL-B1, OL-B2, and OL-B3 included in the display device DD-TD of an embodiment may contain the above-described polycyclic compound of an embodiment.

The light emitting element ED according to an embodiment of the present disclosure may include the above-described polycyclic compound of an embodiment in at least one functional layer disposed between the first electrode EL1 and the second electrode EL2, thereby exhibiting an improved service life characteristic. The light emitting element ED according to an embodiment may include the above-described polycyclic compound of an embodiment in at least one of the hole transport region HTR disposed between the first electrode EL1 and the second electrode EL2, in the emission layer EML, in the electron transport region ETR, or in the capping layer CPL.

For example, the polycyclic compound according to an embodiment may be included in the hole transport region HTR of the light emitting element ED of an embodiment, and the light emitting element of an embodiment may exhibit a long service life characteristic.

The polycyclic compound according to an embodiment as described above includes a bis carbazole moiety connected to a fluorenyl group, and has a molecular structure in which an aryl group (e.g., two aryl groups) is connected to 9-position of the fluorenyl group, and thus may exhibit excellent or suitable electron resistance and heat stability characteristics. In some embodiments, owing to such molecular structural characteristics of the polycyclic compound, the polycyclic compound of an embodiment has excellent or suitable hole transport ability and improved material stability, and when the polycyclic compound is utilized as a material of the light emitting element, it may help to improve a service life of the light emitting element.

Hereinafter, with reference to Examples and Comparative Examples, a polycyclic compound according to an embodiment of the present disclosure and a light emitting element of an embodiment of the present disclosure will be described in more detail. The Examples shown are illustrated only for the understanding of the present disclosure, and the scope of the present disclosure is not limited thereto.

EXAMPLES

1. Synthesis of Polycyclic Compound

First, a synthetic method of a polycyclic compound according to the present embodiment will be described in more detail by illustrating the synthetic methods of Compounds B2, B13, D26, E1, H2, H27, I1, K2, P1 and P31 of Compound Group 1. The following synthetic methods of the polycyclic compounds are provided as examples, but the synthetic method according to an embodiment of the present disclosure is not limited to these Examples.

Synthesis of Compound B2

Polycyclic Compound B2 may be synthesized by, for example, the acts (e.g., tasks or steps) shown in Reaction Scheme 1:

Reaction Scheme 1

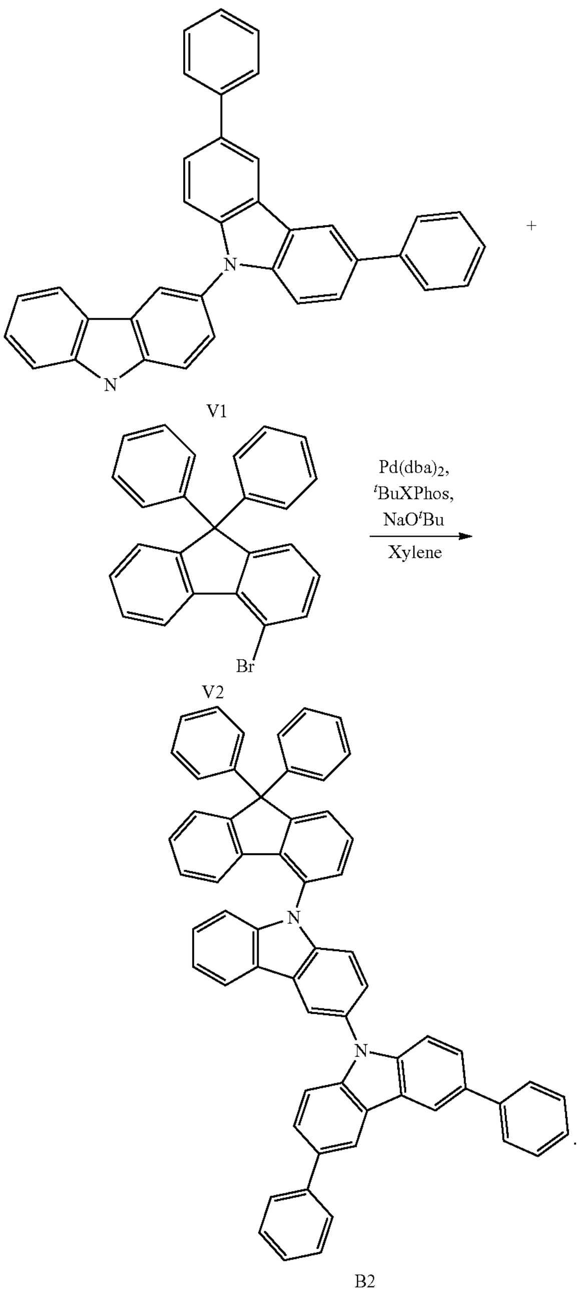

Xylene (200 mL) was added to Compound V1 (10 mmol), Compound V2 (10 mmol), NaOtBu (0.96 g, 10 mmol), and $^t$BuXPhos (1 mmol) and degassed. In an argon atmosphere, bis(dibenzylideneacetone)palladium (0.5 mmol) was added thereto and heated and stirred at about 130° C. for about 12 hours. The reaction solution was standing to cool to room temperature, extracted with toluene, washed with $H_2O$ and brine, and dried over $Na_2SO_4$. The obtained solution was concentrated and purified by column chromatography to obtain Compound B2 (MS 800.32).

Synthesis of Compound B13

Polycyclic Compound B13 may be synthesized by, for example, the acts (e.g., tasks or steps) shown in Reaction Scheme 2:

Reaction Scheme 2

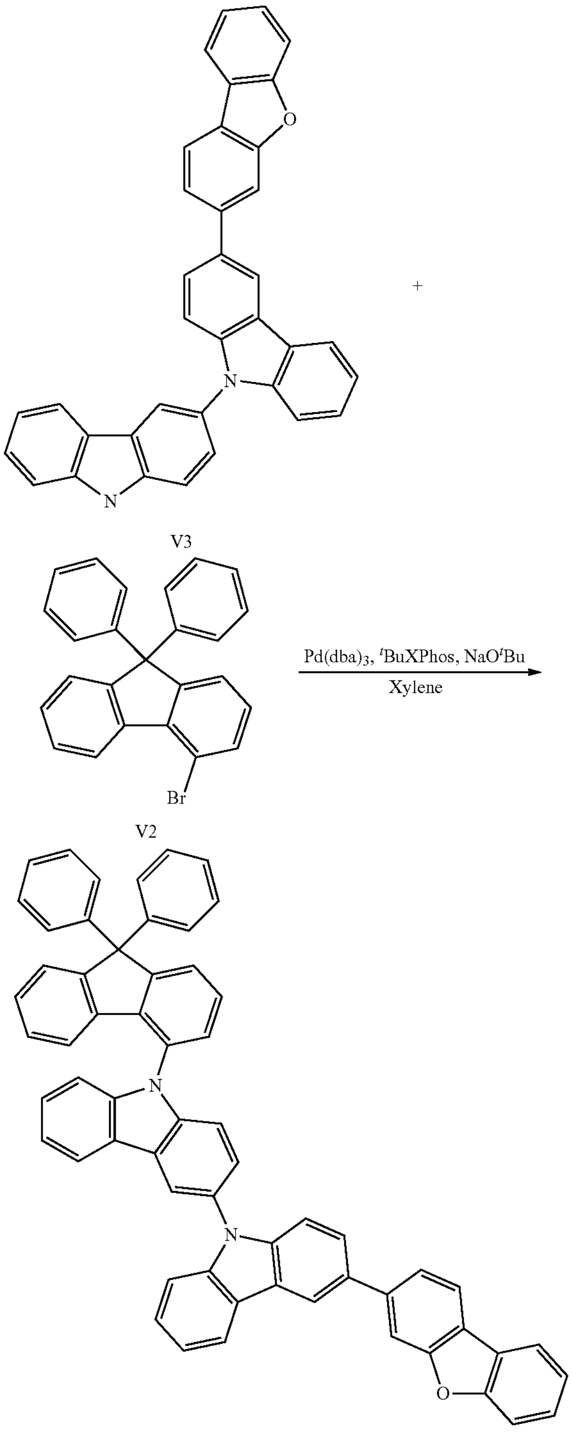

V3

V2

B13

Compound B13 (MS 814.30) was synthesized and obtained by substantially the same method as in Reaction Scheme 1, except that Compound V3 (10 mmol) was utilized instead of Compound V1 (10 mmol) in Reaction Scheme 1.

Synthesis of Compound D26

Polycyclic Compound D26 may be synthesized by, for example, the acts (e.g., tasks or steps) shown in Reaction Scheme 3:

Reaction Scheme 3

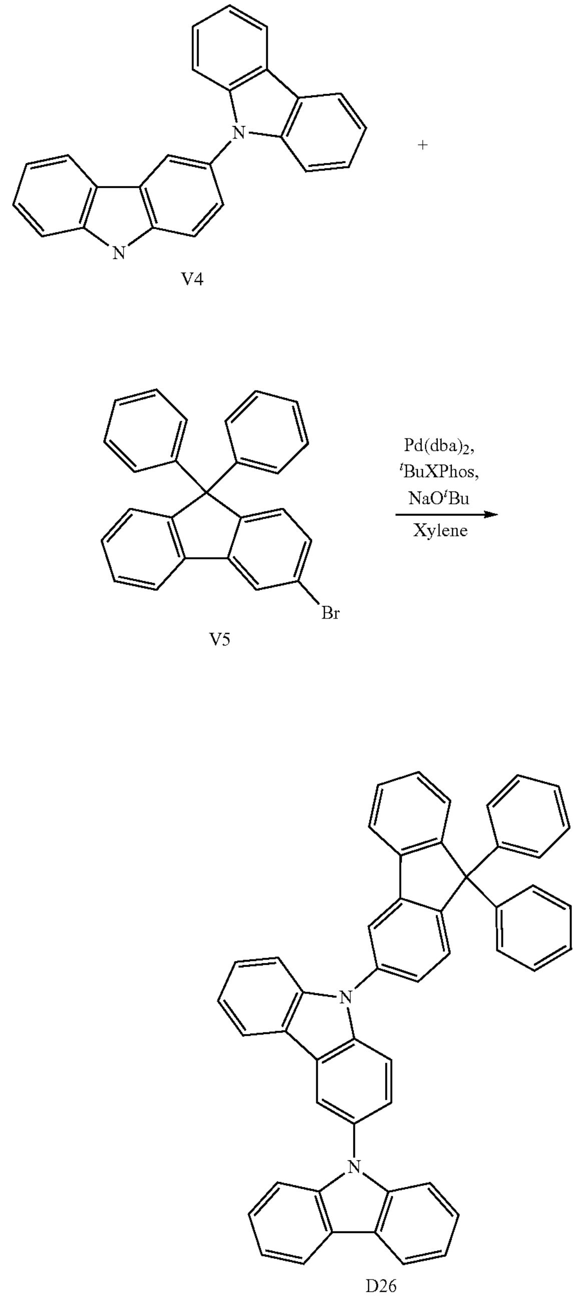

V4

V5

D26

Compound D26 (MS 648.26) was synthesized and obtained by substantially the same method as in Reaction Scheme 1, except that Compound V4 (10 mmol) and Compound V5 (10 mmol) were utilized instead of Compound V1 (10 mmol) and Compound V2 (10 mmol) in Reaction Scheme 1.

Synthesis of Compound E1

Polycyclic Compound E1 may be synthesized by, for example, the acts (e.g., tasks or steps) shown in Reaction Scheme 4:

Reaction Scheme 4

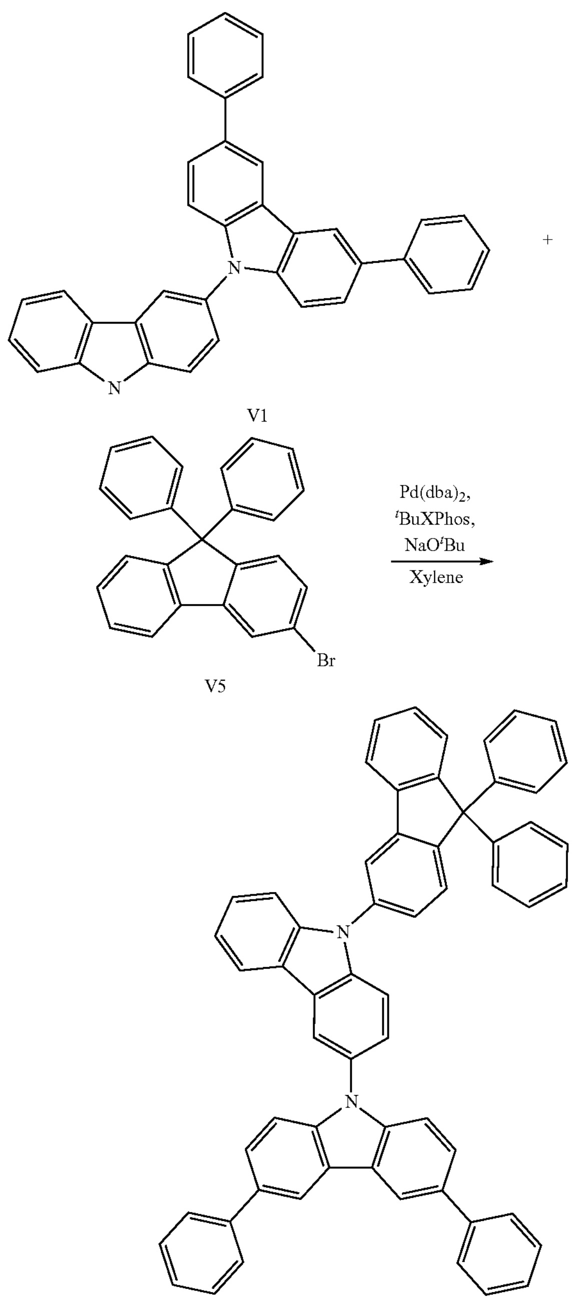

V1 + V5 → E1

Compound E1 (MS 800.32) was synthesized and obtained by substantially the same method as in Reaction Scheme 1, except that Compound V5 (10 mmol) was utilized instead of Compound V2 (10 mmol) in Reaction Scheme 1.

Synthesis of Compound H2

Polycyclic Compound H2 may be synthesized by, for example, the acts (e.g., tasks or steps) shown in Reaction Scheme 5:

Reaction Scheme 5

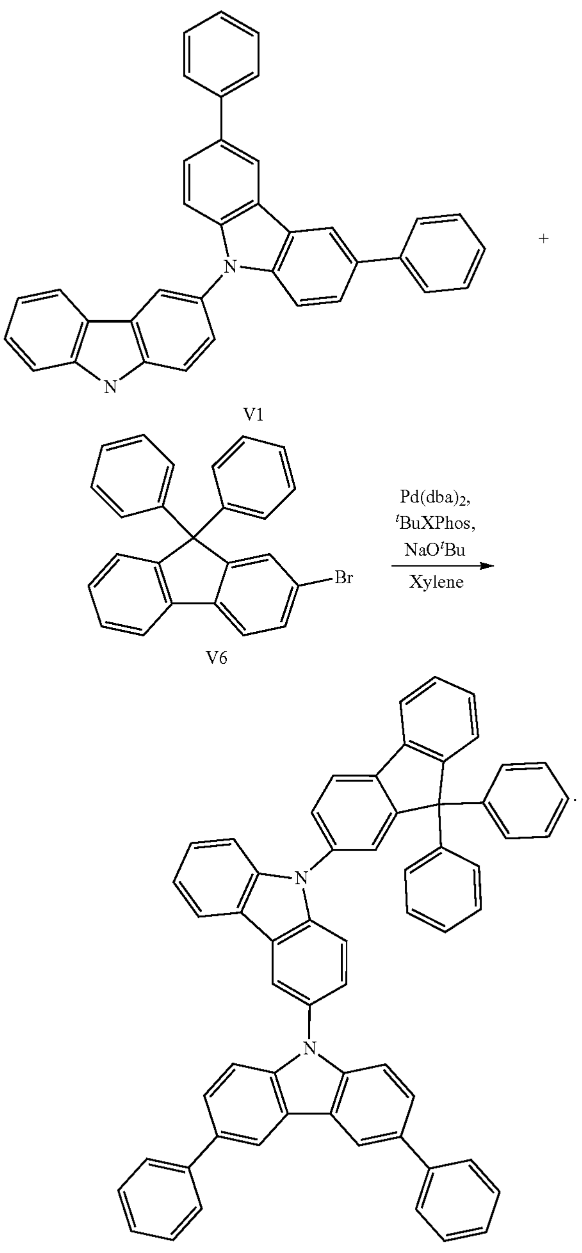

V1 + V6 → H2

Compound H2 (MS 800.32) was synthesized and obtained by substantially the same method as in Reaction Scheme 1, except that Compound V6 (10 mmol) was utilized instead of Compound V2 (10 mmol) in Reaction Scheme 1.

Synthesis of Compound H27

Polycyclic Compound H27 may be synthesized by, for example, the acts (e.g., tasks or steps) shown in Reaction Scheme 6:

Reaction Scheme 6

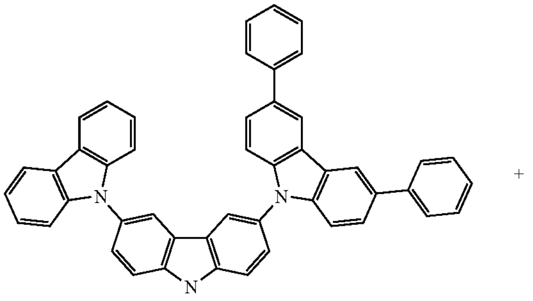

V7

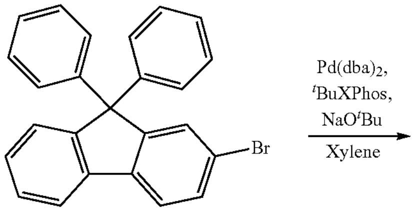

V6

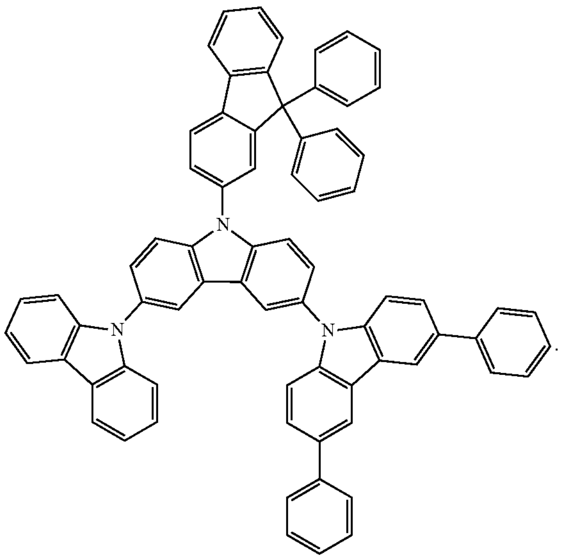

H27

Compound H27 (MS 965.38) was synthesized and obtained by substantially the same method as in Reaction Scheme 1, except that Compound V6 (10 mmol) and Compound V7 (10 mmol) were utilized instead of Compound V1 (10 mmol) and Compound V2 (10 mmol), respectively, in Reaction Scheme 1.

Synthesis of Compound I1

Polycyclic Compound I1 may be synthesized by, for example, the acts (e.g., tasks or steps) shown in Reaction Scheme 7:

Reaction Scheme 7

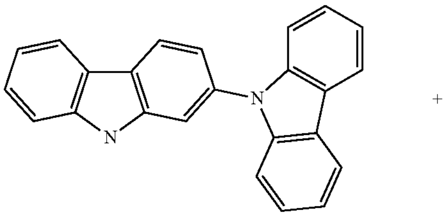

V8

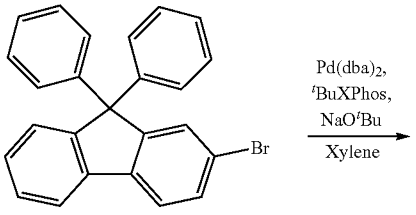

V6

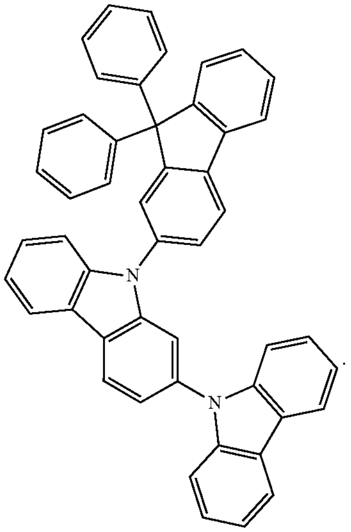

I1

Compound I1 (MS 648.26) was synthesized and obtained by substantially the same method as in Reaction Scheme 1, except that Compound V6 (10 mmol) and Compound V8 (10 mmol) were utilized instead of Compound V1 (10 mmol) and Compound V2 (10 mmol) in Reaction Scheme 1.

Synthesis of Compound K2

Polycyclic Compound K2 may be synthesized by, for example, the acts (e.g., tasks or steps) shown in Reaction Scheme 8:

Reaction Scheme 8

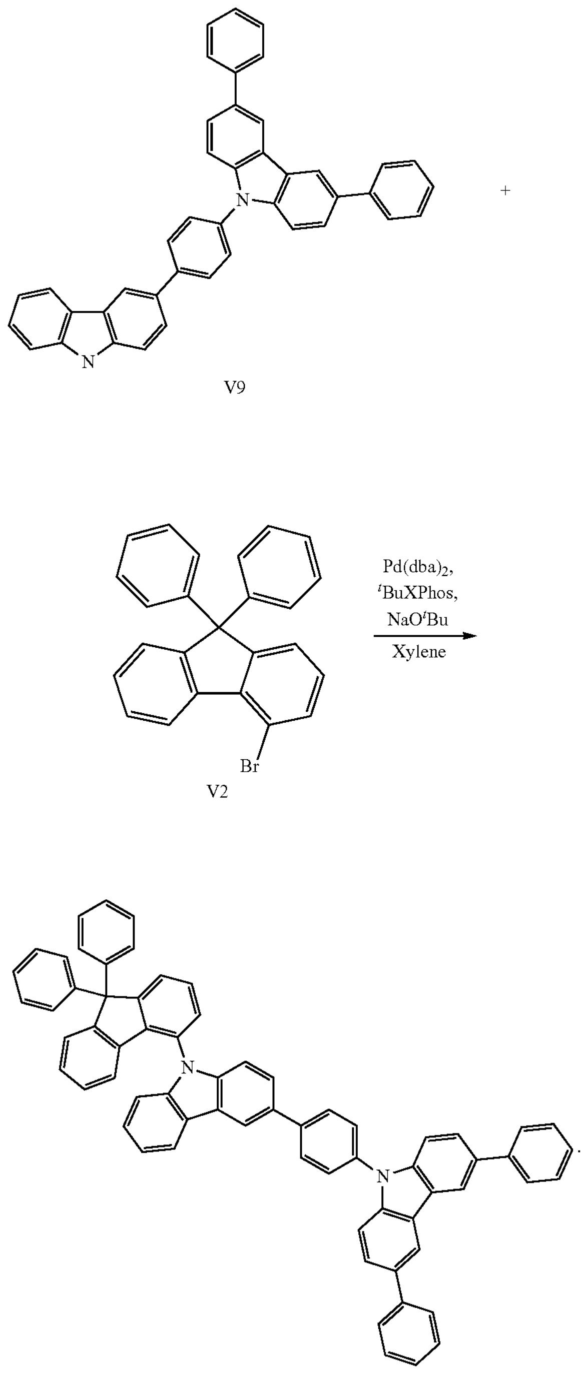

V9

V2

K2

Compound K2 (MS 876.35) was synthesized and obtained by substantially the same method as in Reaction Scheme 1, except that Compound V9 (10 mmol) was utilized instead of Compound V1 (10 mmol) in Reaction Scheme 1.

Synthesis of Compound P1

Polycyclic Compound P1 may be synthesized by, for example, the acts (e.g., tasks or steps) shown in Reaction Scheme 9:

Reaction Scheme 9

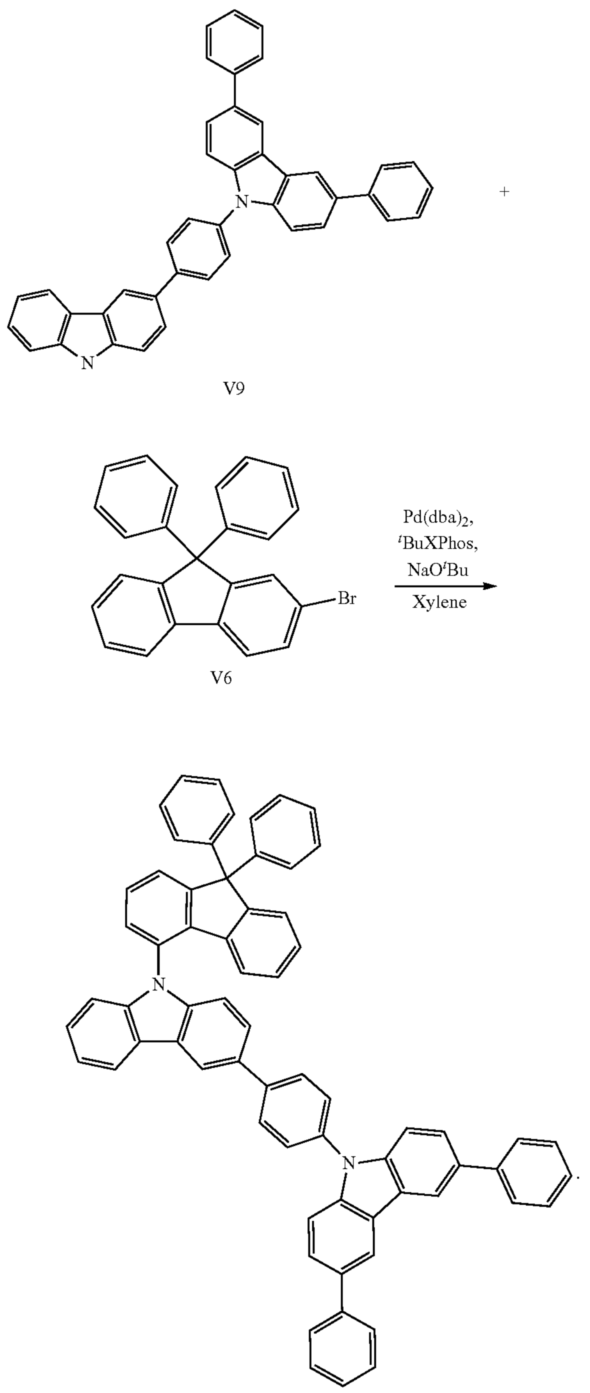

V9

V6

P1

Compound P1 (MS 876.35) was synthesized and obtained by substantially the same method as in Reaction Scheme 1, except that Compound V6 (10 mmol) and Compound V9 (10 mmol) were utilized instead of Compound V1 (10 mmol) and Compound V2 (10 mmol) in Reaction Scheme 1.

Synthesis of Compound P31

Polycyclic Compound P31 may be synthesized by, for example, the acts (e.g., tasks or steps) shown in Reaction Scheme 10:

Reaction Scheme 10

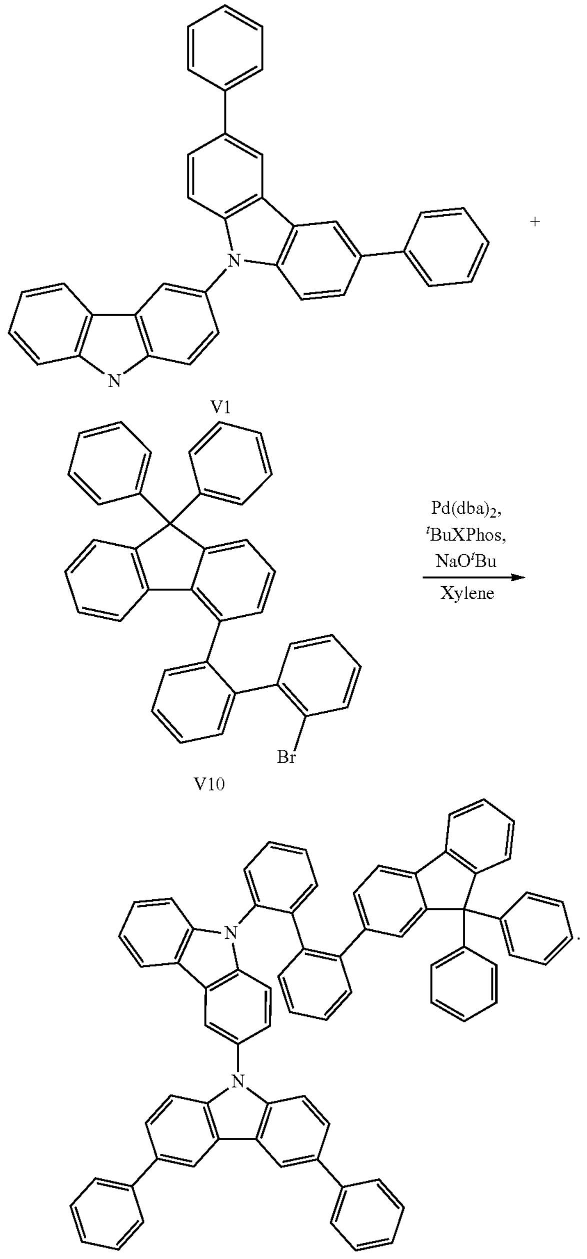

V1

V10

P31

Compound P31 (MS 952.38) was synthesized and obtained by substantially the same method as in Reaction Scheme 1, except that Compound V10 (10 mmol) was utilized instead of Compound V2 (10 mmol) in Reaction Scheme 1.

2. Manufacture and Evaluation of Light Emitting Element

Manufacture of Light Emitting Element

The light emitting element of an embodiment including the polycyclic compound of an embodiment in a hole transport layer was manufactured as follows. Polycyclic compounds of Compound B2, Compound B13, Compound D26, Compound E1, Compound H2, Compound H27, Compound I1, Compound K2, Compound P1 and Compound P31 as described above were each utilized as a hole transport layer material to manufacture the light emitting elements of Examples 1 to 10, respectively. Comparative Example Compounds R1 to R8 below were each utilized as a hole transport layer material to manufacture the light emitting elements of Comparative Examples 1 to 8, respectively.

The compounds utilized in the hole transport layers in Examples 1 to 10 and Comparative Examples 1 to 8 are shown as follows.

Example Compounds Used to Manufacture Devices

B2

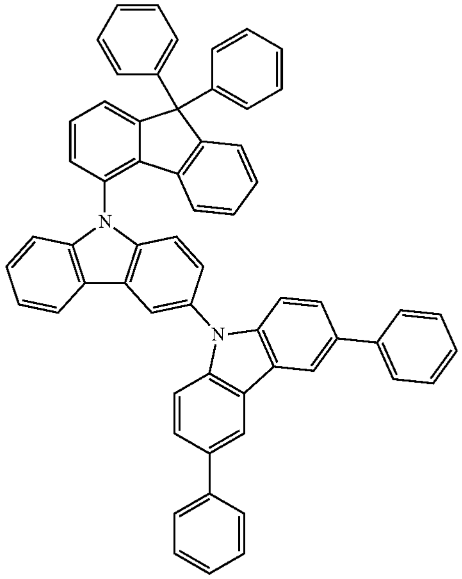

B13

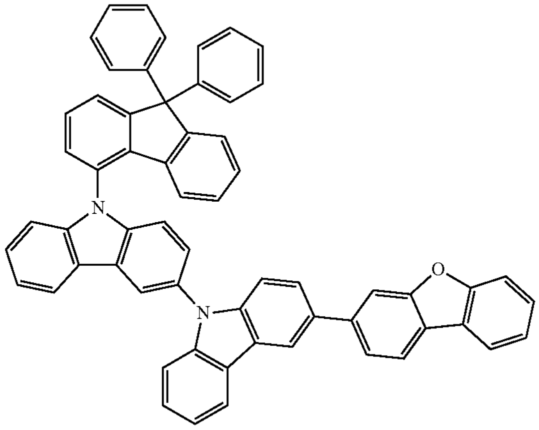

-continued
D26
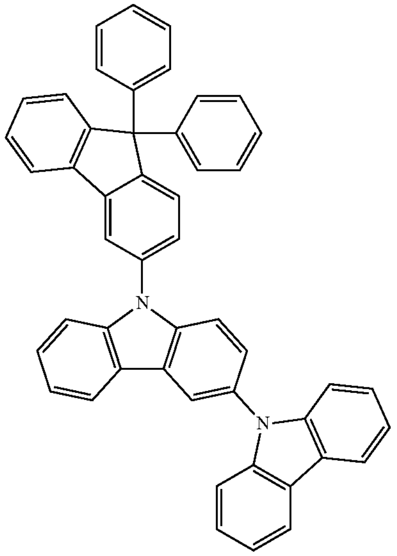
E1
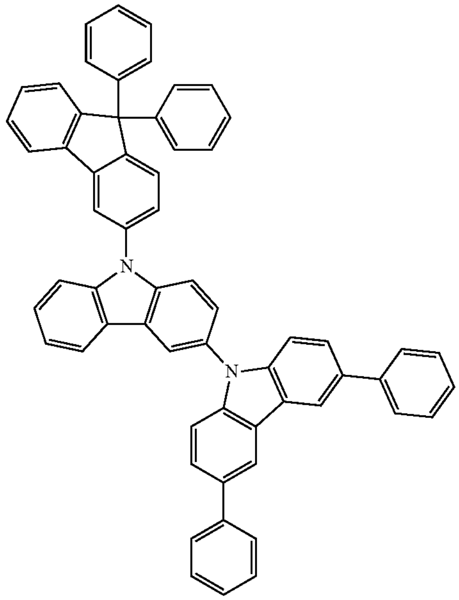
-continued
H2
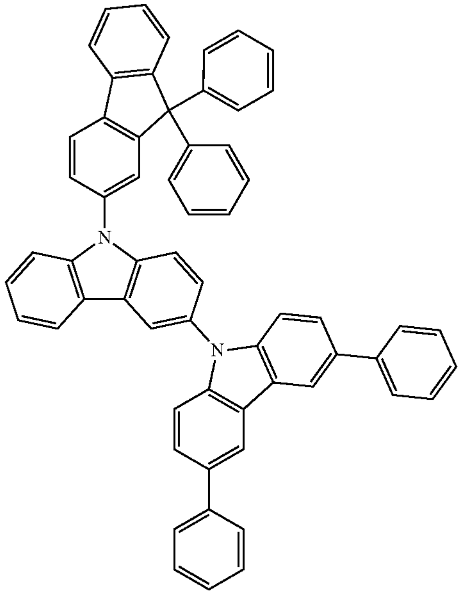
H27
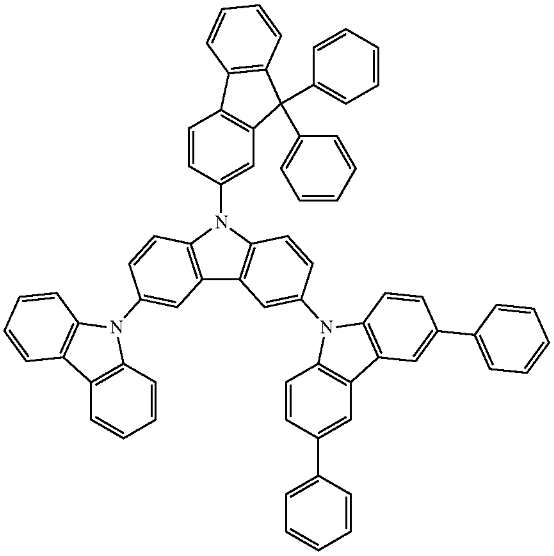
I1
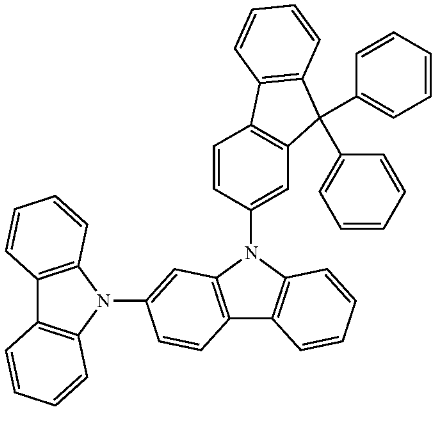

-continued
K2
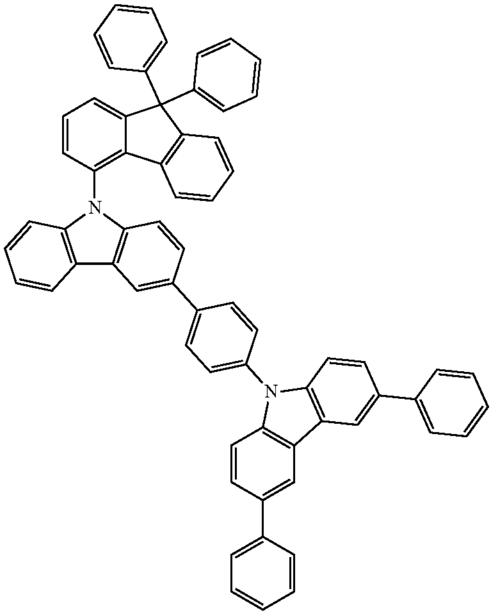
-continued
P31
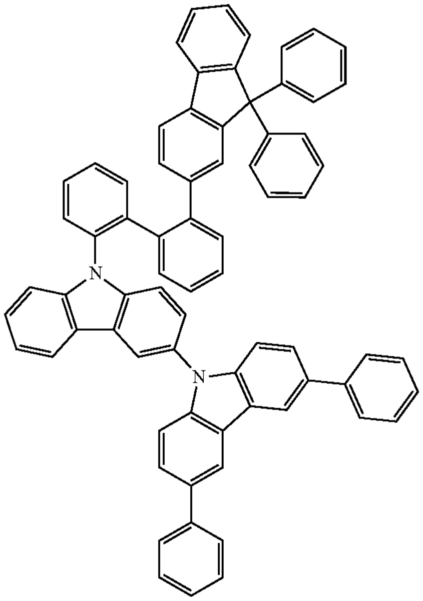
Comparative Example Compounds Used to Manufacture Devices
P1
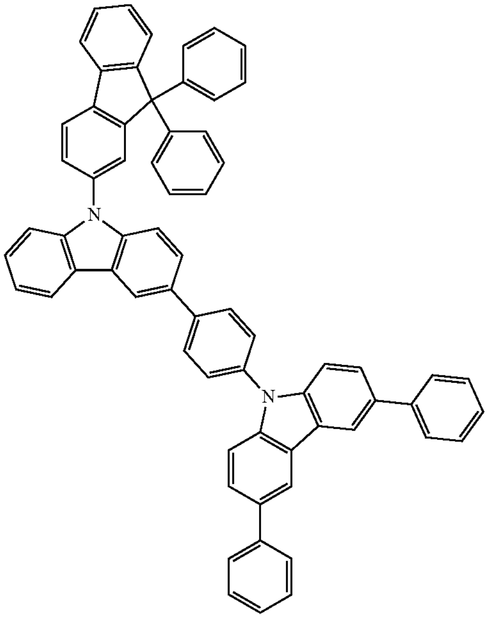
R1
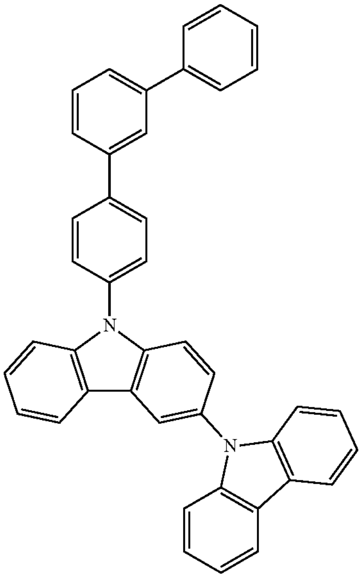

-continued
R2
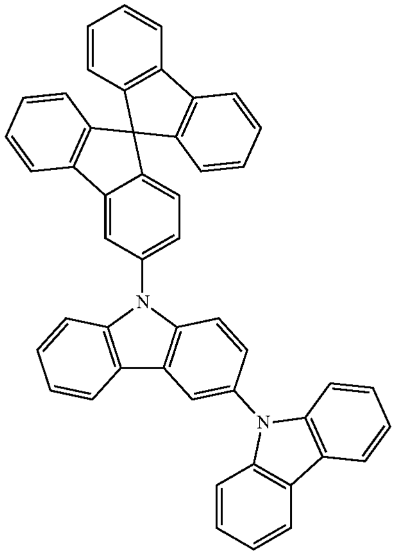
R3
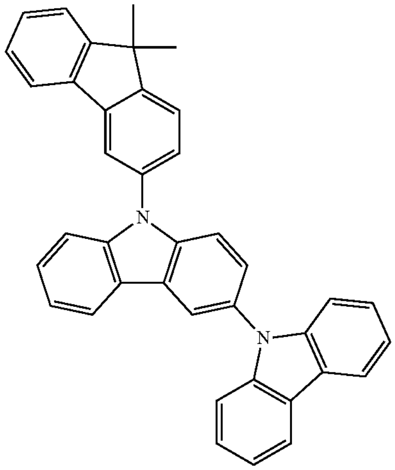
-continued
R4
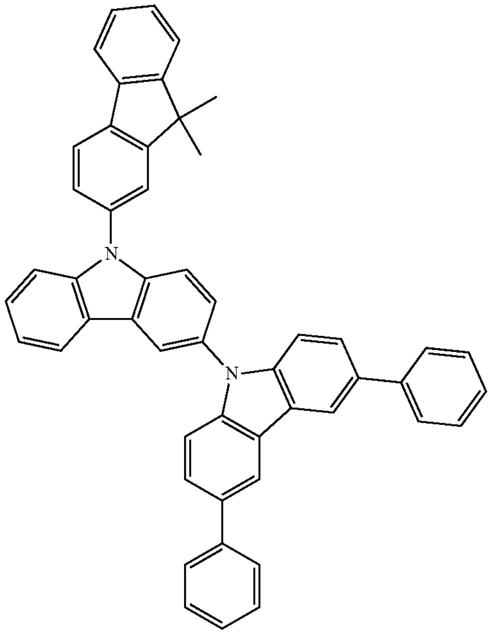
R5
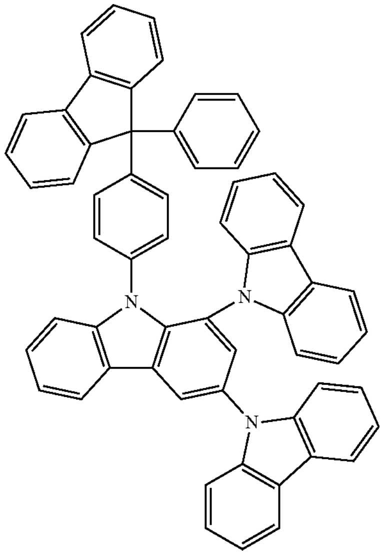

-continued

R6

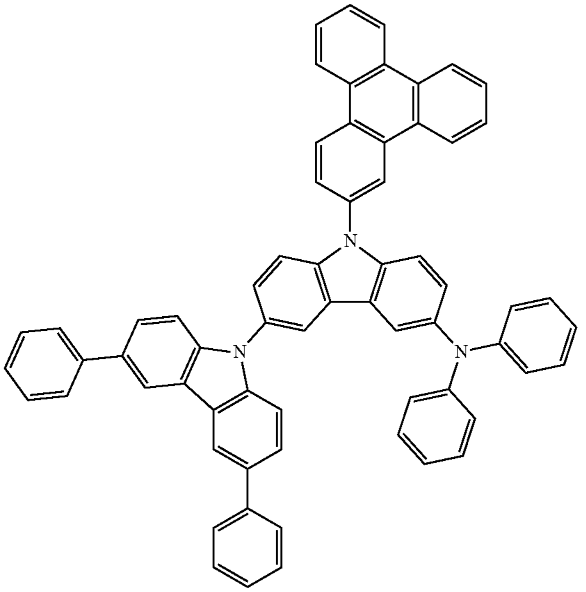

R7

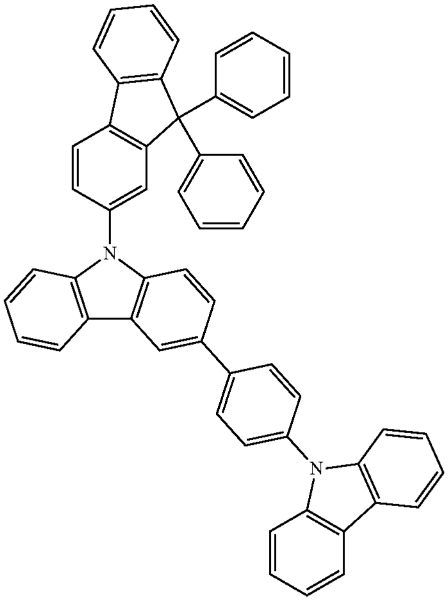

-continued

R8

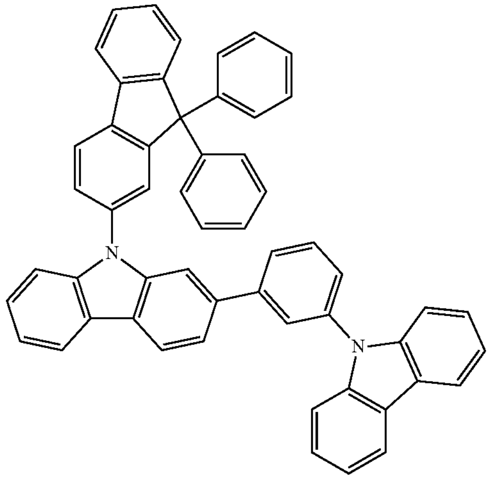

.

A 1500 Å-thick ITO layer was patterned on a glass substrate, washed with ultrapure water, and UV ozone-treated for about 10 minutes. Thereafter, 2-TNATA was deposited to form a 600 Å-thick hole injection layer. Then, an Example Compound or Comparative Example Compound was deposited to form a 300 Å-thick hole transport layer.

Thereafter, TBP was doped into ADN by 3% to form a 250 Å-thick emission layer. Then, $Alq_3$ was deposited to form a 250 Å-thick electron transport layer, and LiF was deposited to form a 10 Å-thick electron injection layer.

Then, Al was deposited to form a 1000 Å-thick second electrode.

In the Examples, the hole injection layer, the hole transport layer, the emission layer, the electron transport layer, the electron injection layer, and the second electrode were each formed by utilizing a vacuum deposition apparatus.

Evaluation of Light Emitting Element Characteristics

Evaluation results of the light emitting elements of Examples 1 to 10 and Comparative Examples 1 to 8 are listed in Table 1. Element service lives of the manufactured light emitting elements are listed in comparison in Table 1. The element service lives of Examples and Comparative Examples listed in Table 1 are set forth as a relative service life value (%), assuming the element service life of Comparative Example 7 as 100%.

TABLE 1

| Element manufacturing examples | Hole transport layer material | Element service life (%) |
|---|---|---|
| Example 1 | Example Compound B2 | 104 |
| Example 2 | Example Compound B13 | 104 |
| Example 3 | Example Compound D26 | 108 |
| Example 4 | Example Compound E1 | 109 |
| Example 5 | Example Compound H2 | 107 |
| Example 6 | Example Compound H27 | 107 |
| Example 7 | Example Compound I1 | 106 |
| Example 8 | Example Compound K2 | 105 |
| Example 9 | Example Compound P1 | 106 |
| Example 10 | Example Compound P31 | 107 |
| Comparative Example 1 | Comparative Example Compound R1 | 95 |
| Comparative Example 2 | Comparative Example Compound R2 | 98 |
| Comparative Example 3 | Comparative Example Compound R3 | 92 |

TABLE 1-continued

| Element manufacturing examples | Hole transport layer material | Element service life (%) |
|---|---|---|
| Comparative Example 4 | Comparative Example Compound R4 | 93 |
| Comparative Example 5 | Comparative Example Compound R5 | 95 |
| Comparative Example 6 | Comparative Example Compound R6 | 92 |
| Comparative Example 7 | Comparative Example Compound R7 | 100 |
| Comparative Example 8 | Comparative Example Compound R8 | 97 |

Referring to the results of Table 1, it may be seen that Examples of the light emitting elements utilizing the polycyclic compounds according to embodiments of the present disclosure as a hole transport layer material exhibit an excellent or suitable element service life characteristic, compared to Comparative Examples. The polycyclic compounds according to the Examples have a structure in which a bis carbazole group is connected (e.g., linked) to a fluorenyl group, and Examples including the polycyclic compounds of examples exhibited a long service life characteristic. It is believed that the polycyclic compounds of the Examples exhibit excellent or suitable hole transport ability and a long service life characteristic by (e.g., as a result of) introducing the carbazole skeleton having excellent or suitable (e.g., relatively high) resistance against heat or charge.

In addition, the fluorenyl group included in the polycyclic compound of an example may include two aryl groups at the 9H-position, and may thereby exhibit a steric effect. Accordingly, it is believed that the stability and resistance of the molecule was increased, and the hole transport ability of the entire molecule was thereby improved.

Therefore, the light emitting elements of examples including the polycyclic compounds of examples in the hole transport regions exhibited an improved service life characteristic.

Comparing the Example Compounds with Comparative Example Compound R1, it may be observed that Comparative Example Compound R1 has a structure in which a terphenyl group is connected to a bis carbazole group, and thus the element service life is reduced compared to Example Compounds. In contrast, the Example Compounds have a structure in which a fluorenyl group is connected to a bis carbazole group, and it is believed that the element service life is improved by the interaction between the bis carbazole group and the fluorenyl group.

Comparing Example Compound D26 with Comparative Example Compound R2, it may be observed that when spiro fluorene is connected to the nitrogen atom of the carbazole group, the element service life is reduced, compared to the structure in which 9,9-diphenyl fluorene is connected to the nitrogen atom of the carbazole group. It may be believed that this is because there is a steric difference between the spiro fluorene and the 9,9-diphenyl fluorene.

Comparing Example Compounds D26 and E1 with Comparative Example Compounds R3 and R4, it may be observed that when 9,9-dimethyl fluorene is connected to the nitrogen atom of the carbazole group, the element service life is reduced, compared to the structure in which 9,9-diphenyl fluorene is connected to the nitrogen atom of the carbazole group. It may be believed that this is because there is a difference of stability between an alkyl group (such as a methyl group) substituted at the 9H-position of the fluorenyl group and an aryl group (such as a phenyl group).

Comparing Example Compounds with Comparative Example Compound R5, it may be observed that when a bis carbazole moiety is connected to one of the aryl groups substituted at the 9H-position of the fluorenyl group, the service life is reduced, compared to the case when a bis carbazole moiety is connected at any among the 1-position to 8-position of the fluorenyl group. It may be believed that when the bis carbazole moiety is connected to the ring skeleton of the fluorenyl group, the fluorenyl group is stabilized by conjugation, and thereby the service life is improved.

Comparing the Example Compounds with Comparative Example Compound R6, it may be observed that when a triphenylene group is connected at the 9-position of the carbazole group, the element service life is reduced compared to the case when a fluorene group (e.g., a 9,9-diphenyl fluorene group) is connected thereto. Therefore, it may be believed that when the fluorenyl group having an aryl group as a substituent is connected at 9-position of the carbazole group, the service life is improved.

Example Compound P1 and Comparative Example Compound R7 each have a structure in which a bis carbazole moiety is connected at the 2-position of the fluorenyl group. For example, Example Compound P1 and Comparative Example Compound R7 have the structure in which a first carbazole group (see Substituent S1) is connected at the 2-position of the fluorenyl group (see $X_1$ in Formula 1), and a linker (see $L_2$ in Substituent 51) and a second carbazole group (see Substituent S2) are connected at the 3-position of the first carbazole group (see $Y_2$ in Substituent 51). However, in Example Compound P1, Substituent S2 is a substituted carbazole group, and in Comparative Example Compound R7, Substituent S2 is an unsubstituted carbazole group. Owing to such a difference, it is believed that Example Compound P1 has more improved conjugation in the bis carbazole moiety than Comparative Example Compound R7, such that the interaction between the bis carbazole moiety and the fluorenyl group is appropriately or suitably adjusted, and thus the element service life is more improved.

Example Compound I1 and Comparative Example Compound R8 each have a structure in which a bis carbazole moiety is connected at the 2-position of the fluorenyl group. For example, Example Compound I1 and Comparative Example Compound R8 each have a structure in which a first carbazole group (see Substituent 51) is connected at 2-position of the fluorenyl group (see $X_1$ in Formula 1), and a linker (see $L_2$ in Substituent S1) and a second carbazole group (see Substituent S2) are connected at 2-position of the first carbazole group (see $Y_1$ in Substituent S1). However, in Example Compound I1, a linker ($L_2$) is a direct linkage, and in Comparative Example Compound R8, a linker ($L_2$) is a phenylene group. Owing to such a difference, it is believed that Example Compound I1 has more improved conjugation in the bis carbazole moiety than Comparative Example Compound R8, the interaction between the bis carbazole moiety and the fluorenyl group is appropriately or suitably adjusted, and thus the element service life is more improved.

In some embodiments, like Example Compounds B2, D26, E1, H2, and 11, when two carbazole groups are directly bonded in the bis carbazole moiety, an improved service life effect is exhibited.

From the comparative evaluation results of the Examples and Comparative Examples listed in Table 1, it may be confirmed that in the case where the polycyclic compound according to embodiments of the present disclosure is utilized as a hole transport layer material, the light emitting element exhibits a long service life characteristic compared to the case of utilizing Comparative Example Compounds.

The polycyclic compound according to embodiments of the present disclosure exhibits a steric effect when a bis carbazole moiety is connected to 9,9-diphenyl fluorene, thereby increasing the interaction between the 9,9-diphenyl fluorene and the carbazole group. Therefore, the polycyclic compound according to embodiments of the present disclosure may exhibit effects of improving a hole transport property of the entire molecule and/or improving electron resistance, heat stability, and/or film characteristics of the material. Also, the light emitting element according to embodiments of the present disclosure includes the polycyclic compound to thereby achieve a long service life.

The light emitting element of an embodiment of the present disclosure may include the polycyclic compound of an embodiment in the hole transport region, thereby exhibiting a long service life characteristic.

The polycyclic compound of an embodiment may improve a service life of the light emitting element.

As used herein, the terms "substantially," "about," and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the present disclosure has been described with reference to embodiments of the present disclosure, it will be understood that the present disclosure is not limited to these embodiments, and various changes and modifications can be made by those skilled in the art without departing from the spirit and scope of the present disclosure.

Accordingly, the technical scope of the present disclosure is not intended to be limited to the contents set forth in the detailed description of the specification, but is intended to be defined by the appended claims and equivalents thereof.

What is claimed is:

1. A light emitting element comprising:

a first electrode;

a second electrode on the first electrode; and at least one functional layer between the first electrode and the second electrode and comprising a polycyclic compound represented by Formula 1:

Formula 1

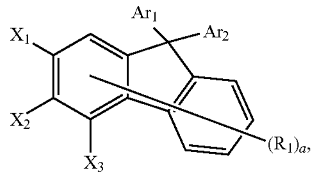

wherein, in Formula 1, $X_1$, $X_2$, and $X_3$ are each independently $R_x$ or represented by Substituent S1, and at least one of $X_1$, $X_2$, or $X_3$ is represented by Substituent S1, $R_x$ and $R_1$ are each independently a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or are bonded to an adjacent group to form a ring, a is an integer of 0 to 5, and $Ar_1$ and $Ar_2$ are each independently a substituted or unsubstituted aryl group having 6 to 50 ring-forming carbon atoms, Substituent S1

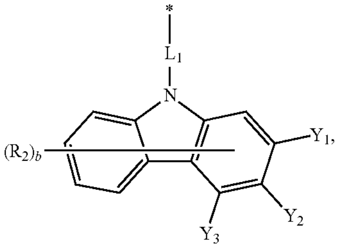

wherein, in Substituent S1, $Y_1$, $Y_2$, and $Y_3$ are each independently $R_y$ or $L_2Z$, and any one of $Y_1$, $Y_2$, or $Y_3$ is represented by $L_2Z$, $R_2$ and $R_y$ are each independently a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or are bonded to an adjacent group to form a ring, where $R_y$ does not include a substituted or unsubstituted carbazole group, b is an integer of 0 to 4, $L_1$ is a direct linkage, or a substituted or unsubstituted arylene group having 6 to 50 ring-forming carbon atoms, and $L_2$ is a direct linkage, a substituted or unsubstituted arylene group having 6 to 50 ring-forming carbon atoms, or a substituted or unsubstituted heteroarylene group having 2 to 50 ring-forming carbon atoms, wherein, when $X_1$ is represented by Substituent S1 and $Y_1$ is represented by $L_2Z$, $L_2$ is a direct linkage, wherein, when $X_1$ is represented by Substituent S1 and $Y_2$ is represented by $L_2Z$, Z is a substituted carbazole group, in Substituent S1, "—*" is a position connected to a benzene ring in Formula 1, and Z is represented by Substituent S2, Substituent S2

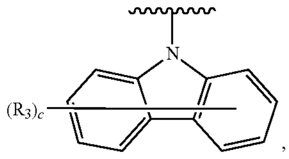

, and wherein, in Substituent S2, $R_3$ is a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or is bonded to an adjacent group to form a ring, c is an integer of 0 to 8, and in Substituent S2, "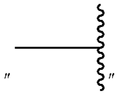"

is a position connected to $L_2$ in Substituent S1, and wherein, when $Y_1$ is $L_2Z$ and $L_2$ is a direct linkage, $L_1$ is a direct linkage.

2. The light emitting element of claim 1, wherein the at least one functional layer comprises an emission layer, a hole transport region between the first electrode and the emission layer, and an electron transport region between the emission layer and the second electrode, and the hole transport region comprises the polycyclic compound.

3. The light emitting element of claim 2, wherein the hole transport region comprises at least one of a hole injection layer, a hole transport layer, or an electron blocking layer, and at least one of the hole injection layer, the hole transport layer, or the electron blocking layer comprises the polycyclic compound.

4. The light emitting element of claim 1, wherein $Ar_1$ and $Ar_2$ are each independently a substituted or unsubstituted phenyl group.

5. The light emitting element of claim 1, wherein any one of $X_1$, $X_2$, or $X_3$ is represented by Substituent S1.

6. The light emitting element of claim 1, wherein $R_x$, $R_y$, and $R_1$ are each independently a hydrogen atom or a deuterium atom.

7. The light emitting element of claim 1, wherein $R_2$ is a hydrogen atom, a deuterium atom, a methyl group, a cyano group, a methoxy group, or a substituted or unsubstituted carbazole group.

8. The light emitting element of claim 1, wherein $R_3$ is a hydrogen atom, a deuterium atom, a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group.

9. The light emitting element of claim 1, wherein the polycyclic compound represented by Formula 1 is represented by Formula 1-1:

Formula 1-1

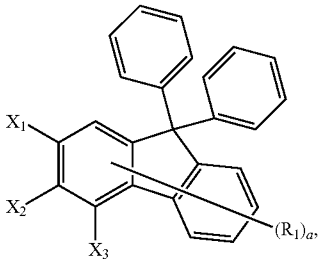

and wherein, in Formula 1-1, $X_1$, $X_2$, $X_3$, $R_1$, and a are each independently the same as defined in Formula 1.

10. The light emitting element of claim 1, wherein L1 is a direct linkage, a substituted or unsubstituted phenylene group, a substituted or unsubstituted divalent biphenyl group, or a substituted or unsubstituted divalent naphthyl group.

11. The light emitting element of claim 1, wherein $L_2$ is a direct linkage, a substituted or unsubstituted phenylene group, a substituted or unsubstituted divalent biphenyl group, a substituted or unsubstituted divalent naphthyl group, a substituted or unsubstituted divalent dibenzofuran group, or a substituted or unsubstituted divalent dibenzothiophene group.

12. The light emitting element of claim 1, wherein the substituent represented by Substituent S2 is a substituted or unsubstituted carbazole group.

13. A polycyclic compound represented by Formula 1:

Formula 1

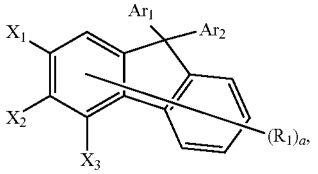

wherein, in Formula 1, $X_1$, $X_2$, and $X_3$ are each independently $R_x$ or represented by Substituent S1, and at least one of $X_1$, $X_2$, or $X_3$ is represented by Substituent S1, $R_x$ and $R_1$ are each independently a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or are bonded to an adjacent group to form a ring, a is an integer of 0 to 5, and $Ar_1$ and $Ar_2$ are each independently a substituted or unsubstituted aryl group having 6 to 50 ring-forming carbon atoms, Substituent S1

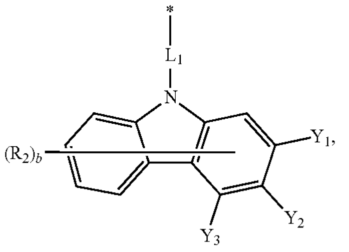

wherein, in Substituent S1, $Y_1$, $Y_2$, and $Y_3$ are each independently $R_y$ or $L_2Z$, and any one of $Y_1$, $Y_2$, or $Y_3$ is represented by $L_2Z$, $R_2$ and $R_y$ are each independently a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or are bonded to an adjacent group to form a ring, where $R_y$ does not include a substituted or unsubstituted carbazole group, b is an integer of 0 to 4, $L_1$ is a direct linkage, or a substituted or unsubstituted arylene group having 6 to 50 ring-forming carbon atoms, and $L_2$ is a direct linkage, a substituted or unsubstituted arylene group having 6 to 50 ring-forming carbon atoms, or a substituted or unsubstituted heteroarylene group having 2 to 50 ring-forming carbon atoms, wherein, when $X_1$ is represented by Substituent S1 and $Y_1$ is represented by $L_2Z$, $L_2$ is a direct linkage, wherein, when $X_1$ is represented by Substituent S1 and $Y_2$ is represented by $L_2Z$, Z is a substituted carbazole group, in Substituent S1, "—*" is a position connected to a benzene ring in Formula 1, and Z is represented by Substituent S2, Substituent S2

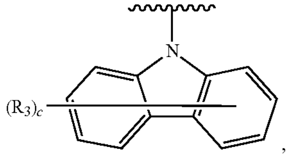

wherein, in Substituent S2, $R_3$ is a hydrogen atom, a deuterium atom, a halogen atom, a cyano group, a substituted or unsubstituted silyl group, a substituted or unsubstituted amine group, a substituted or unsubstituted oxy group, a substituted or unsubstituted alkyl group having 1 to 30 carbon atoms, a substituted or unsubstituted aryl group having 6 to 50 ring-forming carbon atoms, or a substituted or unsubstituted heteroaryl group having 2 to 50 ring-forming carbon atoms, and/or is bonded to an adjacent group to form a ring, c is an integer of 0 to 8, and in Substituent S2,

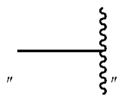

is a position connected to $L_2$ in Substituent S1, and wherein, when $Y_1$ is $L_2Z$ and $L_2$ is a direct linkage, $L_1$ is a direct linkage.

14. The polycyclic compound of claim 13, wherein $Ar_1$ and $Ar_2$ are each independently a substituted or unsubstituted phenyl group.

15. The polycyclic compound of claim 13, wherein $R_x$, $R_y$, and $R_1$ are each independently a hydrogen atom or a deuterium atom.

16. The polycyclic compound of claim 13, wherein $R_2$ is a hydrogen atom, a deuterium atom, a methyl group, a cyano group, a methoxy group, or a substituted or unsubstituted carbazole group.

17. The polycyclic compound of claim 13, wherein $R_3$ is a hydrogen atom, a deuterium atom, a substituted or unsubstituted phenyl group, a substituted or unsubstituted biphenyl group, a substituted or unsubstituted naphthyl group, a substituted or unsubstituted dibenzofuran group, or a substituted or unsubstituted dibenzothiophene group.

18. The polycyclic compound of claim 13, wherein the polycyclic compound represented by Formula 1 is represented by Formula 1-1:

Formula 1-1

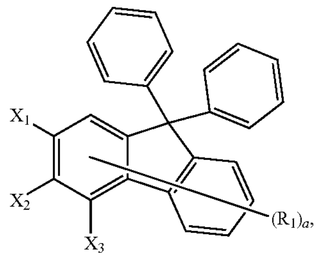

and wherein, in Formula 1-1, $X_1$, $X_2$, $X_3$, $R_1$, and a are each independently the same as defined in Formula 1.

19. The polycyclic compound of claim 13, wherein the substituent represented by Substituent S2 is a substituted or unsubstituted carbazole group.

20. A light emitting element comprising:

a first electrode;

a second electrode on the first electrode; and at least one functional layer between the first electrode and the second electrode and comprising a polycyclic compound represented by any one among compounds of Compound Group 1:

Compound Group 1
A1
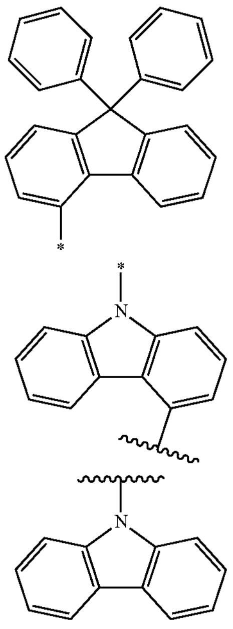
A2
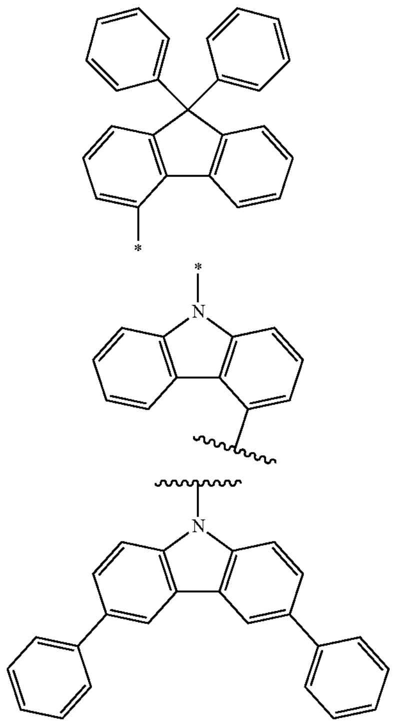
A3
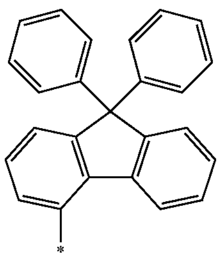
-continued
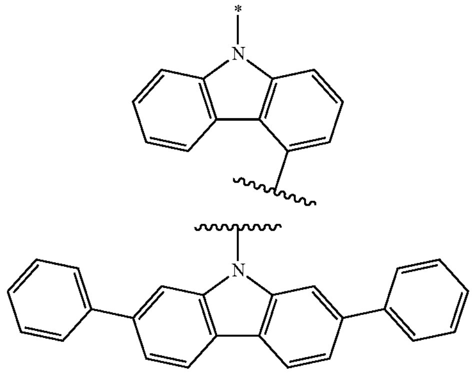
A4
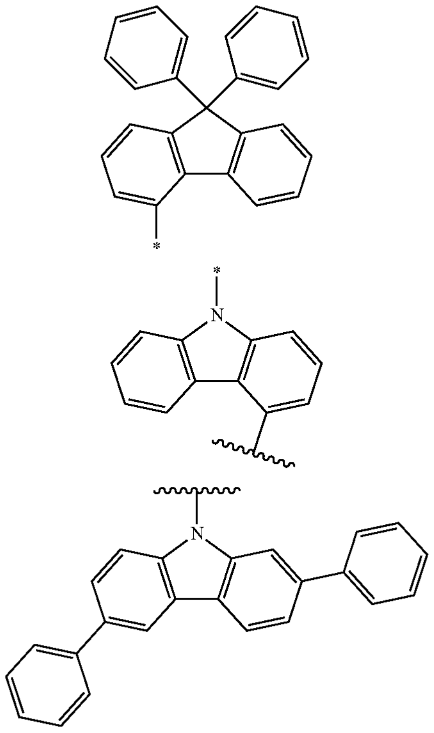
A5
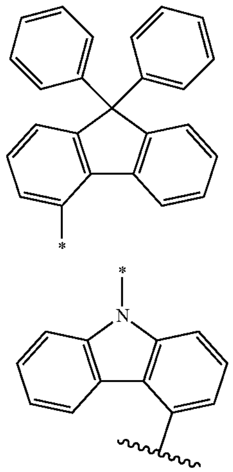

-continued
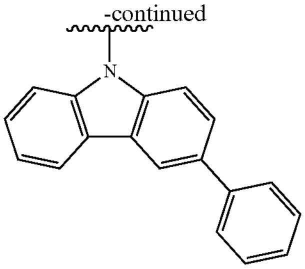
A6
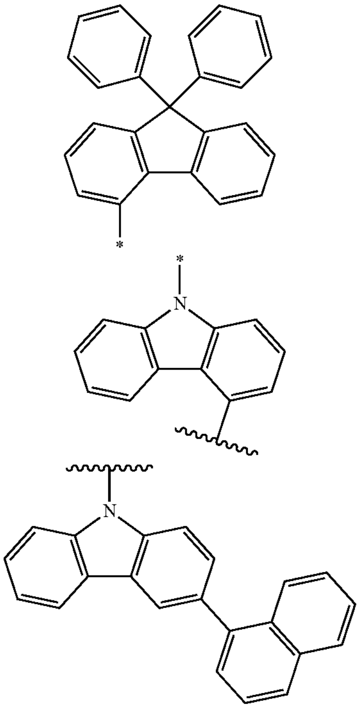
A7
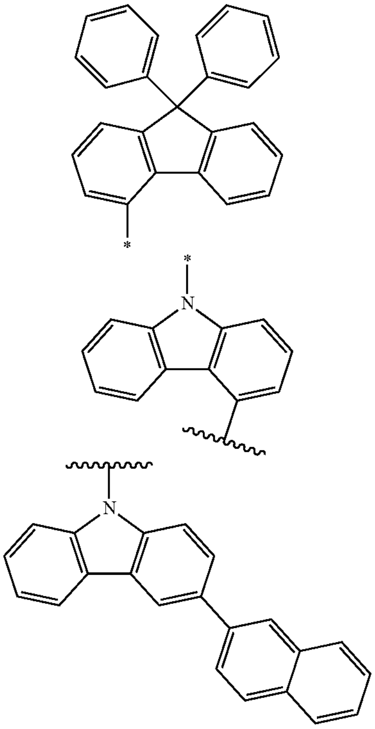
-continued
A8
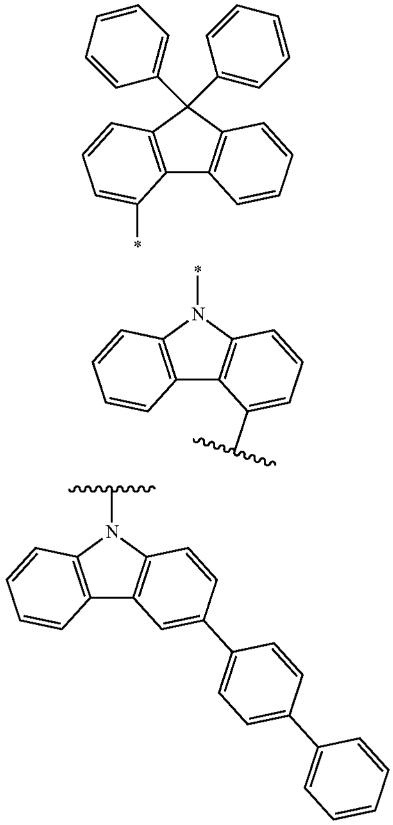
A9
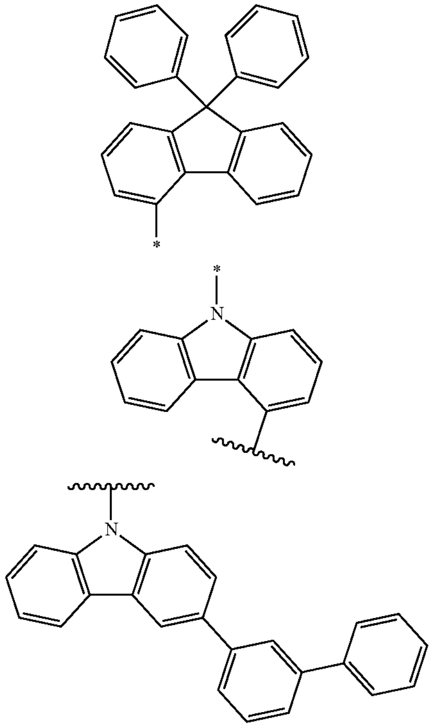

-continued
A10
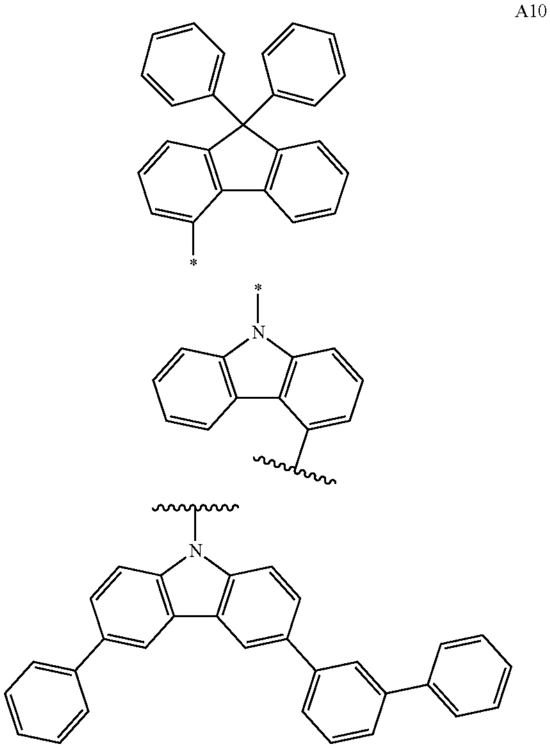
A11
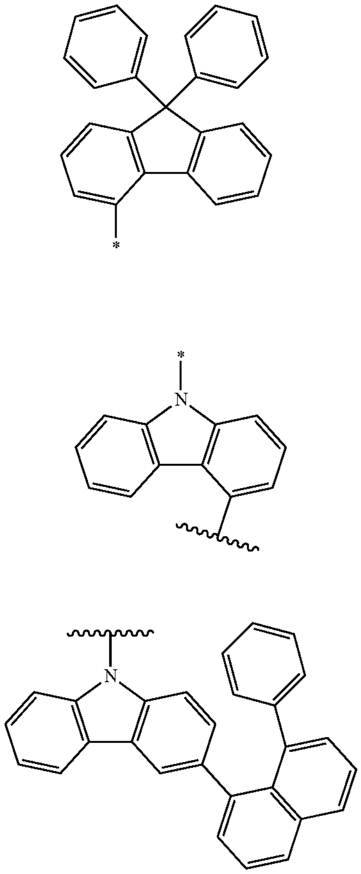
-continued
A12
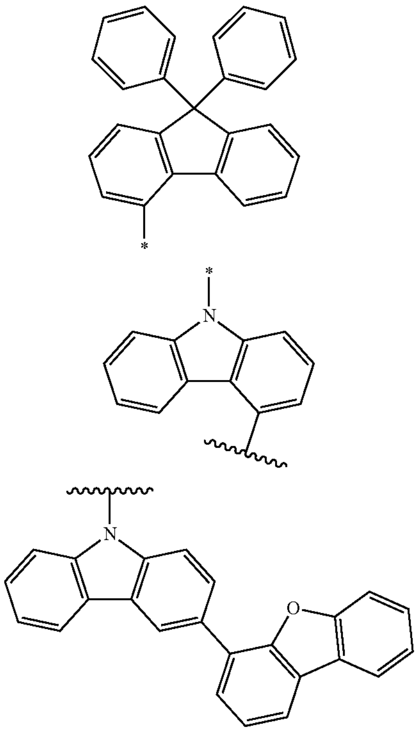
A13
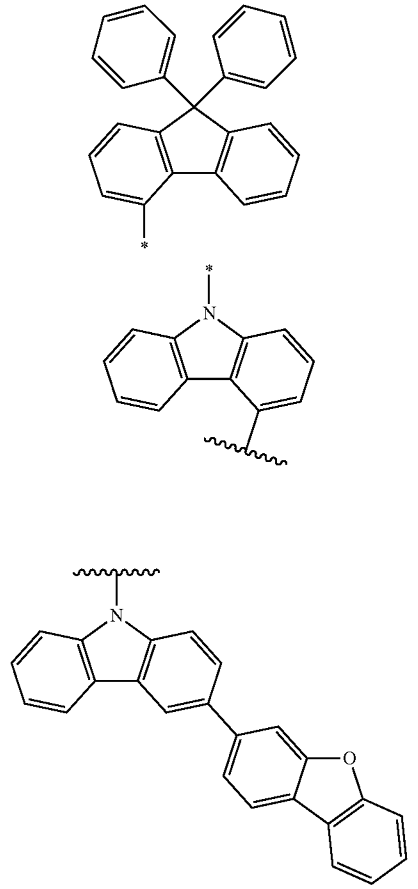

-continued
A14
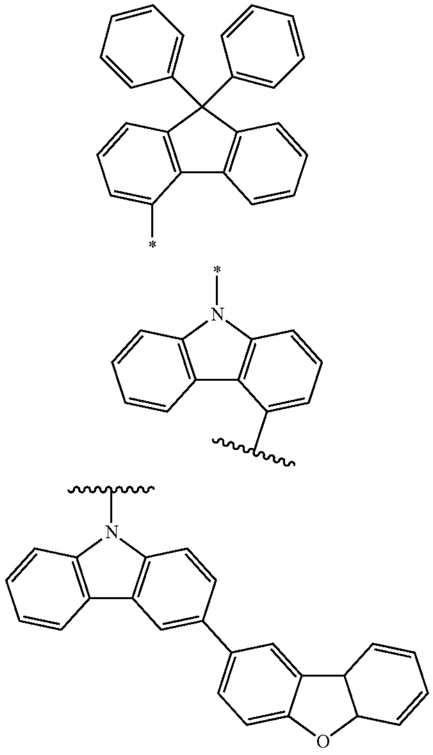
A15
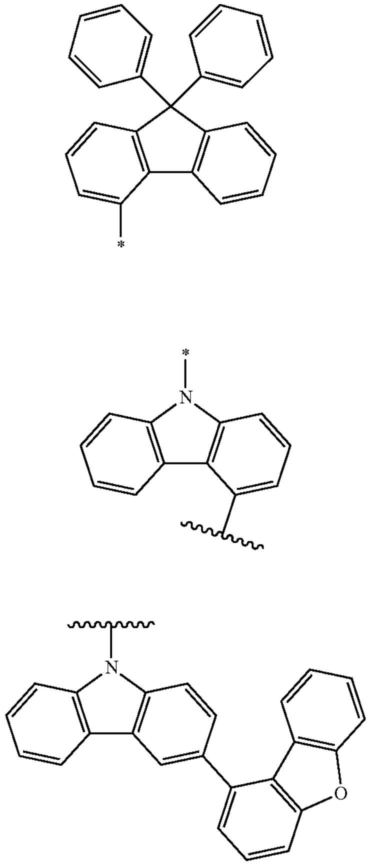
-continued
A16
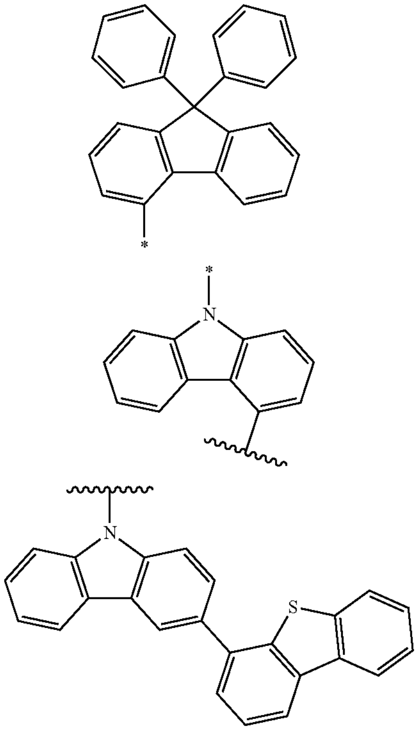
A17
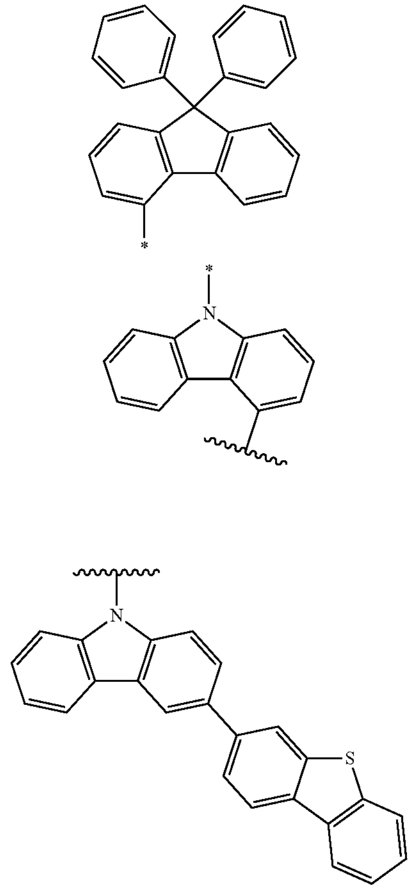

-continued
A18
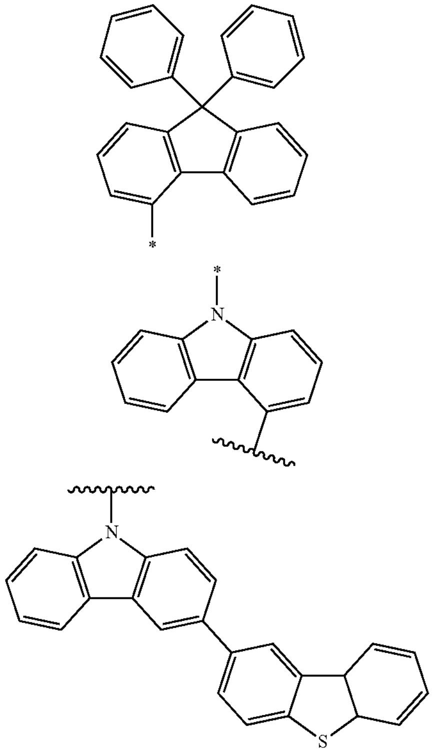
A19
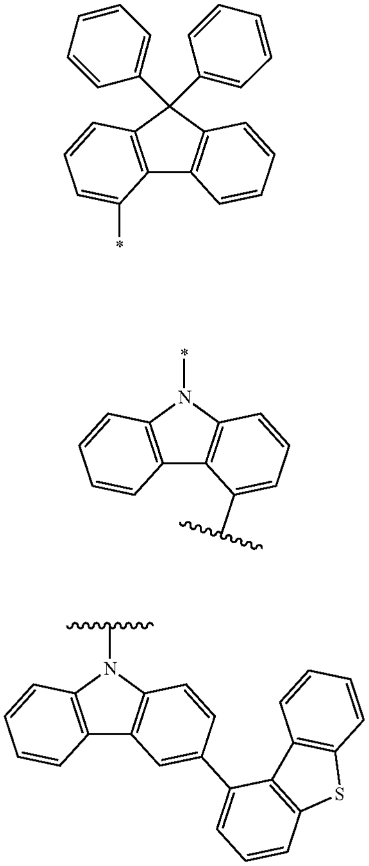
-continued
A20
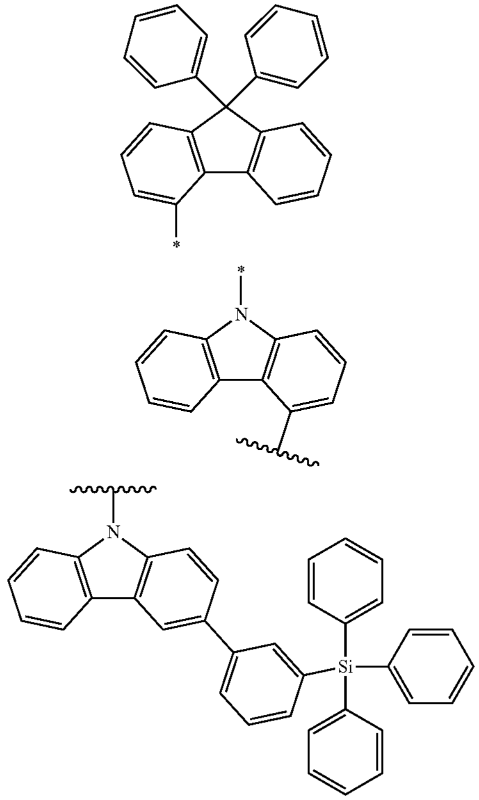
A21
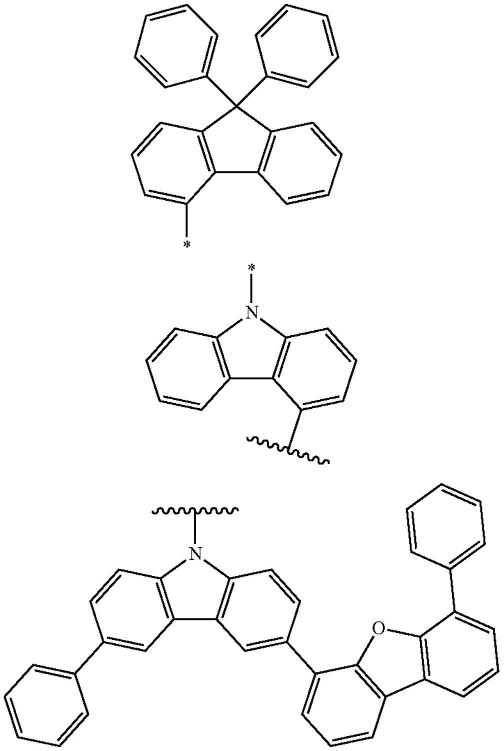

-continued
A22
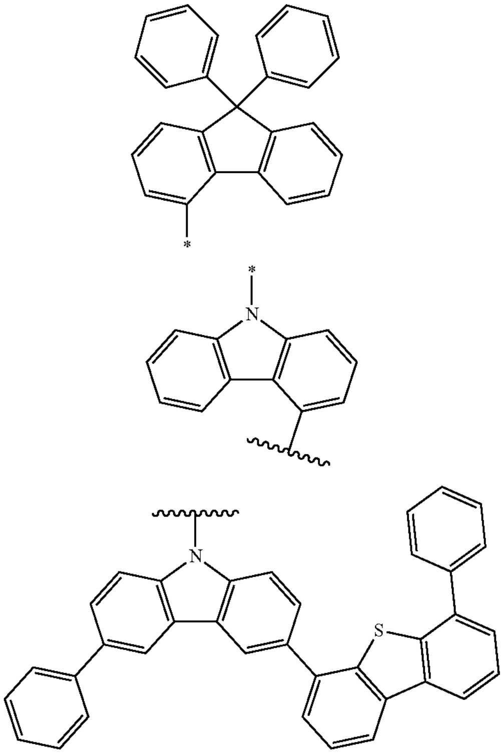
A23
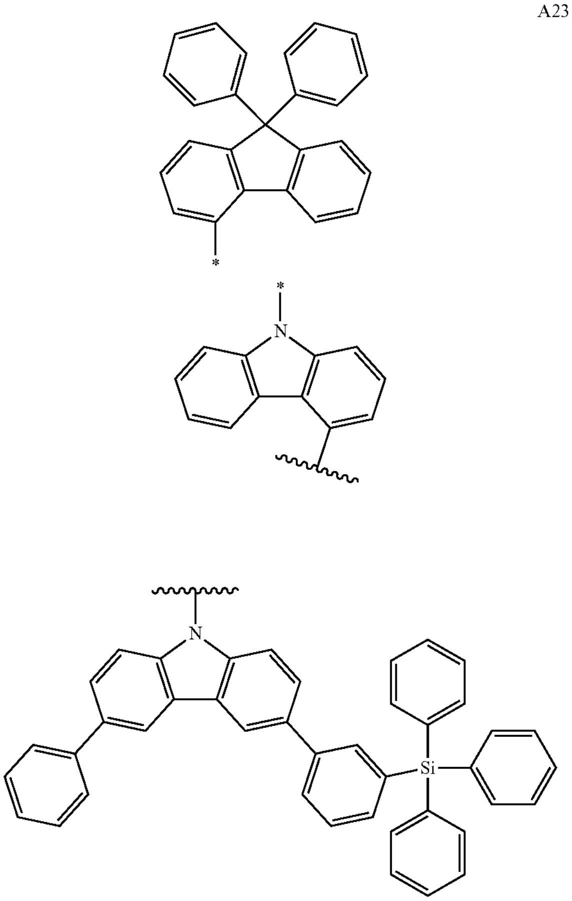
-continued
A24
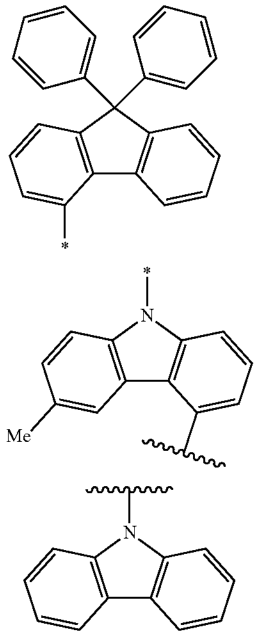
A25
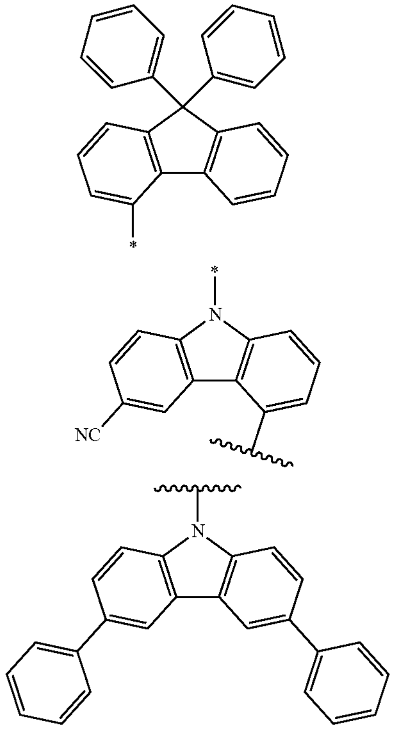
A26
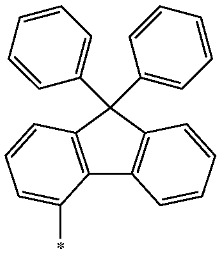

-continued
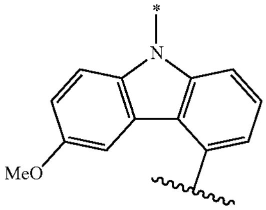
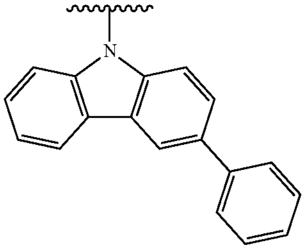
B1
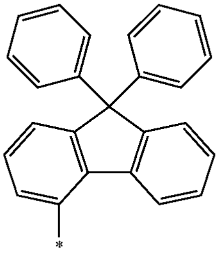
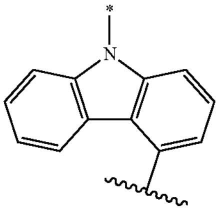
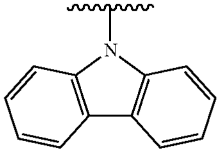
B2
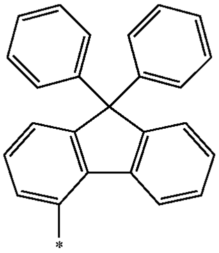
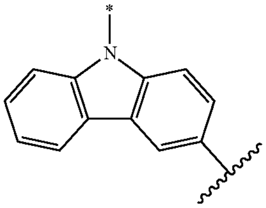
-continued
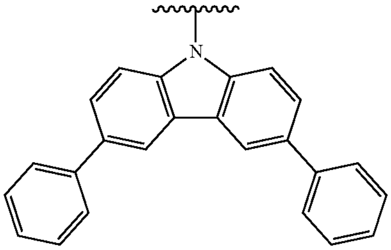
B3
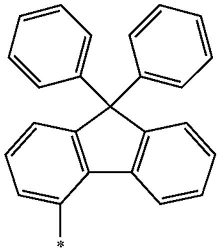
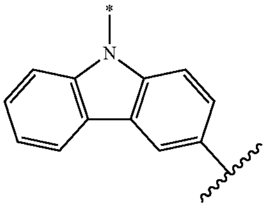
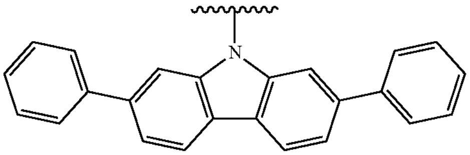
B4
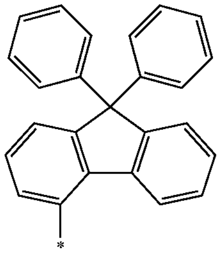
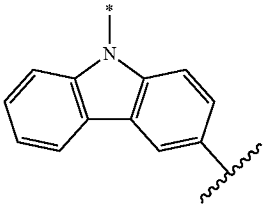
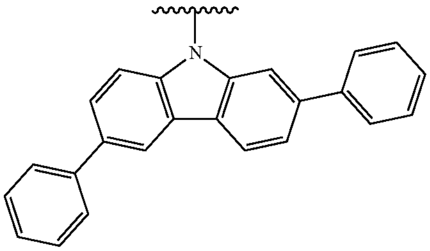

-continued
B5
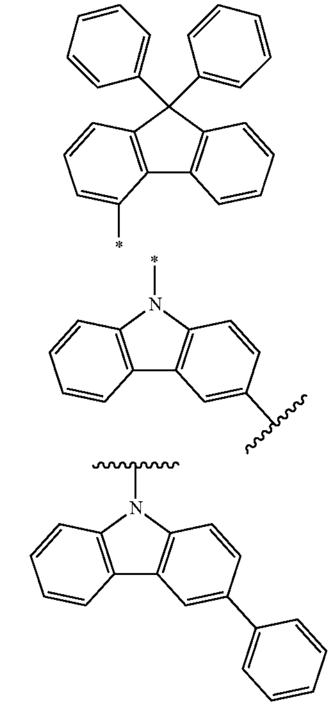
B6
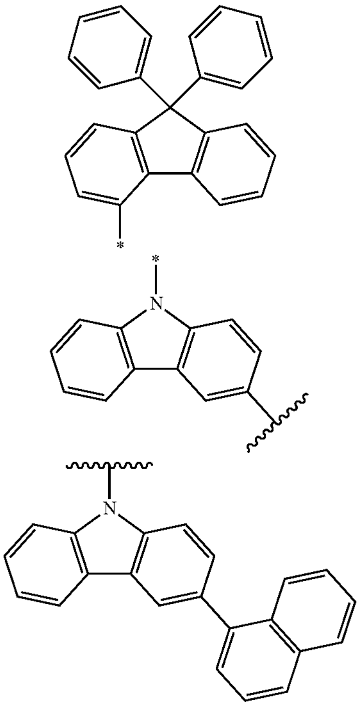
B7
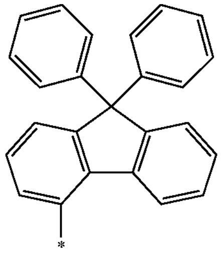
-continued
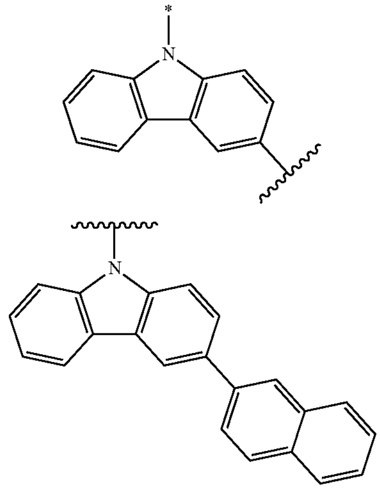
B8
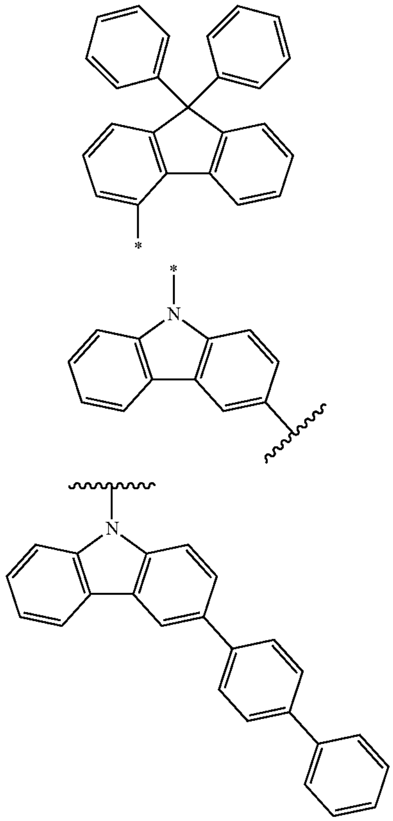
B9
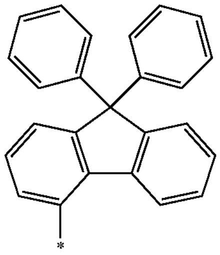

-continued
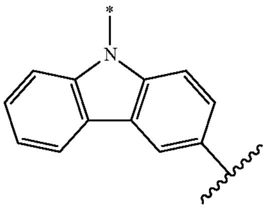
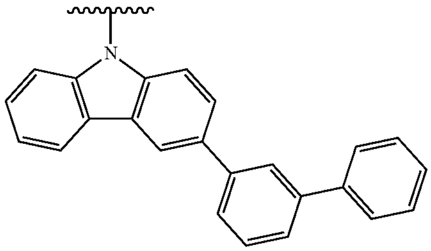
B10
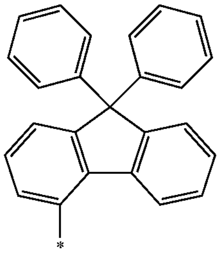
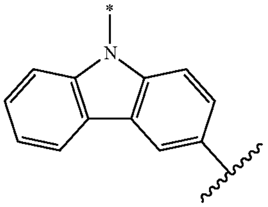
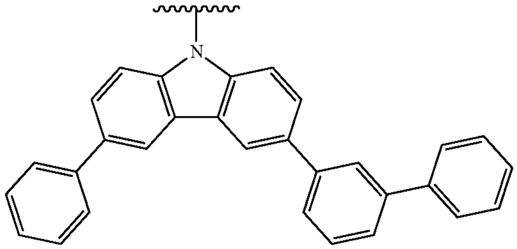
B11
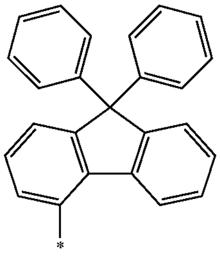
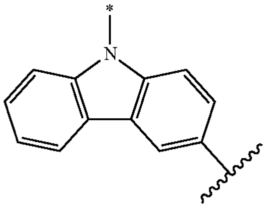
-continued
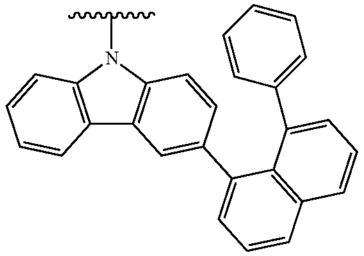
B12
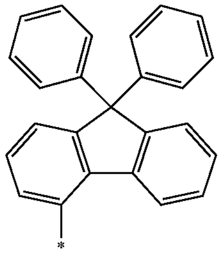
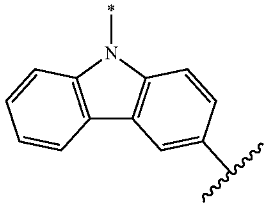
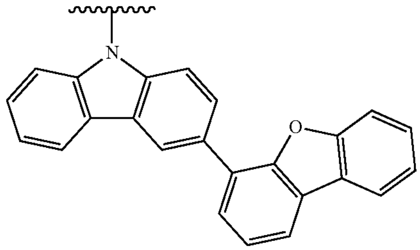
B13
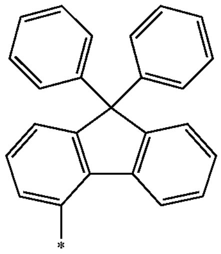
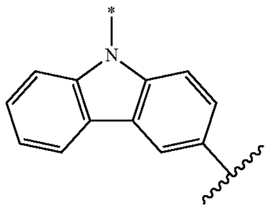

-continued
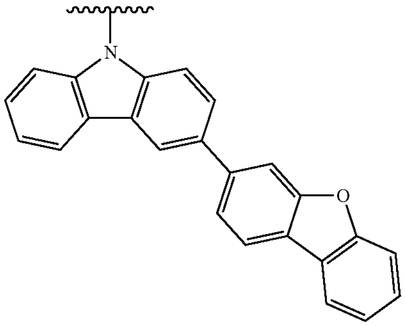
B14
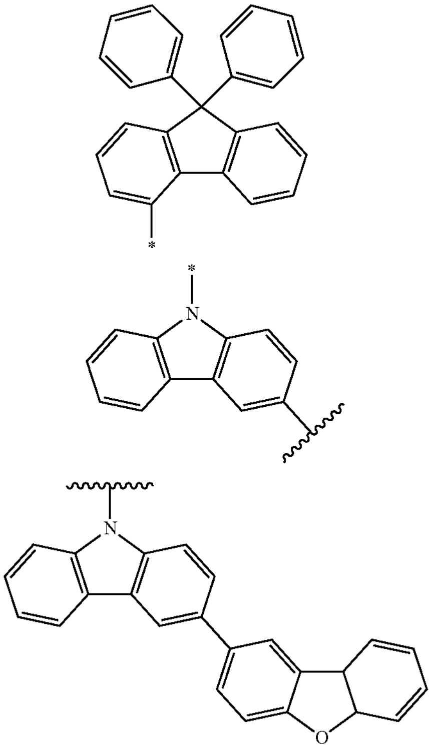
B15
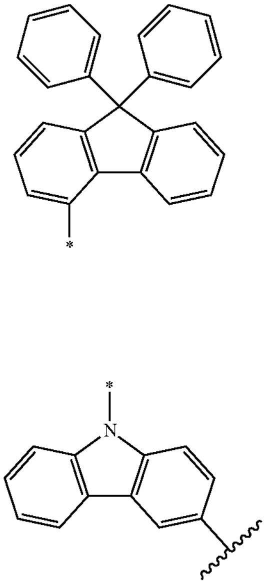
-continued
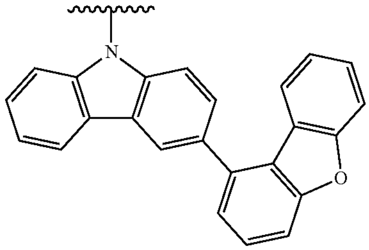
B16
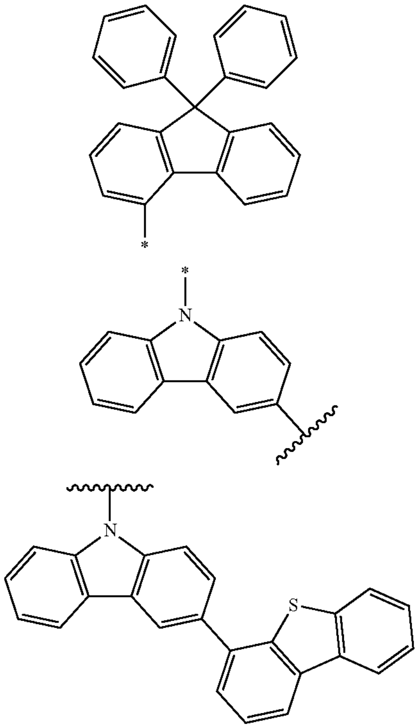
B17
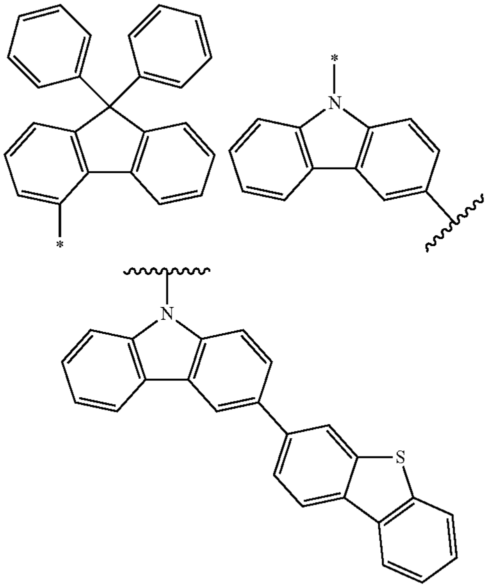

-continued
B18
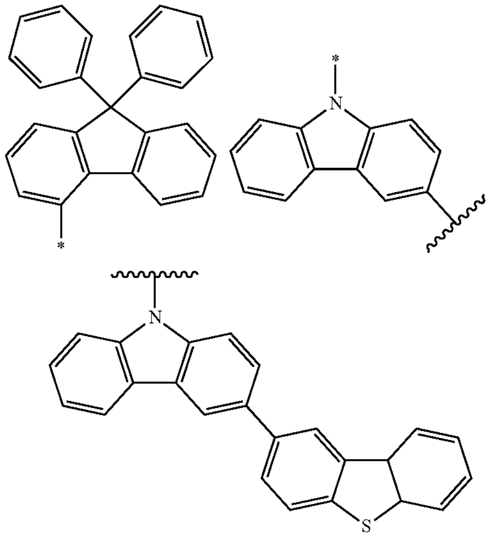
B19
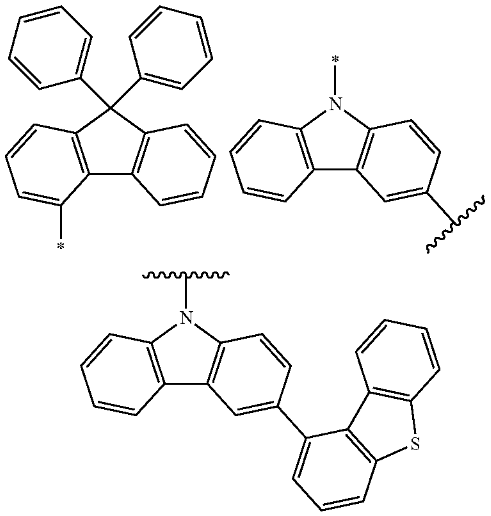
B20
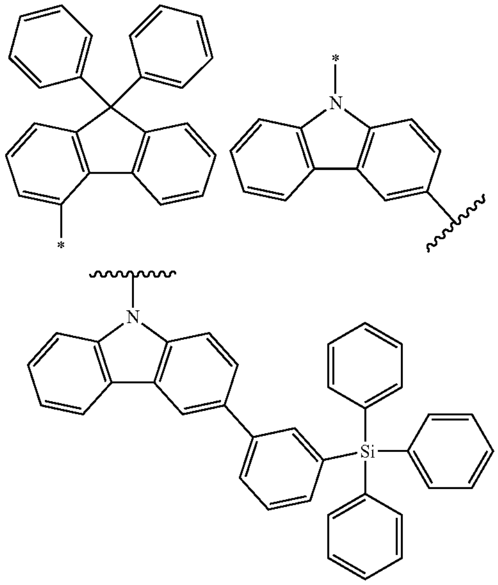
-continued
B21
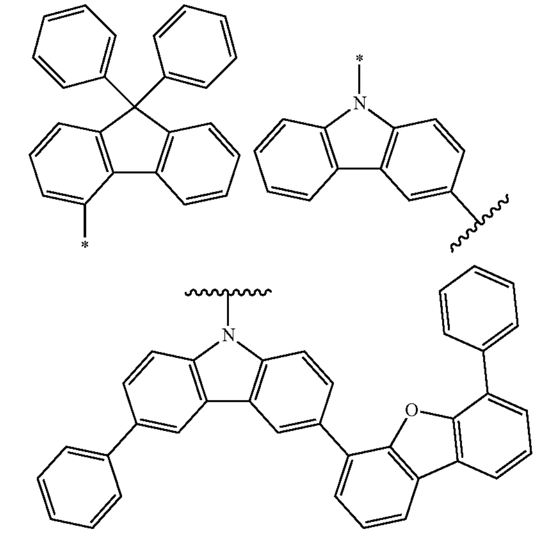
B22
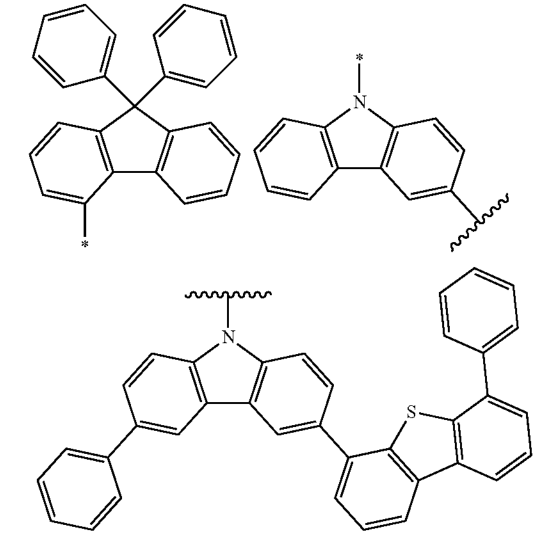
B23
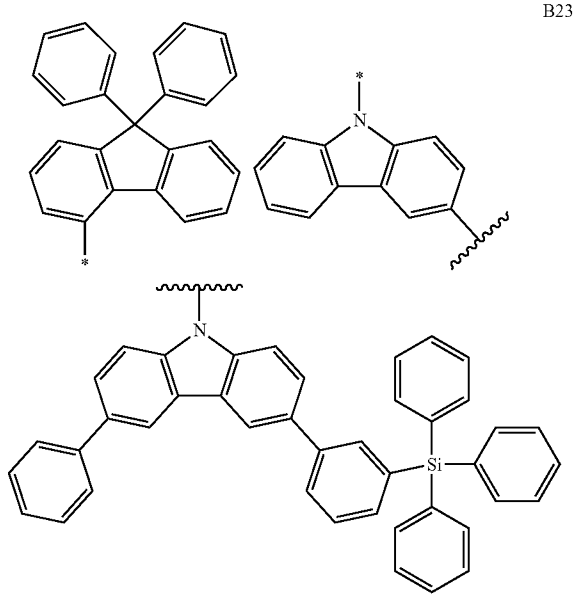

-continued
B24
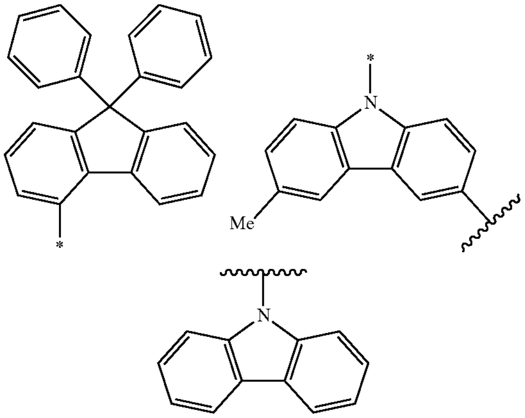
B25
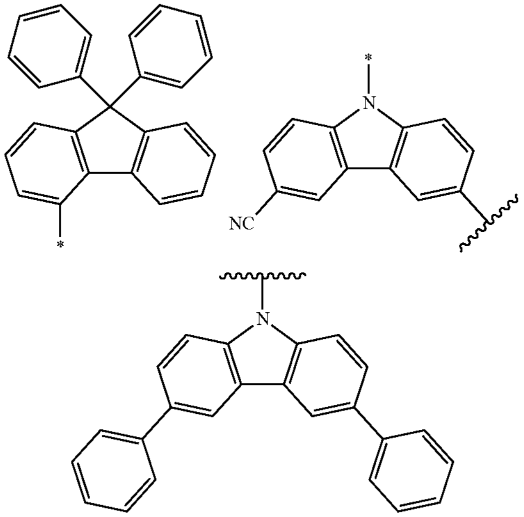
B26
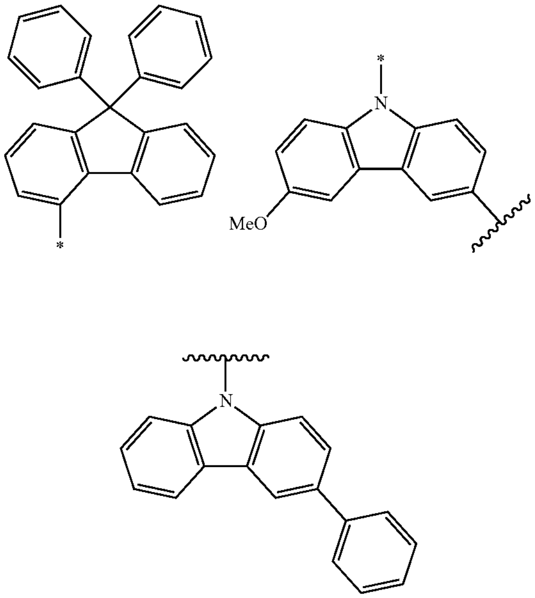
-continued
C1
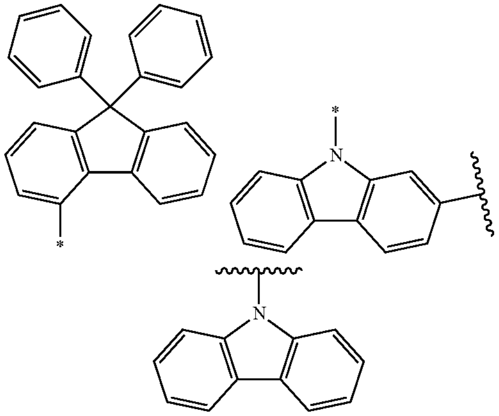
C2
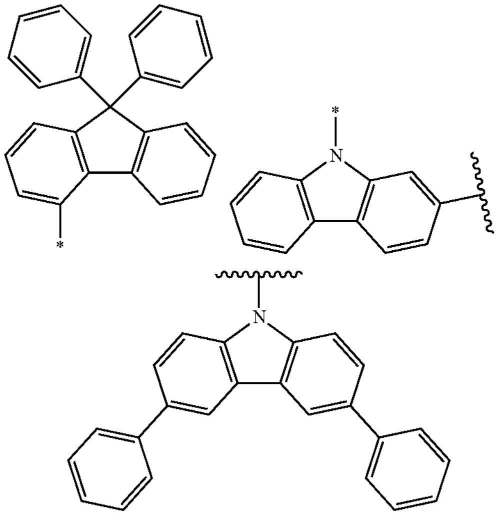
C3
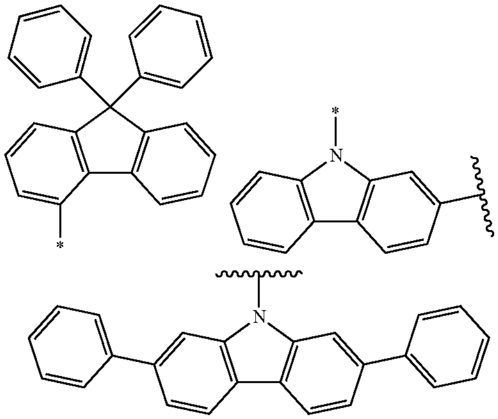
C4
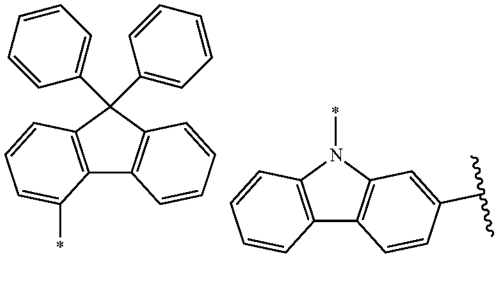

-continued
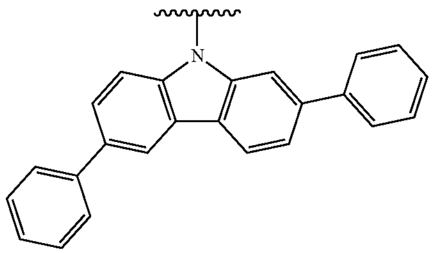
C5
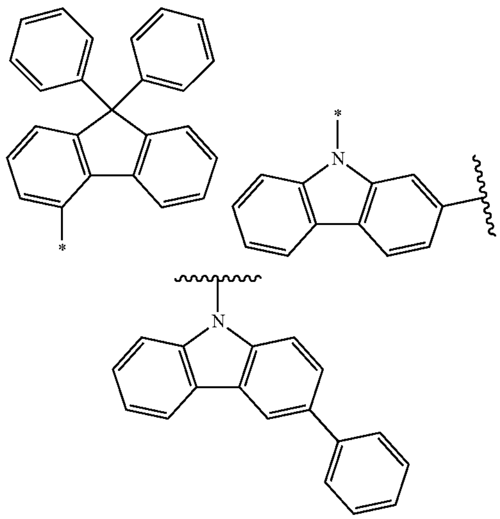
C6
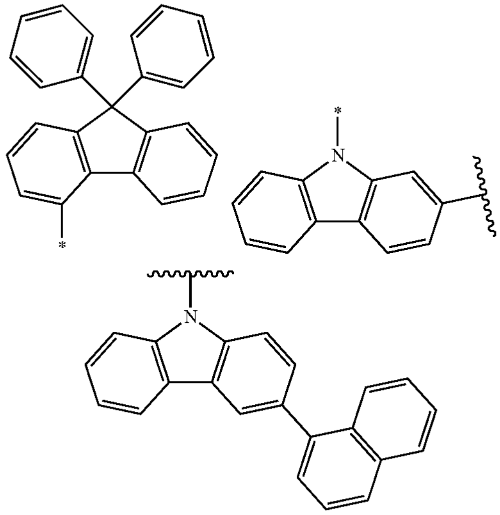
C7
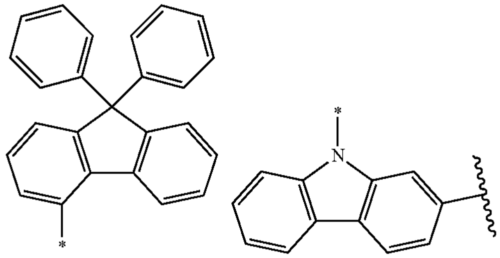
-continued
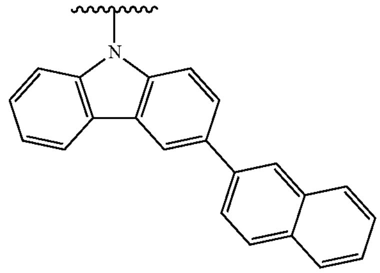
C8
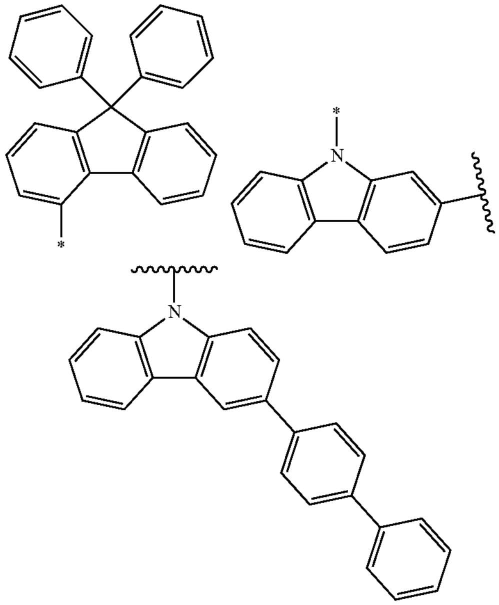
C9
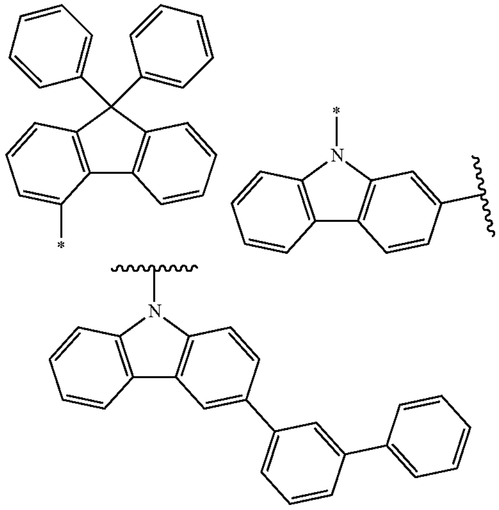
C10
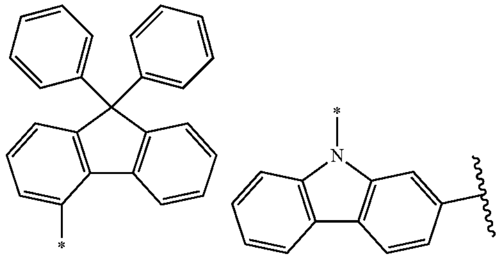

-continued
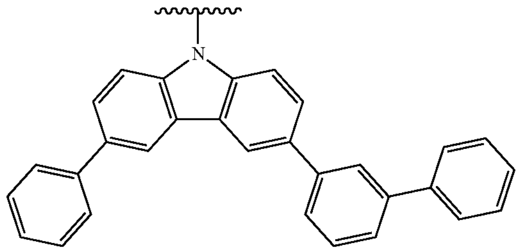
C11
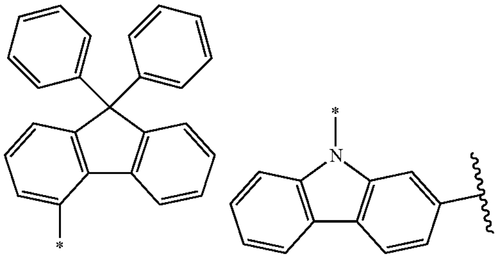
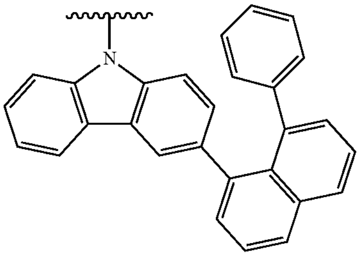
C12
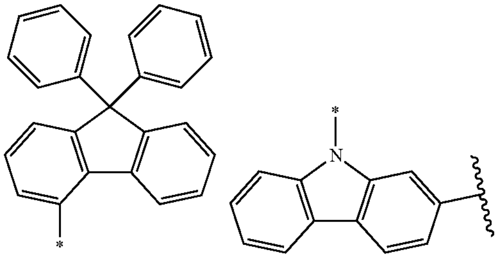
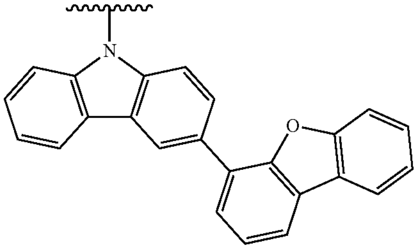
C13
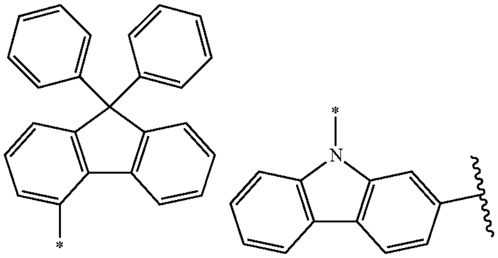
-continued
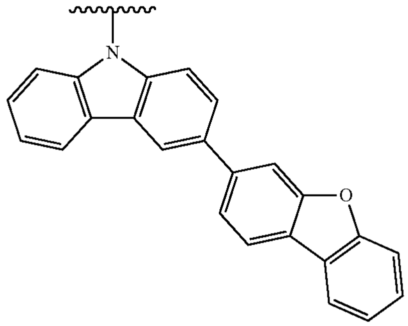
C14
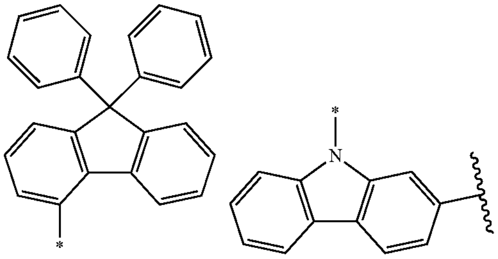
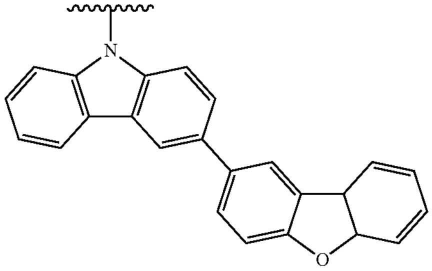
C15
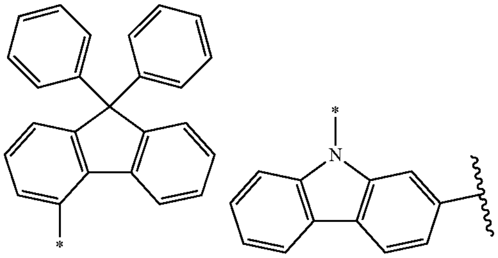
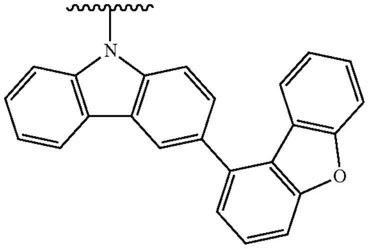
C16
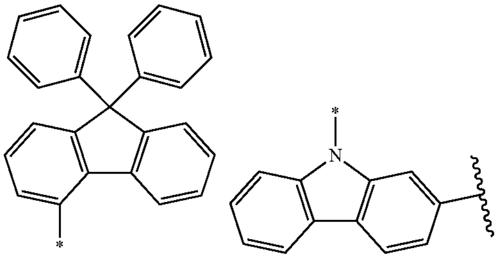

-continued
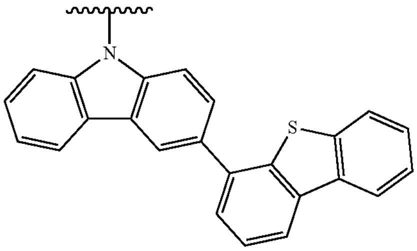
C17
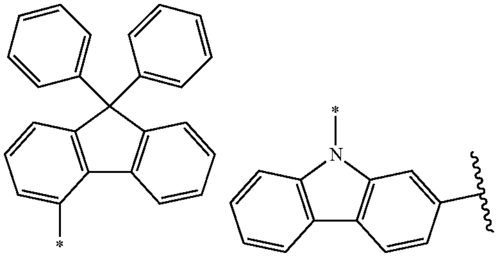
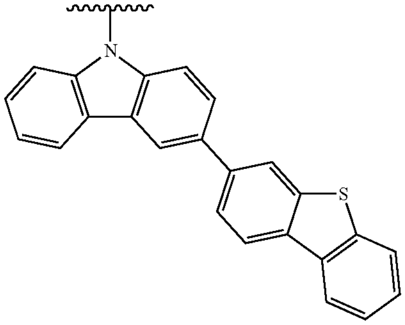
C18
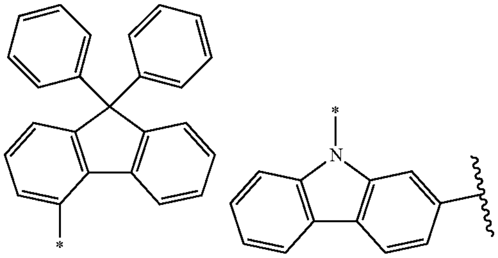
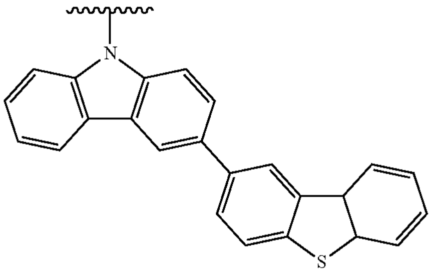
C19
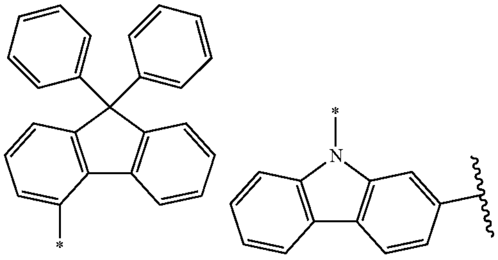
-continued
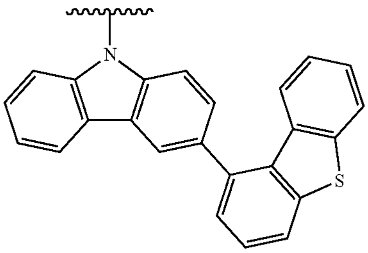
C20
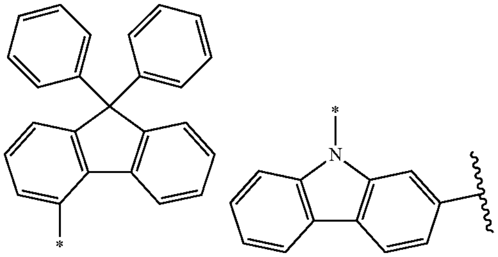
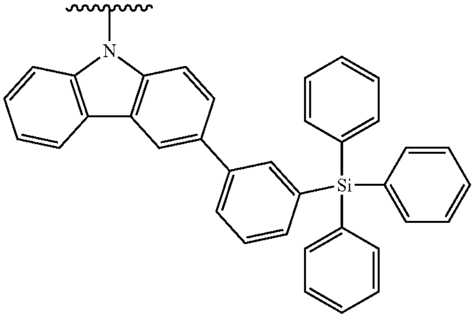
C21
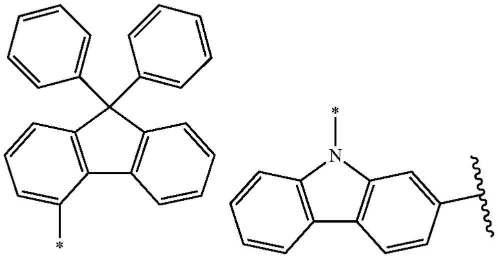
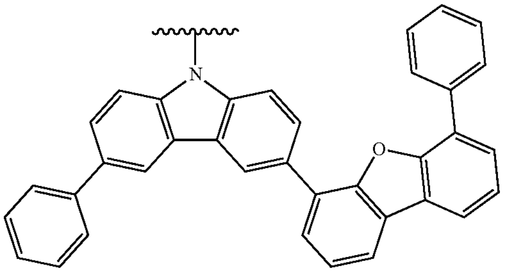
C22
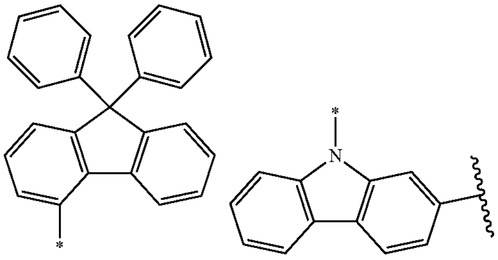

-continued
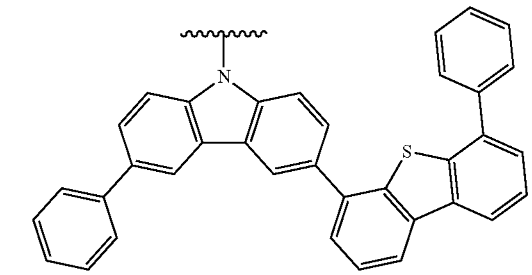
C23
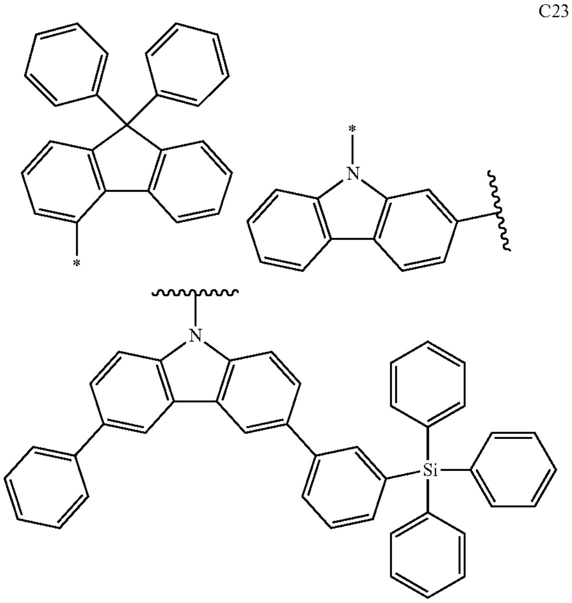
C24
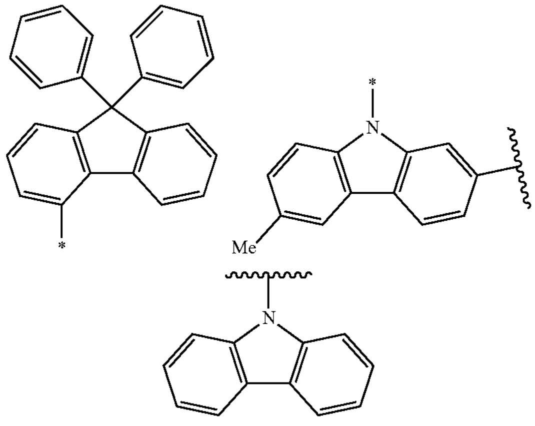
C25
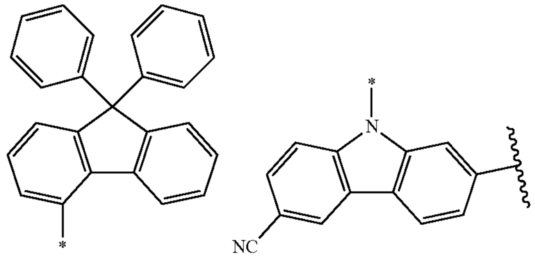
-continued
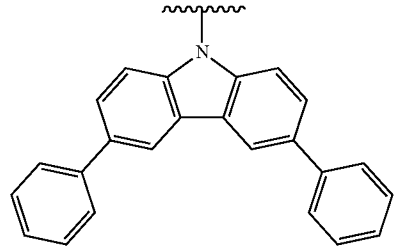
C26
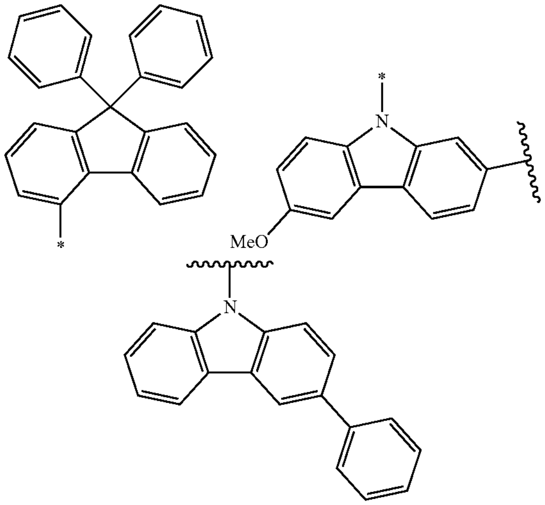
D1
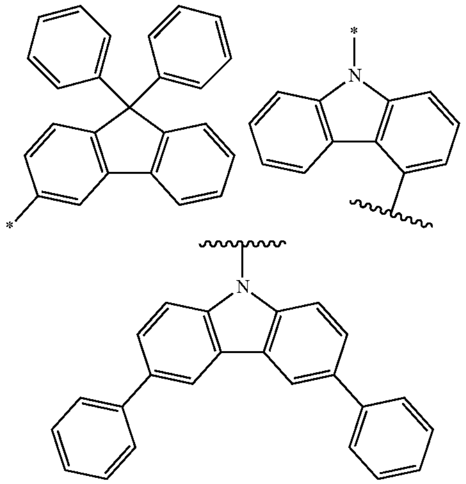
D2
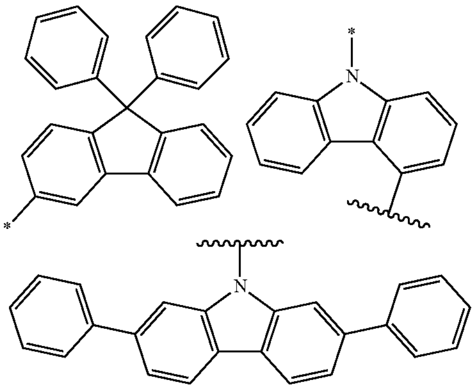

-continued
D3
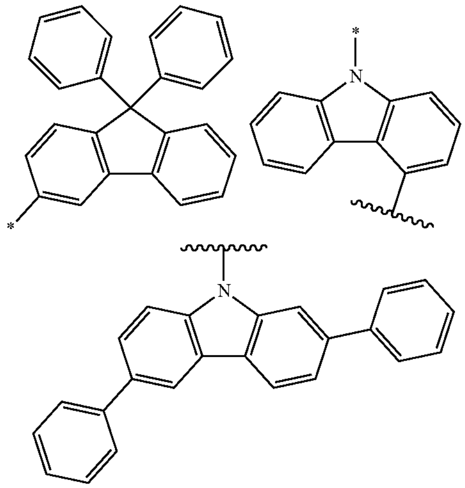
D4
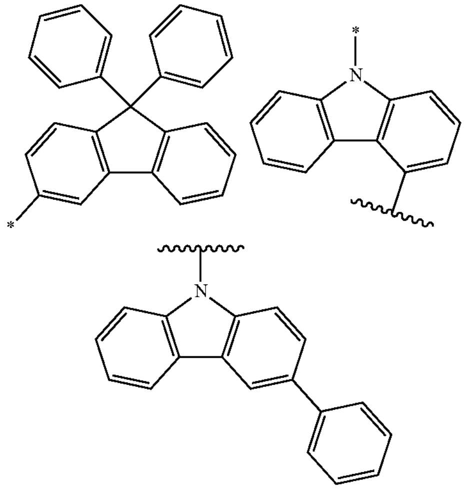
D5
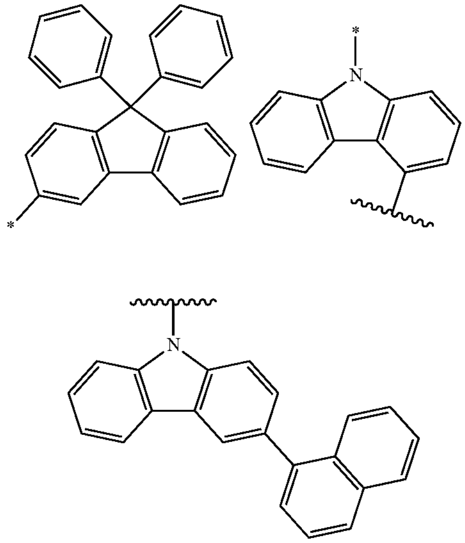
-continued
D6
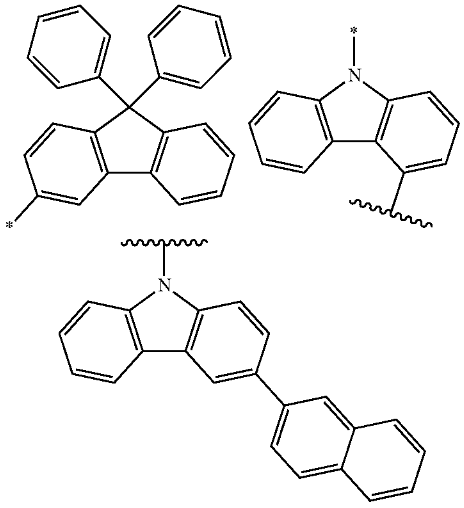
D7
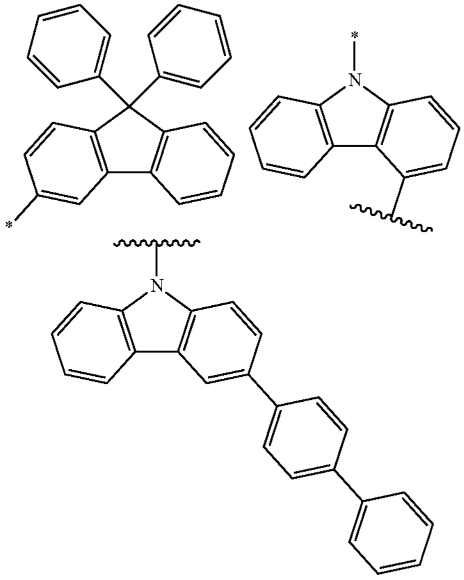
D8
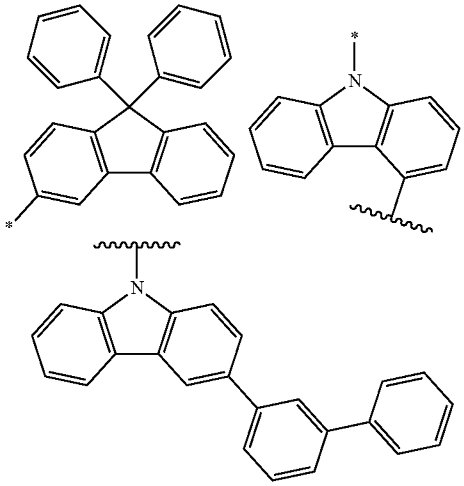

-continued
D9
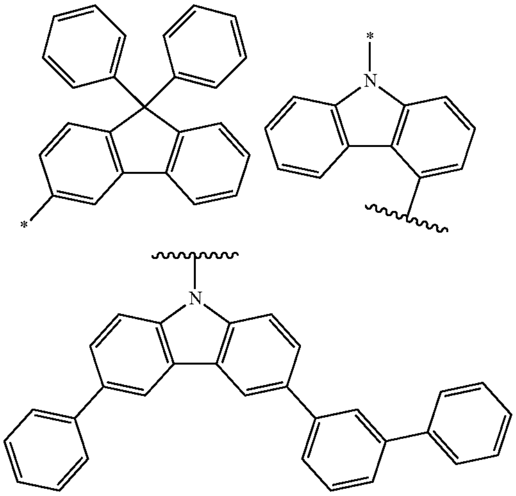
D10
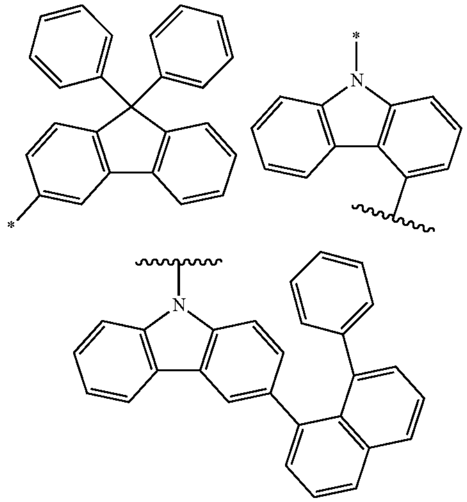
D11
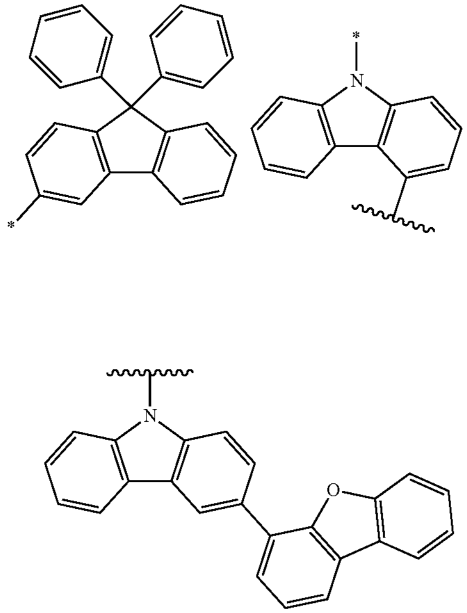
-continued
D12
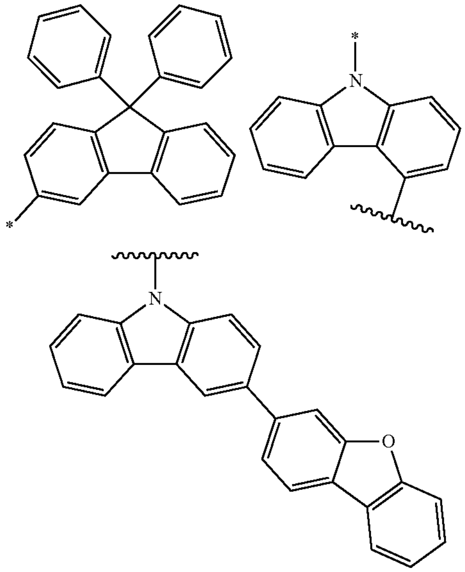
D13
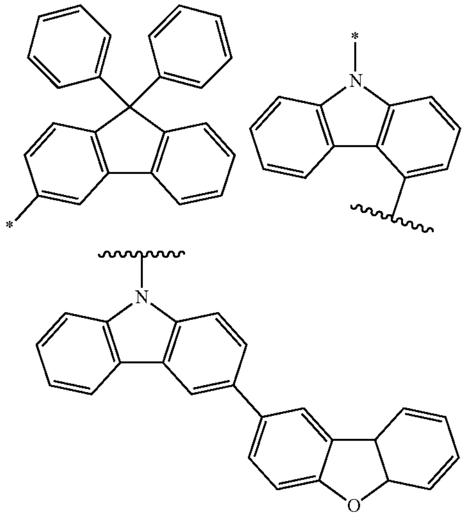
D14
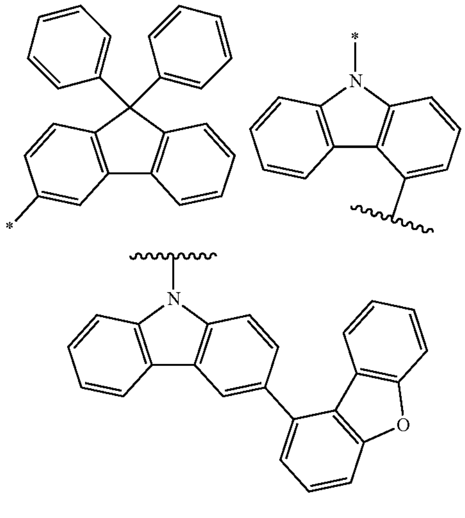

-continued
D15
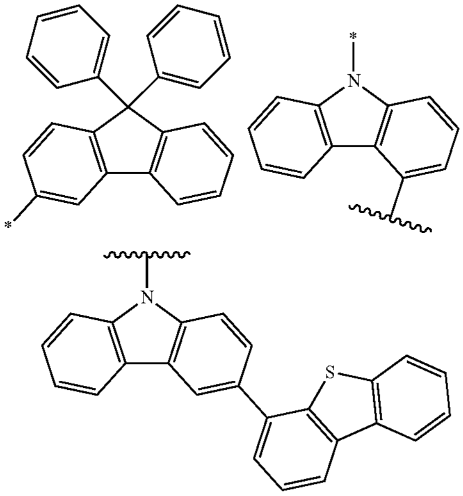
D16
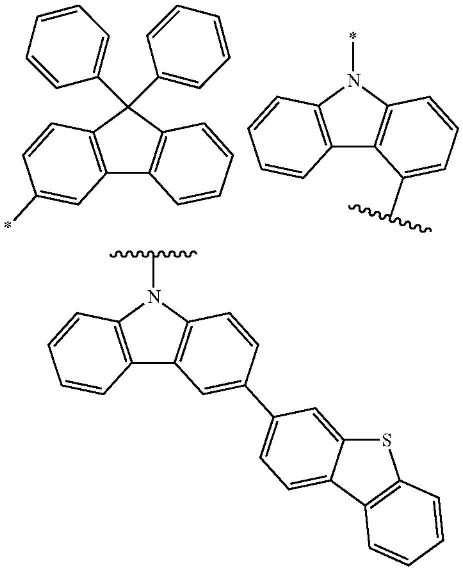
D17
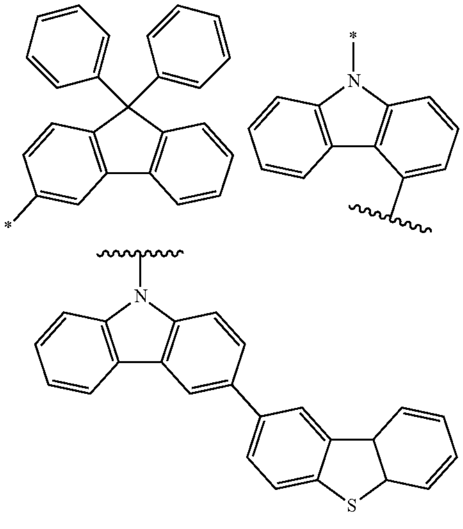
-continued
D18
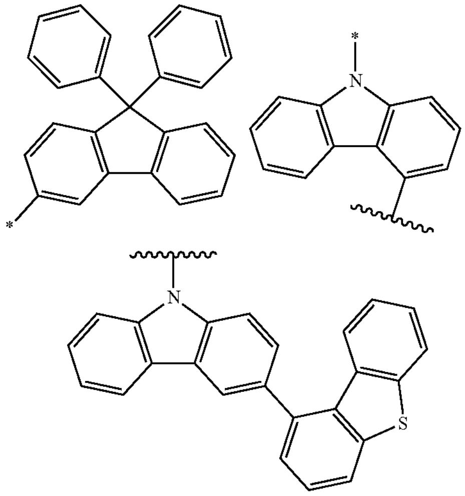
D19
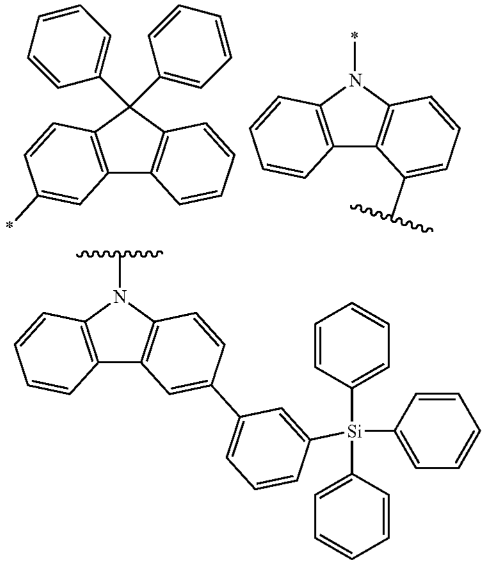
D20
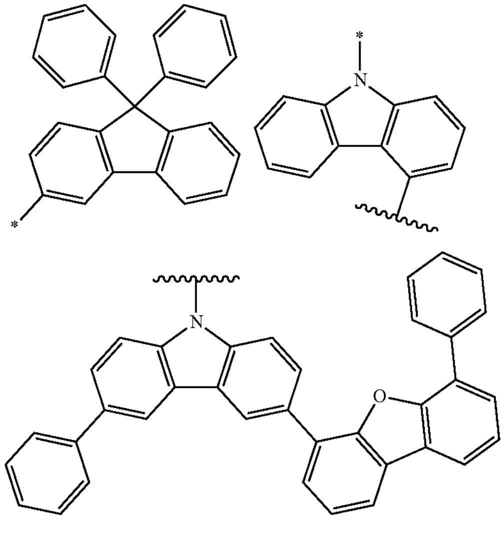

-continued
D21
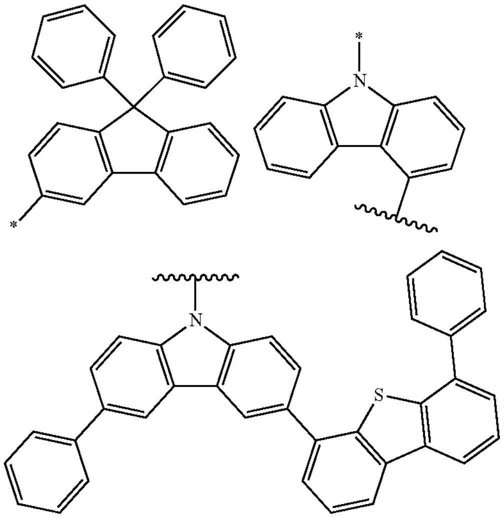
D22
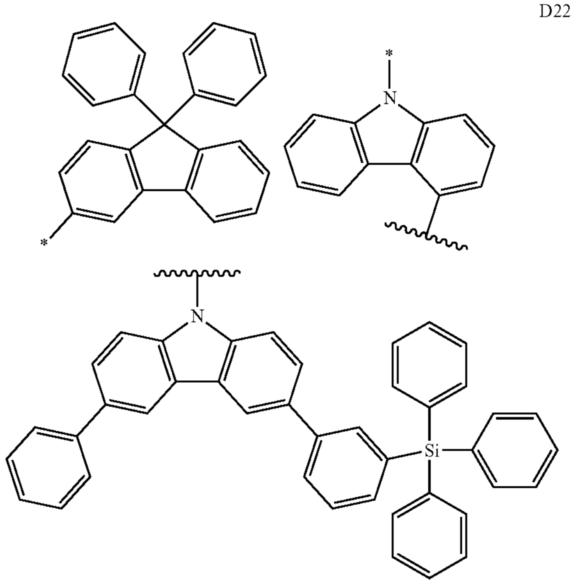
D23
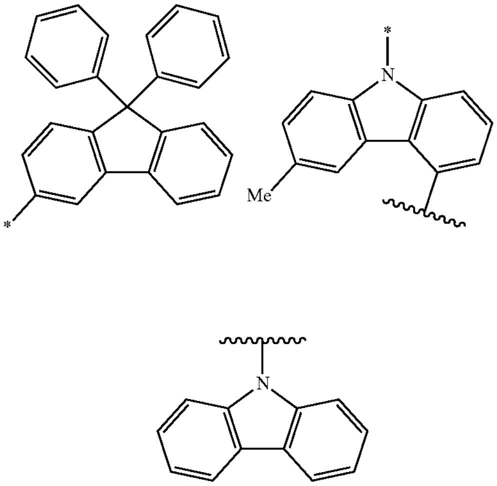
-continued
D24
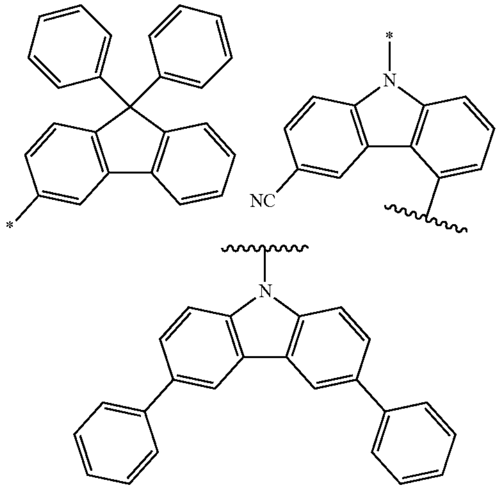
D25
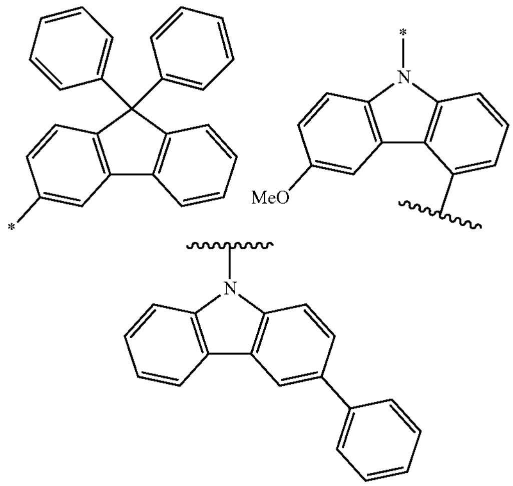
D26
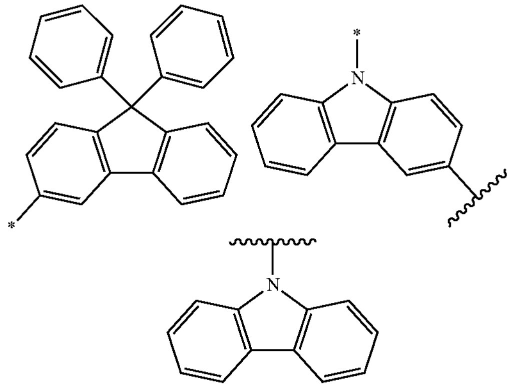
E1
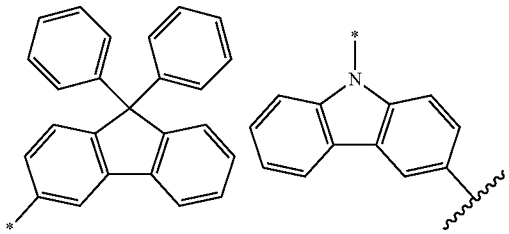

-continued
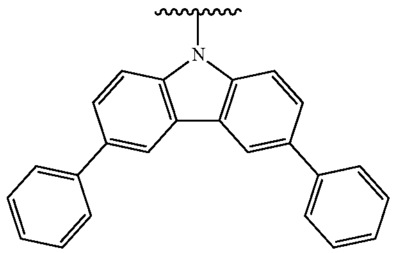
E2
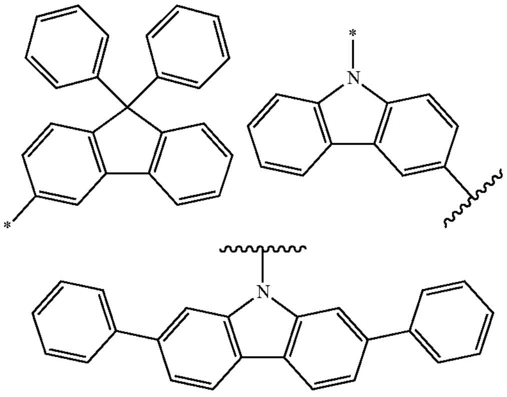
E3
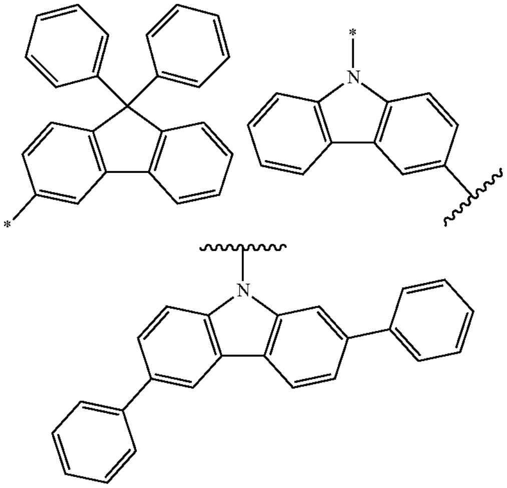
E4
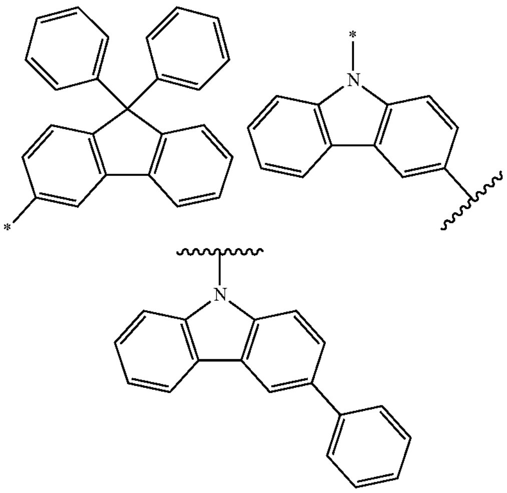
-continued
E5
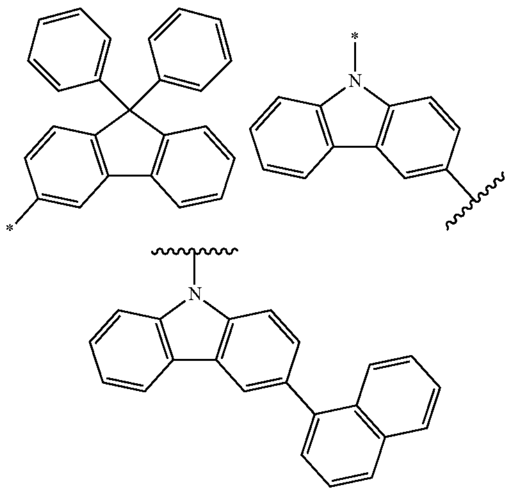
E6
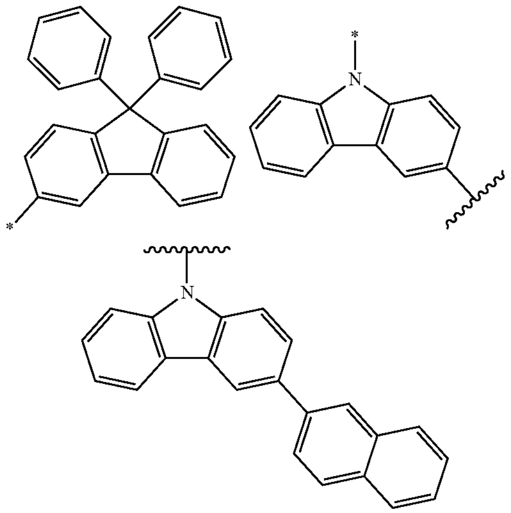
E7
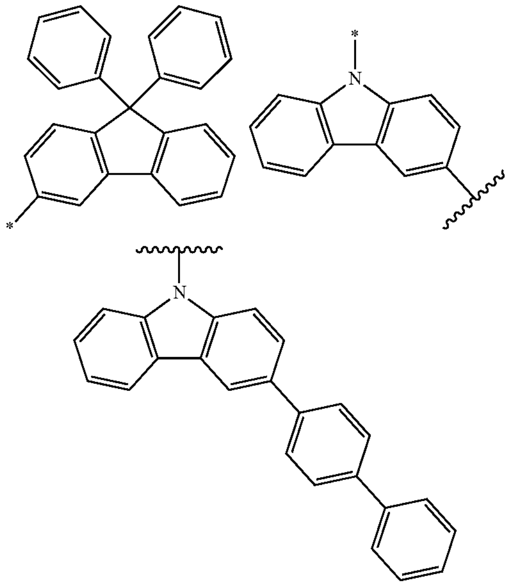

E8
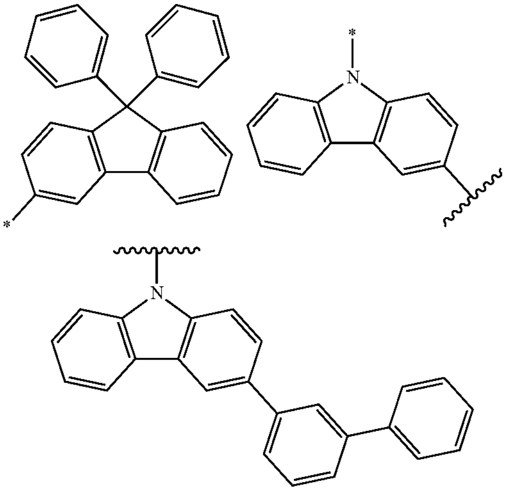
E9
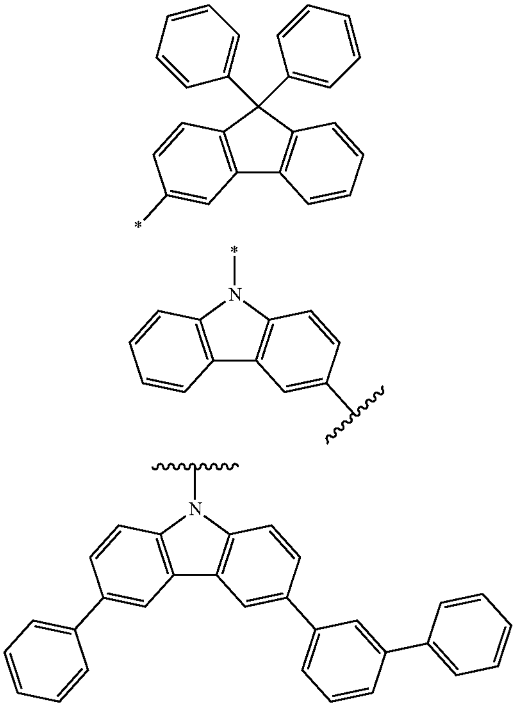
E10
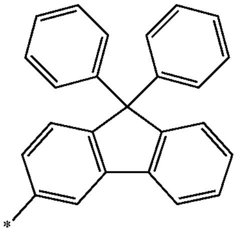
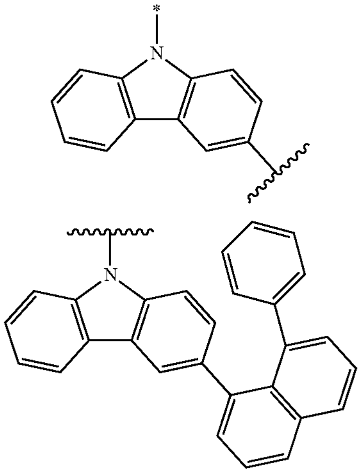
E11
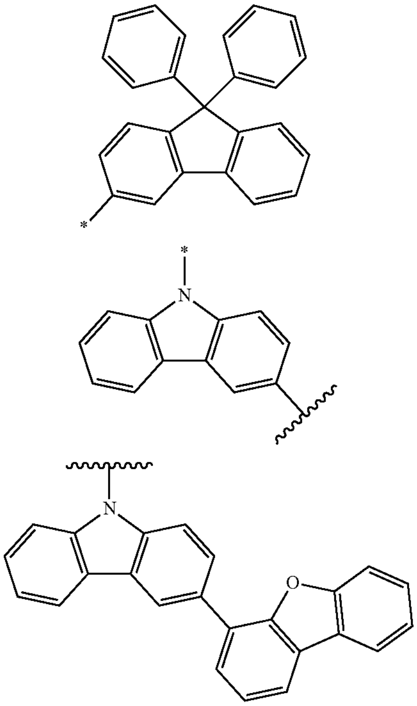
E12
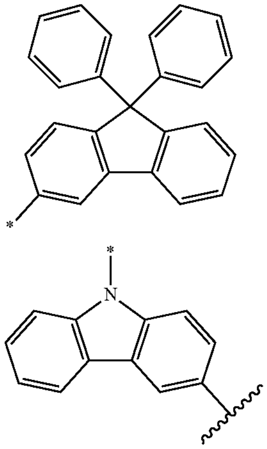

-continued
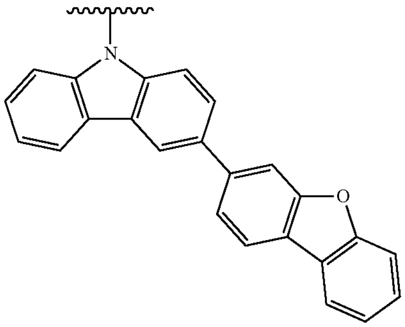
E13
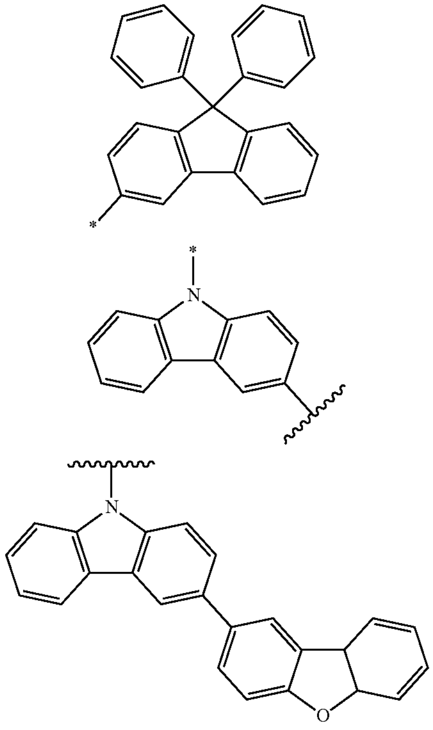
E14
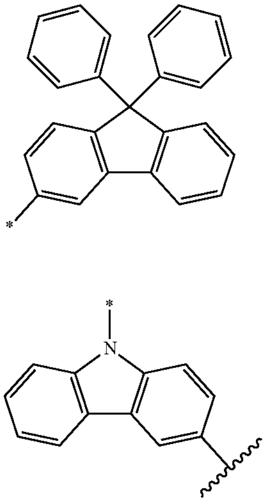
-continued
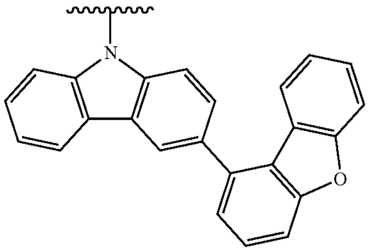
E15
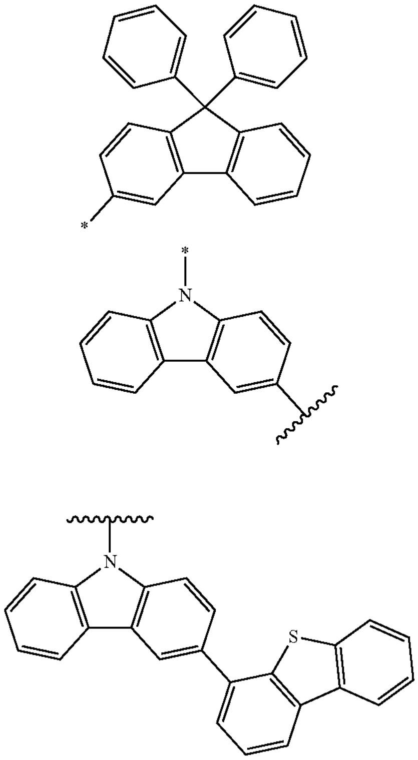
E16
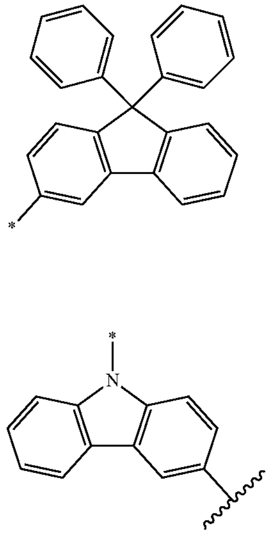

-continued
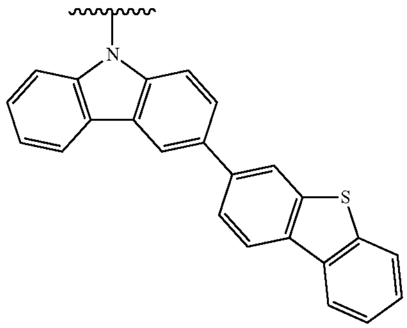
E17
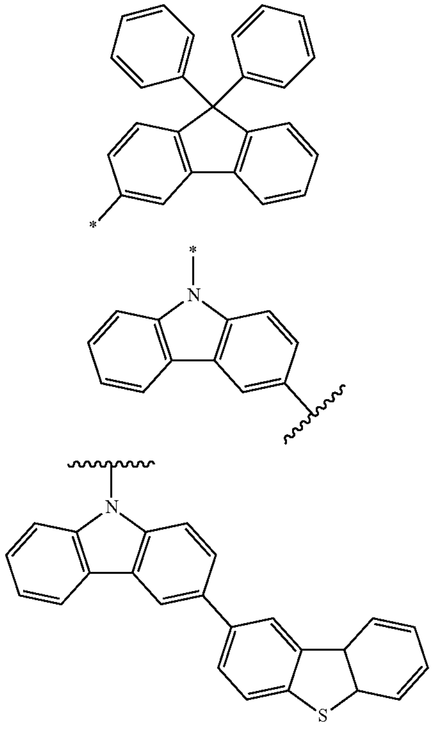
E18
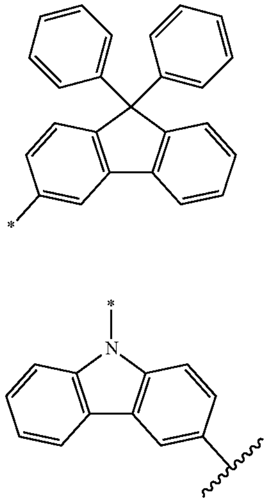
-continued
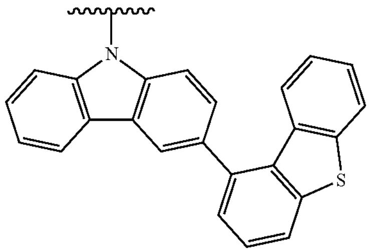
E19
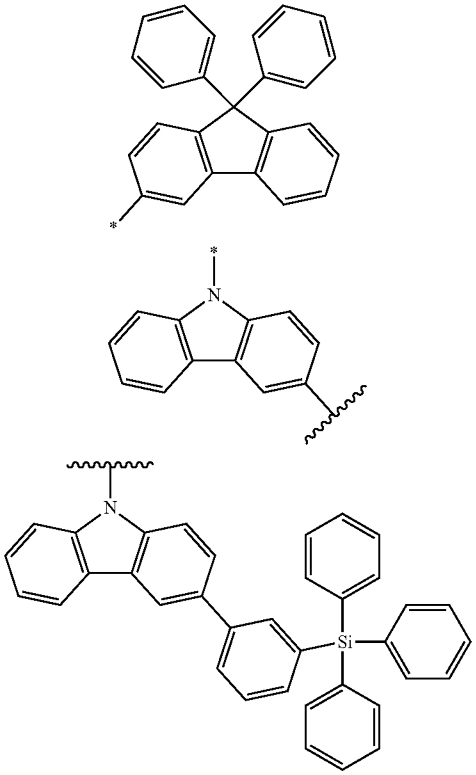
E20
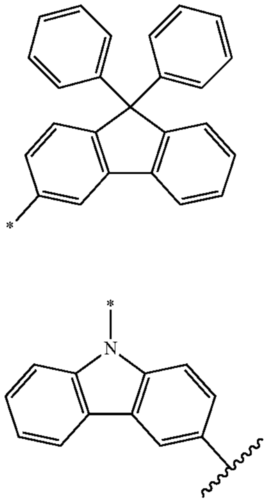

-continued
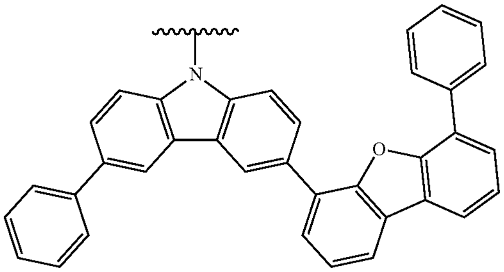
E21
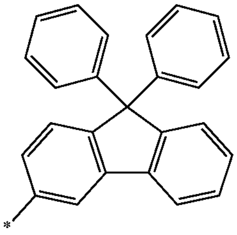
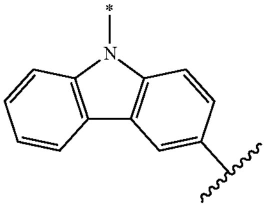
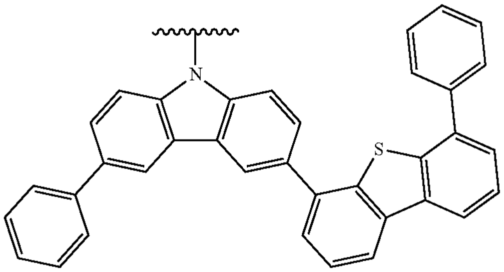
E22
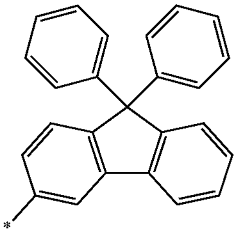
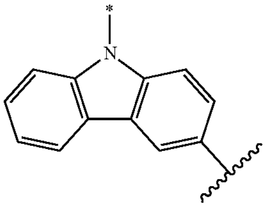
-continued
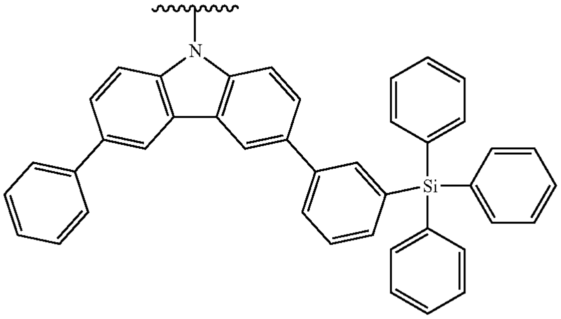
E23
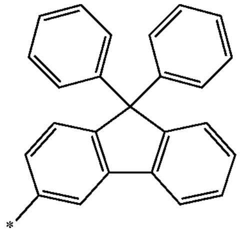
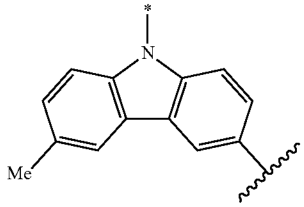
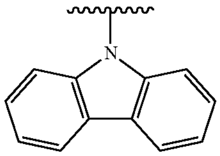
E24
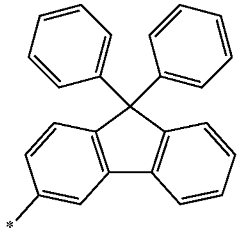
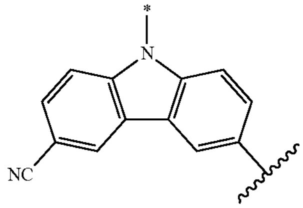
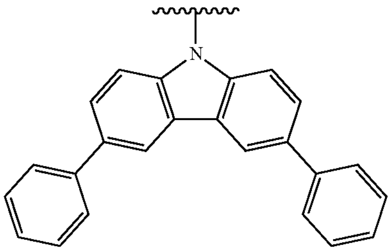

-continued
E25
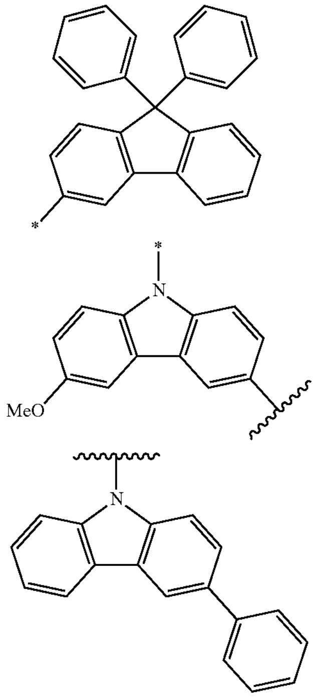
E26
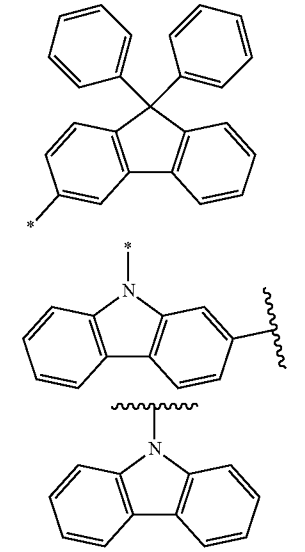
F1
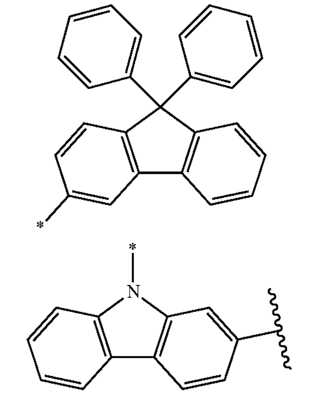
-continued
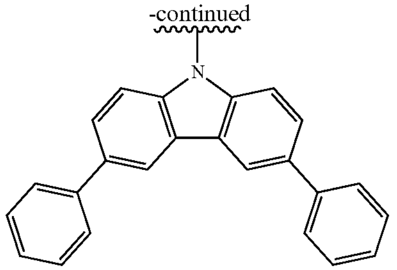
F2
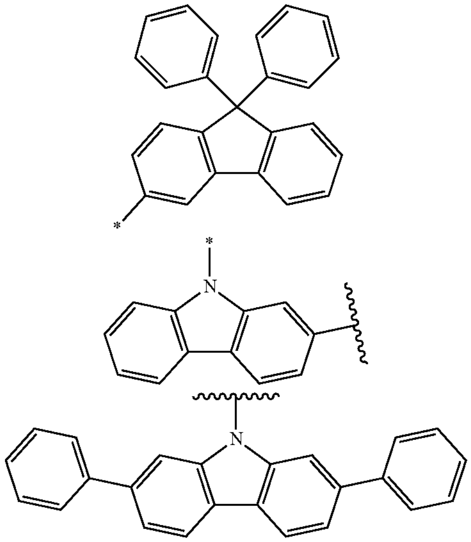
F3
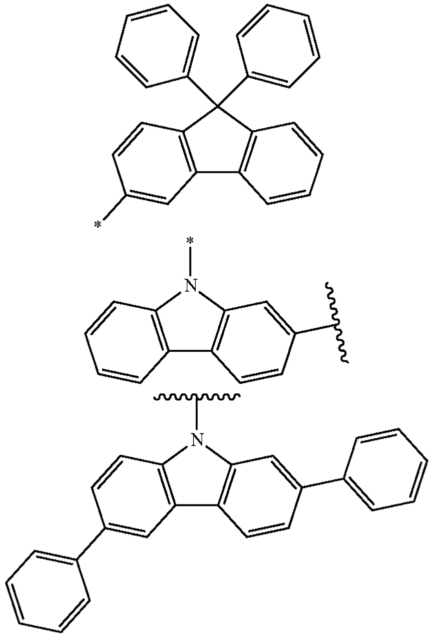
F4
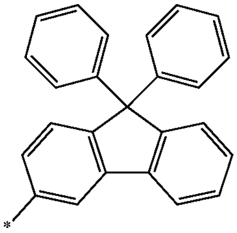

-continued
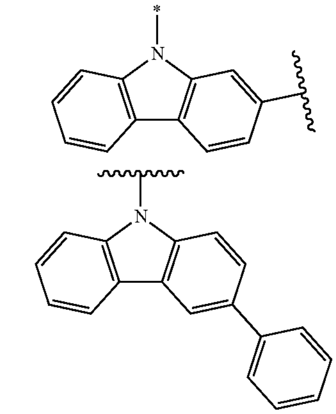
F5
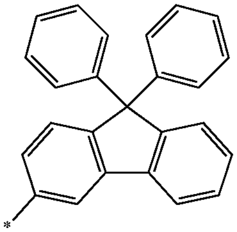
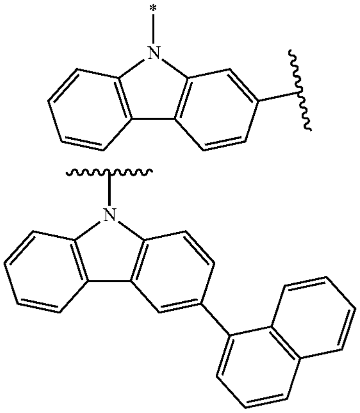
F6
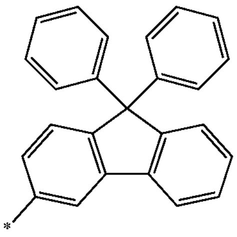
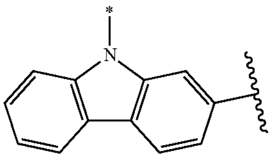
-continued
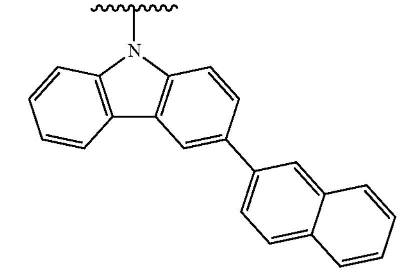
F7
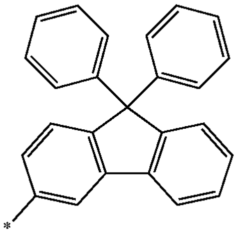
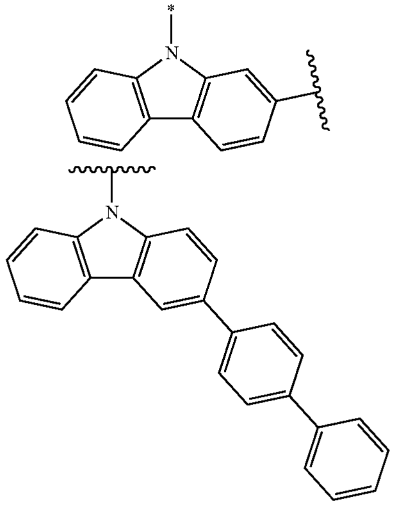
F8
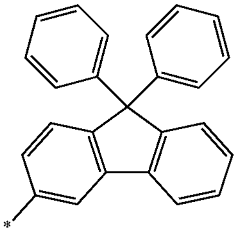
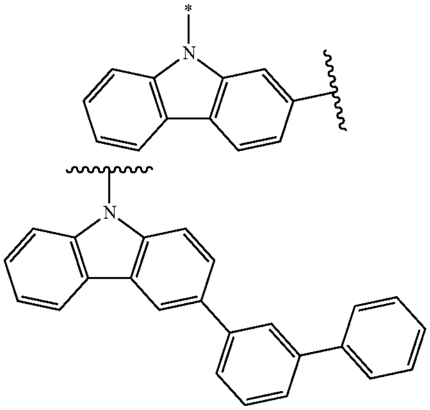

-continued
F9
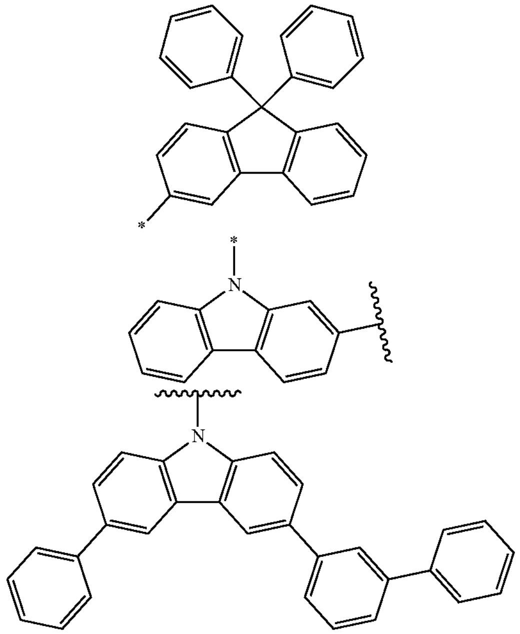
F10
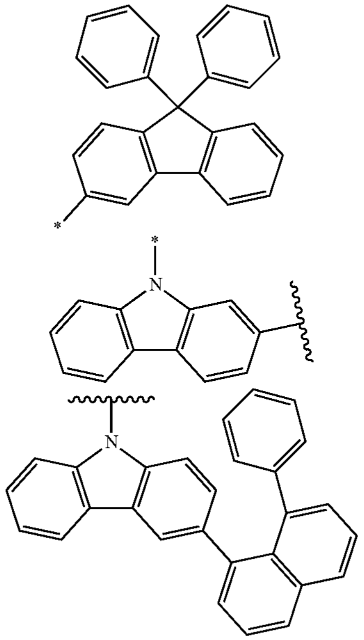
F11
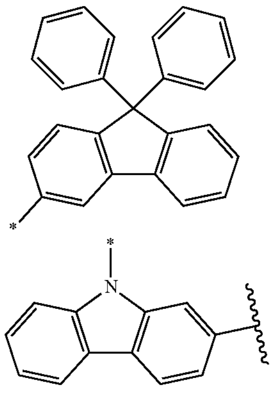
-continued
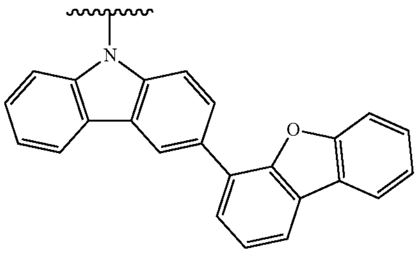
E12
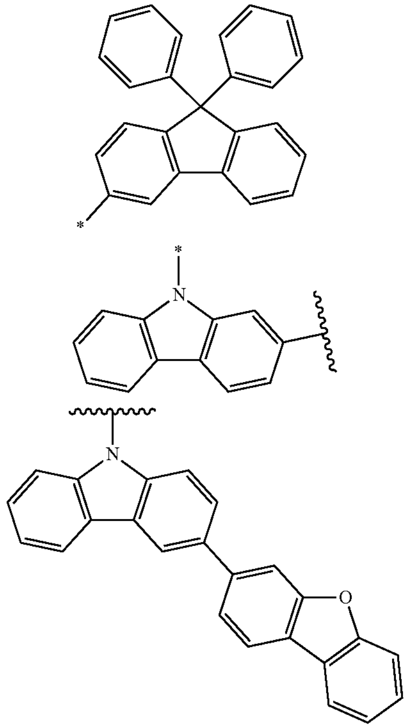
F13
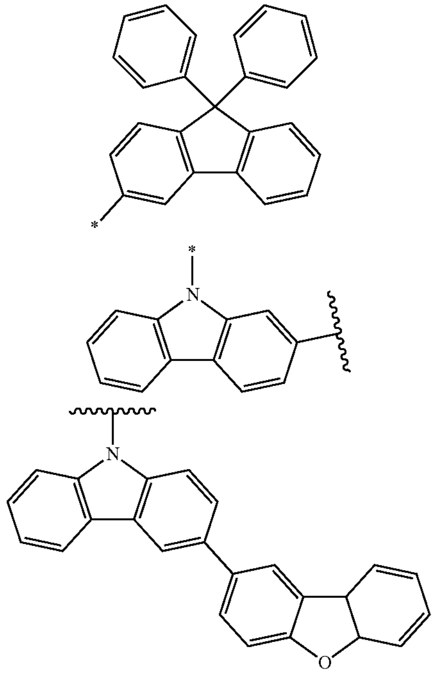

-continued
E14
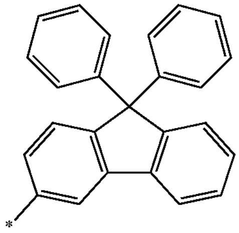
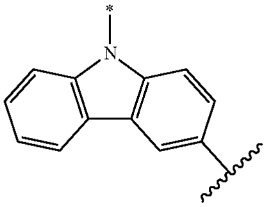
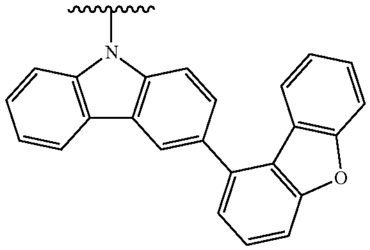
E15
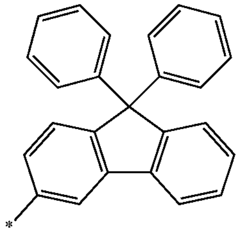
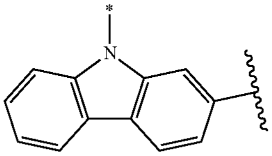
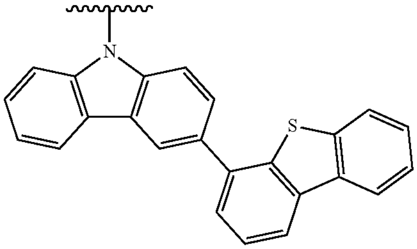
E16
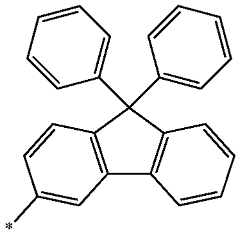
-continued
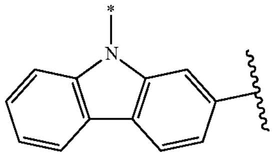
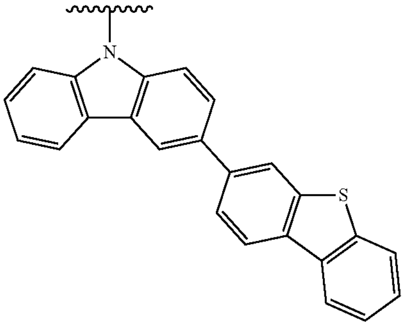
E17
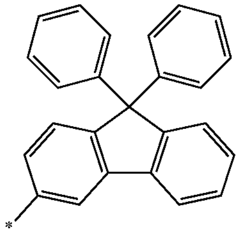
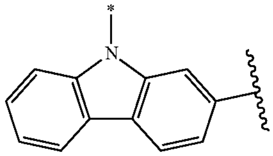
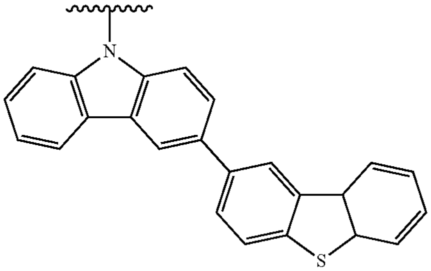
E18
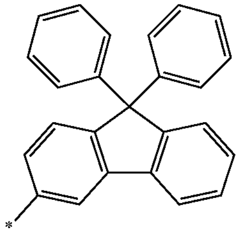
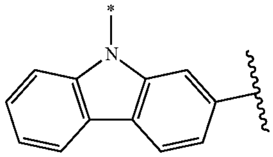

-continued
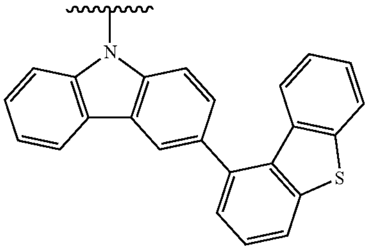
E19
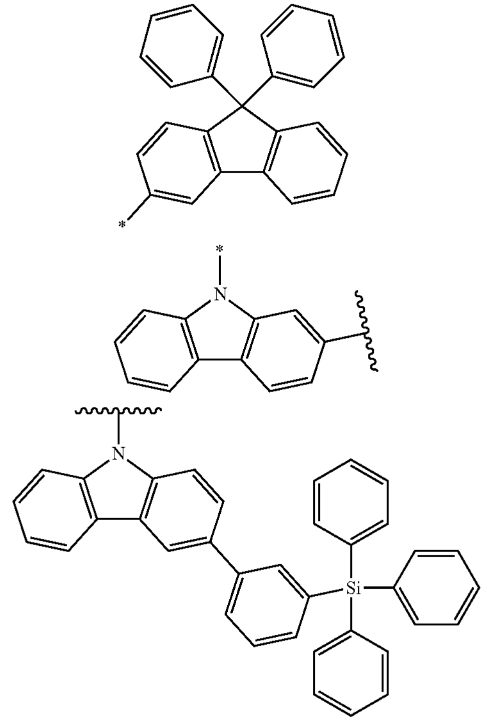
E20
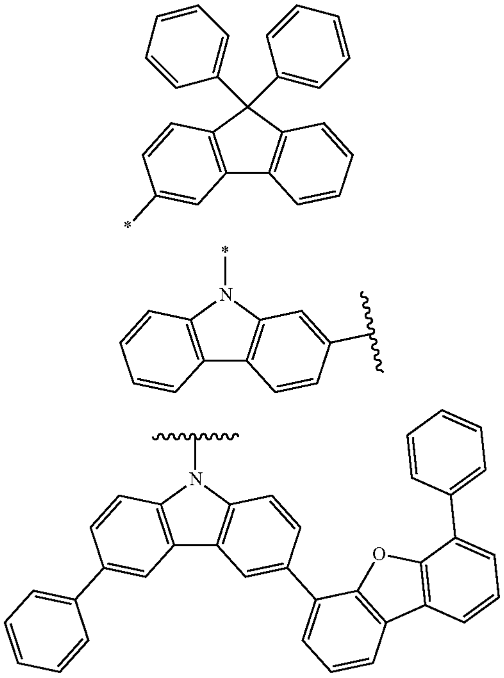
-continued
E21
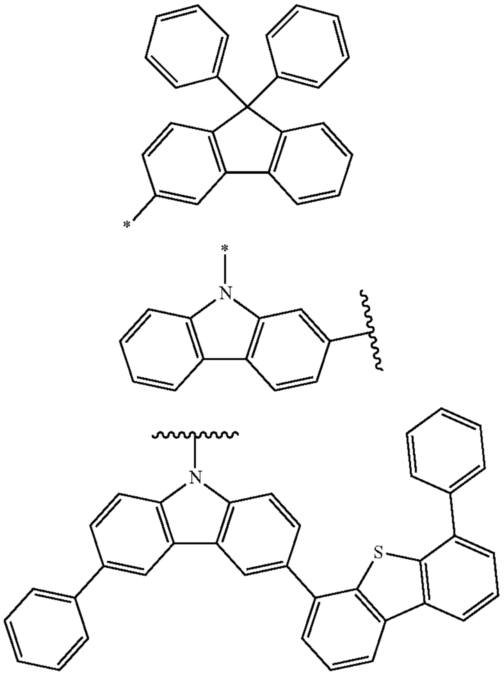
E22
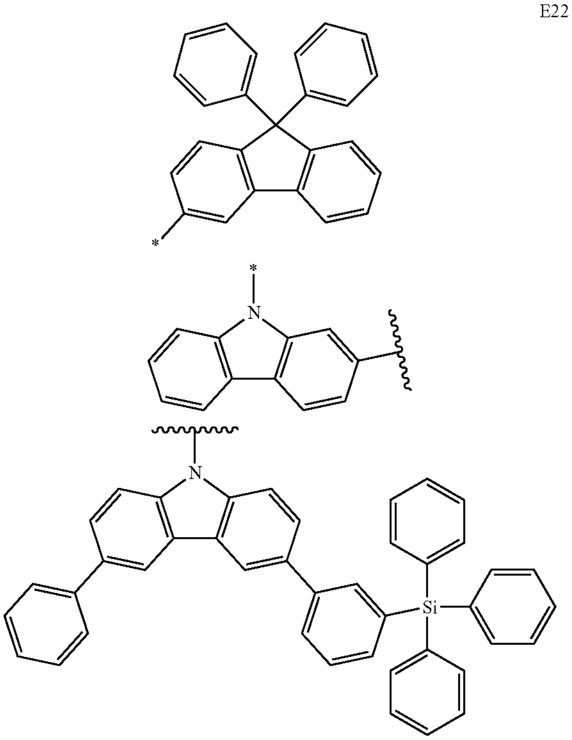
E23
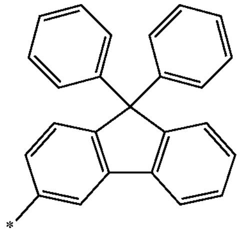

-continued
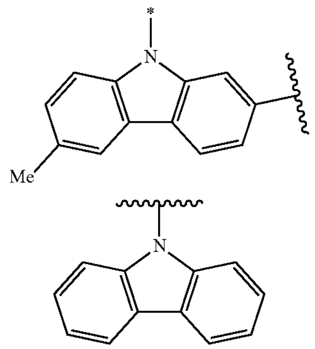
E24
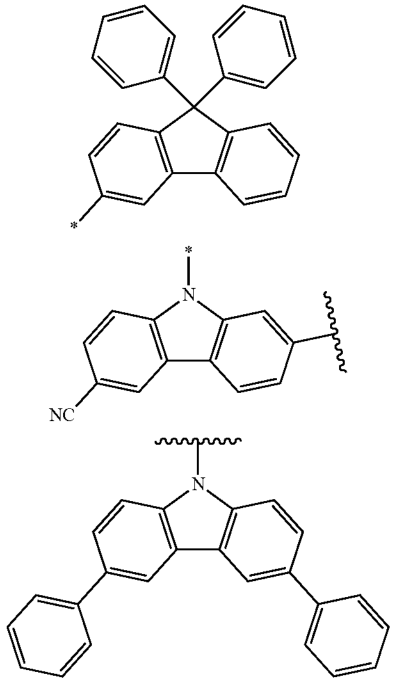
F25
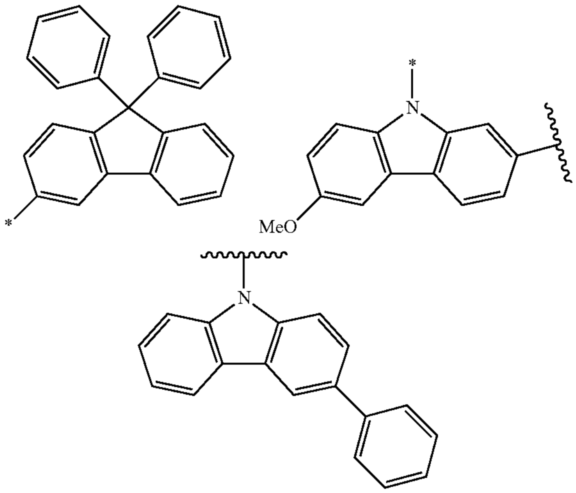
-continued
F26
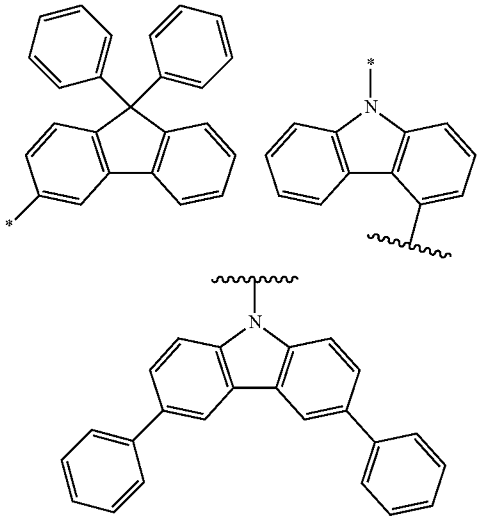
G1
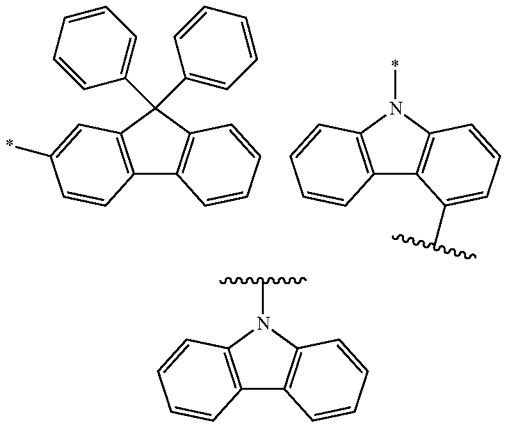
G2
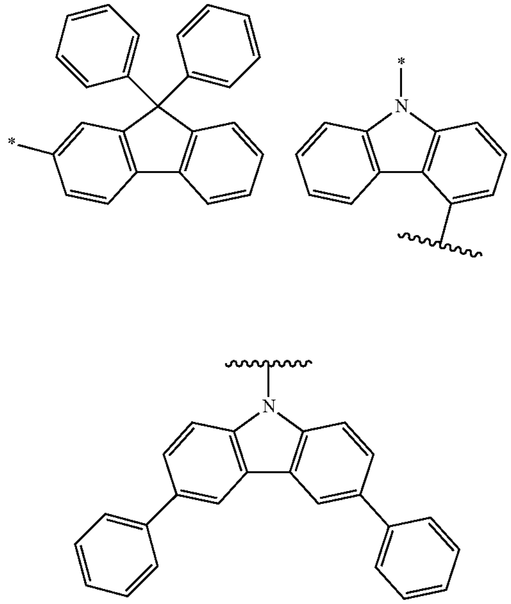

-continued
G3
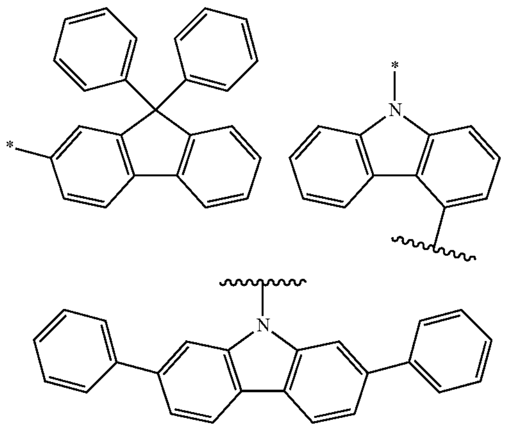
G4
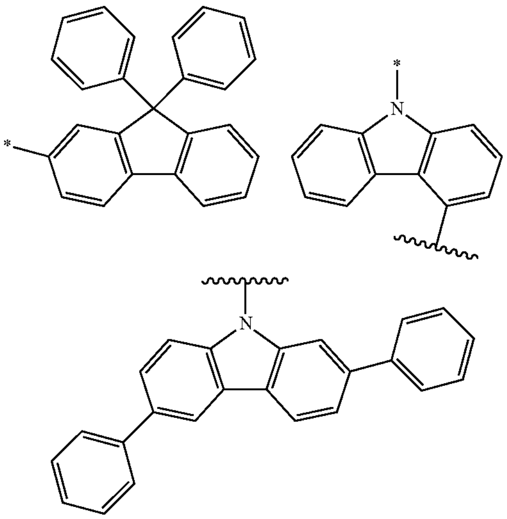
G5
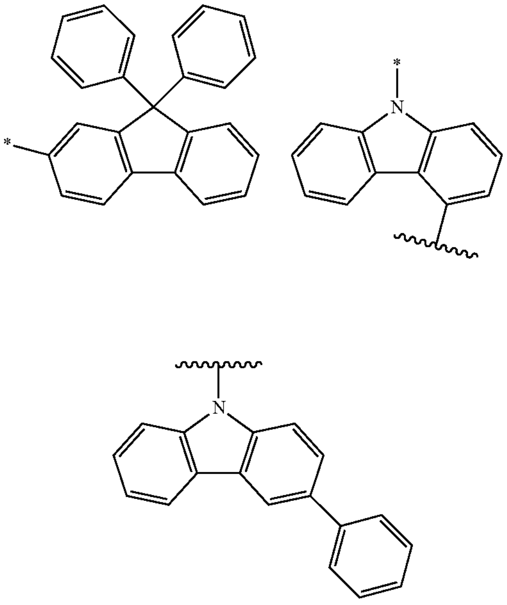
-continued
G6
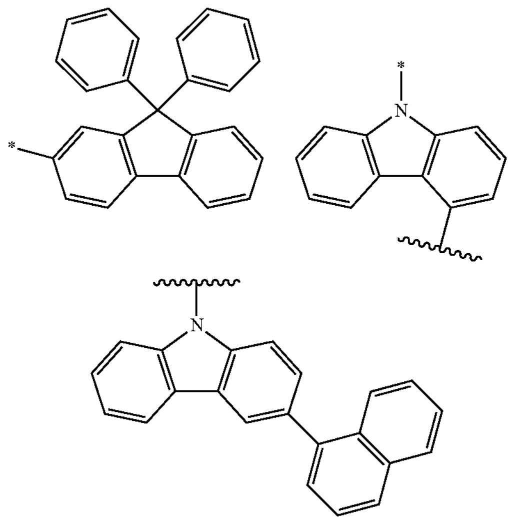
G7
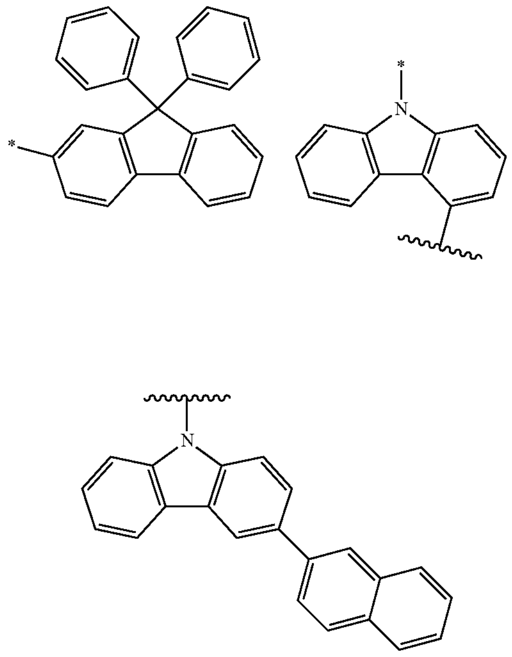
G8
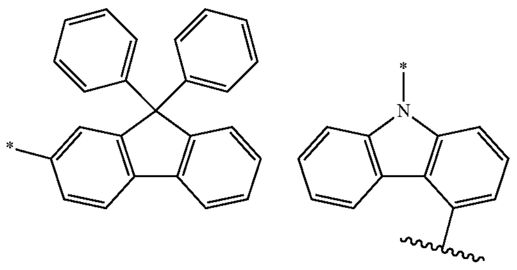

-continued
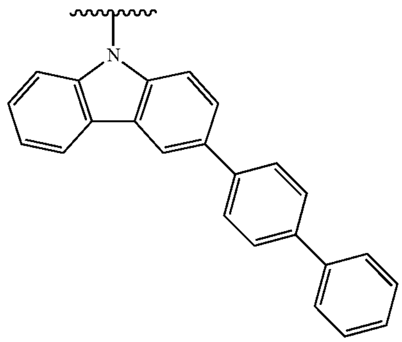
G9
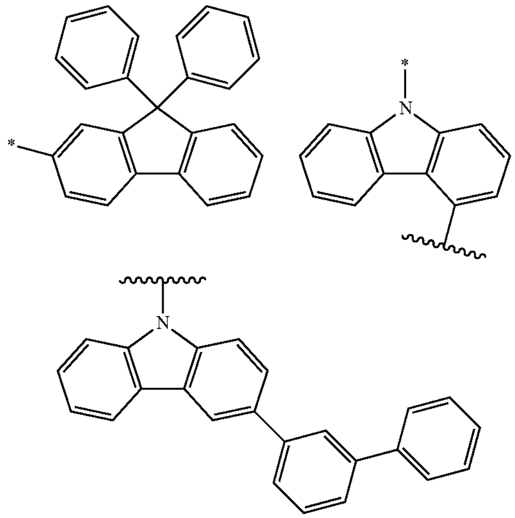
G10
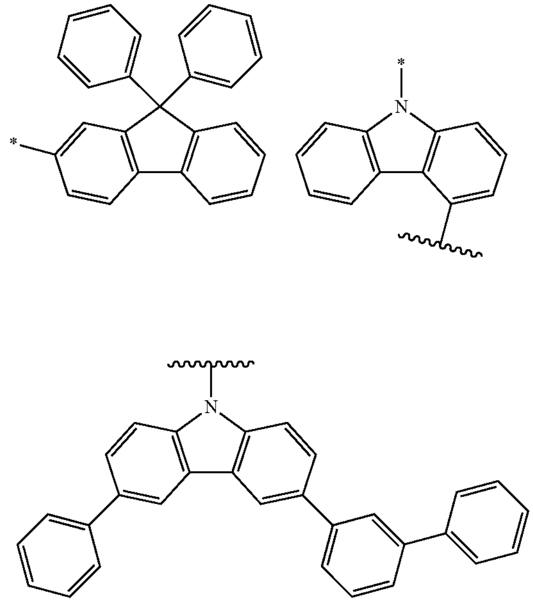
-continued
G11
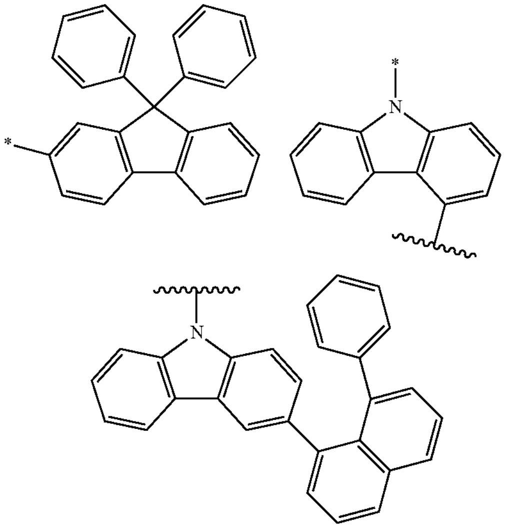
G12
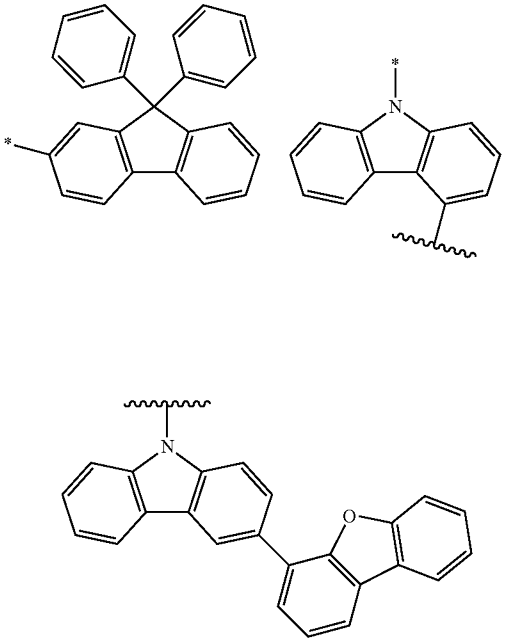
G13
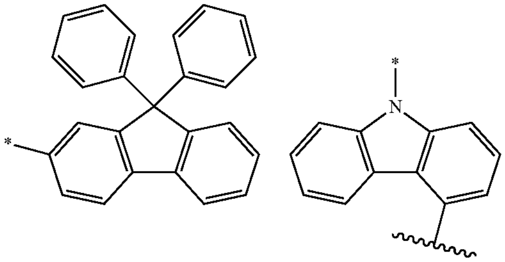

-continued
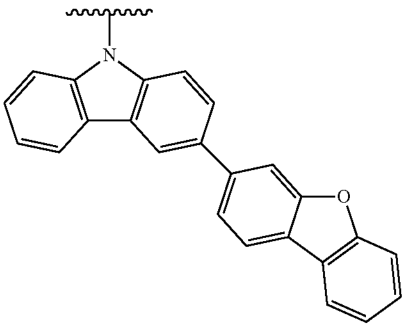
G14
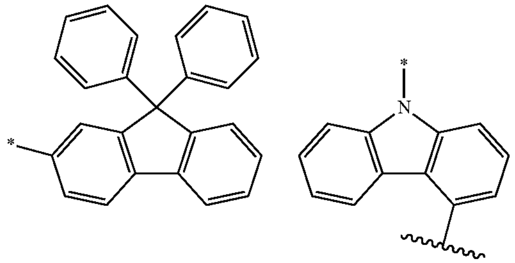
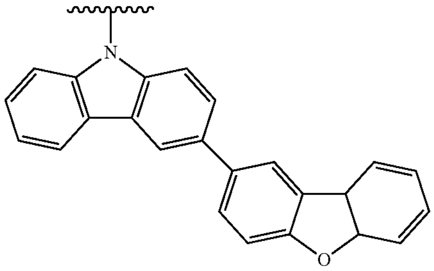
G15
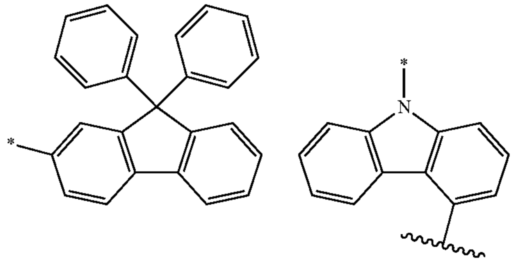
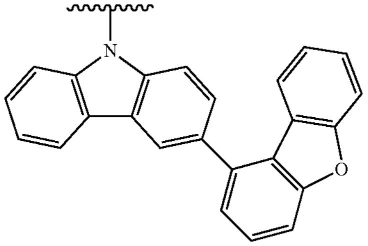
-continued
G16
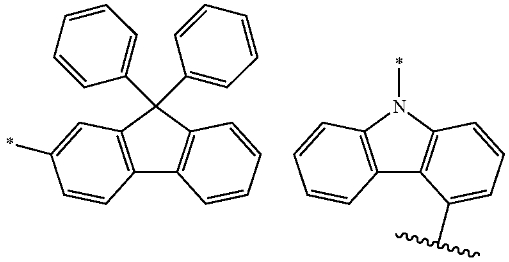
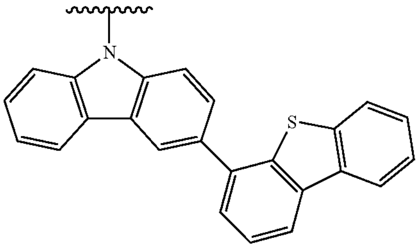
G17
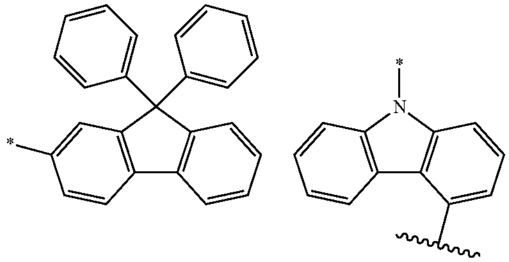
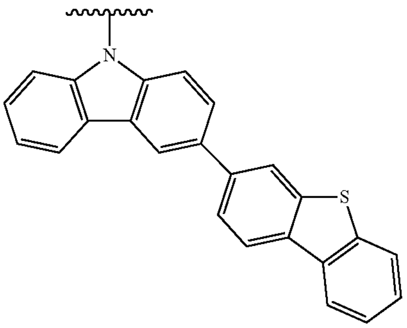
G18
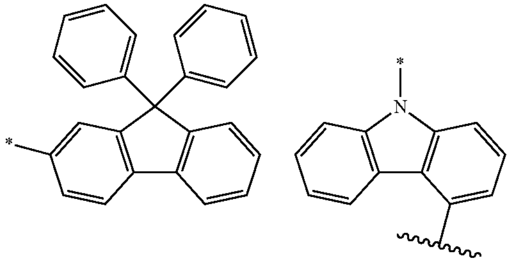

-continued
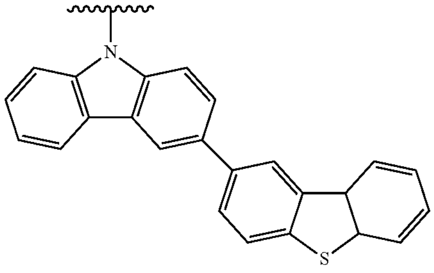
G19
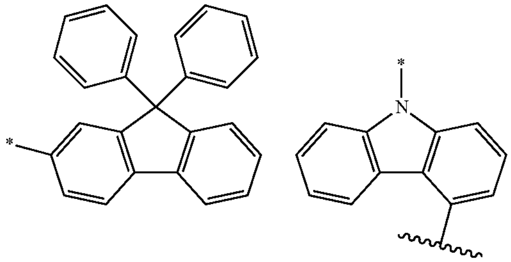
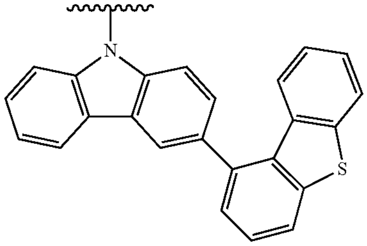
G20
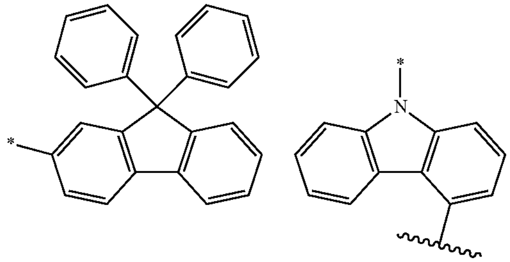
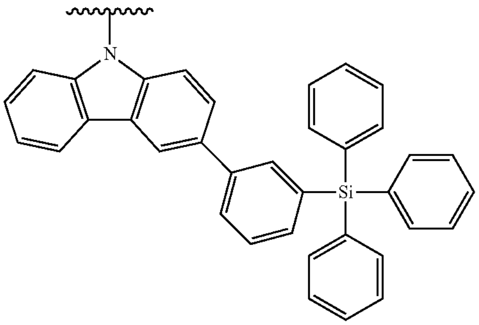
G21
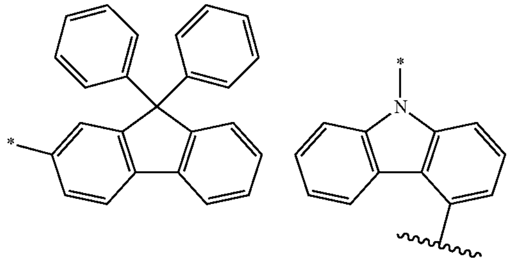
-continued
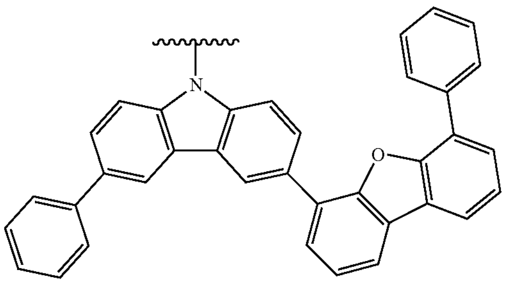
G22
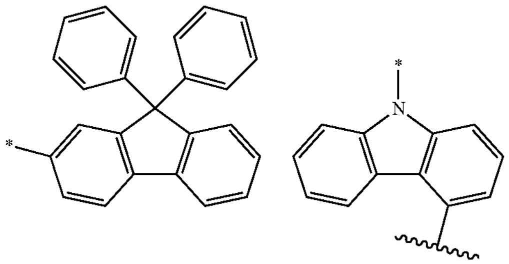
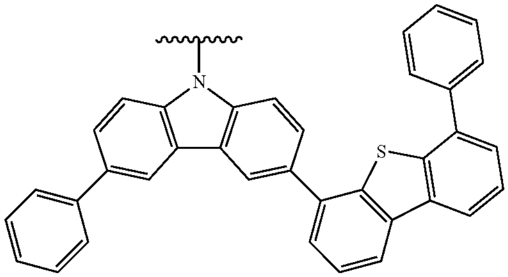
G23
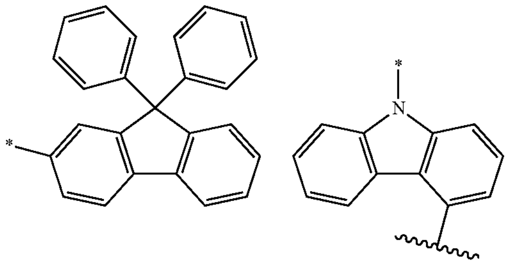
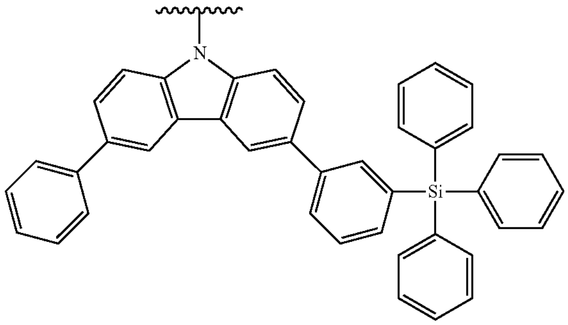

-continued
G24
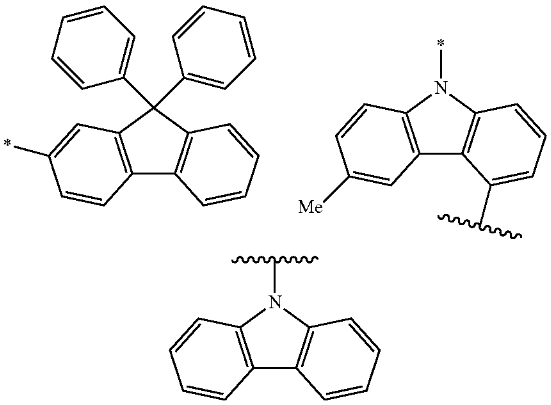
G25
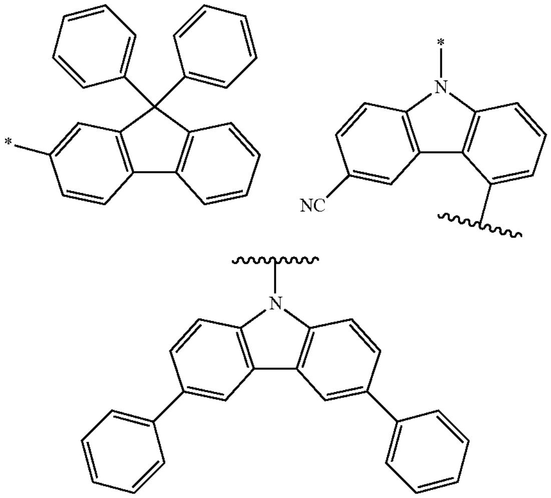
G26
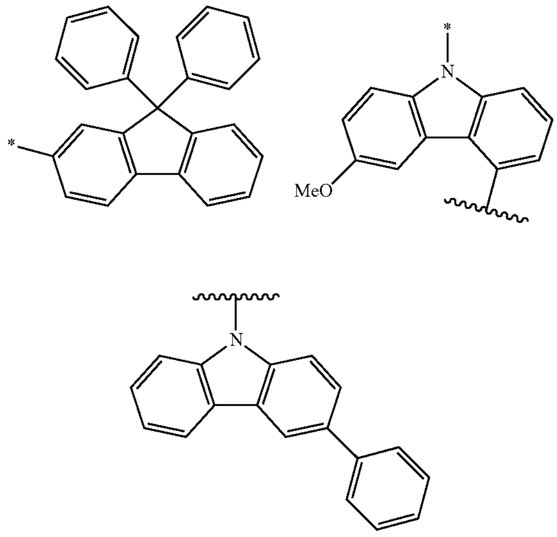
-continued
H1
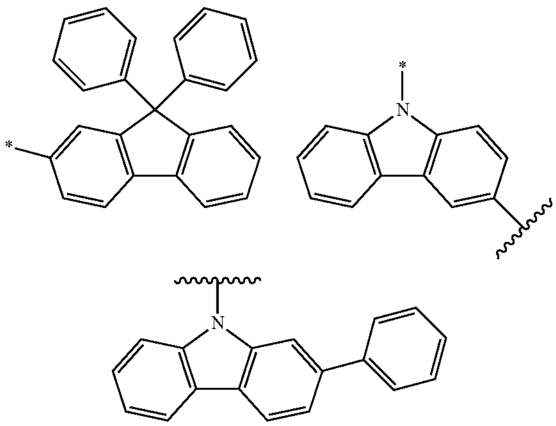
H2
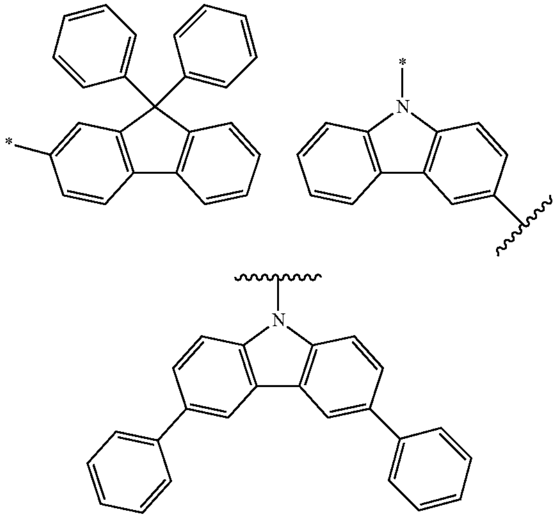
H3
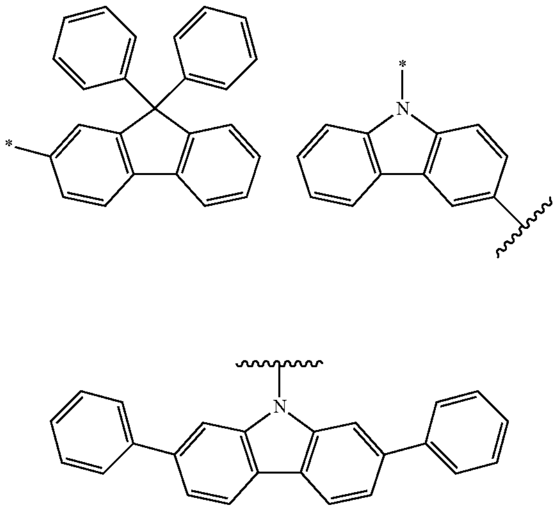

-continued
H4
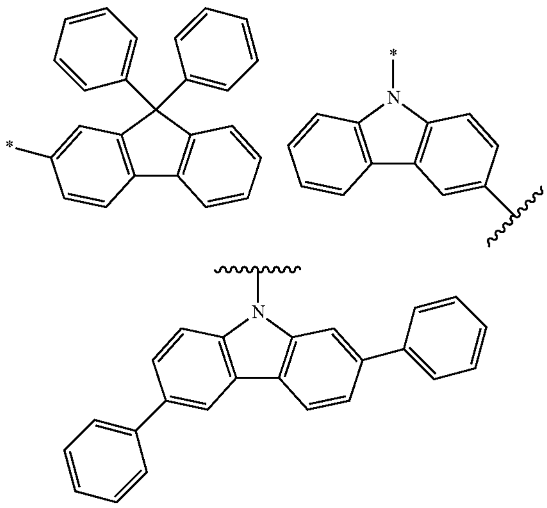
H5
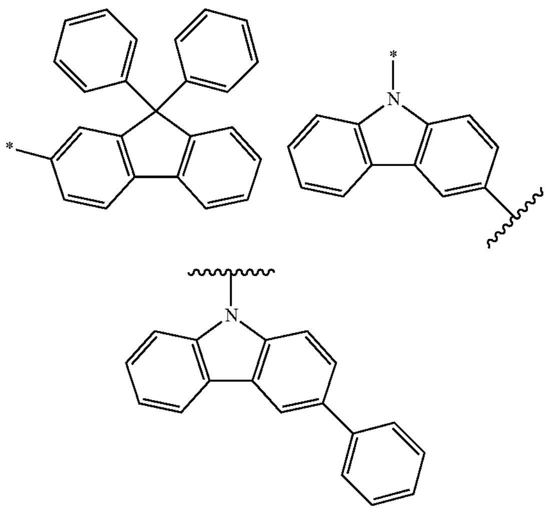
H6
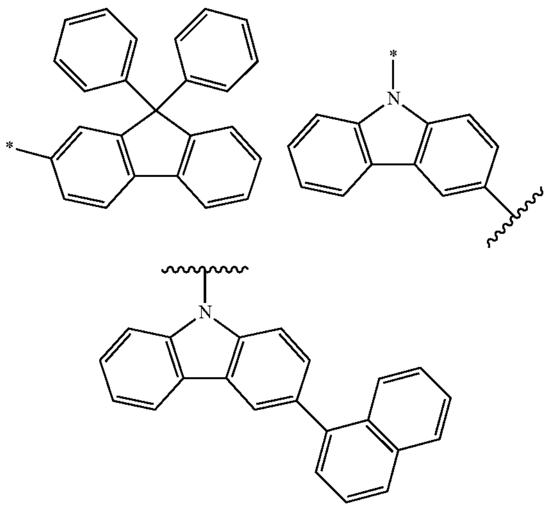
-continued
H7
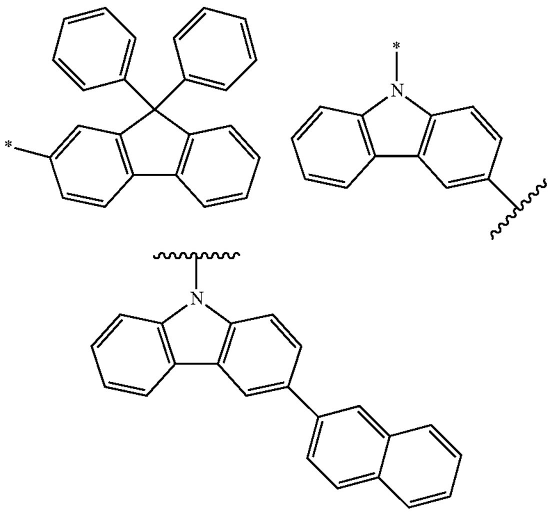
H8
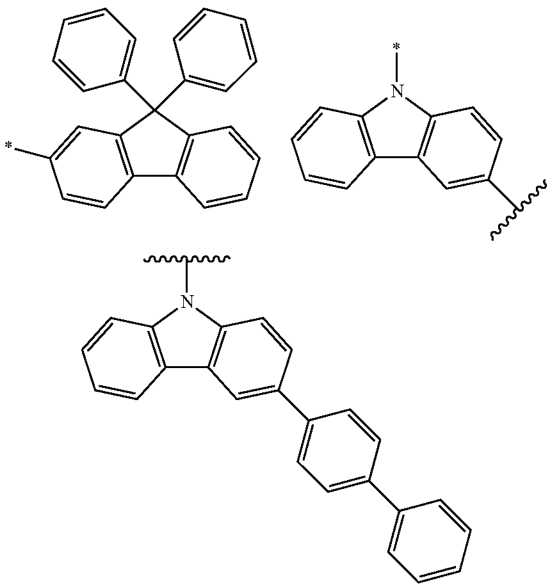
H9
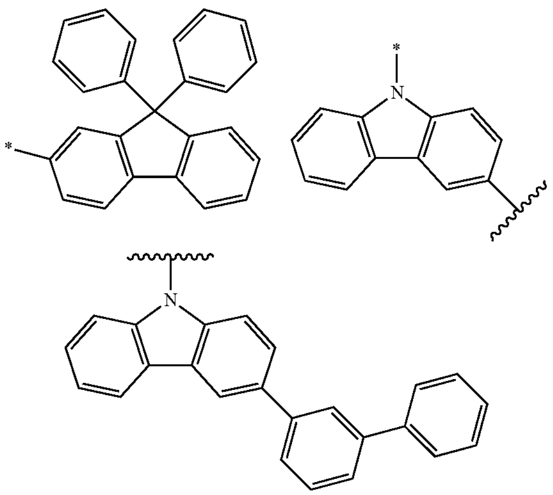

-continued
H10
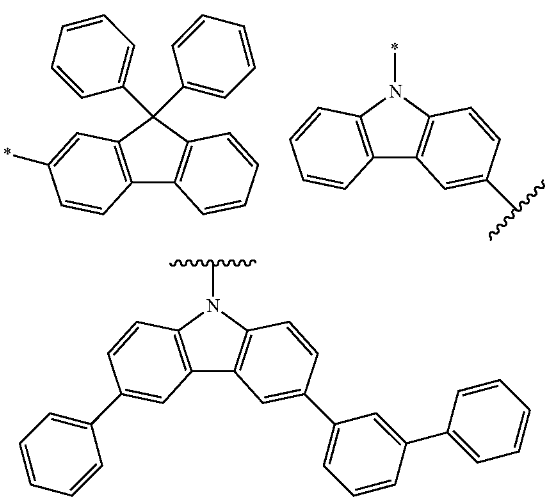
H11
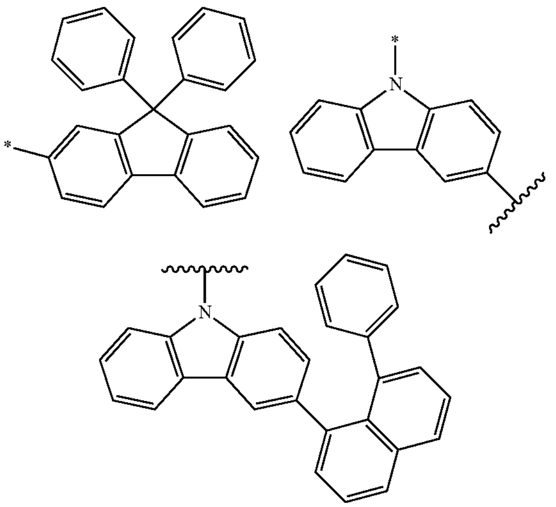
H12
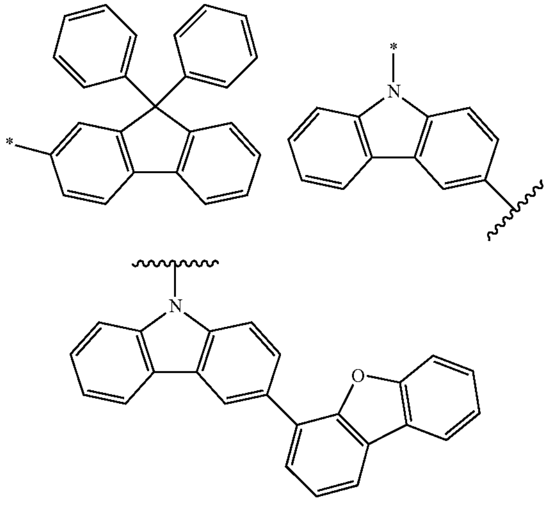
-continued
H13
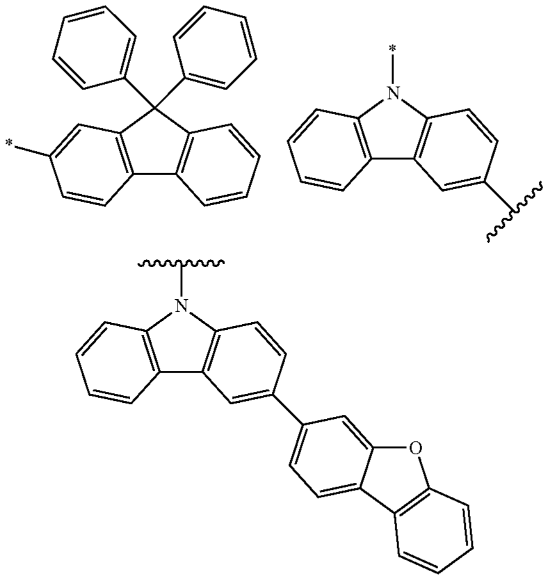
H14
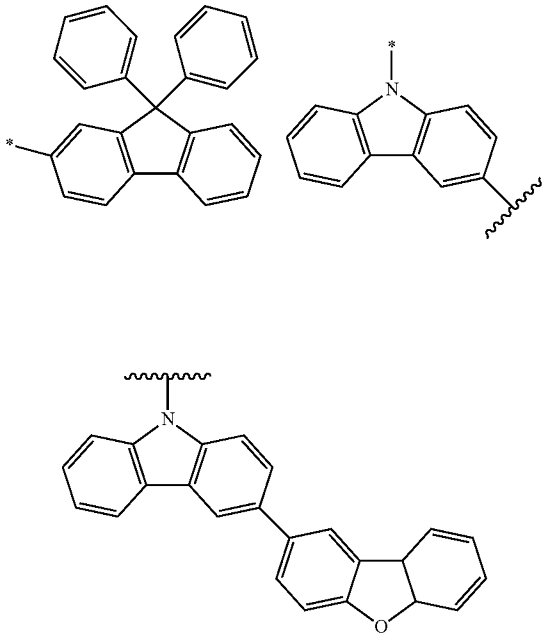
H15
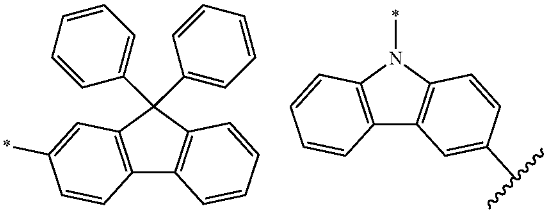

-continued
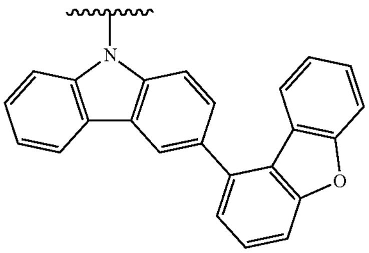
H16
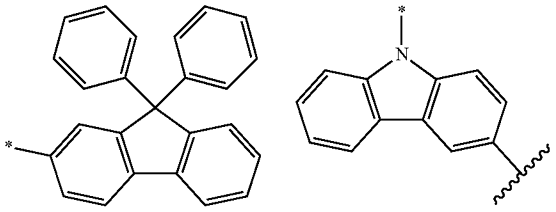
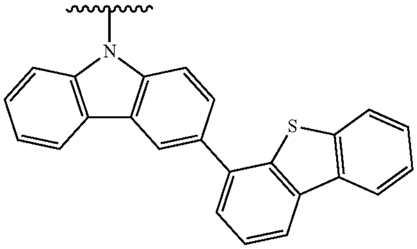
H17
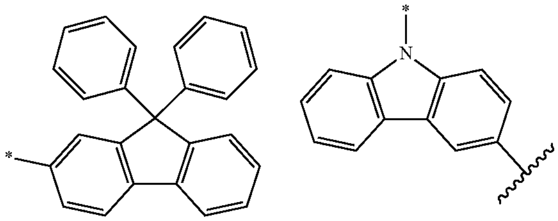
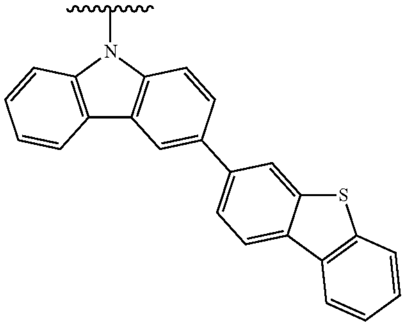
H18
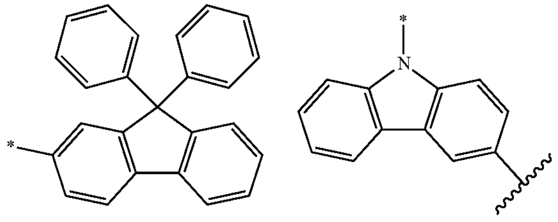
-continued
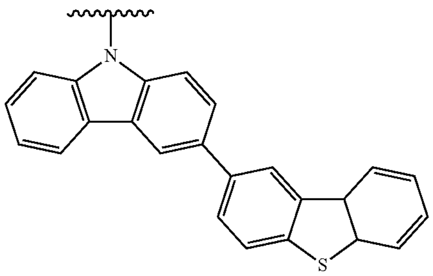
H19
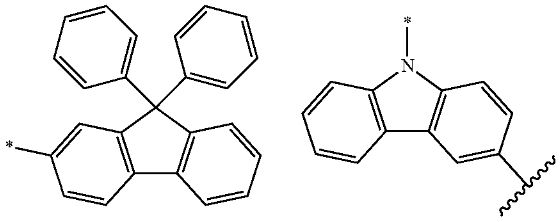
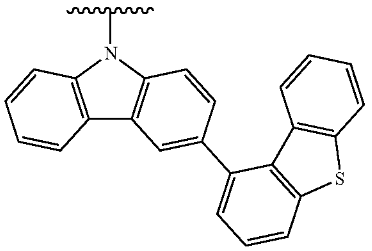
H20
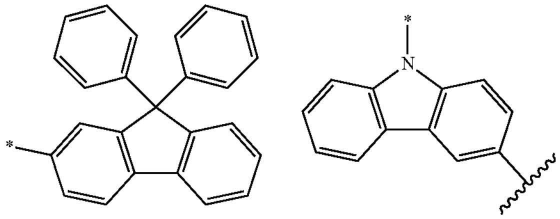
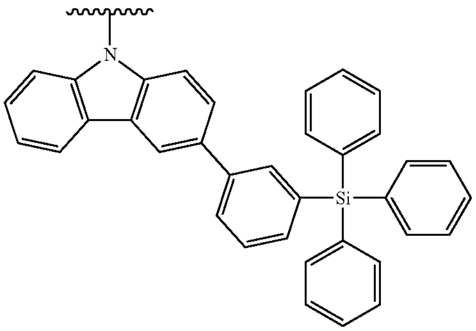
H21
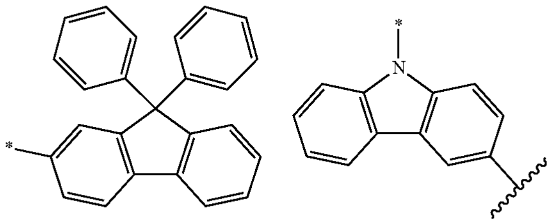

-continued
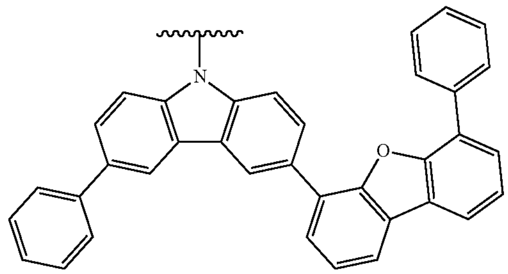
H22
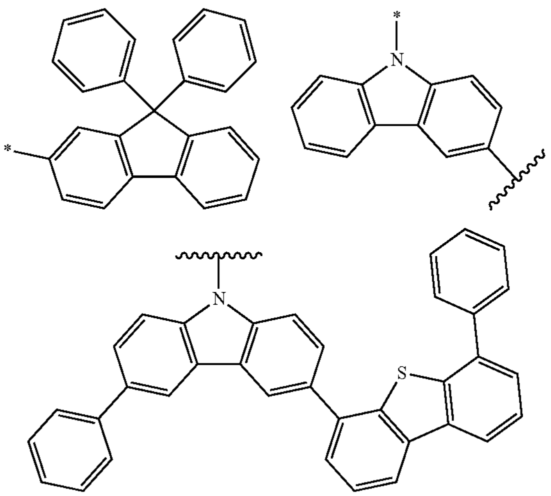
H23
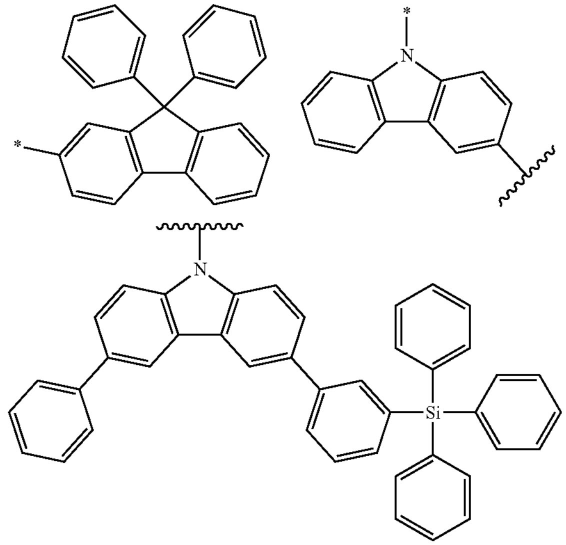
H24
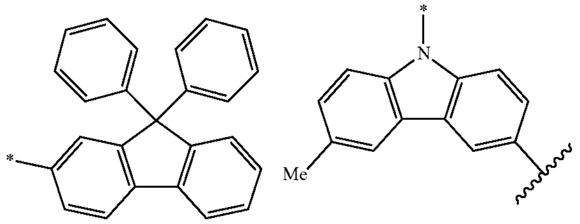
-continued
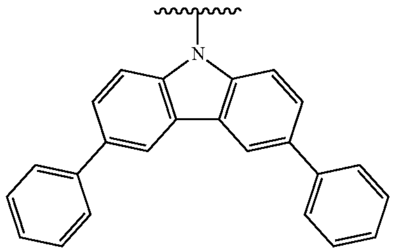
H25
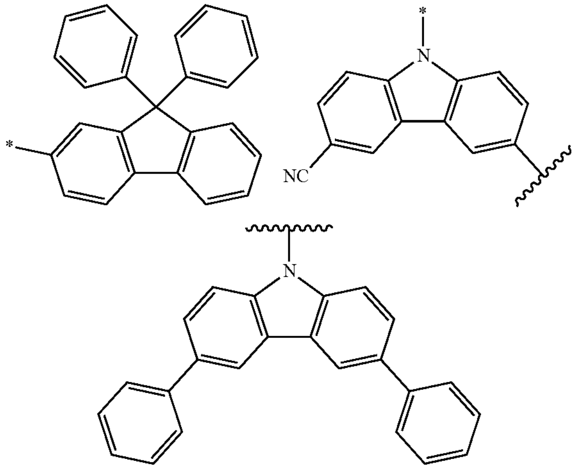
H26
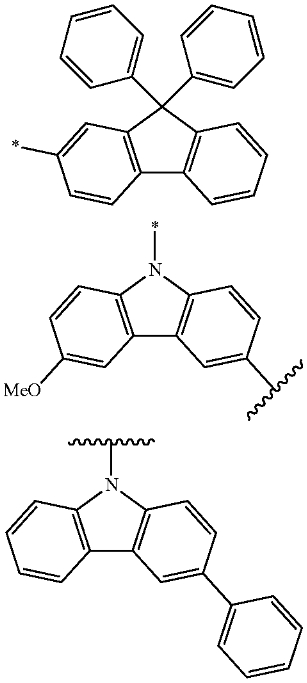
H27
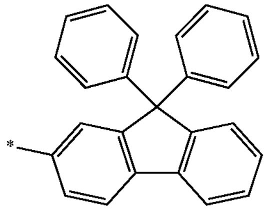

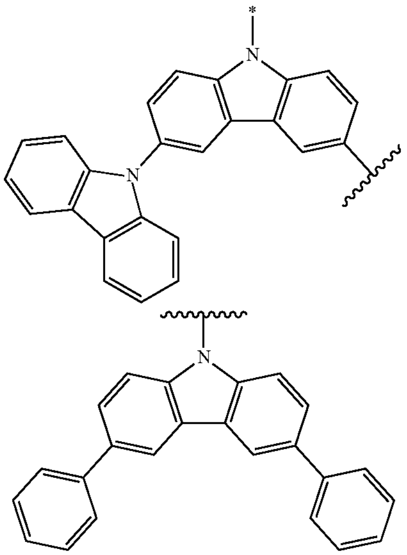
I1
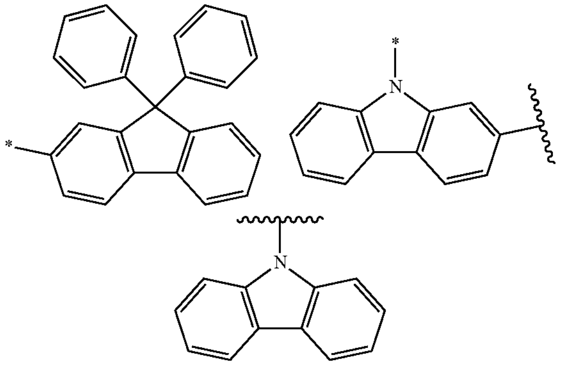
I2
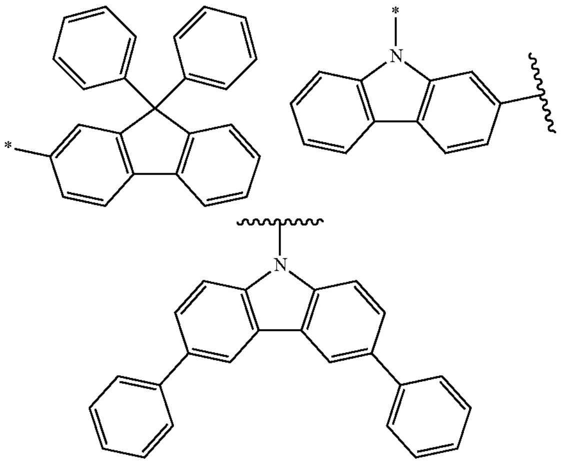
I3
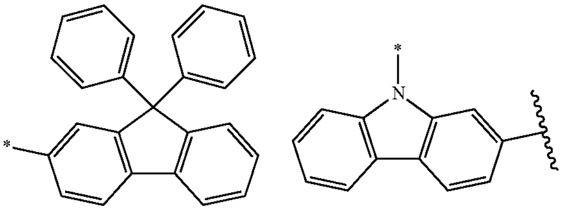
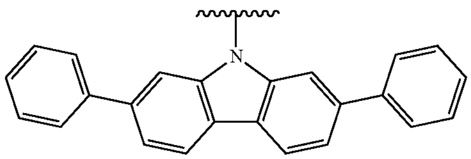
I4
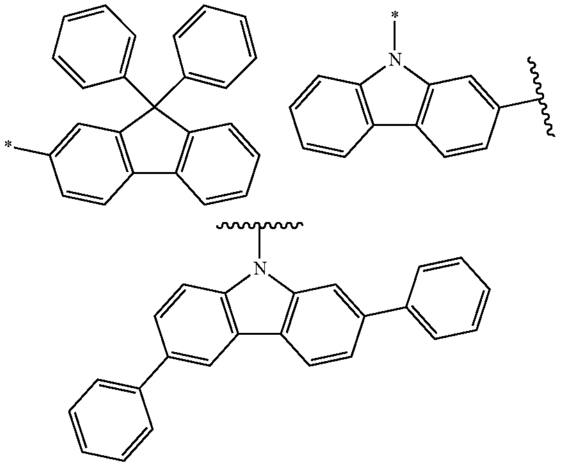
I5
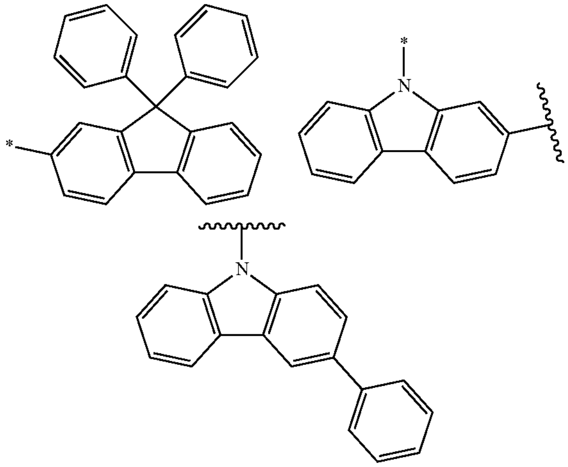
I6
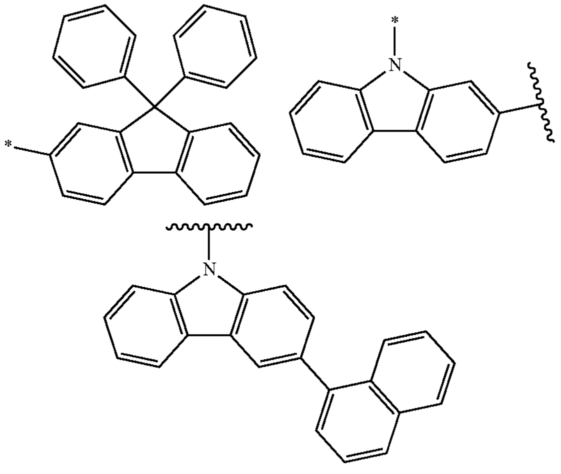

-continued
I7
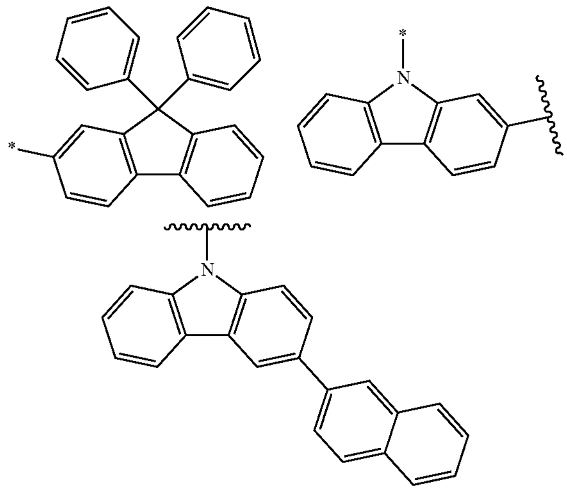
I8
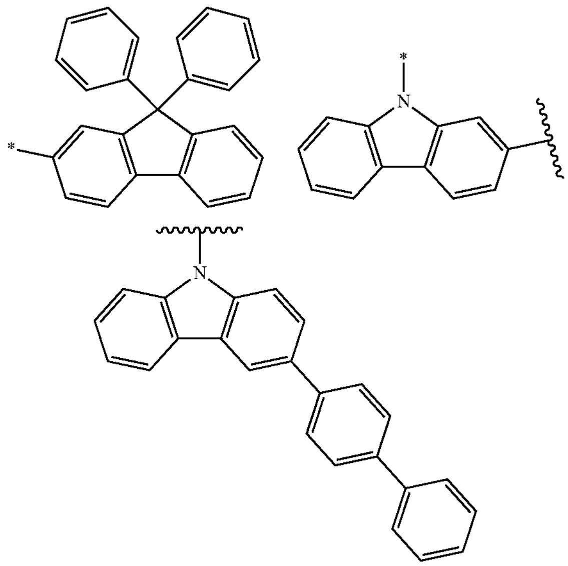
I9
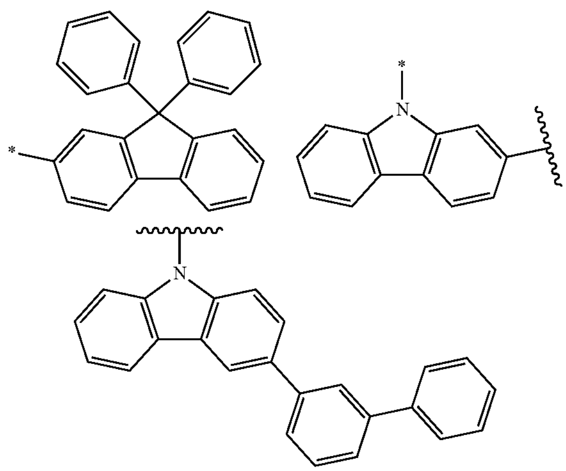
-continued
I10
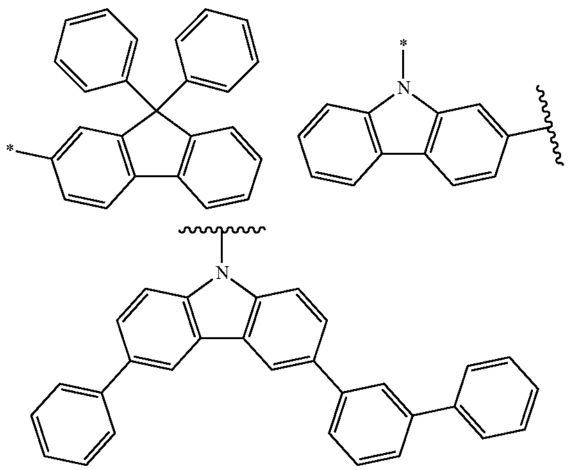
I11
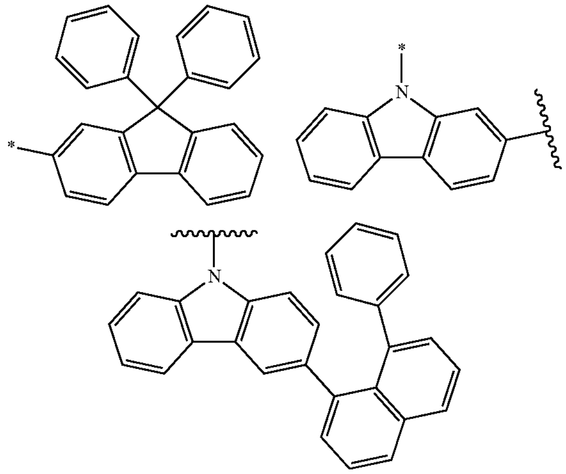
I12
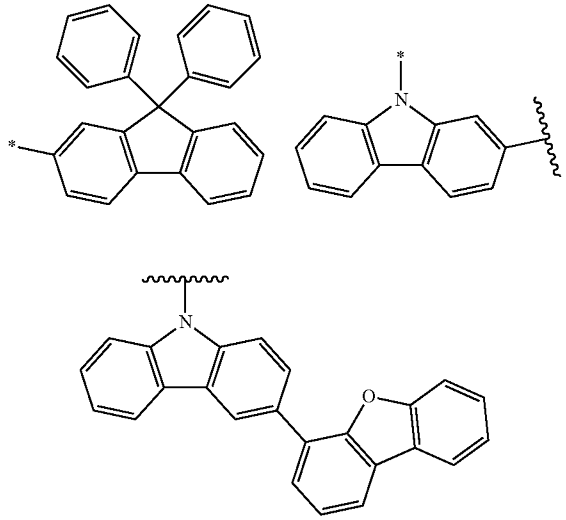

-continued
I13
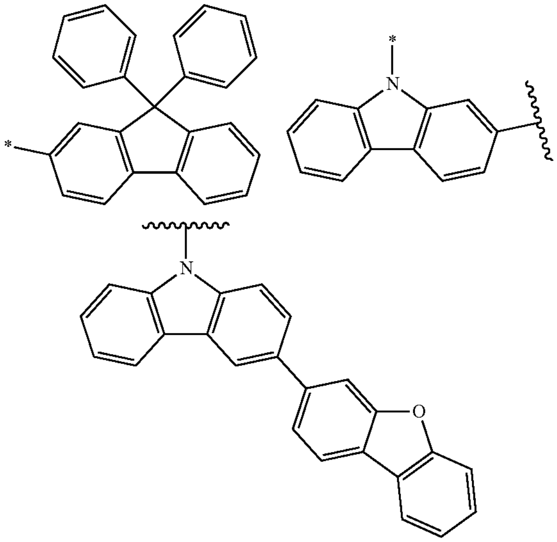
I14
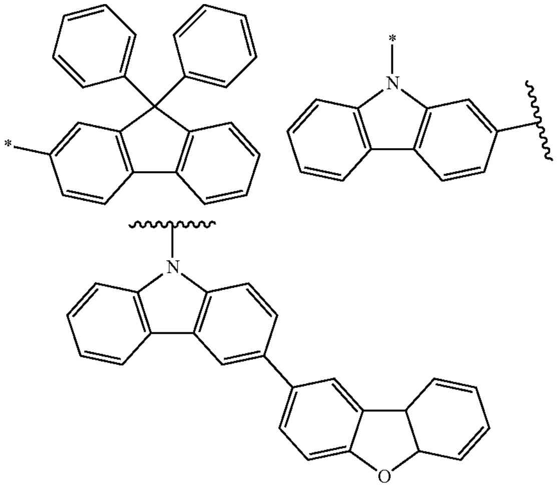
I15
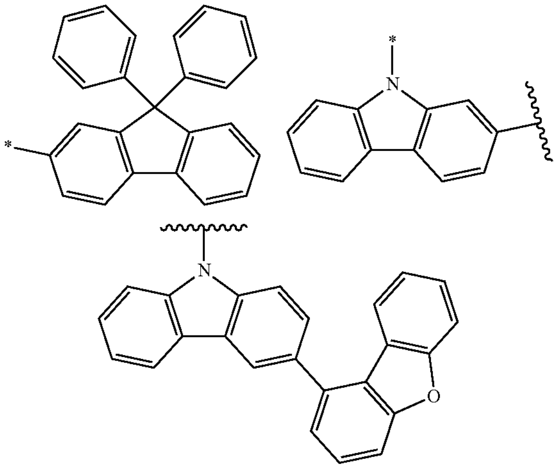
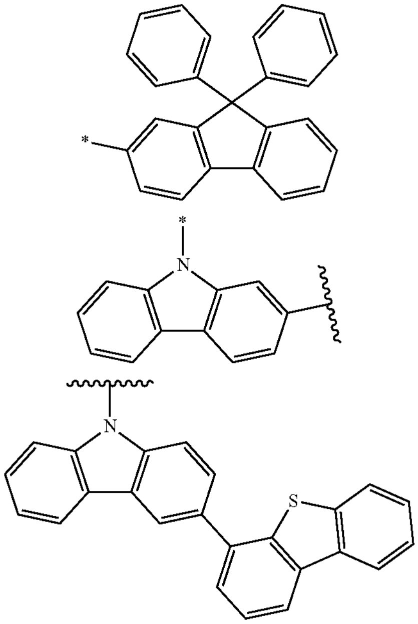
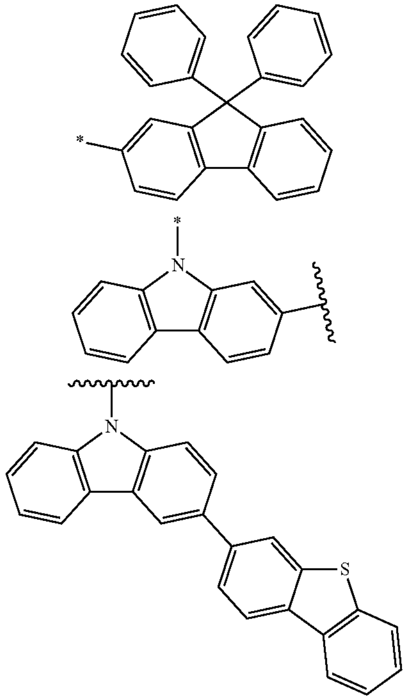
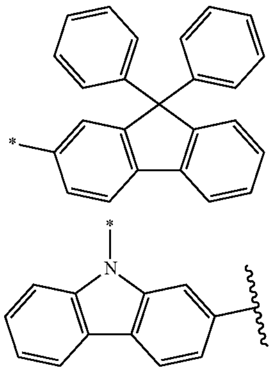

-continued
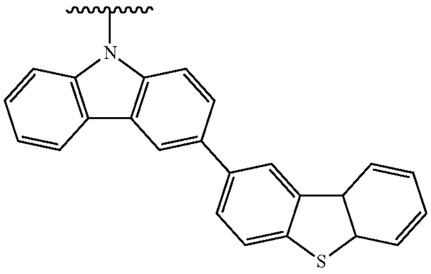
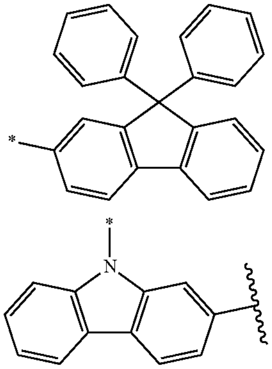
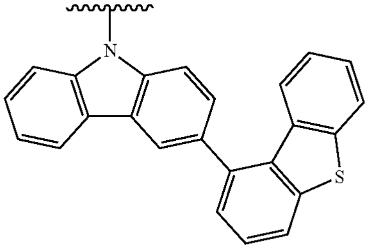
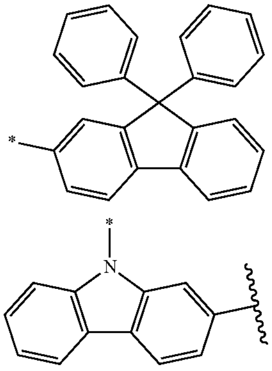
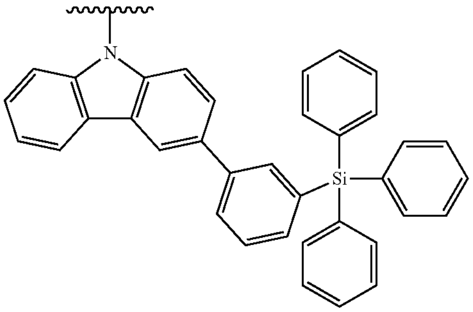
-continued
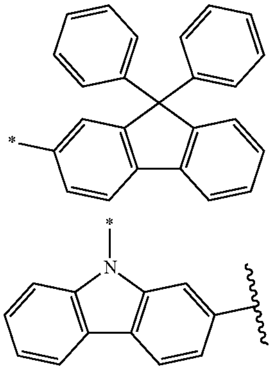
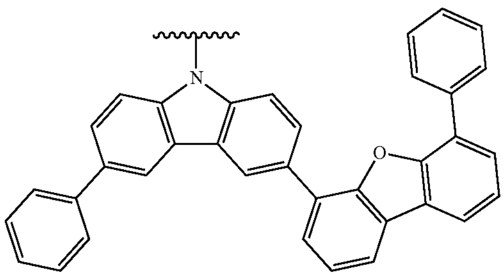
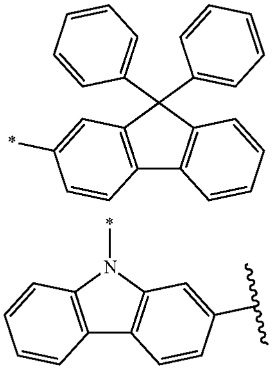
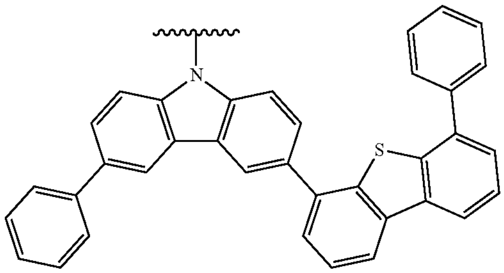
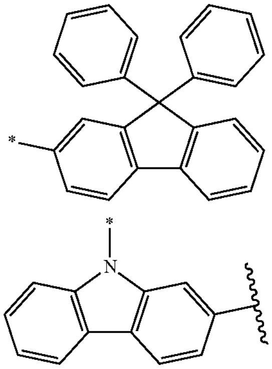

-continued
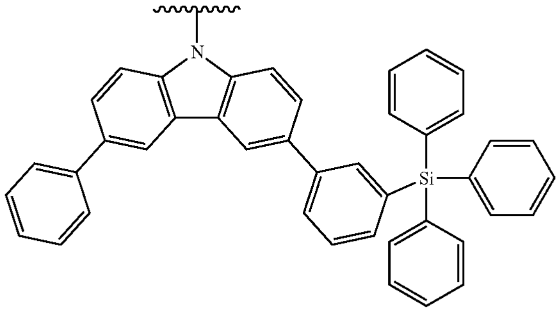
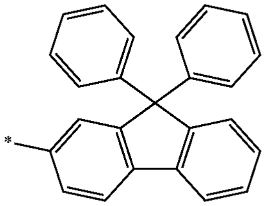
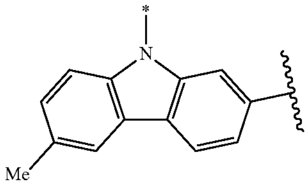
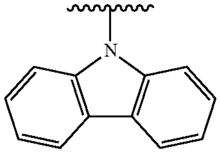
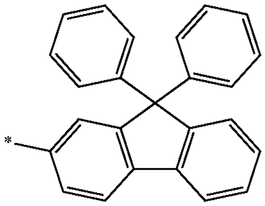
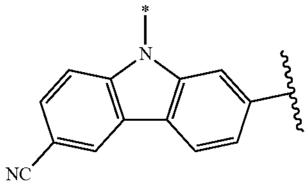
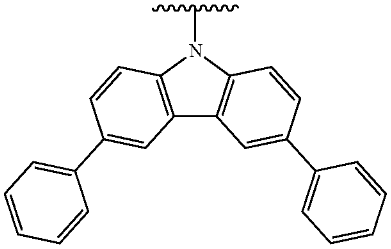
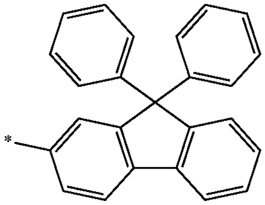
-continued
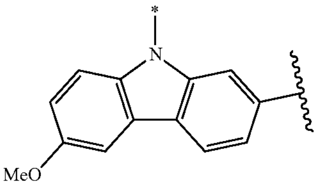
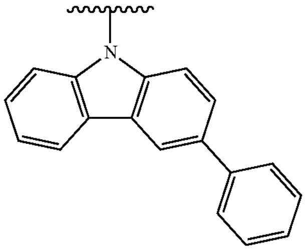
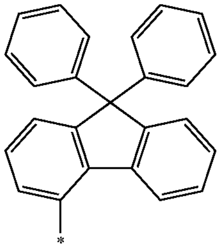
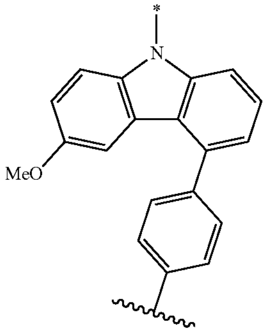
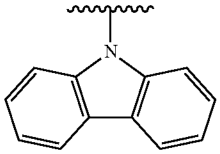
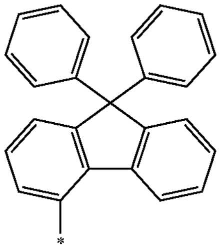

-continued
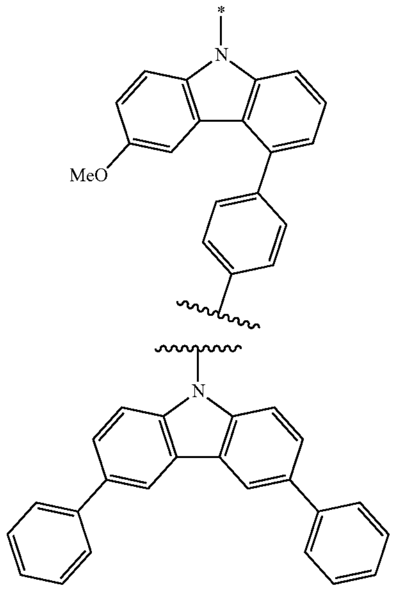
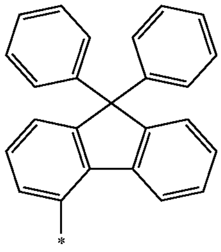
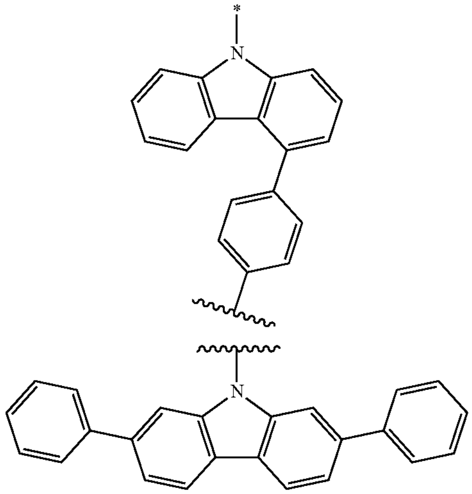
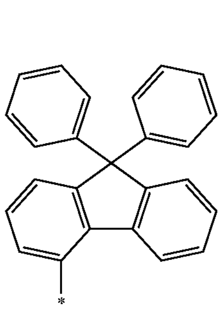
-continued
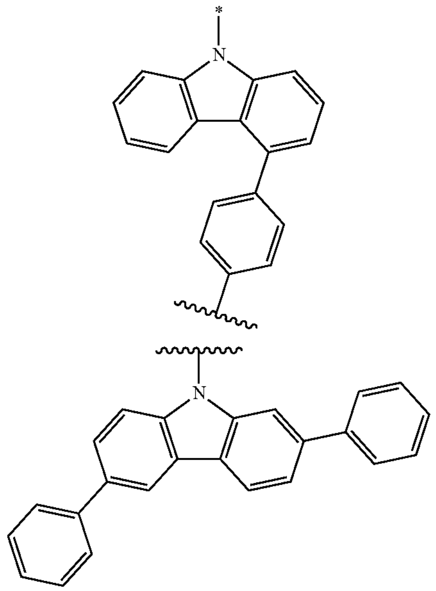
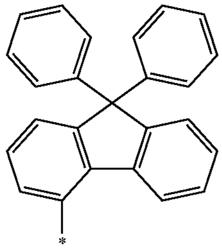
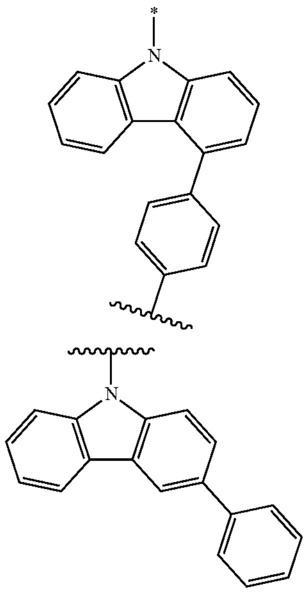
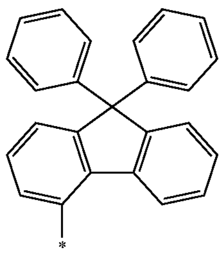

-continued
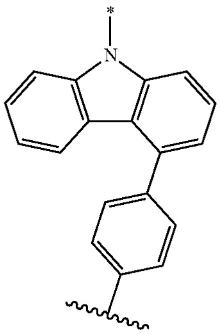
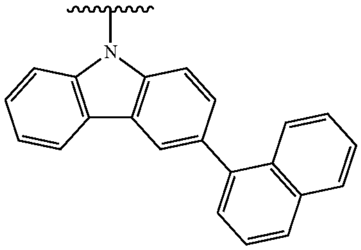
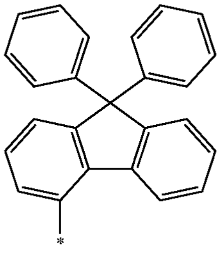
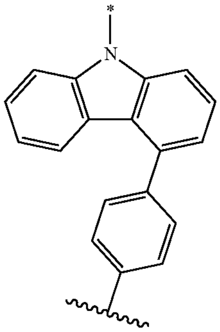
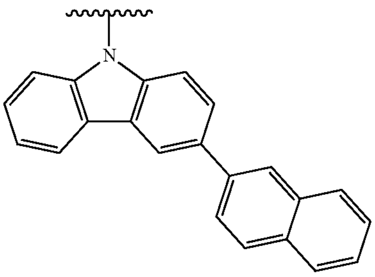
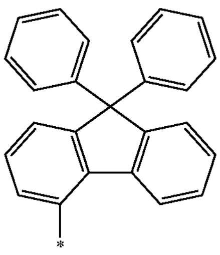
-continued
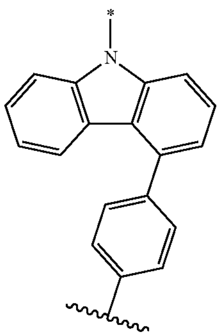
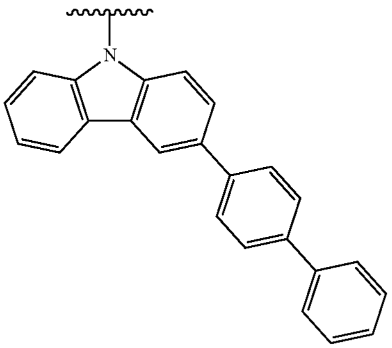
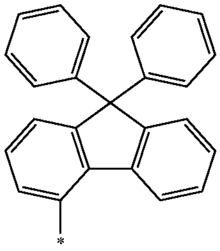
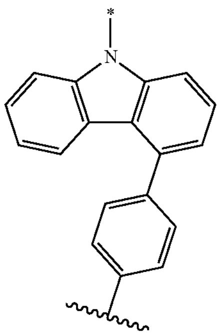
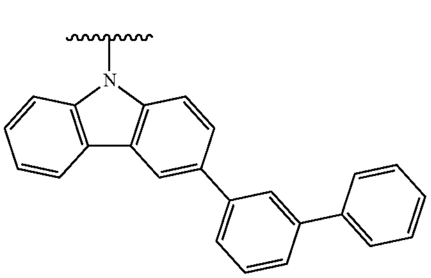

-continued
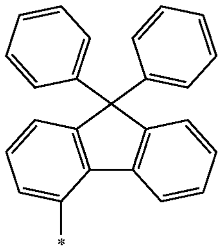
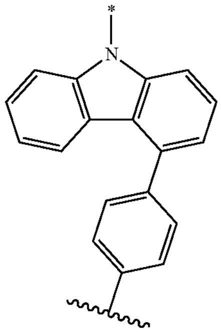
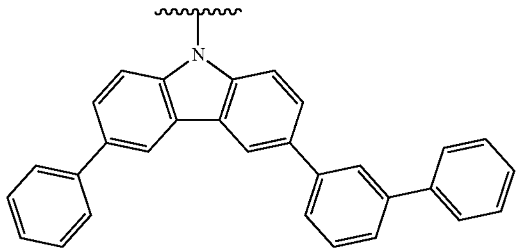
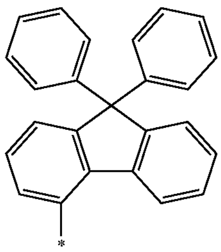
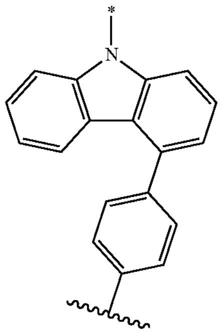
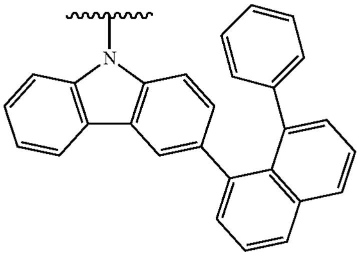
-continued
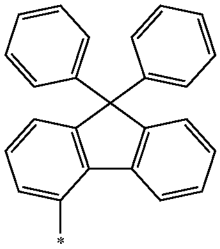
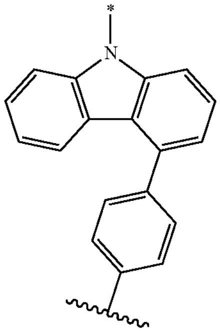
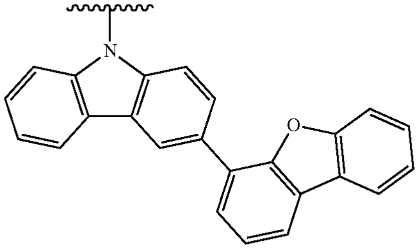
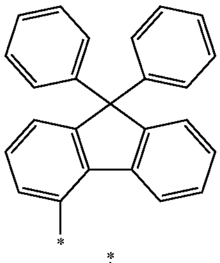
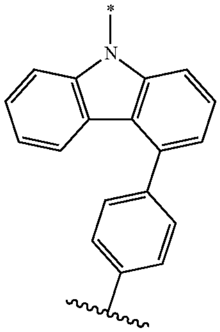
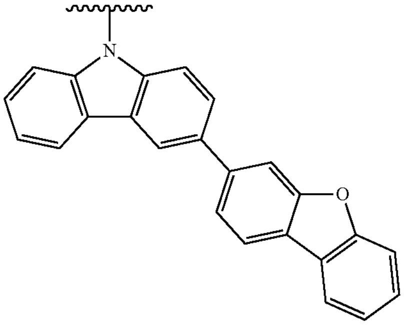

-continued
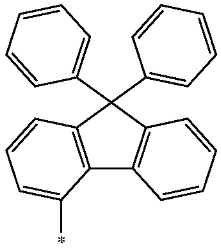
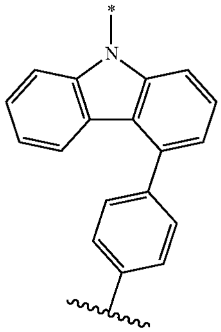
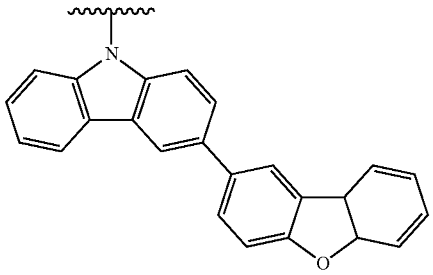
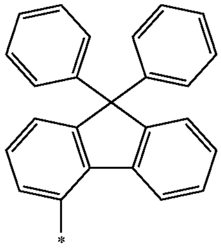
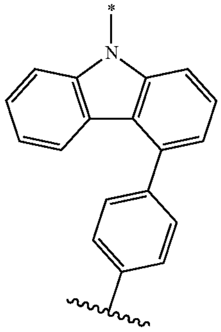
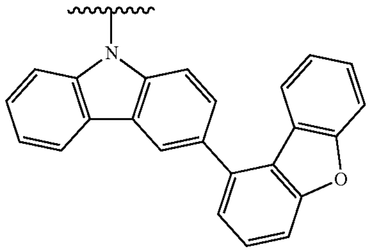
-continued
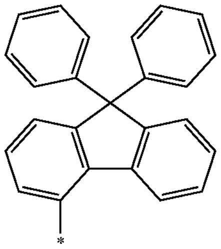
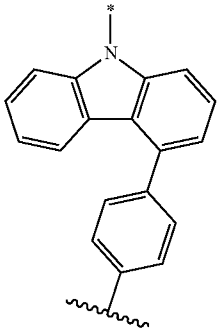
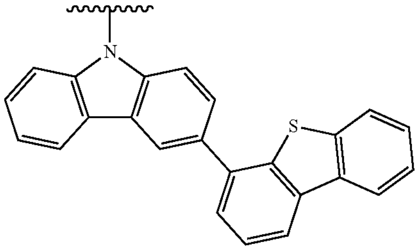
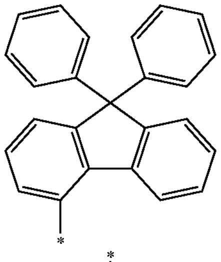
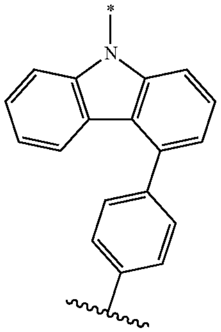
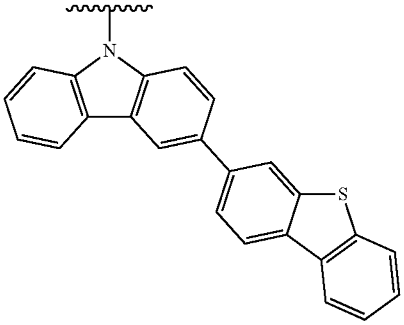

-continued
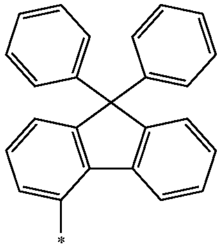
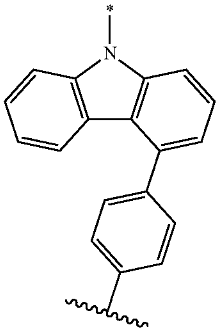
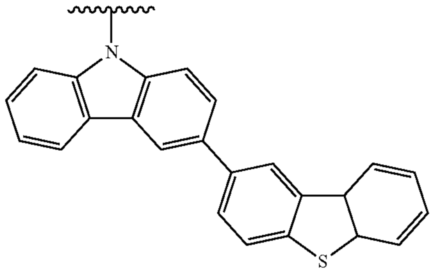
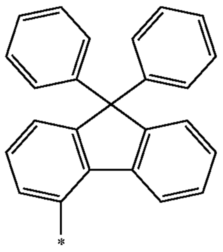
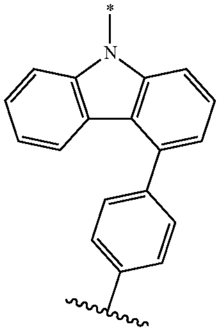
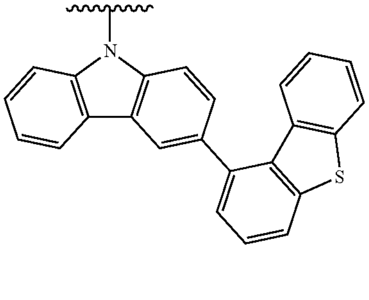
-continued
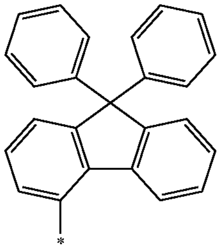
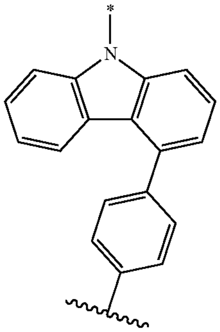
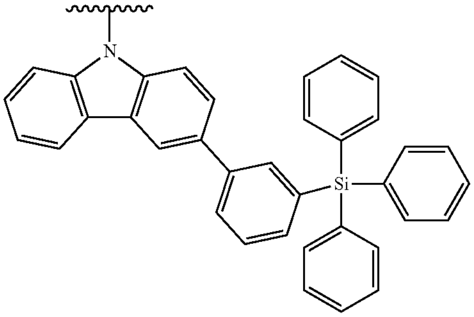
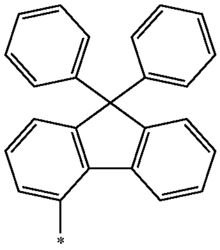
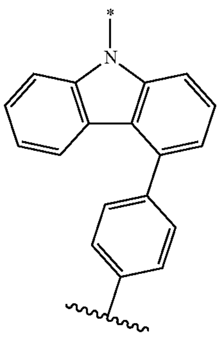

-continued
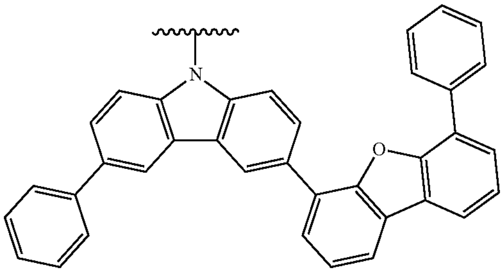
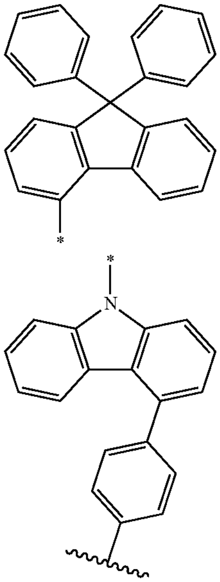
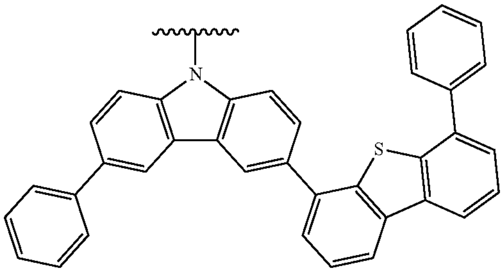
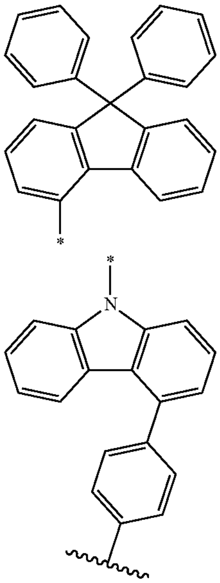
-continued
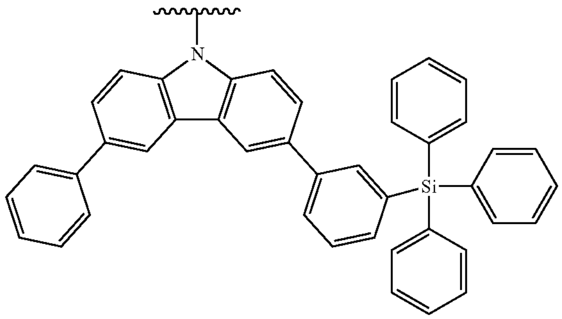
J24
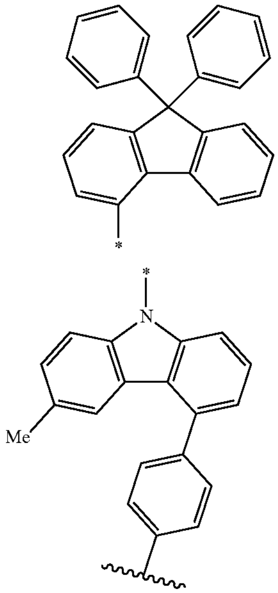
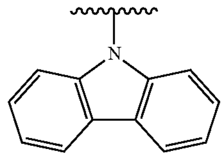
J25
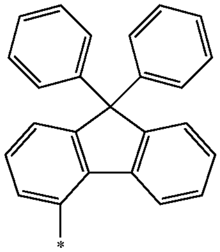

-continued
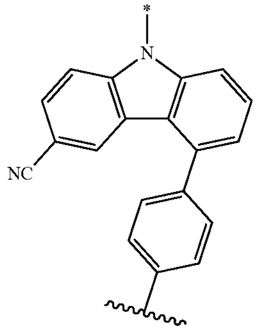
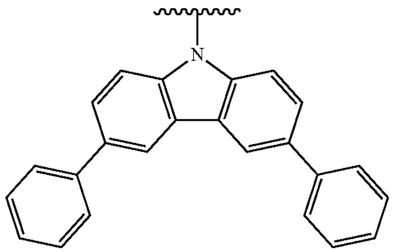
J26
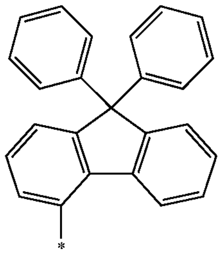
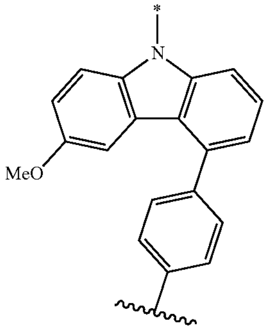
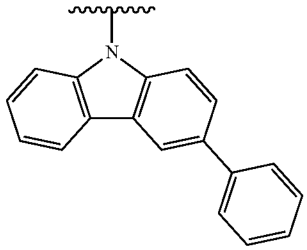
K1
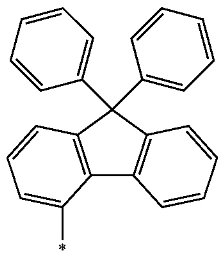
-continued
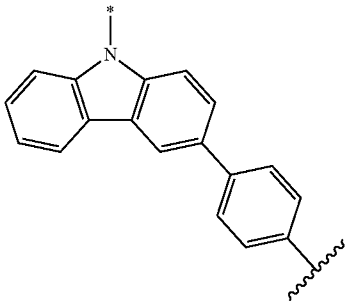
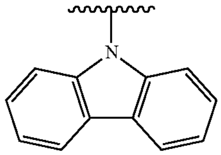
K2
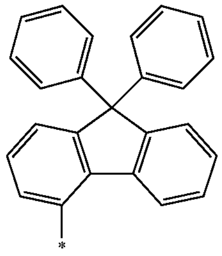
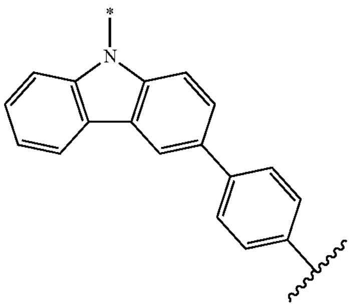
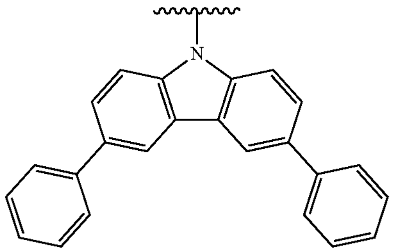
K3
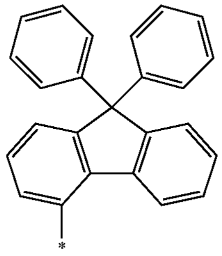

-continued
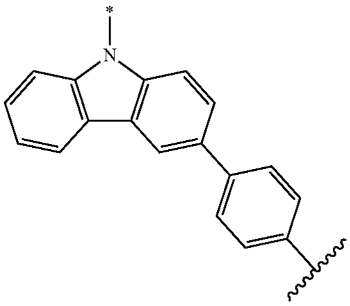
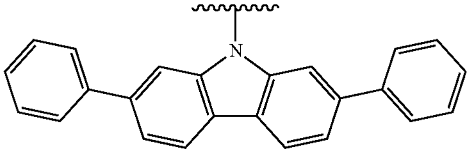
K4
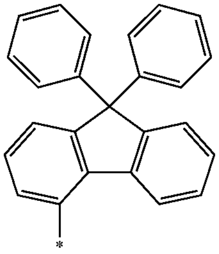
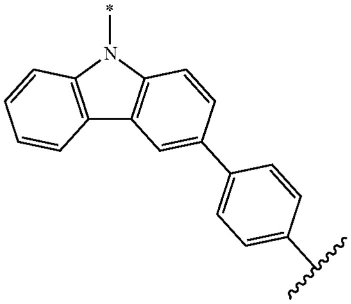
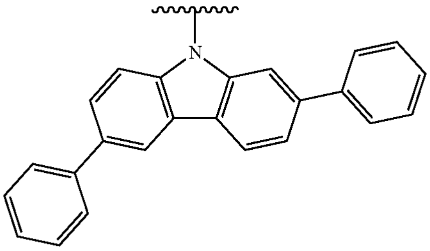
K5
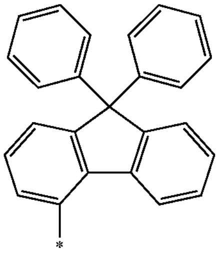
-continued
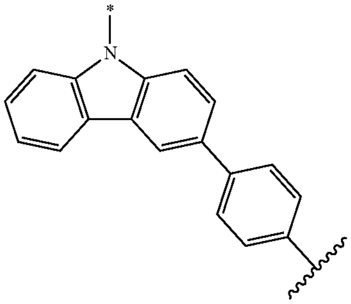
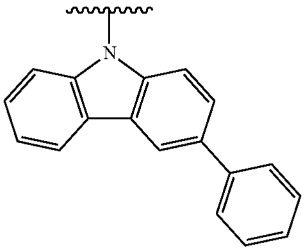
K6
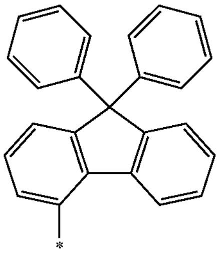
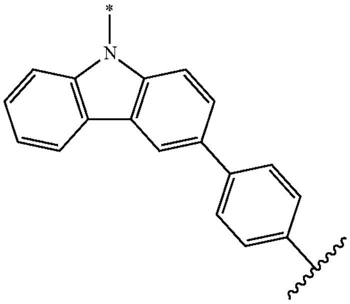
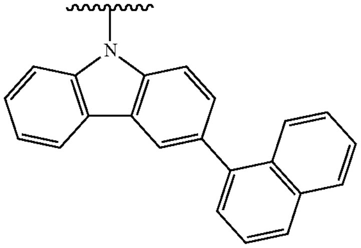
K7
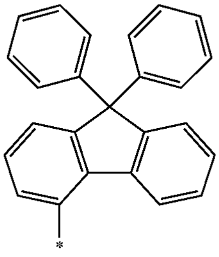

-continued
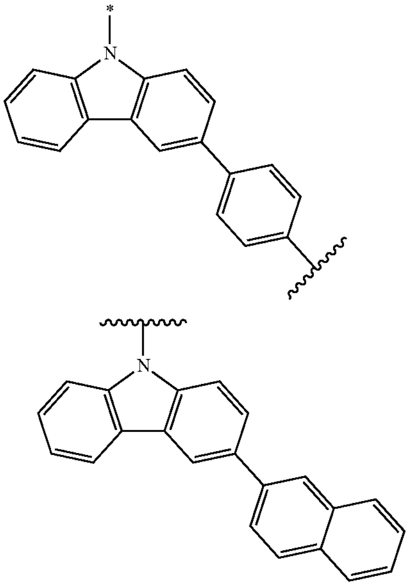
K8
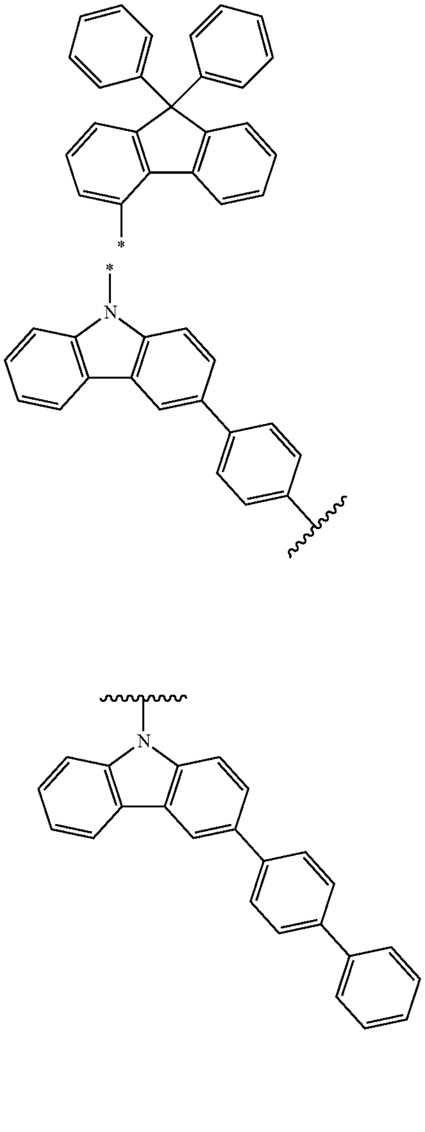
-continued
K9
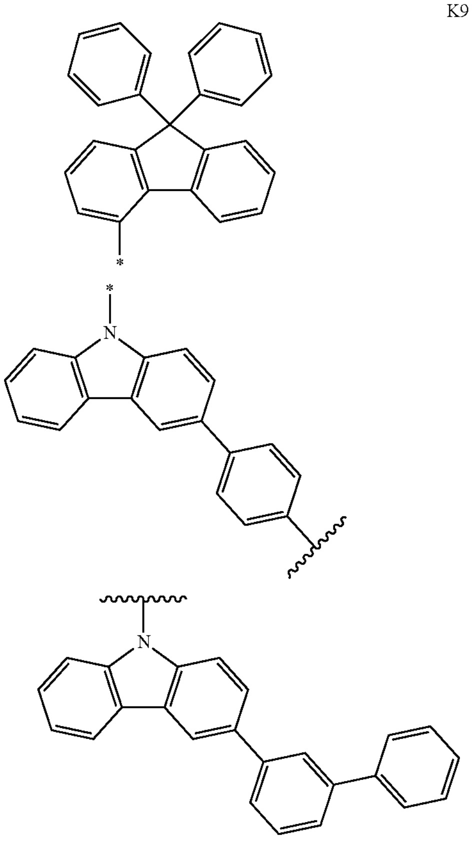
K10
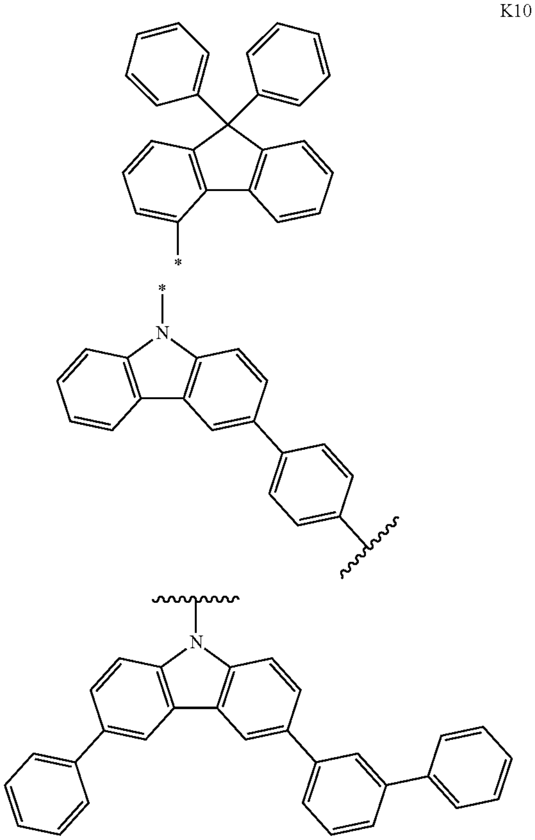

K11
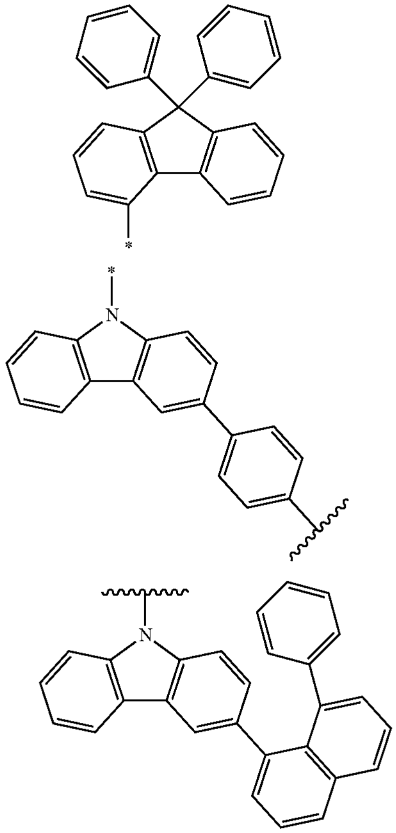
K12
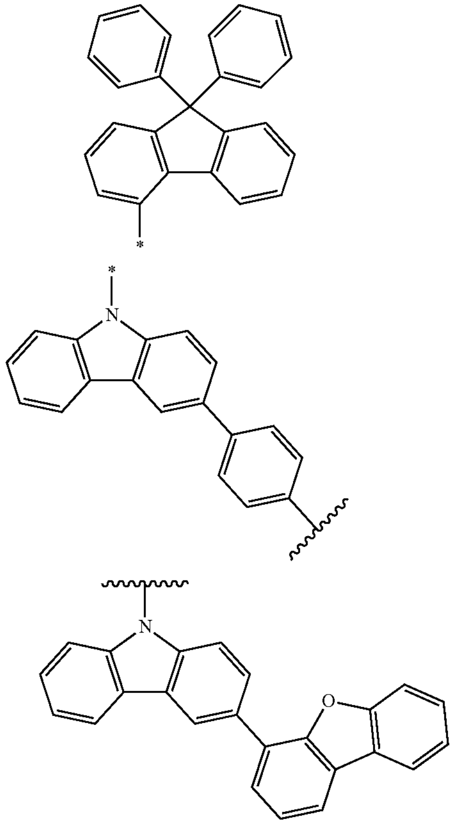
K13
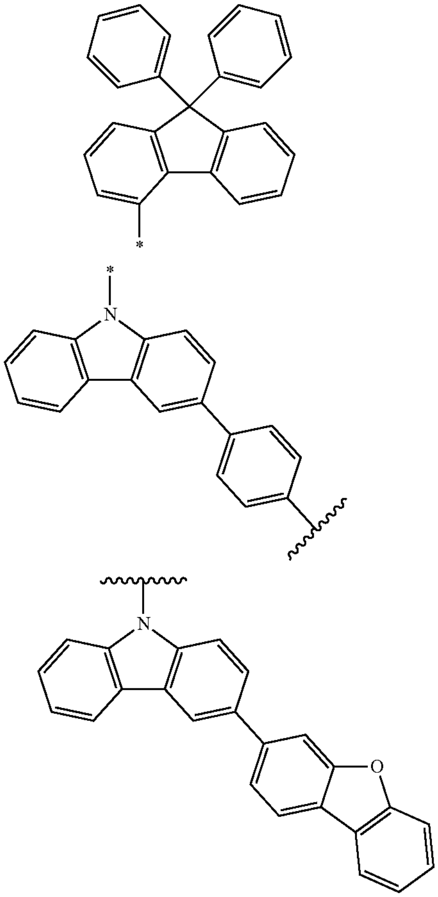
K14
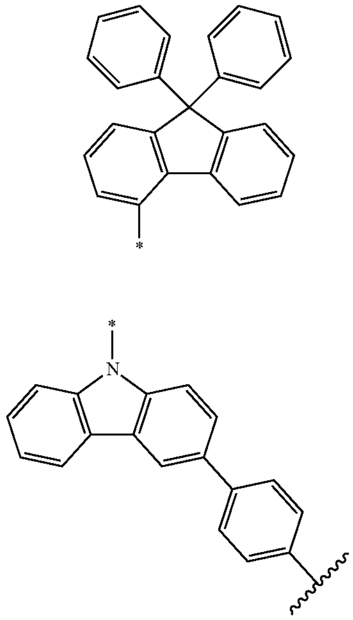

-continued
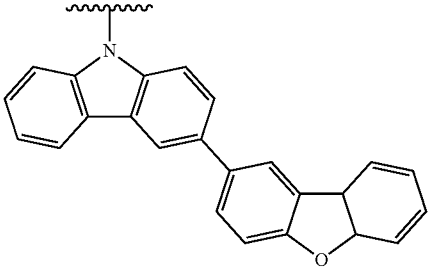
K15
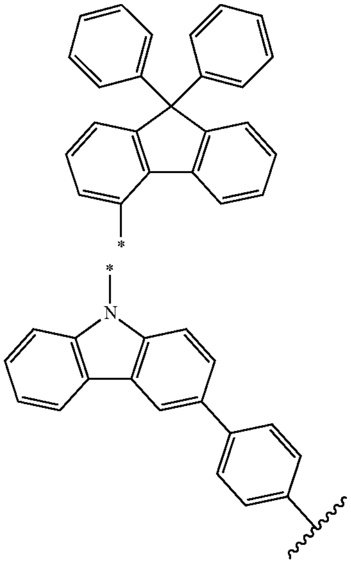
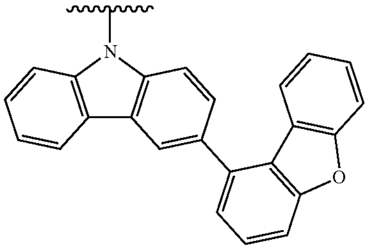
K16
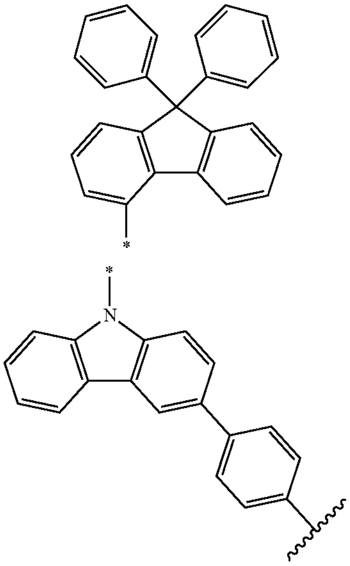
-continued
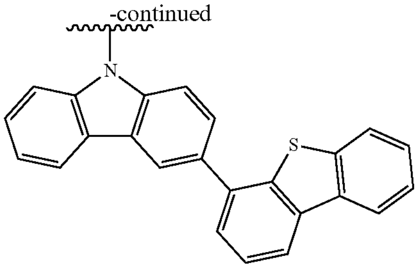
K17
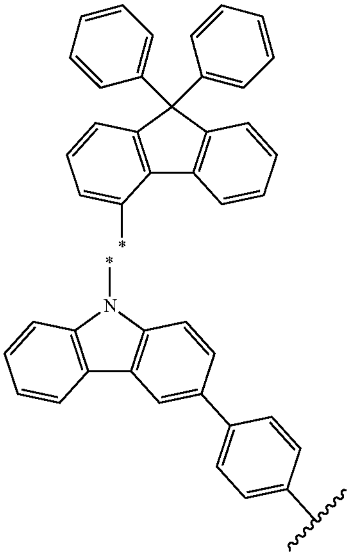
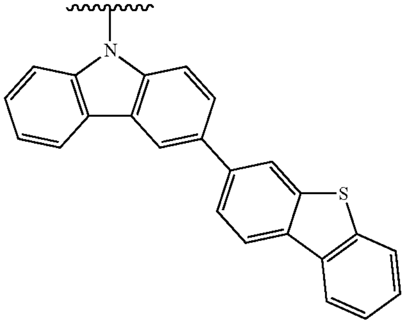
K18
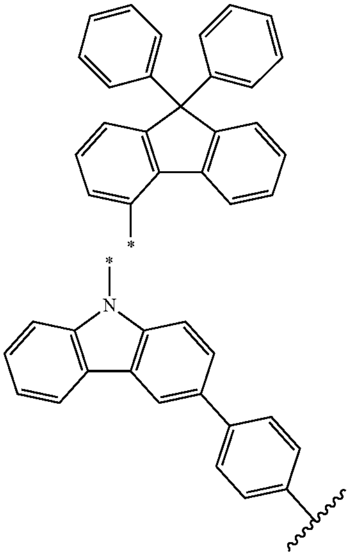

-continued
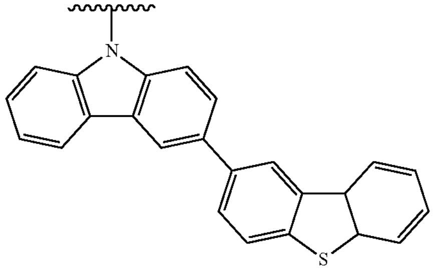
K19
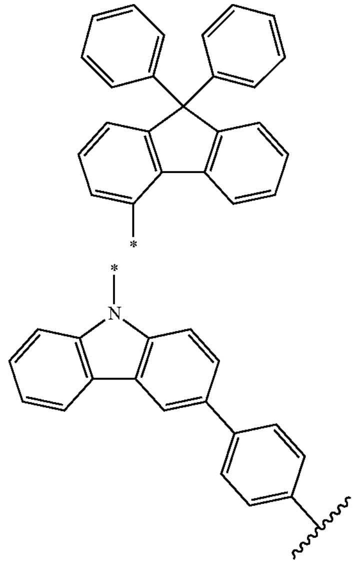
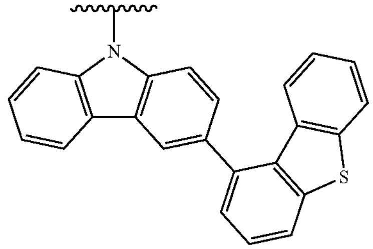
K20
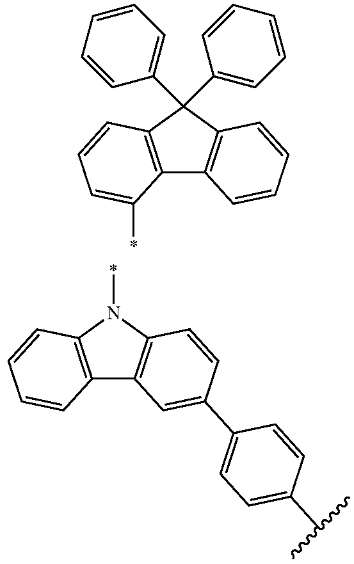
-continued
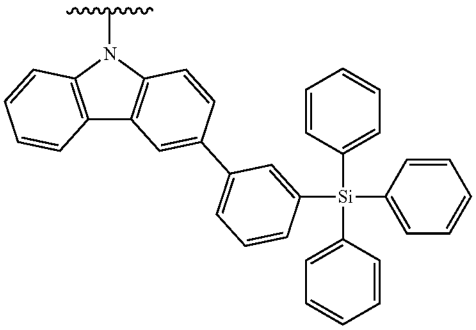
K21
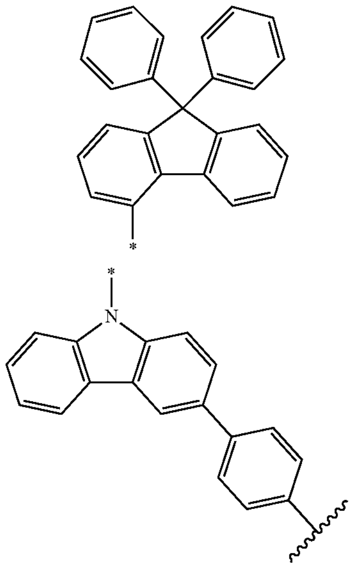
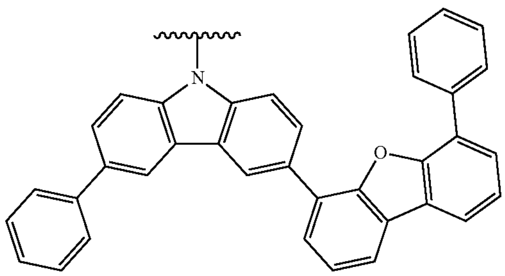
K22
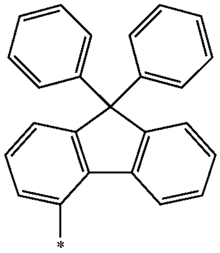

-continued
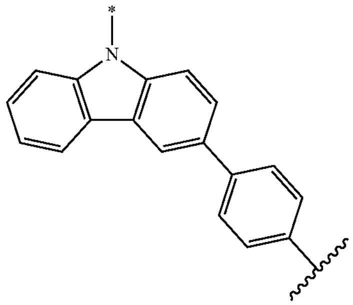
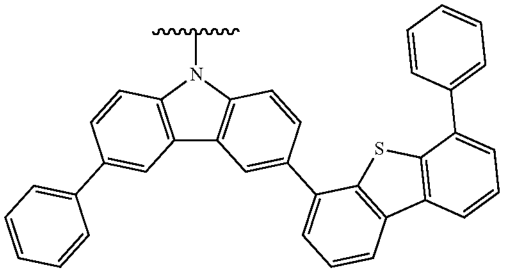
K23
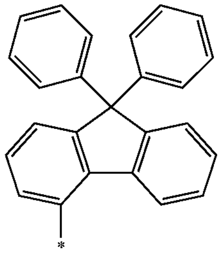
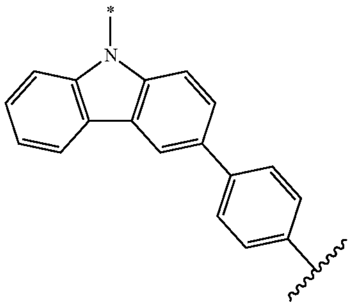
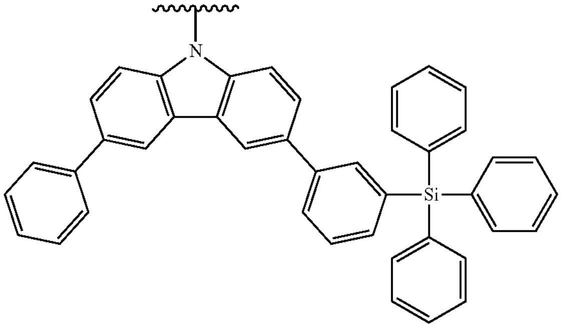
-continued
K24
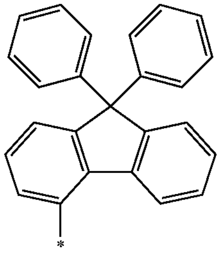
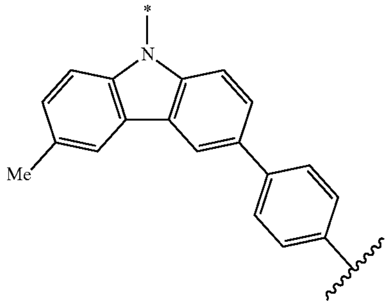
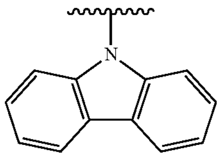
K25
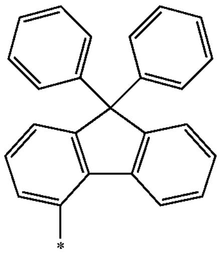
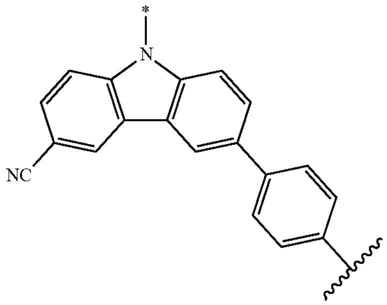
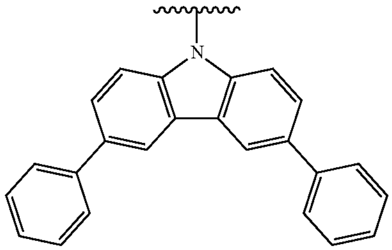

-continued
K26
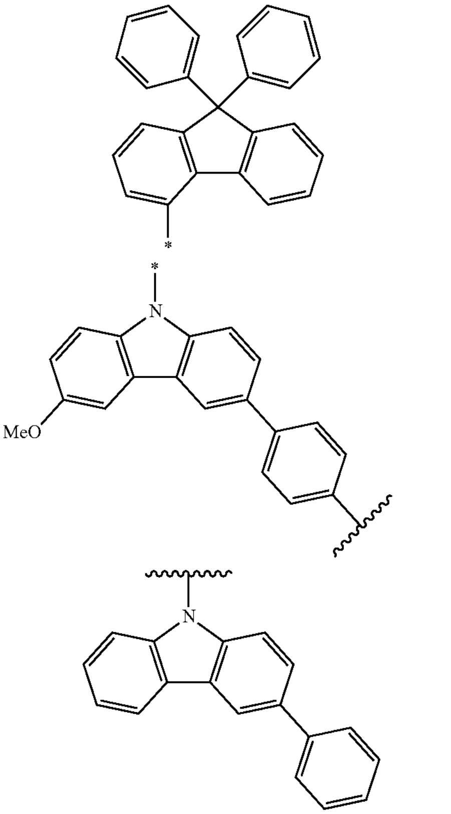
M1
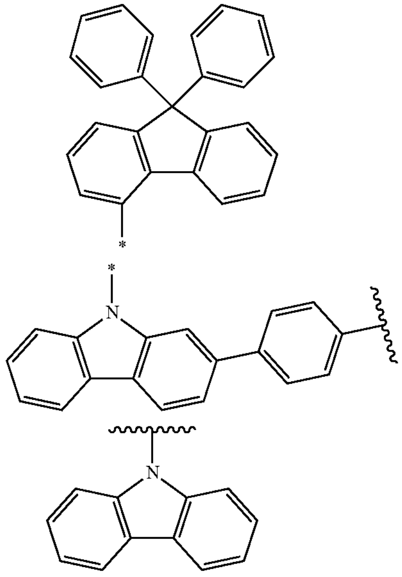
M2
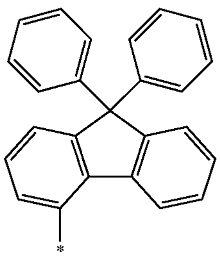
-continued
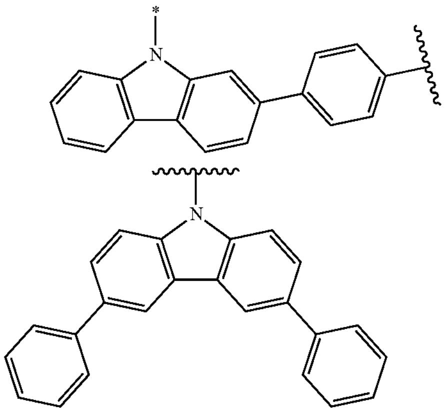
M3
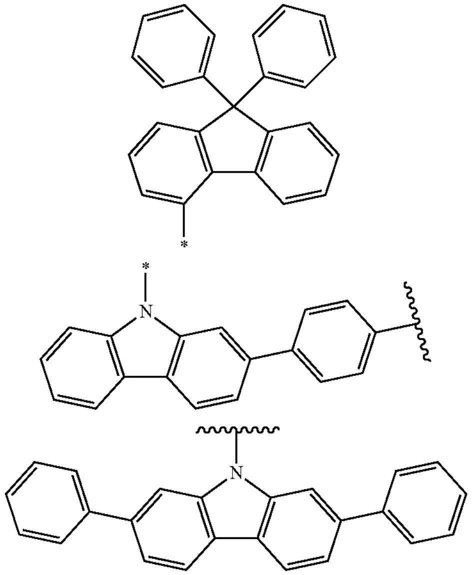
M4
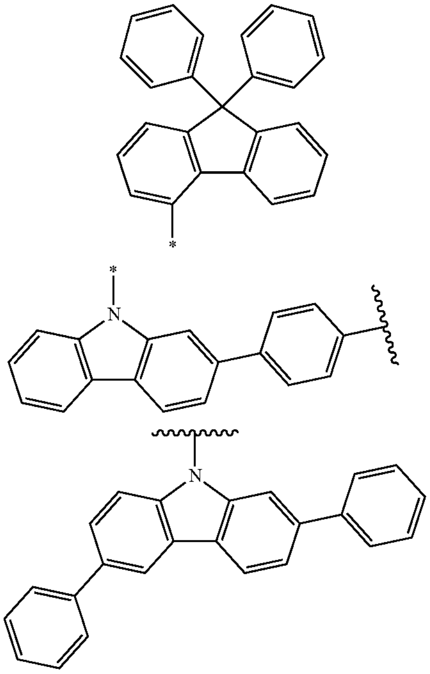

-continued
M5
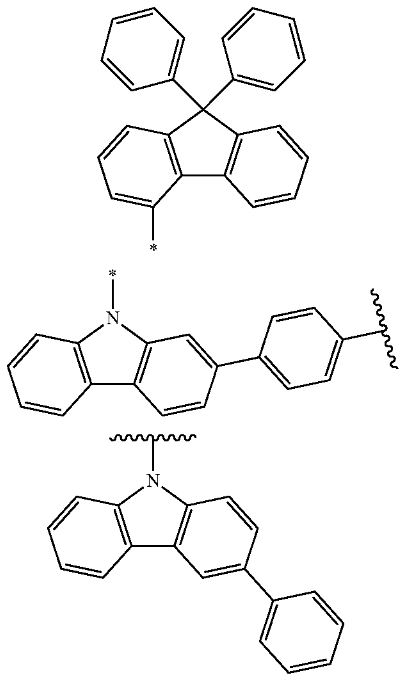
M6
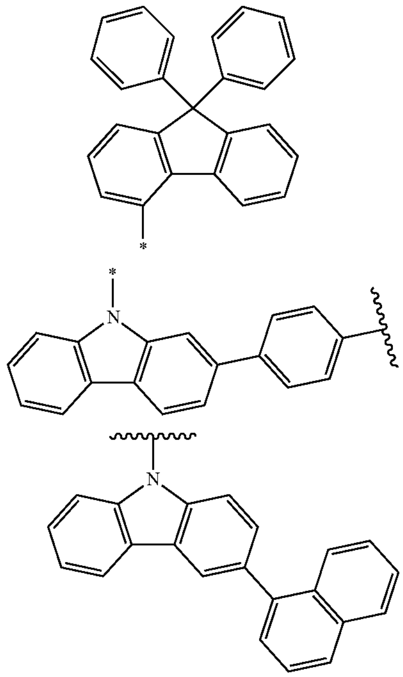
M7
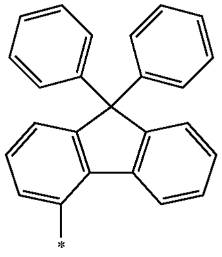
-continued
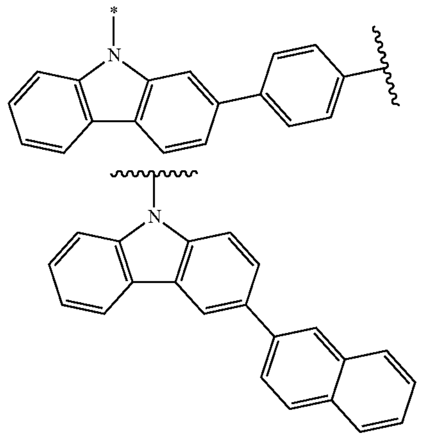
M8
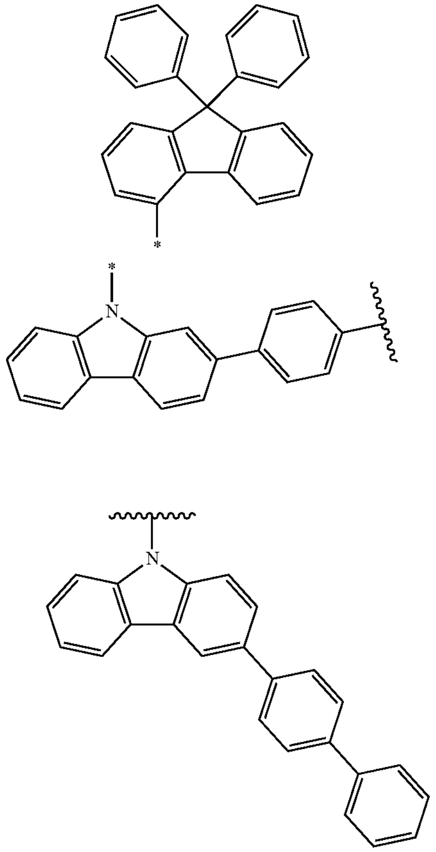
M9
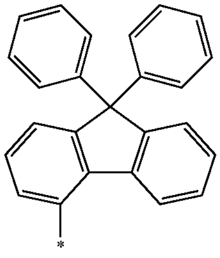

-continued
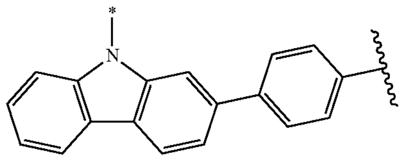
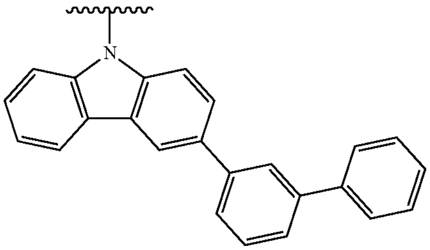
M10
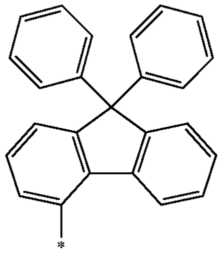
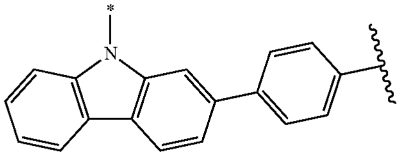
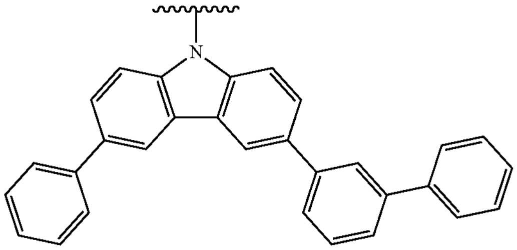
M11
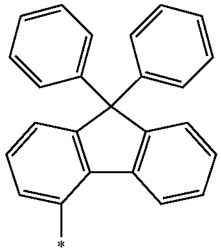
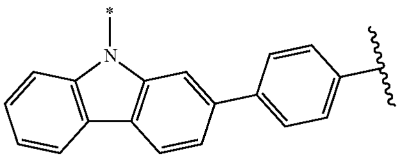
-continued
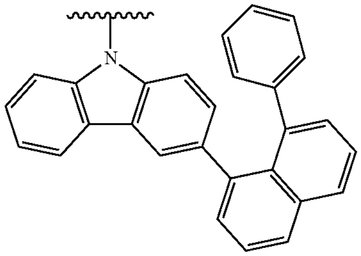
M12
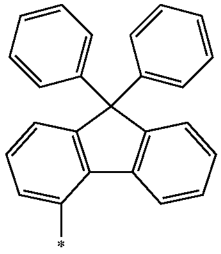
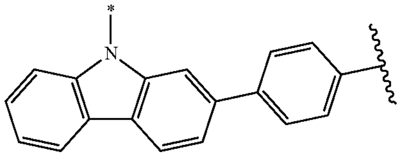
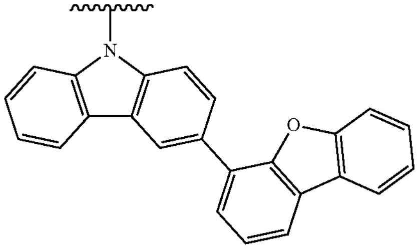
M13
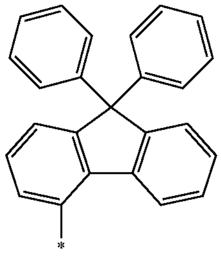
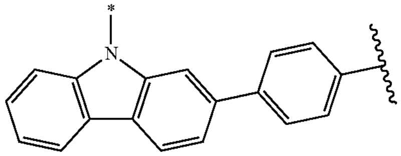
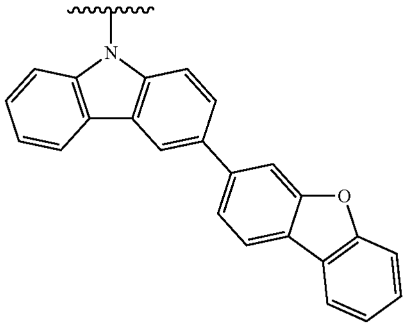

-continued
M14
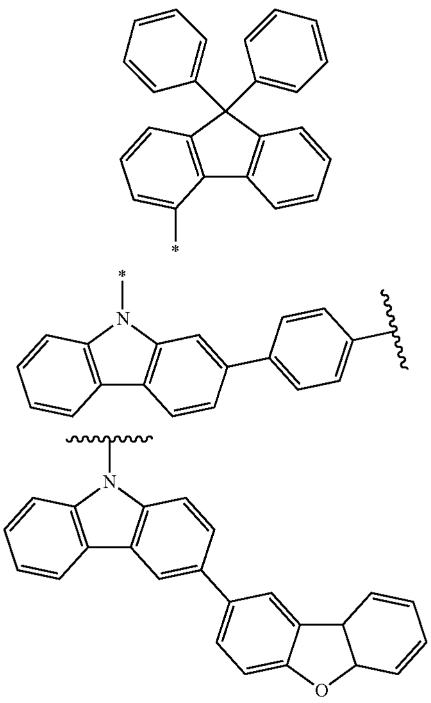
M15
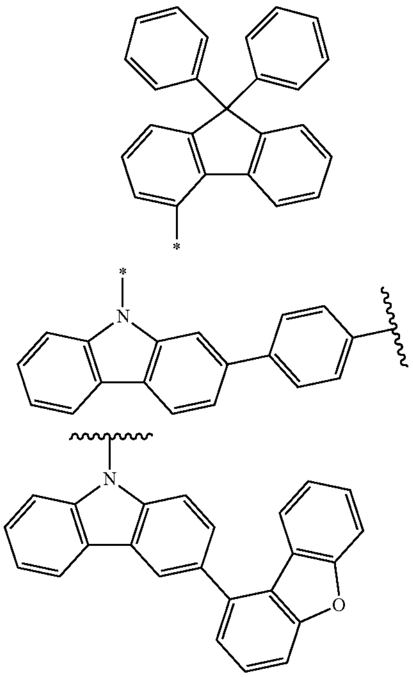
M16
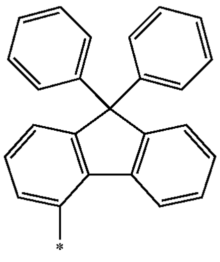
-continued
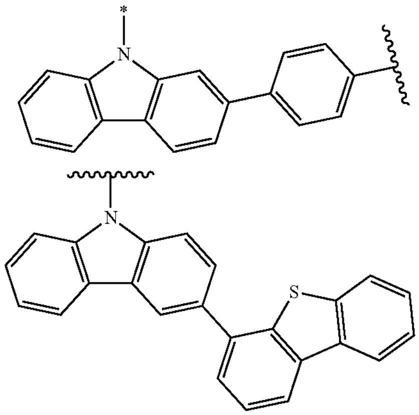
M17
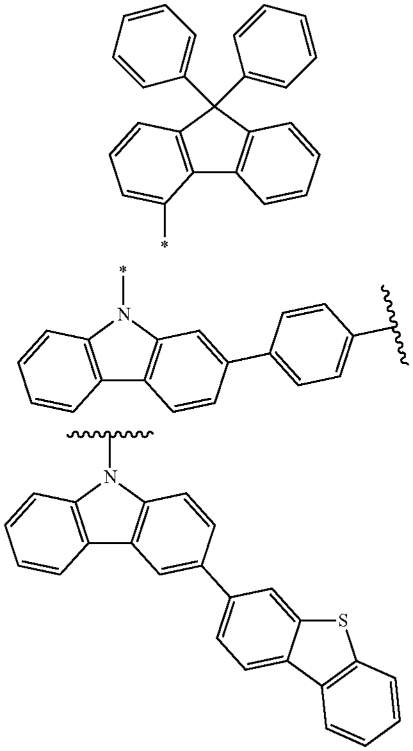
M18
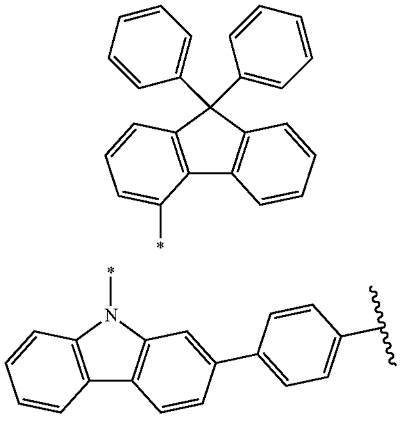

-continued
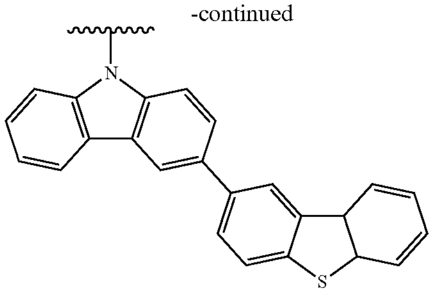
M19
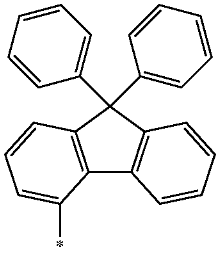
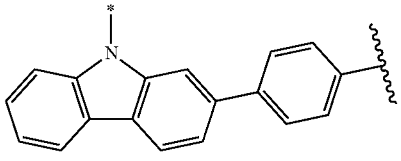
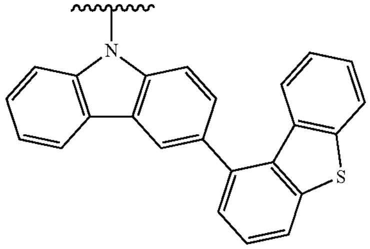
M20
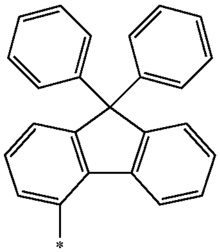
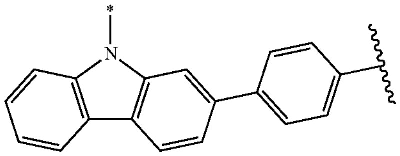
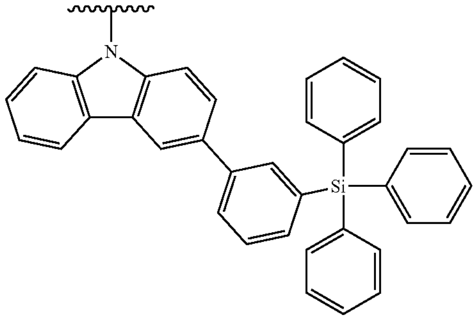
-continued
M21
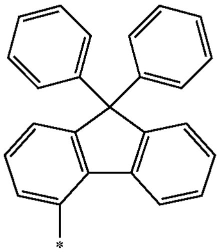
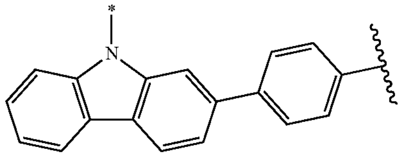
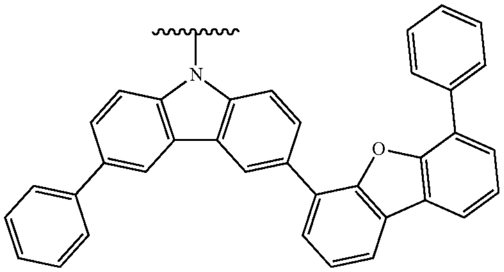
M22
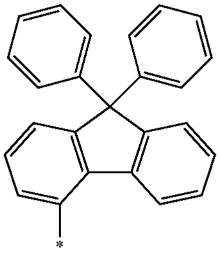
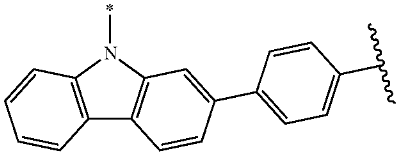
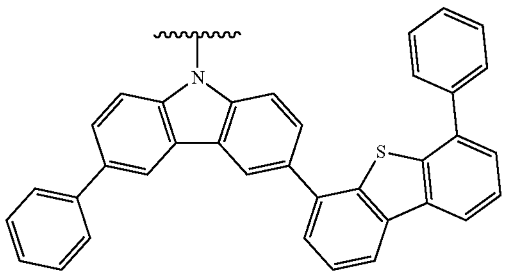

-continued
M23
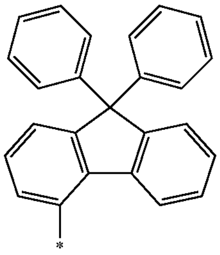
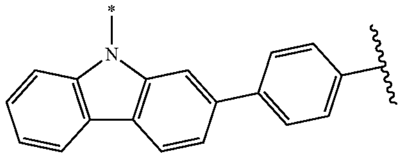
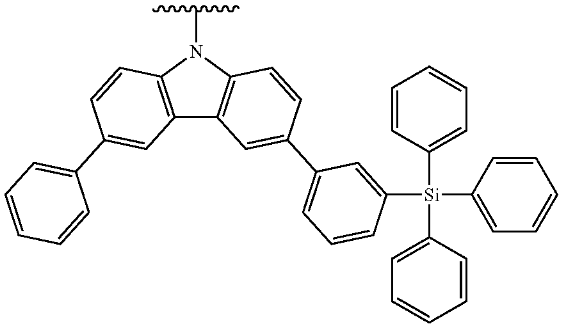
M24
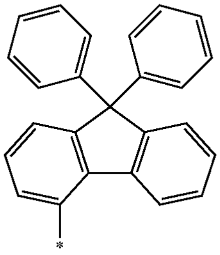
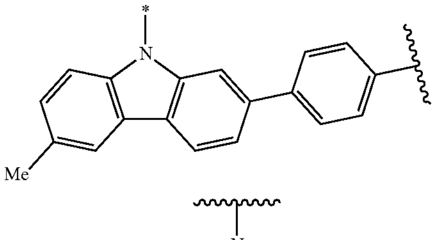
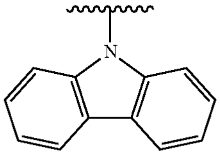
M25
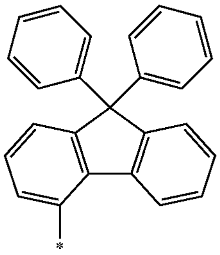
-continued
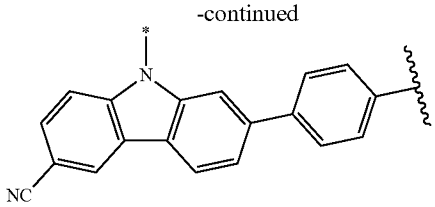
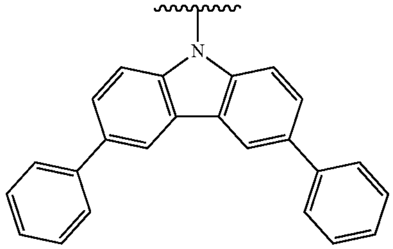
M26
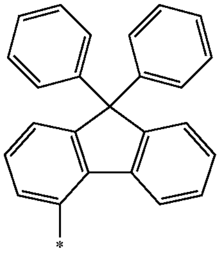
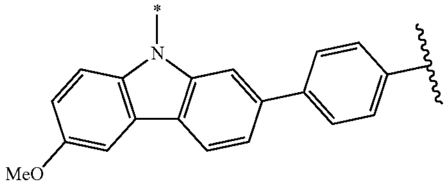
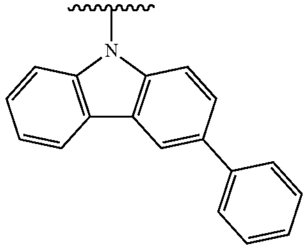
N1
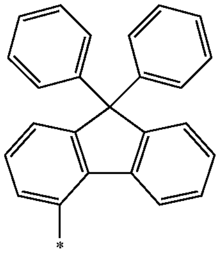
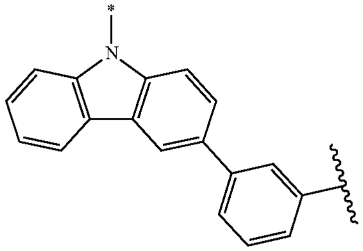

-continued
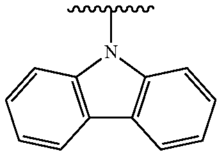
N2
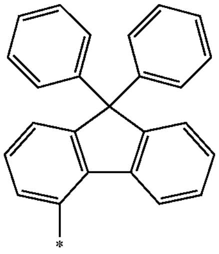
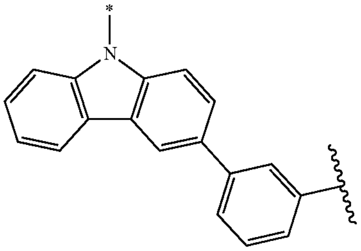
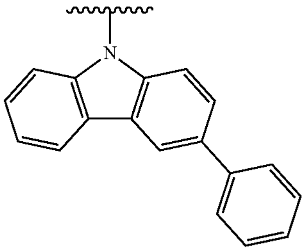
N3
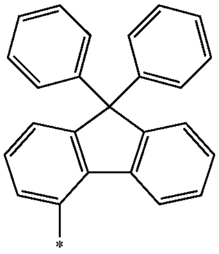
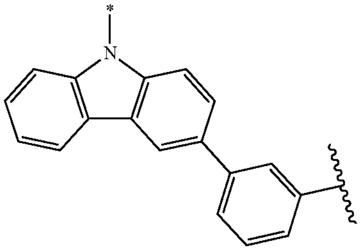
-continued
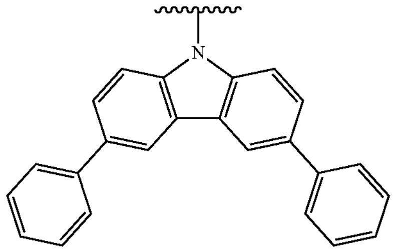
N4
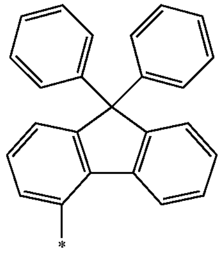
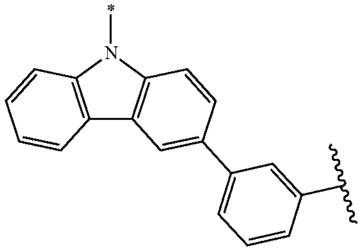
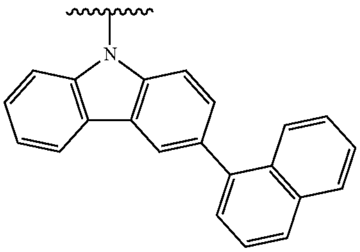
N5
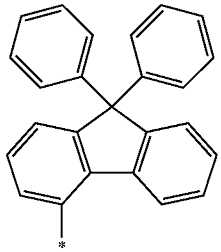
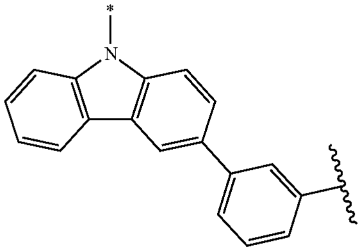

-continued
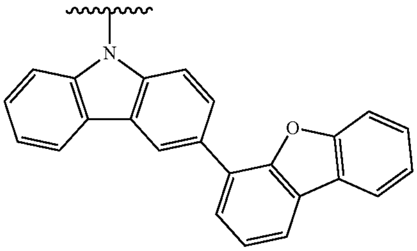
N6
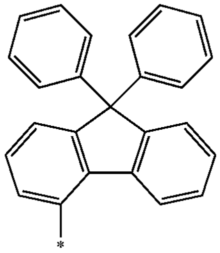
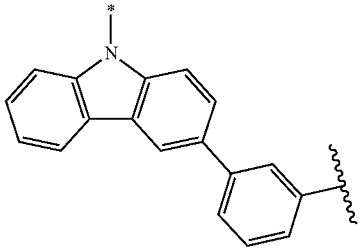
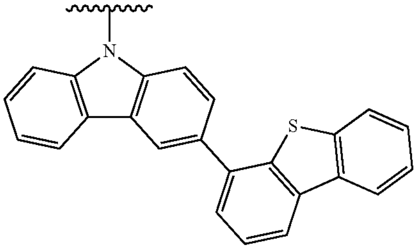
N7
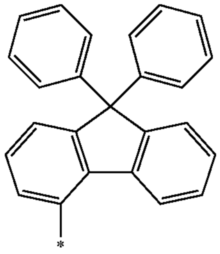
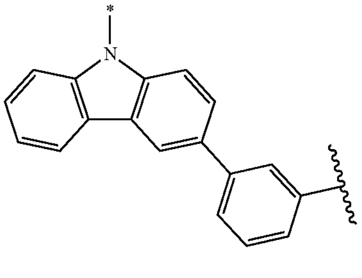
-continued
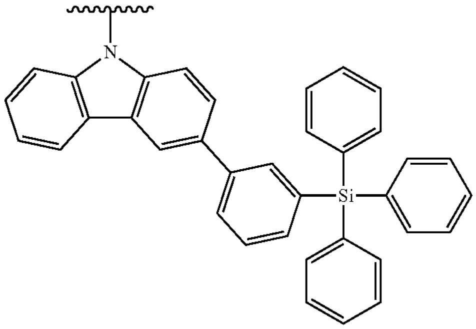
N8
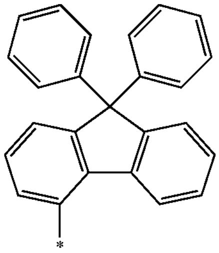
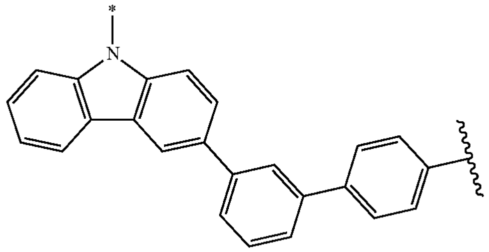
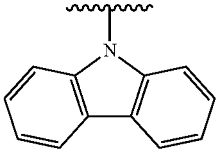
N9
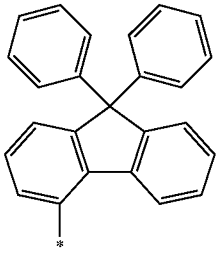
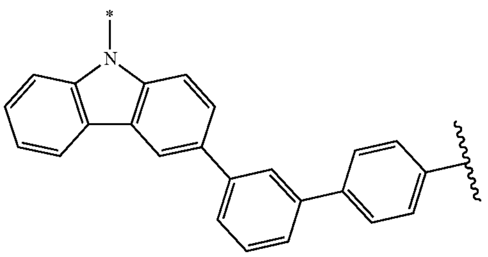

-continued
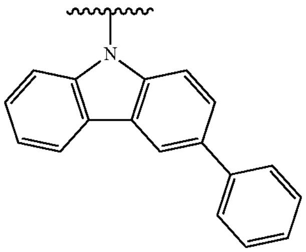
N10
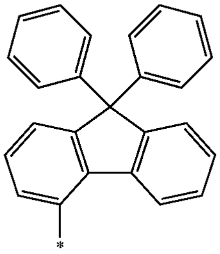
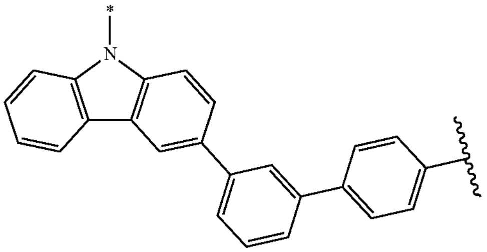
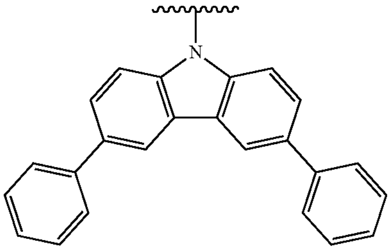
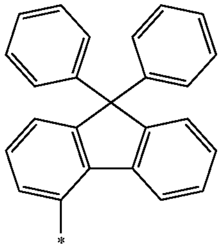
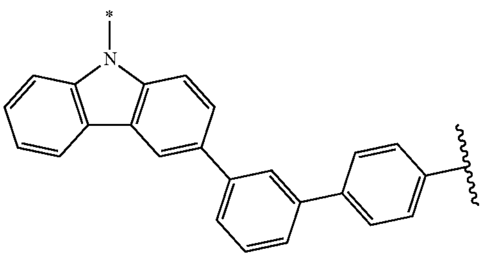
-continued
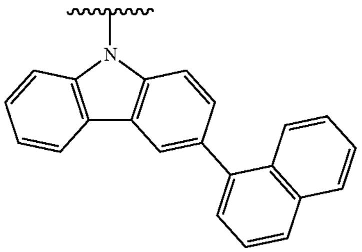
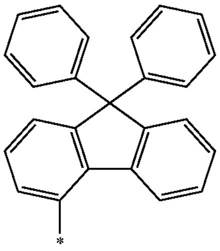
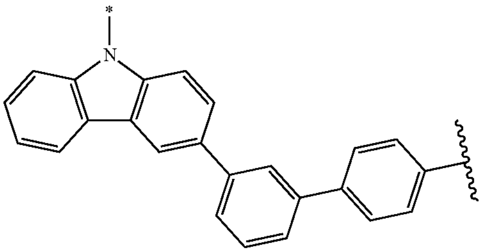
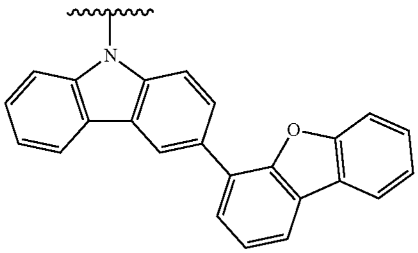
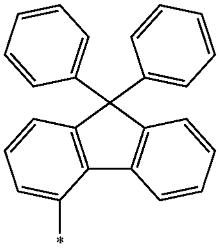
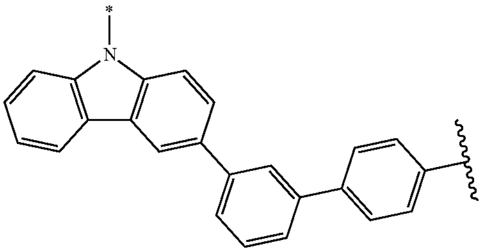

-continued
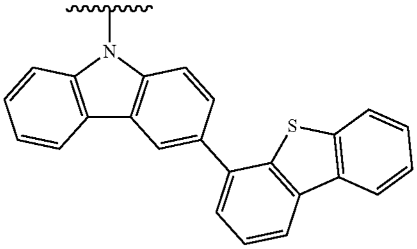
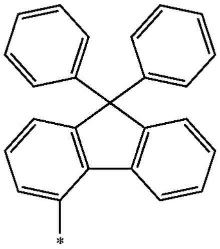
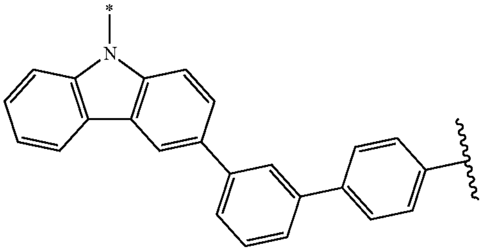
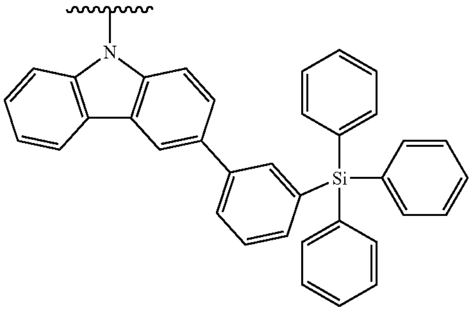
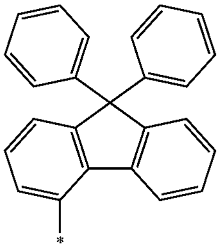
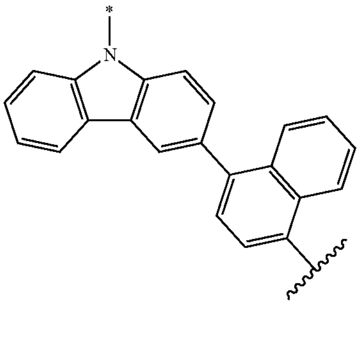
-continued
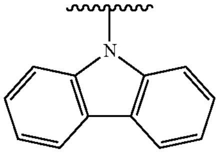
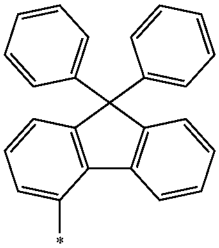
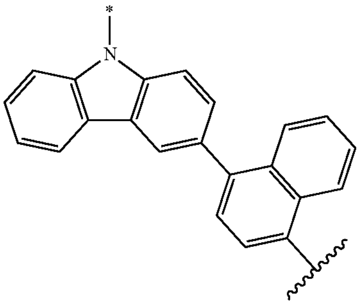
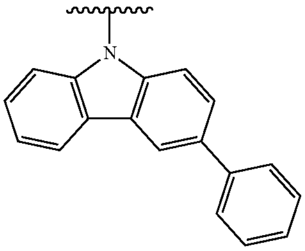
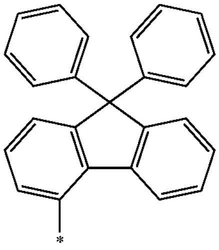
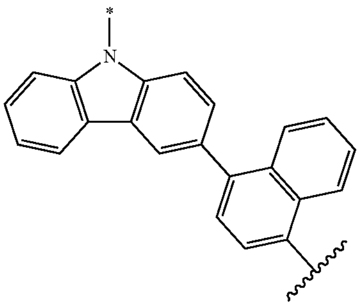

-continued
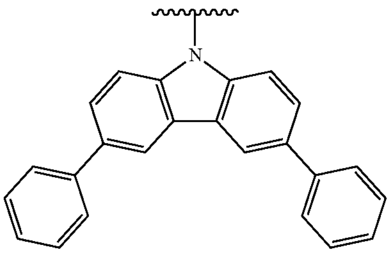
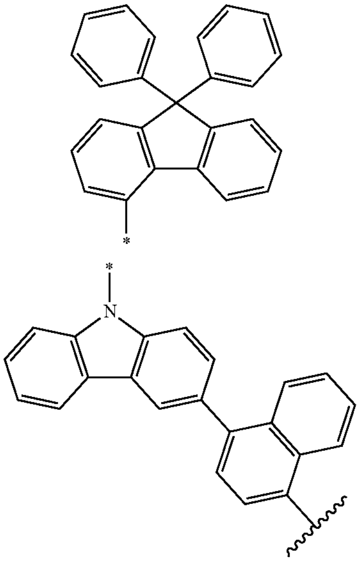
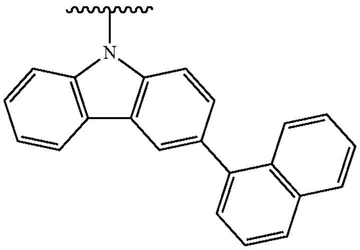
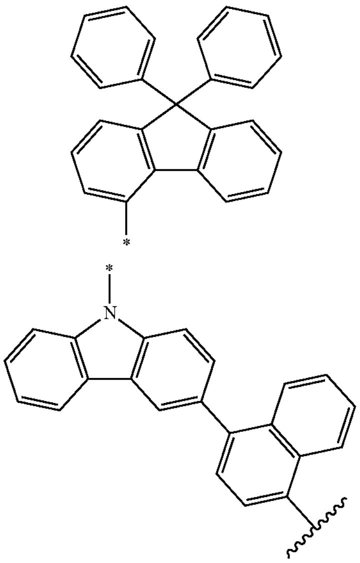
-continued
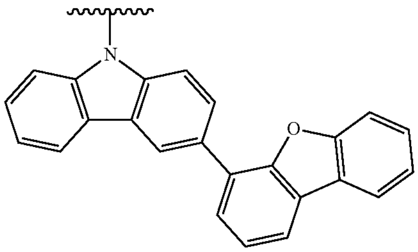
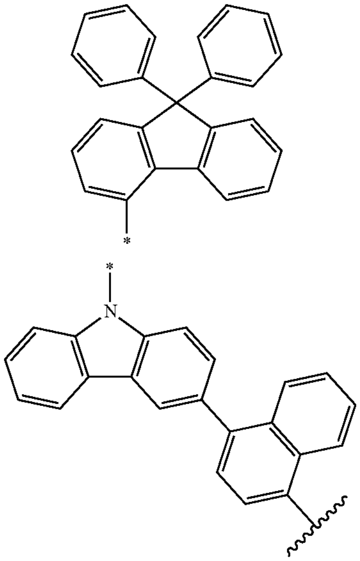
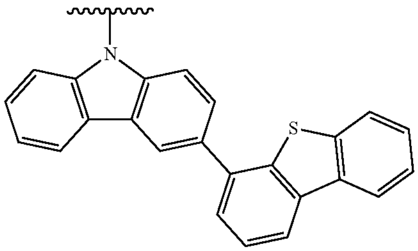
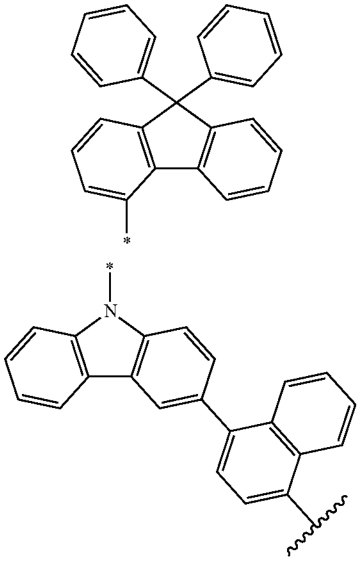

-continued
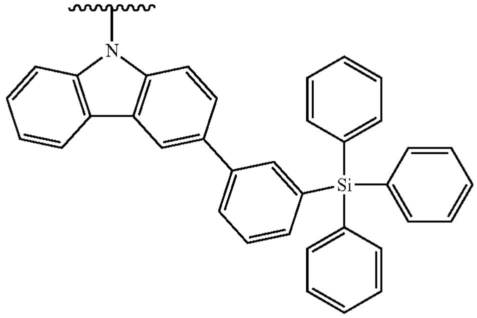
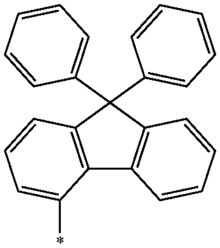
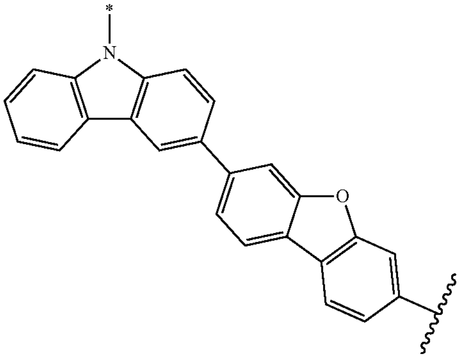
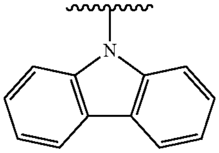
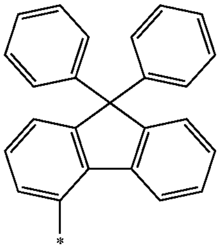
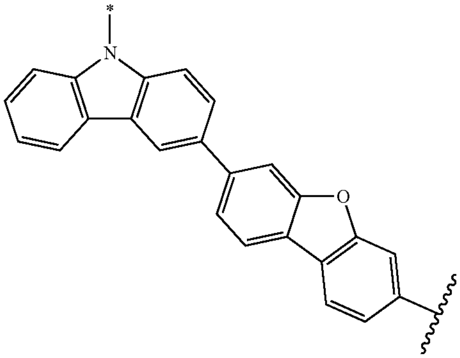
-continued
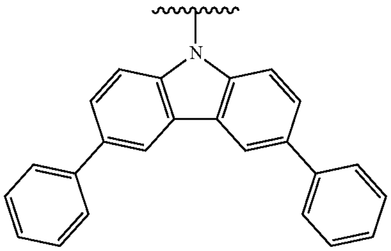
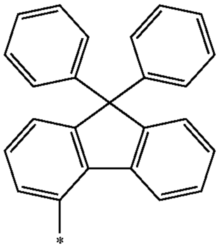
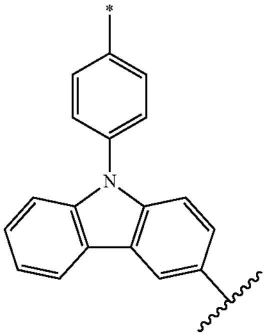
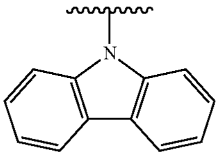
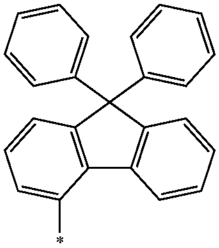
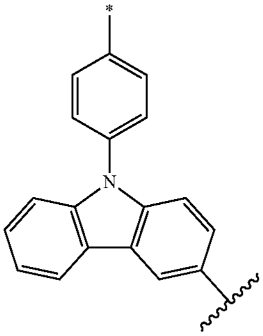

-continued
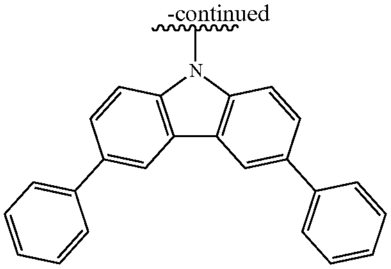
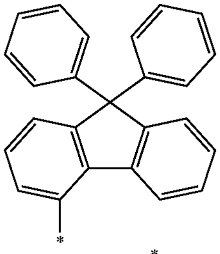
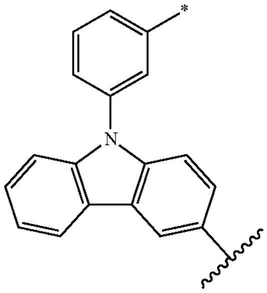
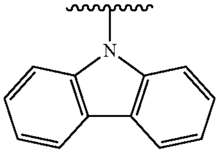
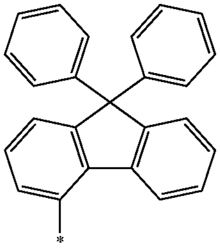
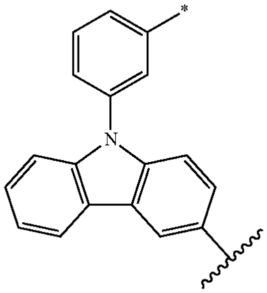
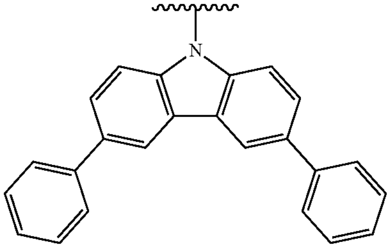
-continued
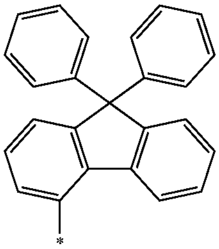
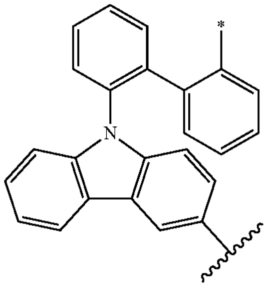
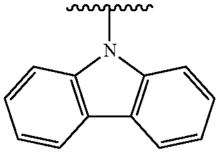
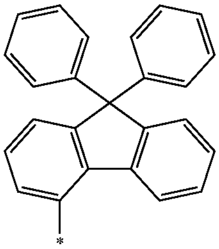
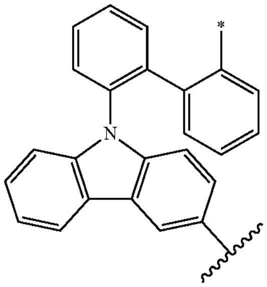
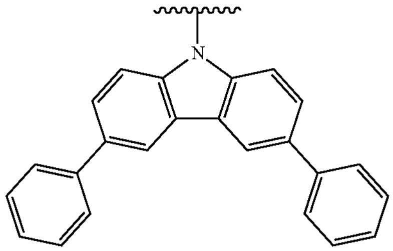
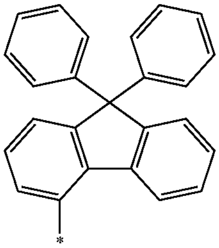

-continued
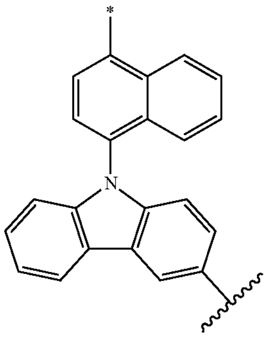
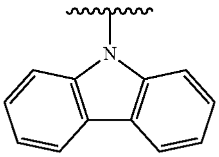
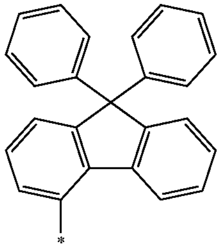
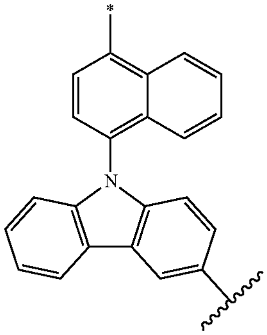
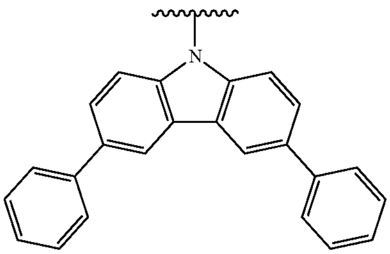
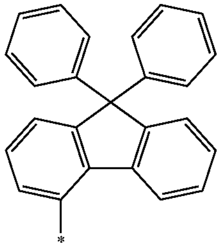
-continued
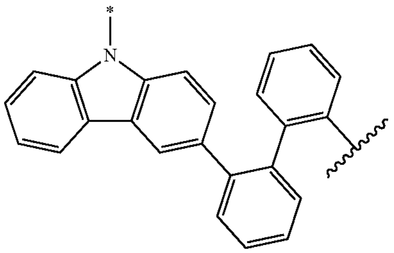
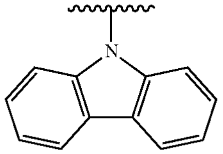
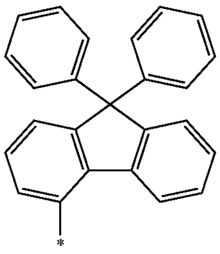
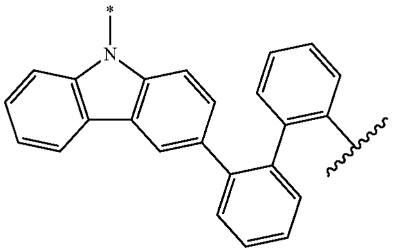
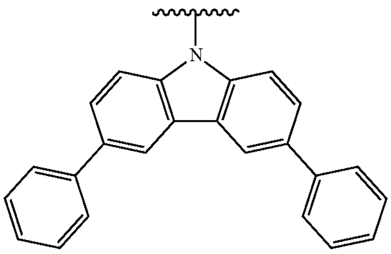
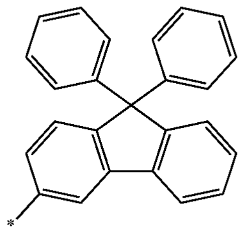
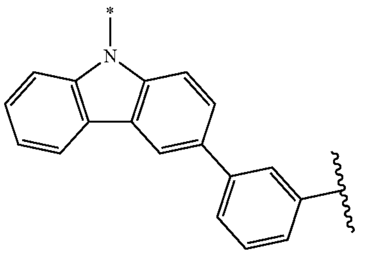

-continued
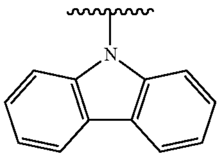
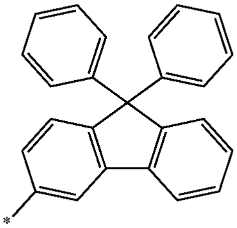
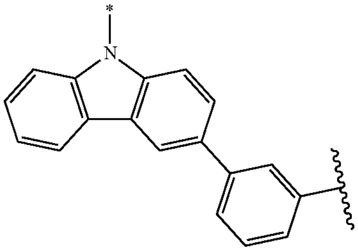
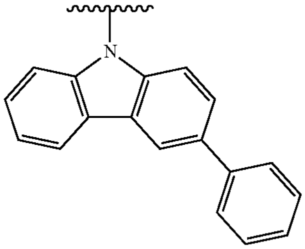
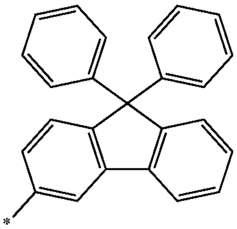
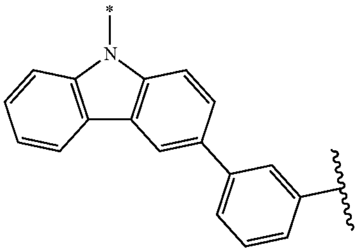
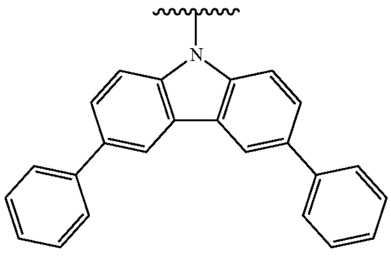
-continued
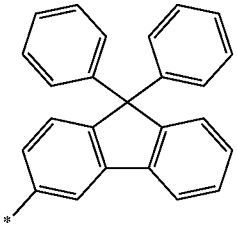
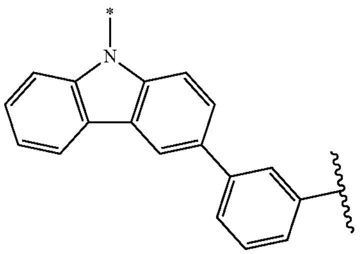
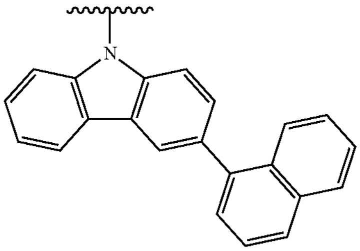
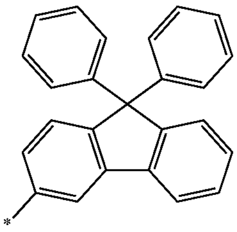
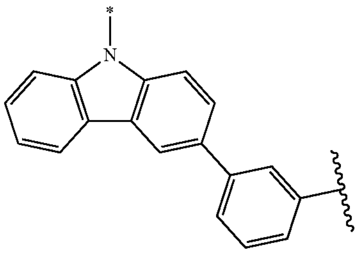
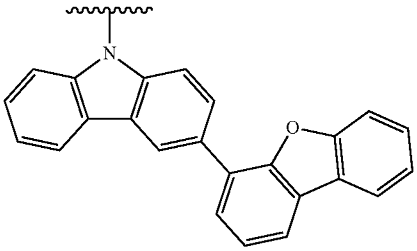
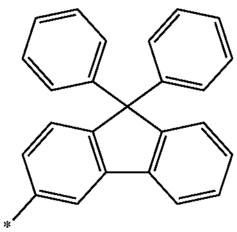

-continued
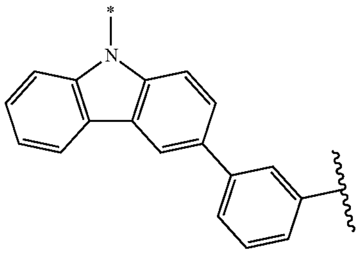
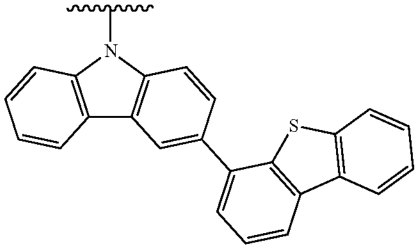
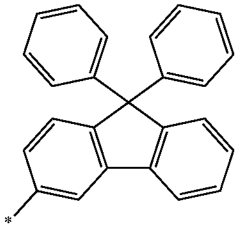
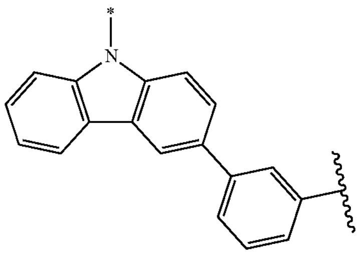
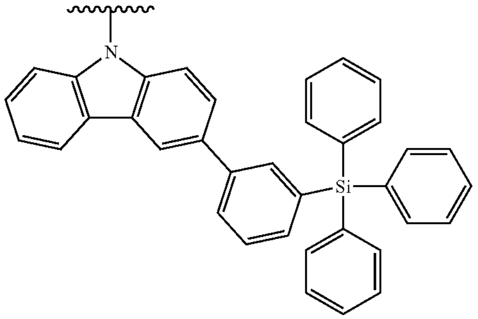
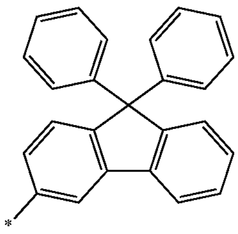
-continued
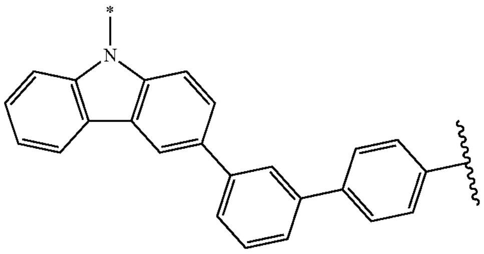
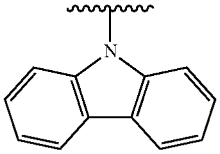
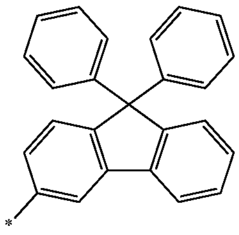
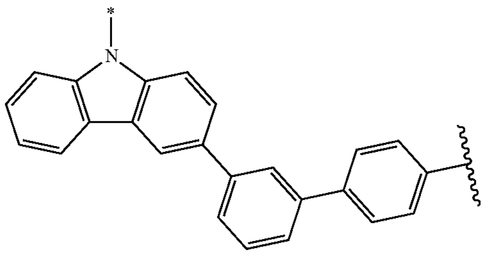
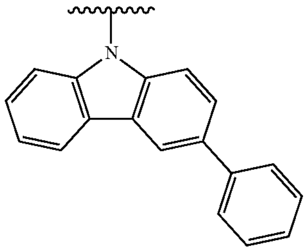
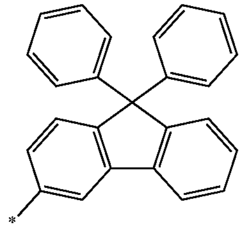
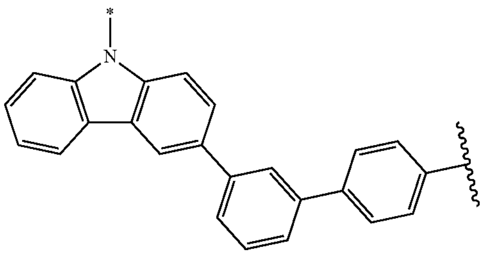

-continued
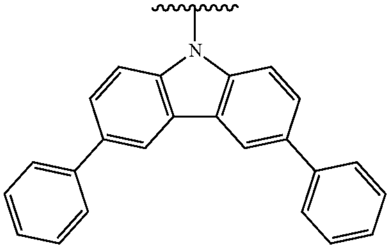
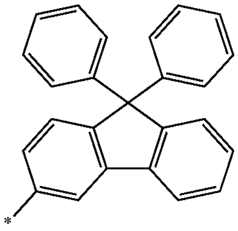
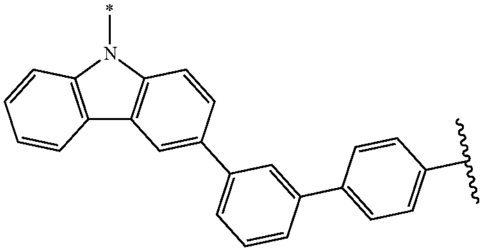
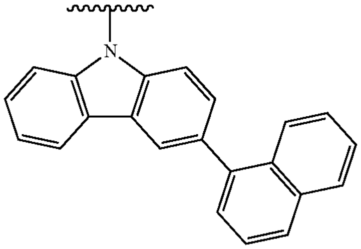
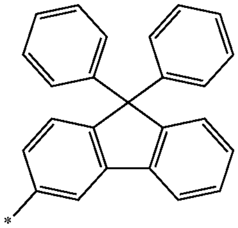
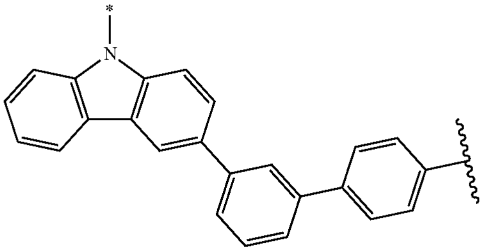
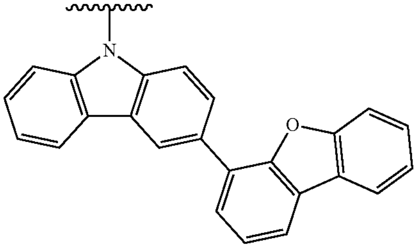
-continued
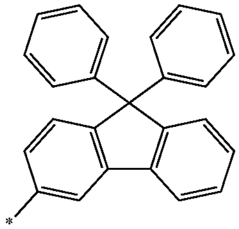
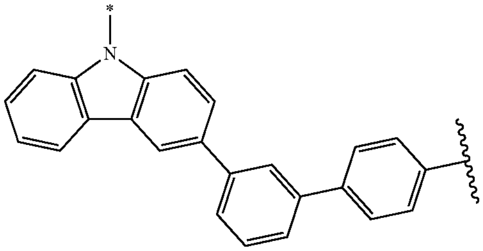
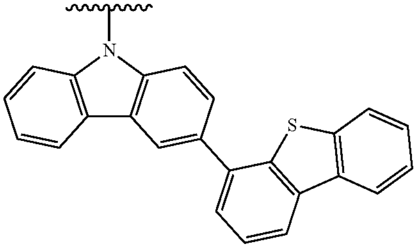
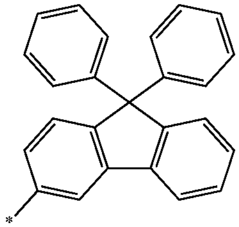
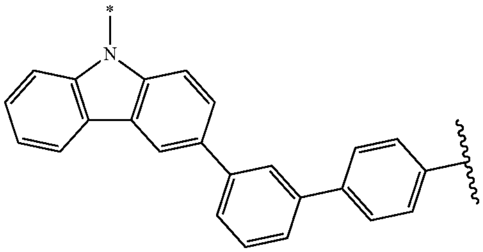
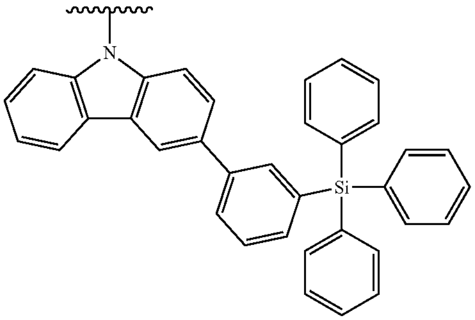

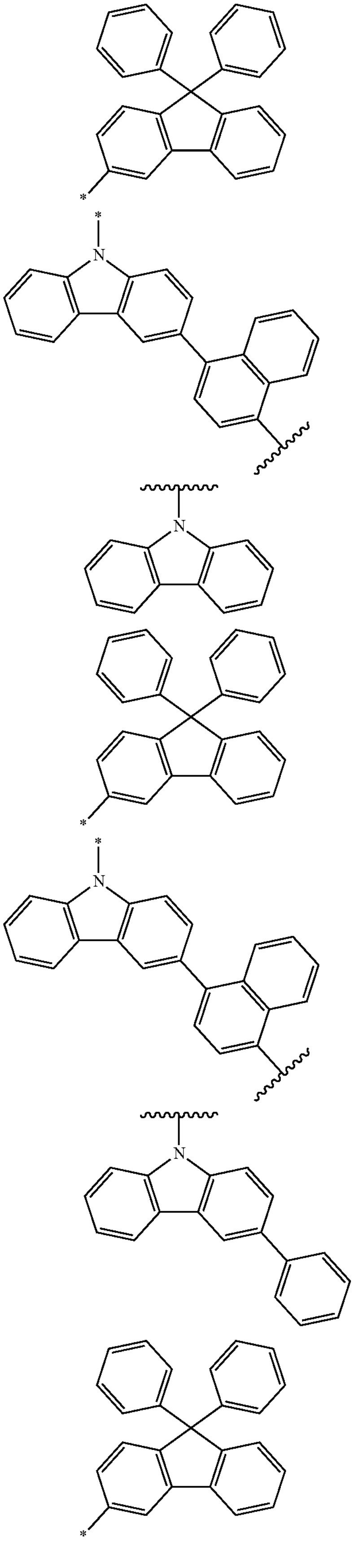
-continued
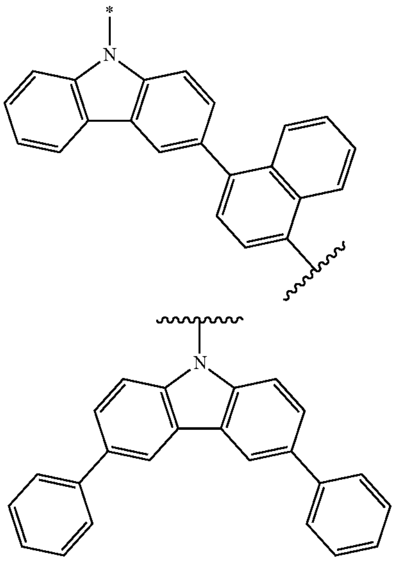
O18
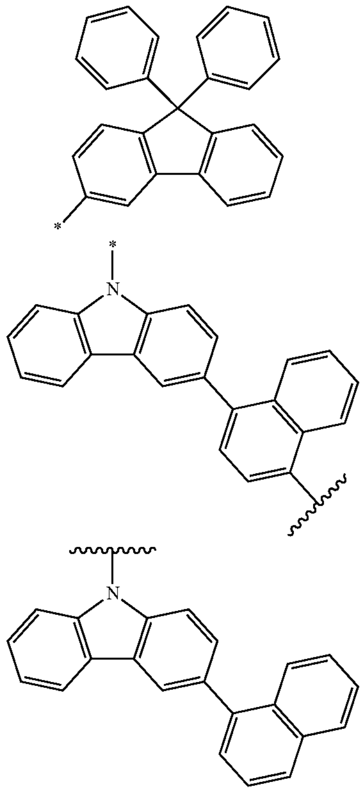
O19
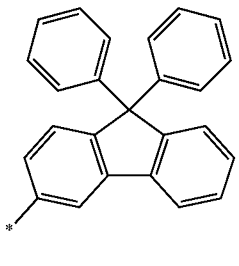

-continued
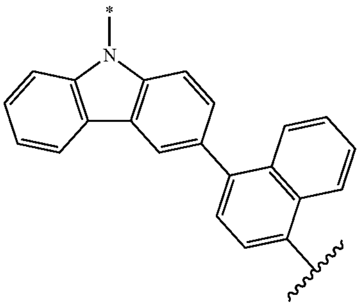
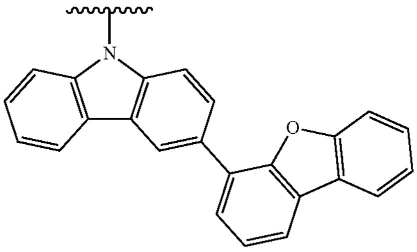
O20
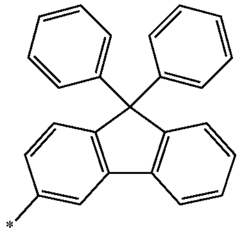
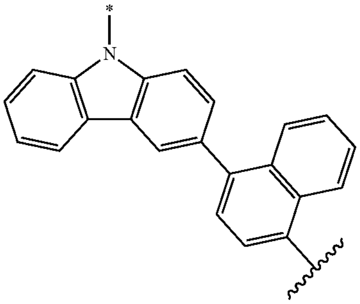
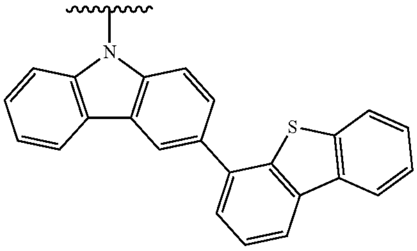
O21
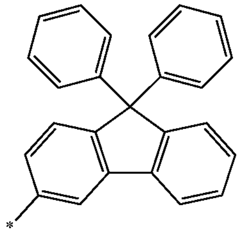
-continued
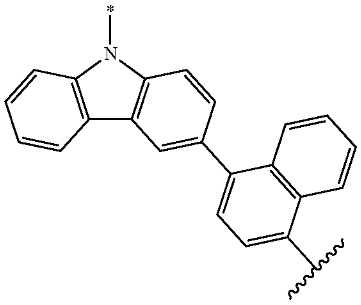
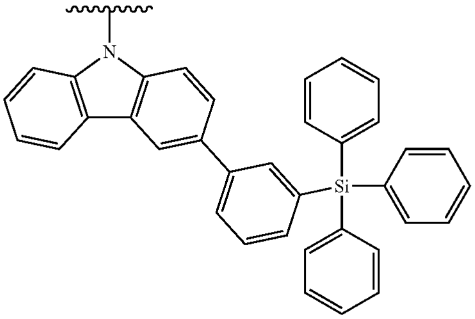
O22
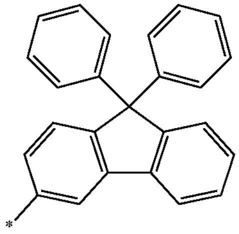
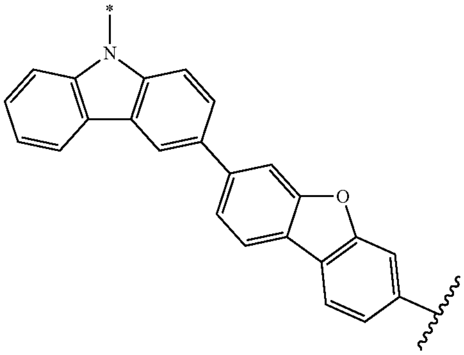
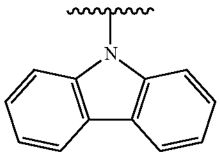
O23
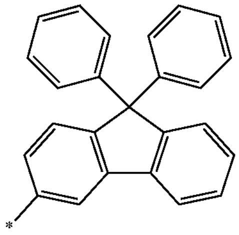

-continued
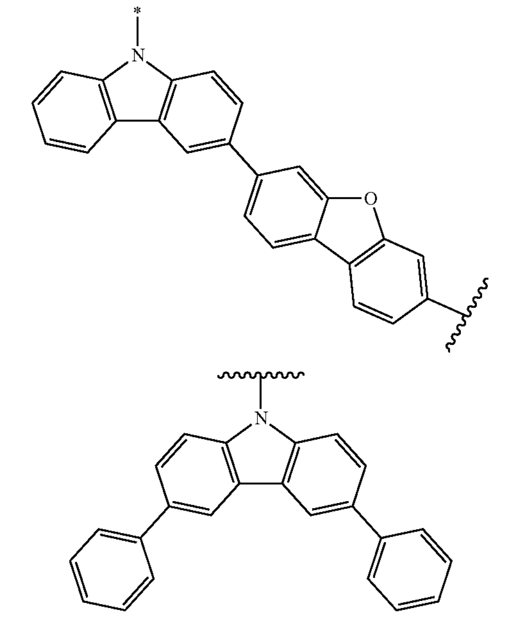
O24
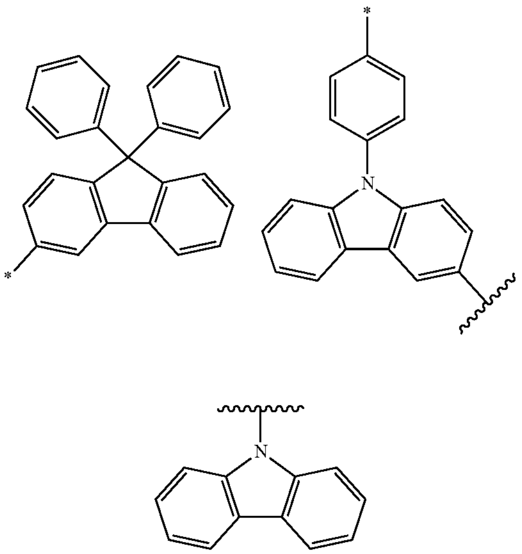
O25
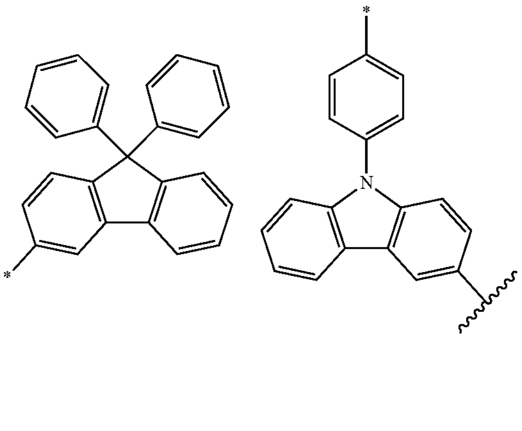
-continued
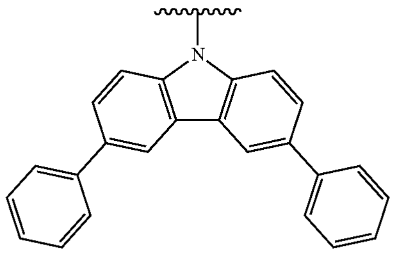
O26
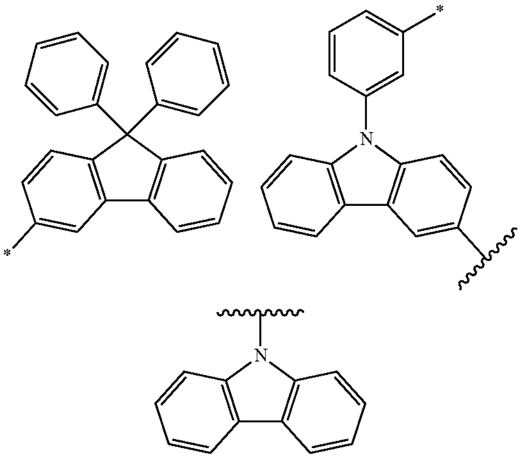
O27
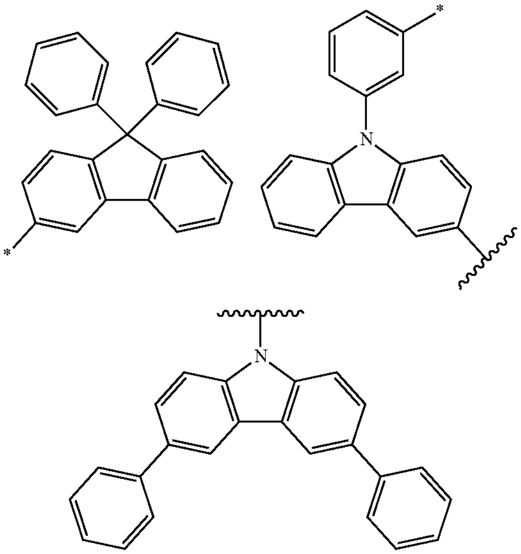
O28
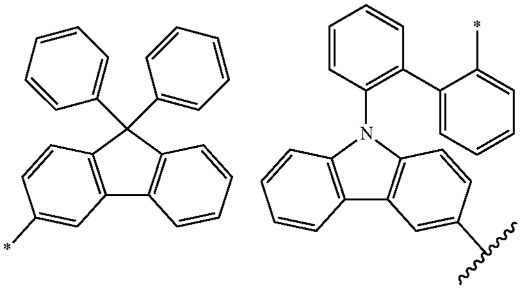

-continued
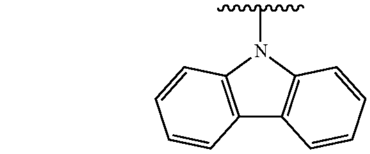
O29
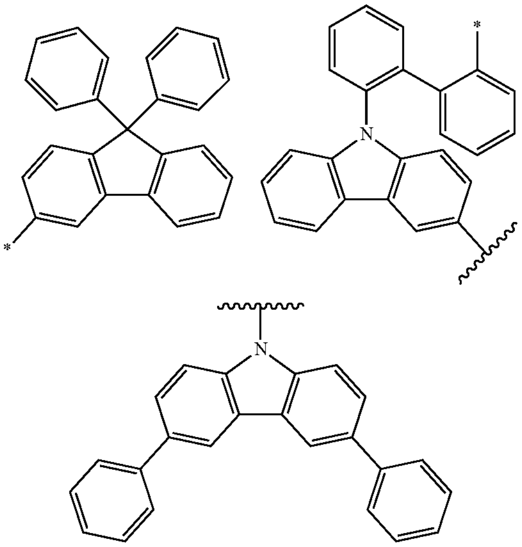
O30
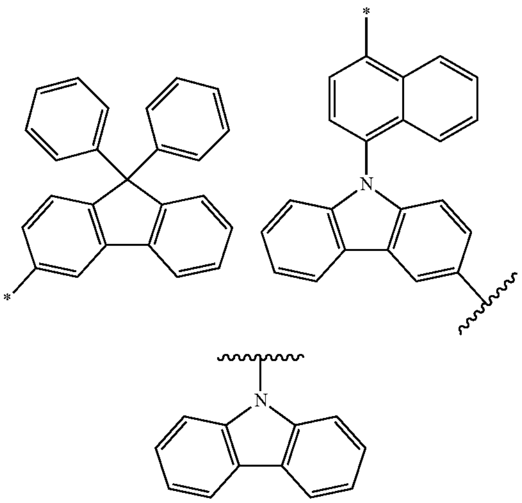
O31
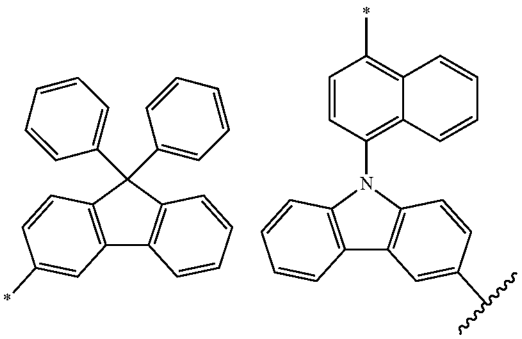
-continued
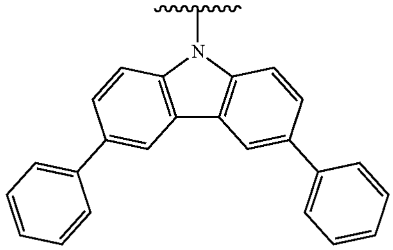
O32
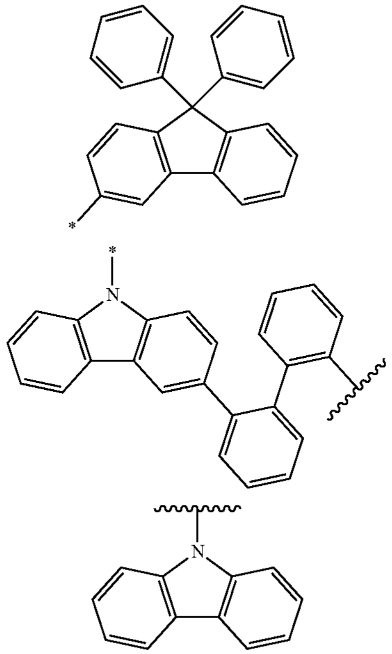
O33
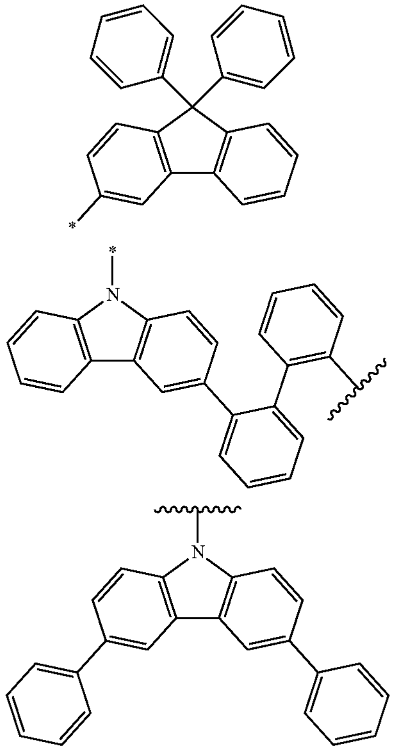

-continued
P1
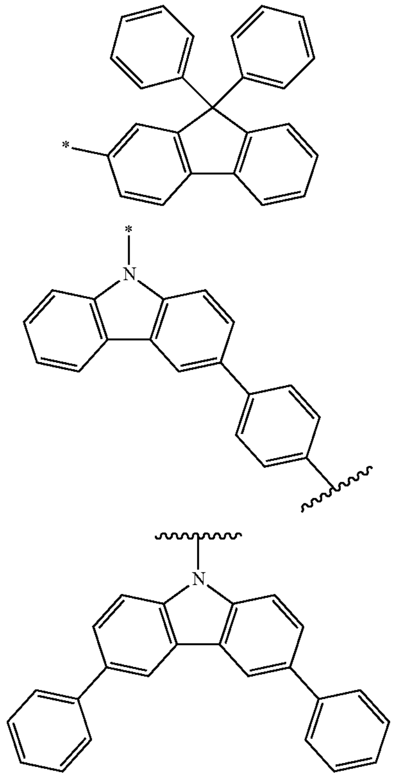
P2
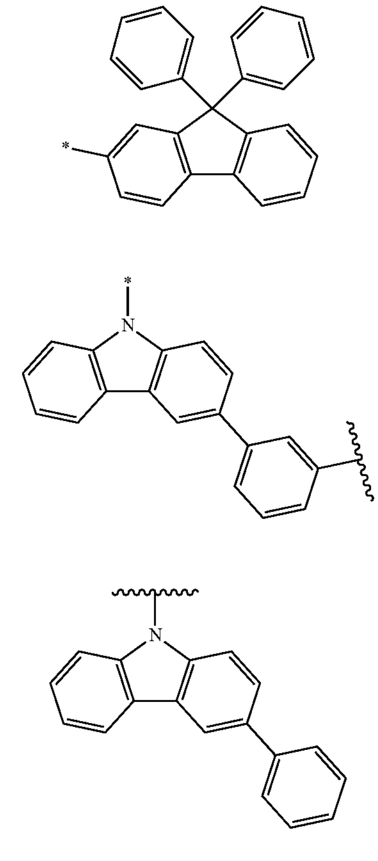
-continued
P3
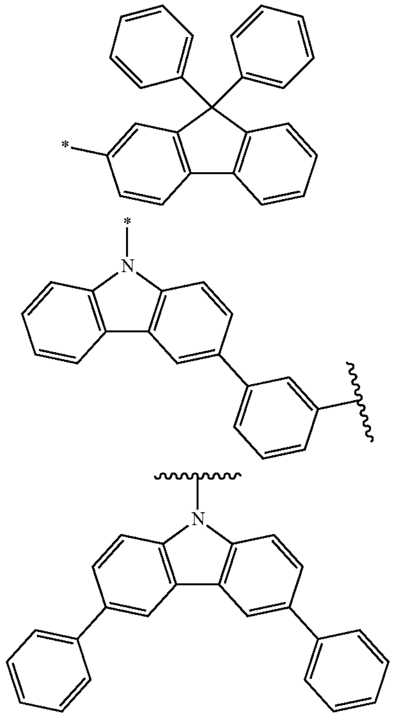
P4
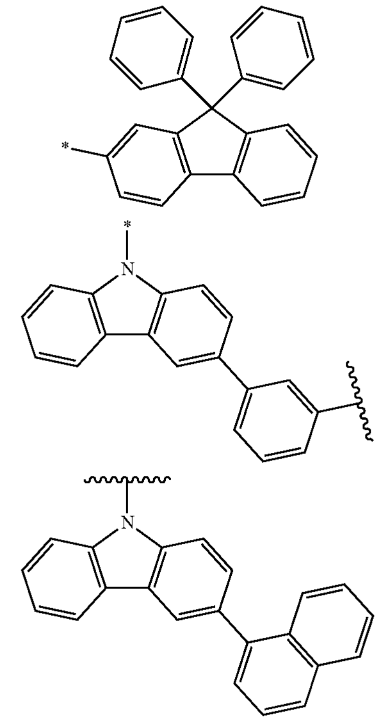
P5
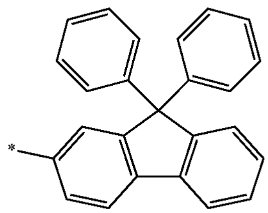

-continued
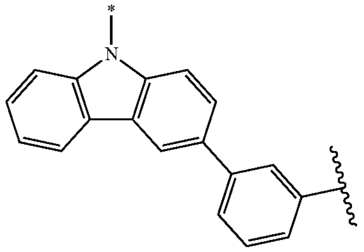
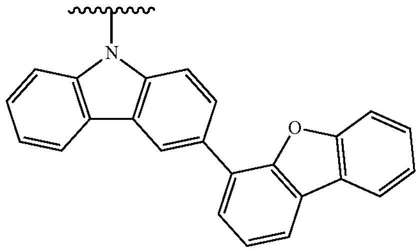
P6
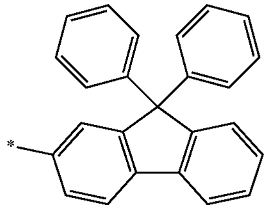
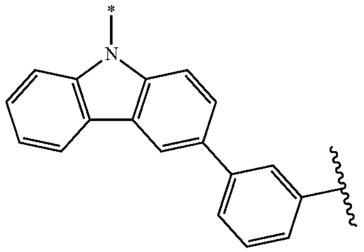
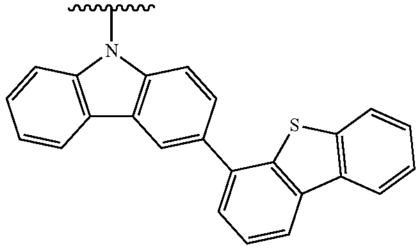
P7
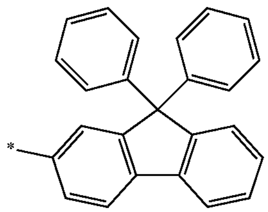
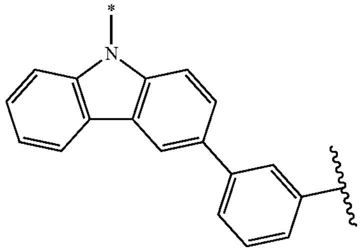
-continued
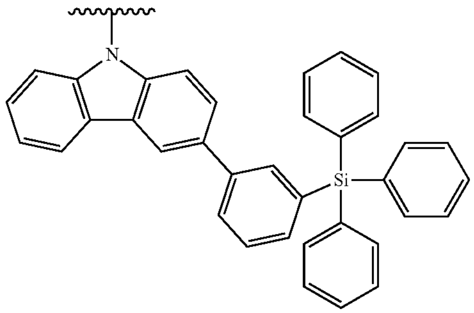
P8
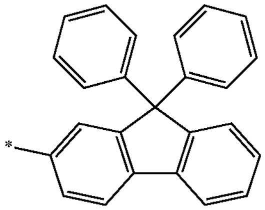
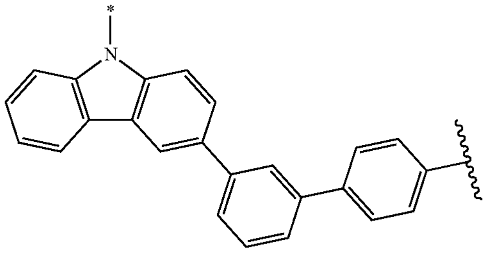
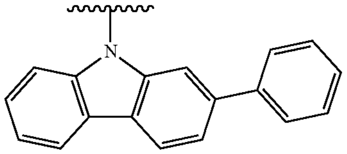
P9
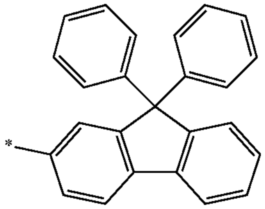
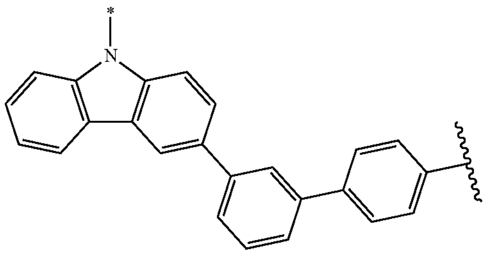
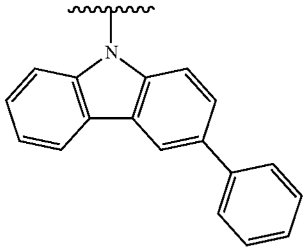

-continued
P10
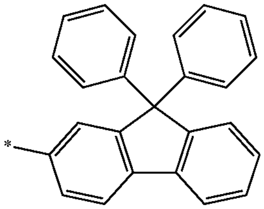
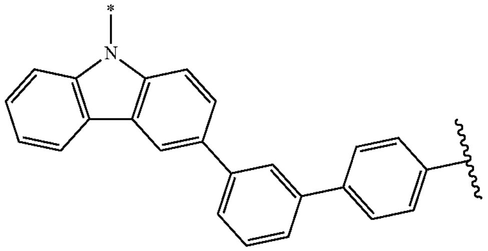
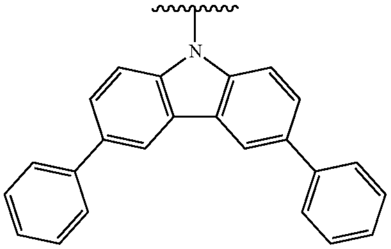
P11
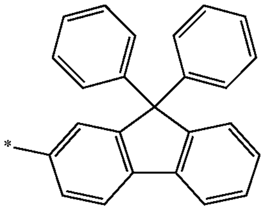
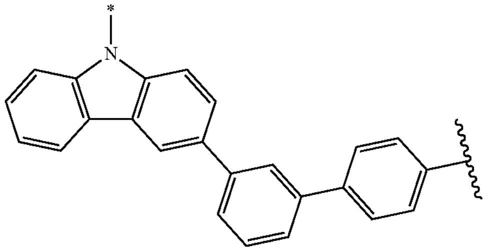
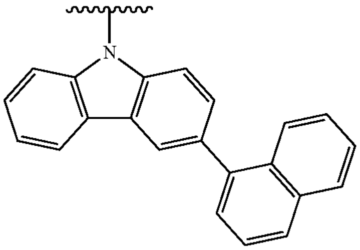
P12
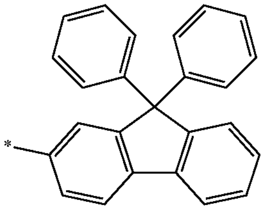
-continued
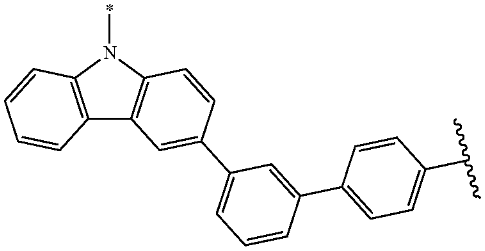
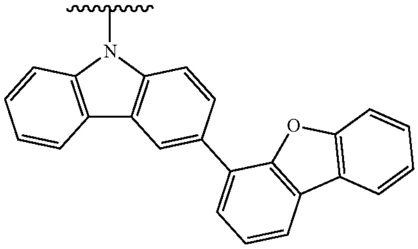
P13
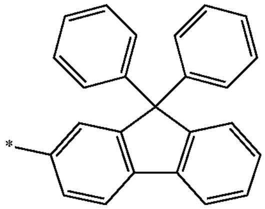
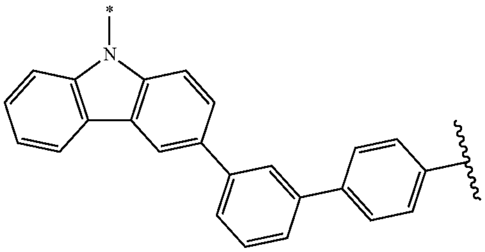
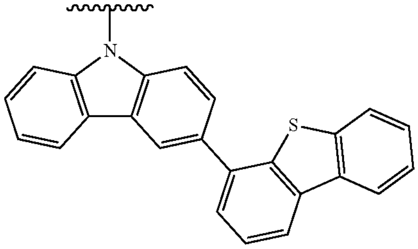
P14
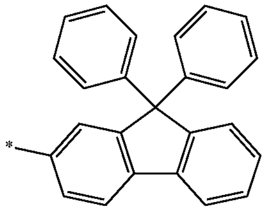
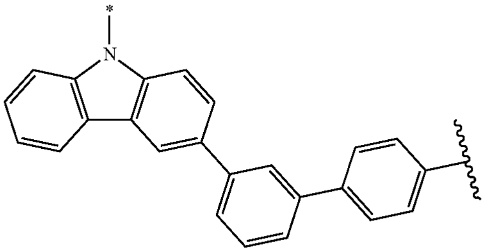

-continued
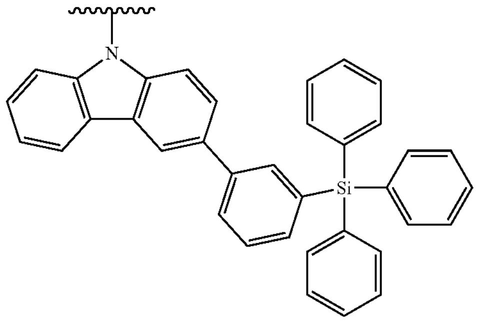
P15
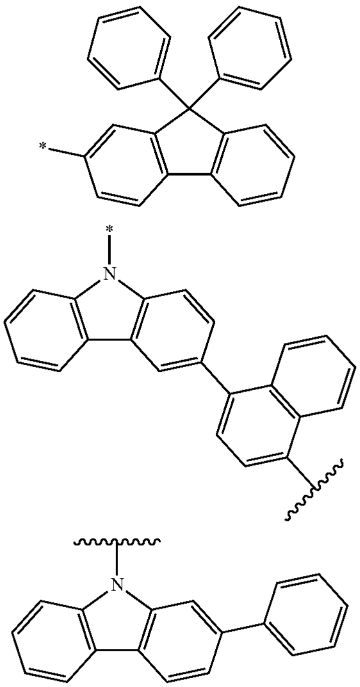
P16
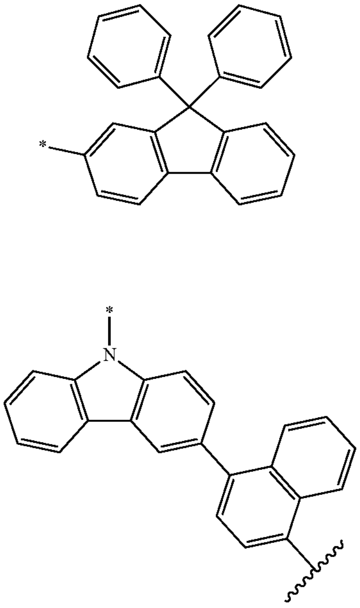
-continued
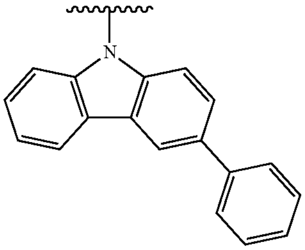
P17
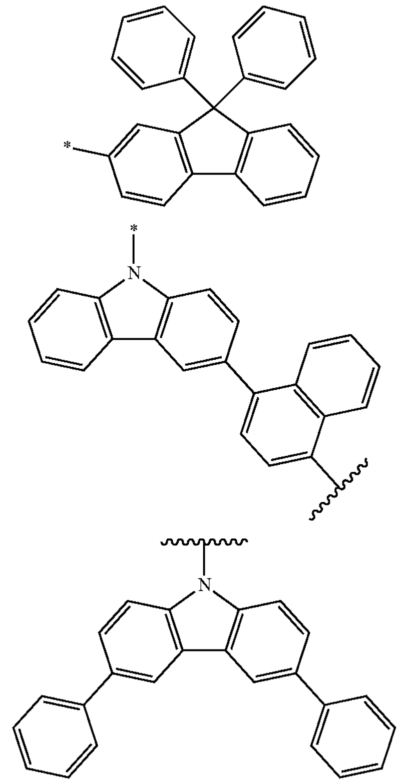
P18
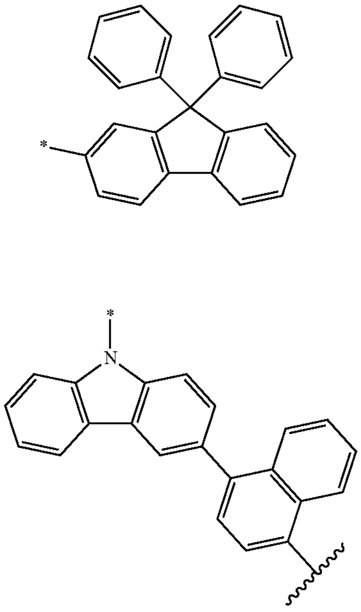

-continued
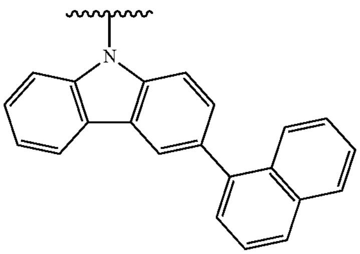
P19
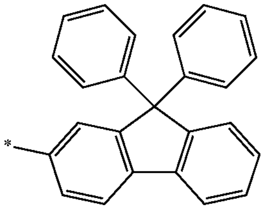
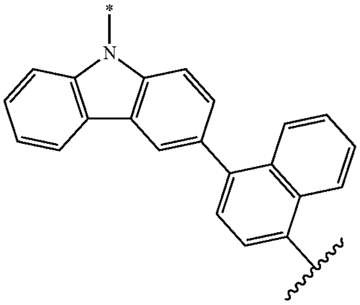
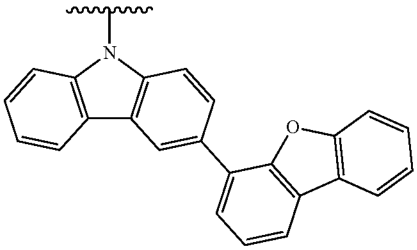
P20
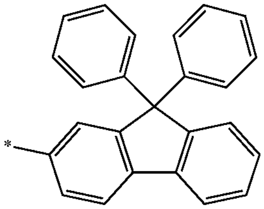
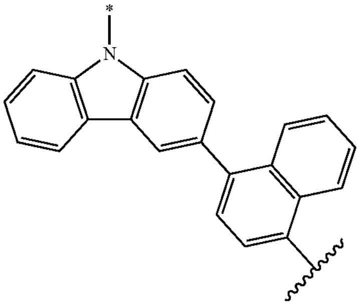
-continued
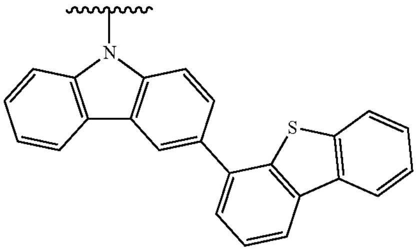
P21
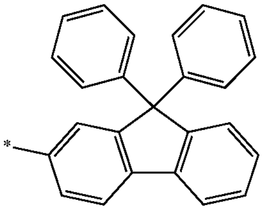
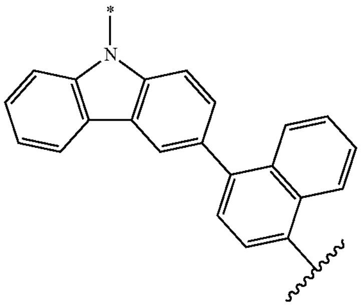
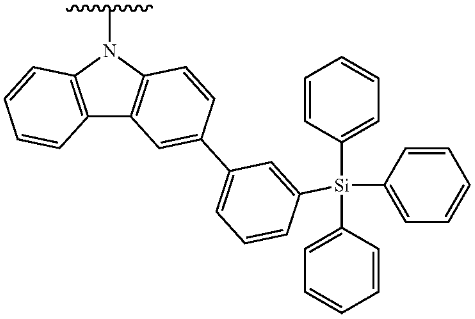
P22
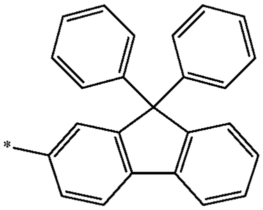
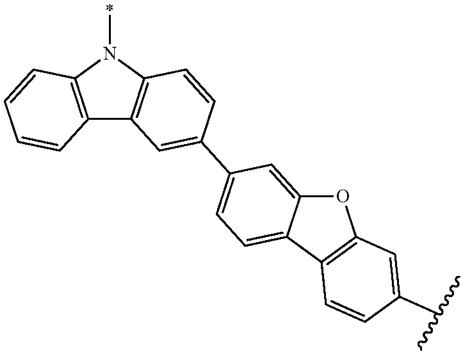

-continued
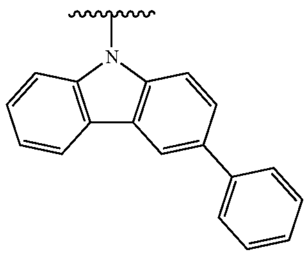
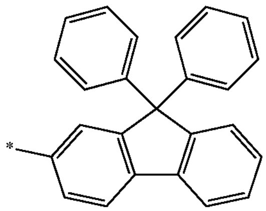
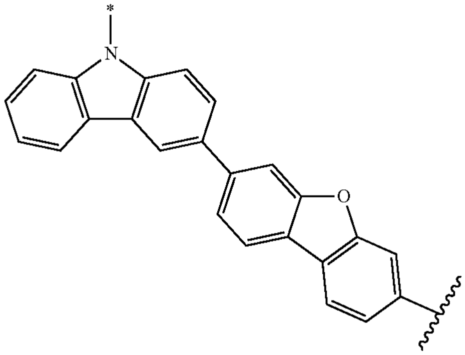
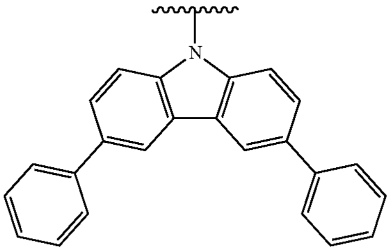
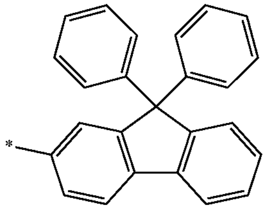
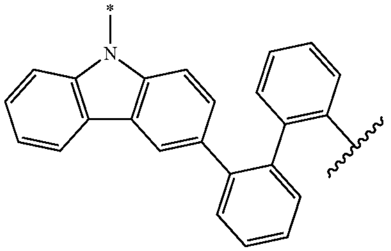
-continued
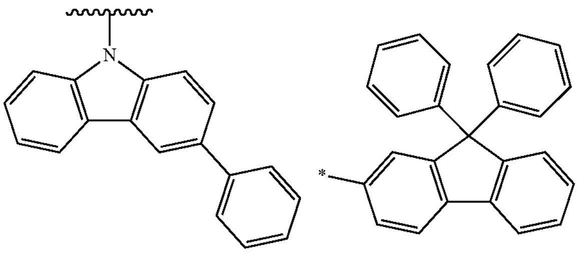
P23
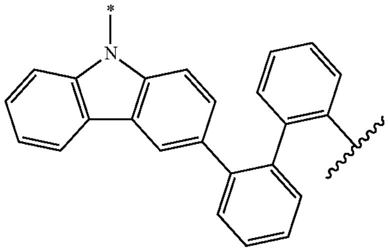
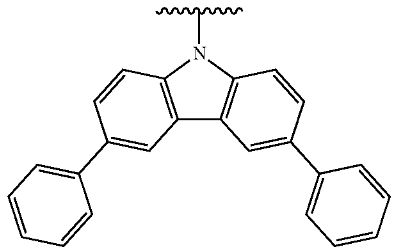
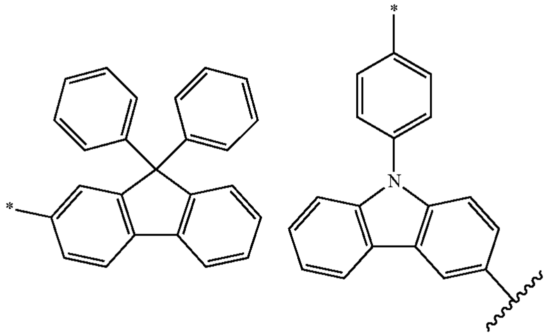
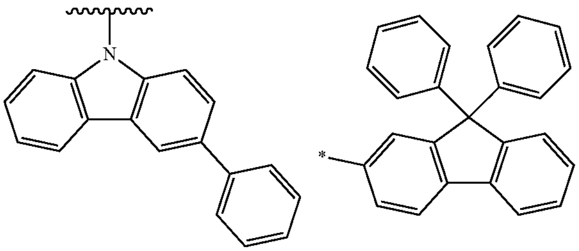
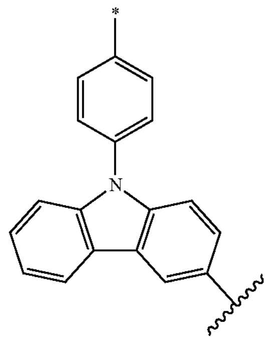

-continued
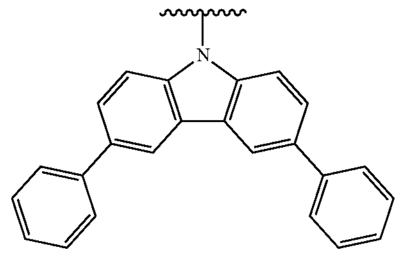
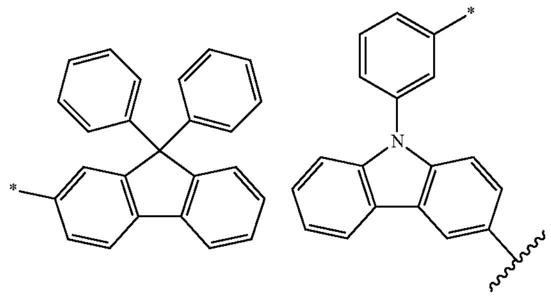
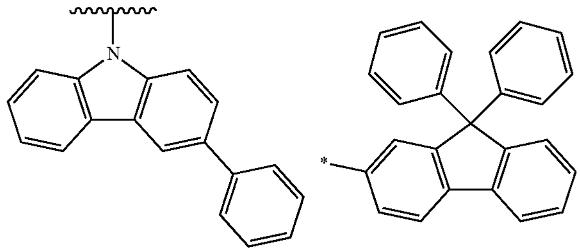
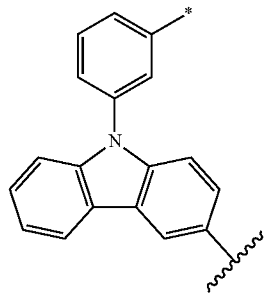
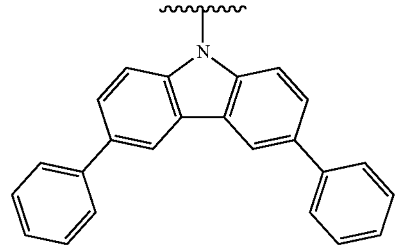
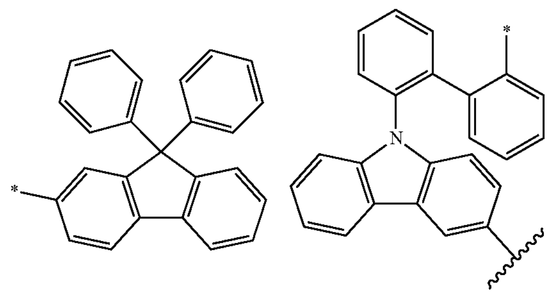
-continued
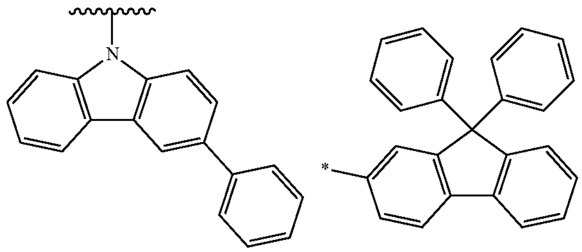
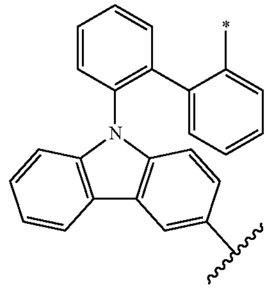
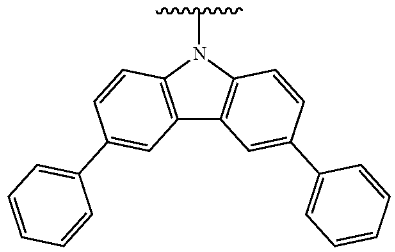
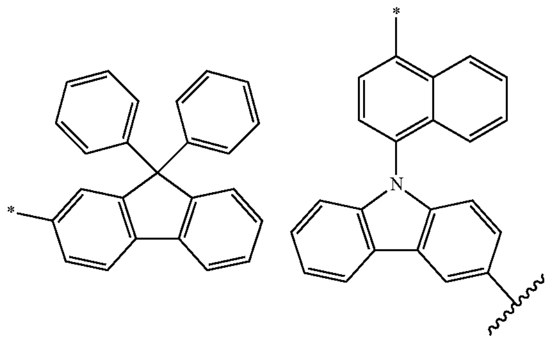
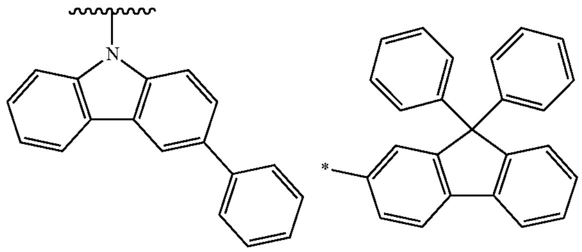
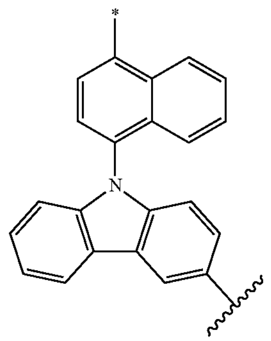

-continued
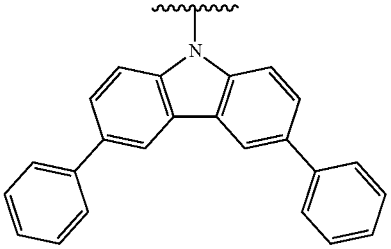
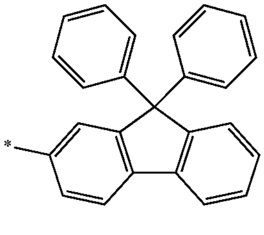
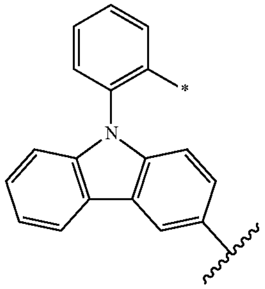
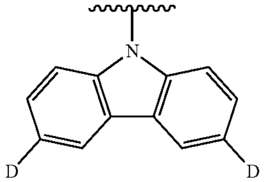
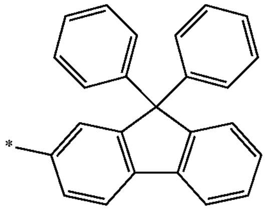
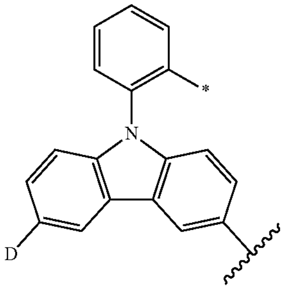
-continued
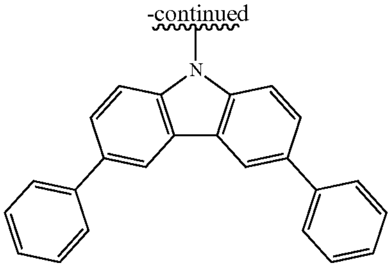
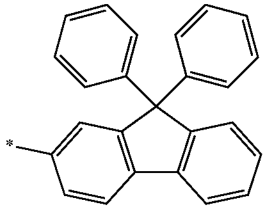
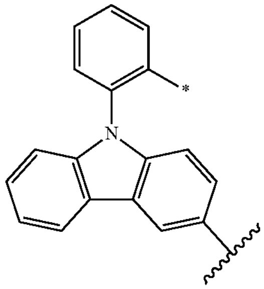
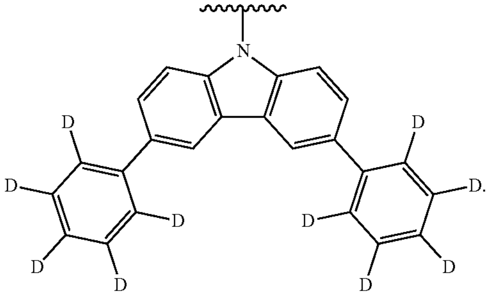
* * * * *